United States Patent
Aoki et al.

(10) Patent No.: US 10,174,053 B2
(45) Date of Patent: Jan. 8, 2019

(54) 2 SUBSTITUTED CEPHEM COMPOUNDS

(71) Applicants: Glaxo Group Limited, Middlesex (GB); Shionogi and Co., Ltd, Osaka-shi (JP)

(72) Inventors: Toshiaki Aoki, Osaka (JP); Hiroki Kusano, Osaka (JP); Xiangmin Liao, Collegeville, PA (US); Neil David Pearson, Collegeville, PA (US); Israil Pendrak, King of Prussia, PA (US); Jun Sato, Osaka (JP); Reema K. Thalji, King of Prussia, PA (US); Kenji Yamawaki, Osaka (JP); Katsuki Yokoo, Osaka (JP)

(73) Assignees: Glaxo Group Limited, Middlesex (GB); Shionogi and Co., Ltd., Osaka-Shi (JP)

( * ) Notice: Subject to any disclaimer, the term of this patent is extended or adjusted under 35 U.S.C. 154(b) by 0 days.

(21) Appl. No.: 15/490,220

(22) Filed: Apr. 18, 2017

(65) Prior Publication Data
US 2017/0281532 A1 Oct. 5, 2017

Related U.S. Application Data

(63) Continuation of application No. 14/439,219, filed as application No. PCT/IB2013/002423 on Oct. 29, 2013, now abandoned.

(60) Provisional application No. 61/719,523, filed on Oct. 29, 2012.

(51) Int. Cl.
| | |
|---|---|
| *C07D 501/48* | (2006.01) |
| *C07D 505/24* | (2006.01) |
| *C07D 501/50* | (2006.01) |
| *A61K 9/00* | (2006.01) |

(52) U.S. Cl.
CPC ......... *C07D 501/48* (2013.01); *C07D 501/50* (2013.01); *C07D 505/24* (2013.01); *A61K 9/0019* (2013.01); *Y02A 50/473* (2018.01)

(58) Field of Classification Search
CPC .............. C07D 501/48; A61K 9/0019
See application file for complete search history.

(56) References Cited

U.S. PATENT DOCUMENTS

| | | | |
|---|---|---|---|
| 3,487,079 A | 12/1969 | Sheehan | |
| 4,268,509 A | 5/1981 | Teraji et al. | |
| 5,019,570 A | 5/1991 | Arnould et al. | |
| 7,384,928 B2 | 6/2008 | Nishitani et al. | |
| 7,696,354 B2 | 4/2010 | Nishitani et al. | |
| 8,883,773 B2 | 11/2014 | Yamawaki et al. | |
| 9,085,589 B2 * | 7/2015 | Kusano ................ | C07D 501/42 |
| 9,145,425 B2 | 9/2015 | Hisakawa et al. | |
| 9,238,657 B2 | 1/2016 | Nishitani et al. | |
| 9,242,999 B2 * | 1/2016 | Nishitani ............. | C07D 501/36 |
| 9,290,515 B2 * | 3/2016 | Yamawaki ........... | C07D 501/56 |
| 9,334,289 B2 * | 5/2016 | Nishitani ............. | C07D 501/18 |
| 9,340,556 B2 * | 5/2016 | Liao .................... | C07D 501/60 |
| 2005/0153950 A1 | 7/2005 | Nishitani et al. | |
| 2009/0131655 A1 | 5/2009 | Nishitani et al. | |
| 2011/0190254 A1 | 8/2011 | Nishitani et al. | |
| 2013/0079319 A1 | 3/2013 | Yamawaki et al. | |
| 2013/0102583 A1 | 4/2013 | Hisakawa et al. | |

FOREIGN PATENT DOCUMENTS

| | | |
|---|---|---|
| EP | 0 035 357 A1 | 9/1981 |
| EP | 0 472 060 A2 | 2/1992 |
| EP | 0 620 225 B1 | 10/1994 |
| EP | 0 838 465 A1 | 4/1998 |
| EP | 0 841 339 B1 | 5/1998 |
| EP | 1 489 084 A1 | 12/2004 |
| EP | 2 341 053 A1 | 7/2011 |
| JP | 55 011600 | 1/1980 |
| WO | WO 2003/078440 | 7/2005 |
| WO | WO 2011/125967 | 10/2011 |
| WO | WO 2010/050468 | 3/2012 |
| WO | WO 2011/125966 | 7/2013 |
| WO | WO 2014/069649 A1 | 5/2014 |

OTHER PUBLICATIONS

Gotou et al., "Cephem Compound* Its Salt* Their Preparation and Remedy and Prophylactic for Microbism Containing Mainly the Same", Patent Order MT, Abstract, 1 page.
Terachi et al., "Cephem Compound, Its Salt, Their Preparation and Remedy and Prophylactic for Microbism Containing Mainly the Same", J-Plat Pat, Abstract, 1 page.
Teraji et al., CAPlus,1980:550265, "Cephem compounds and pharmaceutical preparations containing them", (Corresponding to JP Patent Appln. 55011600/PN), 3 pages.
Maejima, et al., "In vitro antibacterial activity of KP-736, a new cephem antibiotic", *Antimicrobial Agents and Chemotherapy*, vol. 35, No. 1, pp. 104-110 (1991).
Mizokami et al., "Synthesis of 2 α-Methyl- and 2 β-Methyl-3-(substituted methyl)cephalosporins, and 2,3-Diexomethylenecepharm$^1$)", *Chem. Pharm. Bull.*, vol. 31, No. 5, pp. 1482-1493 (1983).
Watanabe, et al., "In vitro antibacterial properties of T-5575 and T-5578 novel parenteral 2-carboxypenams", *Antimicrobial Agents and Chemotherapy*, vol. 39, No. 12, pp. 2787-2791 (1995).
Wright et al., "Chemistry of Cephalosporin Antibiotics. 23. 2-Methyl- and 2-Methylenecephalosporins", *Journal of Medicinal Chemistry*, vol. 14, No. 5, pp. 420-426 (1971).

\* cited by examiner

*Primary Examiner* — Golam M Shameem
(74) *Attorney, Agent, or Firm* — Grace C. Hsu; Fang Qian

(57) ABSTRACT

The compounds of the subject invention are related to 2-substituted cephem compounds, which have a wide antimicrobial spectrum, in particular exhibit potent antimicrobial activity against beta-lactamase producing Gram negative bacteria, and pharmaceutical compositions comprising the same.

23 Claims, No Drawings

2 SUBSTITUTED CEPHEM COMPOUNDS

TECHNICAL FIELD

The compounds of the subject invention are related to 2-substituted cephem compounds, which have a wide antimicrobial spectrum, in particular exhibit potent antimicrobial activity against beta-lactamase producing Gram negative bacteria, and pharmaceutical compositions comprising the same.

BACKGROUND

To date, a variety of beta-lactam drugs have been developed and beta-lactam drugs have become clinically extremely important antimicrobial drugs. However, there are increasing number of bacterial types which have obtained resistance against beta-lactam drugs by producing beta-lactamase, which degrade beta-lactam drugs.

According to the Ambler molecular classification, beta-lactamases are largely classified into four classes. Specifically, these are Class A (TEM type, SHV type, CTX-M type, KPC type and the like), Class B (IMP type, VIM type, L-1 type and the like), Class C (AmpC type) and Class D (OXA type and the like). Amongst these, Classes A, C and D types are largely classified into serine-beta-lactamase, on the other hand, Class B type is classified into metallo-beta-lactamase. It has been known that both have respectively different mechanisms to each other in terms of hydrolysis of beta-lactam drugs.

Recently, clinical problem has been occurring due to the existence of Gram negative bacteria which have become highly resistant to a number of beta-lactam drugs including Cephems and Carbapenems by producing Class A (ESBL) and D types serine-beta-lactamases which have an extended substrate spectrum, and Class B type metallo-beta-lactamase which have an extended substrate spectrum. Particularly, metallo-beta-lactamase is known to be one of the causes of obtaining multidrug-resistance in Gram negative bacteria. Cephem compounds which exhibit intermediate activity against metallo-beta-lactamase producing Gram negative bacteria are known (e.g., International Publication No. 2007/119511 pamphlet and Applied Microbiology and Biotechnology (1994), 40(6), 892-7). However, there is a demand for development of Cephem compounds which exhibit more potent antimicrobial activity, in particular more effective against a variety of beta-lactamase producing Gram negative bacteria.

One of the known antimicrobials having high anti-Gram negative bactericidal activity is Cephem compounds having a catechol group intramolecularly (e.g., The Journal of Antibiotics, vol. 61, pp. 36-39 (2008); The Journal of Antibiotics, vol. 43, pp. 1617-1620 (1990) The Journal of Antibiotics, vol. 42, pp. 795-806 (1989)). The action thereof is that the catechol group forms a chelate with $Fe^{3+}$, thereby the compound is efficiently incorporated into the bacterial body through the $Fe^{3+}$ transportation system on the cellular membrane (tonB-dependent iron transport system). Therefore, research has been conducted on compounds having catechol or similar structure thereto, on the 3-side chain or 7-side chain moiety on the Cephem backbone.

Examples in the non-patent literature (i.e., e.g., see, Applied Microbiology and Biotechnology (1994), 40(6), 892-7) and patent literature (i.e., see Japanese Laid-Open Publication No. 4-364189; Japanese Laid-Open Publication No. 3-173893; Japanese Laid-Open Publication No. 2-15090; Japanese Laid-Open Publication No. 2-28187; Japanese Laid-Open Publication No. 2-117678; Japanese Laid-Open Publication No. 2-28185), respectively, describe catechol type derivatives having a catechol group on the 3-side chain moiety on the Cephem backbone. Other patent documents (i.e., e.g., Japanese Laid-Open Publication No. 2-15090; Japanese Laid-Open Publication No. 2-28187; Japanese Laid-Open Publication No. 6-510523; and Japanese Laid-Open Publication No. 5-213971) describe pseudo-catechol type derivatives having a hydroxypyridone group on the 3-side chain moiety on the Cephem backbone. Patent Documents, International Publication No. 2007/096740 pamphlet and International Publication No. 2003/078440 pamphlet disclose Cephem compounds having a quaternary ammonium group, but do not describe a catechol type derivative.

Moreover, in the above documents, which describe Cephem compounds having a catechol group in their structure, there is no description of Class B type metallo-beta-lactamase and specific antimicrobial activity against a wide variety of Gram negative bacteria including Class B type.

Additionally, specific patent literature documents (i.e., e.g., European Patent Publication No. 35357 and U.S. Pat. No. 3,487,079) and non-patent literature documents (i.e., e.g., Chemical & Pharmaceutical Bulletin, vol. 31, 1482-1493 (1983); Journal of Medicinal Chemistry, vol. 14, 420-425 (1971); and International Journal of Peptide & Protein Research, vol. 10, 51-59 (1977)), respectively, describe cephem compounds having a substituent at position 2 of the cephem skeleton. However, these compounds do not have a quaternary ammonium group and a catechol group at position 3 of the cephem skeleton.

Non-patent literature (e.g., The Journal of Antibiotics, vol. 41, pp. 1154-1157 (1988); The Journal of Antibiotics, vol. 43, pp. 357-371 (1989)) describe oxa-cephem compounds having a substituent at position 2 of the oxa-cephem skeleton. However, these compounds do not have a catechol group at position 3 of the oxa-cephem skeleton.

The present applicant has filed patent applications of cephem compounds having catechol type substituents (e.g., International Publication No. 2010/050468 pamphlet; International Publication No. 2011/125966 pamphlet; International Publication No. 2011/125967 pamphlet and International Publication No. 2011/136268 pamphlet). However, these applications do not disclose a compound having a substituent at position 2 of the cephem skeleton.

SUMMARY OF INVENTION

Problems to be Solved by the Invention

The subject invention provides 2-substituted cephem compounds having a quaternary ammonium group on the 3-side chain, preferably together with a catechol group, which exhibit potent antimicrobial spectrum against a variety of bacteria including Gram negative bacteria and/or Gram positive bacteria. Preferably, the compounds are effective against beta-lactamase producing Gram negative bacteria, including multidrug-resistant bacteria, in particular, Class B type metallo-beta-lactamase producing Gram negative bacteria, and extended-spectrum beta-lactamase (ESBL) producing bacteria. Furthermore, the subject invention provides preferably cephem compounds having antimicrobial activity against strains resistant to 2-unsubstituted cephem compounds.

Means for Solving the Problem

The subject invention provides cephem compounds which have solved the above-mentioned problems with the following structural characteristics:

1) a substituent group (s) at the position 2, preferably an alkyl group.

2) a quaternary ammonium group on the 3-side chain.

3) a catechol group at the terminal or in the quaternary ammonium group of the 3-side chain as a preferable embodiment.

The subject invention provides the following inventions:
1. A compound of the formula (I):

[Chemical Formula 1]

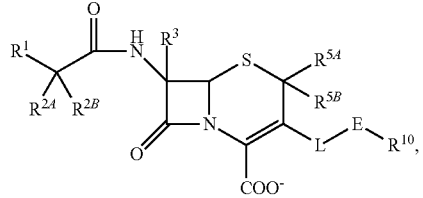

(I)

an ester at carboxyl group, an amino-protected compound when the amino is present on a ring in the 7-side chain, or a pharmaceutically acceptable salt thereof,
wherein,
$R^1$ is an optionally substituted carbocyclic group or an optionally substituted heterocyclic group;
with regard to $R^{2A}$ and $R^{2B}$,
a) $R^{2A}$ is hydrogen, optionally substituted amino, —$SO_3H$, optionally substituted amino sulfonyl, carboxyl, optionally substituted (lower alkyl)oxycarbonyl, optionally substituted carbamoyl, hydroxyl, or substituted carbonyloxy; and $R^{2B}$ is hydrogen, provided that $R^{2A}$ and $R^{2B}$ are not hydrogen at the same time, or
b) $R^{2A}$ and $R^{2B}$ are taken together to form optionally substituted methylidene or optionally substituted hydroxyimino;
$R^3$ is hydrogen, —$OCH_3$ or —NH—CH(=O);
with regard to $R^{5A}$ and $R^{5B}$,
a) $R^{5A}$ and $R^{5B}$ are each independently hydrogen, or lower alkyl and $R^{5A}$ and $R^{5B}$ are not hydrogen at the same time,
b) $R^{5A}$ and $R^{5B}$ may be taken together with the neighboring atom to form optionally substituted carbocycle or a optionally substituted heterocyclic group, or
c) $R^{5A}$ and $R^{5B}$ may be taken together to form optionally substituted methylidene;
L is —$CH_2$—, —CH=CH—, —$CH_2$—CH=CH—, —CH=CH—$CH_2$—, —S—, —$CH_2$—S—, —CH=CH—S— or —CH=CH—$CH_2$—S—;
E is an optionally substituted divalent group having at least one quaternary ammonium ion;
$R^{10}$ is hydrogen or a group represented by the formula (I-B):

[Chemical Formula 2]

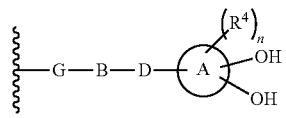

(I-B)

wherein,
ring A is a benzene ring, monocyclic heterocycle or fused heterocycle;
n is an integer from 0 to 2;

each $R^4$ is independently hydrogen, halogen, oxo, —OH, —CN, —$NO_2$, —O—C(=O)—$R^9$, —C(=O)—$R^9$, —C(=O)—OH, —C(=O)—$OR^9$, —$OR^{9'}$, —$NR^9R^9$, —$SO_2R^9$, —$SR^9$, —$NR^9$—C(=O)—$R^9$, optionally substituted lower alkyl, optionally substituted cycloalkyl, optionally substituted aryl, or optionally substituted heteroaryl; provided that two hydroxyl groups on ring A bind respectively to carbon atoms each adjacently locates;
each $R^9$ is independently lower alkyl or halo(lower)alkyl;
G is a single bond, optionally substituted lower alkylene, optionally substituted alkenylene or optionally substituted alkynylene;
B is non-existent, a single bond or a 5- or 6-membered heterocyclic group containing at least 1-3 nitrogen atoms;
D is non-existent, a single bond, —C(=O)—, —O—C(=O)—, —C(=O)—O—, —$NR^6$—, —$NR^6$—C(=O)—, —C(=O)—$NR^6$—, —C(=O)—C(=O)—, —$NR^6$—C(=O)—$NR^6$—, —C(=O)—C(=O)—$NR^6$—, —C(=O)—$NR^6$—C(=O)—, —$NR^6$—C(=O)—C(=O)—, —$NR^6$—$NR^6$—C(=O)—, —C(=O)—$NR^6$—$NR^6$—, —N=N—C(=O)—, —C(=O)—N=N—, —C=N—$NR^6$—C(=O)—, —C=N—C(=O)—, —N=C—C(=O)—, —C=N—C(=O)—$NR^6$—, —$NR^6$—C(=O)—C(=N—$OR^6$)—, —C(=N—$OR^6$)—C(=O)—$NR^6$—, —$NR^6$—C(=N—$OR^6$)—, —C(=N—$OR^6$)—$NR^6$—, —C(=O)—C(=N—$OR^6$)—, —C(=N—$OR^6$)—C(=O)—, —O—, —S—, —S(=O)—, —S(=O)$_2$—$NR^6$—, —$NR^6$—S(=O)$_2$—, —$NR^6$—$CH_2$—, —$CH_2$—$NR^6$— or —S(=O)$_2$—;
each $R^6$ is independently hydrogen or optionally substituted lower alkyl;
provided that when $R^{10}$ is hydrogen, E is an optionally substituted divalent cyclic group having at least one quaternary ammonium ion and at least two hydroxyl groups which bind respectively to carbon atoms each adjacently locates on the cyclic group.

In one aspect of the present invention Formula (I-B) is defined as follows:

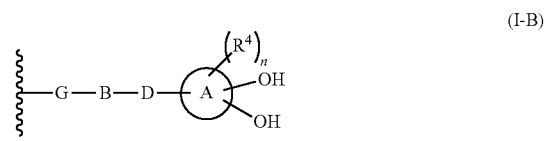

(I-B)

where:
ring A is defined as a fused heterocycle ring system comprised of at least two (2) rings fused together;
where:
$R^4$ optionally is substituted on each of the at least two (2) rings of the fused heterocycle ring system defined as ring A, such that each $R^4$ substituent on each ring of the fused heterocycle ring system independently are selected from identical or different substituents;
where:
each $R^4$ as defined above optionally is substituted independently on each ring of the fused heterocycle ring is selected from hydrogen, halogen, oxo, —OH, —CN, —$NO_2$, —O—C(=O)—$R^9$, —C(=O)—$R^9$, —C(=O)—OH, —C(=O)—$OR^9$, —$OR^{9'}$, —$NR^9R^9$, —$SO_2R^9$, —$SR^9$, —$NR^9$—C(=O)—$R^9$, optionally substituted lower alkyl, optionally substituted cycloalkyl, optionally substituted aryl, or optionally substituted heteroaryl;

provided that two hydroxyl groups on ring A bind respectively to carbon atoms each adjacently locates; and n is an integer from 0 to 2.

2. The compound, an ester at carboxyl group, an amino-protected compound when the amino is present on the ring in the 7-side chain, or a pharmaceutically acceptable salt thereof according to the above 1, wherein $R^{5A}$ is hydrogen and $R^{5B}$ is lower alkyl.

3. The compound, an ester at carboxyl group, an amino-protected compound when the amino is present on the ring in the 7-side chain, or a pharmaceutically acceptable salt thereof according to the above 1 or 2, wherein, $R^{10}$ is a group represented by the formula (I-B):

[Chemical Formula 3]

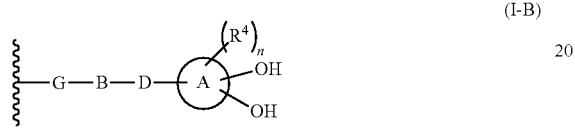

(I-B)

wherein, each symbol is as defined above in 1 and throughout the instant specification.

4. The compound, an ester at carboxyl group, an amino-protected compound when the amino is present on the ring in the 7-side chain, or a pharmaceutically acceptable salt thereof according to the above 1, 2 or 3, wherein, ring A is a benzene ring or monocyclic heterocycle.

5. The compound, an ester at carboxyl group, an amino-protected compound when the amino is present on the ring in the 7-side chain, or a pharmaceutically acceptable salt thereof according to the above 1, 2 or 3, wherein, ring A is fused heterocycle or an optionally substituted fused heterocycle, where each ring of the fused heterocycle independently is substituted with identical or different substituents.

In one aspect, ring A as defined herein is a fused heterocycle ring system comprised of at least two (2) rings fused together optionally substituted by substituents selected from $R^4$;

where:
$R^4$ optionally is substituted on each of the at least two (2) rings of the fused heterocycle ring system defined as ring A, such that each $R^4$ substituent on each ring of the fused heterocycle ring system independently are selected from identical or different substituents;

where:
each $R^4$ as defined above optionally is substituted independently on each ring of the fused heterocycle ring is selected from hydrogen, halogen, oxo, —OH, —CN, —NO$_2$, —O—C(=O)—R$^9$, —C(=O)—R$^9$, —C(=O)—OH, —C(=O)—OR$^9$, —OR$^{9'}$, —NR$^9$R$^9$, —SO$_2$R$^9$, —SR$^9$, —NR$^9$—C(=O)—R$^9$, optionally substituted lower alkyl, optionally substituted cycloalkyl, optionally substituted aryl, or optionally substituted heteroaryl;
provided that two hydroxyl groups on ring A bind respectively to carbon atoms each adjacently locates; and
n is an integer from 0 to 2.

6. The compound, an ester at carboxyl group, an amino-protected compound when the amino is present on the ring in the 7-side chain, or a pharmaceutically acceptable salt thereof according to the above 1 or 2, wherein, $R^{10}$ is hydrogen;

E is an optionally substituted divalent cyclic group having at least one quanternary ammonium ion and at least two hydroxyl groups which bind respectively to carbon atoms each adjacently locates on the cyclic group.

7. The compound, an ester at carboxyl group, an amino-protected compound when the amino is present on the ring in the 7-side chain, or a pharmaceutically acceptable salt thereof according to any one of the above 1 to 5, wherein, G is a single bond, —CH$_2$—, —CH$_2$—CH$_2$—, —CH$_2$—CH$_2$—CH$_2$—, —CH=CH—, —CH=CH—CH$_2$—, —CH$_2$—CH=CH—, —CH$_2$—CH(CH$_3$)—, —CH$_2$—CH($^i$Pr)— or —CH$_2$—CH(Ph)- wherein $^i$Pr is isopropyl and Ph is phenyl.

8. The compound, an ester at carboxyl group, an amino-protected compound when the amino is present on the ring in the 7-side chain, or a pharmaceutically acceptable salt thereof according to the above 1, 2, 3, 4, 5 or 7, wherein, B is non-existent, a single bond or a group represented by the formula:

[Chemical Formula 4]

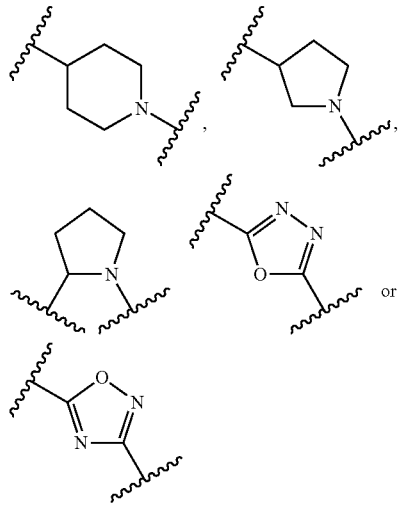

or wherein, the bond of the left side is attached to G and the bond of the right side is attached to D.

9. The compound, an ester at carboxyl group, an amino-protected compound when the amino is present on the ring in the 7-side chain, or a pharmaceutically acceptable salt thereof according to the above 1, 2, 3, 4, 5, 7 or 8, wherein, D is non-existent, a single bond, —C(=O)—, —O—C(=O)—, —C(=O)—O—, —NR$^6$—, —O—, —C(=O)—C(=O)—, —NR$^6$—C(=O)—NR$^6$—, —C(=O)—C(=O)—NR$^6$—, —C(=O)—NR$^6$—C(=O)—, —NR$^6$—C(=O)—C(=O)—, —NR$^6$—C(=O)—, —NR$^6$—NR$^6$—C(=O)—, —C(=O)—NR$^6$—NR$^6$—, —N=N—C(=O)—, —C(=O)—N=N—, —C=N—NR$^6$—C(=O)—, —C=N—C(=O)—, —N=C—C(=O)—, —C=N—C(=O)—NR$^6$—, —NR$^6$—C(=O)—C(=N—OR$^6$)—, —C(=N—OR$^6$)—C(=O)—NR$^6$—, —NR$^6$—C(=N—OR$^6$)—, —C(=O)—C(=N—OR$^6$)—, —C(=N—OR$^6$)—C(=O)— or —C(=N—OR$^6$)—NR$^6$—, wherein R$^6$ is as defined in the above 1.

In one aspect, The compound, an ester at carboxyl group, an amino-protected compound when the amino is present on the ring in the 7-side chain, or a pharmaceutically acceptable salt thereof according to the above 1, 2, 3, 5, 7, 8 or 9, wherein, the formula (I-C-1):

[Chemical Formula 11]

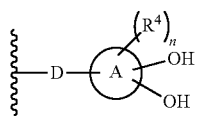
(I-C-1)

wherein:
ring A is defined as a fused heterocycle ring system comprised of at least two (2) rings fused together;
where:
$R^4$ optionally is substituted on each of the at least two (2) rings of the fused heterocycle ring system defined as ring A, such that each $R^4$ substituent on each ring of the fused heterocycle ring system independently are selected from identical or different substituents;
where:
each $R^4$ as defined above optionally is substituted independently on each ring of the fused heterocycle ring is selected from hydrogen, halogen, oxo, —OH, —CN, —NO$_2$, —O—C(=O)—R$^9$, —C(=O)—R$^9$, —C(=O)—OH, —C(=O)—OR$^9$, —OR$^9$, —NR$^9$R$^9$, —SO$_2$R$^9$, —SR$^9$, —NR$^9$—C(=O)—R$^9$, optionally substituted lower alkyl, optionally substituted cycloalkyl, optionally substituted aryl, or optionally substituted heteroaryl;
provided that two hydroxyl groups on ring A bind respectively to carbon atoms each adjacently locates; and
n is an integer from 0 to 2.

10. The compound, an ester at carboxyl group, an amino-protected compound when the amino is present on the ring in the 7-side chain, or a pharmaceutically acceptable salt thereof according to the above 1, 2, 3, 4, 7, 8 or 9, wherein, the formula (I-C-1):

[Chemical Formula 5]

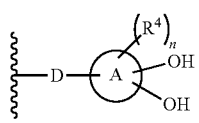
(I-C-1)

is a group selected from the following formulae:

[Chemical Formula 6]

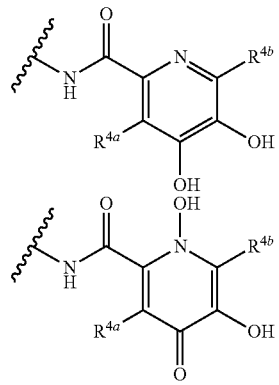

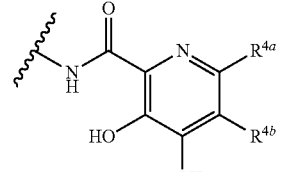

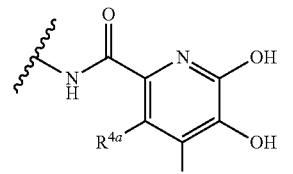

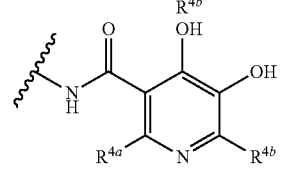

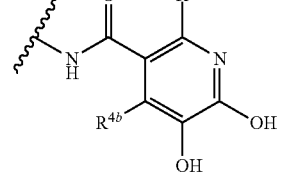

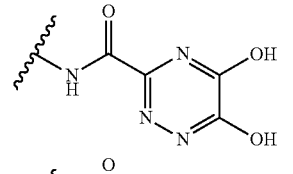

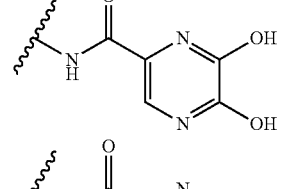

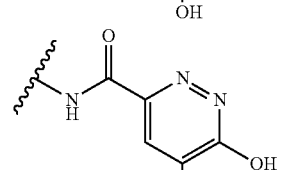

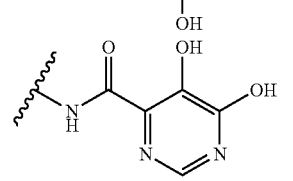

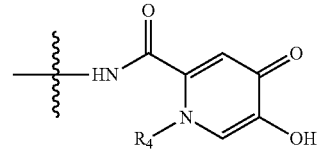

wherein, each $R^{4a}$, $R^{4b}$ and $R^{4c}$ is independently hydrogen, halogen, —OH, —CN, —C(=O)—$R^9$, —C(=O)—OH, —C(=O)—$OR^9$, —$OR^9$, optionally substituted lower alkyl, or optionally substituted cycloalkyl and $R^6$ and $R^9$ are as defined in the above 1, the wavy line means that the bond is in cis or trans configuration, or a mixture thereof.

11. The compound, an ester at carboxyl group, an amino-protected compound when the amino is present on the ring in the 7-side chain, or a pharmaceutically acceptable salt thereof according to the above 10, wherein, the formula (I-C-1):

[Chemical Formula 7]

is a group selected from the following formulae:

[Chemical Formula 8]

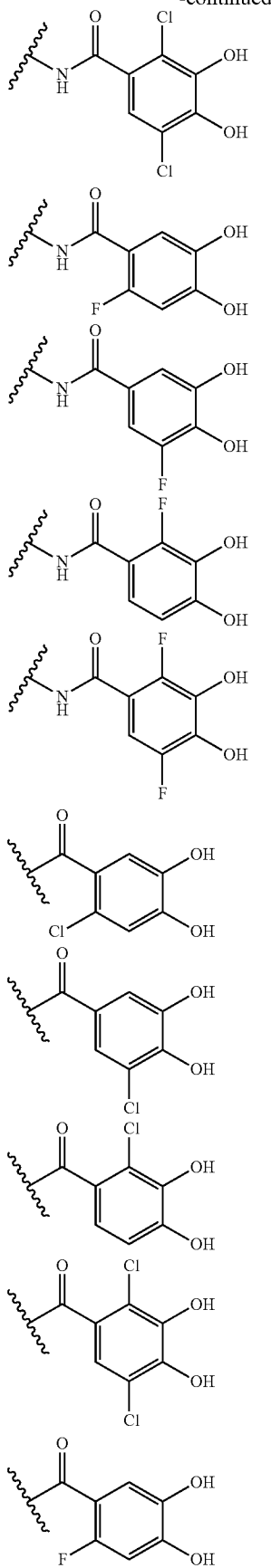
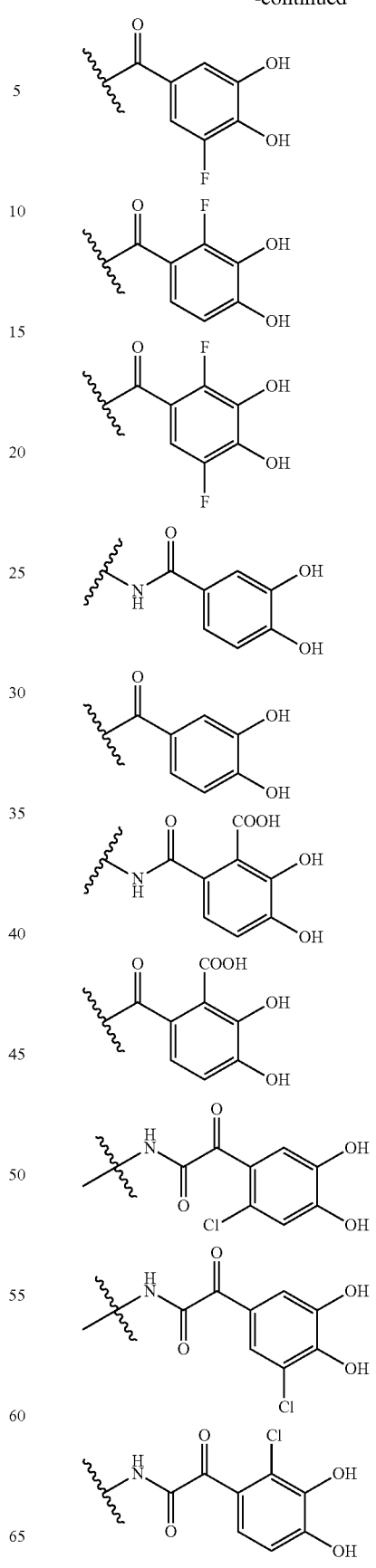

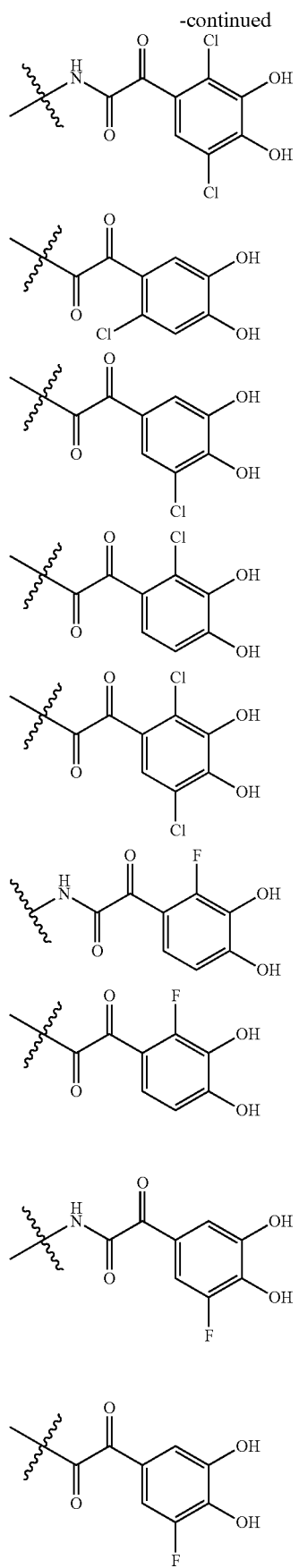
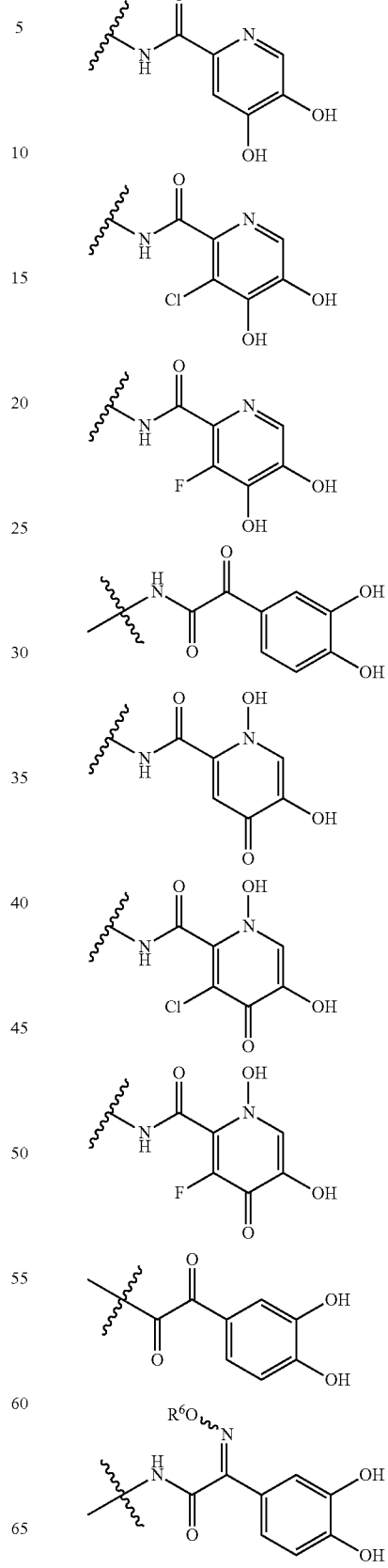
[Chemical Formula 9].

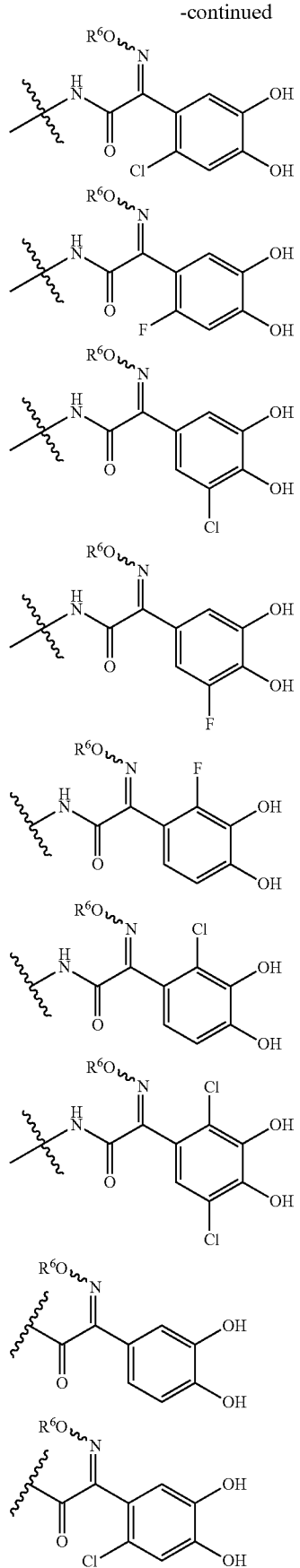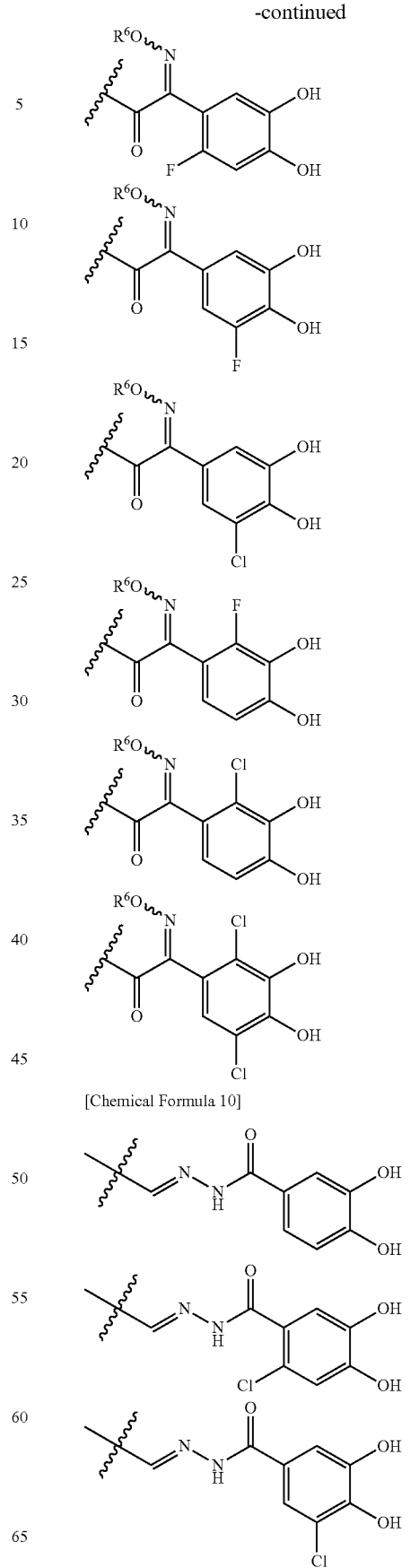
[Chemical Formula 10]

-continued

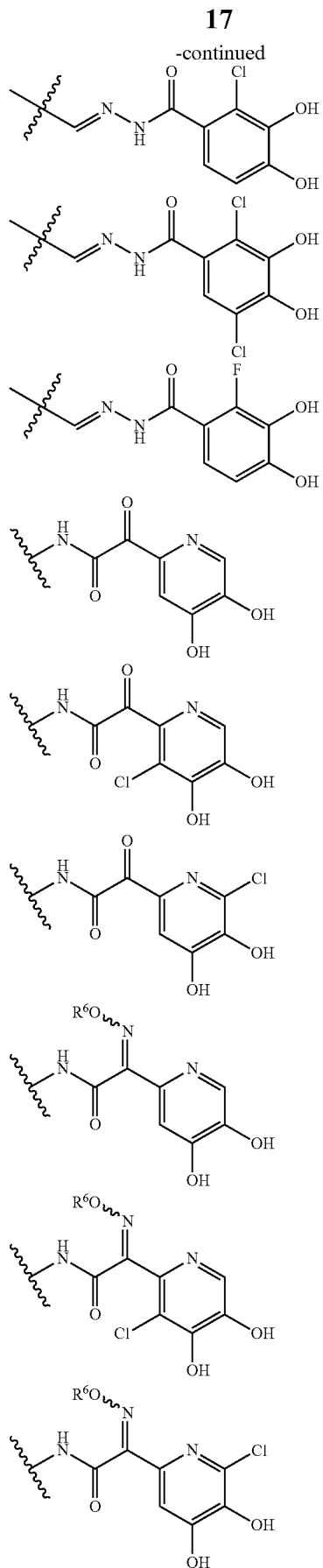

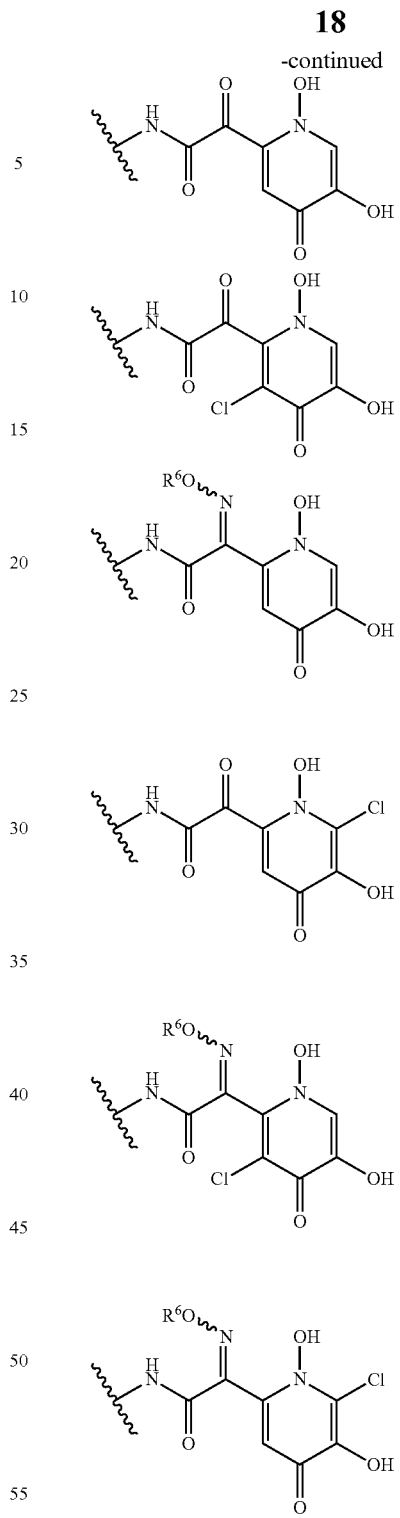

wherein, $R^6$ is hydrogen, methyl, ethyl, tert-buthyl, carboxymethyl, 0.2-carboxypropan-2-yl or 1-carboxyethyl, the wavy line means that the bond is in cis or trans configuration, or a mixture thereof.

12. The compound, an ester at carboxyl group, an amino-protected compound when the amino is present on the ring in the 7-side chain, or a pharmaceutically acceptable salt thereof according to the above 1, 2, 3, 5, 7, 8 or 9, wherein, the formula (I-C-1):

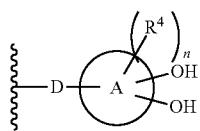
is a group selected from the following formulae:
[Chemical Formula 12]
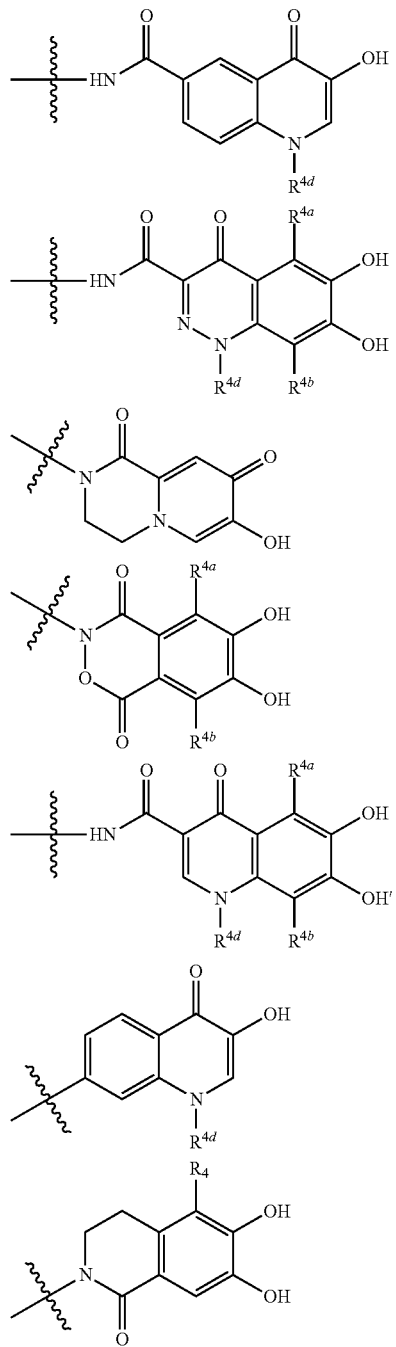
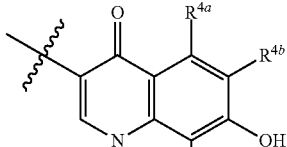
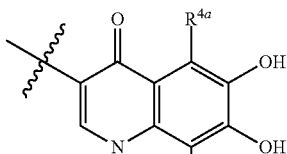
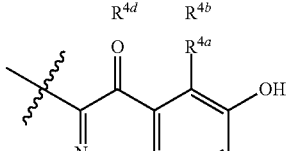
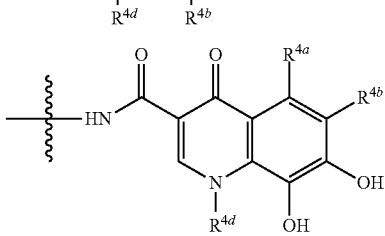
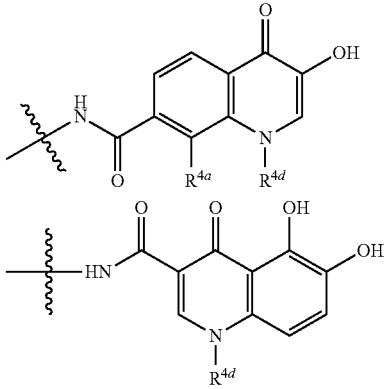
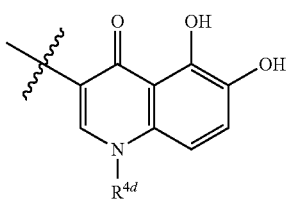
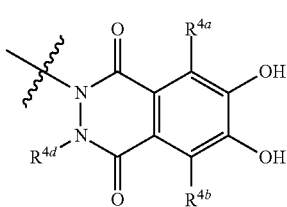

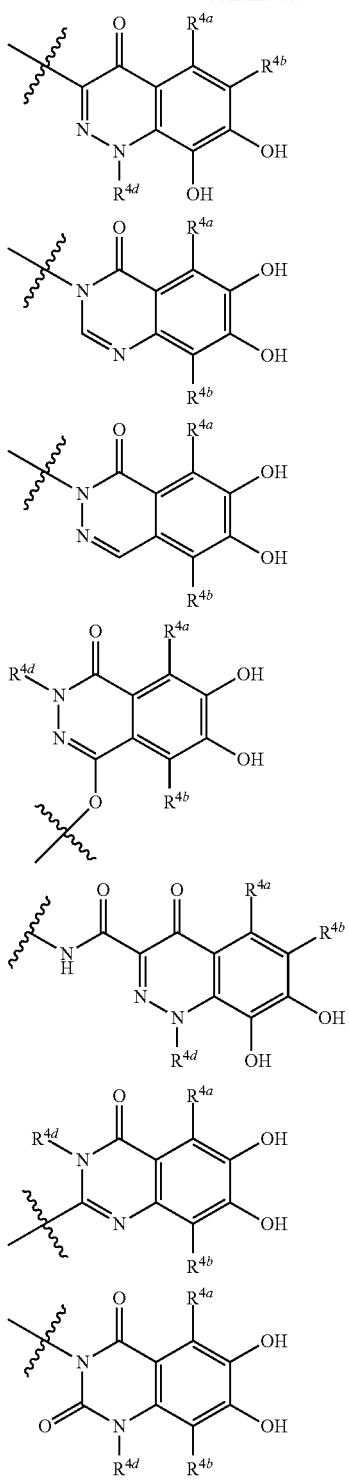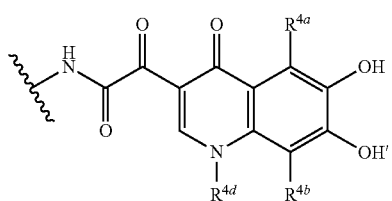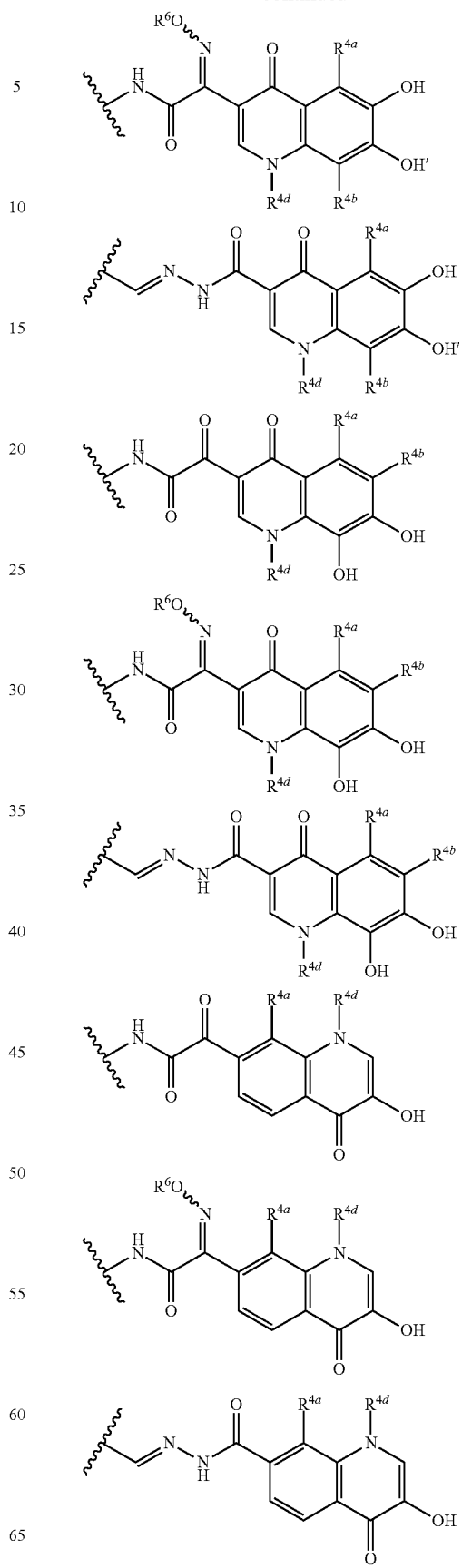

23
-continued
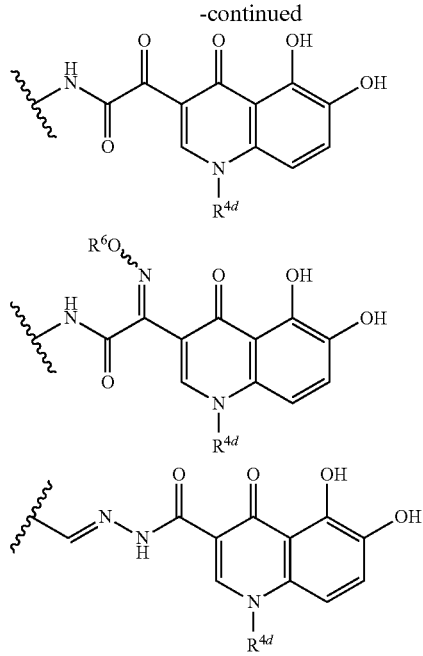
[Chemical Formula 14]
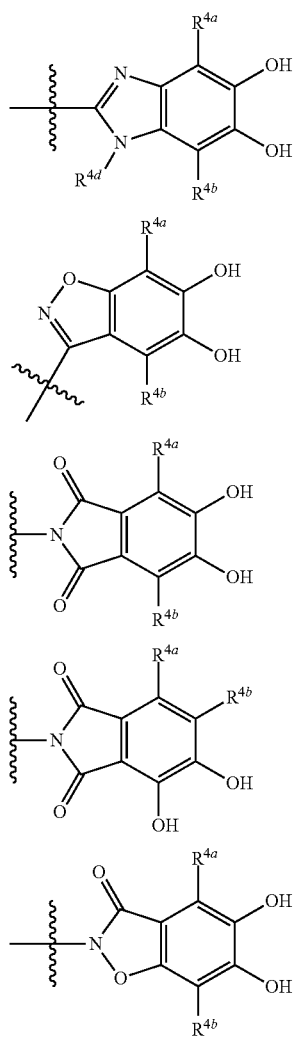
24
-continued
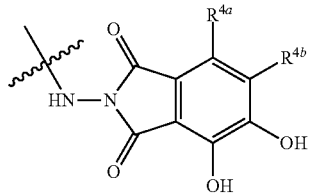
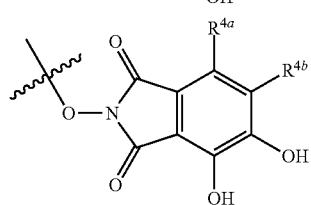
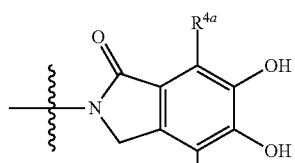
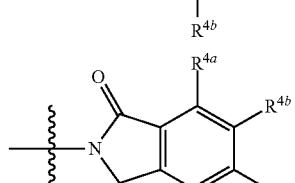
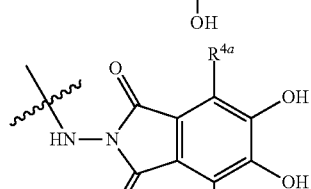
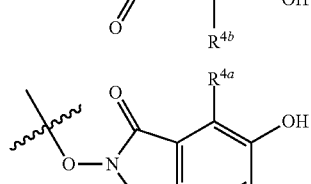
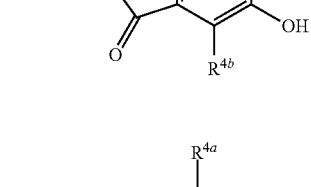
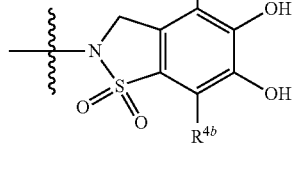
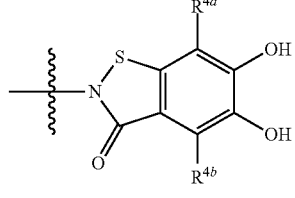
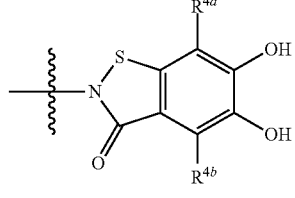
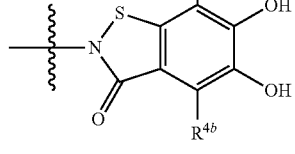
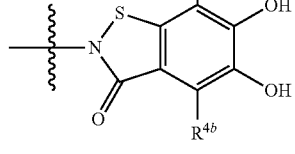

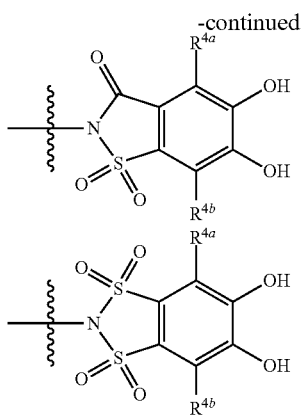

wherein, each $R^{4a}$, $R^{4b}$ and $R^{4d}$ is independently hydrogen, halogen, —OH, —CN, —C(=O)—$R^9$, —C(=O)—OH, —C(=O)—$OR^9$, —$OR^9$, optionally substituted lower alkyl, or optionally substituted cycloalkyl and $R^6$ and $R^9$ are as defined in the above 1, the wavy line means that the bond is in cis or trans configuration, or a mixture thereof.

13. The compound, an ester at carboxyl group, an amino-protected compound when the amino is present on the ring in the 7-side chain, or a pharmaceutically acceptable salt thereof according to the above 12, wherein, the formula (I-C-1):

[Chemical Formula 15]

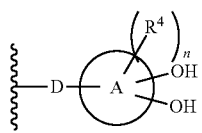

(I-C-1)

is a group selected from the following formulae:

[Chemical Formula 16]

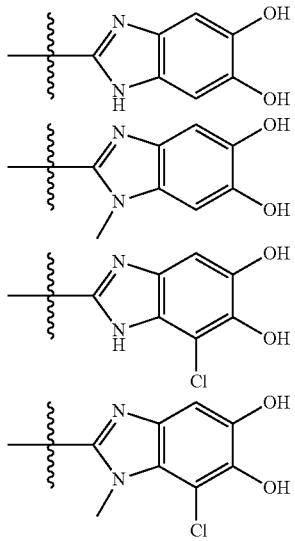

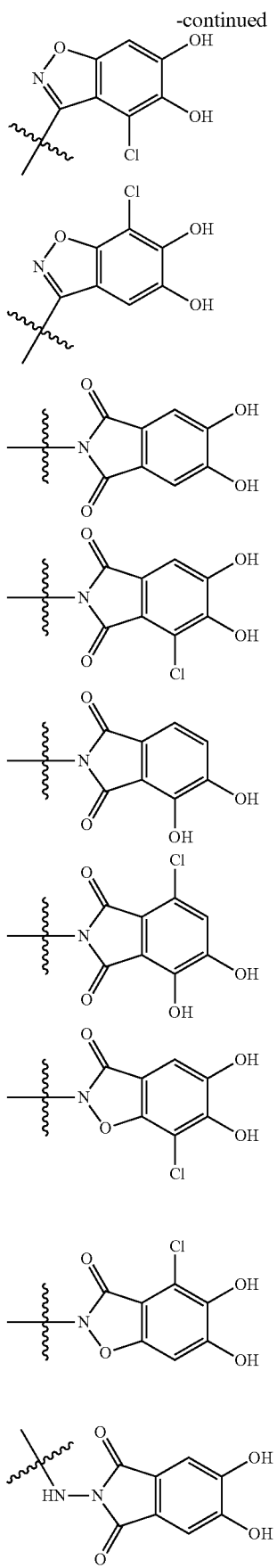

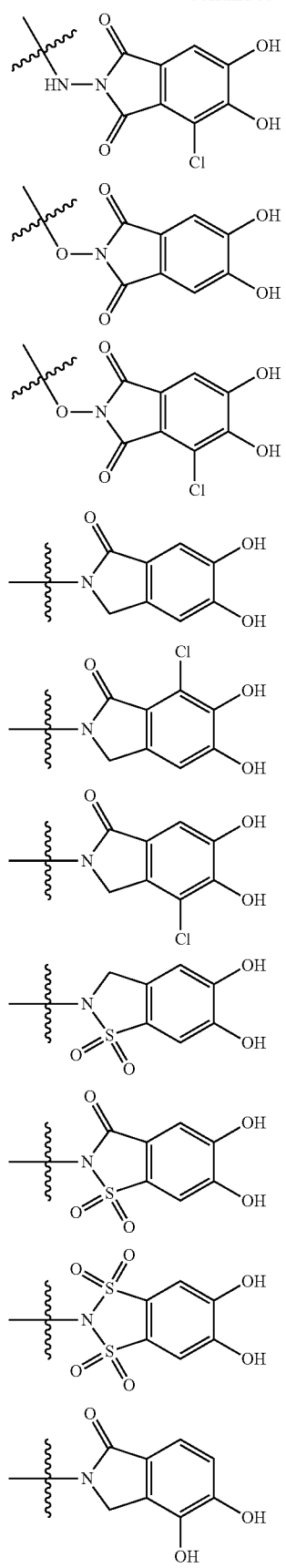
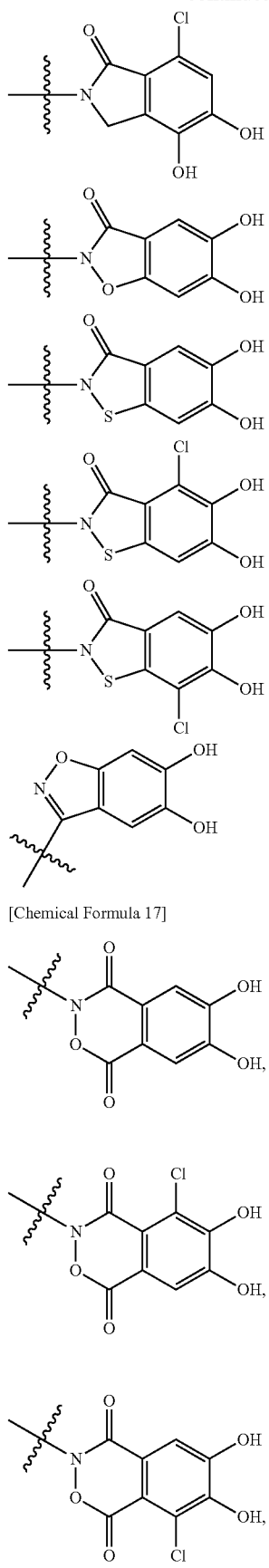

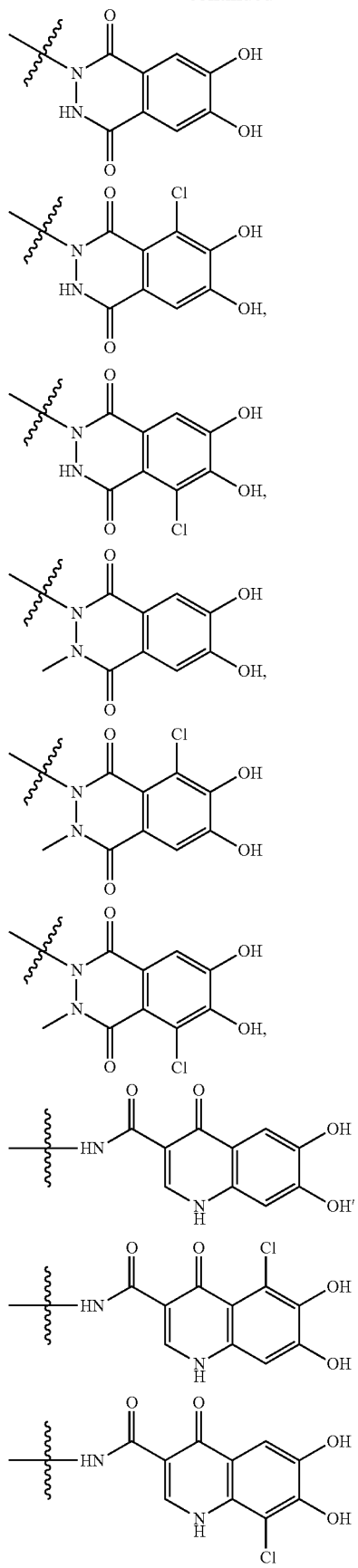
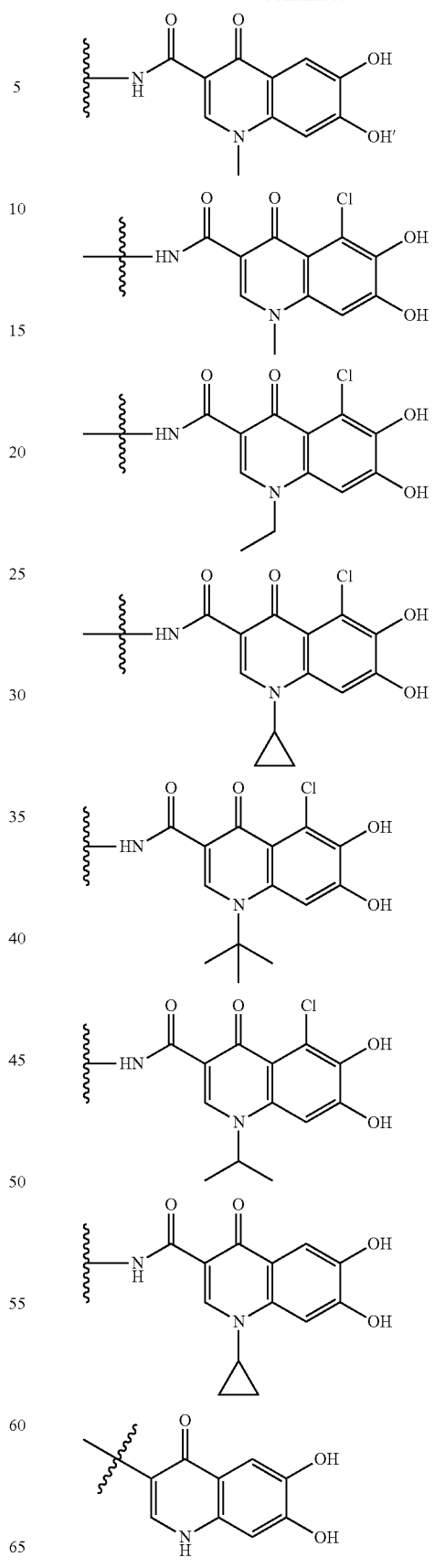

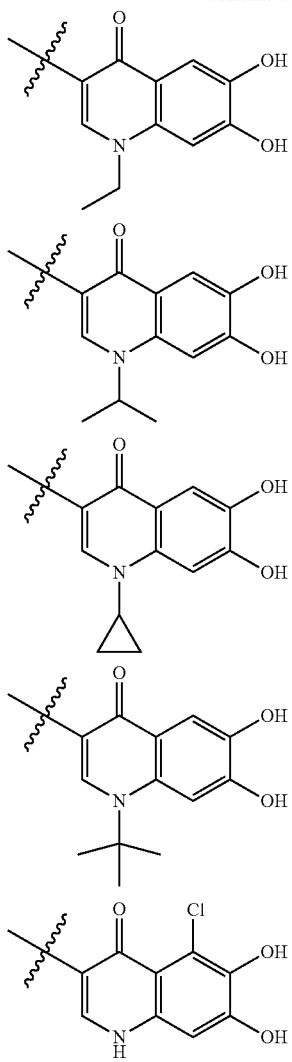
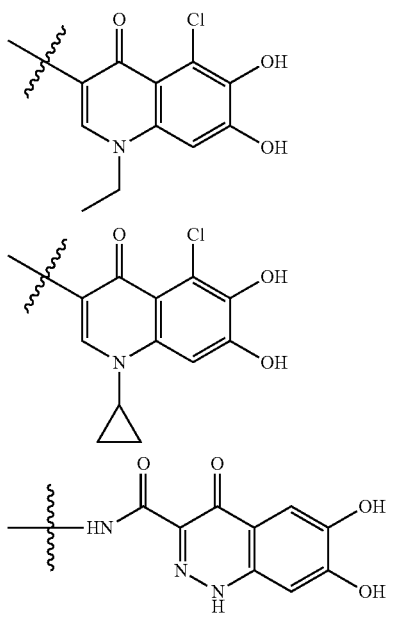
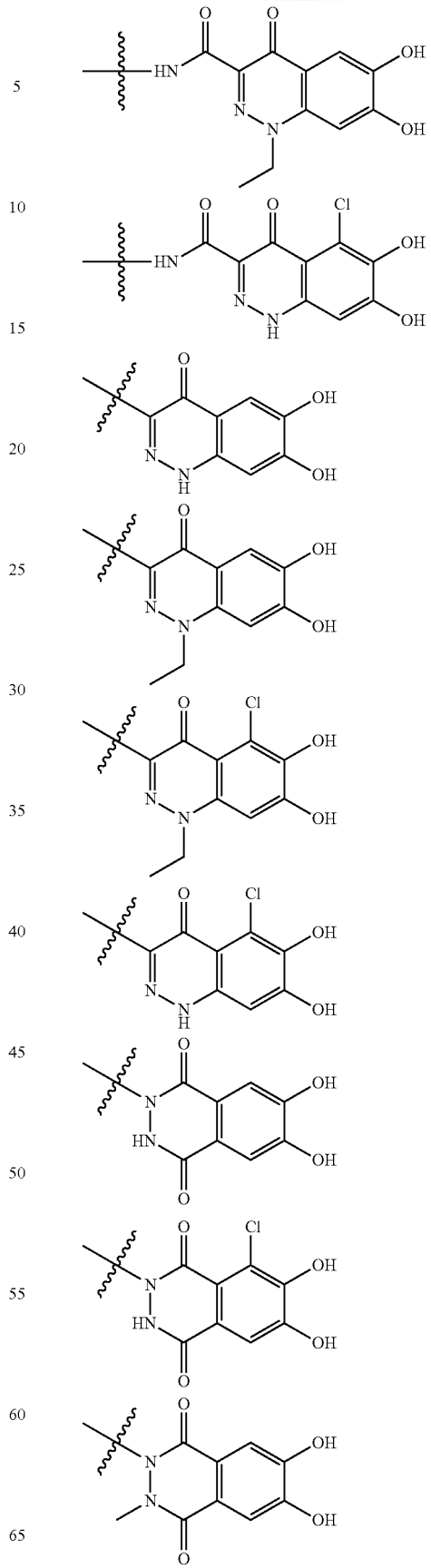

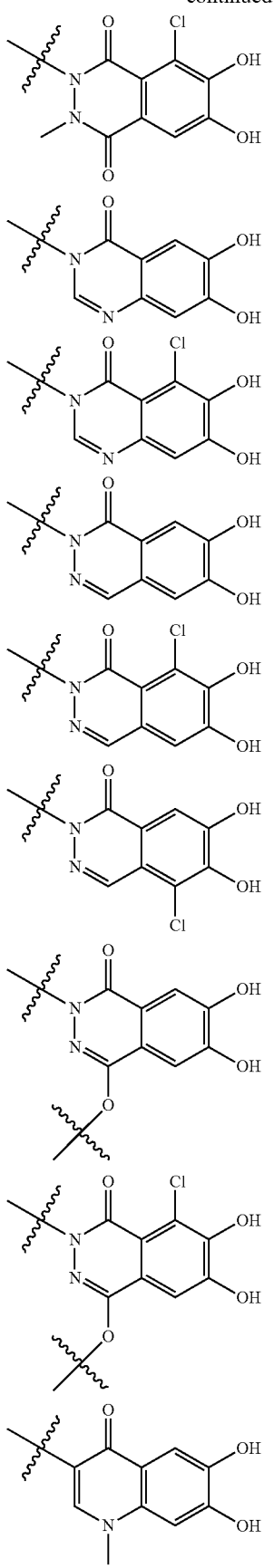

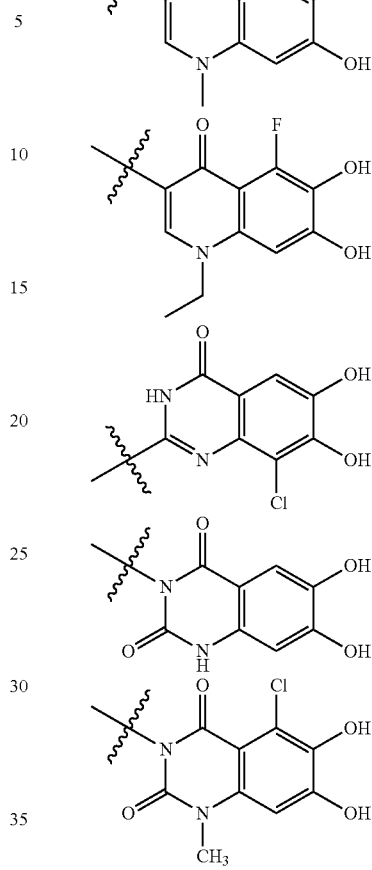

14. The compound, an ester at carboxyl group, an amino-protected compound when the amino is present on the ring in the 7-side chain, or a pharmaceutically acceptable salt thereof according to any one of the above 1 to 13, wherein E is an optionally substituted, saturated or unsaturated, monocyclic or fused cyclic group having at least one quaternary ammonium ion represented by the formula (I-D):

[Chemical Formula 19]

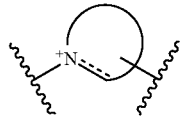

(I-D)

wherein,
the dashed line is a bond in the ring;
the bond to the cationic nitrogen atom binds to L, and the other bond binds to $R^{10}$;
provided,
when a cationic nitrogen atom binds to $R^{10}$, the dashed line is absent, and
when a cationic nitrogen atom does not bind to $R^{10}$, the dashed line is a single bond between the cationic nitrogen atom and a neighboring atom or an alkylene group between the cationic nitrogen atom and a ring member atom other than said neighboring atom.

15. The compound, an ester at carboxyl group, an amino-protected compound when the amino is present on the ring in the 7-side chain, or a pharmaceutically acceptable salt thereof according to any one of the above 1 to 13, wherein E is an optionally substituted, saturated or unsaturated, monocyclic or fused cyclic group having at least one quaternary ammonium ion represented by the formula (I-E):

[Chemical Formula 20]

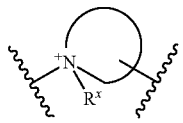

(I-E)

wherein, the bond to the cationic nitrogen atom binds to L, and the other bond binds to $R^{10}$; $R^x$ is optionally substituted lower alkyl.

16. The compound, an ester at carboxyl group, an amino-protected compound when the amino is present on the ring in the 7-side chain, or a pharmaceutically acceptable salt thereof according to any one of the above 1 to 13, wherein L is —S—, —CH$_2$—S—, —CH=CH—S— or —CH=CH—CH$_2$—S— and E is an optionally substituted pyridinium group or an optionally substituted fused pyridinium group.

17. The compound, an ester at carboxyl group, an amino-protected compound when the amino is present on the ring in the 7-side chain, or a pharmaceutically acceptable salt thereof according to the above 16, E is a group selected from the following formulae which are optionally substituted on the ring;

[Chemical Formula 21]

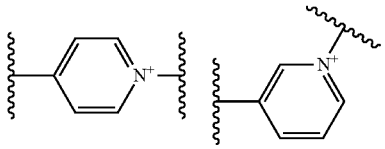

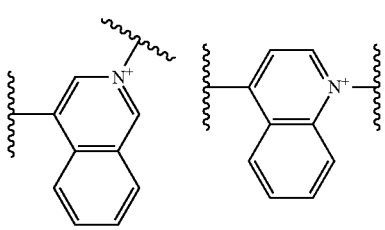

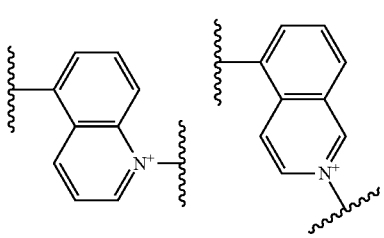

-continued

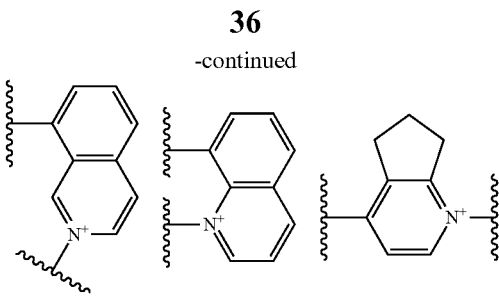

wherein the bond to the cationic nitrogen atom binds to $R^{10}$, the other bond binds to L.

18. The compound, an ester at carboxyl group, an amino-protected compound when the amino is present on the ring in the 7-side chain, or a pharmaceutically acceptable salt thereof according to any one of the above 1 to 15, wherein E is a group selected from the following formulae which are optionally substituted on the ring:

[Chemical Formula 22]

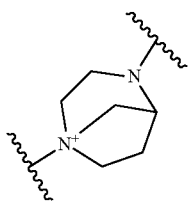

(1)

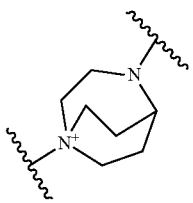

(2)

(3)

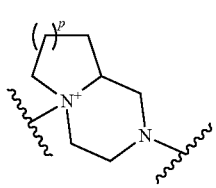

(4)

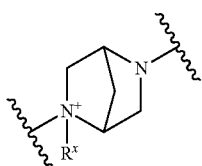

(5)

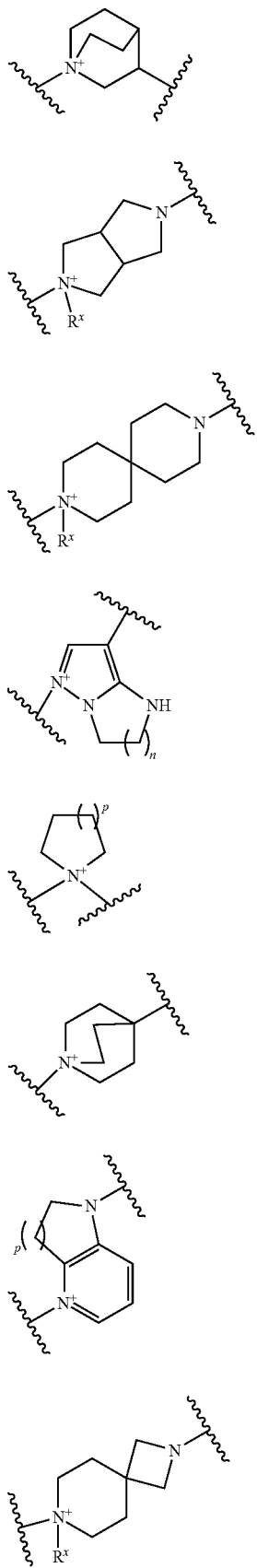
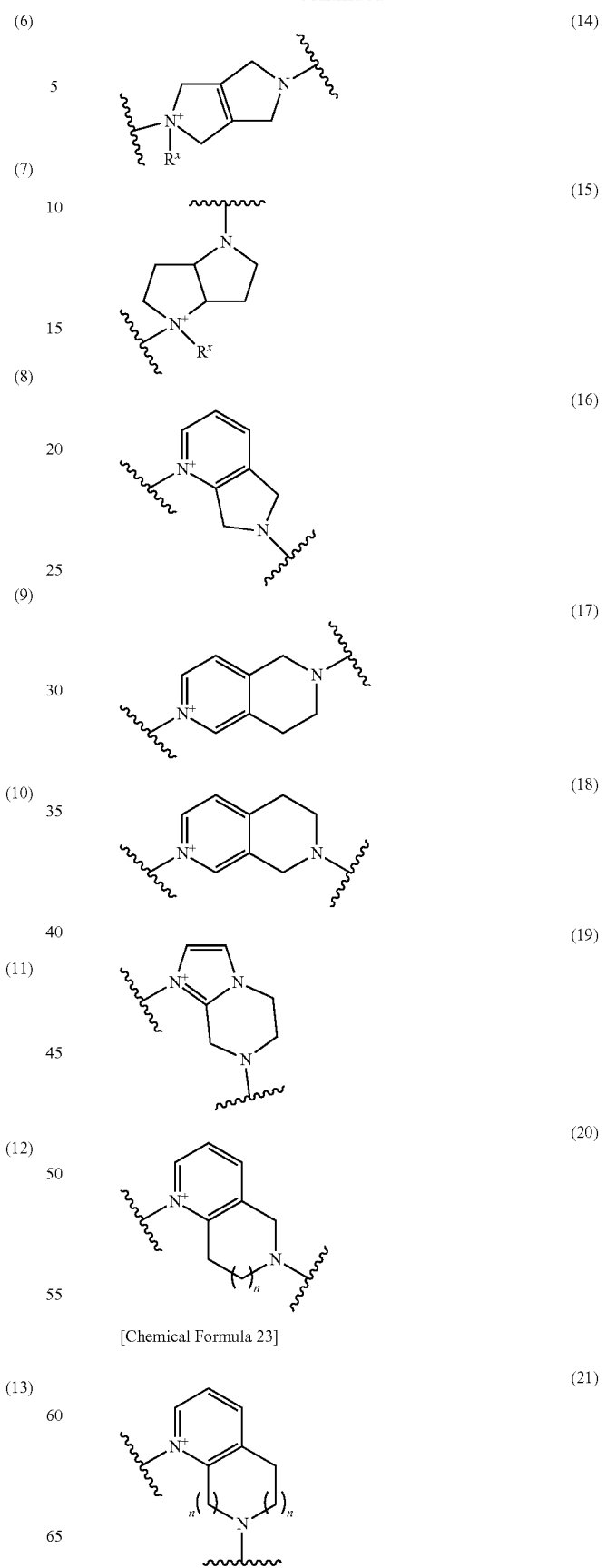
[Chemical Formula 23]

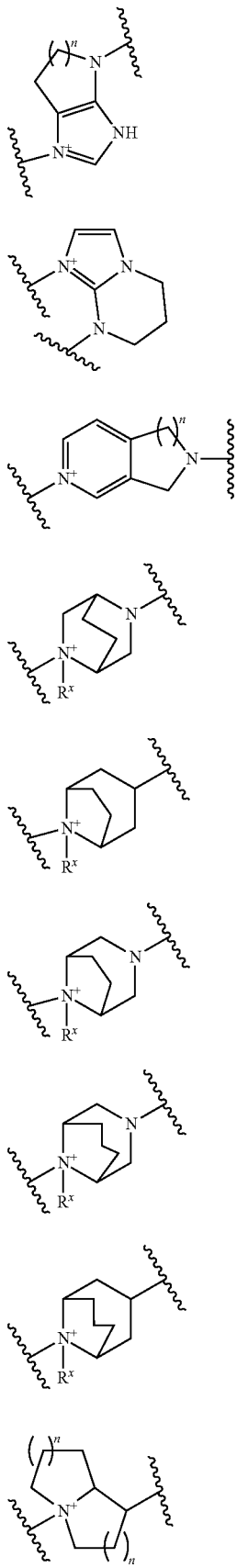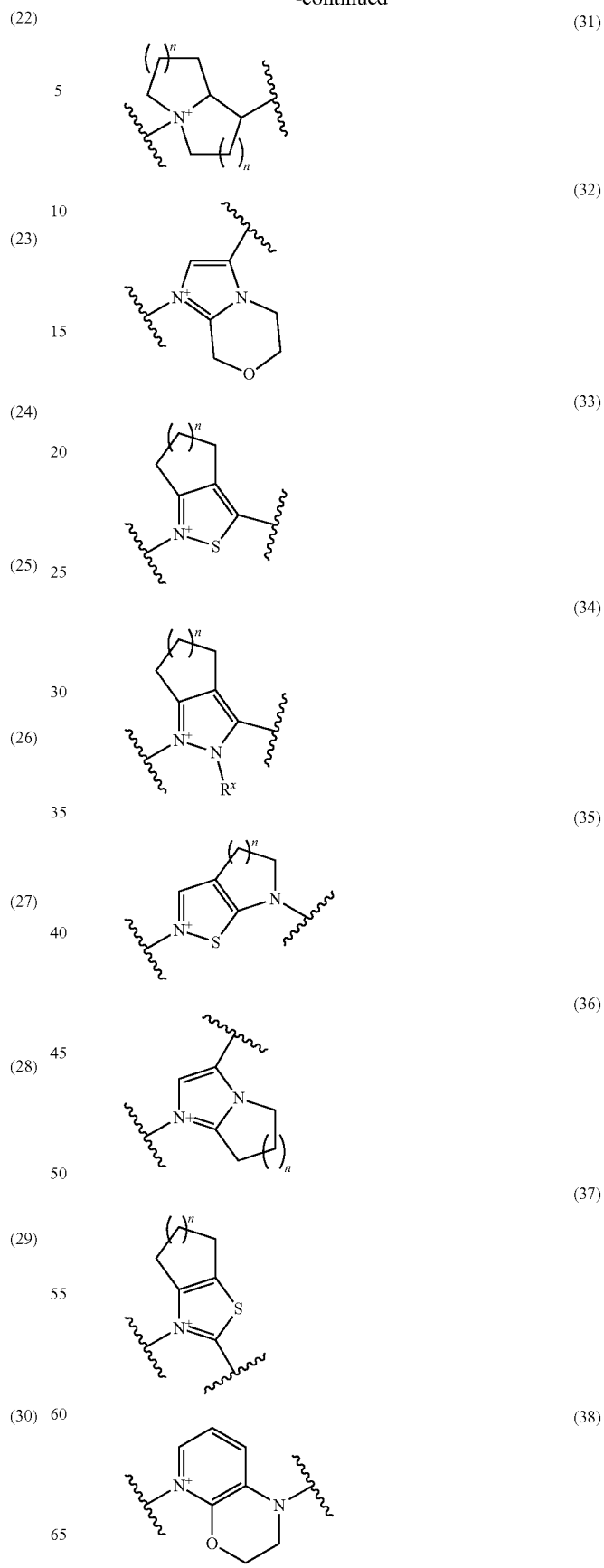

-continued
(39)
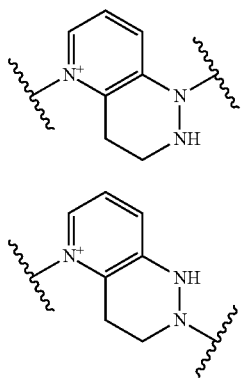
(40)
[Chemical Formula 24]
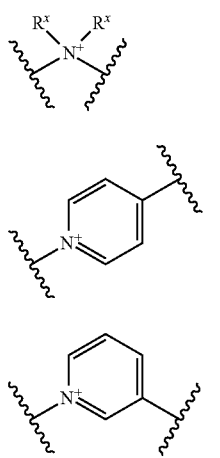
(41)
(42)
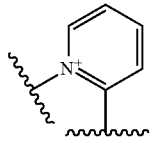
(43)
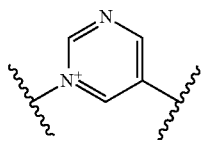
(44)
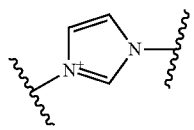
(45)
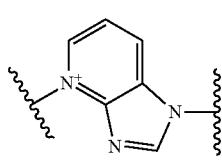
(46)
(47)
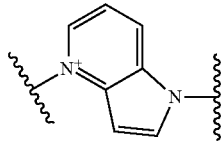
(48)
-continued
(49)
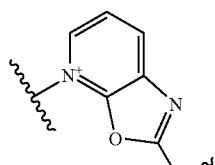
(50)
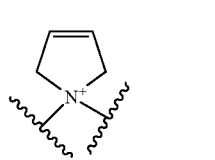
(51)
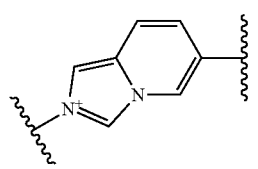
(52)
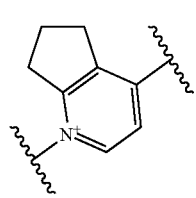
(53)
(54)
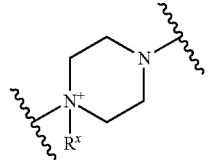
(55)
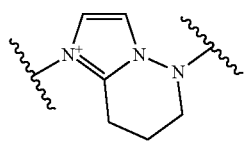
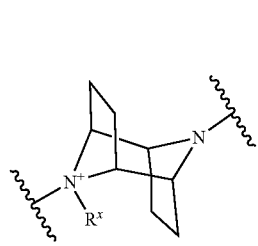
(56)
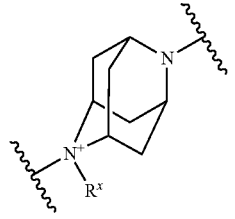

-continued
(57) 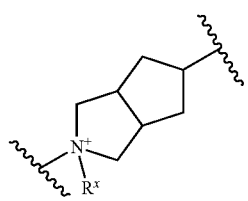
(58) 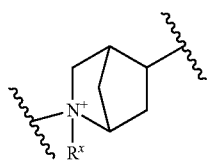
(59) 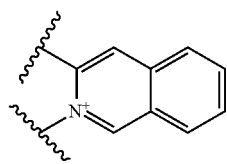
(60) 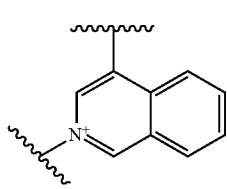
[Chemical Formula 25]
(61) 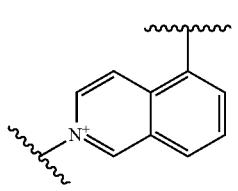
(62) 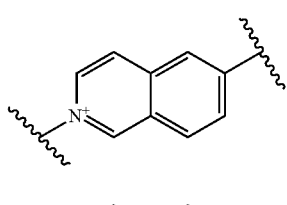
(63) 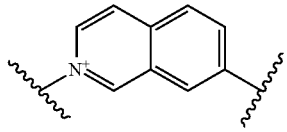
(64) 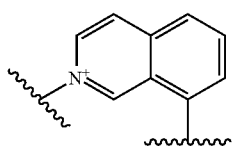
(65) 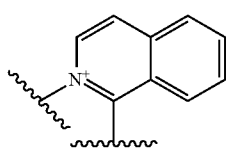
-continued
(66) 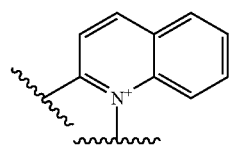
(67) 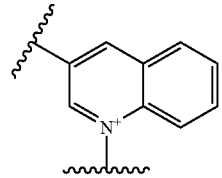
(68) 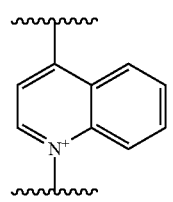
(69) 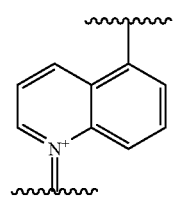
(70) 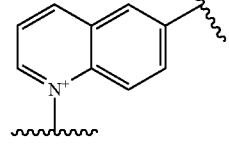
(71) 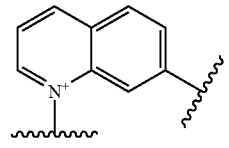
(72) 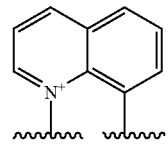
(73) 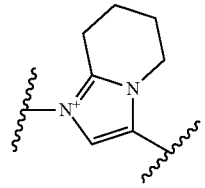
(74) 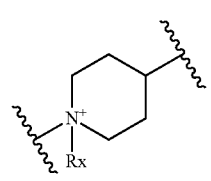

-continued

(75)
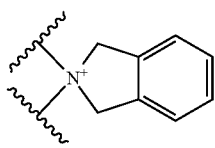

(76)
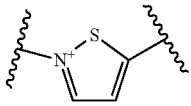

(77)
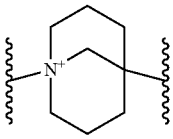

wherein,
the bond to the quaternary nitrogen atom binds to L, and the other bond binds to $R^{10}$;
p is an integer from 1 to 3;
n is an integer of 1 or 2;
$R^x$ is optionally substituted lower alkyl.

19. The compound, an ester at carboxyl group, an amino-protected compound when the amino is present on the ring in the 7-side chain, or a pharmaceutically acceptable salt thereof according to the above 13, wherein, E is selected from the group consisting of the formulae (2), (3), (7), (10), (11), (26), (27), (41), (42), (59), (60) and (77).

20. The compound, an ester at carboxyl group, an amino-protected compound when the amino is present on the ring in the 7-side chain, or a pharmaceutically acceptable salt thereof according to any one of the above 1 to 15, wherein E is a group selected from the following formulae which are optionally substituted on the ring:

[Chemical Formula 26]

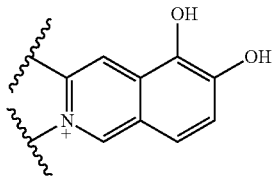

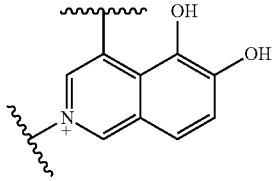

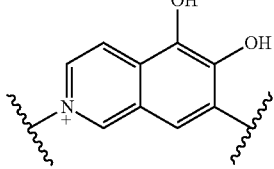

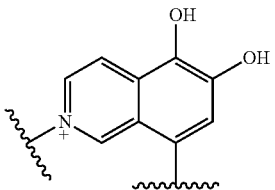

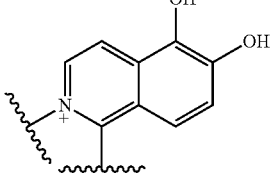

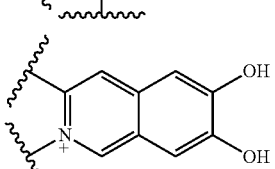

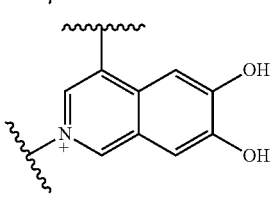

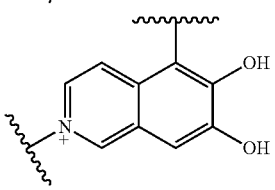

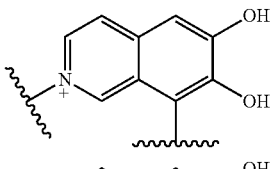

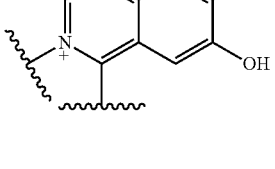

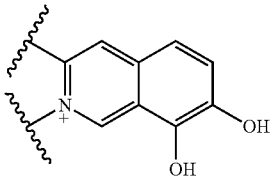

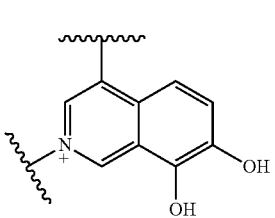

-continued
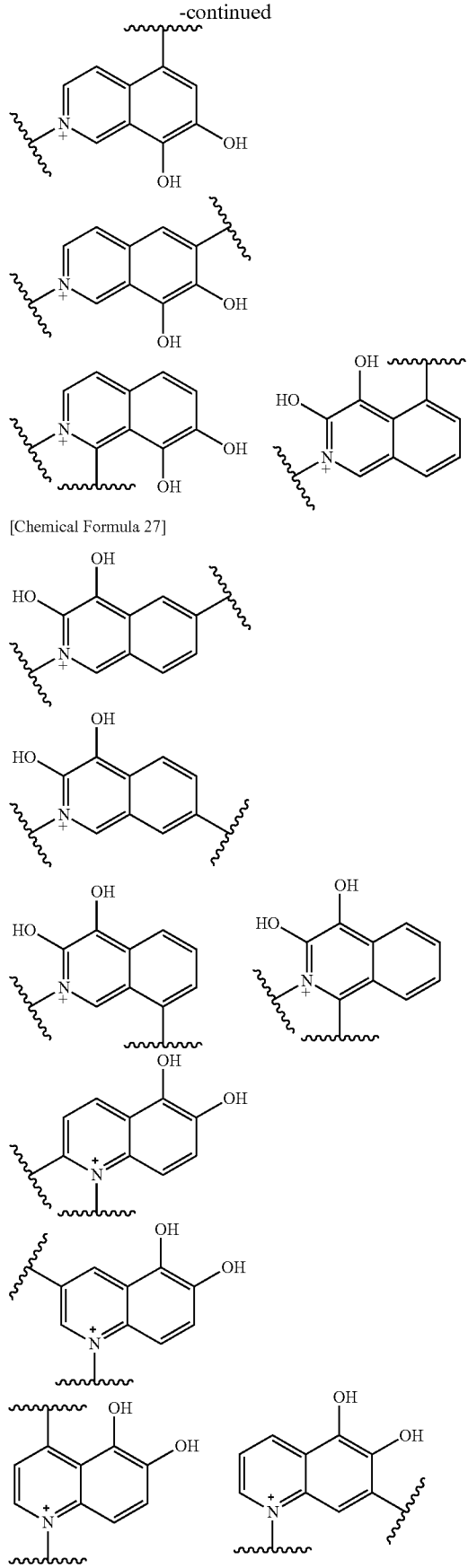
[Chemical Formula 27]
-continued
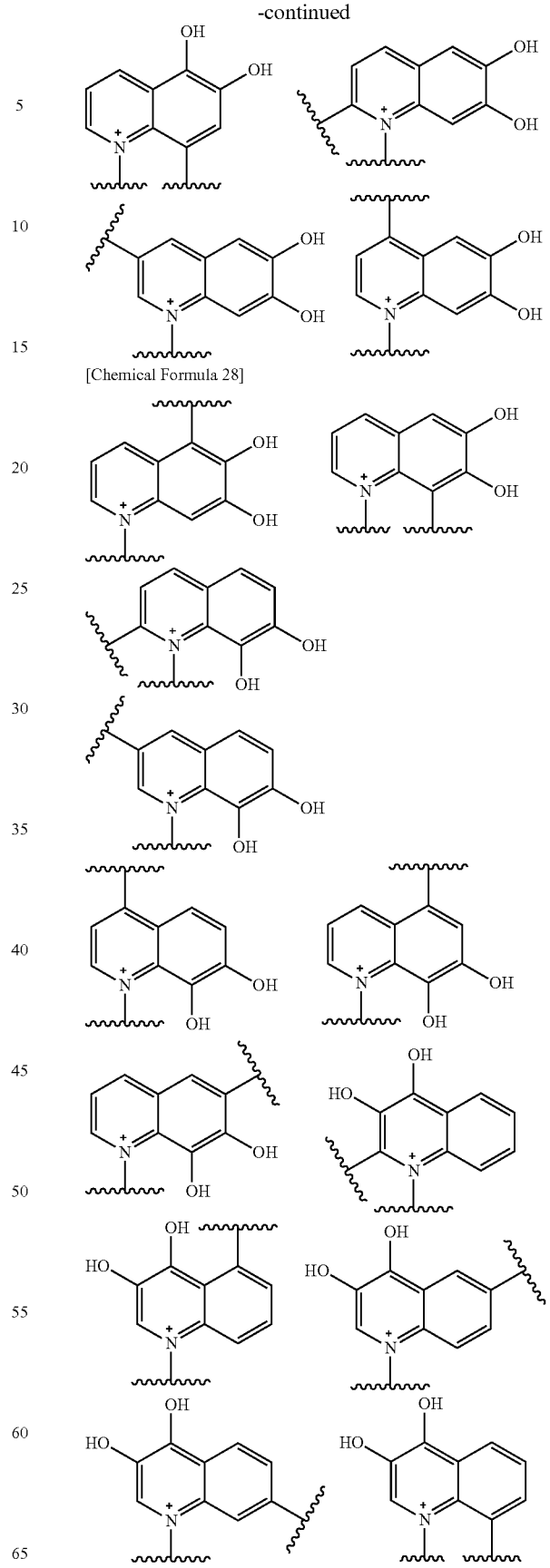
[Chemical Formula 28]

[Chemical Formula 29]

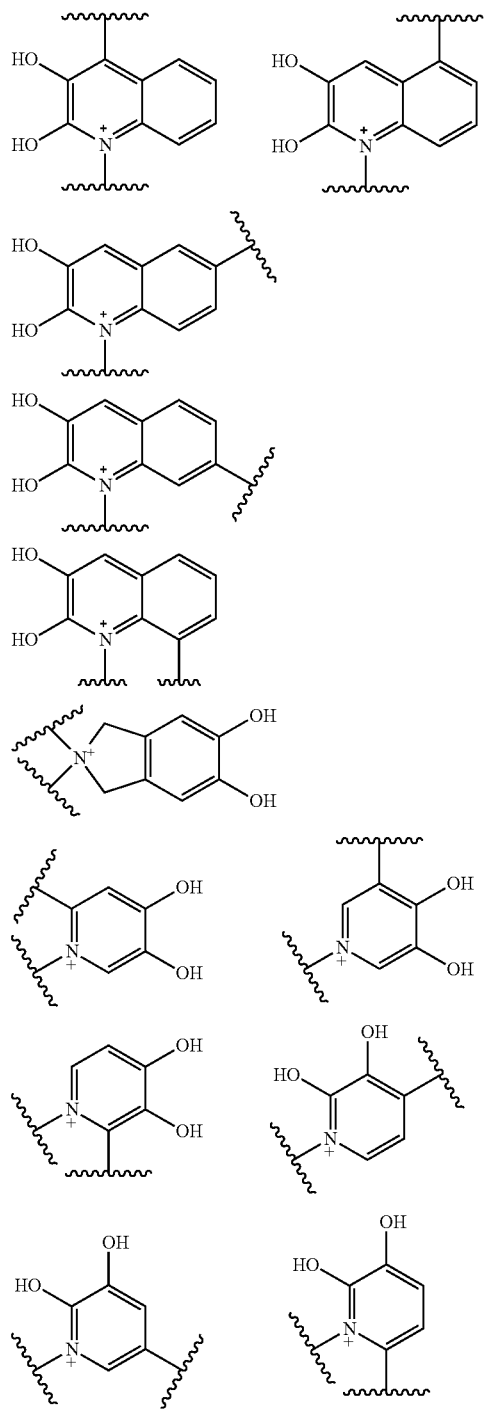

wherein, the bond to the quaternary nitrogen atom binds to L, and the other bond binds to $R^{10}$.

21. The compound, an ester at carboxyl group, an amino-protected compound when the amino is present on the ring in the 7-side chain, or a pharmaceutically acceptable salt thereof according to the above 20, wherein E-$R^{10}$ is a group selected from the following formulae:

[Chemical Formula 30]

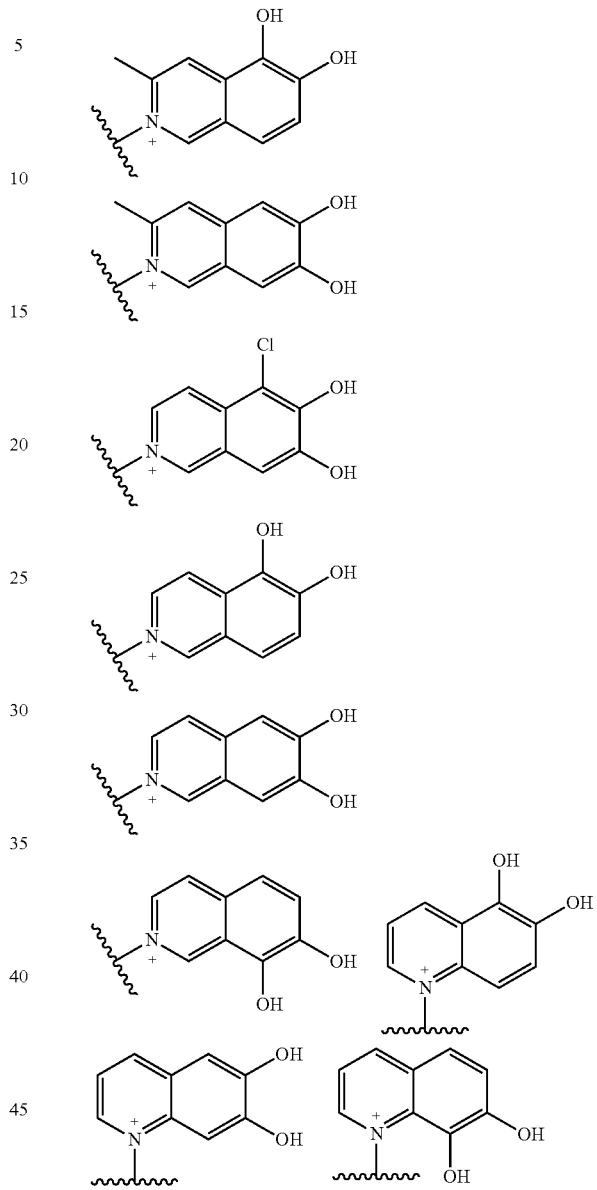

wherein, the bond to the quaternary nitrogen atom binds to L.

22. The compound, an ester at carboxyl group, an amino-protected compound when the amino is present on the ring in the 7-side chain, or a pharmaceutically acceptable salt thereof according to the above 21, wherein E-$R^{10}$ is represented by the formula:

[Chemical Formula 31]

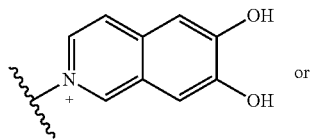 or

-continued

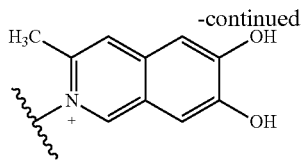

wherein, the bond to the quaternary nitrogen atom binds to L.

23. The compound, an ester at carboxyl group, an amino-protected compound when the amino is present on the ring in the 7-side chain, or a pharmaceutically acceptable salt thereof according to the above 16, wherein -L-E- is represented by the formula;

[Chemical Formula 32]

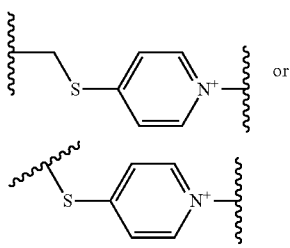

or wherein, the bond to the quaternary nitrogen atom binds to R10, the other bond binds to cephem at 3 position.

24. The compound, an ester at carboxyl group, an amino-protected compound when the amino is present on the ring in the 7-side chain, or a pharmaceutically acceptable salt thereof according to any one of the above 1 to 23, wherein $R^3$ is hydrogen or —$OCH_3$.

25. The compound, an ester at carboxyl group, an amino-protected compound when the amino is present on the ring in the 7-side chain, or a pharmaceutically acceptable salt thereof according to any one of the above 1 to 24, wherein $R^1$ is an optionally substituted phenyl.

26. The compound, an ester at carboxyl group, an amino-protected compound when the amino is present on the ring in the 7-side chain, or a pharmaceutically acceptable salt thereof according to any one of the above 1 to 24, wherein $R^1$ is represented by the formula:

[Chemical Formula 33]

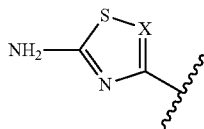

wherein, X is N, C(—H) or C(—Cl).

27. The compound, an ester at carboxyl group, an amino-protected compound when the amino is present on the ring in the 7-side chain, or a pharmaceutically acceptable salt thereof according to the above 26, wherein, X is N.

28. The compound, an ester at carboxyl group, an amino-protected compound when the amino is present on the ring in the 7-side chain, or a pharmaceutically acceptable salt thereof according to the above 26, wherein, X is C(—H) or C(—Cl).

29. The compound, an ester at carboxyl group, an amino-protected compound when the amino is present on the ring in the 7-side chain, or a pharmaceutically acceptable salt thereof according to any one of the above 1 to 28, wherein, $R^{2A}$ is hydrogen, optionally substituted amino, —$SO_3H$, optionally substituted amino sulfonyl, carboxyl, optionally substituted carbamoyl, hydroxyl, or substituted carbonyloxy, and $R^{2B}$ is hydrogen.

30. The compound, an ester at carboxyl group, an amino-protected compound when the amino is present on the ring in the 7-side chain, or a pharmaceutically acceptable salt thereof according to any one of the above 1 to 29, wherein, $R^{2A}$ is:
substituted amino shown below:

[Chemical Formula 34]

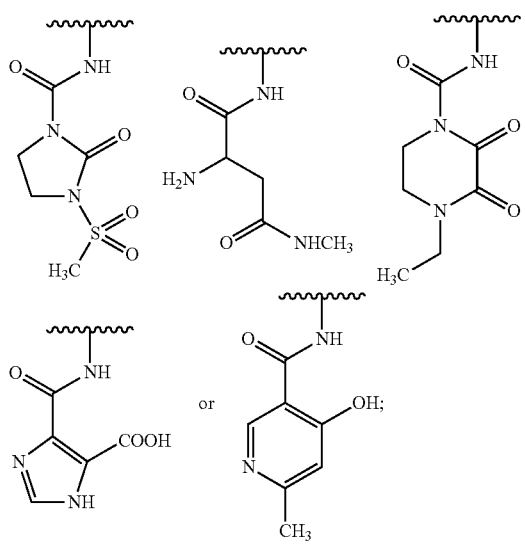

substituted amino sulfonyl shown below:

[Chemical Formula 35]

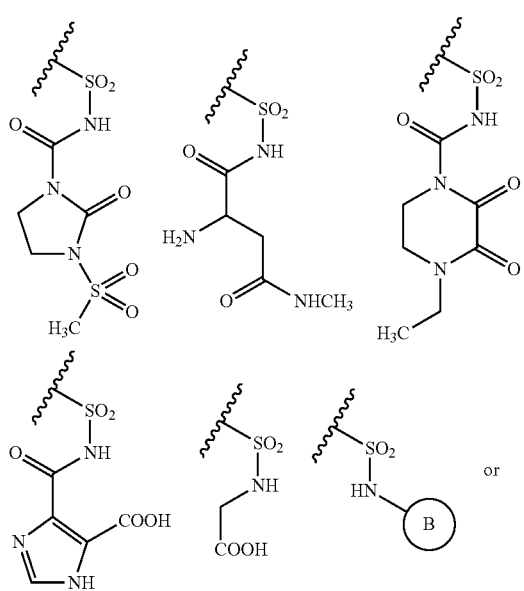

-continued

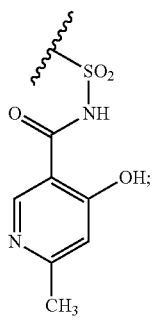

wherein, ring B represents an optionally substituted heterocyclic group;

substituted carbamoyl shown below:

[Chemical Formula 36]

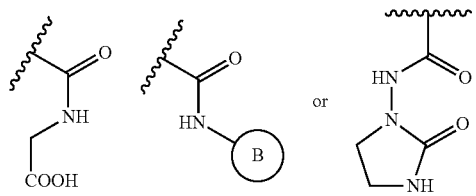

wherein, ring B represents an optionally substituted heterocyclic group; or substituted carbonyloxy shown below:

[Chemical Formula 37]

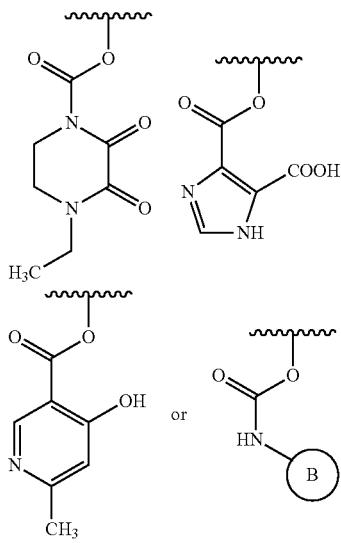

wherein, ring B represents an optionally substituted heterocyclic group.

31. The compound, an ester at carboxyl group, an amino-protected compound when the amino is present on the ring in the 7-side chain, or a pharmaceutically acceptable salt thereof according to any one of the above 1 to 29, wherein, $R^{2A}$ and $R^{2B}$ are taken together to form:

substituted methylidene shown below:

[Chemical Formula 38]

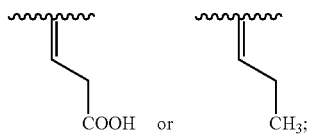

substituted hydroxyimino shown below:

[Chemical Formula 39]

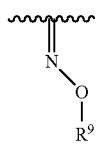

wherein, $R^9$ is optionally substituted lower alkyl.

32. The compound, an ester at carboxyl group, an amino-protected compound when the amino is present on the ring in the 7-side chain, or a pharmaceutically acceptable salt thereof according to any one of the above 1 to 29, wherein $R^{2A}$ and $R^{2B}$ are taken together to form substituted hydroxyimino shown below:

[Chemical Formula 40]

(I-F)

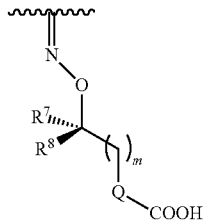

wherein, $R^7$ and $R^8$ are each independently hydrogen, halogen, hydroxyl, carboxyl, optionally substituted lower alkyl, an optionally substituted carbocyclic group, or an optionally substituted heterocyclic group, or $R^7$ and $R^8$ may be taken together with a neighboring atom to form an optionally substituted carbocyclic group or an optionally substituted heterocyclic group;

Q is a single bond, an optionally substituted carbocyclic group or an optionally substituted heterocyclic group; and m is an integer from 0 to 3.

33. A compound of the formula (I-G-1):

[Chemical Formula 41]

(I-G-1)

an ester at carboxyl group, an amino-protected compound when the amino is present on the ring in the 7-side chain, or a pharmaceutically acceptable salt thereof according to any one of the above 1 to 24, wherein, each symbol is as defined above.

34. The compound, an ester at carboxyl group, an amino-protected compound when the amino is present on the ring in the 7-side chain, or a pharmaceutically acceptable salt thereof according to the above 33, wherein, $R^{5A}$ is hydrogen and $R^{5B}$ is lower alkyl; $R^{10}$ is a group represented by the formula (I-B);

[Chemical Formula 42]

(I-B)

each symbol is as defined above.

35. The compound, an ester at carboxyl group, an amino-protected compound when the amino is present on the ring in the 7-side chain, or a pharmaceutically acceptable salt thereof according to the above 34,
wherein,
X is C(—H), C(—Cl) or N;
each $R^7$ and $R^8$ is independently hydrogen or lower alkyl;
R3 is hydrogen;
m is 0 or 1;
Q is a single bond;
L is —CH2-; E is a group selected from the following formulae;

[Chemical Formula 43]

(2)

(5)

(7)

(10)

(11)

(26)

(77)

wherein, Rx is lower alkyl, p is an integer from 1 to 3;
G is a single bond or lower alkylene;
B is non-existent, or a single bond;
D is non-existent, a single bond, —C(=O)—, —C(=O)—C(=O)—, —NR$^6$—C(=O)—C(=O)—, —NR$^6$—C(=O)— or —NH—C(=O)—C(=N—OR$^{6a}$);
$R^6$ is hydrogen or lower alkyl;
$R^{6a}$ is hydrogen, methyl, carboxymethyl, or 2-carboxypropane-2-yl; the formula (1-B-2);

[Chemical Formula 44]

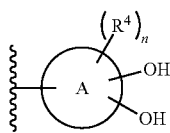

(I-B-2)

is a group selected from the following formulae;

[Chemical Formula 45]

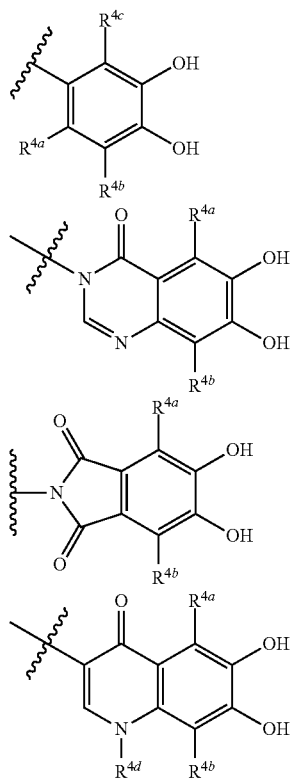

wherein each $R^{4a}$, $R^{4b}$ and $R^{4c}$ is independently hydrogen, halogen or lower alkyl; $R^{4d}$ is hydrogen, lower alkyl or lower cycloalkyl.

36. A pharmaceutical composition, which comprises a compound, an ester at carboxyl group, an amino-protected compound when the amino is present on the ring in the 7-side chain, or a pharmaceutically acceptable salt thereof according to any one of the above 1 to 35.

37. The pharmaceutical composition according to the above 36, which possesses antimicrobial activity.

Effects of the Invention

The compounds of the subject invention are useful as a pharmaceutical product having at least one of the following features:

1) the compounds exhibit potent antimicrobial spectrum against a variety of bacteria including Gram negative bacteria and/or Gram positive bacteria;

2) the compounds exhibit potent antimicrobial activity against beta-lactamase producing Gram negative bacteria;

3) the compounds exhibit potent antimicrobial activity against multidrug-resistant bacteria, in particular, Class B type metallo-beta-lactamase producing Gram negative bacteria;

4) the compounds exhibit potent antimicrobial activity against extended-spectrum beta-lactamase (ESBL) producing bacteria;

5) the compounds do not exhibit cross resistance with known cephem drugs and/or carbapenem drugs; and 6) the compounds do not exhibit side effects such as toxicity and fever after administration into the body;

7) the compounds are stable for storage and/or well soluble in water;

8) the compounds of the present invention have excellent features regarding kinetics in the body, such as high blood concentration, high bioavailability, long duration of effects, and/or high tissue migration; and 9) the compounds of the present invention also may exhibit or have antimicrobial activity against biothreat organisms, which may include, but are not limited to those biothreat organisms, such as *Yersinia pestis, Bacillus anthracis, Francisella tularensis, Burkholderia mallei Burkholderia pseudomallei, Brucella suis, Brucella melitensis* or *Brucella abortus.*

PREFERABLE EMBODIMENTS FOR CARRYING OUT THE INVENTION

It should be understood that, throughout the present specification, the expression of a singular form (e.g., "a", "an", "the", and the like; and in other languages, corresponding articles, adjectives, and the like) includes the concept of its plural form unless specified otherwise. Furthermore, it should be understood that the terms used herein are used in a meaning normally used in the art unless specified otherwise. Thus, unless defined otherwise, all technical and scientific terms used herein have the same meaning as those generally understood by those skilled in the art in the field to which the subject invention pertains. Each specific definition of terms specifically used herein is described below. Each term used herein means, alone or in combination with another word, as below.

"Halogen" includes fluoro, chloro, bromo and iodo. Preferably, halogen is fluoro, chloro or bromo, and more preferably is chloro.

"Lower alkyl" includes linear or branched alkyl having 1-8 carbons, preferably 1-6 carbons, and more preferably 1-4 carbons, for example, methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, and the like.

"Lower alkylene" includes linear alkylene having 1-8 carbons, preferably 1-6 carbons, more preferably 1-4 carbons, and most preferably one or two carbons, for example, methylene, ethylene, n-propylene, n-butylene, n-pentylene, n-hexylene, and the like.

"Lower alkenylene" includes linear alkenylene having 2-8 carbons, preferably 2-6 carbons, more preferably 2-4 carbons, and at least one double bond at any position, and includes, for example, vinylene, allylene, propenylene, butenylene, pyrenylene, butadienylene, pentenylene, pentadienylene, hexenylene, hexadienylene, and the like.

"Lower alkynylene" includes linear alkynylene having 2-8 carbons, preferably 2-6 carbons, more preferably 2-4 carbons, and at least one triple bond at any position, for example, ethynylene, propynylene, buthynylene, pentynylene, hexynylene, and the like.

"Halo(lower)alkyl" refers to a group in which at least one position of said "lower alkyl" is substituted with the above "halogen", and includes, for example, monofluoromethyl, difluoromethyl, ifluoromethyl, monochloromethyl, dichloromethyl, trichloromethyl, monobromomethyl, monofluoroethyl, monochloroethyl, chlorodifluoromethyl, and the like. Preferably is trifluoromethyl or trichloromethyl.

"Aralkyl" includes the above lower alkyl substituted with one to three groups selected from "aryl" mentioned below, preferably wherein the carbon number of alkyl is 1 to 4, more preferably is 1 or 2, for example, benzyl, phenethyl, phenylpropyl, trityl, and the like.

"Heteroaralkyl" includes the above lower alkyl substituted with one to three groups selected from "heteroaryl" mentioned below, preferably wherein the carbon number of alkyl is 1 to 4, more preferably is 1 or 2, for example, furylmethyl, thienylmethyl, pyrrolylmethyl, pyridylmethyl, thienylethyl, furylethyl, imidazorylmethyl, benzotienylmethyl, thiazolylmethyl, and the like.

"Acyl" includes formyl, optionally substituted lower alkylcarbonyl (e.g., acetyl, propionyl, butylyl, isobutylyl, valeryl, isovaleryl, pivaloyl, hexanoyl, octanoyl, methoxyethylcarbonyl, 2,2,2-trifluoroethylcarbonyl), optionally substituted alkenyloxycarbonyl (e.g., alloc, cinnamyloxy carbonyl), alkoxycarbonylacetyl (e.g., ethoxycarbonylmethylcarbonyl), (lower)alkoxy(lower)alkylcarbonyl (e.g., methoxyethylcarbonyl), (lower)alkylcarbamoyl(lower)alkylcarbonyl (e.g., methylcarbamoylethylcarbonyl), optionally substituted arylcarbonyl (e.g., benzoyl, toluoyl), optionally substituted cycloalkyloxy carbonyl (e.g., cycrohexyloxycarbonyl), optionally substituted aralkyloxy carbonyl (e.g., benzyloxycarbonyl, p-nitrobenzyloxycarbonyl), optionally substituted heteroaralkyl carbonyl (e.g., thienylmethyl carbonyl) and the like.

Substituents of "optionally substituted amino" or "optionally substituted carbamoyl" include optionally substituted lower alkyl (e.g., methyl, ethyl, isopropyl, benzyl, carbamoylalkyl (e.g., carbamoylmethyl), mono- or di-(lower)alkylcarbamoyl(lower)alkyl (e.g., dimethylcarbamoylethyl), hydroxy(lower)alkyl, heterocyclyl(lower)alkyl (e.g., morpholinoethyl, tetrahydropyranylethyl), alkoxycarbonyl(lower)alkyl (e.g., ethoxycarbonylmethyl, ethoxycarbonylethyl), mono- or di-(lower)alkylamino(lower)alkyl (e.g., dimethylaminoethyl)); (lower)alkoxy(lower)alkyl (e.g., methoxyethyl, ethoxymethyl, ethoxyethyl, isopropoxyethyl, and the like);
acyl (e.g., formyl, optionally substituted lower alkylcarbonyl (e.g., acetyl, propionyl, butylyl, isobutylyl, valeryl, isovaleryl, pivaloyl, hexanoyl, octanoyl, methoxyethylcarbonyl, 2,2,2-trifluoroethylcarbonyl, alkoxycarbonylacetyl (e.g., ethoxycarbonylmethylcarbonyl),
(lower)alkoxy(lower)alkylcarbonyl (e.g., methoxyethylcarbonyl),
(lower)alkylcarbamoyl(lower)alkylcarbonyl (e.g., methylcarbamoylethylcarbonyl), optionally substituted arylcarbonyl (e.g., benzoyl, toluoyl);
optionally substituted aralkyl (e.g., benzyl, 4-fluorobenzyl); hydroxy;
optionally substituted lower alkylsulfonyl (e.g., methanesulfonyl, ethanesulfonyl, isopropylsulfonyl, 2,2,2-trifluoroethanesulfonyl, benzylsulfonyl, methoxyethylsulfonyl);
arylsulfonyl optionally having a lower alkyl or halogen as a substituent (e.g., benzenesulfonyl, toluenesulfonyl, 4-fluorobenzenesulfonyl), cycloalkyl (e.g., cyclopropyl);
aryl optionally having lower alkyl as a substituent (e.g., phenyl, tolyl);
lower alkylaminosulfonyl (e.g., methylaminosulfonyl, dimethylaminosulfonyl);
lower alkylaminocarbonyl (e.g., dimethylaminocarbonyl);
lower alkoxycarbonyl (e.g., ethoxycarbonyl);
cycloalkylcarbonyl (e.g., cyclopropylcarbonyl, cyclohexylcarbonyl);
optionally substituted sulfamoyl (e.g., sulfamoyl, methylsulfamoyl, dimethylsulfamoyl);
lower alkylcarbonylamino (e.g., methylcarbonylamino);
heterocyclic group (e.g., morpholino, tetrahydropyranyl);
optionally substituted amino (e.g., mono- or di-alkylamino (e.g., dimethylamino), formylamino), and the like.

The above substituted amino or substituted carbamoyl may be mono-substituted or di-substituted.

"Lower alkenyl" refers to a linear or branched alkenyl having 2 to 8 carbons and having one or more double bonds on said "lower alkyl". The examples include vinyl, 1-propenyl, 2-propenyl, 1-butenyl, 2-butenyl, 3-butenyl, 1,3-butadienyl, 3-methyl-2-butenyl, and the like. Preferred is alkenyl having 2 to 6 carbons, more preferably 2 to 4 carbons.

With regard to "optionally substituted amino" or "optionally substituted carbamoyl", two substituents of the amino group may be taken together with the adjacent nitrogen atom to form a nitrogen-containing heterocycle which optionally includes a sulfur atom and/or an oxygen atom in the ring (preferably, the heterocycle is a 5- to 7-membered ring, and is preferably saturated). The heterocycle is optionally substituted with oxo or hydroxy. When a sulfur atom forms the heterocycle, said sulfur atom may be substituted with oxo. Examples thereof include 5- or 6-membered rings such as piperazinyl, piperidino, morpholino, pyrrolidino, 2-oxopiperidino, 2-oxopyrrolidino, 4-hydroxymorpholino, and the like.

Substituents of "optionally substituted lower alkyl" include at least one group selected from Substituent Group alpha. The substitution may be of plurality and the substituents are same or different.

Substituents of "optionally substituted lower alkylene", "optionally substituted lower alkenylene" and "optionally substituted lower alkynylene" include at least one group selected from Substituent Group alpha. The substitution may be of plurality and the substituents are same or different.

Substituents of "optionally substituted cycloalkyl" include at least one group selected from Substituent Group alpha. The substitution may be of plurality and the substituents are same or different.

Substituents of "optionally substituted aryl" include at least one group selected from Substituent Group alpha. The substitution may be of plurality and the substituents are same or different.

Substituents of "optionally substituted heteroaryl" include at least one group selected from Substituent Group alpha. The substitution may be of plurality and the substituents are same or different.

Substituents of "optionally substituted aminosulfonyl" include substituted lower alkyl and at least one group selected from Substituent Group alpha.

Substituents of "optionally substituted lower alkyloxycarbonyl" include at least one group selected from Substituent Group alpha.

Substituents of "substituted carbonyloxy" means "—O—C(=O)-substituent", including optionally substituted lower alkyl, optionally substituted lower alkenyl, optionally substituted lower alkynyl, an optionally substituted carbocyclic group, an optionally substituted heterocyclic group, amino optionally substituted with a heterocyclic group, and at least one group selected from Substituent Group alpha.

Substituents of "optionally substituted carboxyl" include an optionally substituted lower alkyl, optionally substituted lower alkenyl, optionally substituted lower alkynyl, an optionally substituted carbocyclic group, and an optionally substituted heterocyclic group.

"Optionally substituted acyl group" includes carbonyl substituted with optionally substituted lower alkyl, optionally substituted lower alkenyl, optionally substituted lower alkynyl, an optionally substituted carbocyclic group, or an optionally substituted heterocyclic group.

Substituents of an "optionally substituted, saturated or unsaturated, monocyclic or fused cyclic quaternary ammonium group" include an optionally substituted lower alkyl, one group selected from Substituent Group alpha, or any two substituents taken together may form a carbocyclic group or heterocyclic group. Lower alkylene, as a substituent in a heterocyle containing a quanternary ammonium group, may form a bridged structure between the quanternary ammonium group and any carbon atom in the heterocyle.

"Substituent Group alpha" consists of halogen, hydroxy, lower alkoxy, lower alkylene, hydroxy(lower)alkoxy, (lower)alkoxy(lower)alkoxy, carboxy, amino, acylamino, lower (alkyl)amino, imino, hydroxyimino, lower(alkoxy)imino, lower(alkyl)thio, carbamoyl, lower(alkyl)carbamoyl, hydroxy(lower)alkylcarbamoyl, sulfamoyl, lower (alkyl) sulfamoyl, lower(alkyl)sulfinyl, cyano, nitro, a carbocyclic group, and a heterocyclic group.

The lower alkyl moiety in "lower alkoxy", "hydroxy (lower)alkoxy", "(lower)alkoxy(lower)alkoxy", "lower (alkyl)amino", "lower(alkoxy)imino", "lower(alkyl)thio", "lower (alkyl)carbamoyl", "hydroxy(lower)alkylcarbamoyl", and "lower (alkyl)sulfamoyl", "lower(alkyl)sulfinyl", "lower (alkyl)oxycarbonyl", "lower (alkyl) sulfonyl", is as defined as the above "lower alkyl".

The lower alkenyl moiety in "lower(alkenyl)oxy", is as defined as the above "lower alkenyl".

The aryl moiety in "aryloxy" is as defined as "aryl" mentioned below.

Preferred embodiments of substituents in "optionally substituted lower alkyl" include fluoro, chloro, bromo, hydroxy, carboxy, methoxy, ethoxy, hydroxymethoxy, hydroxyethoxy, methoxymethoxy, methoxyethoxy, amino, acetylamino, methylamino, dimethylamino, imino, hydroxyimino, methoxyimino, methylthio, carbamoyl, methylcarbamoyl, hydroxymethylcarbamoyl, sulfamoyl, methylsulfamoyl, lower alkylsulfamoyl, cyano, nitro, phenyl, cyclopropyl, cyclobutyl, cyclohexyl, pyridyl, morpholinyl, and the like.

Preferred embodiments of "optionally substituted lower alkyl" include methyl, ethyl, isopropyl, tert-butyl, halo(lower)alkyl (e.g., monochloromethyl, dichloromethyl, trichloromethyl, monofluoromethyl, difluoromethyl, trifluoromethyl), carboxymethyl, carboxyethyl, carbamoylmethyl, carbamoylethyl, hydroxymethyl, hydroxyethyl, methoxymethyl, ethoxymethyl, methoxyethyl, ethoxyethyl, methylthiomethyl, ethylthiomethyl, benzyl, phenethyl, 4-hydroxybenzyl, 4-methoxybenzyl, 4-carboxybenzyl, and the like.

Preferred embodiments of substituents in "optionally substituted cycloalkyl" include fluoro, chloro, bromo, hydroxy, carboxy, methoxy, ethoxy, hydroxymethoxy, hydroxyethoxy, methoxymethoxy, methoxyethoxy, amino, acetylamino, methylamino, dimethylamino, imino, hydroxyimino, methoxyimino, methylthio, carbamoyl, methylcarbamoyl, hydroxymethylcarbamoyl, sulfamoyl, methylsulfamoyl, lower alkylsulfamoyl, cyano, nitro, phenyl, cyclopropyl, cyclobutyl, cyclohexyl, pyridyl, morpholinyl, and the like.

"Carbocyclic group" includes cycloalkyl, cycloalkenyl, aryl and non-aromatic fused carbocyclic groups, and the like.

"Cycloalkyl" has 3-10 carbons, preferably 3-8 carbons, and more preferably 3-6 carbons, and includes, for example, cyclopropyl, cyclobutyl, cyclopentyl, cyclohexyl, cycloheptyl, cyclooctyl, cyclononyl, cyclodecyl, and the like.

"Cycloalkenyl" is cycloalkyl which contains at least one double bond at any position(s), and includes, for example, cyclopropenyl, cyclobutenyl, cyclopentenyl, cyclohexenyl, cycloheptynyl, cyclooctynyl, and cyclohexadienyl, and the like.

"Aryl" includes phenyl, naphthyl, anthryl, phenanthryl, and the like, and phenyl is preferable.

"Aromatic carbocycle" means a ring derived from aryl as described below.

"Aromatic heterocycle" means an aromatic ring, which is monocyclic or bicyclic or more, having same or different one or more hetero atom selected independently from O, S or N.

The aromatic heterocyclic group which is bicyclic or more includes those wherein a monocyclic or bicyclic or more aromatic heterocyle is condensed with "aromatic carbocyle" described above.

"Non-aromatic carbocyclic group" includes the above "cycloalkyl" and "cycloalkenyl", for example, cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptynyl, cyclooctynyl, and cyclohexadienyl and the like.

"Non-aromatic fused carbocyclic group" includes a group in which one or more cyclic group selected from said "cycloalkyl" and "cycloalkenyl" is fused to said "cycloalkyl" "cycloalkenyl" or "aryl", and includes, for example, indanyl, indenyl, tetrahydronaphthyl, and fluorenyl, and the like.

"Heterocyclic group" includes heterocyclic groups having at least one hetero atom arbitrarily selected from O, S, and N in the ring, and includes, for example, 5- or 6-membered monocyclic non-aromatic heterocyclic group such as pyrrolidyl, piperidinyl, piperadinyl, morpholinyl, tetrahydrofuranyl, tetrohydrothienyl, and the like; 5- or 6-membered monocyclic heteroaryl such as pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, thiazolyl, thiadiazolyl, furyl, thienyl, and the like; 9- or 10-membered bicyclic fused heterocyclic groups such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzotriazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, pyrazolopyridine, triazolopyridyl, imidazothiazolyl, pyrazinopyridazinyl, quinazolinyl, quinolyl, isoquinolyl, naphthyridinyl, dihydrobenzofuryl, tetrahydroquinolyl, tetrahydroisoquinolyl, dihydrobenzoxazine, tetrahydrobenzothienyl, and the like; tricyclic fused heterocyclic groups such as carbazolyl, acridinyl, xanthenyl, phenothiadinyl, phenoxathiinyl, phenoxazinyl, dibenzofuryl, imidazoquinolyl, and the like; non-aromatic heterocyclic groups such as dioxanyl, thiiranyl, oxiranyl, oxathiolanyl, azetidinyl, thianyl, thiazolidine, pyrrolidinyl, pyrrolinyl, imidazolidinyl, imidazolinyl, pyrazolidinyl, pyrazolinyl, piperidyl, piperazinyl, morpholinyl, thiomorpholinyl, thiomorpholino, dihydropyridyl, dihyrobenzimidazolyl, tetrahydropyridyl, tetrahydrofuryl, tetrahydropyranyl, tetrahydrothiazolyl, tetrahydroisothiazolyl, dihydrooxazinyl, hexahydroazepinyl, tetrahydrodiazepinyl, and the like. Preferably, the heterocyclic group is a 5- or 6-membered monocyclic heterocyclic group or 9- or 10-membered bicyclic fused heterocyclic group, and more preferably, a 5- or 6-membered heteroaryl or 9- or 10-membered bicyclic fused heterocyclic group.

"Heteroaryl" means an aromatic heterocyclic group described above. Preferred is 5- or 6-membered monocyclic heteroaryl or 9- or 10-membered bicyclic heteroaryl.

"Heterocycle" means a ring derived from a heterocyclic group as described above. Preferred is 5- or 6-membered monocyclic heterocycle or 9- or 10-membered bicyclic heterocycle.

"Fused heterocycle" means a ring condensed with at least one heterocycle, includes those wherein monocyclic, bicyclic or more heterocyle is condensed with "carbocyle" described above. Preferred is 9- or 10-membered bicyclic heterocycle having at least one nitrogen atom.

"Monocyclic heterocycle" is preferably 5- to 7-membered heterocycle, and more preferably 6-membered heterocycle having at least one nitrogen atom.

"Non-aromatic heterocyclic group" means a group which does not show aromatic character of the "heterocyclic group".

Substituents of "optionally substituted carbocyclic group" "optionally substituted heterocyclic group", "optionally substituted non-aromatic carbocyclic group", and "optionally substituted non-aromatic heterocyclic group" include optionally substituted lower alkyl, and at least one group selected from Substituent Group alpha.

Preferred embodiments of substituents in "optionally substituted carbocyclic group", "optionally substituted heterocyclic group", "optionally substituted non-aromatic carbocyclic group" and "optionally substituted non-aromatic heterocyclic group" include methyl, ethyl, isopropyl, tert-butyl, a fluorine atom, a chlorine atom, a bromine atom, hydroxy, carboxy, methoxy, ethoxy, hydroxymethoxy, hydroxyethoxy, methoxymethoxy, methoxyethoxy, amino, acetylamino, methylamino, dimethylamino, imino, hydroxyimino, methoxyimino, methylthio, carbamoyl, methylcarbamoyl, hydroxymethylcarbamoyl, sulfamoyl, methylsulfamoyl, lower alkylsulfamoyl, cyano, nitro, phenyl, cyclopropyl, cyclobutyl, cyclohexyl, pyridyl, morpholinyl, and the like.

"5- or 6-membered aromatic heterocyclic group having 1-3 nitrogen atoms" includes pyrrolyl, imidazolyl, pyrazolyl, pyridyl, pyridazinyl, pyrimidinyl, pyrazinyl, triazolyl, triazinyl, isoxazolyl, oxazolyl, oxadiazolyl, isothiazolyl, thiazolyl, thiadiazolyl, furyl, thienyl, and the like.

Examples of "optionally substituted carbocyclic group" or "optionally substituted heterocyclic group" of $R^1$ include phenyl, aminothiazole, aminothiadiazole, thiophene, furan, benzothiazole, pyridine, pyrimidine, pyridazine, aminopyridine, and the like, each optionally substituted with hydroxyl and/or halogen. Preferred Examples include the followings:

[Chemical Formula 46]

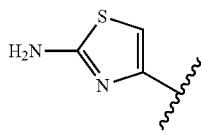

-continued

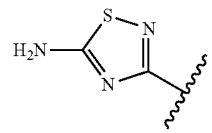

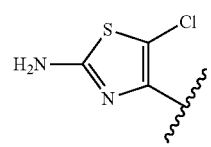

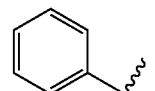

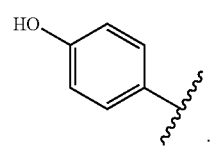

Examples of $R^{24}$ include hydrogen, optionally substituted amino, —COOH, —SO$_3$H, optionally substituted aminosulfonyl, carboxyl, optionally substituted carbamoyl, hydroxyl, substituted carbonyloxy, and the like.

In Preferred examples of

[Chemical Formula 47]

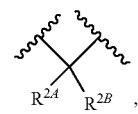

$R^{2B}$ is hydrogen and $R^{24}$ is the following group:
1) substituted amino group shown below:

[Chemical Formula 48]

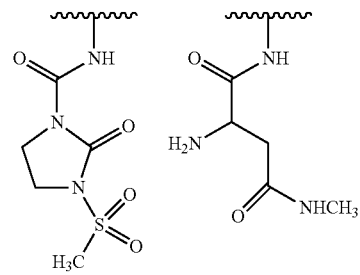

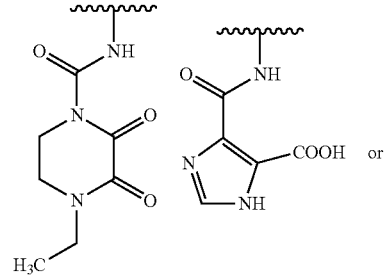

-continued

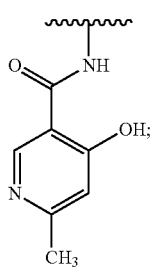

2) substituted aminosulfonyl group shown below:

[Chemical Formula 49]

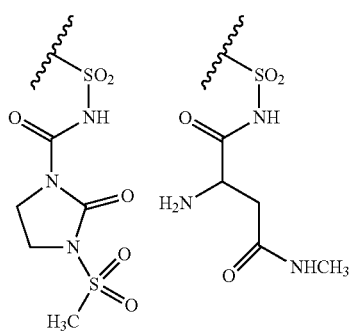

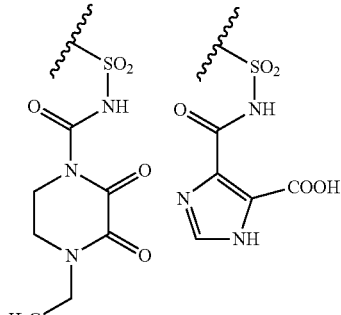

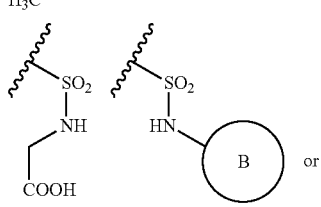

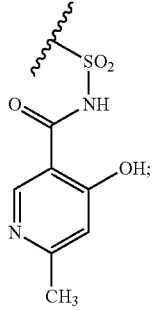

wherein ring B represents an optionally substituted heterocyclic group;

3) substituted carbamoyl group shown below:

[Chemical Formula 50]

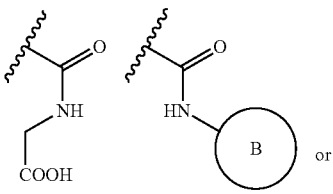

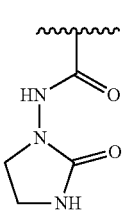

wherein ring B represents an optionally substituted heterocyclic group; or 4) substituted carbonyloxy shown below:

[Chemical Formula 51]

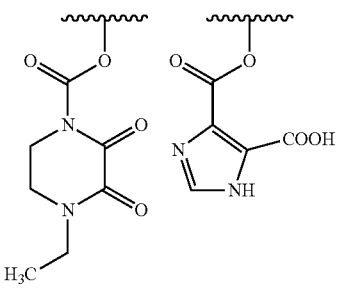

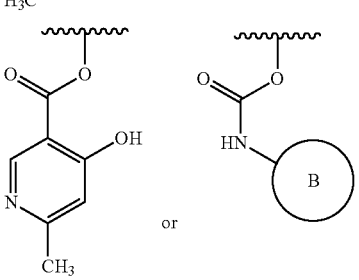

wherein ring B represents an optionally substituted.

Alternatively, $R^{2A}$ and $R^{2B}$ may be taken together to form a substituted methylidene group shown below:

[Chemical Formula 52]

wherein $R^9$ is optionally substituted lower alkyl, preferably

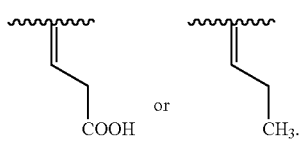
[Chemical Formula 53]

Also, $R^{2A}$ and $R^{2B}$ may be taken together to form optionally substituted hydroxyimino shown below:

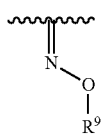
[Chemical Formula 54]

wherein $R^9$ is as defined above. Preferred is a group shown below.

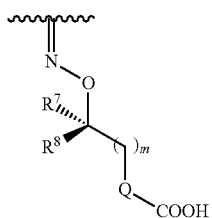
[Chemical Formula 55]

wherein each symbol is as defined above.

Examples of "$R^7$ and $R^8$" includes hydrogen, fluoro, chloro, hydroxy, carboxy, methyl, ethyl, isopropyl, tert-butyl, monofluoromethyl, difluoromethyl, trifluoromethyl, carboxymethyl, carboxyethyl, carbamoylmethyl, carbamoylethyl, hydroxymethyl, hydroxyethyl, methoxymethyl, ethoxymethyl, methoxyethyl, ethoxyethyl, methylthiomethyl, ethylthiomethyl, benzyl, 4-hydroxybenzyl, 4-methoxybenzyl, 4-carboxybenzyl, 3,4-dihydroxybenzyl, phenyl, 4-hydroxyphenyl, 3,4-dihydroxyphenyl, naphthyl, cyclopropyl, cyclobutyl, cyclopentyl, cyclohexyl, pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, thiazolyl, thiadiazolyl, furyl, thienyl, and the like.

Preferred combinations of ($R^7$, $R^8$) include (hydrogen, hydrogen), (methyl, hydrogen), (hydrogen, methyl), (methyl, methyl), (ethyl, hydrogen), (hydrogen, ethyl), (ethyl, ethyl), (phenyl, hydrogen), (hydrogen, phenyl), (dihydroxyphenyl, hydrogen), (hydrogen, dihydroxyphenyl), (carboxymethyl, hydrogen), (hydrogen, carboxymethyl), (carboxyethyl, hydrogen), (hydrogen, carboxyethyl), (hydroxyethyl, hydrogen), (hydrogen, hydroxylethyl), (carbamoylmethyl, hydrogen), (hydrogen, carbamoylmethyl), (trifluoromethyl, hydrogen), (carboxy, hydrogen), (carbamoylethyl, hydrogen), (benzyl, hydrogen), (dihydroxybenzyl, hydrogen), and the like. More preferred combinations of ($R^7$, $R^8$) include, (methyl, methyl), (hydrogen, carboxymethyl), and (carboxyethyl, hydrogen).

Preferred examples of the above substituted hydroxyimino include groups shown bellow.

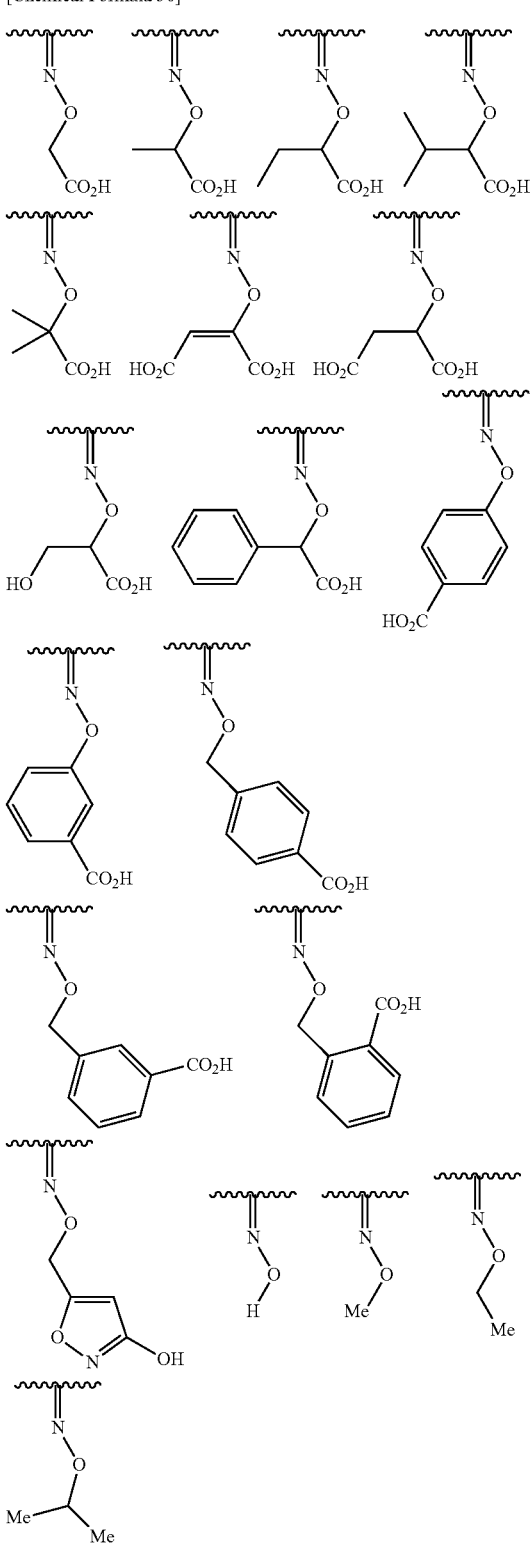
[Chemical Formula 56]

More preferred examples of the above substituted hydroxyimino include groups shown bellow.

[Chemical Formula 57]

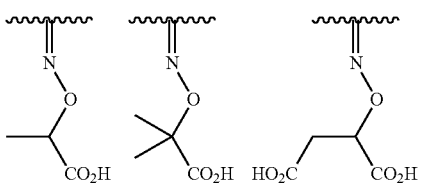

In the case where "$R^7$ and $R^8$ may be taken together with a neighboring atom to form an optionally substituted carbocyclic group or an optionally substituted heterocyclic group" in the formula:

[Chemical Formula 58]

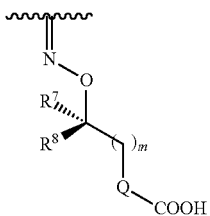

wherein each symbol is as defined, $R^7$ and $R^8$ may form cycloalkane, cycloalkene, or a non-aromatic heterocycle optionally substituted with a group selected from Substituent Group alpha. For example, a group of the formula:

[Chemical Formula 59]

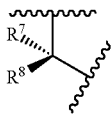

includes those shown below:

[Chemical Formula 60]

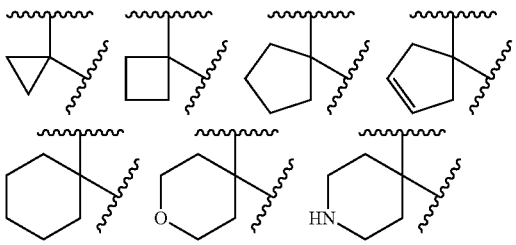

wherein each ring is optionally substituted with a group selected from Substituent Group alpha.

Examples of "Q" include a single bond, phenyl, pyridyl, and the like. A single bond is particularly preferable.

"m" is preferably 0 or 1, and 0 is particularly preferable.

Preferred examples of the above embodiments include:

[Chemical Formula 61]

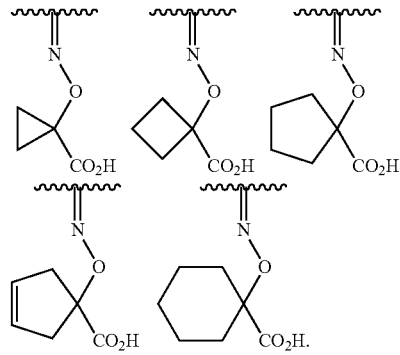

"$R^3$" is preferably hydrogen or —$OCH_3$, and more preferably hydrogen.

Lower alkyl of $R5^A$ and $R5^B$ includes linear or branched alkyl having 1-6 carbons, preferably 1-4 carbons, for example, methyl, ethyl, n-propyl, isopropyl, n-buthyl, isobutyl, sec-butyl, tert-butyl, n-pentyl, isopentyl, neopentyl, hexyl, isohexyl, and the like.

Examples of combinations of ($R^{5A}$, $R^{5B}$) include (hydrogen, methyl), (hydrogen, ethyl), (hydrogen, isopropyl), (hydrogen, tert-butyl), (methyl, methyl), and the like. Preferably, ($R^{5A}$, $R^{5B}$) is (hydrogen, methyl) or (methyl, methyl).

Carbocycle of "$R5^A$ and $R5^B$ may be taken together with the neighboring atom to form optionally substituted carbocycle" include cycloalkane and cycloalkene which have 3-8 carbons, preferably 3-6 carbons. Preferred embodiments include cyclopropane, cyclobutane, cyclopentane, cyclopentene, cyclohexane, cyclohexene, and the like, more preferably include cyclopropane. Substituents of the carbocycle include halogen, hydroxyl, lower alkyl, lower alkoxy, and the like. Preferred embodiments include fluoro, chloro, hydroxyl, methyl, ethyl, isopropyl, tert-buthyl, methoxy, ethoxy, isopropoxy, and the like.

Heterocycle of "$R5^A$ and $R5^B$ may be taken together with the neighboring atom to form optionally substituted heterocycle" include an aromatic or non-aromatic, monocyclic or fused cyclic ring. Preferred embodiments include non-aromatic 3- to 6-membered monocyclic ring. Substituents of the heterocycle include halogen, hydroxyl, lower alkyl, lower alkoxy, and the like. Preferred embodiments include fluoro, chloro, hydroxyl, methyl, ethyl, isopropyl, tert-buthyl, methoxy, ethoxy, isopropoxy, and the like.

Optionally substituted methylidene of "$R5^A$ and $R5^B$ may be taken together to form optionally substituted methylidene" is shown by the formula;

[Chemical Formula 62]

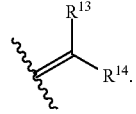

wherein, $R^{13}$ and $R^{14}$ are each independently hydrogen, halogen, or optionally substituted lower alkyl, and preferred $R^{13}$ and $R^{14}$ are hydrogen.

"L" is —$CH_2$—, —CH=CH—, —$CH_2$—CH=CH—, —CH=CH—$CH_2$—, —S—, —$CH_2$—S—, —CH=CH—S— or —CH=CH—$CH_2$—S—, preferably —$CH_2$—, —$CH_2$—CH=CH—, —S— or —$CH_2$—S—.

E is an optionally substituted, saturated or unsaturated, monocyclic or fused cyclic group having at least one quaternary ammonium ion and is preferably selected from the above formulae (1) to (77) which are optionally substituted on the ring. The substituents on the ring include an optionally substituted lower alkyl or one or more group selected from substituent Group alpha. Preferred embodiments of such substitutent include methyl, ethyl, isopropyl, tert-butyl, fluorine atom, chlorine atom, bromine atom, hydroxyl, carboxyl, methoxy, ethoxy, hydroxymethoxy, hydroxyethoxy, methoxymethoxy, methoxyethoxy, methylene, ethylene, propylene, butylene, amino, acetylamino, methylamino, dimethylamino, imino, hydroxyimino, methoxyimino, methylthio, carbamoyl, methylcarbamoyl, hydroxymethylcarbamoyl, sulfamoyl, methylsulfamoyl, (lower)alkylsulfamoyl, cyano, nitro, phenyl, cyclopropyl, cyclobutyl, cyclohexyl, pyridyl, morpholinyl, and the like. More preferred embodiments include a ring unsubstituted or mono- or di-substituted with a hydroxyl group. Such ring mono- or di-substituted with a hydroxyl group may be substituted additionally with another substituent. Herein, when a substitutent is lower alkylene such as ethylene, propylene, or butylene, the lower alkylene may form a bridged structure between the quanternary ammonium group and any carbon atom or between any two carbon atoms in E.

Preferred embodiment of E is the formula (I-D):

[Chemical Formula 63]

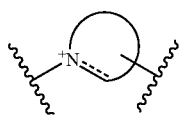

(I-D)

wherein,
the dashed line is a bond in the ring;
the bond to the cationic nitrogen atom binds to L, and the other bond binds to $R^{10}$;
provided,
when a cationic nitrogen atom binds to $R^{10}$, the dashed line is absent, and
when a cationic nitrogen atom does not bind to $R^{10}$, the dashed line is a single bond between the cationic nitrogen atom and a neighboring atom or an alkylene group between the cationic nitrogen atom and a ring member atom other than said neighboring atom,
or the formula (I-E):

[Chemical Formula 64]

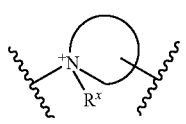

(I-E)

wherein, the bond to the cationic nitrogen atom binds to L, and the other bond binds to $R^{10}$; $R^x$ is optionally substituted lower alkyl.

When L is —S—, —$CH_2$—S—, —CH=CH—S— or —CH=CH—$CH_2$—S—, preferred embodiment of E is a monocyclic or fused heterocyclic group represented by the formula (I-D'):

[Chemical Formula 65]

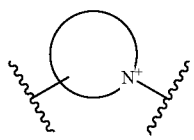

(I-D')

wherein,
the bond to the cationic nitrogen atom binds to $R^{10}$, and the other bond binds to L,
more preferred E is an optionally substituted pyridinium group or an optionally substituted fused pyridinium group.

Preferred examples of E include the following formulae optionally substituted on the ring:

[Chemical Formula 66]

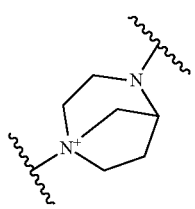

(1)

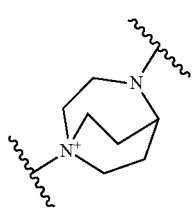

(2)

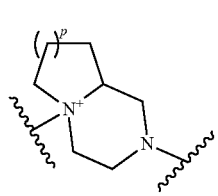

(3)

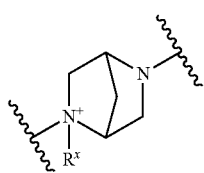

(4)

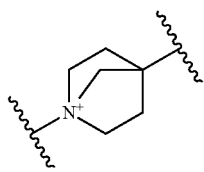

(5)

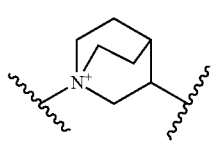

(6)

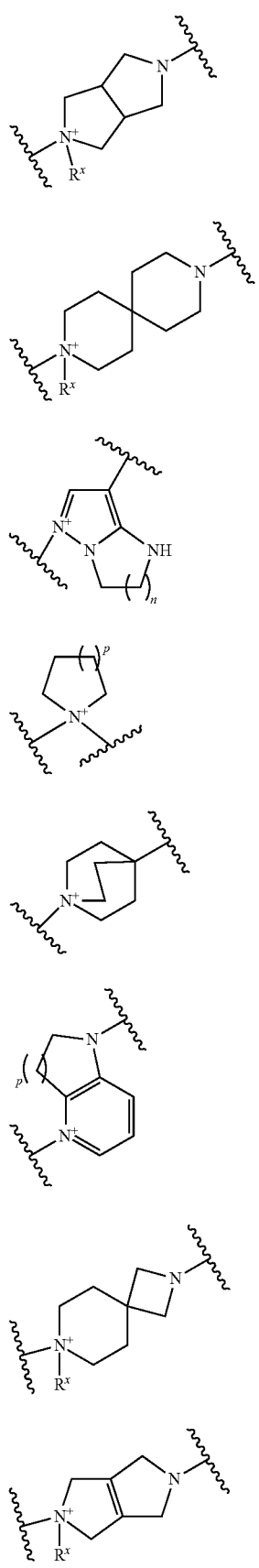
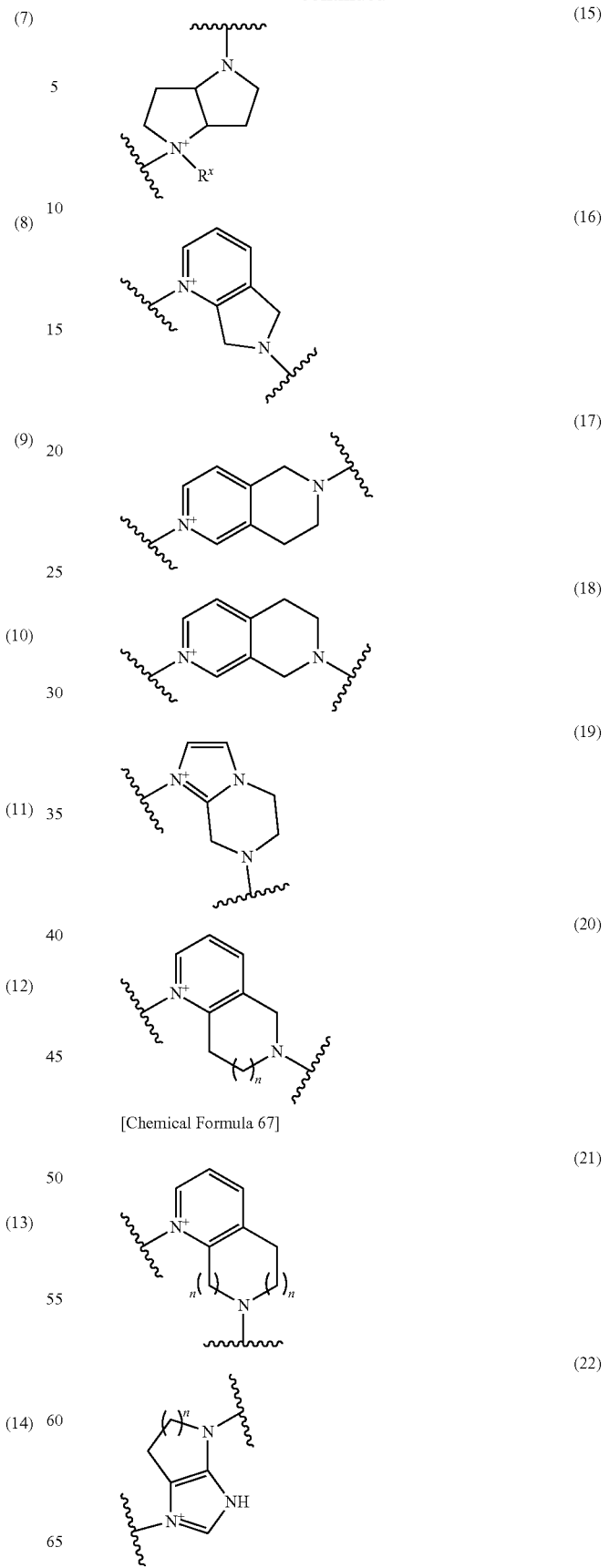
[Chemical Formula 67]

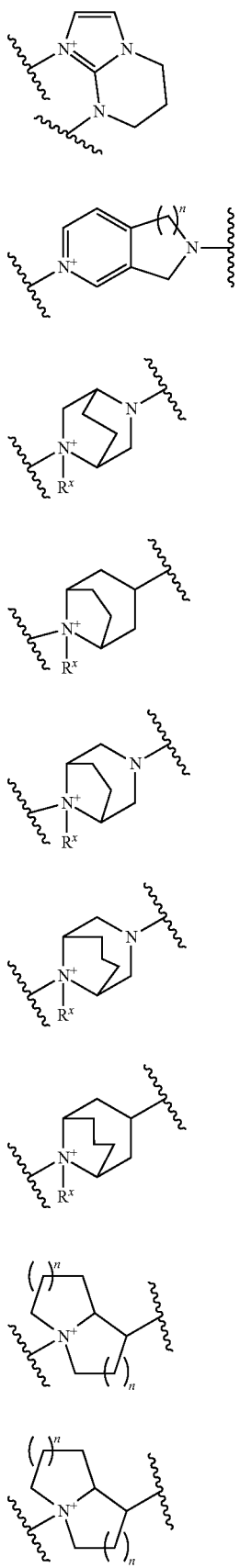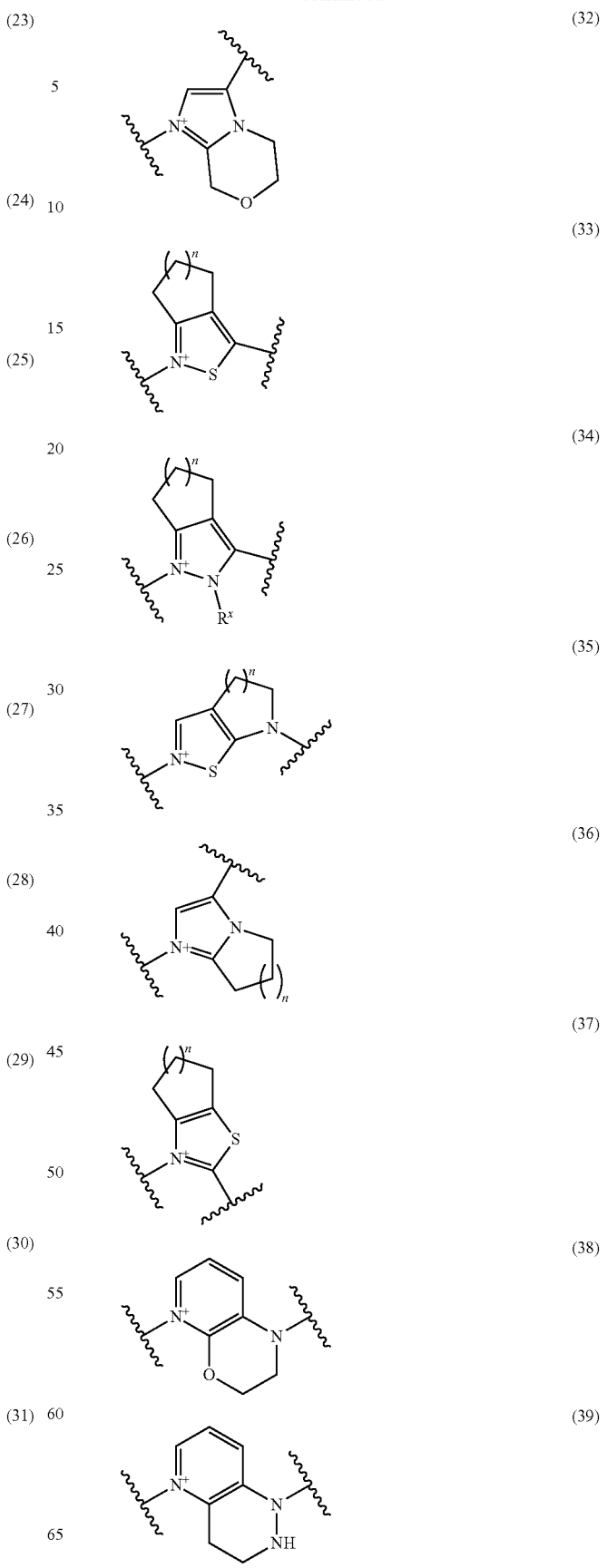

(40)
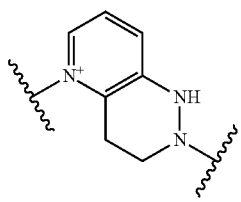
[Chemical Formula 68]
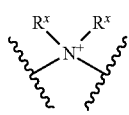
(41)
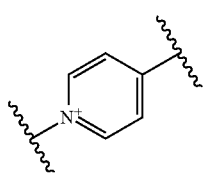
(42)
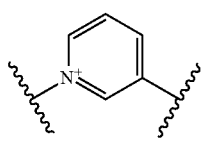
(43)
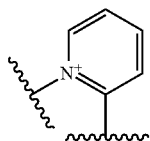
(44)
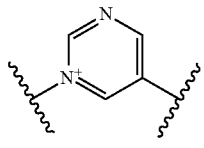
(45)
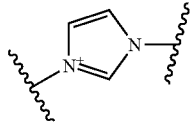
(46)
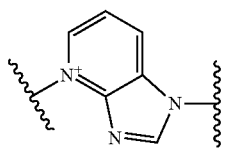
(47)
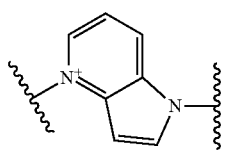
(48)
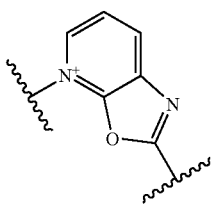
(49)
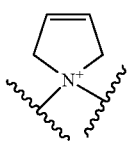
(50)
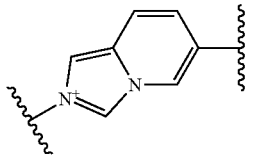
(51)
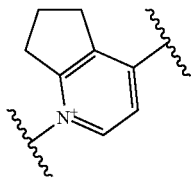
(52)
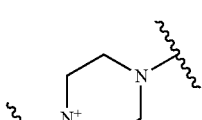
(53)
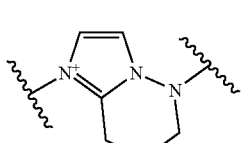
(54)
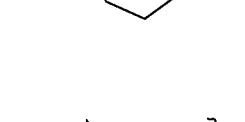
(55)
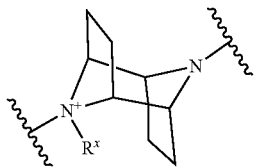
(56)
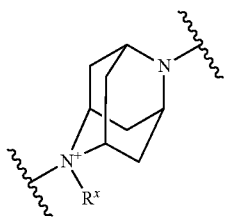

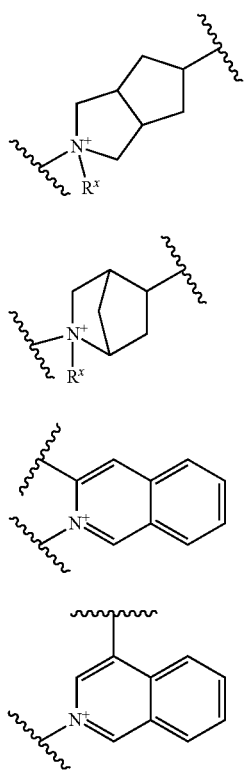
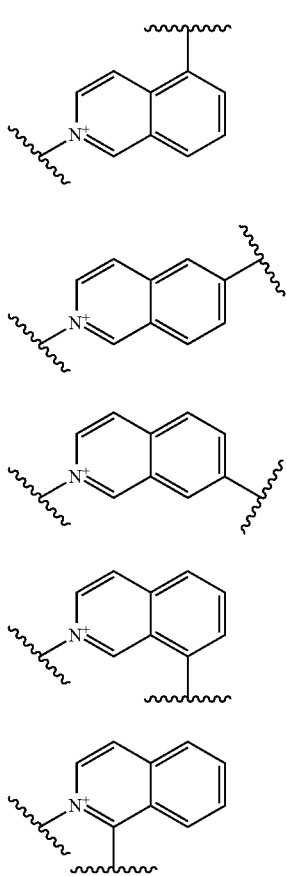
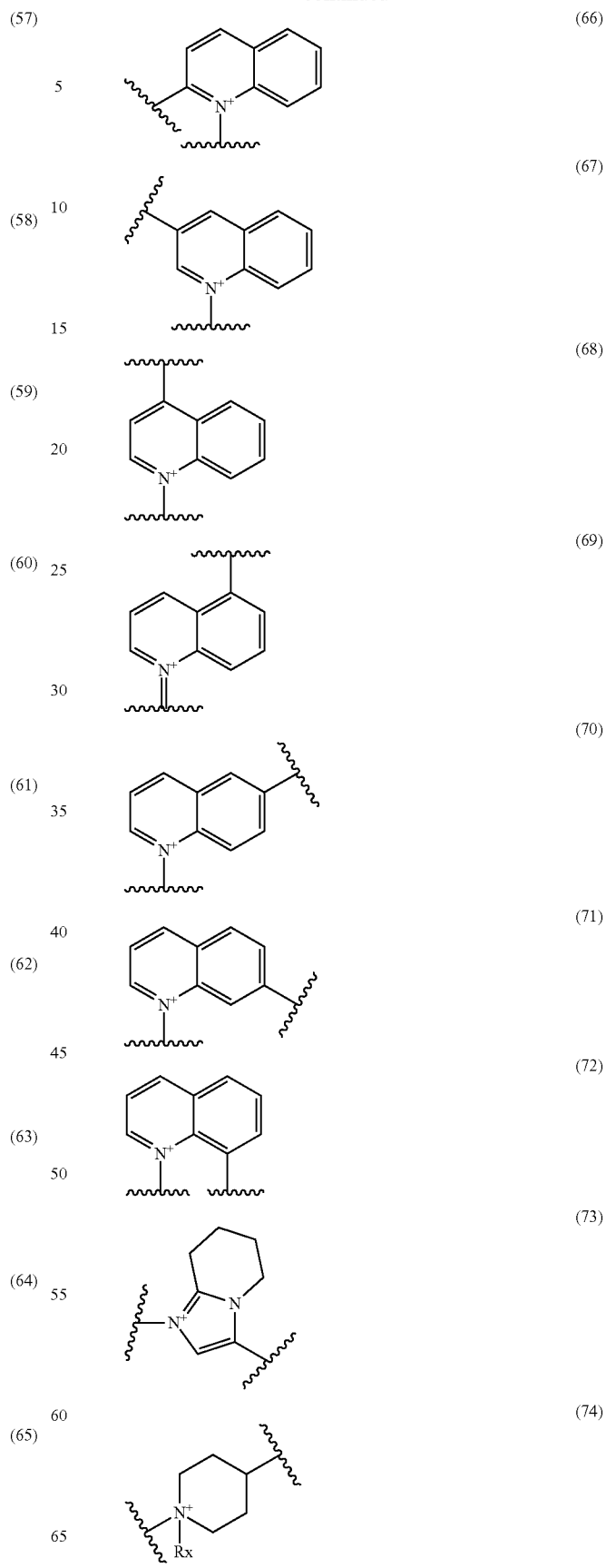

(75)
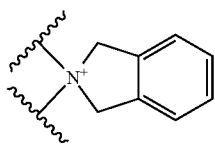

(76)
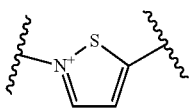

(77)
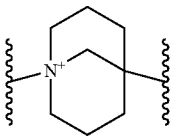

wherein one bond to the quaternary nitrogen atom binds to L, and the other bond binds to $R^{10}$; p is an integer from 1 to 3; n is 1 or 2; each Rx is independently an optionally substituted lower alkyl group.

Among the above formulae, a group selected from the group consisting of the formulae (1) to (7), (10) to (12), (14), (25) to (29), (31), (41) to (44), (47), (50), (52), (53), (59), (60), (64), (73) and (77) is more preferable.

Particularly, a group selected from the group consisting of the formulae (2), (3), (5), (6), (7), (10), (11), (26), (27), (41), (42), (59), (60) and (77) is preferable.

In the subject invention, E is an optionally substituted, saturated or unsaturated, monocyclic or fused cyclic group having at least one quaternary ammonium ion and includes the following embodiment.

1) E is an aromatic heterocyclic group wherein two hydroxyl groups each binds to each of two adjacent carbon atoms on the aromatic ring;

2) E is a heterocyclic group wherein a hydroxyl group(s) do not attached to the ring, or when a hydroxyl group (s) attached, two hydroxyl group each do not bind to each of two adjacent carbon atoms on the ring; and 3) E is a non-cyclic group.

Preferred is 1) or 2).

Preferable examples of the above 1) include:

[Chemical Formula 70]

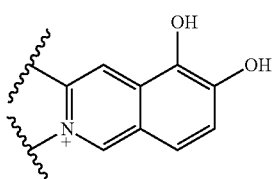

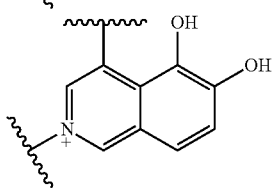

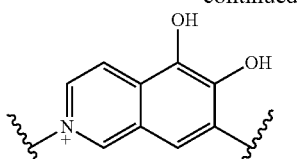

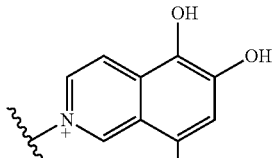

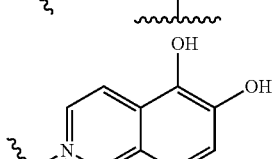

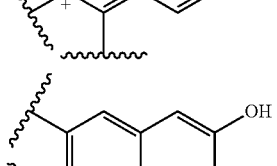

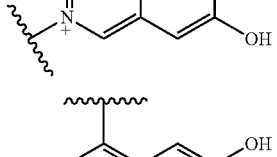

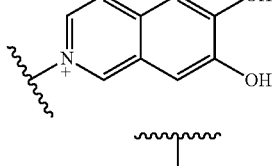

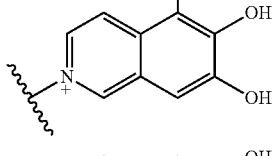

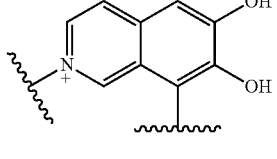

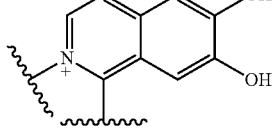

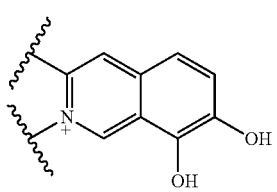

[Chemical Formula 71]
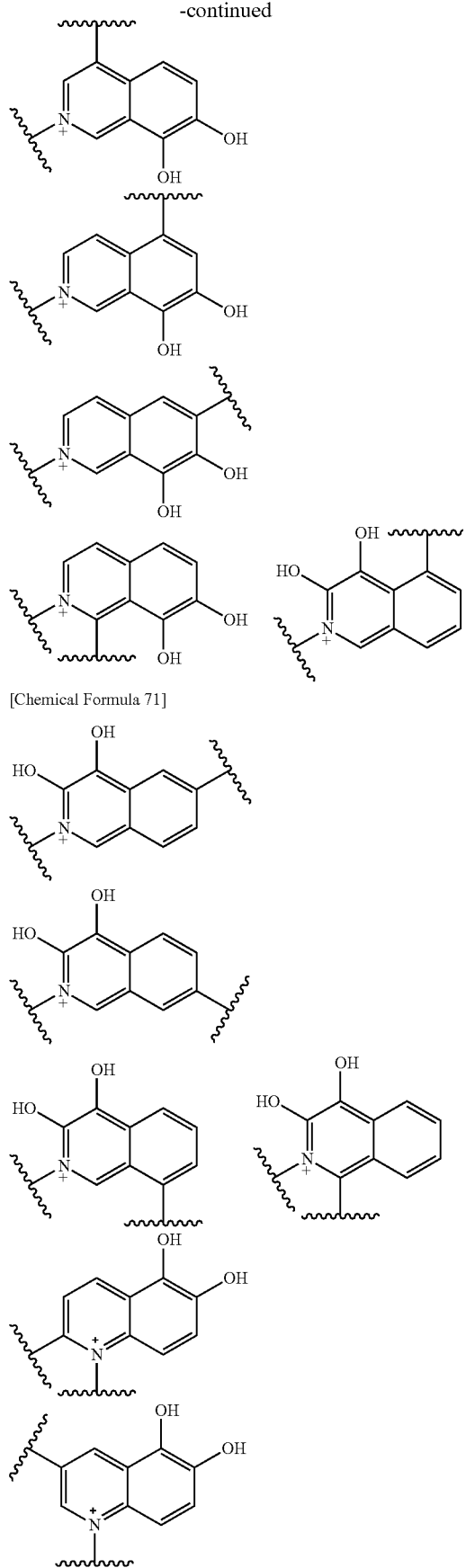
[Chemical Formula 72]
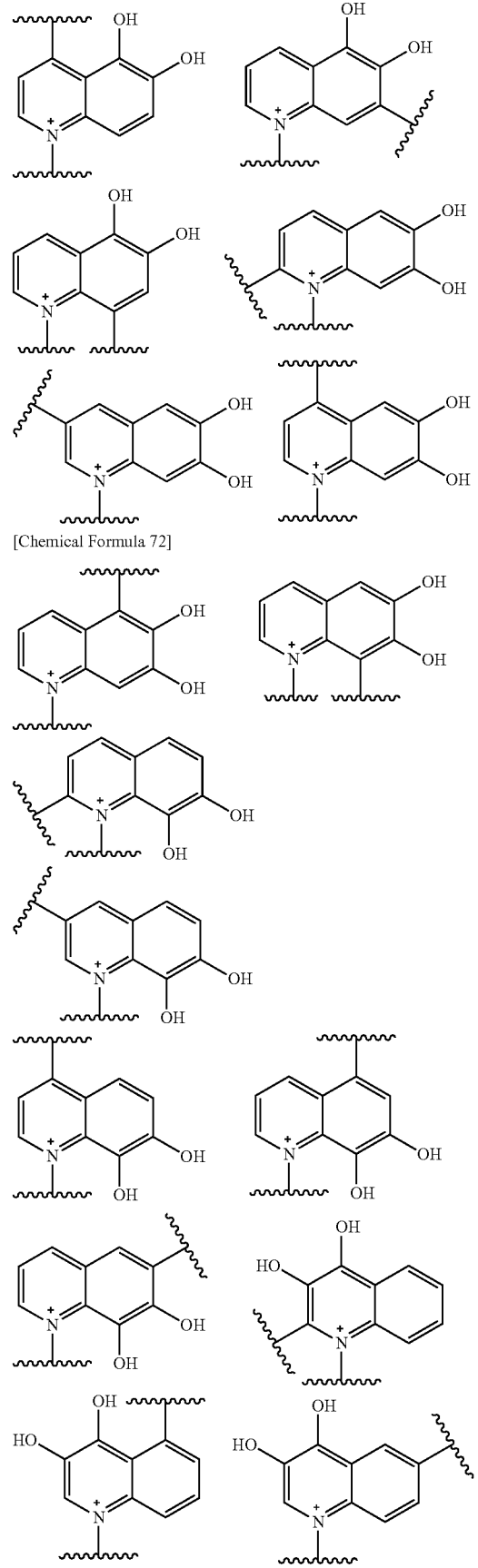

85
-continued

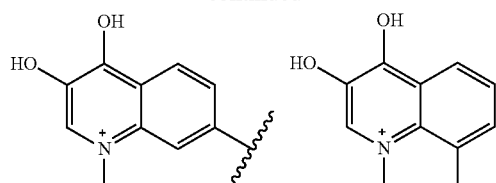

[Chemical Formula 73]

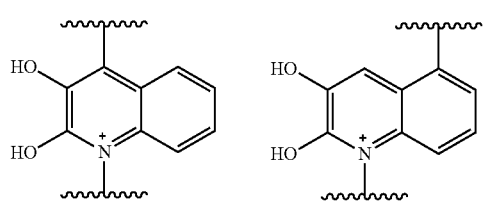

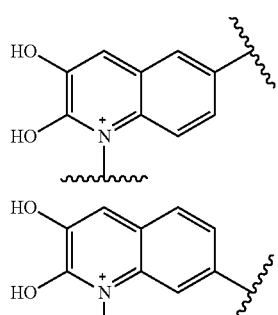

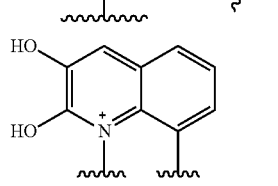

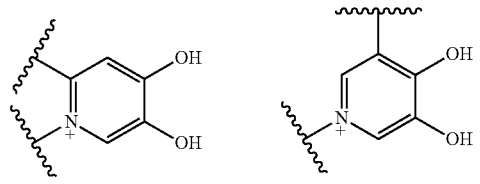

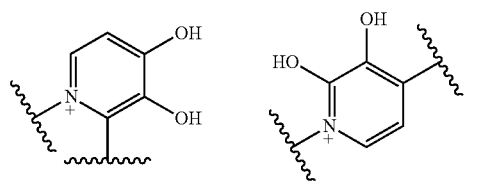

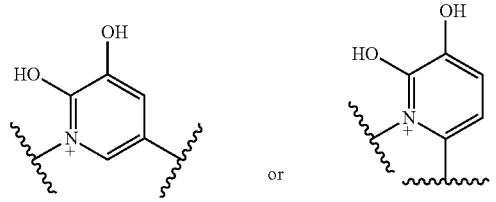

or wherein one bond to the quaternary nitrogen atom binds to L, and the other bond binds to $R^{10}$.

86

Preferred examples of E-$R^{10}$ include:

[Chemical Formula 74]

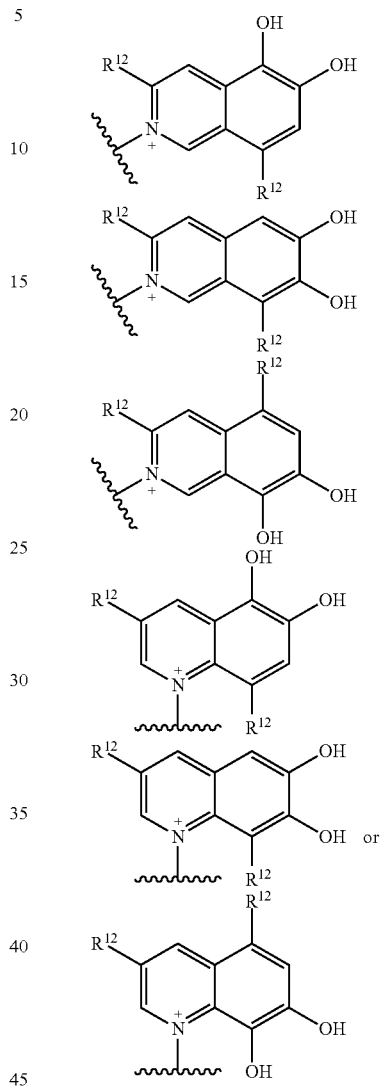

wherein one bond to the quaternary nitrogen atom binds to L, and $R^{12}$ is as defined above.

More preferred examples of E-$R^{10}$ include:

[Chemical Formula 75]

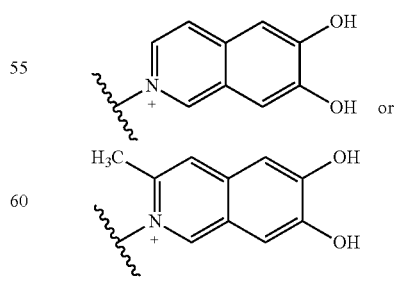

wherein the bond to the quaternary nitrogen atom binds to L.

$R^6$ is hydrogen or optionally substituted lower alkyl, preferably hydrogen, linear or branched alkyl having 1-4 carbons or linear or branched alkyl having 1-4 carbons substituted with carboxy, halogen, hydroxyl or carbonyl, more preferably hydrogen, methyl, ethyl, tert-buthyl,

[Chemical Formula 76]

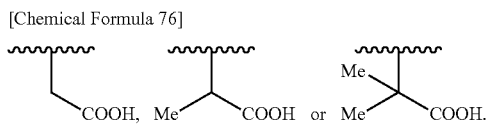

In accordance with the present invention, variable terms "B" or "D", respectively. are as defined throughout the specification and as below, i.e.:

B is non-existent, a single bond or a 5- or 6-membered heterocyclic group containing at least 1-3 nitrogen atoms.

D is non-existent, a single bond, —C(=O)—, —O—C(=O)—, —C(=O)—O—, —NR$^6$—, —NR$^6$—C(=O)—, —C(=O)—NR$^6$—, —C(=O)—C(=O)—, —NR$^6$—C(=O)—NR$^6$—, —C(=O)—C(=O)—NR$^6$—, —C(=O)—NR$^6$—C(=O)—, —NR$^6$—C(=O)—C(=O)—, —NR$^6$—NR$^6$—C(=O)—, —C(=O)—NR$^6$—NR$^6$—, —N=N—C(=O)—, —C(=O)—N=N—, —C=N—NR$^6$—C(=O)—, —C=N—C(=O)—, —N=C—C(=O)—, —C=N—C(=O)—NR$^6$—, —NR$^6$—C(=O)—C(=N—OR$^6$)—, —C(=N—OR$^6$)—C(=O)—NR$^6$—, —NR$^6$—C(=N—OR$^6$)—, —C(=N—OR$^6$)—NR$^6$—, —C(=O)—C(=N—OR$^6$)—, —C(=N—OR$^6$)—C(=O)—, —O—, —S—, —S(=O)—, —S(=O)$_2$—NR$^6$—, —NR$^6$—S(=O)$_2$—, —NR$^6$—CH$_2$—, —CH$_2$—NR$^6$— or —S(=O)$_2$—.

In light of the above definitions and throughout the specification, the terms "B" and "D" may respectively or individually be non-existent, or if both "B" and "D" represent single bonds, then "B" and "D" may be taken together or collectively (i.e., "B-D" joined together) such that it may represent one single bond attached to corresponding adjacent or adjoining functional groups as defined by the present invention.

Preferred embodiments of R$^{10}$ as a group represented by the formula:

[Chemical Formula 77]

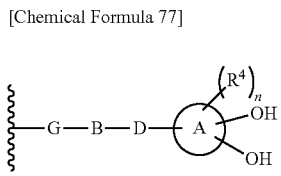

(I-B)

are provided below.

G is preferably a single bond or optionally substituted lower alkylene, and more preferably a single bond, methylene or ethylene.

B is non-existent, preferably a single bond or a group represented by the formula:

[Chemical Formula 78]

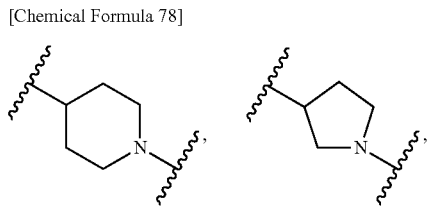

-continued

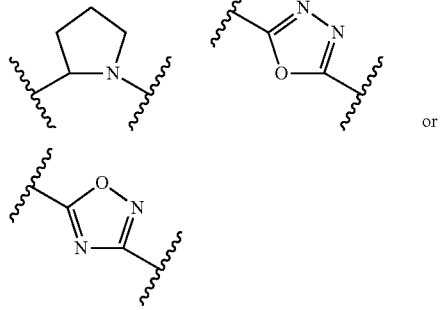

or wherein the bond of the left side is attached to G and the bond of the right side is attached to D.

B is non-existent or more preferably a single bond.

D is non-existent, preferably a single bond, —C(=O)—, —O—C(=O)—, —C(=O)—O—, —NR6-, —O—, —C(=O)—C(=O)—, —NR6-C(=O)—NR6-, —C(=O)—C(=O)—NR6-, —C(=O)—NR6-C(=O)—, —NR6-C(=O)—C(=O)—, —NR6-C(=O)—, —C(=O)—NR6-, —NR6-NR6-C(=O)—, —C(=O)—NR6-NR6-, —N=N—C(=O)—, —C(=O)—N=N—, —C=N—NR6-C(=O)—, —C=N—C(=O)—, —N=C—C(=O)—, —C=N—C(=O)—NR6-, —NR6-C(=O)—C(=N—OR6)-, —C(=N—OR6)-C(=O)—NR6-, —NR6-C(=N—OR6)-, —C(=O)—C(=N—OR6)-, —C(=N—OR6)-C(=O)— or —C(=N—OR6)-NR6-, wherein R$^6$ is hydrogen, methyl, carboxymethyl or 2-carboxypropane-2-yl, and more preferably a single bond, —C(=O)—, —C(=O)—C(=O)—, —NH—C(=O)—C(=O)—, —NH—C(=O)—, —NH—C(=O)—C(=N—OR$^6$)—, —C(=O)—C(=N—OR$^6$)—, —NH—, —O—, or —C=N—NH—C(=O)—, R$^6$ is hydrogen, methyl, ethyl, tert-buthyl, carboxymethyl, 2-carboxypropan-2-yl or 1-carboxyethyl.

Preferred combinations of "-G-B-D-" include the formulae as shown below:

[Chemical Formula 79]

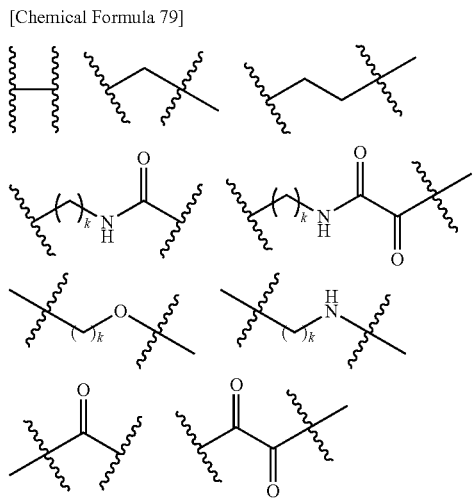

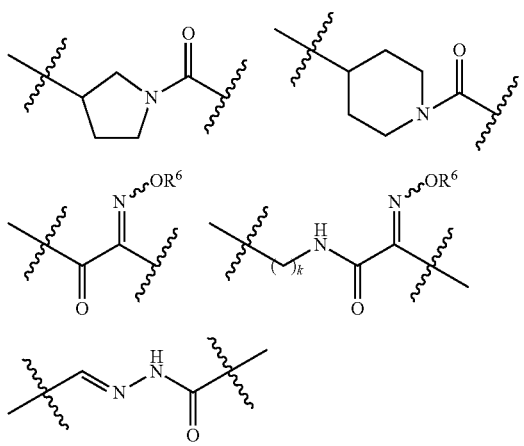
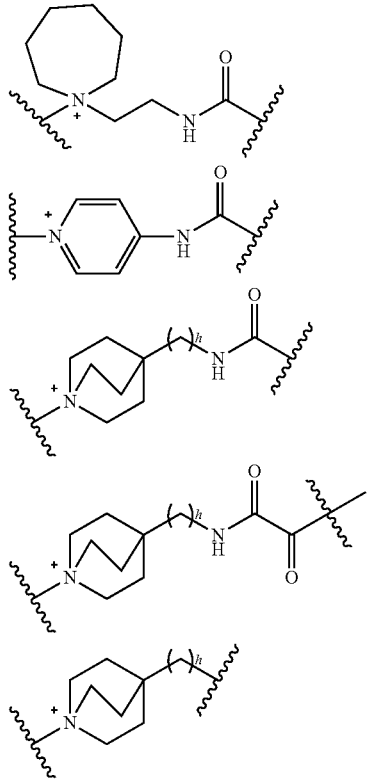
wherein,
k is an integer of 0 to 3, $R^6$ is as defined above, the wavy line means that the bond is in cis or trans configuration, or. a mixture thereof.
Preferable examples of "-E-G-B-D-" include the formulae as shown below:
[Chemical Formula 80]
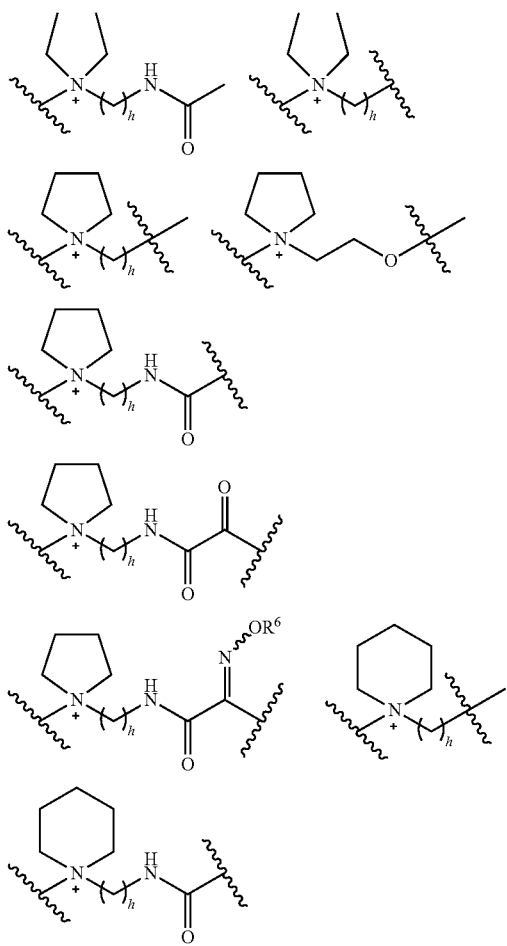
[Chemical Formula 81]
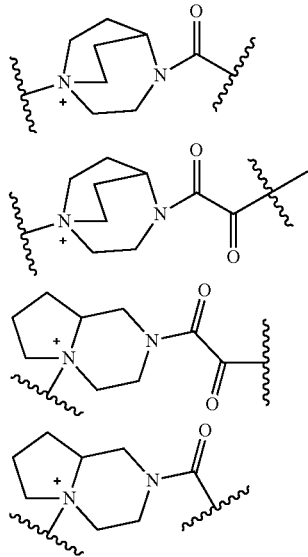

-continued

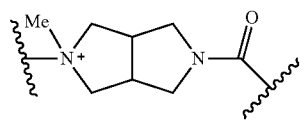
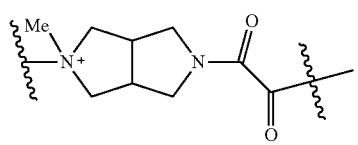
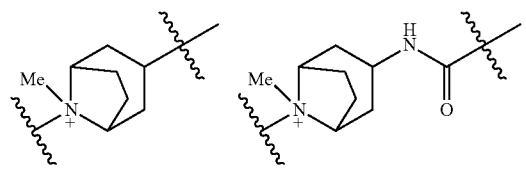
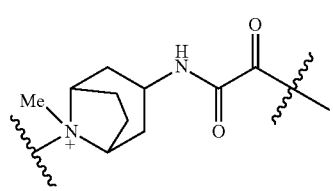
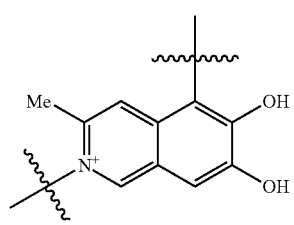
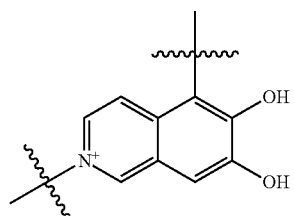
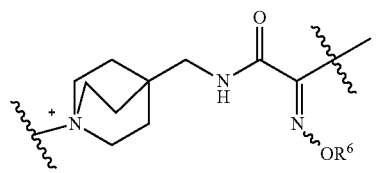
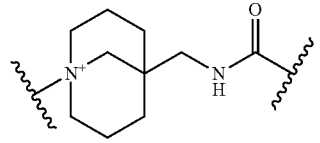
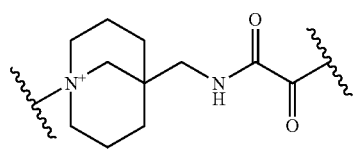
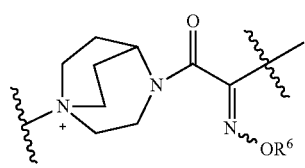

-continued

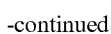
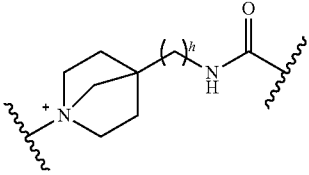
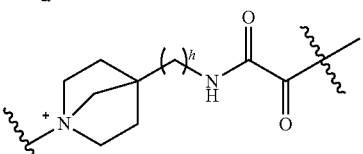
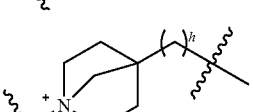
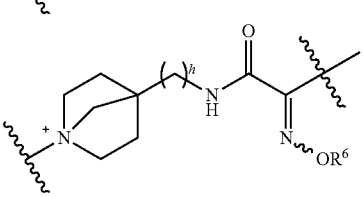

wherein,
Me represents a methyl group,
h is an integer 0 to 3,
$R^6$ is hydrogen, methyl, ethyl, tert-buthyl, carboxymethyl, 2-carboxypropan-2-yl or 1-carboxyethyl,
the wavy line means that the bond is in cis or trans configuration, or a mixture thereof.

In one aspect of the present invention with regard to Formula (I-B):

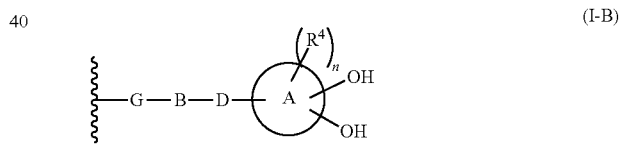

(I-B)

where:
ring A is defined as a fused heterocycle ring system comprised of at least two (2) rings fused together;
where:
$R^4$ optionally is substituted on each of the at least two (2) rings of the fused heterocycle ring system defined as ring A, such that each $R^4$ substituent on each ring of the fused heterocycle ring system independently are selected from identical or different substituents;
where:
each $R^4$ as defined above optionally is substituted independently on each ring of the fused heterocycle ring is selected from hydrogen, halogen, oxo, —OH, —CN, —NO$_2$, —O—C(=O)—R$^9$, —C(=O)—R$^9$, —C(=O)—OH, —C(=O)—OR$^9$, —OR$^{9'}$, —NR$^9$R$^9$, —SO$_2$R$^9$, —SR$^9$, —NR$^9$—C(=O)—R$^9$, optionally substituted lower alkyl, optionally substituted cycloalkyl, optionally substituted aryl, or optionally substituted heteroaryl;
provided that two hydroxyl groups on ring A bind respectively to carbon atoms each adjacently locates; and
n is an integer from 0 to 2.

Preferred embodiments of a group of the formula:

[Chemical Formula 82]

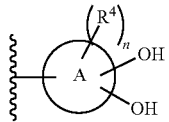

wherein:

A is a benzene ring, monocyclic heterocycle or fused heterocycle, respectively as defined throughout the specification;

each $R^4$ is independently hydrogen, halogen, oxo, —OH, —CN, —NO2, —O—C(=O)—$R^9$, —C(=O)—$R^9$, —C(=O)—OH, —C(=O)—$OR^9$, —$OR^9$, —$NR^9R^9$, —$SO_2R^9$, —$SR^9$, —$NR^9$—C(=O)—$R^9$, lower alkyl, halo (lower)alkyl, cycloalkyl, aryl, or heteroaryl; each $R^9$ is independently lower alkyl or halo(lower)alkyl; n is an integer from 0 to 2; provided that two hydroxyl groups on the ring A bind respectively to carbon atoms each adjacently locates.

Preferred examples of ring A include benzene, a 5- to 7-membered monocyclic heterocycle and a 8- to 12-membered fused heterocycle and as defined throughout the instant specification.

Preferred examples of 5- to 7-membered monocyclic heterocycle of ring A include the ring having 1 to 3 nitrogen atom(s), more preferably one nitrogen atom.

Preferred examples of 8- to 12-membered fused heterocycle of ring A include the ring having 1 to 4 nitrogen atom(s), more preferably one or two nitrogen atom(s).

More preferred examples of ring A include benzene, a 5- to 6-membered monocyclic heterocycle having one nitrogen atom and a 9- to 10-membered fused heterocycle having one or two nitrogen atom(s).

Preferred examples of a group of the formula:

[Chemical Formula 83]

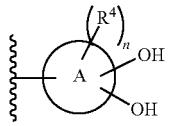

include the formulae as shown below:

[Chemical Formula 84]

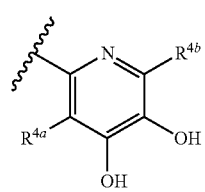 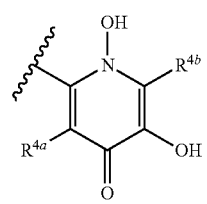

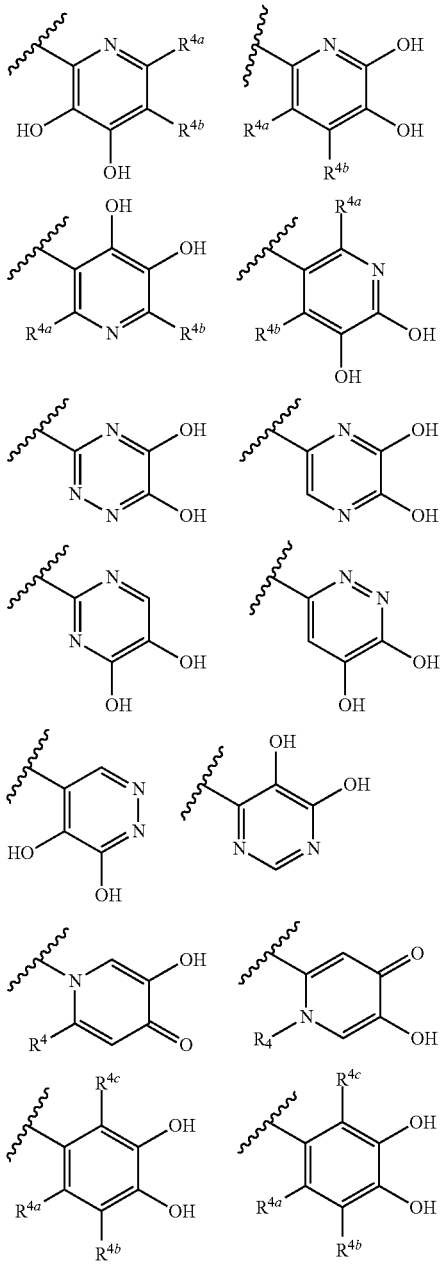

[Chemical Formula 85]

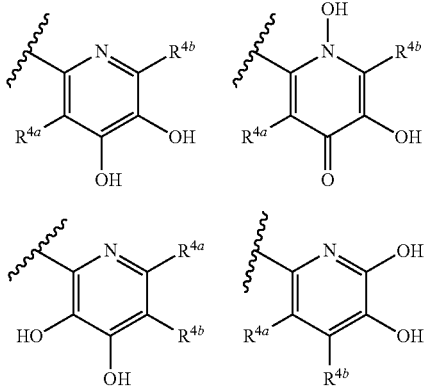

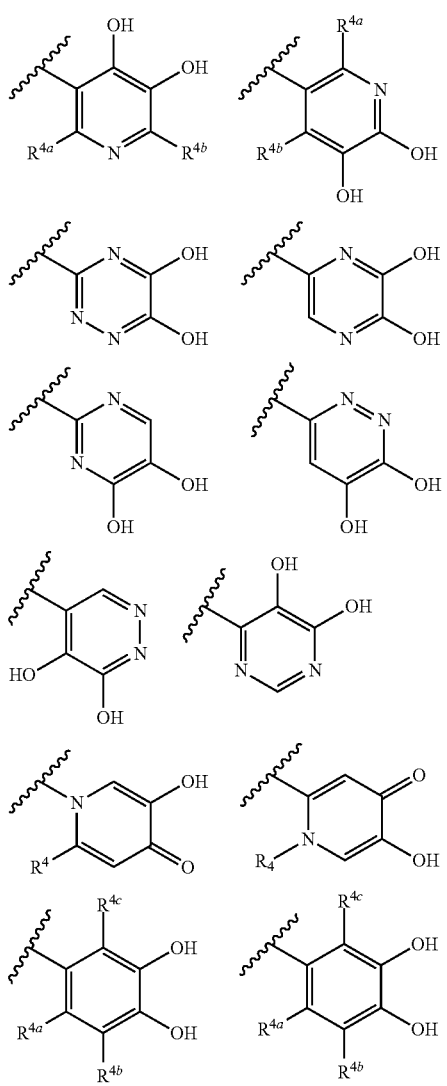
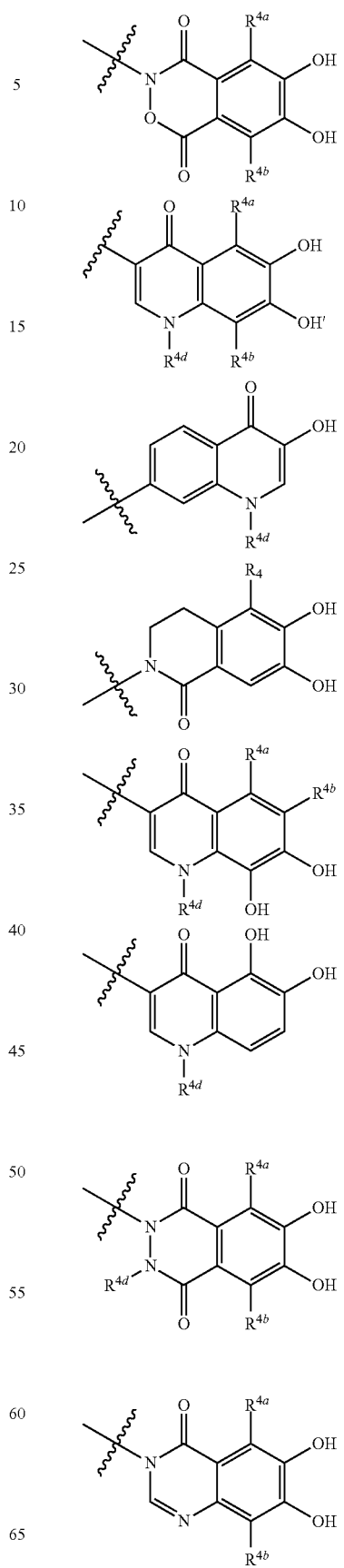
[Chemical Formula 86]
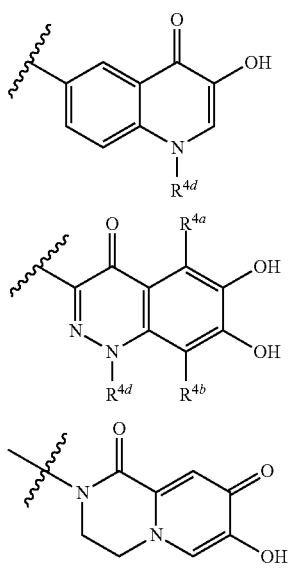

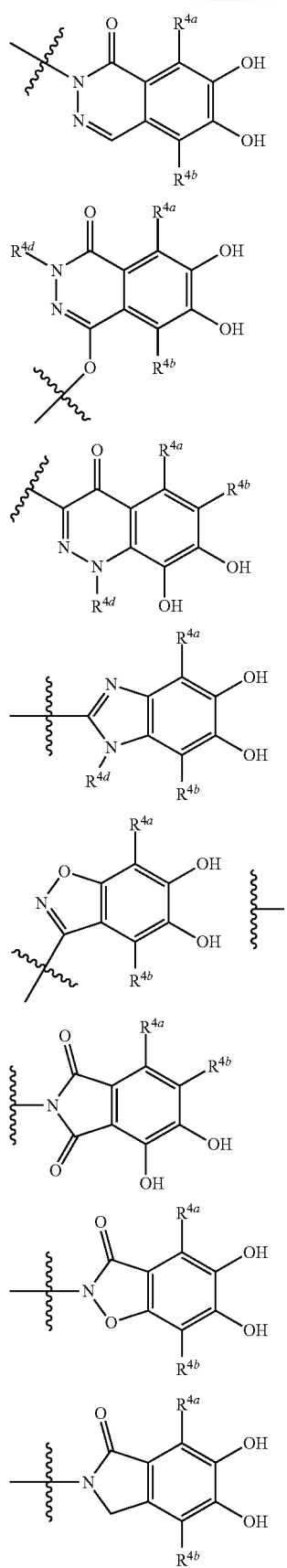

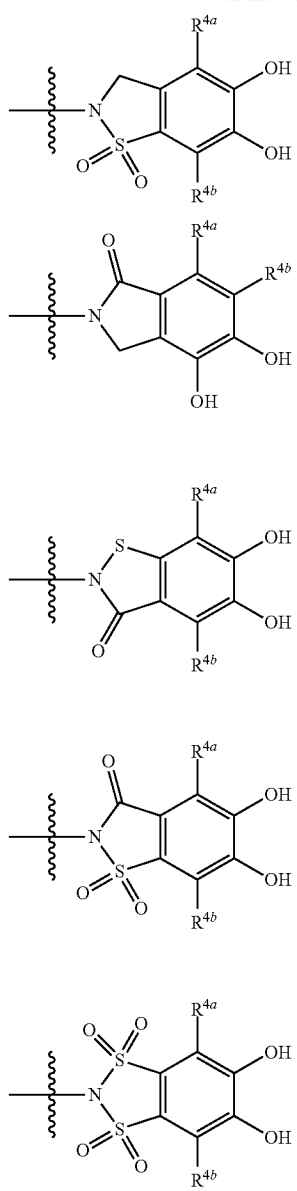

wherein, each $R^{4a}$, $R^{4b}$, $R^{4c}$ and $R^{4d}$ is independently hydrogen, halogen, —OH, —CN, —C(=O)—$R^9$, —C(=O)—OH, —C(=O)—$OR^9$, —$OR^9$, optionally substituted lower alkyl, or optionally substituted cycloalkyl;

$R^9$ is independently lower alkyl or halo(lower)alkyl;

$R^6$ is hydrogen, or optionally substituted lower alkyl.

More preferred examples of a group of the formula:

[Chemical Formula 87]

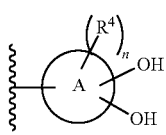

include the formulae as shown below:
[Chemical Formula 88]
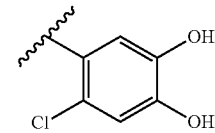 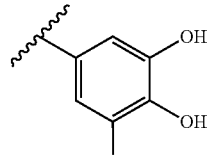
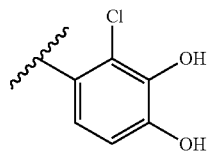 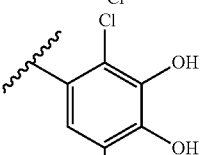
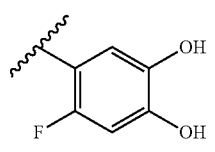 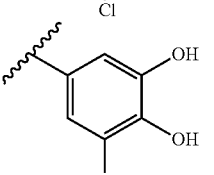
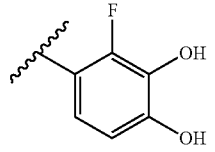 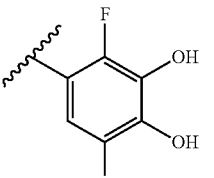
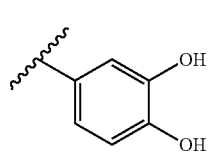 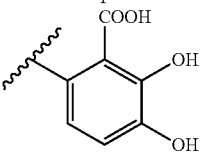
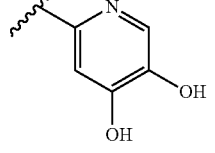 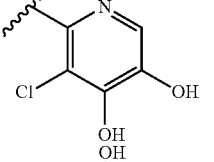
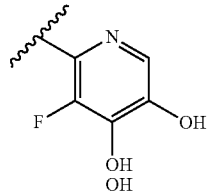 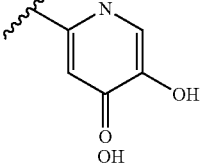
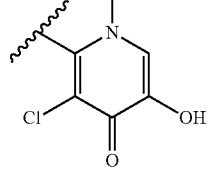 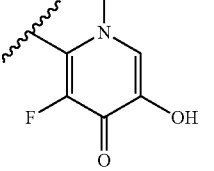
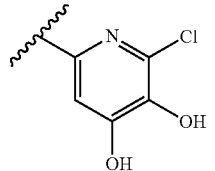 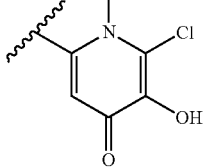
-continued
[Chemical Formula 89]
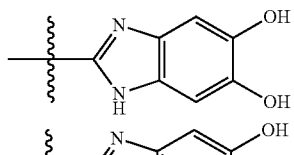
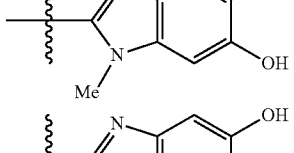
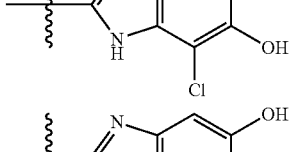
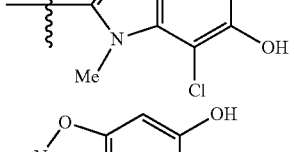
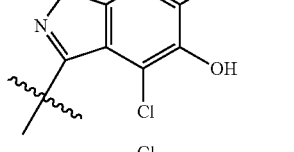
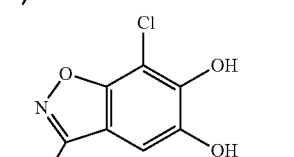
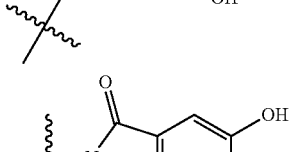
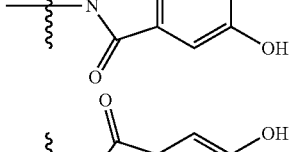
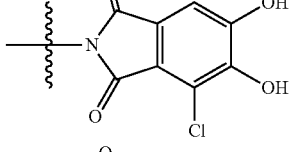
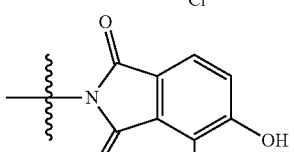
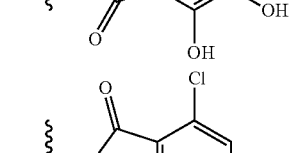
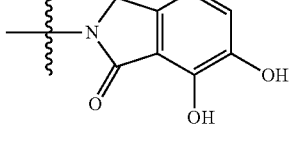

101
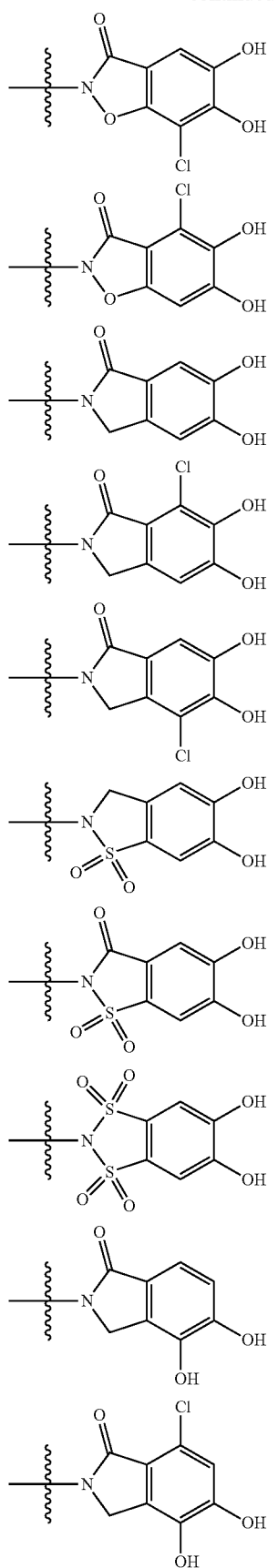
102
-continued
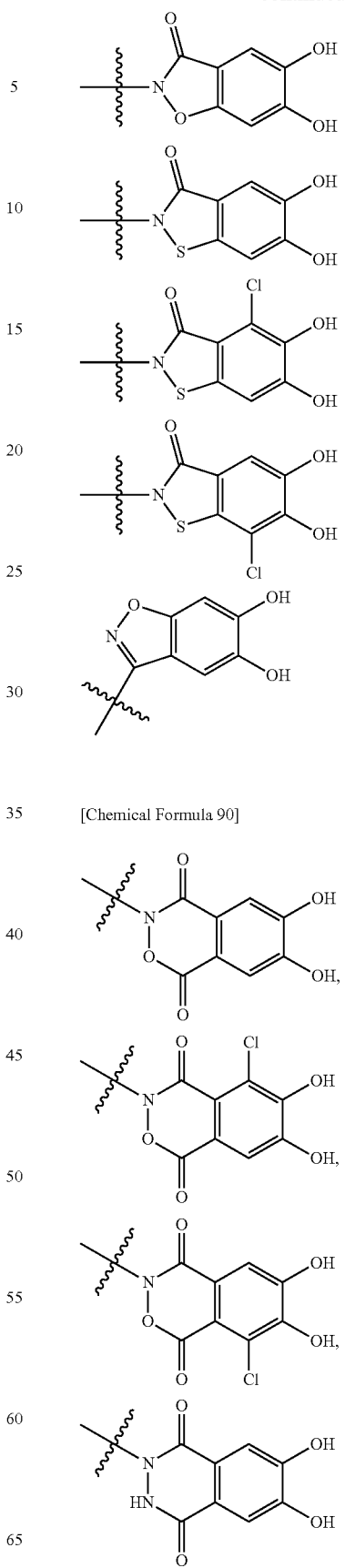
[Chemical Formula 90]

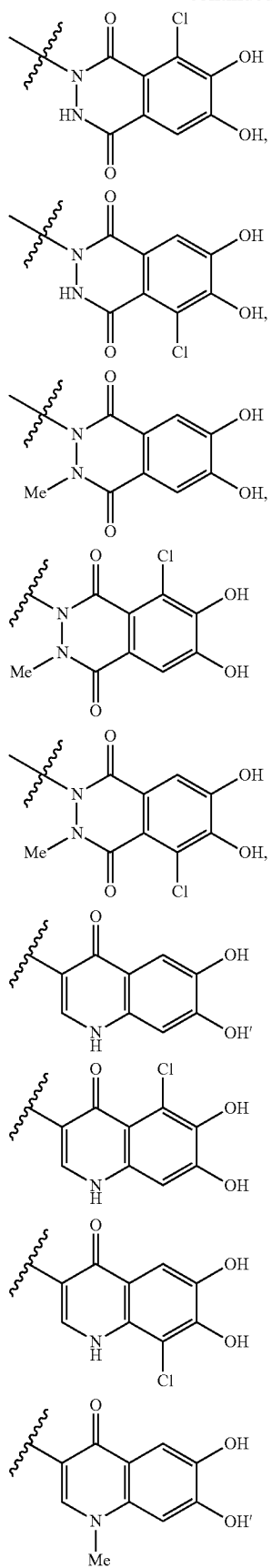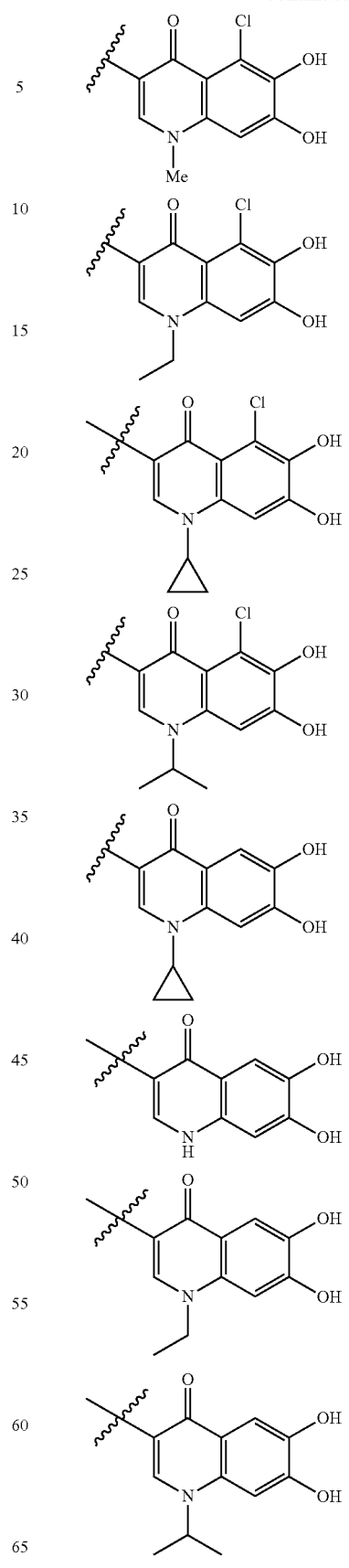

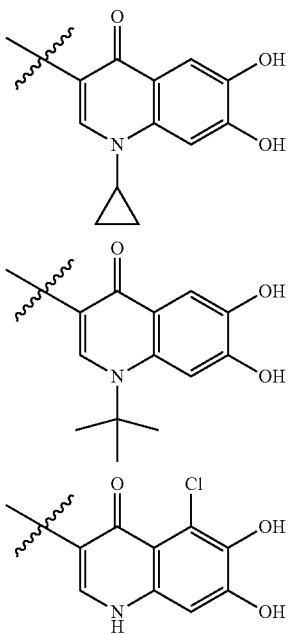
[Chemical Formula 91]
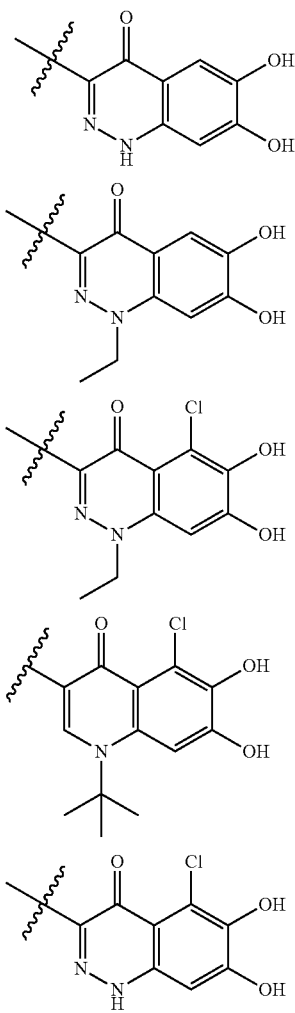
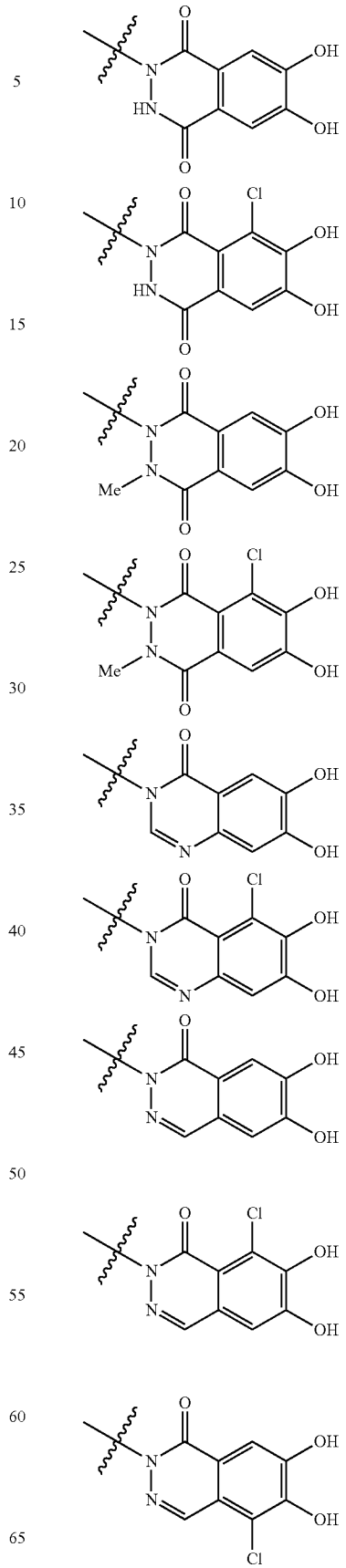

-continued
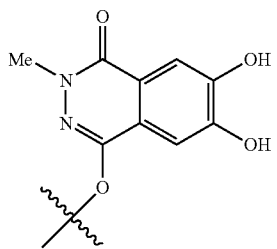
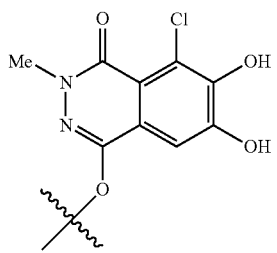
Wherein, Me represents a methyl group.
Preferred examples of a group of the formula (1-C-1):
[Chemical Formula 92]
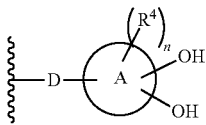
(I-C-1)
include the formulae as shown below:
[Chemical Formula 93]
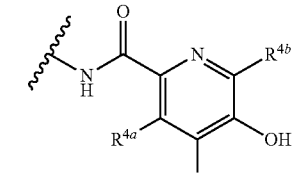
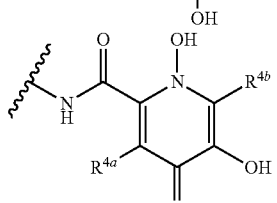
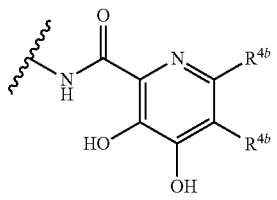
-continued
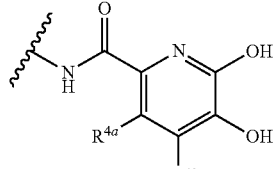
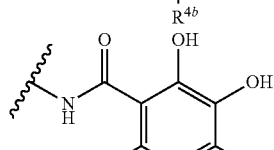
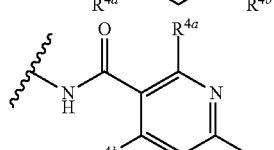
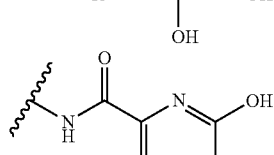
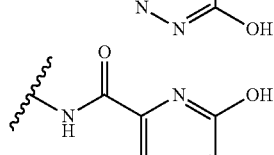
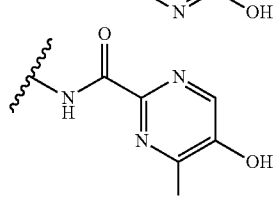
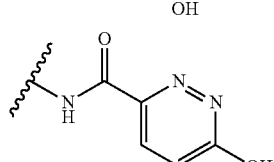
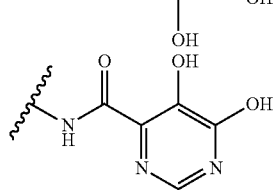 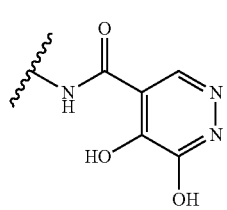
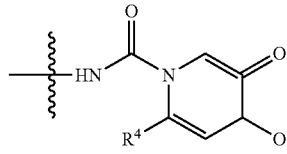 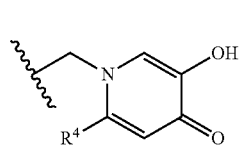
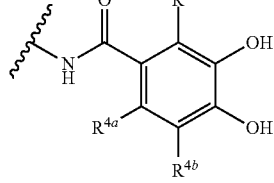 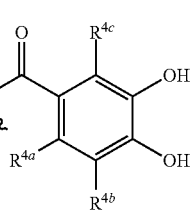

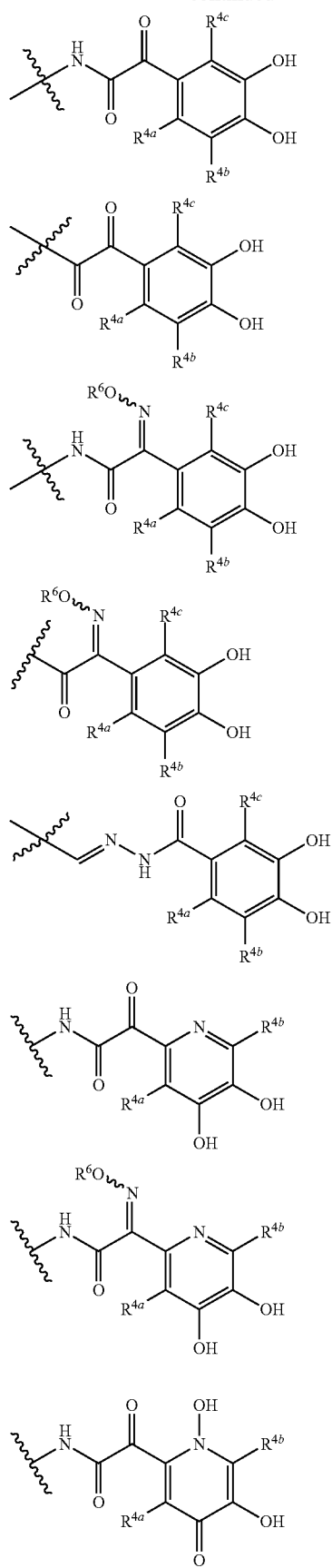
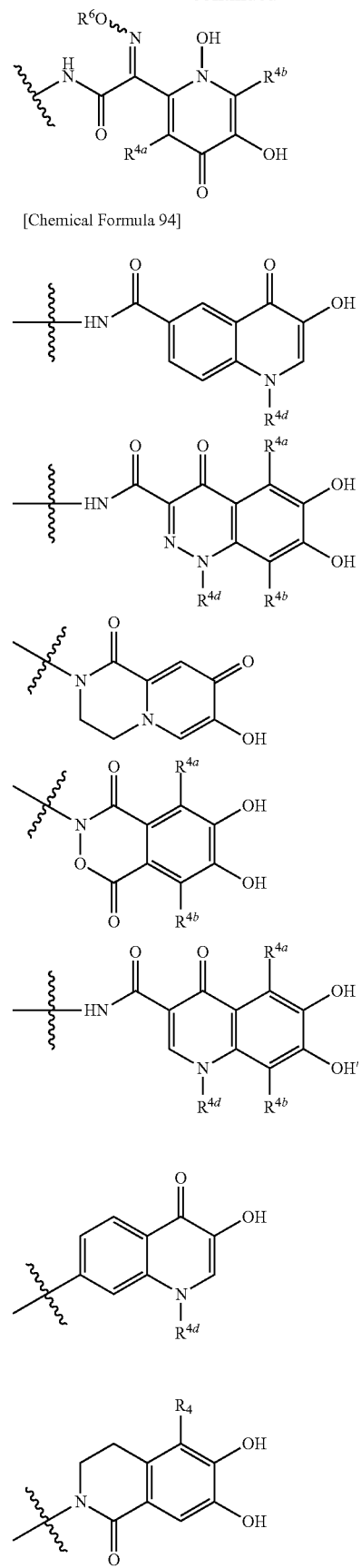
[Chemical Formula 94]

111
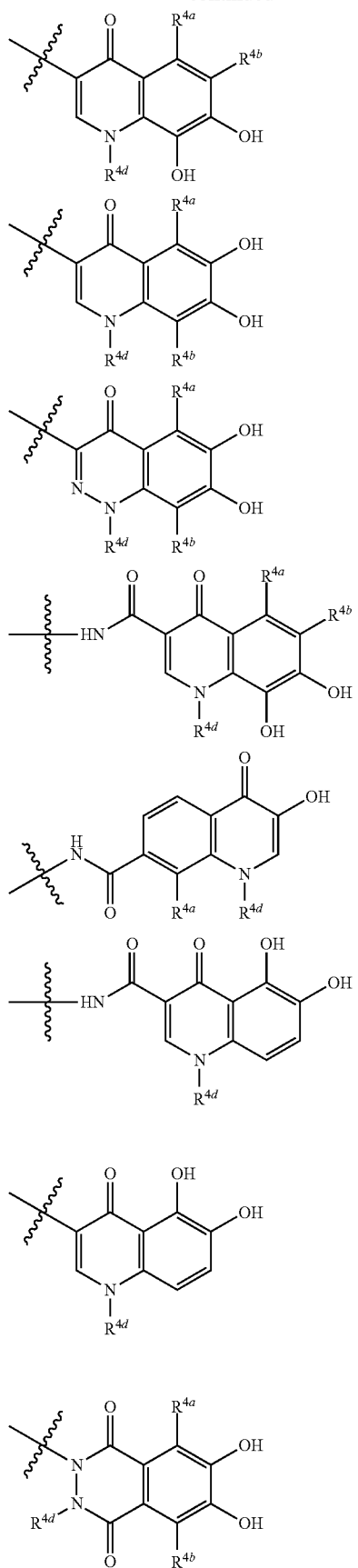
112
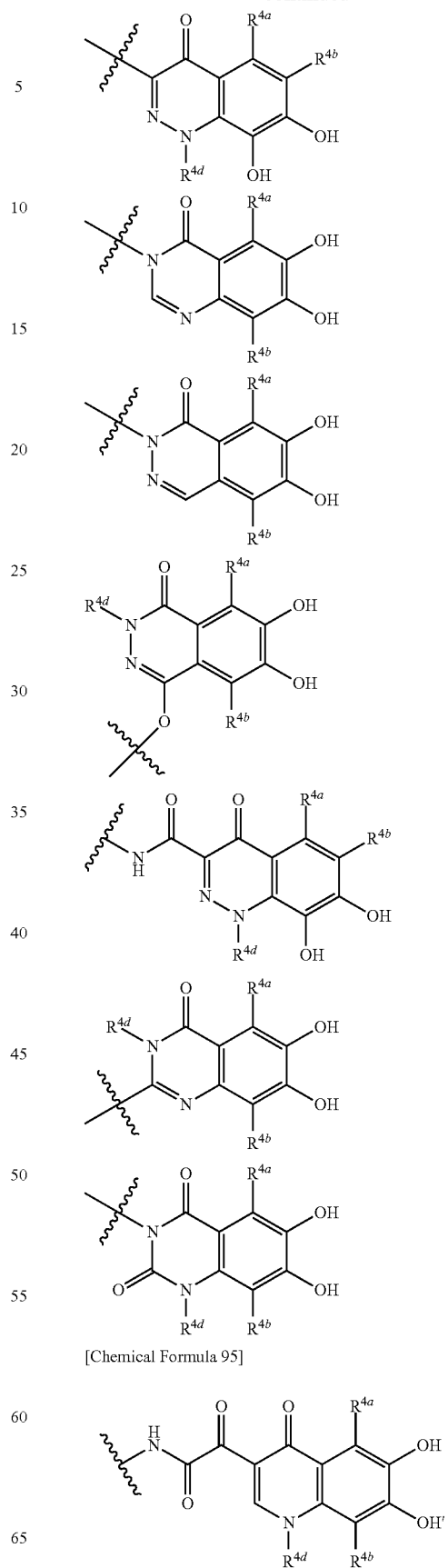
[Chemical Formula 95]

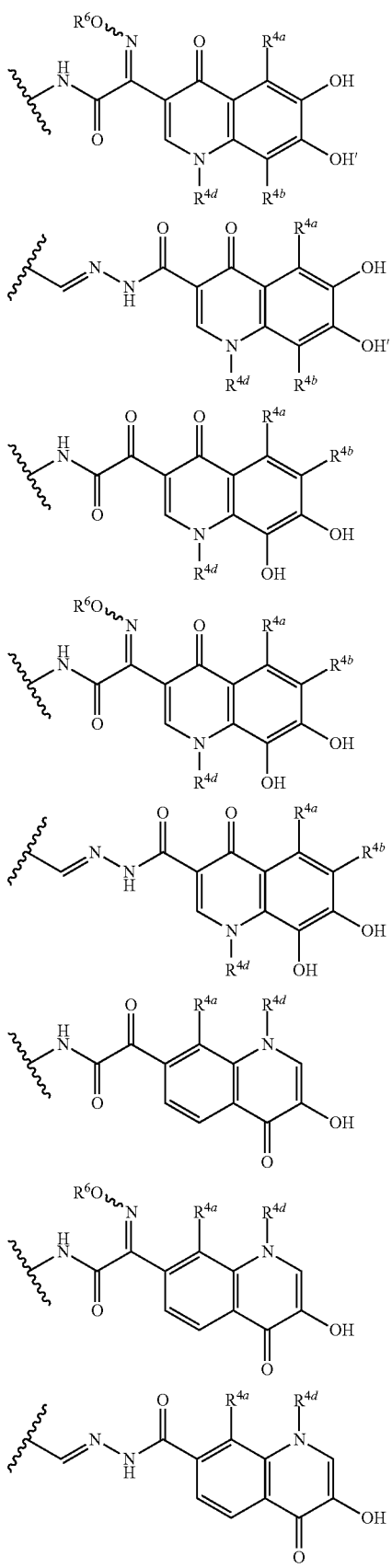
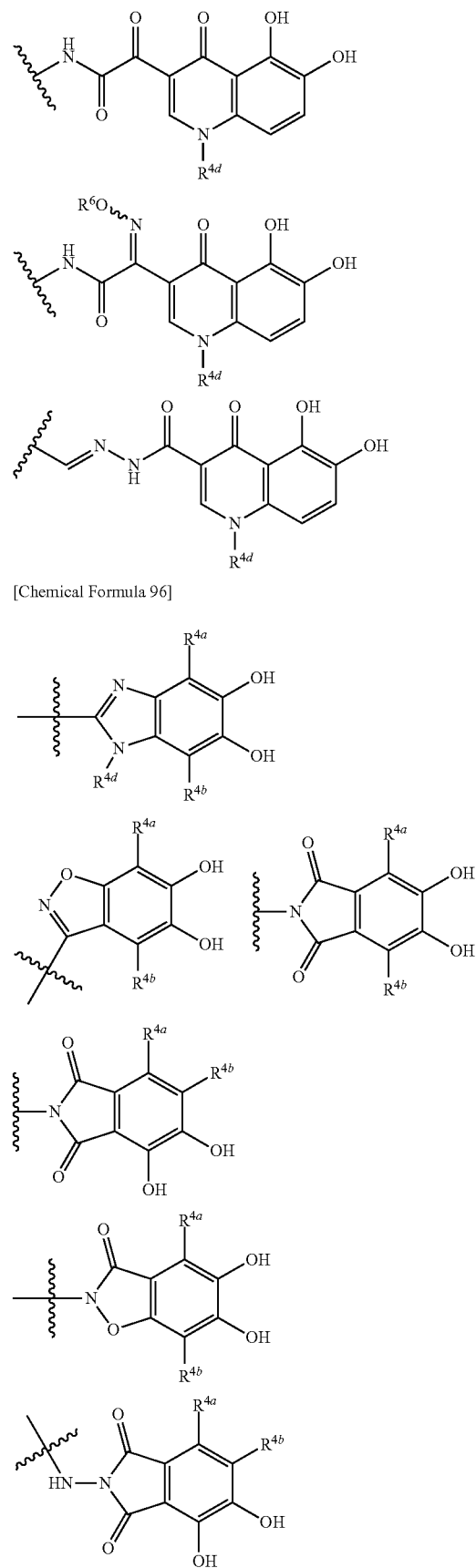
[Chemical Formula 96]

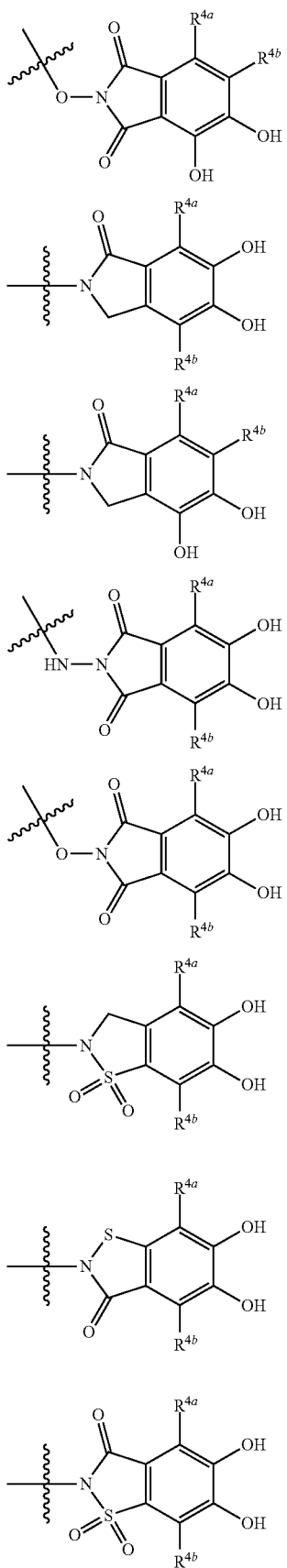

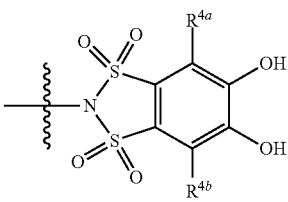

wherein, each $R^{4a}$, $R^{4b}$ $R^{4c}$ and $R^{4d}$ is independently hydrogen, halogen, —OH, —CN, —C(=O)—$R^9$, —C(=O)—OH, —C(=O)—$OR^9$, —$OR^9$, optionally substituted lower alkyl, or optionally substituted cycloalkyl;

$R^9$ is independently lower alkyl or halo(lower)alkyl;

$R^6$ is hydrogen, or optionally substituted lower alkyl;

the wavy line means that the bond is in cis or trans configuration, or a mixture thereof.

Examples of $R^{4a}$, $R^{4b}$ $R^{4c}$ and $R^{4d}$ include hydrogen, chloro, fluoro, bromo, cyano, hydroxy, carboxy, acetyl, methoxy, ethoxy, trifluoromethyl, and the like. Preferably, each $R^{4a}$, $R^{4b}$ $R^{4c}$ and $R^{4d}$ is independently hydrogen, hydroxy, carboxy, methoxy, fluoro, trifluoromethyl, or chloro.

More preferred examples of a group of the formula (1-C-1):

[Chemical Formula 97]

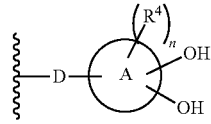

(I-C-1)

include the formulae as shown below:

[Chemical Formula 98]

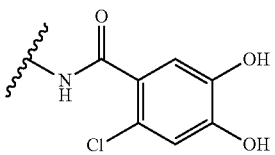

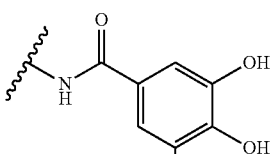

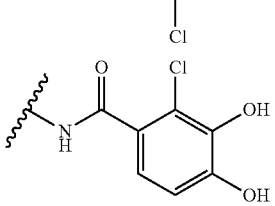

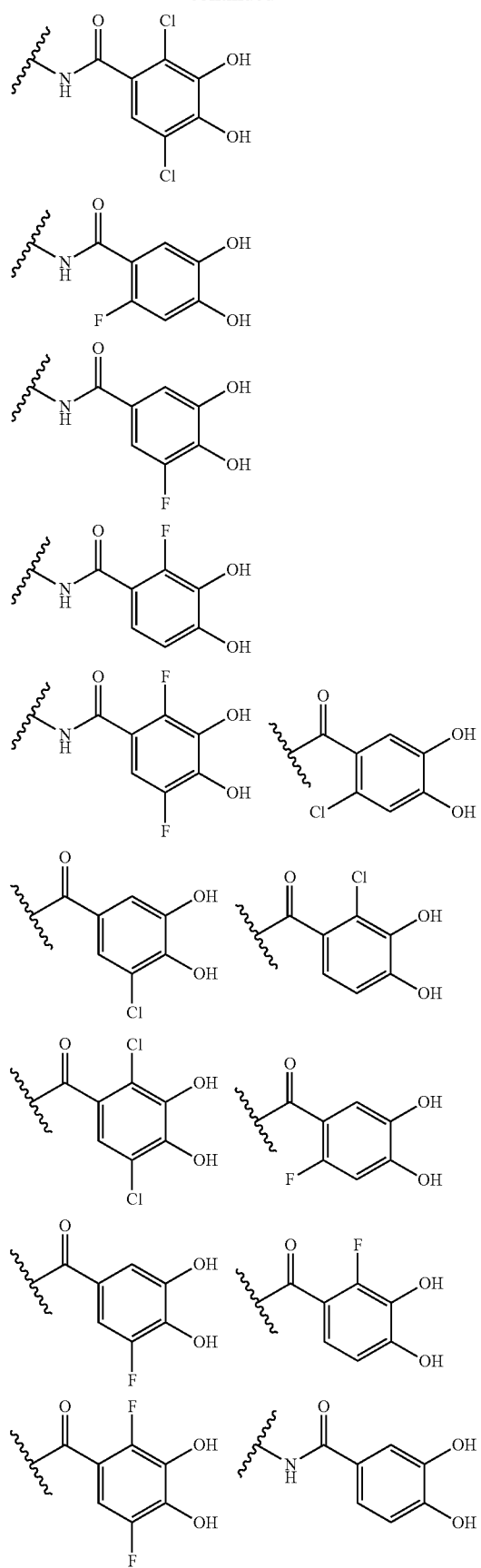
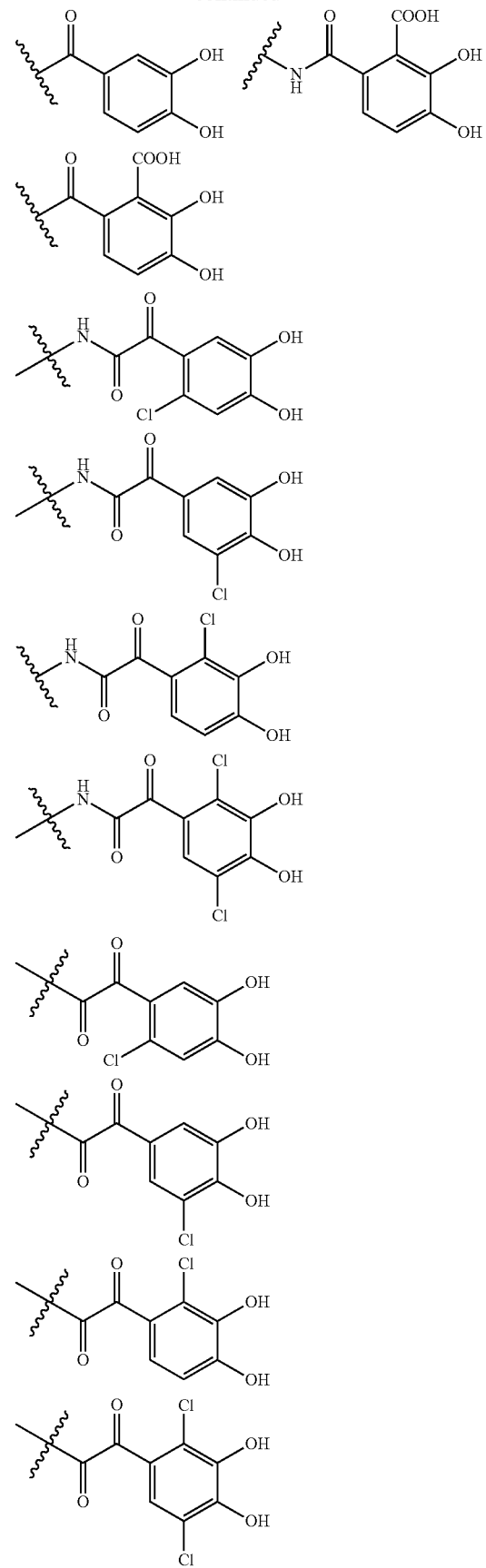

119
-continued
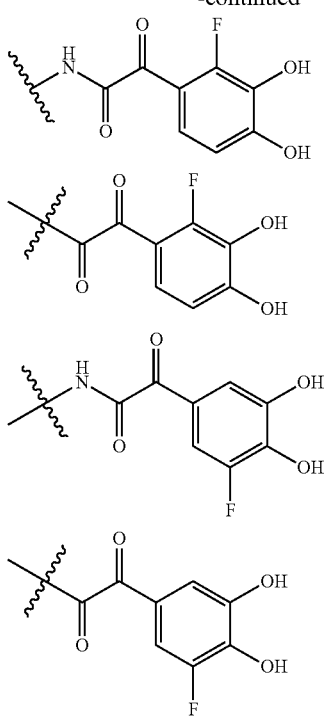
[Chemical Formula 99]
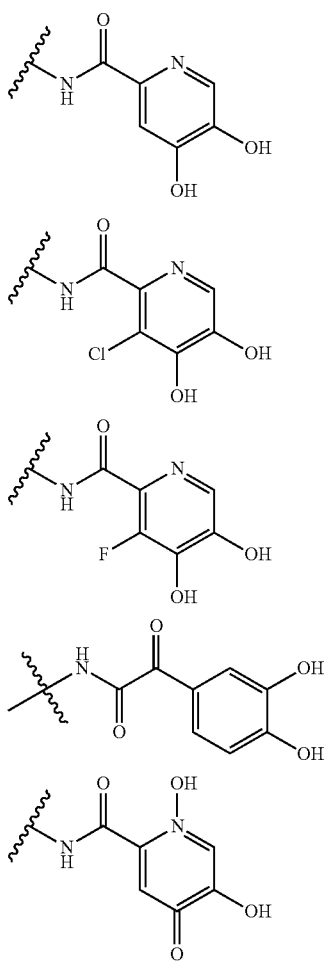
120
-continued
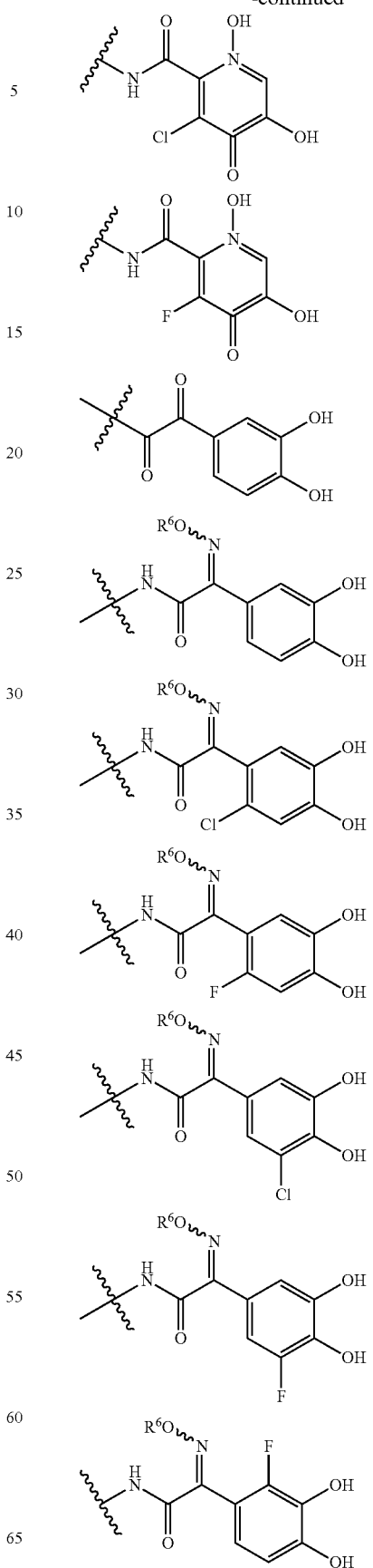

-continued
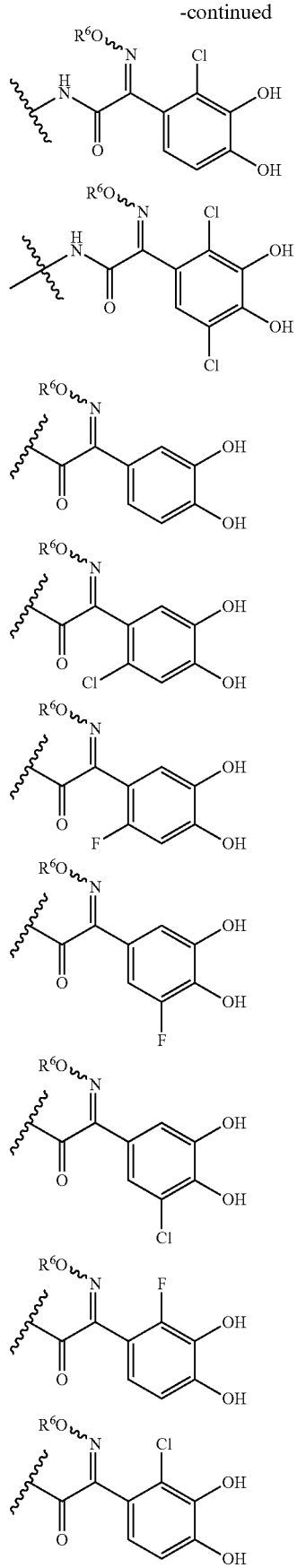
-continued
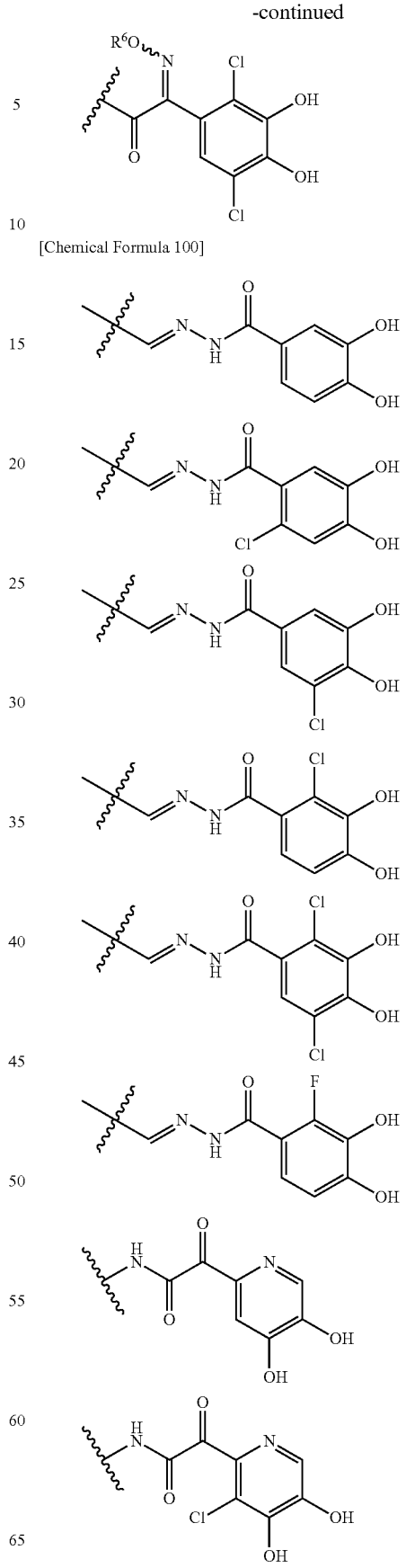
[Chemical Formula 100]

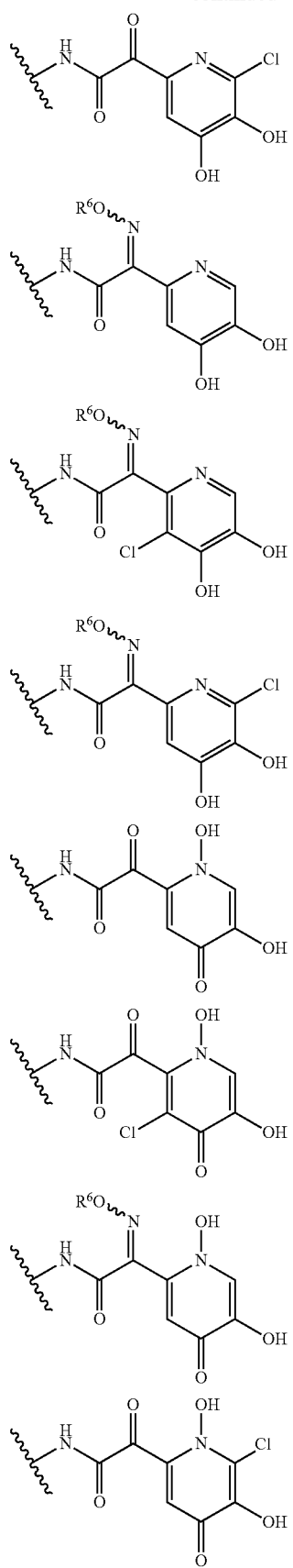
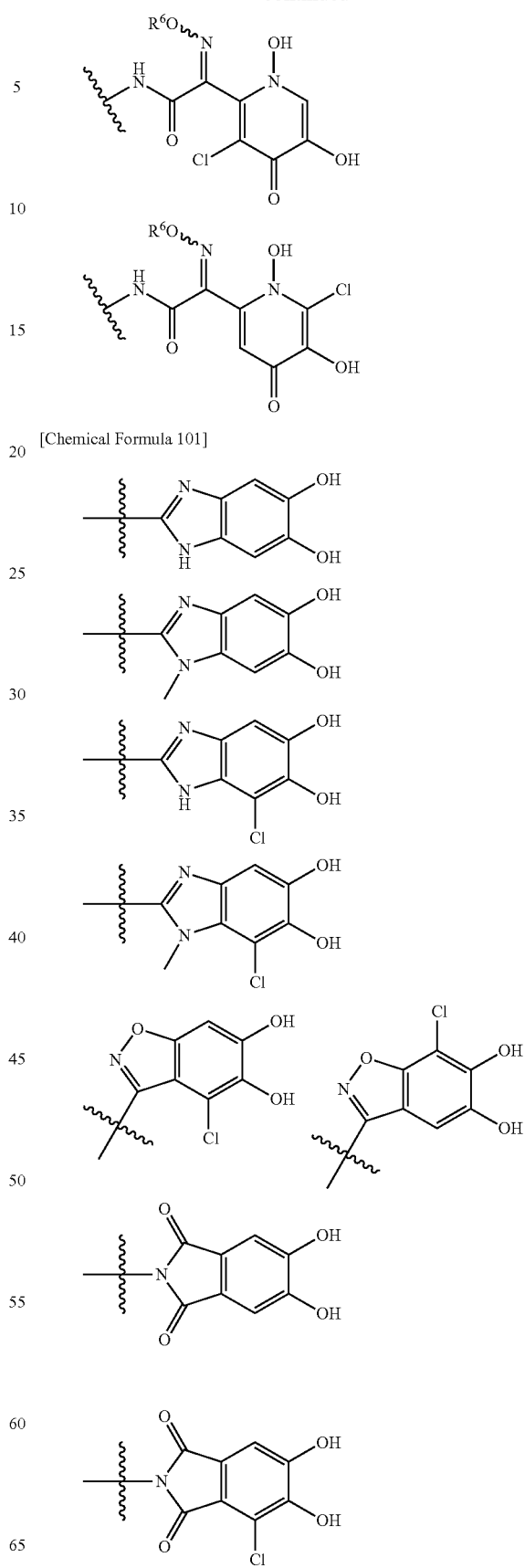

125
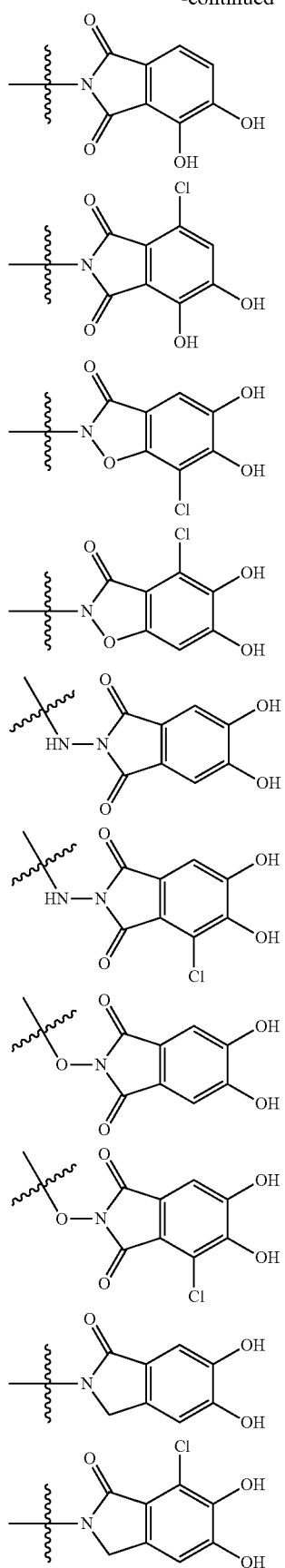
126
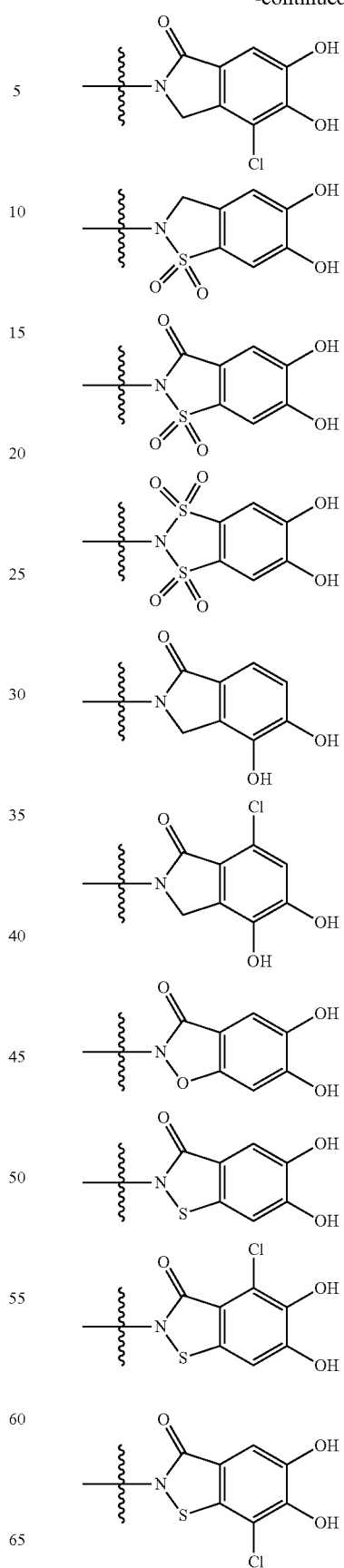

127
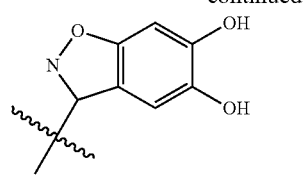
[Chemical Formula 102]
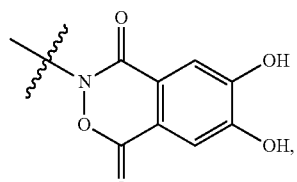
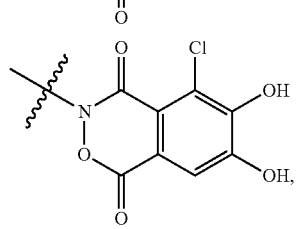
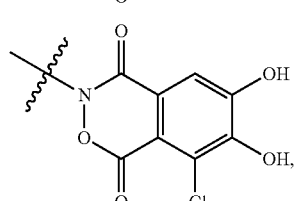
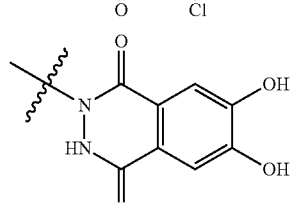
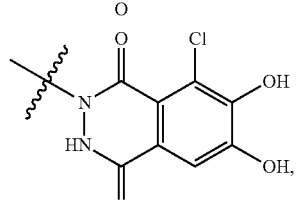
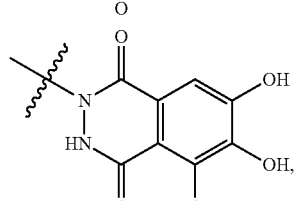
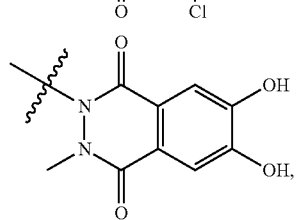
128
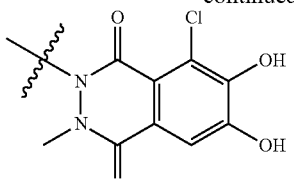
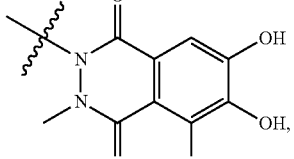
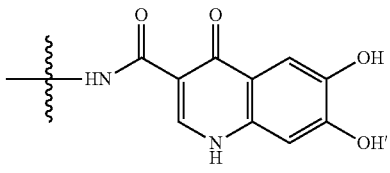
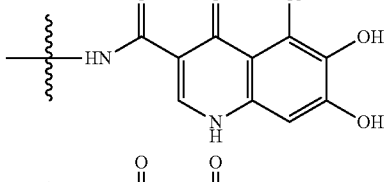
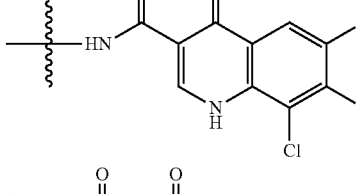
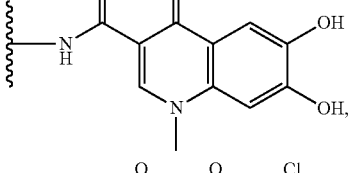
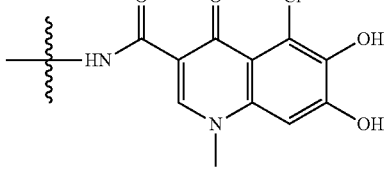
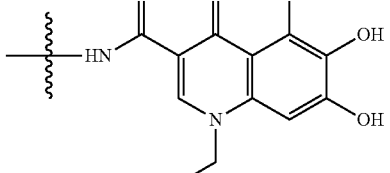
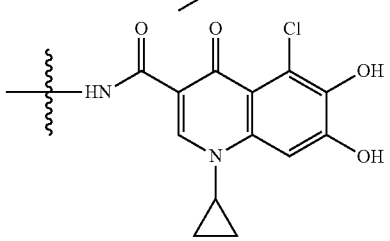

129
-continued
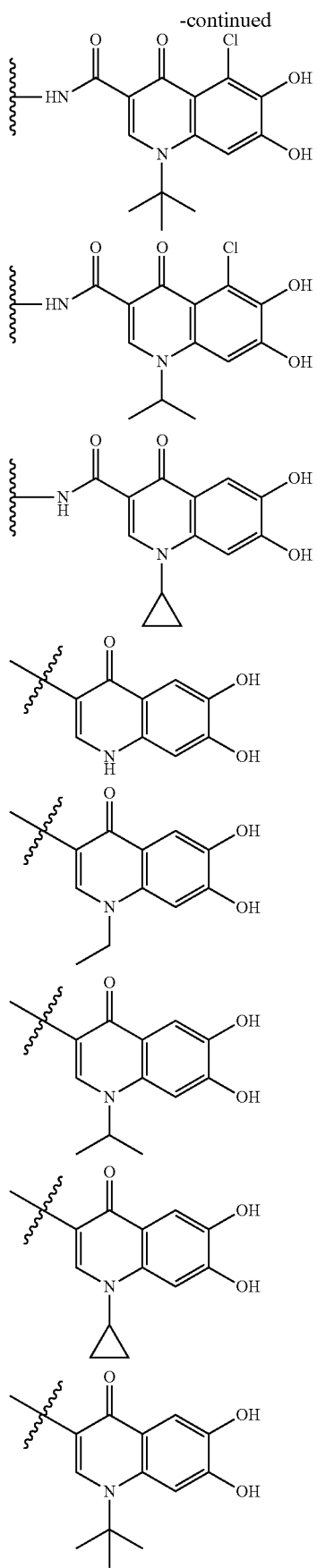
130
-continued
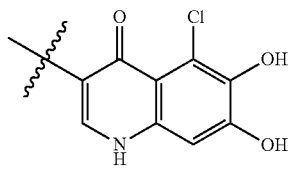
[Chemical Formula 103]
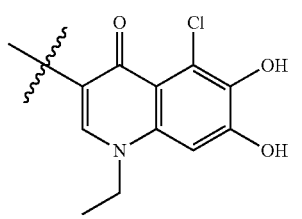
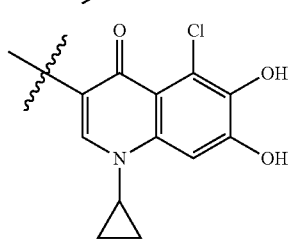
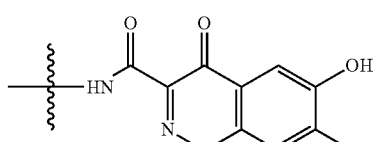
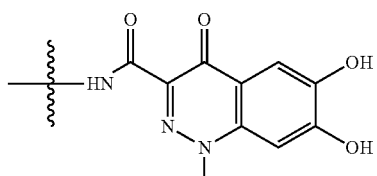
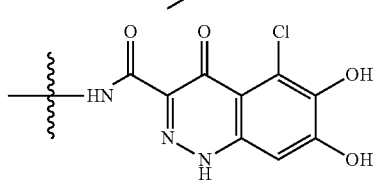
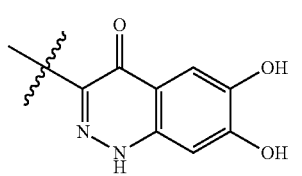
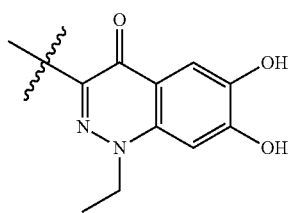

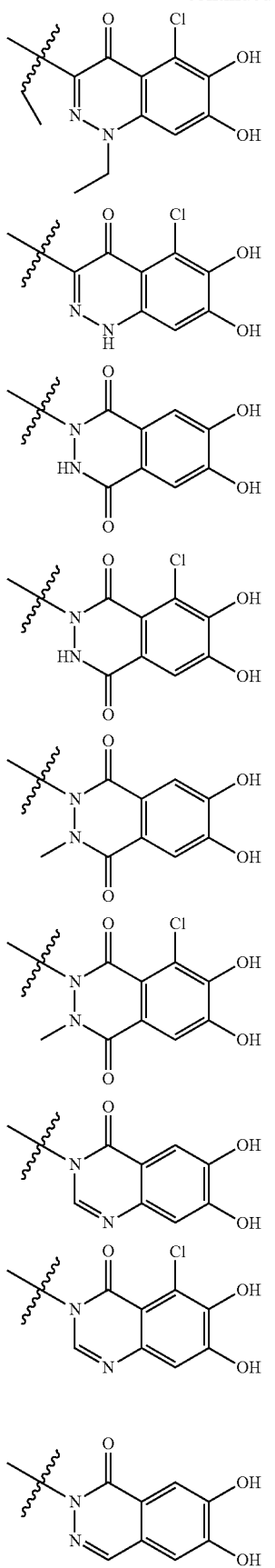
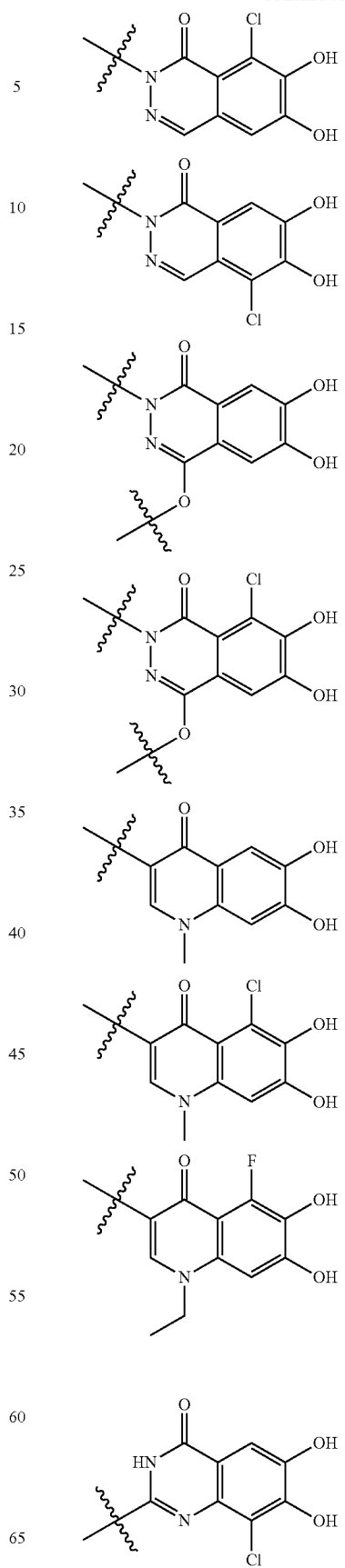

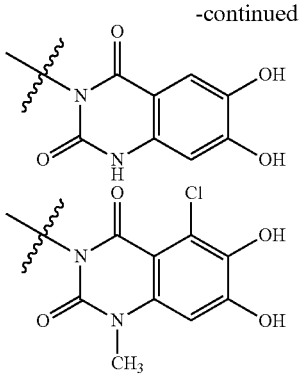

wherein, $R^6$ is hydrogen, methyl, ethyl, tert-butyl, carboxymethyl, 2-carboxypropan-2-yl or 1-carboxyethyl, the wavy line means that the bond is in cis or trans configuration, or a mixture thereof.

The nomenclature of the substitution position on the cephem skeleton of Formula (I) is as follows. As used herein, 3-side chain, 4-side chain and 7-side chain respectively refer to groups binding to the 3-position, 4-position and the 7-position of the cephem skeleton

[Chemical Formula 104]

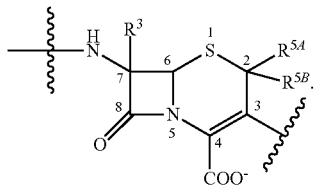

Esters of Formula (I) preferably include those at the 7-side chain. Esters at the carboxyl group on the 7-side chain include compounds, wherein any carboxyl group of optionally substituted amino, optionally substituted aminosulfonyl, carboxyl, optionally substituted (lower)alkyloxycarbonyl, optionally substituted carbamoyl, substituted carbonyloxy, or the like at the terminal of $R^1$, $R^{2A}$ or $R^{2B}$ shown in the formula:

[Chemical Formula 105]

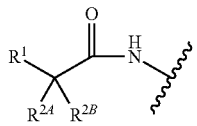

wherein each symbol is as defined above, is esterified. For example, in the case of carboxyl (—COOH), such esters are represented by the structural formula —COOR$^a$, wherein R$^a$ is an ester residue such as a carboxyl-protecting group or the like. Such esters include those easily metabolized in the body to form a carboxylic state.

The aforementioned protecting groups for carboxyl or the like may be any group as long as it can be protected and/or deprotected by a method described in Protective Groups in Organic Synthesis, written by T. W. Greene, John Wiley & Sons Inc. (1991), or the like. Examples thereof include lower alkyl (e.g., methyl, ethyl, t-butyl), (lower)alkylcarbonyloxymethyl (e.g., pivaloyl), optionally substituted aralkyl (e.g., benzyl, benzhydryl, phenethyl, p-methoxybenzyl, p-nitrobenzyl), silyl groups (t-butyldimethylsilyl, diphenyl (t-butyl)silyl), and the like.

Amino-protected compounds at the amino on the 7-side chain of Formula (I) refer to the structures in which the amino on the ring (e.g., thiazole, thiadiazole) has been protected.

The amino protected group is represented by the formula —NHR$^e$ wherein R$^e$ represents an amino-protecting group. Such amino-protecting groups include those groups that are readily metabolized in the body to form amino. The aforementioned amino-protecting groups may be any group as long as it can be protected and/or deprotected by a method described in Protective Groups in Organic Synthesis, written by T. W. Greene, John Wiley & Sons Inc. (1991), or the like. Examples thereof include (lower)alkoxycarbonyl (e.g., t-butoxycarbonyl, benzyloxycarbonyl, p-nitrobenzyloxycarbonyl), optionally substituted aralkanoyl (e.g., benzoyl, p-nitrobenzoyl), acyl (e.g., formyl, chloroacetyl), and the like.

The Compound (I) of the subject invention is not limited to particular isomers, but includes any possible isomers (e.g., keto-enol isomer, imine-enamine isomer, diastereoisomer, geometrical isomer, optical isomer, rotamer, etc.), racemates and a mixture thereof.

For example, the Formula (I):

[Chemical Formula 106]

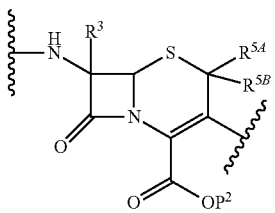

includes

[Chemical Formula 107]

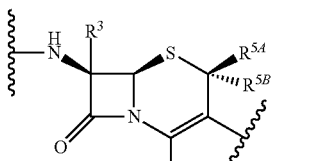

and

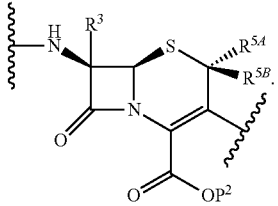

For example the formula:

[Chemical Formula 108]

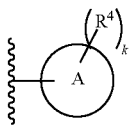

wherein each symbol is as defined above, includes the following resonance structures:
[Chemical Formula 109]
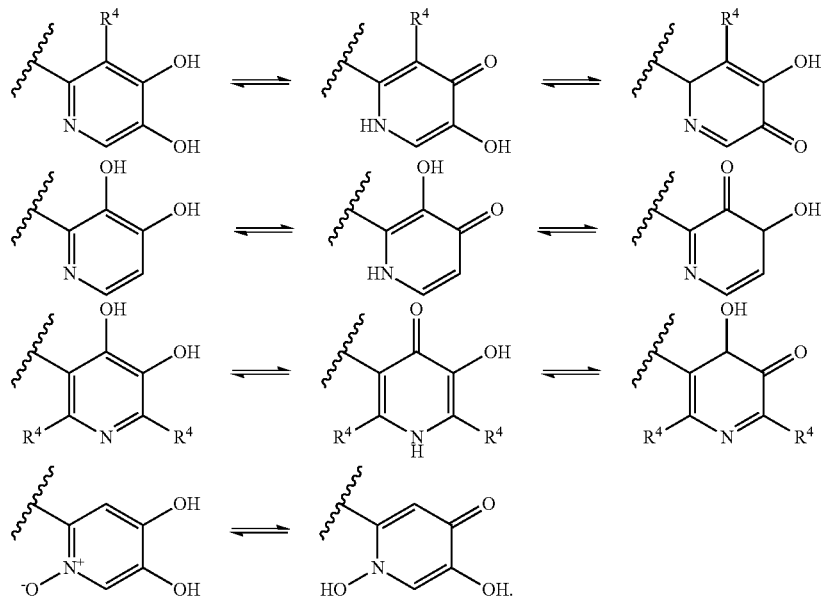
wherein $R^4$ is as defined above.
Also, the group "E" in Formula (I), for example, includes the following resonance structures:
[Chemical Formula 110]
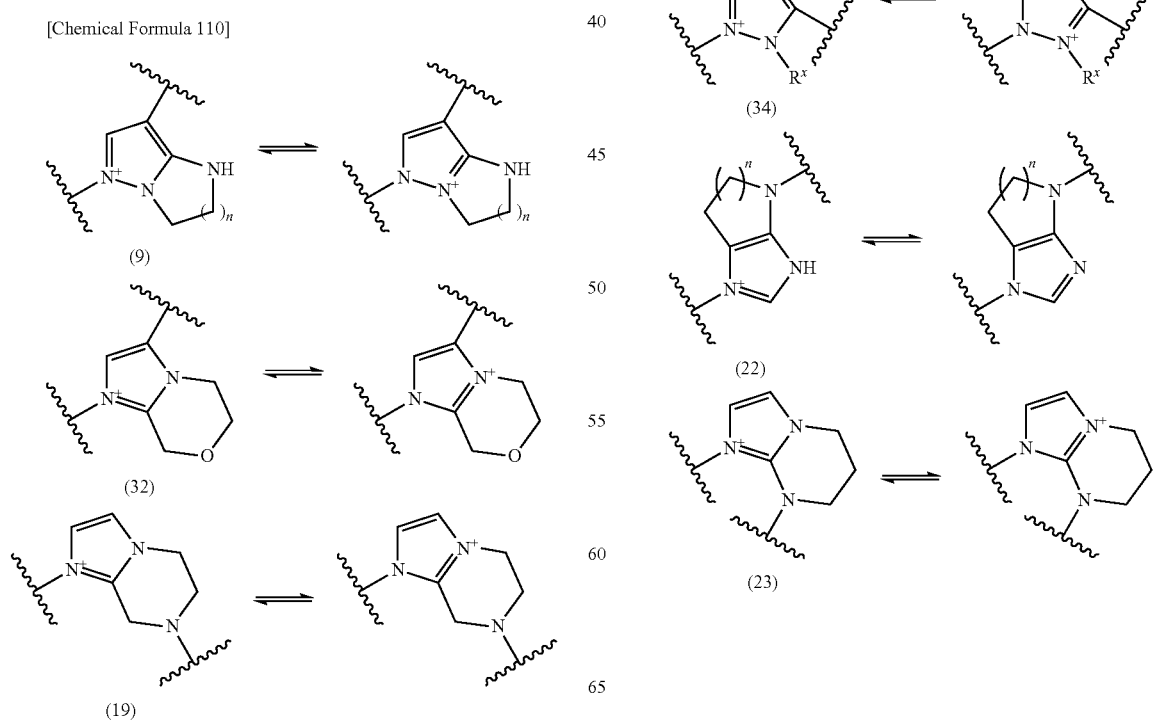
wherein each symbol is as defined above.

For example, the formula:

[Chemical Formula 111]

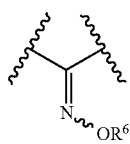

wherein, $R^6$ is as defined above;
includes

[Chemical Formula 112]

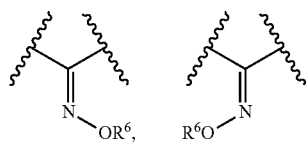

and a mixture thereof.

At least one hydrogen atom, carbon atom and/or another atom may be replaced with an isotope of said hydrogen atom, carbon atom and/or another atom. Examples of such isotope include hydrogen, carbon, nitrogen, oxygen, sulfur, fluorine, iodine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$ and $^{36}Cl$. The compound of Formula (I) include compounds having an atom replaced with such isotope. Such compound replaced with an isotope are useful as a pharmaceutical product, and such compound include all of radiolabeled compound of Formula (I). Also, the subject invention includes any method of radioactive labeling for the production of such radiolabeled compound, and thus, it is useful in a research for metabolic pharmacokinetics, binding assay and/or as a diagnostic tool.

A radiolabeled compound of Formula (I) may be prepared according to the technique well known in the art. For example, tritium can be introduced into a specific compound of Formula (I) by catalytic dehalogenation using tritium to prepare a tritium-labeled compound of Formula (I). This method comprises reaction of a precursor which is a compound of Formula (I) appropriately halogenated with tritium gas in the presence of appropriate catalyst, such as Pd/C, in the presence or absence of a base. For another method for the preparation of a tritium-labeled compound, see the literature, Isotopes in the Physical and Biomedical Sciences, Vol. 1, Labeled Compounds (Part A), Chapter 6 (1987). $^{14}C$-labeled compound can be prepared using a starting material having $^{14}C$.

Salts of a compound of Formula (I) include those formed with an inorganic or organic acid by a carboxyl group in the 7-side chain and/or an amino group in the 7-side chain; and those formed with a counter anion by a quaternary amine moiety in the 3-side chain.

Pharmaceutically acceptable salts of a compound of Formula (I) include, for example, salts formed with alkali metal (e.g. lithium, sodium, potassium, etc.), alkaline earth metal (e.g. calcium, barium, etc.), magnesium, transition metal (e.g. zinc, ferrum, etc.), ammonia, organic base (e.g. trimethylamine, triethylamine, dicyclohexylamine, ethanolamine, diethanolamine, triethanolamine, meglumine, diethanolamine, ethylenediamine, pyrydine, picoline, quinoline, etc.) and amino acid, or salts formed with inorganic acid (e.g. hydrochloric acid, sulphuric acid, nitric acid, carbonic acid, hydrobromic acid, phosphoric acid, hydroiodic acid, etc.), and organic acid (e.g. formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulphonic acid, p-toluenesulfonic acid, methanesulphonic acid, ethanesulphonic acid, etc, particularly, salts formed with hydrochloric acid, sulphuric acid, phosphoric acid, tartaric acid, methanesulphonic acid. These salts can be formed according to the conventional method.

The compound of Formula (I) or pharmaceutically acceptable salts thereof may form a solvate (e.g., hydrate) and/or a crystalline polymorphism, and the subject invention also includes such solvates and crystalline polymorphisms. In such "solvate", any number of solvent molecules (e.g., water molecule, etc.) may be coordinated to the compound of Formula (I). By leaving the compound of Formula (I) or pharmaceutically acceptable salt thereof in the atmosphere, it may absorb moisture to adhere with absorbed water or form a hydrate thereof. Also, a crystalline polymorphism of the compound of Formula (I) or pharmaceutically acceptable salt thereof can be formed by recrystallization.

The compound of Formula (I) or pharmaceutically acceptable salt thereof may form a prodrug, and the subject invention includes such prodrugs. Prodrug is a derivative of the compound of the invention having a group chemically- or metabolically-degradable to be transformed into a pharmacologically active compound by solvolysis or under physiological condition in vivo. Prodrug includes compounds which can be transformed into the compound of Formula (I) by enzymatically oxidization, reduction or hydrolysis under physiological condition in vivo, or transformed into the compound of Formula (I) by hydrolysis with gastric acid, etc. Methods for selection and production of appropriate prodrug derivative can be found, for example, in Design of Prodrugs, Elsevier, Amsterdam 1985.

Prodrug may be active compound in itself.

When the compound of Formula (I) or pharmaceutically acceptable salt thereof has hydroxyl, acyloxy derivatives or sulfonyloxy derivatives can be prepared as a prodrug. For example, such compound having hydroxyl may be reacted with an appropriate acyl halide, acid anhydrate or an appropriate sulfonyl chloride, sulfonyl anhydrate, mixed anhydrate, etc., or may be reacted using a coupling agent, such as for examples, those having $CH_3COO-$, $C_2H_5COO-$, t-Bu-COO—, $C_{15}H_{31}COO-$, PhCOO—, (m-NaOOCPh)COO—, $NaOOCCH_2CH_2COO-$, $CH_3CH(NH_2)COO-$, $CH_2N(CH_3)_2COO-$, $CH_3SO_3-$, $CH_3CH_2SO_3-$, $CF_3SO_3-$, $CH_2FSO_3-$, $CF_3CH_2SO_3-$, p-$CH_3$—O-PhSO$_3$—, PhSO$_3$—, p-$CH_3$PhSO$_3$—.

For the synthesis of a compound of Formula (I), A compound of the formula (I-H):

[Chemical formula 34]

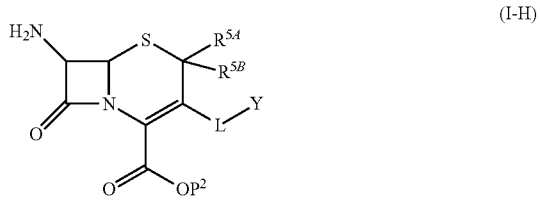

(I-H)

wherein,

Y is a leaving group; $P^2$ is a protecting group;

$R^{5A}$, $R^{5B}$ and L are as defined above, or a pharmaceutically acceptable salt thereof is preferred as an intermediate.

The compound of the formula (I-H), or a salt thereof, wherein $P^2$ is benzhydryl group, p-methoxybenzyl group, trityl group, 2,6-dimethoxybenzyl group, methoxymethyl group, benzyloxymethyl group or 2-(trimethylsilyl)ethoxymethyl group is preferred as an intermediate.

The compound of the formula (I-H), or a salt thereof, wherein $R5^A$ is methyl and $R5^B$ is hydrogen is preferred as an intermediate.

For the synthesis of a compound of Formula (I), a compound of the formula (I-I):

[Chemical formula 35]

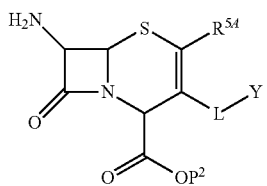

(I-I)

or a salt thereof,
wherein,
Y is a leaving group; $P^2$ is a protecting group;
$R^{5A}$ and L are as defined above,
or a pharmaceutically acceptable salt thereof is preferred as an intermediate.

For the synthesis of a compound of Formula (I), a compound of the formula:

[Chemical Formula 113]

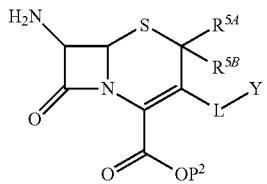

wherein, Y is a leaving group; P2 is a protecting group; R5A, R5B and L are as defined above,
or a pharmaceutically acceptable salt thereof is preferred as an intermediate. The 7-amino can be formed with a counter anion ($Z^-$) to be a salt ($—NH_3^+Z^-$)

The leaving group includes halogen (Cl, Br, I, F), acetoxy, methanesulfonyloxy, p-toluenesulfonyloxy, trifluoromethanesulfonyloxy, etc.

Preferred example of a compound of the formula:

[Chemical Formula 114]

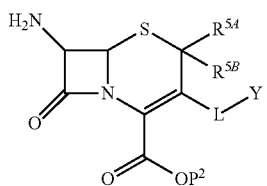

wherein, Y is a leaving group; P2 is a protecting group; R5A, R5B and L are as defined above,
is a compound of the formula:

[Chemical Formula 115]

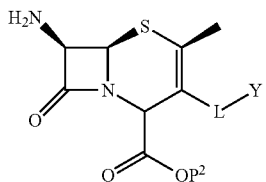

wherein, Y is a leaving group; P2 is a protecting group; L is as defined above.

As described in the following General Synthesis and Examples, an intermediate compound described above is reacted with side chain moieties at the 3-, 4- and 7-positions of the cephem skeleton to obtain a compound of Formula (I). Examples of the protecting group "$P^2$" include those described in the following General Synthesis, and preferably, benzhydryl, p-methoxybenzyl, trityl, 2,6-dimethoxybenzyl, methoxymethyl, benzyloxymethyl or 2-(trimethylsilyl)ethoxymethyl, etc.

(General Synthesis Method)

Scheme 1 represents a general scheme for the preparation of compounds of the present invention.

Scheme 1

[Chemical Formula 116]

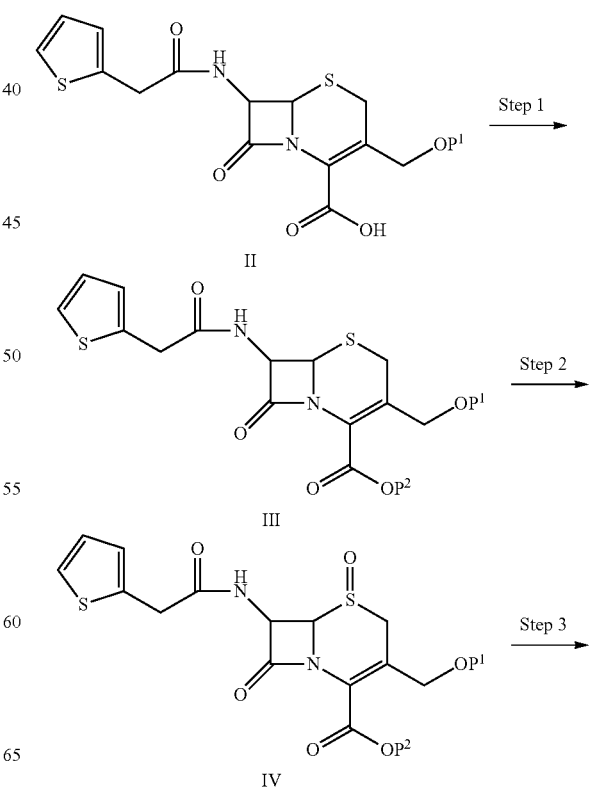

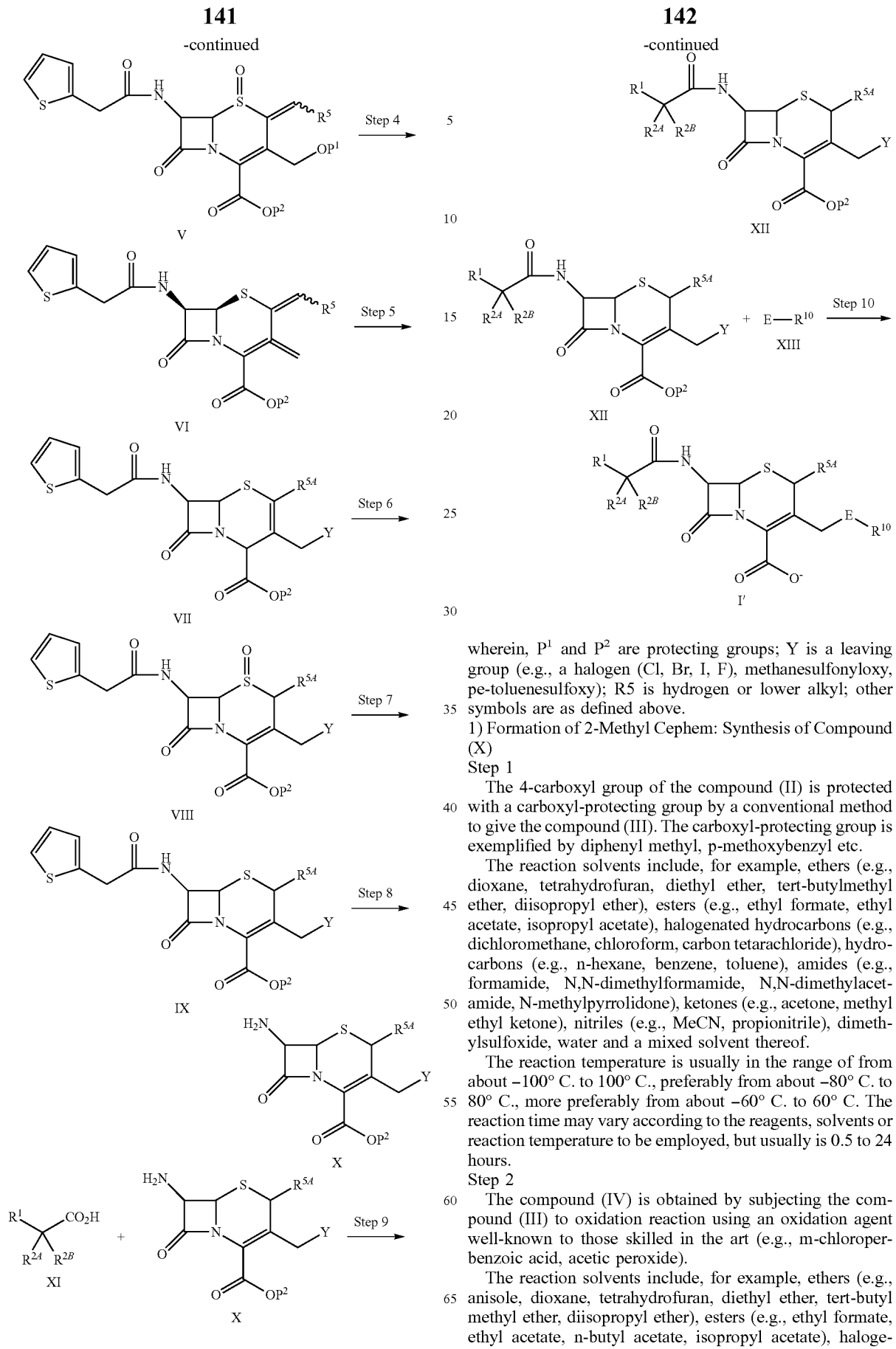

wherein, P¹ and P² are protecting groups; Y is a leaving group (e.g., a halogen (Cl, Br, I, F), methanesulfonyloxy, pe-toluenesulfoxy); R5 is hydrogen or lower alkyl; other symbols are as defined above.

1) Formation of 2-Methyl Cephem: Synthesis of Compound (X)

Step 1

The 4-carboxyl group of the compound (II) is protected with a carboxyl-protecting group by a conventional method to give the compound (III). The carboxyl-protecting group is exemplified by diphenyl methyl, p-methoxybenzyl etc.

The reaction solvents include, for example, ethers (e.g., dioxane, tetrahydrofuran, diethyl ether, tert-butylmethyl ether, diisopropyl ether), esters (e.g., ethyl formate, ethyl acetate, isopropyl acetate), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, water and a mixed solvent thereof.

The reaction temperature is usually in the range of from about −100° C. to 100° C., preferably from about −80° C. to 80° C., more preferably from about −60° C. to 60° C. The reaction time may vary according to the reagents, solvents or reaction temperature to be employed, but usually is 0.5 to 24 hours.

Step 2

The compound (IV) is obtained by subjecting the compound (III) to oxidation reaction using an oxidation agent well-known to those skilled in the art (e.g., m-chloroperbenzoic acid, acetic peroxide).

The reaction solvents include, for example, ethers (e.g., anisole, dioxane, tetrahydrofuran, diethyl ether, tert-butyl methyl ether, diisopropyl ether), esters (e.g., ethyl formate, ethyl acetate, n-butyl acetate, isopropyl acetate), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), nitros (e.g., nitromethane, nitroethane, nitrobenzene), dimethylsulfoxide, water, and a mixed solvent selected from two or more of these solvents. The reaction temperature is usually in the range of from about −100° C. to 100° C., preferably from about −80° C. to 50° C., more preferably about −60° C. to −30° C. The reaction time may vary according to the reagents, solvents or reaction temperature to be employed, but usually is carried out for 0.5 to 24 hours.

Step 3

The compound (IV) is reacted with aldehyde (i.e. $R^5CHO$) and a primary or secondary amine to give the compound (V).

Aldehyde include, for example, formaldehyde and lower alkyl aldehyde (e.g. acetaldehyde, propionaldehyde). Aldehyde is generally used in an amount of about 1 to 100 moles, preferably 1 to 30 moles, for 1 mole of the compound (IV).

A primary or secondary amine include, for example, methylamine, dimethylamine, ethylamine and diethylamine. A primary or secondary amine, including its salt, is generally used in an amount of about 1 to 100 moles, preferably 1 to 30 moles, for 1 mole of the compound (IV).

The reaction solvents include, for example, ethers (e.g., dioxane, tetrahydrofuran, diethyl ether, tert-butylmethyl ether, diisopropyl ether), esters (e.g., ethyl formate, ethyl acetate, isopropyl acetate), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, water, and a mixed solvent thereof.

The reaction temperature is usually in the range of from about −100° C. to 100° C., preferably from about −80° C. to 80° C., more preferably from about 0° C. to 80° C. The reaction time may vary according to the reagents, solvents or reaction temperature to be employed, but usually is 0.5 to 24 hours.

Step 4

The compound (V) is reacted with a reductant (e.g., zinc, copper, mixture thereof) and an acid (e.g., Hydrochloric acid, acetic acid, formic acid) to give the compound (VI).

Zinc is generally used in an amount of about 1 to 100 moles, preferably 1 to 30 moles, for 1 mole of the compound (V). Acid (e.g., Hydrochloric acid, acetic acid, formic acid) is generally used in an amount of about 1 to 100 moles, preferably 1 to 30 moles, for 1 mole of the compound (V).

The reaction solvents include, for example, ethers (e.g., dioxane, tetrahydrofuran, diethyl ether, tert-butylmethyl ether, diisopropyl ether), esters (e.g., ethyl formate, ethyl acetate, isopropyl acetate), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), acid (e.g., Hydrochloric acid, acetic acid, formic acid), dimethylsulfoxide, water, and a mixed solvent thereof.

The reaction temperature is usually in the range of from about −100° C. to 100° C., preferably from about −80° C. to 80° C., more preferably from about −20° C. to 60° C. The reaction time may vary according to the reagents, solvents or reaction temperature to be employed, but usually is 0.5 to 24 hours.

Step 5

The compound (VI) is reacted with hydrohalic acid such as hydrochloric acid, etc. to give the compound (VII).

Hydrohalic acid is generally used in an amount of about 1 to 100 moles, preferably 1 to 30 moles, for 1 mole of the compound (VI). The reaction solvents include, for example, ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, water, and a mixed solvent thereof.

The reaction temperature is usually in the range of from about −100° C. to 100° C., preferably from about −80° C. to 80° C., more preferably from about −20° C. to 60° C. The reaction time may vary according to the reagents, solvents or reaction temperature to be employed, but usually is 0.5 to 24 hours.

Step 6

The compound (VII) is reacted with a peroxyacid (e.g., meta-Chloroperoxybenzoic acid, peroxyacetic acid), etc. to give the crude sulfoxide compound. Furthermore, the crude sulfoxide compound is reacted with a base (e.g. triethylamine, sodium acetate, sodium bicarbonate, sodium hydrogen carbonate) to give the single stereoisomer sulfoxide compound (VIII).

Peroxyacid is generally used in an amount of about 1 to 100 moles, preferably 1 to 30 moles, for 1 mole of Compound (III). The reaction solvents include, for example, alcohols (e.g., methanol, ethanol), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone). The reaction temperature is usually in the range of from about −100° C. to 100° C., preferably from about −80° C. to 50° C., more preferably from about −20° C. to 0° C. The reaction time may vary according to the reagents, solvents or reaction temperature to be employed, but usually is 0.5 to 24 hours.

Step 7

The compound (VIII) is reacted with a reductant (e.g., phosphorus trichloride, phosphorus tribromide) to give the compound (IX).

The reductant (e.g., phosphorus trichloride, phosphorus tribromide) is generally used in an amount of about 1 to 100 moles, preferably 1 to 30 moles, for 1 mole of Compound (VIII).

The reaction solvents include, for example, halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone). The reaction temperature is usually in the range of from about −100° C. to 100° C., preferably from about −80° C. to 50° C., more preferably from about −60° C. to 0° C. The reaction time may vary according to the reagents, solvents or reaction temperature to be employed, but usually is 0.5 to 24 hours.

Step 8

The compound (X) is obtained by subjecting Compound (IX) to a hydrolysis reaction to make amide on 7-side chain to an amino group, followed by treating the compound with a hydrohalic acid such as hydrochloric acid. The reaction solvents include, for example, ethers (e.g., anisole, dioxane, tetrahydrofuran, diethyl ether, tert-butyl methyl ether, diisopropyl ether), esters (e.g., ethyl formate, ethyl acetate, n-butyl acetate, isopropyl acetate), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), nitros (e.g., nitromethane, nitroethane, nitrobenzene), dimethylsulfoxide, water, and a mixed solvent selected from two or more thereof. The reaction temperature is usually in the range of from about −100° C. to 100° C., preferably from about −50° C. to 50° C., more preferably from about −40° C. to 30° C. The reaction time may vary according to the reagents, solvents or reaction temperature to be employed, but usually is 0.5 to 24 hours.

2) Formation of the 7-Side Chain: Synthesis of the Compound (XII).

Step 9

The compound (X) is subjected to condensation reaction with the compound (XI) to give the compound (XII). The reaction solvents include, for example, water, ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, water, and a mixed solvent thereof.

The reaction temperature is usually in the range of from about −100° C. to 100° C., preferably from about −80° C. to 80° C., more preferably from about −60° C. to 50° C. The reaction time may vary according to the reagents, solvents or reaction temperature to be employed, but usually is 0.5 to 24 hours.

3) Formation of the 3-Side Chain: Synthesis of the Compound (I) Step 10

The compound (I') is obtained by subjecting the compound (XII) to a substitution reaction with the compound (XIII) and then subjecting it to deprotection reaction. The reaction solvents used in the reaction between the compound (XII) and the compound (XIII) include, for example, ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, water, and a mixed solvent thereof. The reaction temperature is usually in the range of from about −100° C. to 100° C., preferably from about −80° C. to 80° C., more preferably from about −20° C. to 30° C. The reaction time may vary according to the reagents, solvents or reaction temperature to be employed, but usually is 0.5 to 24 hours.

The protecting group to be used in the above reaction such as amino-protecting groups, hydroxy-protecting groups, etc. includes, for example, protecting groups described in Protective Groups in Organic Synthesis, written by T. W. Greene, John Wiley & Sons Inc. (1991), etc. Methods for the introduction and removal of a protecting group are methods commonly used in synthetic organic chemistry (see, for example, methods described in Protective Groups in Organic Synthesis, written by T. W. Greene, John Wiley & Sons Inc. (1991)), etc., or can be obtained by a modified method thereof. Furthermore, a functional group included in each substituent can be converted by a known method (e.g., those described in Comprehensive Organic Transformations, written by R. C. Larock (1989), etc.) in addition to the above production methods. Some of the compounds of the present invention can be used as a synthetic intermediate, leading to a new derivative. Intermediates and desired compounds produced in each of the above production methods can be isolated and purified by a purification method commonly used in synthetic organic chemistry, for example, neutralization, filtration, extraction, washing, drying, concentration, recrystallization, any kind of chromatography, etc. Furthermore, intermediates can be subjected to a next reaction without any purification.

Examples of an amino-protecting group include phthalimide, lower alkoxycarbonyl (butoxycarbonyl (Boc) etc.), lower alkenyloxycarbonyl (allyloxycarbonyl (Alloc), etc.), benzyloxycarbonyl, p-nitrobenzyloxycarbonyl, optionally substituted aralkanoyl (p-nitrobenzoyl, etc.), acyl (formyl, chloroacetyl, etc.), optionally substituted aralkyl (trityl, etc.), benzhydryl (BH), and the like.

Examples of a hydroxy-protecting group include lower alkoxycarbonyl such as a C1-C4 alkoxycarbonyl (e.g., t-butyloxycarbonyl), halogenated lower alkoxycarbonyl such as a halogenated (C1-C3) alkoxycarbonyl (e.g., 2-iodo ethyloxycarbonyl, 2,2,2-trichloroethyloxycarbonyl), aryl-(lower) alkoxycarbonyl such as a phenyl-(C1-C4) alkoxycarbonyl having optionally a substituent (s) on the benzene ring (benzyloxycarbonyl, o-nitrobenzyloxycarbonyl, p-nitrobenzyloxycarbonyl, p-methoxybenzyloxycarbonyl), p-methoxybenzyl (PMB), tri-lower alkylsilyl such as tri-(C1-C4) alkylsilyl (e.g., trimethylsilyl, t-butyldimethylsilyl), a substituted methyl such as C1-C4 alkoxymethyl (e.g., methoxymethyl), C1-C4 alkoxy-(C1-C4) alkoxymethyl (e.g., 2-methoxyethoxymethyl), C1-C4 alkylthiomethyl (e.g., methylthiomethyl), tetrahydropyranyl, and the like.

The above-mentioned deprotecting reaction is carried out in a solvent such as tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, or a mixed solvent thereof, using a Lewis acid (e.g., AlCl3, SnCl4, TiCl4), a protonic acid (e.g., HCl, HBr, H2SO4, HCOOH), and the like.

The obtained compound is further chemically modified, and thereby an ester, or a compound of which amino on the thiazole or thiadiazole ring at the 7-position thereof is protected, or a pharmaceutically acceptable salt, or a solvate thereof can be synthesized.

Scheme 2

[Chemical Formula 117]

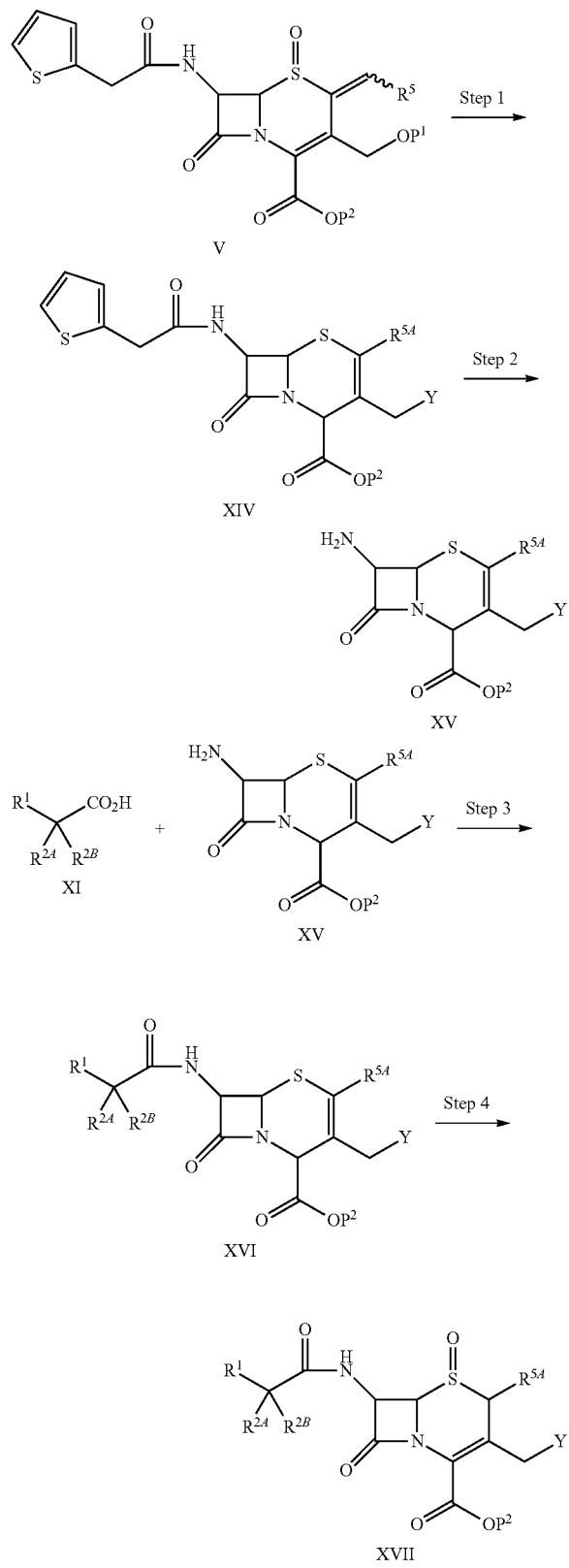

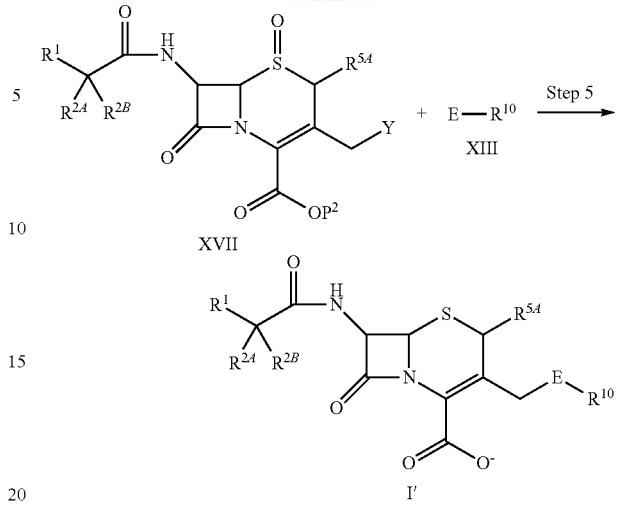

wherein, $P^1$ and $P^2$ are protecting groups; Y is a leaving group (e.g., a halogen (Cl, Br, I, F), methanesulfonyloxy, pe-toluenesulfoxy); R5 is lower alkyl; other symbols are as defined above.

(1) Synthesis of the Compound (XV)

Step 1

The compound (V) is reacted with a reductant (e.g., phosphorus trichloride, phosphorus tribromide), followed by treating the resultant with a hydrohalic acid such as hydrochloric acid, etc. to give the compound (IX).

The reaction solvents include, for example, ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, water, and a mixed solvent thereof.

The reaction temperature is usually in the range of from about −100° C. to 100° C., preferably from about −80° C. to 80° C., more preferably from about −20° C. to 60° C. The reaction time may vary according to the reagents, solvents or reaction temperature to be employed, but usually is 0.5 to 24 hours.

Step 2

The compound (XV) is obtained by subjecting Compound (XIV) to a hydrolysis reaction to make amide on 7-side chain to an amino group, followed by treating the compound with a hydrohalic acid such as hydrochloric acid. The reaction solvents include, for example, ethers (e.g., anisole, dioxane, tetrahydrofuran, diethyl ether, tert-butyl methyl ether, diisopropyl ether), esters (e.g., ethyl formate, ethyl acetate, n-butyl acetate, isopropyl acetate), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), nitros (e.g., nitromethane, nitroethane, nitrobenzene), dimethylsulfoxide, water, and a mixed solvent selected from two or more thereof. The reaction temperature is usually in the range of from about −100° C. to 100° C., preferably from about −50° C. to 50° C., more preferably from about −40° C. to 30° C. The reaction time may vary according to the reagents, solvents or reaction temperature to be employed, but usually is 0.5 to 24 hours.
2) Formation of the 7-Side Chain: Synthesis of the Compound (XVII).
Step 3

The compound (XV) is subjected to condensation reaction with the compound (XI) to give the compound (XVI). The reaction solvents include, for example, water, ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, water, and a mixed solvent thereof.

The reaction temperature is usually in the range of from about −100° C. to 100° C., preferably from about −80° C. to 80° C., more preferably from about −60° C. to 50° C. The reaction time may vary according to the reagents, solvents or reaction temperature to be employed, but usually is 0.5 to 24 hours.
Step 4

The compound (XVII) is obtained by subjecting the compound (XVI) to oxidation reaction using an oxidation agent well-known to those skilled in the art (e.g., m-chloroperbenzoic acid, acetic peroxide).

The reaction solvents include, for example, ethers (e.g., anisole, dioxane, tetrahydrofuran, diethyl ether, tert-butyl methyl ether, diisopropyl ether), esters (e.g., ethyl formate, ethyl acetate, n-butyl acetate, isopropyl acetate), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), nitros (e.g., nitromethane, nitroethane, nitrobenzene), dimethylsulfoxide, water, and a mixed solvent selected from two or more thereof. The reaction temperature is usually in the range of from about −100° C. to 100° C., preferably from about −80° C. to 50° C., more preferably from about −60° C. to −30° C. The reaction time may vary according to the reagents, solvents or reaction temperature to be employed, but usually is carried out for 0.5 to 24 hours.

The obtained compound (XVII) can be purified by column chromatography to obtain each 2-methyl stereoisomer.
3) Formation of the 3-Side Chain: Synthesis of the Compound (I)
Step 5

Compound (I') is obtained by subjecting Compound (XVII) to a substitution reaction with Compound (XIII) by a method well-known to those skilled in the art, followed by reducing it with a reduction agent well-known to those skilled in the art (e.g., phosphorus chloride, phosphorus tribromide), and then subjecting it to a deprotection reaction. The reaction solvents include, for example, ethers (e.g., anisole, dioxane, tetrahydrofuran, diethyl ether, tert-butyl methyl ether, diisopropyl ether), esters (e.g., ethyl formate, ethyl acetate, n-butyl acetate, isopropyl acetate), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), nitros (e.g., nitromethane, nitroethane, nitrobenzene), dimethylsulfoxide, water, and a mixed solvent selected from two or more thereof. The reaction temperature is usually in the range of from about −100° C. to 100° C., preferably from about −80° C. to 50° C., more preferably from about −40° C. to 0° C. The reaction time may vary according to the reagents, solvents or reaction temperature to be employed, but usually is 0.5 to 24 hours.

Scheme 3

[Chemical Formula 118]

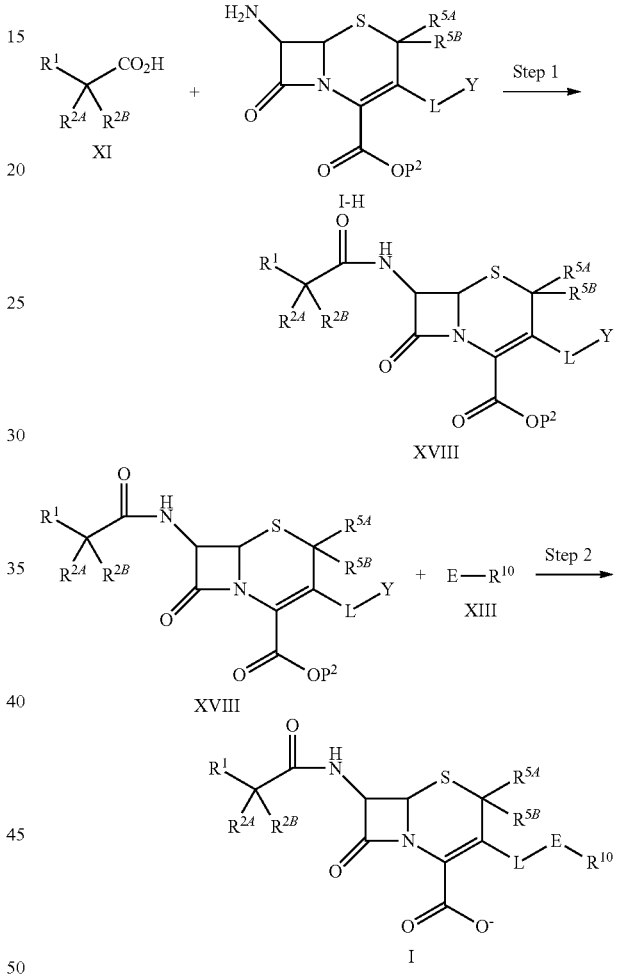

wherein, $P^2$ is protecting groups; Y is a leaving group (e.g., a halogen (Cl, Br, I, F), methanesulfonyloxy, pe-toluenesulfoxy); other symbols are as defined above.
(1) Synthesis of the Compound (I)
Step 1

The compound (XVIII) is obtained by reaction of the compound (XI) and the compound (I-H) as the similar procedure described in Step 9 of Scheme 1.
Step 2

The compound (I) is obtained by reaction of the compound (XVIII) and the compound (XIII) as the similar procedure described in Step 10 of Scheme 1.

The compounds of the present invention have a wide antimicrobial activity spectrum, and may be used for prevention or therapy against a variety of diseases caused by causative bacteria in a variety of mammals including humans, for example, airway infectious diseases, urinary system infectious diseases, respiratory system infectious diseases, sepsis, nephritis, cholecystitis, oral cavity infectious diseases, endocarditis, pneumonia, bone marrow membrane myelitis, otitis media, enteritis, empyema, wound infectious diseases, opportunistic infection, etc.

The compounds of the present invention exhibit high antimicrobial activity in particular against Gram negative bacteria, preferably, Gram negative bacteria of enterobacteria (*E. coli, Klebsiella, Serratia, Enterobacter, Citrobacter, Morganella, Providencia, Proteus*, etc.), Gram negative bacteria colonized in respiratory system (*Haemophilus, Moraxella*, etc.), and Gram negative bacteria of glucose non fermentation (*Pseudomonas aeruginosa, Pseudomonas* other than *P. aeruginosa, Stenotrophomonas, Burkholderia, Acinetobacter*, etc.). The compounds are stable against beta-lactamase belonging to Classes A, B, C and D which is produced by these Gram negative bacteria, and have high antimicrobial activity against a variety of beta-lactam drug resistant Gram negative bacteria, such as ESBL producing bacteria, etc. These are extremely stable against metallo-beta-lactamase belonging to Class B including in particular IMP type, VIM type, L-1 type, etc. Thus, these are effective against a variety of beta-lactam drug resistant Gram negative bacteria including Cephem and Carbapenem. Moreover, the compounds of the present invention have antimicrobial activity against Gram positive bacteria including methicillin-resistant *Staphylococcus aureus* (MRSA), penicillin-resistant *Streptococcus pneumoniae* (PRSP), etc. Still more preferable compounds have features regarding kinetics in the body, such as high blood concentration, long duration of effects, and/or significant tissue migration. More preferable compounds are safe in terms of side effects, such as fever and nephrotoxty. More preferable compounds have high water solubility, and thus preferable as an injecting drug, in particular.

The compounds of the present invention can be administered either orally or parenterally. The compounds of the present invention, when administered orally, can be used in any dosage form of normal formulations, for example, solid drug such as tablet, powder, granule, capsule, etc.; solution drug; oleaginous suspension drug; or liquid drug such as syrup or elixir. The compounds of the present invention, when administered parenterally, can be used as an aqueous or oleaginous suspended injecting agent, or nasal drops. In preparation thereof, a conventional excipient, binder, lubricant, aqueous solvent, oleaginous solvent, emulsifier, suspending agent, preservative, stabilizer, etc. can be optionally used. A formulation of the present invention is produced by combining (for example, mixing) a therapeutically effective amount of a compound of the present invention with a pharmaceutically acceptable carrier or diluent.

The compounds of the present invention may be administered either parenterally or orally as an injecting agent, capsules, tablets, and granules, and preferably administered as an injecting agent. The dosage of the present compound may usually be, per 1 kg of body weight of a patient or animal, about 0.1 to 100 mg/day, preferably, about 0.5 to 50 mg/day, if desired, divided into 2-4 times per day. Carriers when used in an injecting agent are, for example, distilled water, brine, etc., and a base and the like may be used for pH adjustment. When used as capsules, granules, or tablets, carriers may be known excipients (e.g., starch, lactose, sucrose, calcium carbonate, calcium phosphate, etc.), binders (e.g., starch, acacia gum, carboxymethyl cellulose, hydroxypropyl cellulose, crystalline cellulose, etc.), lubricants (e.g., magnesium stearate, talc, etc.), etc.

General Method

Unless otherwise noted, all starting materials were obtained from commercial suppliers and used without further purification. Unless otherwise indicated, all temperatures are expressed in ° C. (degrees Centigrade). Unless otherwise indicated, all reactions are conducted under an inert atmosphere at ambient temperature.

All temperatures are given in degrees Celsius, all solvents are highest available purity and all reactions run under anhydrous conditions in an argon (Ar) or nitrogen (N2) atmosphere where necessary.

1H NMR (hereinafter also "NMR") spectra were recorded on Brucker AVANCE-400 spectrometers. CDCl3 is deuteriochloroform, d6-DMSO is hexadeuteriodimethylsulfoxide, D2O is Deuterium oxide, and CD3OD is tetradeuteriomethanol. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

Mass spectra were run on Waters Open Architecture System, UPLC SQD MS analytical system. The compound is analyzed using a reverse phase column, e.g., Xbridge-C18, Sunfire-C18, Thermo Aquasil/Aquasil C18, Acquity HPLC C18, Acquity UPLC BEH C18, Shim-pack XR-ODS, Thermo Hypersil Gold eluted using an acetonitrile and water gradient with a low percentage of an acid modifier such as 0.02% TFA or 0.1% formic acid.

Analytical HPLC was run using an Agilent system (1100 series) with variable wavelength UV detection using Luna C18 column and eluting with an acetonitrile/water gradient containing a 0.05% or 0.1% TFA modifier (added to each solvent).

Unless otherwise indicated, flash chromatography was run on a Teledyne Isco Combiflash RF using disposable Redi-Sep flash columns (normal or reverse stationary phase as indicated), and a detector with UV wavelength at 254 nm. A styrenic adsorbent resin, DIAION™ HP20SS, was used in the workup and purification of cephalosporin analogs, and is referred to simply as HP20SS resin in the following examples.

EXAMPLES

Hereinafter, the present invention is described in more details with Examples, Reference Examples, Experiments and Formulation Examples. However, the present invention is not construed to be limited thereto.

The meaning of each abbreviation is as described below.
Ac: Acetyl
Allooc: Allyloxycarbonyl
BH or Bzh: Benzhydryl
Boc: tert-Butoxycarbonyl
Bn: Benzyl
Bt: benzotriazole
Cbz: carbobenzoxy
DMF: N,N-dimethylformamide
EDC: 1-ethyl-3-(3-dimethylaminopropyl)carbodiimide
Et: Ethyl
HOBt: 1-hydroxybenzotriazole
i-Pr: isopropyl
mCPBA: m-chloroperoxybenzoic acid
Me: methyl
ODS: Octadecylsilyl
PMB: para-Methoxybenzyl
TBS: tert-butyldimethylsilyl
t-Bu: tert-butyl TFA: trifluoroacetic acid
Tr: Trityl
WSCD: N-ethyl-N'-(3-dimethylaminopropyl)carbodiimide
rt: room temperature
TFA: trifluoroacetic acid
THF: tetrahydrofuran
DCM: dichloromethane
MeOH: methanol
EA or EtOAc: ethyl acetate
Pd/C: palladium on carbon
NaBH(OAc)$_3$: sodium triacetoxyborohydride
Pd$_2$(dba)$_3$: tris(dibenzylideneacetone)dipalladium (0)
XPhos: dicyclohexyl[2',4',6'-tris(1-methylethylethyl)-2-biphenylyl]phosphane
SEMCl: 2-(trimethylsilyl)ethoxymethyl chloride
CDI: 1,1'-carbonyldiimidazole AlCl$_3$: aluminum chloride
LAH: lithium aluminium hydride
DIBAL-H: diisobutylaluminum hydride
PyBOP: (benzotriazol-1-yloxy)tripyrrolidinophosphonium hexafluorophosphate
HATU: 2-(3H-[1,2,3]triazolo[4,5-b]pyridin-3-yl)-1,1,3,3-tetramethylisouronium hexafluorophosphate (V)
DIPEA or DIEA: diisopropylethylamine
K$_2$CO$_3$: potassium carbonate
TMS: tetramethylsilane
CDCl$_3$: deuteriochloroform
CD$_3$OD: tetradeuteriomethanol
DMSO-d$_6$: hexadeuteriodimethylsulfoxide Reference Example 1: Synthesis of Compound X-1

[Chemical Formula 119]

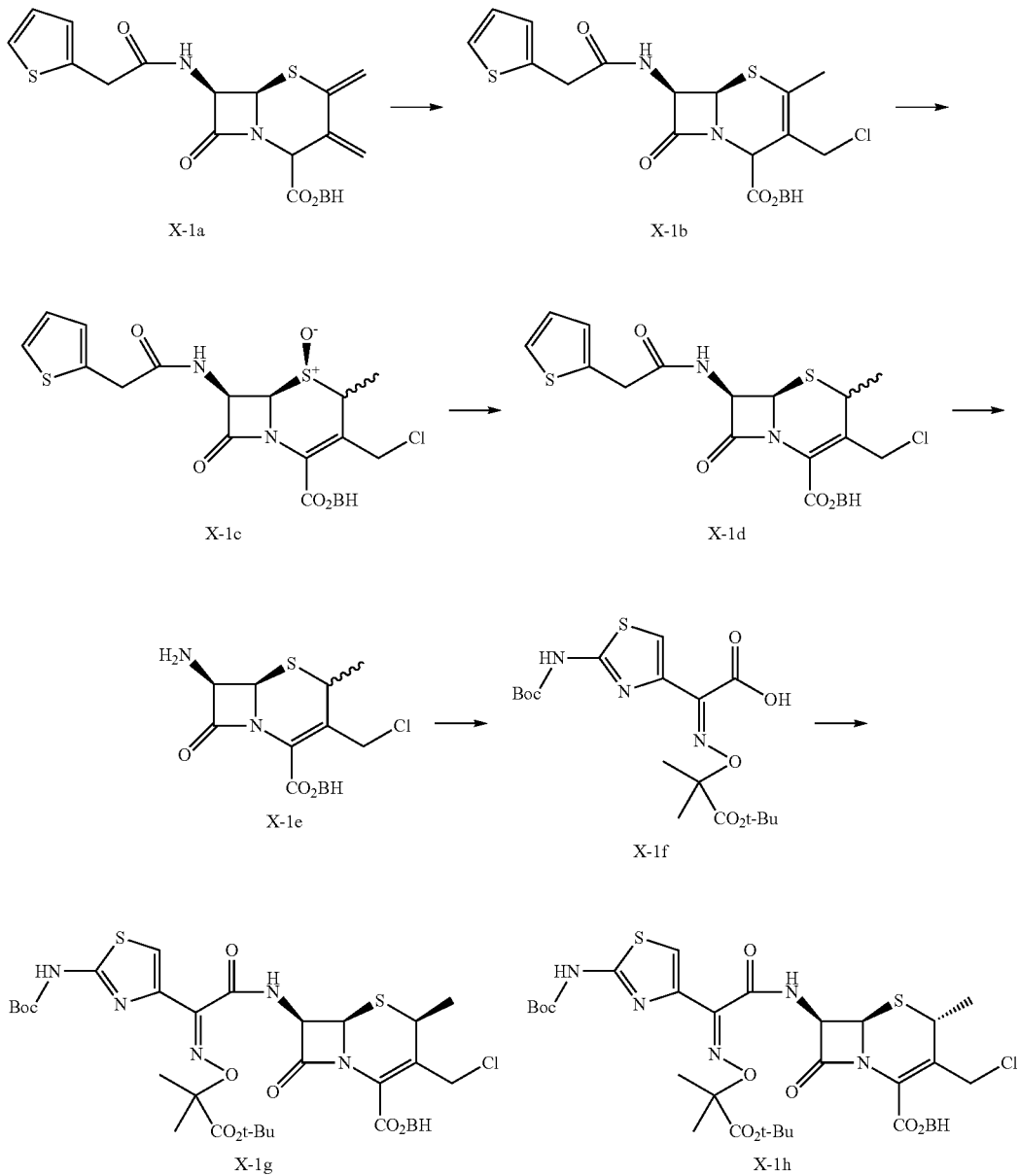

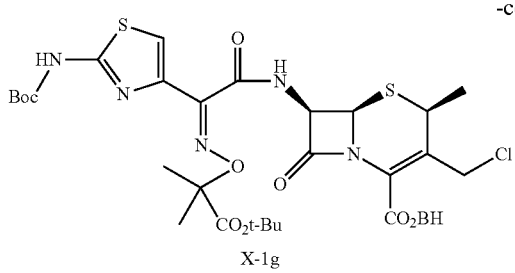

X-1g

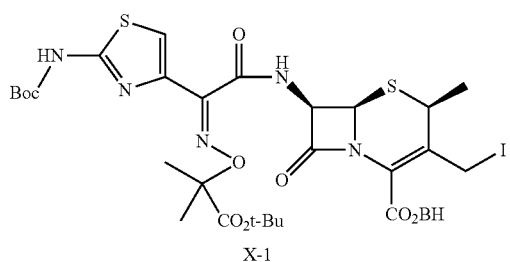

X-1

Step (1): Compound X-1a→Compound X-1b

Compound X-1a (26.47 g, 51.2 mmol) which was synthesized according to the synthesis in U.S. Pat. No. 4,463,172A1 was dissolved into dioxane (200 mL), and thereto was then added 4 mol/L hydrochloric acid solution in dioxane (25.6 ml, 102 mmol) at rt. The mixture was stirred at rt for 1 hour. The reaction mixture was concentrated under reduced pressure. The precipitated solid was then collected by filtration, and washed with diisopropyl ether/dichloromethane to yield compound X-1b (21.1 g, 75%).

$^1$H-NMR (CDCl$_3$) δ: 7.37-7.26 (11H, m), 7.03-6.99 (2H, m), 6.87 (1H, s), 6.36 (1H, d, J=8.7 Hz), 5.63-5.59 (1H, m), 5.23-5.20 (2H, m), 4.31 (1H, d, J=12.3 Hz), 4.09 (1H, d, J=12.3 Hz), 3.86 (2H, s), 1.99 (3H, s).

Step (2): Compound X-1b→Compound X-1c

Compound X-1b (5.53 g, 10 mmol) was dissolved into dichloromethane (60 mL), and thereto was then added dropwise a solution of m-chloroperoxybenzoic acid (3.45 g, 13 mmol) in dichloromethane (40 mL) at −40° C. The mixture was stirred at −40° C. for 1 hour. The reaction mixture was diluted with an aqueous sodium thiosulfate solution, then separated and washed with saturated sodium hydrogen carbonate solution, and dried over magnesium sulfate. Magnesium sulfate was filtrated off, and then the liquid was concentrated under reduced pressure. The precipitated solid was then collected by filtration, and washed with methanol to yield compound X-1c (3.79 g, 67%).

MS(M+1)=569

Step (3): Compound X-1c→Compound X-1d

Compound X-1c (3.79 g, 6.6 mmol) was dissolved into dimethylformamide (35 mL), and thereto was then added phosphorus trichloride (1.7 mL, 20 mmol) at −50° C. The mixture was stirred at −20° C. for 30 minutes. The reaction mixture was diluted with water and ethyl acetate, then separated and washed with water and a saturated salt solution, and dried over magnesium sulfate. Magnesium sulfate was filtrated off, and then the liquid was concentrated under reduced pressure. The compound-containing liquid was subjected to silica gel column chromatography to elute out the desired compound with hexane/ethyl acetate. The desired-compound-containing fraction was concentrated under reduced pressure to yield compound X-1d (1.98 g, 54%).

MS(M+1)=553

Step (4): Compound X-1d→Compound X-1e

Phosphorus pentachloride (1.47 g, 7.1 mmol) was suspended into dichloromethane (20 mL), and thereto were then added pyridine (0.63 ml, 7.8 mmol) and compound X-1d (1.95 g, 3.5 mmol) at 0° C. The mixture was stirred at 0° C. for 1 hour. Thereto was then added methanol (10 mL) at −40° C. The mixture was stirred at 0° C. for 30 minutes. The mixture was diluted with a saturated sodium hydrogen carbonate solution and dichloromethane, then separated and dried over magnesium sulfate. Magnesium sulfate was filtrated off, and then ethyl acetate (20 ml) was added and concentrated under reduced pressure to yield the ethyl acetate solution of compound X-1e. This solution was used as it was, without being purified, in the next reaction.

Step (5): Compound X-1e+Compound X-1f→Compound X-1g, Compound X-1h

Compound X-1f (1.82 g, 4.2 mmol) and triethylamine (0.68 mL, 4.9 mmol) were dissolved into dimethylacetoamide (20 mL), and thereto was then added methanesulfonyl chloride (0.36 mL, 4.6 mmol) at −20° C. The mixture was stirred at −10° C. for 20 minutes. Pyridine (0.57 mL, 7.1 mmol) and the reaction mixture were added to the ethyl acetate solution of compound X-1e (3.5 mmol) at 0° C. The mixture was stirred at 0° C. for 20 minutes. The reaction mixture was diluted with water and ethyl acetate, then separated and washed with water and a saturated salt solution, and dried over magnesium sulfate. Magnesium sulfate was filtrated off, and then the liquid was concentrated under reduced pressure. The compound-containing liquid was subjected to silica gel column chromatography to elute out the desired compound with hexane/ethyl acetate. The desired-compound-containing fraction was concentrated under reduced pressure to yield Compound X-1g (0.13 g, 4.4%), compound X-1h (1.17 g, 40%).

Compound X-1g $^1$H-NMR (CDCl$_3$) δ: 8.18-8.16 (2H, m), 7.42-7.30 (11H, m), 6.93 (1H, s), 6.03 (1H, dd, J=9.0, 5.0 Hz), 5.23 (1H, d, J=5.0 Hz), 4.83 (1H, d, J=12.3 Hz), 4.21 (1H, d, J=12.3 Hz), 4.01 (1H, q, J=7.2 Hz), 1.64 (3H, s), 1.61 (3H, s), 1.57 (3H, d, J=7.2 Hz), 1.53 (9H, s), 1.41 (9H, s).

Compound X-1h $^1$H-NMR (CDCl$_3$) δ: 8.22-8.19 (2H, m), 7.46-7.30 (11H, m), 7.01 (1H, s), 6.13 (1H, dd, J=9.0, 5.1 Hz), 5.19 (1H, d, J=5.1 Hz), 4.43 (1H, d, J=11.5 Hz), 4.18 (1H, d, J=11.5 Hz), 3.85 (1H, q, J=7.3 Hz), 1.63 (3H, s), 1.60 (3H, s), 1.58 (3H, d, J=7.3 Hz), 1.53 (9H, s), 1.39 (9H, s).

Step (6): Compound X-1g→Compound X-1

Compound X-1g (77.6 g, 92 mmol) was dissolved into tetrahydrofuran (770 mL), and thereto was then added sodium iodide (41.5 g, 277 mmol) at 15° C. The resultant solution was stirred at 15° C. for 1 day. The reaction mixture was diluted with an aqueous sodium bisulfite solution and ethyl acetate, then separated and washed with water and a saturated salt solution, and dried over magnesium sulfate.

Magnesium sulfate was filtrated off, and then the liquid was concentrated under reduced pressure to yield compound X-1 (85.2 g, 99%). Compound X-1g yielded was used as it was, without being purified, in the next reaction.

$^1$H-NMR (CDCl$_3$) δ: 8.24 (1H, d, J=8.8 Hz), 7.42-7.29 (12H, m), 6.94 (1H, s), 5.94 (1H, dd, J=8.8, 4.9 Hz), 5.27 (1H, d, J=4.9 Hz), 4.97 (1H, d, J=9.8 Hz), 4.07-4.00 (2H, m), 1.64 (3H, s), 1.61 (3H, s), 1.55-1.53 (12H, m), 1.41 (9H, s).

Reference Example 2: Synthesis of Compound X-2

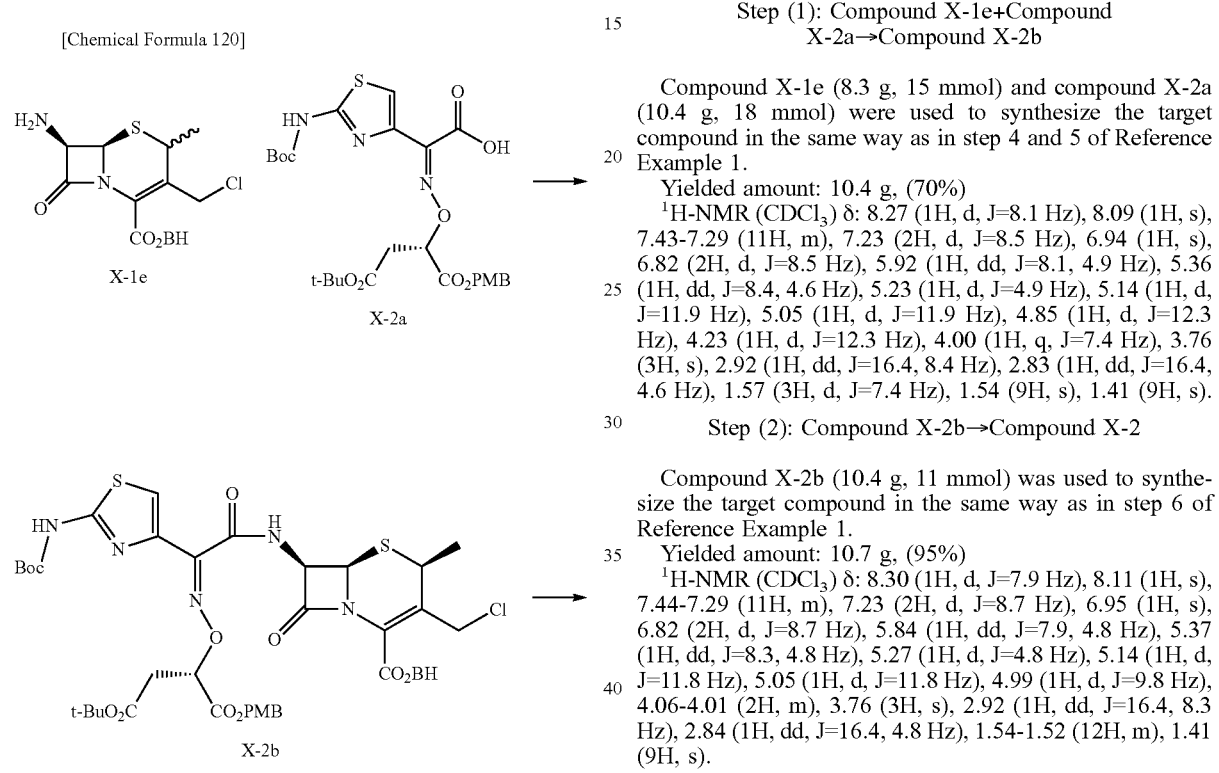

Step (1): Compound X-1e+Compound X-2a→Compound X-2b

Compound X-1e (8.3 g, 15 mmol) and compound X-2a (10.4 g, 18 mmol) were used to synthesize the target compound in the same way as in step 4 and 5 of Reference Example 1.

Yielded amount: 10.4 g, (70%)

$^1$H-NMR (CDCl$_3$) δ: 8.27 (1H, d, J=8.1 Hz), 8.09 (1H, s), 7.43-7.29 (11H, m), 7.23 (2H, d, J=8.5 Hz), 6.94 (1H, s), 6.82 (2H, d, J=8.5 Hz), 5.92 (1H, dd, J=8.1, 4.9 Hz), 5.36 (1H, dd, J=8.4, 4.6 Hz), 5.23 (1H, d, J=4.9 Hz), 5.14 (1H, d, J=11.9 Hz), 5.05 (1H, d, J=11.9 Hz), 4.85 (1H, d, J=12.3 Hz), 4.23 (1H, d, J=12.3 Hz), 4.00 (1H, q, J=7.4 Hz), 3.76 (3H, s), 2.92 (1H, dd, J=16.4, 8.4 Hz), 2.83 (1H, dd, J=16.4, 4.6 Hz), 1.57 (3H, d, J=7.4 Hz), 1.54 (9H, s), 1.41 (9H, s).

Step (2): Compound X-2b→Compound X-2

Compound X-2b (10.4 g, 11 mmol) was used to synthesize the target compound in the same way as in step 6 of Reference Example 1.

Yielded amount: 10.7 g, (95%)

$^1$H-NMR (CDCl$_3$) δ: 8.30 (1H, d, J=7.9 Hz), 8.11 (1H, s), 7.44-7.29 (11H, m), 7.23 (2H, d, J=8.7 Hz), 6.95 (1H, s), 6.82 (2H, d, J=8.7 Hz), 5.84 (1H, dd, J=7.9, 4.8 Hz), 5.37 (1H, dd, J=8.3, 4.8 Hz), 5.27 (1H, d, J=4.8 Hz), 5.14 (1H, d, J=11.8 Hz), 5.05 (1H, d, J=11.8 Hz), 4.99 (1H, d, J=9.8 Hz), 4.06-4.01 (2H, m), 3.76 (3H, s), 2.92 (1H, dd, J=16.4, 8.3 Hz), 2.84 (1H, dd, J=16.4, 4.8 Hz), 1.54-1.52 (12H, m), 1.41 (9H, s).

Reference Example 3: Synthesis of Compound X-3 and X-24

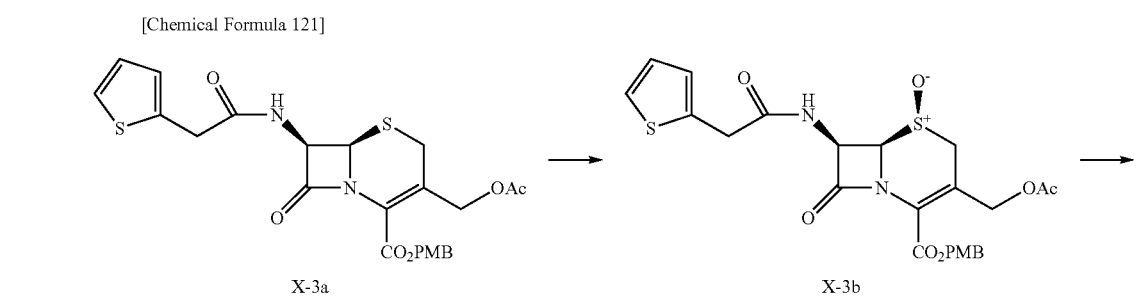

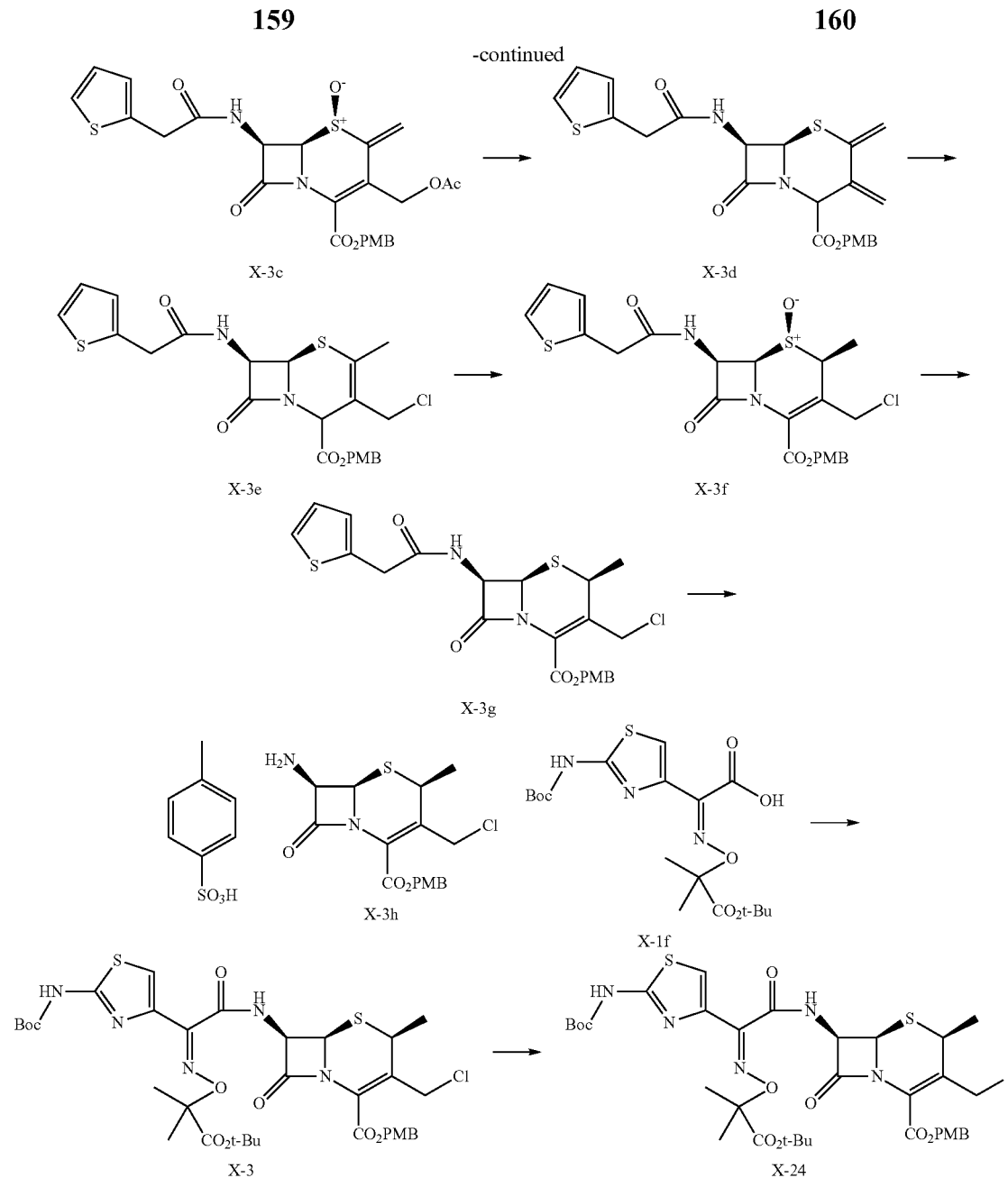

Step (1): Compound X-3a→Compound X-3b→Compound X-3c

To a pre-cooled solution of compound X-3a (50 g, 97 mmol), which was synthesized according to the synthesis in Tetrahedron Letter, 37, 1971-1974 (1996), in dichloromethane (450 mL) at −10° C. was added peracetic acid (19.82 g, 102 mmol, 37% Wt). The mixture was stirred at −10 to −5° C. To the resulting mixture was added a solution of sodium bisulfite (12.1 g, 116 mmol) in water (200 mL). Water (150 mL) was added to the mixture, and then an organic layer was separated. The organic layer was washed with water (250 mL), 10% aqueous solution of sodium chloride (250 mL). The aqueous layers were successively extracted with dichloromethane (150 mL) The combined organic layers were dried over magnesium sulfate and filtered. To the filtrated was added dimethylformamide (200 mL) and then the solution was concentrated. The residue was placed in a reaction bottle with dimethylformamide (30 mL) and then to the solution was added formaldehyde (15.7 g, 194 mmol, 37% Wt) and dimethylamine hydrochloride (7.89 g, 97 mmol). The mixture was stirred at 60° C. for 3 hours and then cooled in ice bath. To the mixture was added water (250 mL) dropwise over 8 minutes. The resulting mixture was stirred for 3.5 hr. The precipitated material was collected by filtration and washed with water (250 mL) and ethanol (250 mL). The solid was dried under air for 3 days to afford compound X-3c (48.5 g, 92%).

$^1$H-NMR (DMSO-D$_6$) δ: 8.61 (1H, d, J=8.3 Hz), 7.39-7.35 (3H, m), 6.98-6.93 (4H, m), 6.40 (1H, s), 6.21 (1H, s), 5.95 (1H, dd, J=8.3, 5.1 Hz), 5.31-5.26 (2H, m), 5.21 (1H, d, J=11.9 Hz), 5.07 (1H, d, J=5.1 Hz), 4.74 (1H, d, J=12.5 Hz), 3.91 (1H, d, J=15.4 Hz), 3.83 (1H, d, J=15.4 Hz), 3.75 (3H, s), 1.96 (3H, s).

Step (2): Compound X-3c→Compound X-3d→Compound X-3e

To a pre-cooled suspension of compound X-3c (25.0 g, 45.9 mmol) in 1,4-dioxane (175 mL) and dichloromethane (50 mL) in ice bath was added zinc (15.01 g, 230 mmol) with dichloromethane (15 mL). To the mixture in ice bath was added concentrated hydrochloric acid (19.1 mL, 230 mmol, 12M) dropwise over 45 minutes and then washed with dichloromethane (10 mL). The mixture was stirred in ice bath for 1 hour, and then filtered through Celite and it washed with dichloromethane (300 mL). The filtrate was washed with water (500 mL) and water (125 mL) successively. The aqueous layers were successively extracted with dichloromethane (75 mL). The combined organic layers were dried over magnesium sulfate, filtered and concentrated. The residue was dissolved with 1,4-dioxane (75 mL) to remove dichloromethane and then cooled in ice bath. To the mixture was added hydrochloric acid in 1,4-dioxane (23.0 mL, 4M) and then stirred in ice bath for 2 hr. To the resulting mixture was added isopropyl ether (122 mL) and stirred in ice bath for 1.5 hr. The precipitated material was collected by filtration and washed with isopropyl ether. The solid was dried under air over night to afford compound X-3e (15.3 g, 58%).

$^1$H-NMR (DMSO-D$_6$) δ: 9.27 (1H, d, J=7.8 Hz), 7.38-7.34 (3H, m), 6.97-6.92 (4H, m), 5.48 (1H, dd, J=7.8, 3.8 Hz), 5.19 (1H, d, J=3.8 Hz), 5.15-5.08 (3H, m), 4.64 (1H, d, J=12.2 Hz), 4.31 (1H, d, J=12.2 Hz), 3.77-3.74 (5H, m), 2.04 (3H, s).

Step (3): Compound X-3e→Compound X-3f

To a pre-cooled suspension of compound X-3e (50.0 g, 94 mmol) in dichloromethane (500 mL) in ice bath was added peracetic acid (18.4 g, 94 mmol, 39% Wt) dropwise over 10 minutes. The mixture was stirred in ice bath for 3 hours. An aqueous solution of sodium bisulfite (11.8 g, 113 mmol) in water (250 mL) was added. Water (250 mL) was further added. The organic layer was washed with water (500 mL) and 10% aqueous solution of sodium chloride (500 mL). The aqueous layers were successively extracted with dichloromethane (50 mL). The combined organic layers were concentrated while replaced a solvent to acetonitrile by adding twice (250 mL, 100 mL). To the residual suspension (approx. 250 mL) was added acetonitrile (612 mL) and water (150 mL). To the mixture was added 10% aqueous solution of sodium acetate (100 mL) and then pH showed 6.29. The mixture was stirred at room temperature with monitoring pH for 1.5 hours. 2 mol/L hydrochloric acid (24.5 mL) was added to quench. The insoluble material was collected by filtration and washed with water (200 mL) and acetonitrile (150 mL). The solid was dried under air over 3 days to afford compound X-3f (32.6 g, 66%).

$^1$H-NMR (DMSO-D$_6$) δ: 8.53 (1H, d, J=8.3 Hz), 7.38-7.36 (3H, m), 6.97-6.93 (4H, m), 5.88 (1H, dd, J=8.3, 4.9 Hz), 5.30 (1H, d, J=12.0 Hz), 5.21 (1H, d, J=12.0 Hz), 5.10 (1H, d, J=4.9 Hz), 4.81 (1H, d, J=12.3 Hz), 4.42 (1H, d, J=12.3 Hz), 3.90-3.79 (3H, m), 3.76 (3H, s), 1.61 (3H, d, J=7.5 Hz).

Step (4): Compound X-3f→Compound X-3g

To a pre-cooled suspension of compound X-3f (30.0 g, 57.4 mmol) in dimethylformamide (240 mL) with stirring at −40° C. was added phosphorus trichloride (23.6 g, 172 mmol) over 10 minutes. The mixture was stirred at −35° C. for 1 hour. To the resulting mixture was added dichloromethane (300 mL) and water (300 mL). The organic layer was separated, and then washed with water (300 mL) and 10% aqueous solution of sodium chloride (300 mL). The aqueous layers were successively extracted with dichloromethane (90 mL). The combined organic layers were dried over magnesium sulfate, filtered and concentrated to approx. 150 mL. To the residual suspension was added 2-propanol (180 mL) and then the suspension was concentrated to approx. 150 mL again. To the residue was added 2-propanol (14 mL) and diisopropyl ether (120 mL). The mixture was stirred for 3 hours. The insoluble material was collected by filtration and dried under air for 3 days to afford compound X-3g (20.8 g, 71%).

$^1$H-NMR (DMSO-D$_6$) δ: 9.21 (1H, d, J=8.4 Hz), 7.38-7.34 (3H, m), 6.96-6.91 (4H, m), 5.73 (1H, dd, J=8.4, 5.0 Hz), 5.33 (1H, d, J=5.0 Hz), 5.27 (1H, d, J=11.9 Hz), 5.17 (1H, d, J=11.9 Hz), 4.66 (1H, d, J=12.0 Hz), 4.49 (1H, d, J=12.0 Hz), 4.08 (1H, q, J=7.2 Hz), 3.75 (5H, s), 1.53 (3H, d, J=7.2 Hz).

Step (5): Compound X-3g→Compound X-3h

To a pre-cooled suspension of phosphorus pentachloride (8.21 g, 39.4 mmol) in dichloromethane (90 mL) with stirring at −5° C. was added pyridine (3.43 g, 43.4 mmol) and compound X-3g (10.0 g, 19.7 mmol). The mixture was stirred at 10 to 15° C. for 1 hour. The resulting mixture was poured into pre-cooled methanol (25 mL) in ice bath, and then water (50 mL) was added. The organic layer was separated and washed with water (100 mL). The aqueous layers were successively extracted with dichloromethane (40 mL). The combined organic layers were dried over magnesium sulfate, filtered. To the filtrate was added p-toluenesulfonic acid mono-hydrate (3.75 g, 19.7 mmol) and ethyl acetate (60 mL). The mixture was concentrated to remove dichloromethane. To the residual suspension was added ethyl acetate (50 mL). The mixture was stirred at 35° C., and then stirred in ice bath for 2.5 hours. The insoluble material was collected by filtration and washed with ethyl acetate. The solid was dried through air circulation to afford compound X-3h (7.30 g, 63%).

$^1$H-NMR (DMSO-D$_6$) δ: 9.02 (3H, br s), 7.48 (2H, d, J=7.7 Hz), 7.36 (2H, d, J=8.3 Hz), 7.12 (2H, d, J=7.7 Hz), 6.94 (2H, d, J=8.3 Hz), 5.45 (1H, d, J=5.0 Hz), 5.29-5.17 (3H, m), 4.68 (1H, d, J=12.0 Hz), 4.51 (1H, d, J=12.0 Hz), 4.21 (1H, q, J=7.2 Hz), 3.75 (3H, s), 2.29 (3H, s), 1.57 (3H, d, J=7.2 Hz).

Step (6): Compound X-3h+Compound X-1f→Compound X-3

To a pre-cooled suspension of compound X-1f (9.29 g, 21.6 mmol) and compound X-3h (12.0 g, 21.6 mmol) in ethyl acetate (120 mL) at −40° C. was added phenyl dichlorophosphate (6.84 g, 4.82 mmol) and N-methylmorpholine (7.65 g, 76 mmol). The mixture was stirred at −40° C. for 1.5 hours. 0.5 mol/L hydrochloric acid (130 mL) was added to quench. The organic layer was separated and washed with water (120 mL), 5% aqueous solution of sodium bicarbonate (120 mL), and 10% aqueous solution of sodium chloride (120 mL). The aqueous layers were successively extracted with ethyl acetate (60 mL). The combine organic layers were dried over magnesium sulfate, filtered and concentrated to give a crude material (19.7 g) 6.58 g of the crude residue was purified by silica gel column chromatography eluted with n-hexane and ethyl acetate to afford compound X-3 (5.77 g).

$^1$H-NMR (DMSO-D$_6$) δ: 11.84 (1H, s), 9.58 (1H, d, J=8.3 Hz), 7.36 (2H, d, J=8.2 Hz), 7.26 (1H, s), 6.94 (2H, d, J=8.2 Hz), 5.87 (1H, dd, J=8.1, 5.0 Hz), 5.40 (1H, d, J=4.9 Hz), 5.26 (1H, d, J=11.8 Hz), 5.18 (1H, d, J=11.8 Hz), 4.67 (1H, d, J=12.2 Hz), 4.48 (1H, d, J=12.0 Hz), 4.06 (1H, q, J=7.2 Hz), 3.76 (3H, s), 1.52 (3H, d, J=7.2 Hz), 1.46-1.44 (15H, m), 1.39 (9H, s).

Step (7): Compound X-3→Compound X-24

Compound X-3 (25.6 g, 30.0 mmol) was used to synthesize Compound X-24 in the same way as in step (6) of Reference Example 1.

Yielded amount: 28.08 g, (106%)

$^1$H-NMR (CDCl$_3$) δ: 8.14 (1H, d, J=8.9 Hz), 7.35-7.33 (3H, m), 6.91 (2H, d, J=8.4 Hz), 5.91 (1H, dd, J=8.9, 4.9 Hz), 5.27 (1H, d, J=11.9 Hz), 5.21-5.18 (2H, m), 5.05 (1H, d, J=10.4 Hz), 4.09-4.07 (2H, m), 3.82 (3H, s), 1.62 (3H, s), 1.60 (3H, s), 1.55 (3H, d, J=7.3 Hz), 1.53 (9H, s), 1.41 (9H, s).

Reference Example 4: Synthesis of Compound X-4

[Chemical Formula 122]

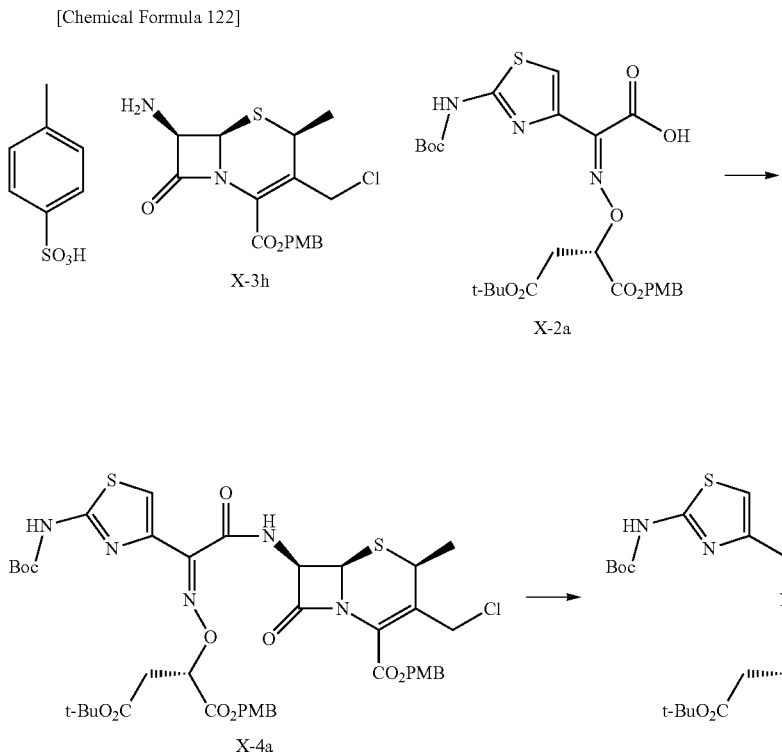

Step (1): Compound X-3h+Compound X-2a→Compound X-4a

Compound X-3h (6.3 g, 11 mmol) and compound X-2a (6.0 g, 11 mmol) were used to synthesize the target compound in the same way as in step 6 of Reference example 3.

Yielded amount: 6.7 g, (65%)

$^1$H-NMR (DMSO-D$_6$) δ: 11.87 (1H, s), 9.68 (1H, d, J=8.2 Hz), 7.36 (2H, d, J=8.0 Hz), 7.31-7.29 (3H, m), 6.94 (2H, d, J=8.0 Hz), 6.87 (2H, d, J=8.0 Hz), 5.84 (1H, dd, J=8.2, 4.8 Hz), 5.39 (1H, d, J=4.8 Hz), 5.26 (1H, d, J=12.0 Hz), 5.18 (1H, d, J=12.0 Hz), 5.10 (2H, s), 4.96 (1H, t, J=6.4 Hz), 4.68 (1H, d, J=12.0 Hz), 4.49 (1H, d, J=12.0 Hz), 4.07 (1H, q, J=7.2 Hz), 3.75 (3H, s), 3.73 (3H, s), 2.92-2.80 (2H, m), 1.51 (3H, d, J=7.2 Hz), 1.47 (9H, s), 1.35 (9H, s).

Step (2): Compound X-4a→Compound X-4

Compound X-4a (28.3 g, 30 mmol) was used to synthesize the target compound X-4 in the same way as in step 6 of Reference Example 1.

Yielded amount: 32 g, (103%)

$^1$H-NMR (CDCl$_3$) δ: 8.21 (1H, d, J=8.0 Hz), 8.11 (1H, s), 7.37-7.35 (3H, m), 7.23 (2H, d, J=8.7 Hz), 6.92 (2H, d, J=8.7 Hz), 6.83 (2H, d, J=8.7 Hz), 5.81 (1H, dd, J=8.0, 4.8 Hz), 5.36 (1H, dd, J=8.2, 5.0 Hz), 5.30-5.04 (7H, m), 4.09-4.03 (1H, m), 3.82 (3H, s), 3.79 (3H, s), 2.89 (1H, dd, J=16.4, 8.2 Hz), 2.82 (1H, dd, J=16.4, 5.0 Hz), 1.55-1.54 (12H, m), 1.40 (9H, s).

Reference Example 5: Synthesis of Compound X-5

[Chemical Formula 123]

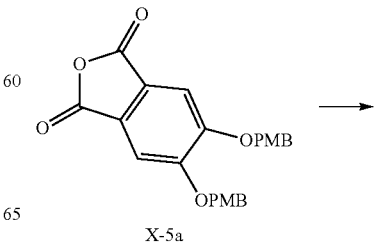

-continued

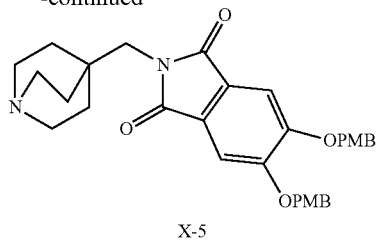

X-5

Step (1): Compound X-5a→Compound X-5

Compound X-5a (2.1 g, 5 mmol) was suspended into toluene (20 mL), and thereto was then added quinuclidin-4-ylmethanamine (0.74 g, 5.3 mmol) at 0° C. The mixture was stirred at 50° C. for 1 hour. Thereto was added acetic acid (0.57 mL, 10 mmol). The resultant was stirred at reflux for 3 days. The reaction mixture was diluted with ethyl acetate and aqueous sodium hydroxide solution, then separated and washed with water and a saturated salt solution, and dried over magnesium sulfate. Magnesium sulfate was filtrated off, and then the liquid was concentrated under reduced pressure. The precipitated solid was then collected by filtration, and washed with diisopropyl ether to yield compound X-5 (2.6 g, 95%).

$^1$H-NMR (CDCl3) δ: 7.35 (4H, d, J=8.7 Hz), 7.33 (2H, s), 6.90 (4H, d, J=8.7 Hz), 5.18 (4H, s), 3.82 (6H, s), 3.38 (2H, br s), 2.85-2.81 (6H, m), 1.42-1.38 (6H, m).

Reference Example 6: Synthesis of Compound X-6

[Chemical Formula 124]

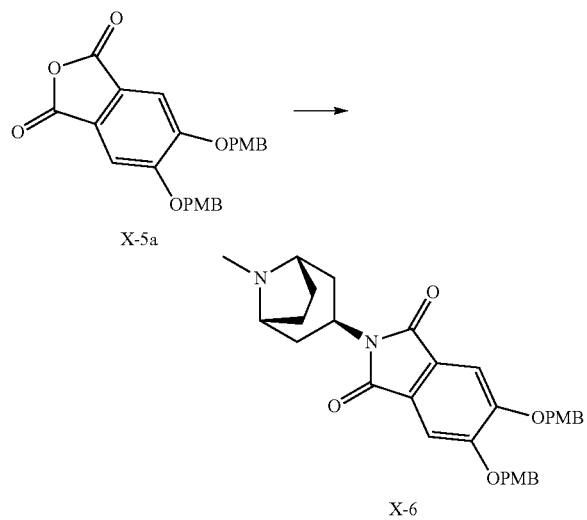

X-5a

X-6

Step (1): Compound X-5a→Compound X-6

Compound X-5a (2.1 g, 5 mmol) was used to synthesize Compound X-6 in the same way as Reference Example 5.
Yielded amount: 2.18 g (80%)
$^1$H-NMR (CDCl$_3$) δ: 7.36-7.32 (4H, m), 7.27 (2H, s), 6.91-6.87 (4H, m), 5.16 (4H, s), 4.59-4.49 (1H, m), 3.81 (6H, s), 3.24-3.20 (2H, m), 2.32-2.24 (2H, m), 2.20 (3H, s), 2.15-2.11 (2H, m), 1.88-1.82 (2H, m), 1.72-1.67 (2H, m).

Reference Example 7: Synthesis of Compound X-7

[Chemical Formula 125]

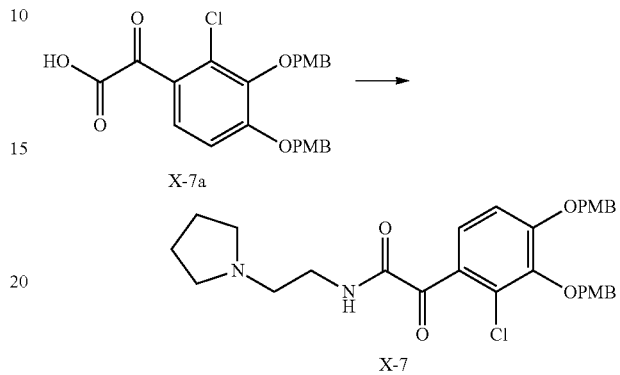

X-7a

X-7

Step (1): Compound X-7a→Compound X-7

Compound X-7a (0.48 mg, 4.2 mmol) and triethylamine (0.58 ml, 4.2 mmol) were dissolved into dimethylacetamide (12 mL), and thereto was then added Methanesulfonyl chloride (0.3 ml, 3.9 mmol) at −20° C. The mixture was stirred at −20° C. for 30 minutes. Thereto was then added aminoethylpyrrolidine (0.48 g, 4.2 mmol) at 0° C. The mixture was stirred at 0° C. for 1 hours. The reaction mixture was diluted with ethyl acetate, washed with an aqueous sodium hydroxide solution, water and a saturated salt solution, and dried over magnesium sulfate. Magnesium sulfate was filtrated off, and then the liquid was concentrated under reduced pressure. The compound-containing liquid was subjected to silica gel column chromatography to elute out the desired compound with hexane/ethyl acetate (containing 3% triethyl amine). The desired-compound-containing fraction was concentrated under reduced pressure to yield compound X-7 (0.75 g, 45%).

$^1$H-NMR (CDCl$_3$) δ: 7.62 (1H, d, J=8.7 Hz), 7.47-7.42 (1H, m), 7.34 (4H, dd, J=8.7, 2.3 Hz), 6.95-6.90 (3H, m), 6.85-6.81 (2H, m), 5.11 (2H, s), 4.96 (2H, s), 3.83 (3H, s), 3.80 (3H, s), 3.49 (2H, q, J=5.9 Hz), 2.72-2.65 (2H, m), 2.58-2.50 (4H, m), 1.83-1.74 (4H, m).

Reference Example 8: Synthesis of Compound X-8

[Chemical Formula 126]

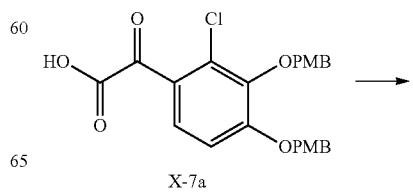

X-7a

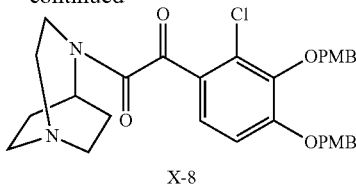

X-8

Step (1): Compound X-7a→Compound X-8

Compound X-7a (0.5 g, 3.9 mmol) was used to synthesize Compound X-7 in the same way as Reference Example 7.

Yielded amount: 0.62 g (39%)

$^1$H-NMR (DMSO-D$_6$) δ: 7.69-7.65 (1H, m), 7.47-7.45 (2H, m), 7.39 (1H, d, J=8.8 Hz), 7.31-7.26 (2H, m), 7.01-6.97 (2H, m), 6.87-6.83 (2H, m), 5.25 (2H, s), 4.91 (2H, s), 3.78 (3H, s), 3.74 (3H, s), 3.08-2.89 (7H, m), 1.97-1.69 (6H, m).

Reference Example 9: Synthesis of Compound X-9

[Chemical Formula 127]

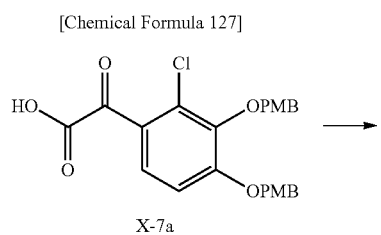

X-7a

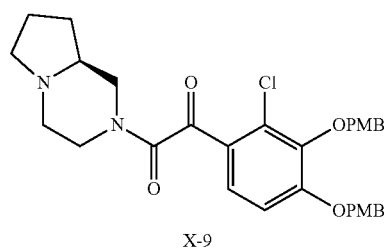

X-9

Step (1): Compound X-7a→Compound X-9

Compound X-7a (0.5 g, 3.9 mmol) was used to synthesize Compound X-9 in the same way as Reference Example 7.

Yielded amount: 0.64 g (43%)

$^1$H-NMR (CDCl$_3$) δ: 7.69 (1H, d, J=8.9 Hz), 7.34 (4H, t, J=8.2 Hz), 6.99 (1H, d, J=8.9 Hz), 6.93 (2H, d, J=8.7 Hz), 6.83 (2H, d, J=8.7 Hz), 5.13 (2H, s), 4.95 (2H, s), 4.72-4.55 (1H, m), 3.84 (3H, s), 3.80 (3H, s), 3.77-3.61 (1H, m), 3.14-2.94 (3H, m), 2.32-2.03 (3H, m), 1.92-1.76 (3H, m), 1.50-1.34 (1H, m).

Reference Example 10: Synthesis of Compound X-10

[Chemical Formula 128]

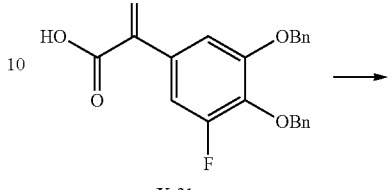

X-21

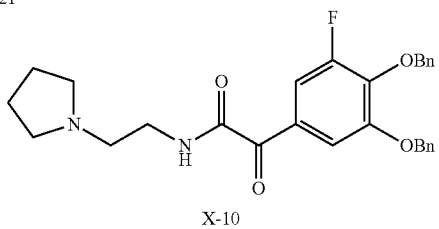

X-10

Step (1): Compound X-21→Compound X-10

Compound X-21 (1.9 g, 5.0 mmol) and diisopropylethylamine (1.3 ml, 7.5 mmol) were dissolved into dichloromethane (25 mL), and thereto was then added diphenyl chlorophosphate (1.2 ml, 6.5 mmol) at 0° C. The mixture was stirred at 0° C. for 1 hour. Thereto was then added aminoethylpyrrolidine (0.68 g, 6 mmol) at 0° C. The mixture was stirred at rt for 2 hours. The reaction mixture was diluted with ethyl acetate, washed with an aqueous sodium hydroxide solution, water and a saturated salt solution, and dried over magnesium sulfate. Magnesium sulfate was filtrated off, and then the liquid was concentrated under reduced pressure. The compound-containing liquid was subjected to silica gel column chromatography to elute out the desired compound with hexane/ethyl acetate (containing 3% triethyl amine). The desired-compound-containing fraction was concentrated under reduced pressure to yield compound X-10 (0.56 g, 19%).

$^1$H-NMR (DMSO-D$_6$) δ: 8.85 (1H, t, J=5.8 Hz), 7.58-7.32 (12H, m), 5.25 (2H, s), 5.22 (2H, s), 3.37-3.35 (2H, m), 2.56-2.54 (2H, m), 1.72-1.65 (3H, m).

The compounds shown below were used to synthesize the each target compound in the same way as Reference Example 10.

Reference Example 11: Synthesis of Compound X-11

[Chemical Formula 129]

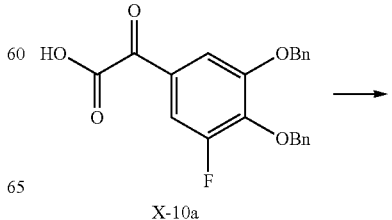

X-10a

-continued

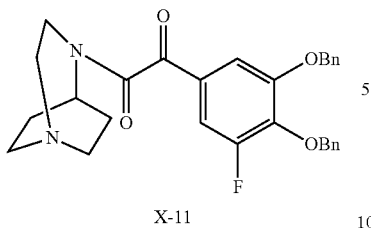
X-11

Yielded amount: 0.37 g (15%)
$^1$H-NMR (DMSO-D$_6$) δ: 7.49-7.21 (15H, m), 5.28 (2H, s), 5.23 (2H, s), 2.99-2.72 (7H, m), 2.02-1.55 (6H, m).

Reference Example 12: Synthesis of Compound X-12

[Chemical Formula 130]

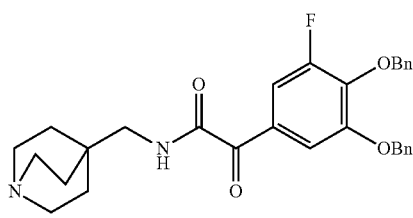
X-12

Yielded amount: 0.52 g (20%)
$^1$H-NMR (DMSO-D$_6$) δ: 8.82 (1H, t, J=6.3 Hz), 7.57-7.20 (10H, m), 5.24 (2H, s), 5.23 (2H, s), 3.02 (2H, d, J=6.4 Hz), 2.74-2.70 (6H, br m), 1.33-1.29 (6H, br m).

Reference Example 13: Synthesis of Compound X-13

[Chemical Formula 131]

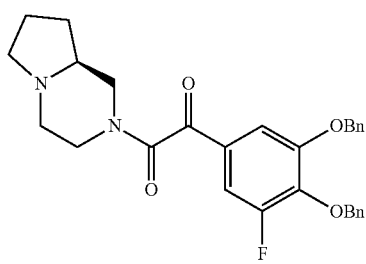
X-13

Yielded amount: 0.88 g (36%)
$^1$H-NMR (DMSO-D$_6$) δ: 7.49-7.32 (12H, m), 5.28 (2H, s), 5.24 (2H, s), 3.41-2.82 (8H, m), 2.14-1.63 (5H, m).

Reference Example 14: Synthesis of Compound X-14

[Chemical Formula 132]

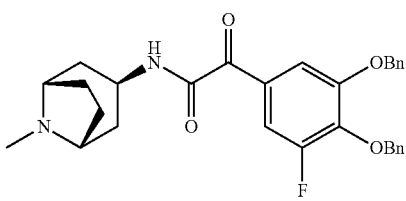
X-14

Yielded amount: 1.0 g (39%)
$^1$H-NMR (CDCl$_3$) δ: 7.97 (1H, br s), 7.93-7.90 (1H, m), 7.56-7.30 (10H, m), 5.25 (2H, s), 5.16 (2H, s), 4.16-4.11 (1H, m), 3.24 (1H, br s), 2.34-2.18 (6H, m), 1.84-1.71 (5H, m).

Reference Example 15: Synthesis of Compound X-15

[Chemical Formula 133]

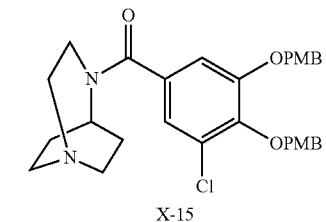
X-15

Yielded amount: 0.85 g (50%)
[M+H]=537.25

Reference Example 16: Synthesis of Compound X-16

[Chemical Formula 134]

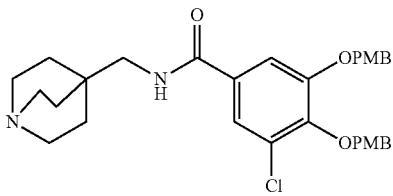
X-16

Yielded amount: 2.0 g (71%)
$^1$H-NMR (CDCl$_3$) δ: 7.41 (1H, s), 7.36-7.27 (5H, m), 6.91 (2H, d, J=8.4 Hz), 6.81 (2H, d, J=8.4 Hz), 6.28 (1H, br s), 5.06 (2H, s), 5.02 (2H, s), 3.82 (3H, s), 3.78 (3H, s), 3.19 (2H, d, J=6.3 Hz), 2.90-2.86 (6H, m), 1.41-1.38 (6H, m).

Reference Example 17: Synthesis of Compound X-17

[Chemical Formula 135]

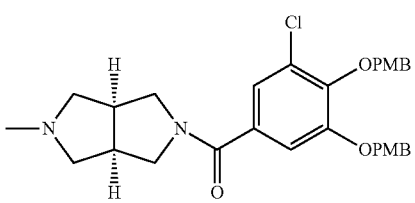
X-17

Yielded amount: 1.3 g (49%)
$^1$H-NMR (CDCl$_3$) δ: 7.34 (4H, dd, J=8.8, 2.6 Hz), 7.11 (1H, d, J=1.9 Hz), 7.02 (1H, d, J=1.9 Hz), 6.91 (2H, d, J=8.5 Hz), 6.83 (2H, d, J=8.5 Hz), 5.06 (2H, br s), 5.00 (2H, br s), 3.98 (1H, s), 3.83 (3H, d, J=10.2 Hz), 3.80 (3H, s), 3.54 (2H, s), 3.25 (1H, s), 2.82 (2H, s), 2.42 (6H, dd, J=53.5, 20.3 Hz).

Reference Example 18: Synthesis of Compound X-18

[Chemical Formula 136]

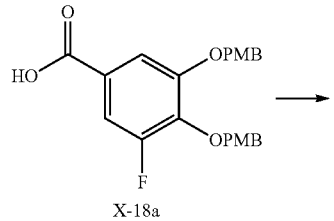

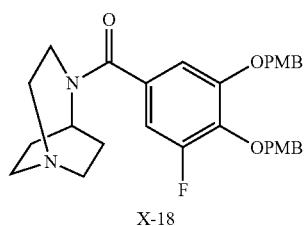
X-18

Yielded amount: 0.39 g (32%)
[M+H]=521.35

Reference Example 19: Synthesis of Compound X-19

[Chemical Formula 137]

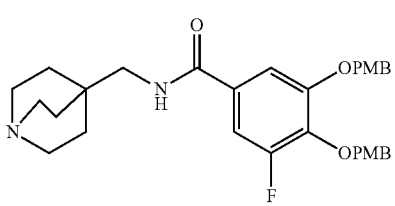
X-19

Yielded amount: 1.3 g (50%)
$^1$H-NMR (CDCl$_3$) δ: 7.34 (2H, dd, J=11.5, 2.8 Hz), 7.31-7.27 (2H, m), 7.24 (1H, d, J=1.6 Hz), 7.01 (1H, dd, J=10.4, 1.9 Hz), 6.92 (2H, dt, J=9.3, 2.4 Hz), 6.82 (2H, dt, J=9.2, 2.4 Hz), 5.95 (1H, t, J=6.1 Hz), 5.08 (4H, s), 3.82 (3H, s), 3.79 (3H, s), 3.20 (2H, d, J=6.4 Hz), 2.91-2.87 (6H, m), 1.42-1.38 (6H, m).

Reference Example 20: Synthesis of Compound X-20

[Chemical Formula 138]

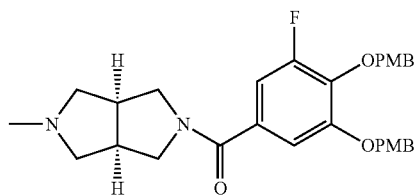
X-20

Yielded amount: 1.1 g (42%)
$^1$H-NMR (CDCl$_3$) δ: 7.33 (4H, dd, J=13.7, 8.6 Hz), 6.91-6.79 (6H, m), 5.05 (4H, s), 4.00-3.89 (1H, m), 3.82 (3H, s), 3.77 (3H, dd, J=18.3, 6.6 Hz), 3.59 (1H, t, J=20.3 Hz), 3.21 (1H, d, J=28.7 Hz), 2.85 (1H, s), 2.57 (1H, d, J=39.9 Hz), 2.35 (3H, s), 1.81 (5H, s).

Reference Example 21: Synthesis of Compound X-21

[Chemical Formula 139]

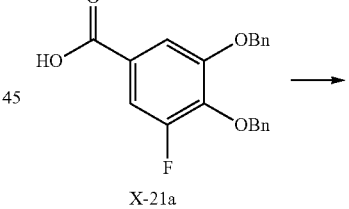
X-21a

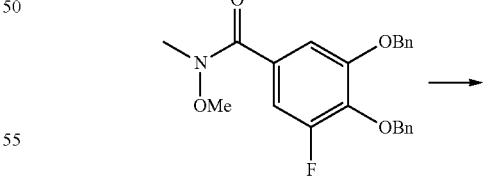
X-21b

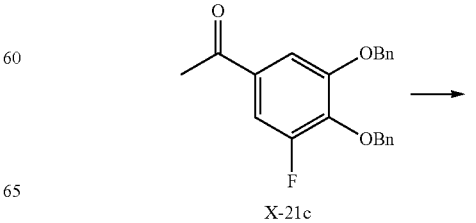
X-21c

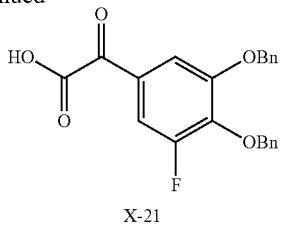

X-21

Step (1): Compound X-21a→Compound X-21b

Compound X-21a (13.5 g, 38 mmol) was suspended into dichloromethane (100 mL), and thereto were then added N,O-Dimethylhydroxylamine hydrochloride (5.6 g, 57 mmol), 1-ethyl-3-(3-dimethylaminopropyl)carbodiimide hydrochloride (11 g, 57 mmol) and triethylamine (7.94 ml, 57 mmol) in turn. The mixture was stirred at rt for 1 hours. The reaction mixture was diluted with dichloromethane and water. The resultant solution was then separated and washed with water and a saturated salt solution, and dried over magnesium sulfate. Magnesium sulfate was filtrated off, and then the liquid was concentrated under reduced pressure. The precipitated solid was then collected by filtration, and washed with diisopropyl ether to yield compound X-21b (15.1 g, 100%).

$^1$H-NMR (CDCl$_3$) δ: 7.42-7.26 (12H, m), 7.16 (2H, d, J=10.4 Hz), 5.17 (2H, s), 5.13 (2H, s), 3.48 (3H, s), 3.32 (3H, s).

Step (2): Compound X-21b→Compound X-21c

Compound X-21b (15.1 g, 38 mmol) was suspended into tetrahydrofurane (320 mL), and thereto was then added methyl magnesium bromide (0.99 mol/L in tetrahydrofurane, 77 ml 76 mmol) at 0° C. The mixture was stirred at rt for 1 hours. The reaction mixture was diluted with saturated ammonium chloride solution, then extracted ethyl acetate and washed with water and a saturated salt solution, and dried over magnesium sulfate. Magnesium sulfate was filtrated off, and then the liquid was concentrated under reduced pressure. The precipitated solid was then collected by filtration, and washed with diisopropyl ether to yield compound X-21c (13 g, 97%).

$^1$H-NMR (CDCl$_3$) δ: 7.44-7.26 (12H, m), 5.21 (2H, s), 5.16 (2H, s), 2.52 (3H, s).

Step (2): Compound X-21c→Compound X-21

Compound X-21c (13 g, 37 mmol) was dissolved into pyridine (200 mL), and thereto was then added selenium dioxide (10.3 g, 93 mmol). The mixture was stirred at 80° C. for 1 day. The reaction mixture was filtered and evaporated. The residue was diluted with aqueous hydrochloric acid solution and ethyl acetate, then separated and washed with water and a saturated salt solution, and dried over magnesium sulfate. Magnesium sulfate was filtrated off, and then the liquid was concentrated under reduced pressure. The precipitated solid was then collected by filtration, and washed with diisopropyl ether to yield compound X-21 (11.5 g, 82%).

$^1$H-NMR (DMSO-D$_6$) δ: 7.52-7.48 (3H, m), 7.44-7.32 (9H, m), 5.27 (2H, s), 5.23 (2H, s).

Reference Example 22: Synthesis of Compound X-22

[Chemical Formula 140]

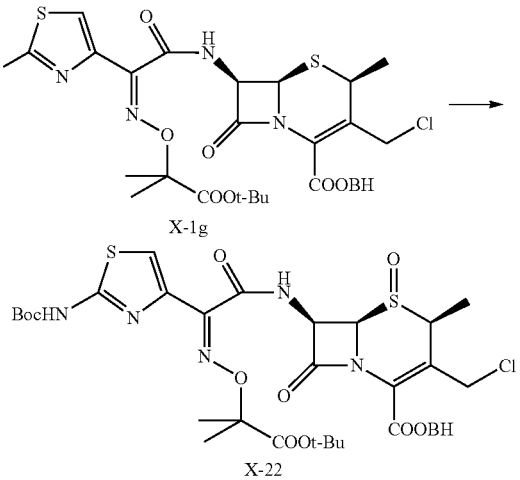

Step (1): Compound X-1g→Compound X-22

A solution of the Compound X-1g (4.20 g, 5.0 mmol) in dichloromethane (20 ml) was cooled to −40° C. A solution of m-chloroperbenzoic acid (1.46 g, 5.5 mmol) in dichloromethane (20 ml) was added drop-wise. After stirring at −40° C. for 30 minutes, aqueous 15% sodium thiosulfate solution was added thereto, dichloromethane was evaporated under reduced pressure, followed by extraction with ethyl acetate. The organic layer was washed with aqueous 5% sodium hydrogen carbonate, then saturated brine, and then dried with anhydrous magnesium sulfate. The inorganic substance was removed by filtration, followed by concentration in vacuo. The resulting crude product was purified by silica gel column chromatography to yield Compound X-22 as a yellow form.

Yield: 2.59 g, (60%)

$^1$H-NMR (CDCl$_3$) δ: 1.43 (9H, s), 1.59 (3H, s), 1.60 (3H, s), 1.61 (9H, s), 1.78 (3H, d, J=7.53 Hz), 3.48 (1H, q, J=7.53 Hz), 4.05 (1H, d, J=12.67 Hz), 4.74 (1H, dd, J=4.96, 1.38 Hz), 5.17 (1H, d, J=12.67 Hz), 6.25 (1H, dd, J=9.98, 4.96 Hz), 6.95 (1H, s), 7.28-7.44 (11H, m), 8.09 (1H, d, J=9.98 Hz), 8.30 (1H, s).

Reference Example 23: Synthesis of Compound X-23

[Chemical Formula 141]

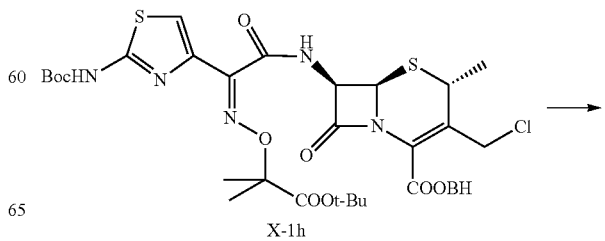

X-1h

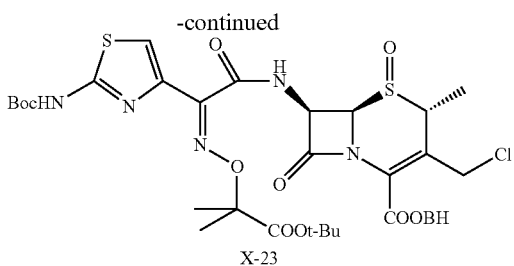

X-23

Step (1): Compound X-1h → Compound X-23

From Compound X-1h (4.20 g, 5.0 mmol), Compound X-23 was obtained as a white solid using the same method as Reference Example 22.
Yield: 2.26 g, (53%)
$^1$H-NMR (CDCl$_3$) δ: 1.39 (3H, d, J=7.47 Hz), 1.42 (9H, s), 1.53 (9H, s), 1.59 (3H, s), 1.60 (3H, s), 3.88 (1H, q, J=7.47 Hz), 4.34 (1H, d, J=12.05 Hz), 4.59 (1H, d, J=5.03 Hz), 4.63 (1H, d, J=12.05 Hz), 6.31 (1H, dd, J=9.76, 5.03 Hz), 7.00 (1H, s), 7.25-7.48 (11H, m), 7.95 (1H, d, J=9.76 Hz), 8.19 (1H, s).

Reference Example 25: Synthesis of Compound X-25

Chemical Formula 142]

Compound X-25: 5-chloro-1-cyclopropyl-6,7-bis((4-methoxybenzyl)oxy)-N-((1R,3r,5S)-8-methyl-8-azabicyclo[3.2.1]octan-3-yl)-4-oxo-1, 4-dihydroquinoline-3-carboxamide

[Chemical Formula 143]

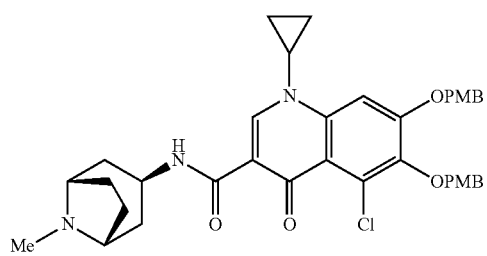

X-25

To a solution of 5-chloro-1-cyclopropyl-6,7-bis((4-methoxybenzyl)oxy)-4-oxo-1,4-dihydroquinoline-3-carboxylic acid (WO2013052568A1, 8 g, 14.93 mmol) and (1R,5S)-8-methyl-8-azabicyclo[3.2.1]octan-3-amine, 2 Hydrochloride (3.34 g, 15.7 mmol) in DCM (700 mL) were added DIPEA (9.12 mL, 52.2 mmol) and PyBOP (9.32 g, 17.9 mmol) at room temperature. The reaction mixture was stirred overnight and then concentrated, and the resulting residue was purified via automated silica gel chromatography (120 g column, 0-10% MeOH in DCM). The isolated product was purified again via automated silica gel chromatography (24 g column, 0-10% MeOH in DCM) to afford compound X-25 (4.64 g, 47% yield) as a white solid. LCMS: (M+H)$^+$: 658.2. $^1$H NMR (DMSO-d$_6$): 10.46 (d, J=7.3 Hz, 1H), 8.57 (s, 1H), 7.67 (s, 1H), 7.50 (d, J=8.6 Hz, 2H), 7.33 (d, J=8.6 Hz, 2H), 7.02 (d, J=8.6 Hz, 2H), 6.87 (d, J=8.6 Hz, 2H), 5.35 (s, 2H), 4.91 (s, 2H), 4.04 (q, J=6.8 Hz, 1H), 3.79 (s, 3H), 3.75 (s, 3H), 3.62-3.69 (m, 1H), 3.02-3.16 (m, 2H), 2.21 (s, 3H), 1.90-2.15 (m, 6H), 1.60 (d, J=13.9 Hz, 2H), 1.25-1.35 (m, 2H), 0.99-1.07 (m, 2H).

Reference Example 26: Synthesis of Compound X-26

[Chemical Formula 144]

Compound X-26: 5-chloro-1-ethyl-6,7-bis((4-methoxybenzyl)oxy)-N-((1R,3r,5S)-8-methyl-8-azabicyclo[3.2.1]octan-3-yl)-4-oxo-1,4-dihydroquinoline-3-carboxamide

[Chemical Formula 145]

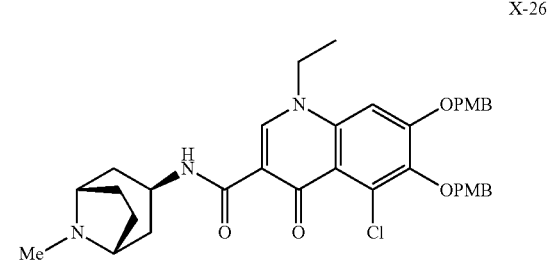

X-26

To a solution of 5-chloro-1-ethyl-6,7-bis((4-methoxybenzyl)oxy)-4-oxo-1,4-dihydroquinoline-3-carboxylic acid (WO2013052568A1, 10.0 g, 19.1 mmol) and (1R,5S)-8-methyl-8-azabicyclo[3.2.1]octan-3-amine, 2 Hydrochloride (4.07 g, 19.1 mmol) in DCM (800 mL) were added DIPEA (11.7 mL, 66.8 mmol) and PyBOP (11.92 g, 22.90 mmol) at room temperature, and the reaction mixture was stirred for 0.5 h. The mixture was concentrated and the obtained residue was purified via automated silica gel chromatography (120 g column, 0-10% MeOH in DCM). The fractions containing product were combined and washed with saturated NaHCO$_3$ aq, brine, and water successively. The product was repurified via automated silica gel chromatography (24 g column, 0-10% MeOH in DCM) to afford compound X-26 (5.95 g, 48% yield) as a white solid. LCMS: (M+H)$^+$: 646.2. $^1$H NMR (CDCl$_3$) δ: 10.71 (d, J=6.6 Hz, 1H), 8.64 (s, 1H), 7.41 (d, J=8.6 Hz, 2H), 7.37 (d, J=8.6 Hz, 2H), 6.96 (d, J=9.1 Hz, 2H), 6.87 (d, J=8.6 Hz, 1H), 6.81 (s, 1H), 5.22 (s, 2H), 5.01 (s, 2H), 4.31 (q, J=6.4 Hz, 1H), 4.17 (q, J=7.3 Hz, 2H), 3.85 (s, 3H), 3.83 (s, 3H), 3.40-3.55 (m, 2H), 2.58-2.73 (m, 2H), 2.55 (s, 3H), 2.31-2.41 (m, 2H), 2.20-2.30 (m, 2H), 2.01 (d, J=14.9 Hz, 2H), 1.41 (t, J=7.2 Hz, 3H).

Example 1: Synthesis of Compound I-1

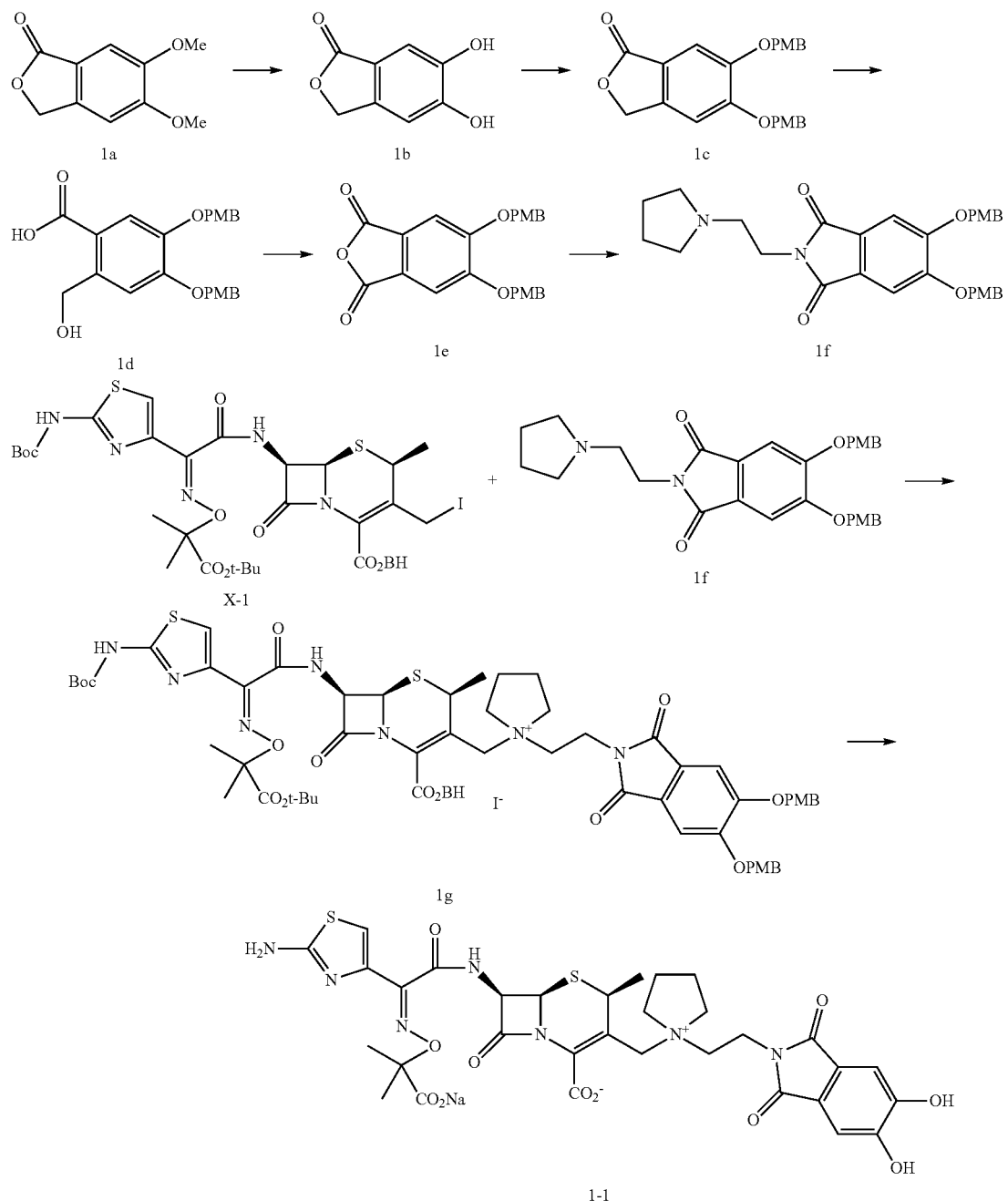

Step (1): Compound 1a→Compound 1b

Compound 1a (14.53 g, 74.8 mmol) was dissolved into dichloromethane (150 mL), and thereto was then added dropwise boron tribromide (50 g, 200 mmol) at 0° C. The mixture was stirred at rt for 1 hour. The reaction mixture was diluted with ice water, and evaporated. The precipitated solid was then collected by filtration, and washed with water. In this way, compound 1b was yielded (11.2 g, 90%).

$^1$H-NMR (DMSO-D$_6$) δ: 10.18 (1H, s), 9.66 (1H, s), 7.06 (1H, s), 6.92 (1H, s), 5.16 (2H, s).

Step (2): Compound 1b→Compound 1c

Compound 1b (13.20 g, 79 mmol) was dissolved into dimethylacetoamide (130 mL), and thereto were then added potassium carbonate (32.9 g, 238 mmol), p-methoxybenzyl chloride (26.0 ml, 191 mmol) and sodium iodide (11.91 g, 79 mmol) in turn. The mixture was stirred at 50° C. for 1 hour. The reaction mixture was poured into water. The precipitated solid was then collected by filtration, and washed with water and diisopropyl ether. In this way, compound 1c was yielded (37.32 g 116%).

$^1$H-NMR (CDCl$_3$) δ: 7.37-7.33 (5H, m), 6.92-6.88 (5H, m), 5.16 (2H, s), 5.16 (2H, s), 5.12 (2H, s), 3.82 (3H, s), 3.81 (3H, s).

Step (3): Compound 1c→Compound 1d

A 2 mol/L aqueous sodium hydroxide solution (119 ml, 237 mmol) was added to a solution of the total amount of compound 1c yielded (37.32 g, 79 mmol) in tetrahydrofuran (30 mL) and methanol (30 mL). The resultant solution was stirred at 70° C. for 1 hour. To the reaction mixture was added water and 2 mol/L aqueous hydrochloric acid solutions (120 mL). The precipitated solid was then collected by filtration, and washed with water to yield compound 1d (42.71 g, 127%).

$^1$H-NMR (CDCl$_3$) δ: 7.69 (1H, s), 7.36-7.34 (4H, m), 7.02 (1H, s), 6.91-6.87 (4H, m), 5.15 (2H, s), 5.09 (2H, s), 4.73 (2H, s), 4.69 (1H, br s), 3.81 (3H, s), 3.80 (3H, s).

Step (4): Compound 1d→Compound 1e

The total amount of compound 1d yielded (42.71 g, 79 mmol) was suspended into acetone (350 mL), and thereto was then added Jone's reagent (2.67 mol/L, 71.0 mL, 190 mmol) at 0° C. The mixture was stirred at 0° C. for 1 hour. The reaction mixture was diluted with dichloromethane and water, then added sodium bisulfite at 0° C. The resultant solution was then separated and washed with water and a saturated salt solution, and dried over magnesium sulfate. Magnesium sulfate was filtrated off, and then the liquid was concentrated under reduced pressure. The precipitated solid was then collected by filtration, and washed with diisopropyl ether to yield compound 1e (26.94 g, 81%).

$^1$H-NMR (CDCl$_3$) δ: 7.38 (2H, s), 7.35 (4H, d, J=8.1 Hz), 6.92 (4H, d, J=8.1 Hz), 5.21 (4H, s), 3.82 (6H, s).

Step (5): Compound 1e→Compound 1f

Compound 1e (1.88 g, 4.5 mmol) was suspended into toluene (20 mL), and thereto was then added aminoethylpyrrolidine (0.60 mL, 4.7 mmol) at 0° C. The mixture was stirred at rt for 30 minutes. Thereto was added acetic acid (0.28 mL, 4.9 mmol). The resultant mixture was stirred at reflux for 30 minutes. The reaction mixture was diluted with ethyl acetate and aqueous sodium hydroxide solution, then separated and washed with water and a saturated salt solution, and dried over magnesium sulfate. Magnesium sulfate was filtrated off, and then the liquid was concentrated under reduced pressure. The precipitated solid was then collected by filtration, and washed with diisopropyl ether to yield compound 1f (2.10 g, 91%).

$^1$H-NMR (CDCl$_3$) δ: 7.36-7.32 (6H, m), 6.92-6.89 (4H, m), 5.17 (4H, s), 3.81 (6H, s), 3.78-3.73 (2H, m), 2.72-2.68 (2H, m), 2.56 (4H, br s), 1.74 (4H, br s).

Step (6): Compound X-1+Compound 1f→Compound 1g→Compound I-1

Compound 1f (517 mg, 1.0 mmol) was added to a solution of compound X-1 (932 mg, 1.00 mmol) in dimethylformamide (2 mL) at 0° C., and the resultant solution was stirred at 0° C. for 1 day. The reaction mixture was slowly added to a 5% salt solution (30 ml) (containing 1.5 g of sodium bisulfite) at 0° C. The precipitated solid was collected by filtration, washed with water, and then suspended into water. The suspension was freeze-dried to yield compound 1g as an orange solid. Compound 1g yielded was used as it was, without being purified, in the next reaction.

The total amount of compound 1g yielded was dissolved in dichloromethane (10 mL), and the solution was cooled to −40° C. Thereto were then added anisole (1.3 mL, 12 mmol) and a 2 mol/L aluminum chloride solution (6.00 mL, 12 mmol) in nitromethane in turn. The resultant was stirred at 0° C. for 30 minutes. The reaction mixture was dissolved in water, a 2 mol/L aqueous hydrochloric acid solution, and acetonitrile. The resultant solution was then washed with diisopropyl ether. To the water phase was added HP20-SS resin, and then acetonitrile was distilled off under reduced pressure. The resultant mixed liquid was purified by ODS column chromatography. To the resultant target-compound solution was added HP20-SS resin, and then acetonitrile was distilled off under reduced pressure. The resultant mixed liquid was purified by HP20-SS column chromatography. To the resultant target-compound solution was added a 0.2N aqueous sodium hydroxide solution until the whole gave a pH of 6.0. Thereafter, a piece of dry ice was added thereto. The resultant solution was concentrated under reduced pressure, and then freeze-dried to yield compound I-1 as an orange powder.

Yielded amount: 163.5 mg, (18%).

$^1$H-NMR (D$_2$O) δ: 6.99 (3H, s), 5.80 (1H, d, J=4.6 Hz), 5.47 (1H, d, J=4.6 Hz), 5.07 (1H, d, J=14.1 Hz), 4.30 (1H, d, J=14.1 Hz), 4.11 (1H, d, J=6.3 Hz), 4.00 (2H, br s), 3.69-3.52 (6H, m), 2.23 (4H, br s), 1.59 (3H, d, J=5.8 Hz), 1.53 (3H, s), 1.51 (3H, s).

Elem. Anal.: C32H34N7O11S2Na (H2O) 4.8

Calcd.: C, 44.37; H, 5.07; N, 11.32; S, 7.40; Na, 2.65(%).
Found: C, 44.29; H, 4.98; N, 11.52; S, 7.27; Na, 2.76(%).

Example 2: Synthesis of Compound I-2

[Chemical Formula 147]

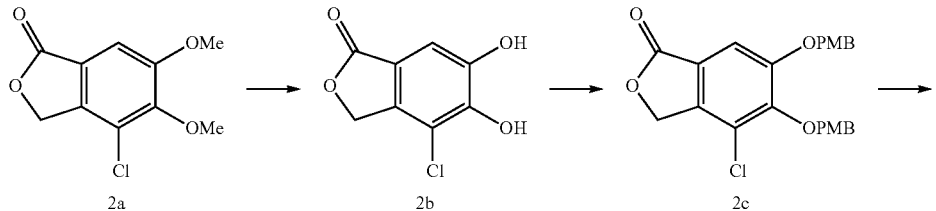

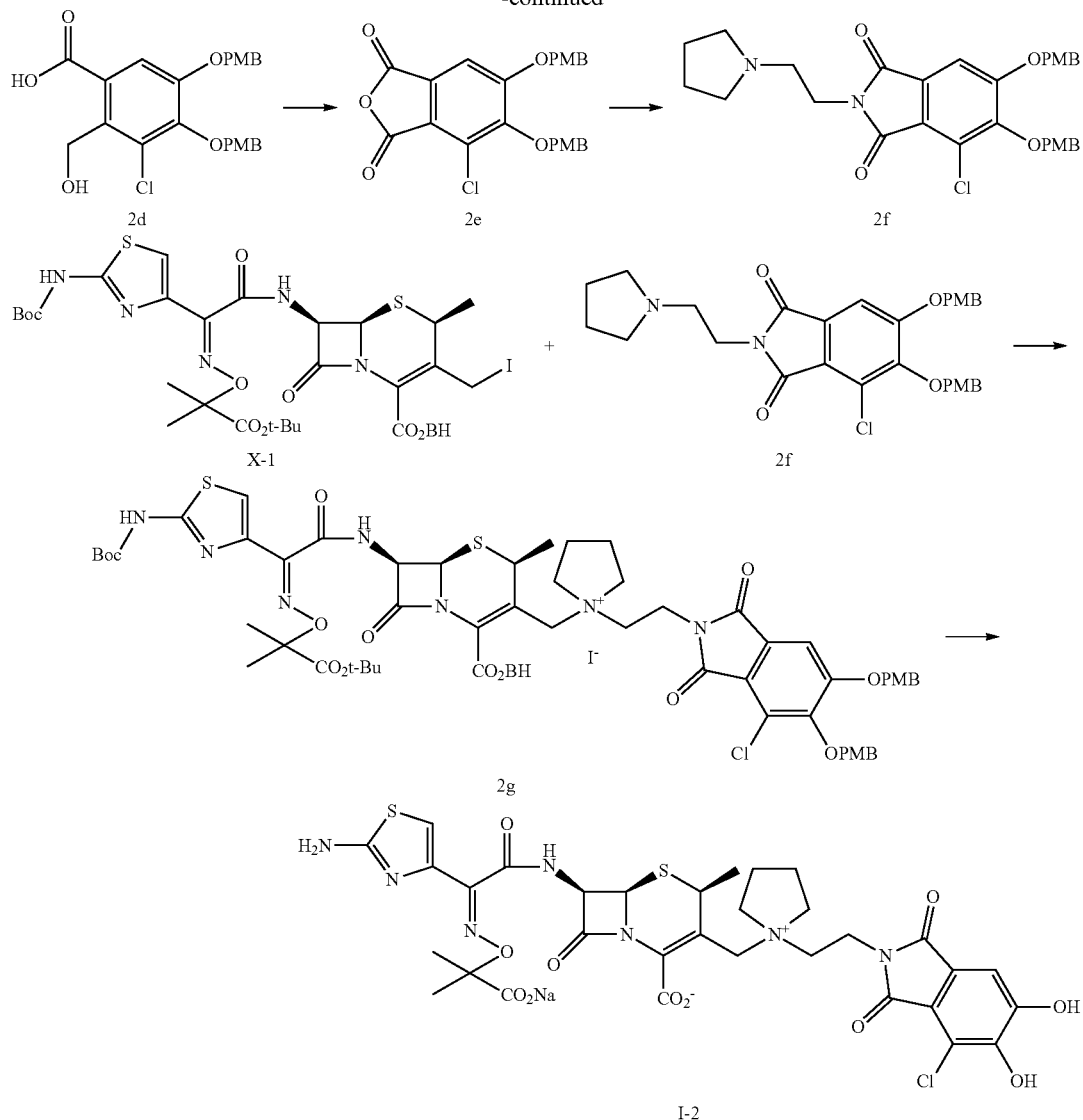

Step (1): Compound 2a→Compound 2b

Compound 2a (2.33 g, 10.2 mmol) was used to synthesize the target compound in the same way as step 1 of Example 1.

Yielded amount: 2.00 g, (98%)

$^1$H-NMR (DMSO-D$_6$) δ: 10.55 (2H, br s), 7.09 (1H, s), 5.22 (2H, s).

Step (2): Compound 2b→Compound 2c

Compound 2b (2.00 g, 9.97 mmol) was used to synthesize the target compound in the same way as step 2 of Example 1.

Yielded amount: 4.85 g, (110%)

$^1$H-NMR (CDCl$_3$) δ: 7.39-7.37 (3H, m), 7.31 (2H, d, J=8.7 Hz), 6.94 (2H, d, J=8.7 Hz), 6.83 (2H, d, J=8.7 Hz), 5.18 (2H, s), 5.11 (2H, s), 5.09 (2H, s), 3.84 (3H, s), 3.80 (3H, s).

Step (3): Compound 2c→Compound 2d

The total amount of compound 2c yielded (4.85 g, 9.97 mmol) was used to synthesize the target compound in the same way as step 3 of Example 1.

Yielded amount: 4.46 g, (98%)

$^1$H-NMR (CDCl$_3$) δ: 7.62 (1H, s), 7.36 (2H, d, J=8.5 Hz), 7.33 (2H, d, J=8.5 Hz), 6.92 (2H, d, J=8.5 Hz), 6.83 (2H, d, J=8.5 Hz), 5.09 (2H, s), 5.04 (2H, s), 4.99 (2H, s), 3.83 (3H, s), 3.80 (3H, s).

Step (4): Compound 2d→Compound 2e

Compound 2d (4.46 g, 9.72 mmol) was used to synthesize the target compound in the same way as step 4 of Example 1.

Yielded amount: 3.32 g, (75%, containing compound 2c) Compound 2e yielded was used as it was, without being purified, in the next reaction.

Step (5): Compound 2e→Compound 2f

Compound 2e (2.36 g, 5.19 mmol) was used to synthesize the target compound in the same way as in step 5 of Example 1.

Yielded amount: 0.98 g, (34%)

$^1$H-NMR (CDCl$_3$) δ: 7.39-7.36 (3H, m), 7.30 (2H, d, J=8.7 Hz), 6.94 (2H, d, J=8.7 Hz), 6.82 (2H, d, J=8.7 Hz), 5.16 (2H, s), 5.03 (2H, s), 3.84 (3H, s), 3.80-3.77 (5H, m), 2.73 (2H, t, J=6.8 Hz), 2.61-2.56 (4H, m), 1.77-1.74 (4H, m).

Step (6): Compound X-1+Compound 2f→Compound 2g

Compound X-1 (932 mg, 1.00 mmol) and compound 2f (551 mg, 1.00 mmol) were used to synthesize the target compound in the same way as step 6 of Example 1.

Yielded amount: 124.3 mg, (13%)

$^1$H-NMR (D$_2$O) δ: 7.31 (1H, dd, J=7.78, 1.53 Hz), 7.07 (1H, dd, J=7.78, 1.53 Hz), 6.98 (1H, s), 6.83 (1H, t, J=7.78 Hz), 5.89 (1H, d, J=4.96 Hz), 5.38 (1H, d, J=4.96 Hz), 4.31 (1H, t, J=7.32 Hz), 4.11-3.94 (4H, m), 3.51 (1H, d, J=17.23 Hz), 3.11 (3H, br s), 2.83-2.72 (2H, m), 2.61-2.41 (5H, m), 2.19 (1H, br s), 2.13 (1H, br s), 1.52 (3H, s), 1.50 (3H, s).

Elem. Anal.: C32H32.8ClN7O11S2Na1.2 (H2O) 6.7

Calcd.: C, 40.92; H, 4.96; Cl, 3.77; N, 10.44; S, 6.83; Na, 2.94(%).

Found: C, 40.77; H, 4.91; Cl, 3.53; N, 10.72; S, 6.99; Na, 2.94(%).

Example 3: Synthesis of Compound I-3

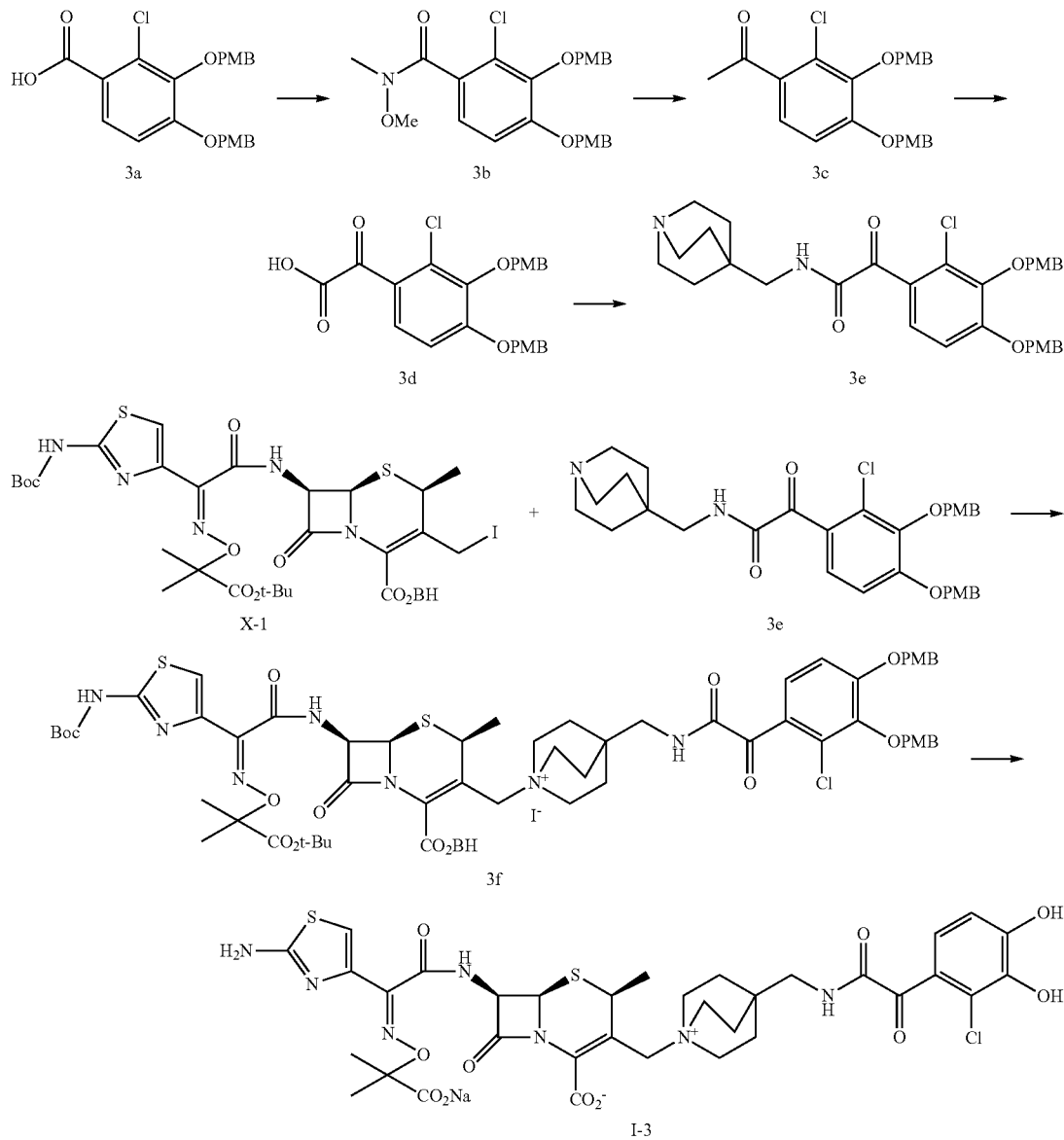

[Chemical Formula 148]

Step (1): Compound 3a→Compound 3b

Compound 3a (60 g, 140 mmol) was suspended into dichloromethane (300 mL), and thereto were then added N,O-Dimethylhydroxylamine hydrochloride (16.5 g, 169 mmol) and 1-ethyl-3-(3-dimethylaminopropyl)carbodiimide hydrochloride (32.2 g, 168 mmol) in turn. The mixture was stirred at rt for 1 day. Thereto were then added N,O-Dimethylhydroxylamine hydrochloride (4.10 g, 42 mmol) and 1-ethyl-3-(3-dimethylaminopropyl)carbodiimide hydrochloride (8.05 g, 42 mmol) in turn. The mixture was stirred at rt for 3 hours. Thereto were then added N,O-Dimethylhydroxylamine hydrochloride (4.10 g, 42 mmol) and 1-ethyl-3-(3-dimethylaminopropyl)carbodiimide hydrochloride (8.05 g, 42 mmol) in turn. The mixture was stirred at rt for 2 hours. The reaction mixture was diluted with dichloromethane and water. The resultant solution was then separated and washed with water and a saturated salt solution, and dried over magnesium sulfate. Magnesium sulfate was filtrated off, and then the liquid was concentrated under reduced pressure. The precipitated solid was then collected by filtration, and washed with diisopropyl ether to yield compound 3b (62.07 g, 94%).

$^1$H-NMR (CDCl$_3$) δ: 7.36-7.32 (4H, m), 7.02 (1H, d, J=8.4 Hz), 6.93-6.89 (3H, m), 6.81 (2H, d, J=8.5 Hz), 5.06 (2H, s), 4.98 (2H, s), 3.83 (3H, s), 3.79 (3H, s), 3.45-3.31 (6H, br m).

Step (2): Compound 3b→Compound 3c

Compound 3b (18.88 g, 40 mmol) was suspended into tetrahydrofurane (380 mL), and thereto was then added methyl magnesium bromide (0.99 mol/L in tetrahydrofurane, 81 ml 80 mmol) at 0° C. The mixture was stirred at rt for 3 hours. The reaction mixture was diluted with a saturated ammonium chloride solution, then extracted ethyl acetate and washed with water and a saturated salt solution, and dried over magnesium sulfate. Magnesium sulfate was filtrated off, and then the liquid was concentrated under reduced pressure. The precipitated solid was then collected by filtration, and washed with diisopropyl ether to yield compound 3c (13.19 g, 77%).

$^1$H-NMR (CDCl$_3$) δ: 7.39-7.33 (5H, m), 6.93-6.91 (3H, m), 6.83 (2H, d, J=8.5 Hz), 5.09 (2H, s), 4.96 (2H, s), 3.83 (3H, s), 3.80 (3H, s), 2.62 (3H, s).

Step (3): Compound 3c→Compound 3d

Compound 3c (13.19 g, 31 mmol) was dissolved into pyridine (130 mL), and thereto was then added selenium dioxide (8.57 g, 77 mmol). The mixture was stirred at 80° C. for 1 day. The reaction mixture was filtered and evaporated. The residue was diluted with an aqueous hydrochloric acid solution and ethyl acetate, then separated and washed with water and a saturated salt solution, and dried over magnesium sulfate. Magnesium sulfate was filtrated off, and then the liquid was concentrated under reduced pressure. The precipitated solid was then collected by filtration, and washed with diisopropyl ether to yield compound 3d (12.41 g, 88%).

$^1$H-NMR (DMSO-D$_6$) δ: 7.60 (1H, d, J=8.8 Hz), 7.46 (2H, d, J=8.5 Hz), 7.37 (1H, d, J=8.8 Hz), 7.28 (2H, d, J=8.5 Hz), 6.99 (2H, d, J=8.5 Hz), 6.85 (2H, d, J=8.5 Hz), 5.24 (2H, s), 4.92 (2H, s), 3.78 (3H, s), 3.74 (3H, s).

Step (4): Compound 3d→Compound 3e

Compound 3d (2.28 g, 5.0 mmol) was dissolved into dimethylacetoamide (20 mL), and thereto were then added 4-aminomethylquinuclidine (2.10 g, 15.0 mmol), hydroxybenzotriazole (0.74 g, 5.50 mmol) and 1-ethyl-3-(3-dimethylaminopropyl)carbodiimide hydrochloride (1.05 g, 5.50 mmol) in turn. The mixture was stirred at rt for 1 day and 40° C. for 1 day. The reaction mixture was diluted with an aqueous hydrochloric acid solution and stirred at rt for 30 minutes. The reaction mixture was diluted with ethyl acetate and aqueous sodium hydroxide solution, then separated and washed with water and a saturated salt solution, and dried over magnesium sulfate. Magnesium sulfate was filtrated off, and then the liquid was concentrated under reduced pressure. The precipitated solid was then collected by filtration, and washed with ethyl acetate to yield compound 3e (0.50 g, 17%).

$^1$H-NMR (DMSO-D$_6$) δ: 8.80 (1H, t, J=6.4 Hz), 7.50 (1H, d, J=8.8 Hz), 7.46 (2H, d, J=8.7 Hz), 7.33 (1H, d, J=8.8 Hz), 7.28 (2H, d, J=8.7 Hz), 6.99 (2H, d, J=8.7 Hz), 6.85 (2H, d, J=8.7 Hz), 5.22 (2H, s), 4.90 (2H, s), 3.78 (3H, s), 3.74 (3H, s), 3.01 (2H, d, J=6.4 Hz), 2.81 (6H, t, J=7.6 Hz), 1.37 (6H, t, J=7.6 Hz).

Step (2): Compound X-1+Compound 3e→Compound 3f

Compound X-1 (745 mg, 0.80 mmol) and compound 3e (463 mg, 0.80 mmol) were used to synthesize the target compound in the same way as step 6 of Example 1.

Yielded amount: 284.2 mg, (35%)

$^1$H-NMR (D$_2$O) δ: 7.31 (1H, d, J=8.7 Hz), 7.01 (1H, s), 6.88 (1H, d, J=8.7 Hz), 5.84 (1H, d, J=4.8 Hz), 5.45 (1H, d, J=4.8 Hz), 4.65 (1H, d, J=14.4 Hz), 4.11-4.05 (2H, m), 3.60-3.42 (6H, m), 3.36 (2H, s), 1.95 (6H, t, J=7.8 Hz), 1.57 (3H, d, J=6.9 Hz), 1.52 (3H, s), 1.51 (3H, s).

Elem. Anal.: C34H37ClN7O11S2Na (H2O) 6.4

Calcd.: C, 42.65; H, 5.24; Cl, 3.70; N, 10.24; S, 6.70; Na, 2.40(%).

Found: C, 42.61; H, 5.26; Cl, 3.83; N, 10.32; S, 6.71; Na, 2.43(%).

Example 4: Synthesis of Compound I-4

[Chemical Formula 149]

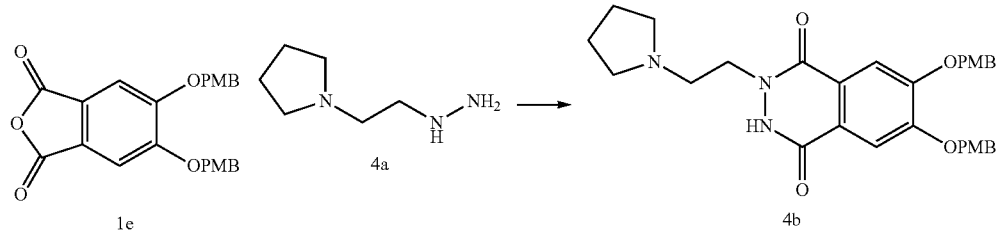

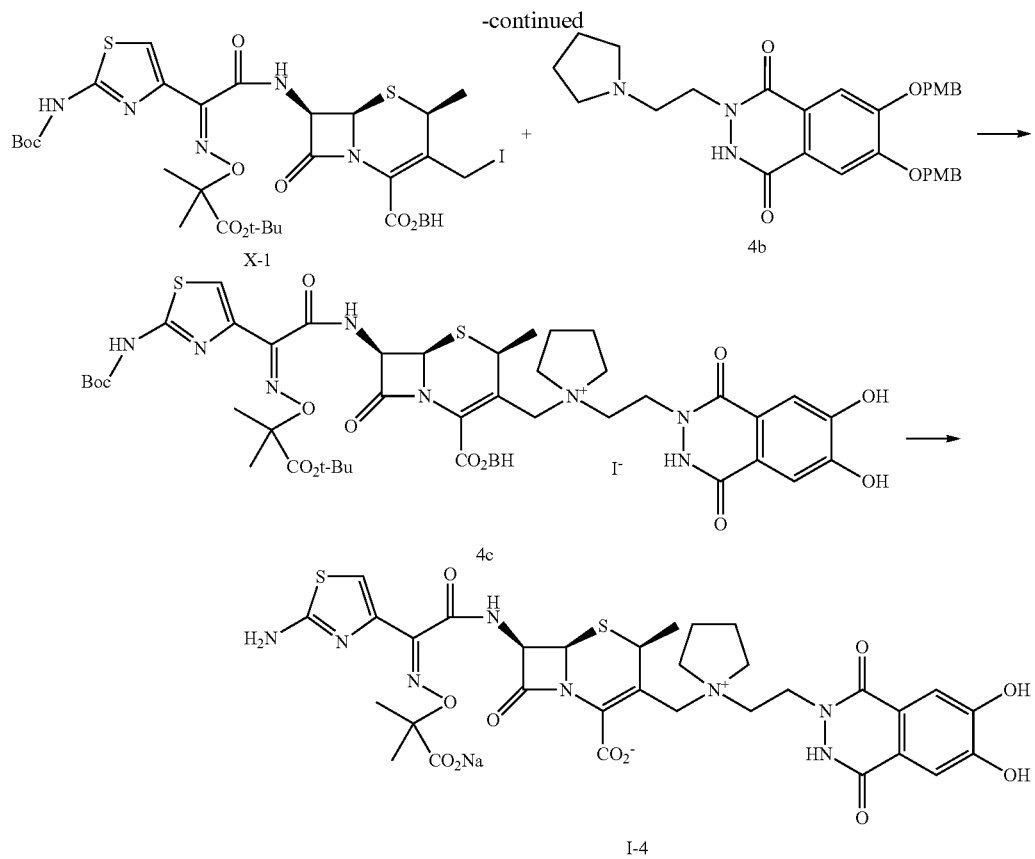

Step (1): Compound 1e+Compound 4a→Compound 4b

Compound 1e (1.88 g, 4.5 mmol) was dissolved into ethanol (10 mL), and thereto was then added Compound 4a (0.58 g, 4.5 mmol). The mixture was stirred at rt for 1 day. The precipitated solid was then collected by filtration, and washed with ethanol and diisopropyl ether to yield compound 4b (2.00 g, 84%).

$^1$H-NMR (CDCl$_3$) δ: 7.80 (1H, s), 7.32 (2H, d, J=8.5 Hz), 7.08 (2H, d, J=8.5 Hz), 6.73 (2H, d, J=8.5 Hz), 6.69 (2H, d, J=8.5 Hz), 6.49 (1H, br s), 5.01 (2H, s), 4.65 (2H, s), 4.35 (2H, br s), 3.78 (3H, s), 3.76 (3H, s), 3.27-3.01 (6H, br m), 1.90 (4H, br s).

Step (2): Compound X-1+Compound 4b→Compound 4c

Compound X-1 (932 mg, 1.00 mmol) and compound 4b (532 mg, 1.00 mmol) were used to synthesize the target compound in the same way as step 6 of Example 1.

Yielded amount: 64.5 mg, (6%)

$^1$H-NMR (D$_2$O) δ: 7.31 (1H, s), 7.15 (1H, s), 6.98 (1H, s), 5.79 (1H, d, J=4.8 Hz), 5.45 (1H, d, J=4.8 Hz), 5.03 (1H, d, J=14.2 Hz), 4.45 (2H, d, J=4.6 Hz), 4.25 (1H, d, J=14.2 Hz), 4.01 (1H, q, J=7.0 Hz), 3.81-3.43 (6H, m), 2.24-2.06 (4H, m), 1.51-1.49 (9H, m).

Elem. Anal.: C32H34.5N8O11S2Na1.5 (H2O) 10.3
Calcd.: C, 38.77; H, 5.60; N, 11.30; S, 6.47; Na, 3.48(%).
Found: C, 38.76; H, 5.45; N, 11.42; S, 6.34; Na, 3.49(%).

Example 5: Synthesis of Compound I-5

[Chemical Formula 150]

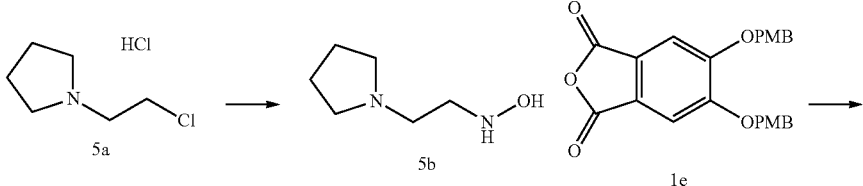

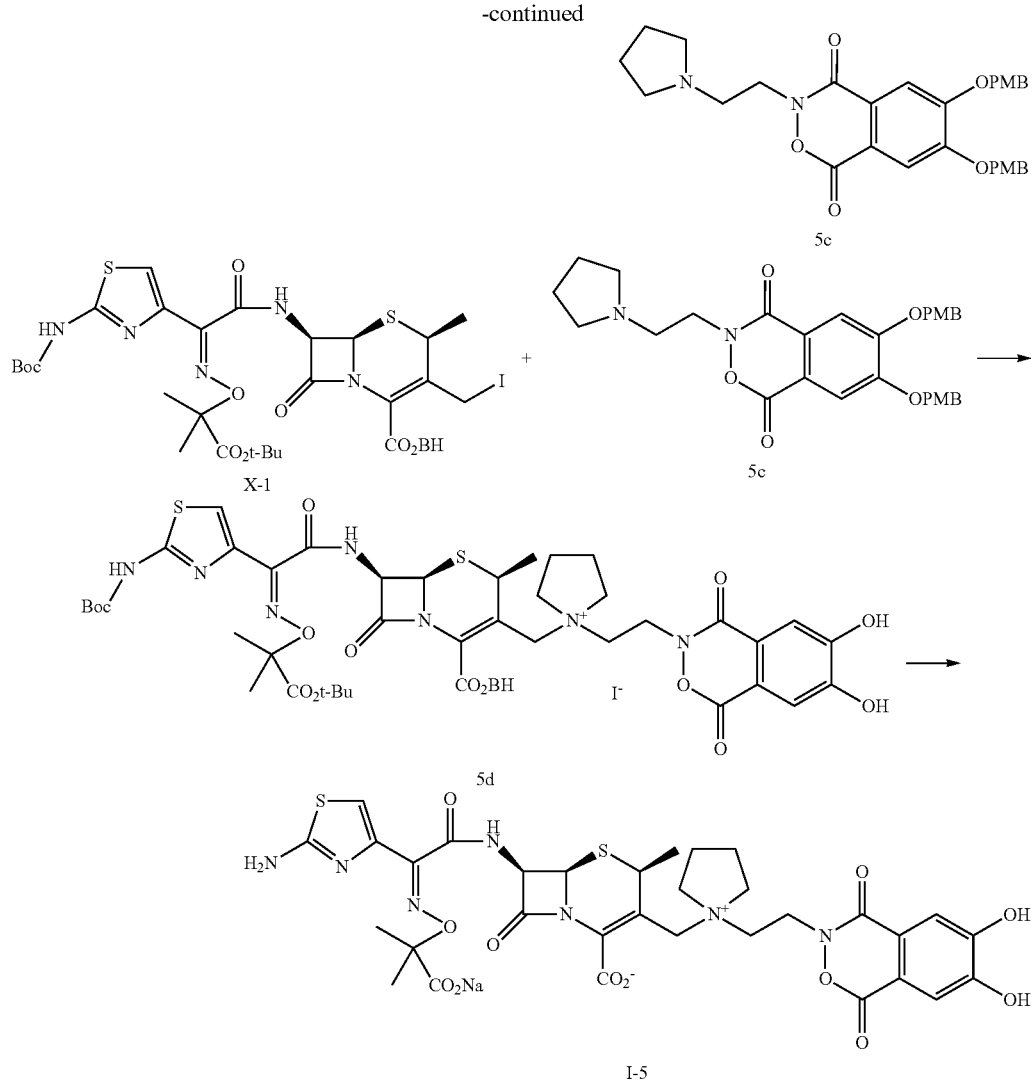

Step (1): Compound 5a→Compound 5b

Compound 5a (8.50 g, 50 mmol) and hydroxylamine hydrochloride (5.21 g, 75 mmol) were dissolved into ethanol (50 mL) and water (25 ml), and thereto was then added sodium carbonate (10.6 g, 100 mmol) at 0° C. The mixture was stirred at reflux for 1 hour. The reaction mixture was diluted with ethyl ether and aqueous sodium hydroxide solution, then separated and dried over magnesium sulfate. Magnesium sulfate was filtrated off, and then the liquid was concentrated under reduced pressure. The residue was distilled by vacuum distillation (4 mmHg, 116° C.) to yield compound 5b (1.88 g, 29%).

$^1$H-NMR (CDCl$_3$) δ: 3.09 (2H, br s), 2.75 (2H, br s), 2.57 (4H, br s), 1.78 (4H, br s).

Step (2): Compound 5b+Compound 1e→Compound 5c

Compound 1e (2.10 g, 5.0 mmol) was dissolved into ethanol (10 mL), and thereto was then added Compound 5b (0.65 g, 5.0 mmol). The mixture was stirred at rt for 1 day, 50° C. for 2 hours and 80° C. for 4 hours. The precipitated solid was then collected by filtration, and washed with ethanol and diisopropyl ether to yield compound 5c (1.81 g, 68%).

$^1$H-NMR (CDCl$_3$) δ: 7.69 (1H, s), 7.61 (1H, s), 7.39-7.36 (4H, m), 6.92-6.89 (4H, m), 5.23 (2H, s), 5.19 (2H, s), 4.19 (2H, t, J=6.7 Hz), 3.81 (6H, s), 2.90 (2H, br s), 2.60 (4H, br s), 1.77 (4H, br s).

Step (3): Compound X-1+Compound 5c→Compound 5d

Compound X-1 (932 mg, 1.00 mmol) and compound 5c (533 mg, 1.00 mmol) were used to synthesize the target compound in the same way as step 6 of Example 1.

Yielded amount: 158.9 mg, (14%)

$^1$H-NMR (D$_2$O) δ: 7.47 (1H, s), 7.40 (1H, s), 7.02 (1H, s), 5.81 (1H, d, J=4.8 Hz), 5.48 (1H, d, J=4.8 Hz), 5.04 (1H, d, J=14.3 Hz), 4.63-4.58 (1H, m), 4.32 (1H, d, J=14.2 Hz), 4.08 (1H, q, J=7.0 Hz), 3.89-3.49 (6H, m), 2.22 (4H, br s), 1.58 (3H, d, J=7.2 Hz), 1.52 (3H, s), 1.50 (3H, s).

Elem. Anal.: C32H33.8N7O12S2Na1.2 (H2O) 8.3
Calcd.: C, 40.47; H, 5.35; N, 10.32; S, 6.75; Na, 2.90(%).
Found: C, 40.39; H, 5.30; N, 10.59; S, 6.64; Na, 3.02(%).

Example 6: Synthesis of Compound I-6

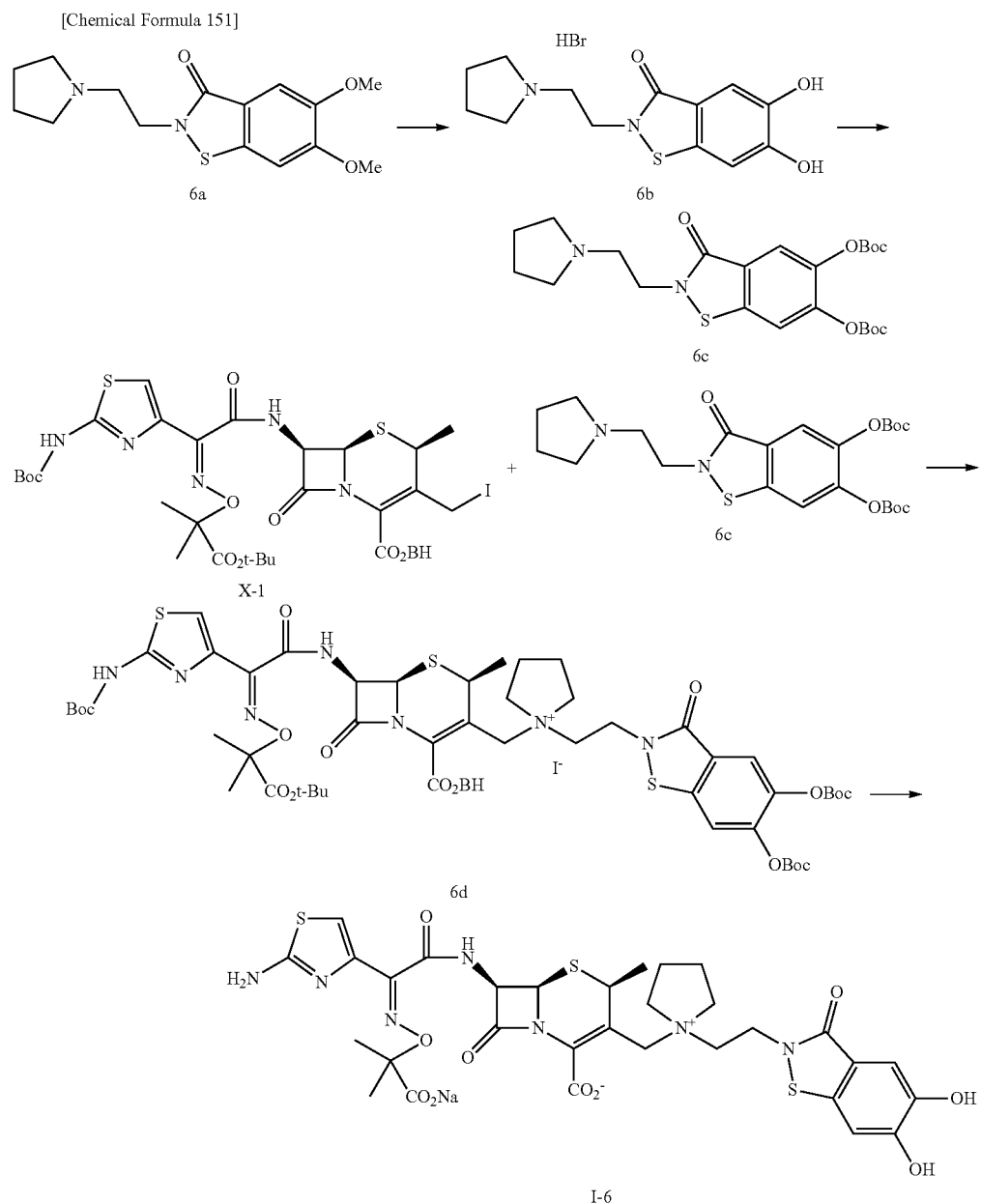

Step (1): Compound 6a→Compound 6b

Compound 6a (2.81 g, 9.11 mmol) was dissolved into dichloromethane (30 mL), and thereto was then added dropwise boron tribromide (2.5 ml, 26.4 mmol) at 0° C. The mixture was stirred at rt for 1 hour. Thereto was then added dropwise methanol (10 ml, 247 mmol) at 0° C. The mixture was stirred at 0° C. for 10 minutes. The reaction mixture was evaporated. In this way, compound 6b was yielded (5.53 g, 168%). Compound 6b yielded was used as it was, without being purified, in the next reaction.

Step (2): Compound 6b→Compound 6c

The total amount of compound 6b yielded (5.53 g, 9.11 mmol) and triethylamine (5.68 mL, 41.0 mmol) were dissolved into dichloromethane (30 mL), and thereto were then added di-t-butyl dicarbonate (6.35 ml, 27.3 mmol) and N,N-dimethyl-4-aminopyridine (0.06 g, 0.5 mmol) in turn at 0° C. The mixture was stirred at rt for 1 day. The reaction mixture was diluted with dichloromethane, washed with an aqueous sodium hydroxide solution, water and a saturated salt solution, and dried over magnesium sulfate. Magnesium sulfate was filtrated off, and then the liquid was concentrated under reduced pressure. The compound-containing liquid was subjected to silica gel column chromatography to elute out the desired compound with hexane/ethyl acetate (containing 3% triethyl amine). The desired-compound-containing fraction was concentrated under reduced pressure to yield compound 6c (1.27 g, 29%).

$^1$H-NMR (CDCl$_3$) δ: 7.89 (1H, s), 7.47 (1H, s), 4.00 (2H, t, J=6.0 Hz), 2.82 (2H, t, J=6.0 Hz), 2.62 (4H, br s), 1.82 (4H, br s), 1.56 (18H, s).

Step (3): Compound X-1+Compound 5c→Compound 5d

Compound X-1 (932 mg, 1.00 mmol) and compound 5c (481 mg, 1.00 mmol) were used to synthesize the target compound in the same way as step 6 of Example 1.

Yielded amount: 175.2 mg, (18%)

$^1$H-NMR (D$_2$O) δ: 7.33 (1H, s), 7.15 (1H, s), 7.02 (1H, s), 5.80 (1H, d, J=4.8 Hz), 5.46 (1H, d, J=4.8 Hz), 4.47-4.25 (3H, m), 4.04 (1H, br s), 3.72-3.47 (6H, m), 2.22 (4H, br s), 1.56-1.50 (9H, m).

Elem. Anal.: C31H34N7O10S3Na (H2O) 7.4

Calcd.: C, 40.60; H, 5.36; N, 10.69; S, 10.49; Na, 2.51 (%).

Found: C, 40.65; H, 5.22; N, 10.88; S, 10.20; Na, 2.51 (%).

Example 7: Synthesis of Compound I-7

[Chemical Formula 152]

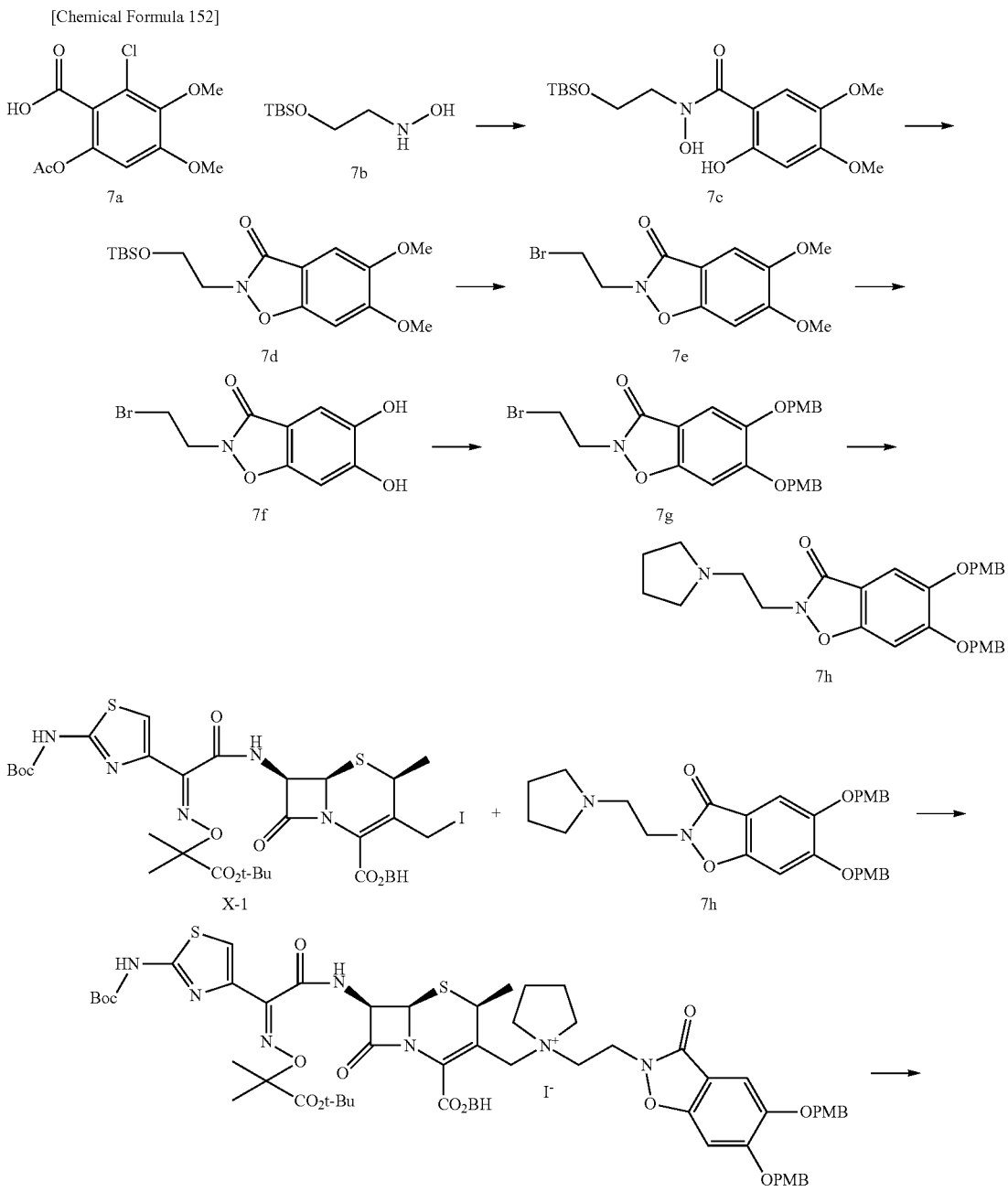

-continued

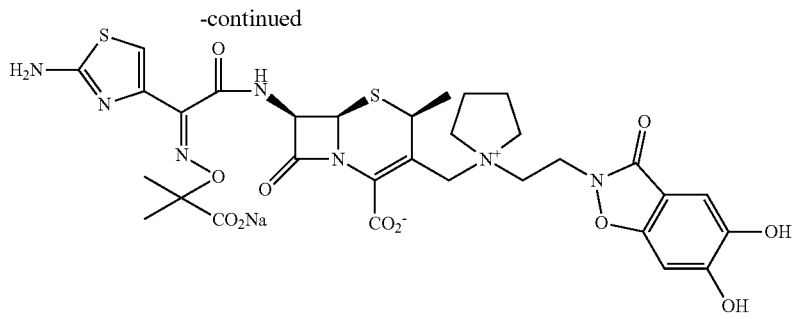

I-7

Step (1): Compound 7a+Compound 7b→Compound 7c

Compound 7a (10.0 g, 41.6 mmol) was suspended into dichloromethane (100 mL), and thereto was then added 1-chloro-N,N,2-trimethyl-1-propenylamine (6.1 mL, 45.8 mmol) at 0° C. The mixture was stirred at rt for 1 hour. The reaction mixture was added to the mixture of Compound 7b (23.90 g, 125 mmol) and sodium bicarbonate (17.65 g, 167 mmol) in tetrahydrofurane (100 ml) and water (100 ml) at 0° C. The mixture was stirred at rt for 1 hour. The reaction mixture was diluted with an aqueous hydrochloric acid solution (adjusted pH=5) and ethyl acetate, then separated and washed with water and a saturated salt solution, and dried over magnesium sulfate. Magnesium sulfate was filtrated off, and then the liquid was concentrated under reduced pressure. The compound-containing liquid was subjected to silica gel column chromatography to elute out the desired compound with hexane/ethyl acetate. The desired-compound-containing fraction was concentrated under reduced pressure to yield compound 7c (15.5 g, 101%).

$^1$H-NMR (CDCl$_3$) δ: 7.39 (1H, s), 6.51 (1H, s), 4.02-3.98 (4H, m), 3.89 (3H, s), 3.82 (3H, s), 0.89 (9H, s), 0.09 (6H, s).

Step (2): Compound 7c→Compound 7d

Compound 7c (14.5 g, 39.0 mmol) and triphenylphosphine (12.28 g, 46.8 mmol) were dissolved into tetrahydrofurane (150 mL), and thereto was then added dropwise dimethyl azodicarboxylate (2.7 mol/L in toluene, 17.35 ml, 46.8 mmol) at 0° C. The mixture was stirred at rt for 2 hour. Thereto was then added dropwise a mixture of acetic acid and methanol (1:1) at 0° C. The mixture was stirred at 0° C. for 10 minutes. The reaction mixture was diluted with a saturated sodium hydrogen carbonate solution and toluene, then separated and washed with a saturated salt solution, and dried over magnesium sulfate. Magnesium sulfate was filtrated off, and then the liquid was concentrated under reduced pressure. The residue was dissolved into toluene (150 mL) and hexane (100 ml) and stored at −20° C. for overnight. The reaction mixture was filtered and washed with toluene/hexane (1/1).

The compound-containing liquid was subjected to silica gel column chromatography to elute out the desired compound with hexane/ethyl acetate. The desired-compound-containing fraction was concentrated under reduced pressure to yield compound 7d (6.37 g, 46%).

$^1$H-NMR (CDCl$_3$) δ: 7.17 (1H, s), 6.67 (1H, s), 4.11 (2H, t, J=5.8 Hz), 3.95 (3H, s), 3.93-3.90 (5H, m), 0.83 (9H, s), −0.01 (6H, s).

Step (3): Compound 7d→Compound 7e

Triphenylphosphine (7.09 g, 27.0 mmol) was dissolved into dichloromethane (60 ml), and thereto was then added dropwise bromine (1.30 ml, 25.3 mmol) at 0° C. The mixture was stirred at rt for 20 min. Thereto was then added a solution of Compound 7d (6.37 g, 18.0 mmol) in dichloromethane (20 ml) at 0° C. The resulting mixture was stirred at rt. for 2 hr. The reaction mixture was diluted with water and dichloromethane, then separated and washed with a saturated sodium hydrogen carbonate solution and a saturated salt solution, and dried over magnesium sulfate. Magnesium sulfate was filtrated off, and then the liquid was concentrated under reduced pressure. The compound-containing liquid was subjected to silica gel column chromatography to elute out the desired compound with hexane/ethyl acetate. The desired-compound-containing fraction was concentrated under reduced pressure to yield compound 7e (4.41 g, 81%).

$^1$H-NMR (CDCl$_3$) δ: 7.17 (1H, s), 6.69 (1H, s), 4.37 (2H, t, J=6.8 Hz), 3.96 (3H, s), 3.91 (3H, s), 3.64 (2H, t, J=6.8 Hz).

Step (4): Compound 7e→Compound 7f

Compound 7e (4.41 g, 14.6 mmol) was used to synthesize the target compound in the same way as step 1 of Example 1.

Yielded amount: 3.80 g, (95%)

$^1$H-NMR (DMSO-D$_6$) δ: 9.91 (2H, br s), 6.94 (1H, s), 6.73 (1H, s), 4.24 (2H, br s), 3.76 (2H, br s).

Step (5): Compound 7f→Compound 7g

Compound 7f (3.80 g, 13.87 mmol) was used to synthesize the target compound in the same way as step 2 of Example 1.

Yielded amount: 7.25 g, (102%)

$^1$H-NMR (CDCl$_3$) δ: 7.36-7.33 (4H, m), 7.23 (1H, s), 6.93-6.87 (4H, m), 6.71 (1H, s), 5.13 (2H, s), 5.06 (2H, s), 4.33 (2H, t, J=6.8 Hz), 3.82 (3H, s), 3.81 (3H, s), 3.60 (2H, t, J=6.8 Hz).

Step (6): Compound 7g→Compound 7h

Compound 7g (3.50 g, 6.80 mmol) was dissolved into dimethylacetoamide (35 ml), and thereto were then added pyrrolidine (1.13 ml, 13.61 mmol) and sodium iodide (1.02 g, 6.80 mmol) at 0° C. The mixture was stirred at rt for 1 day. The reaction mixture was diluted with ethyl acetate and an aqueous sodium hydroxide solution, then separated and washed with water and a saturated salt solution, and dried over magnesium sulfate. Magnesium sulfate was filtrated off, and then the liquid was concentrated under reduced pressure. The compound-containing liquid was subjected to amino silica gel column chromatography to elute out the desired compound with hexane/ethyl acetate. The desired-compound-containing fraction was concentrated under reduced pressure to yield compound 7h (0.62 g, 18%).

$^1$H-NMR (CDCl$_3$) δ: 7.36-7.33 (4H, m), 7.22 (1H, s), 6.92-6.86 (4H, m), 6.70 (1H, s), 5.12 (2H, s), 5.06 (2H, s), 4.08 (2H, t, J=6.7 Hz), 3.82 (3H, s), 3.81 (3H, s), 2.84 (2H, t, J=6.7 Hz), 2.57 (4H, br s), 1.76 (4H, br s).

Step (7): Compound X-1+Compound 7h→Compound 7i

Compound X-1 (932 mg, 1.00 mmol) and compound 7h (505 mg, 1.00 mmol) were used to synthesize the target compound in the same way as step 6 of Example 1.

Yielded amount: 292.8 mg, (33%)

$^1$H-NMR (D$_2$O) δ: 7.13 (1H, s), 7.01 (1H, s), 6.83 (1H, s), 5.81 (1H, d, J=4.8 Hz), 5.46 (1H, d, J=4.8 Hz), 5.05 (1H, d, J=14.3 Hz), 4.62-4.45 (2H, m), 4.29 (1H, d, J=14.3 Hz), 4.06 (1H, q, J=7.0 Hz), 3.91-3.71 (3H, m), 3.58 (2H, br s), 3.51-3.44 (1H, m), 2.22 (4H, br s), 1.56 (3H, d, J=7.0 Hz), 1.52 (3H, s), 1.50 (3H, s).

Elem. Anal.: C31H34N7O11S2Na (H2O) 5.7
Calcd.: C, 42.77; H, 5.26; N, 11.26; S, 7.37; Na, 2.64(%).
Found: C, 42.50; H, 5.22; N, 11.55; S, 7.40; Na, 2.70(%).

Example 8: Synthesis of Compound I-8

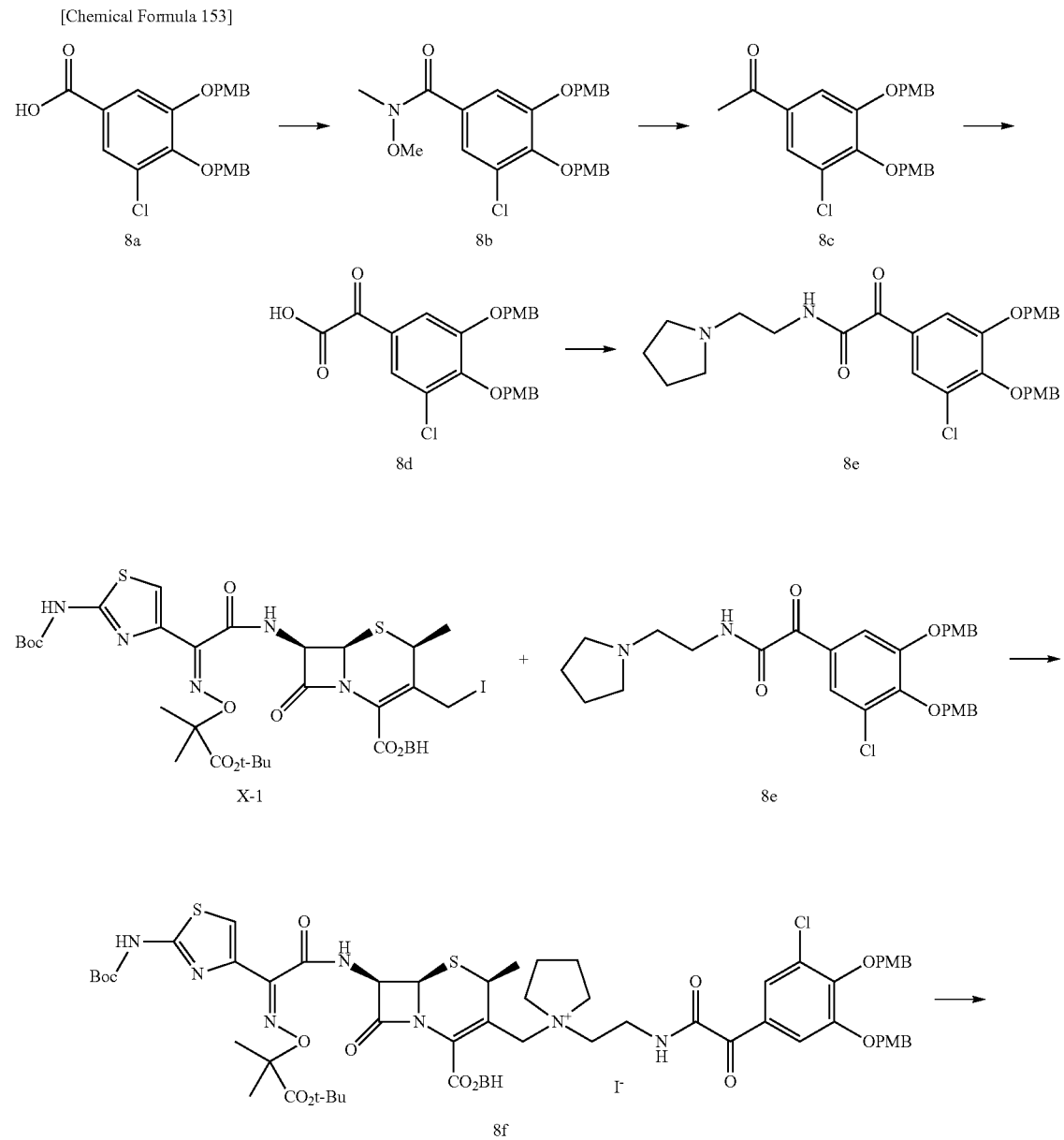

[Chemical Formula 153]

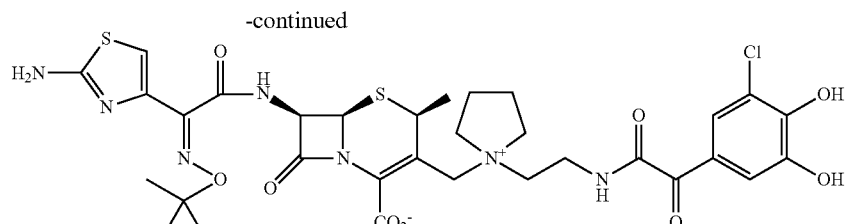

I-8

Step (1): Compound 8a→Compound 8b

Compound 8a (21.4 g, 50 mmol) was used to synthesize the target compound in the same way as step 1 of Example 3.

Yielded amount: 21.27 g, (90%)
$^1$H-NMR (CDCl$_3$) δ: 7.40 (1H, d, J=1.9 Hz), 7.37-7.33 (4H, m), 7.29 (1H, d, J=1.9 Hz), 6.92 (2H, d, J=8.7 Hz), 6.83 (2H, d, J=8.5 Hz), 5.07 (2H, s), 5.03 (2H, s), 3.83 (3H, s), 3.80 (3H, s), 3.52 (3H, s), 3.34 (3H, s).

Step (2): Compound 8b→Compound 8c

Compound 8b (21.27 g, 45 mmol) was used to synthesize the target compound in the same way as step 2 of Example 3.

Yielded amount: 17.17 g, (89%)
$^1$H-NMR (CDCl$_3$) δ: 7.58 (1H, d, J=2.0 Hz), 7.52 (1H, d, J=2.0 Hz), 7.38 (2H, d, J=8.7 Hz), 7.32 (2H, d, J=8.7 Hz), 6.93 (2H, d, J=8.7 Hz), 6.82 (2H, d, J=8.7 Hz), 5.09 (2H, s), 5.07 (2H, s), 3.83 (3H, s), 3.80 (3H, s), 2.54 (3H, s).

Step (3): Compound 8c→Compound 8d

Compound 8c (21.27 g, 45 mmol) was used to synthesize the target compound in the same way as step 3 of Example 3.

Yielded amount: 17.58 g, (96%)
$^1$H-NMR (DMSO-D$_6$) δ: 7.64 (1H, s), 7.57 (1H, s), 7.46 (2H, d, J=7.1 Hz), 7.28 (2H, d, J=7.3 Hz), 6.99 (2H, d, J=7.3 Hz), 6.86 (2H, d, J=7.1 Hz), 5.21 (2H, s), 5.09 (2H, s), 3.78 (3H, s), 3.74 (3H, s).

Step (4): Compound 8d→Compound 8e

Compound 8d (2.28 g, 5.0 mmol) and diisopropylethylamine (1.3 ml, 7.5 mmol) were dissolved into dichloromethane (20 mL), and thereto was then added diphenyl chlorophosphate (1.6 ml, 7.5 mmol) at 0° C. The mixture was stirred at 0° C. for 1 hour. Thereto was then added aminoethylpyrrolidine (0.7 ml, 5.5 mmol) at 0° C. The mixture was stirred at rt for 2 hours. The reaction mixture was diluted with ethyl acetate, washed with an aqueous sodium hydroxide solution, water and a saturated salt solution, and dried over magnesium sulfate. Magnesium sulfate was filtrated off, and then the liquid was concentrated under reduced pressure. The compound-containing liquid was subjected to silica gel column chromatography to elute out the desired compound with hexane/ethyl acetate (containing 3% triethyl amine). The desired-compound-containing fraction was concentrated under reduced pressure to yield compound 8e (0.58 g, 21%).

$^1$H-NMR (CDCl$_3$) δ: 8.11 (1H, s), 8.00 (1H, s), 7.50 (1H, br s), 7.38 (2H, d, J=7.7 Hz), 7.31 (2H, d, J=7.7 Hz), 6.93 (2H, d, J=7.7 Hz), 6.82 (2H, d, J=7.7 Hz), 5.10 (4H, s), 3.83 (3H, s), 3.79 (3H, s), 3.47 (2H, t, J=6.0 Hz), 2.68 (2H, t, J=6.0 Hz), 2.55 (4H, br s), 1.79 (4H, br s).

Step (5): Compound X-1+Compound 8e→Compound 8f

Compound X-1 (932 mg, 1.00 mmol) and compound 8e (553 mg, 1.00 mmol) were used to synthesize the target compound in the same way as step 6 of Example 1.

Yielded amount: 434.5 mg, (44%)
$^1$H-NMR (D$_2$O) δ: 7.73 (1H, s), 7.39 (1H, s), 7.03 (1H, s), 5.80 (1H, d, J=4.6 Hz), 5.48 (1H, d, J=4.6 Hz), 4.28 (1H, d, J=13.8 Hz), 4.14-4.08 (1H, m), 3.99-3.92 (1H, m), 3.85-3.79 (1H, m), 3.74-3.69 (1H, m), 3.58 (5H, br s), 2.24 (4H, br s), 1.58 (3H, d, J=6.4 Hz), 1.52 (3H, s), 1.50 (3H, s).

Elem. Anal.: C32H34.8ClN7O11S2Na1.2 (H2O) 5.5
Calcd.: C, 41.79; H, 5.02; Cl, 3.85; N, 10.66; S, 6.97; Na, 3.00(%).
Found: C, 41.69; H, 4.95; Cl, 3.83; N, 10.81; S, 7.10; Na, 2.96(%).

Example 9: Synthesis of Compound I-9

[Chemical Formula 154]

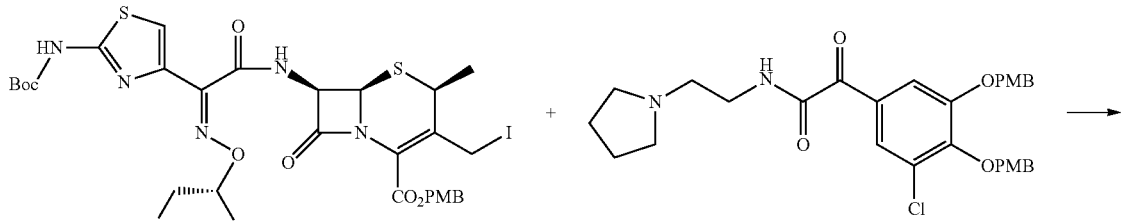

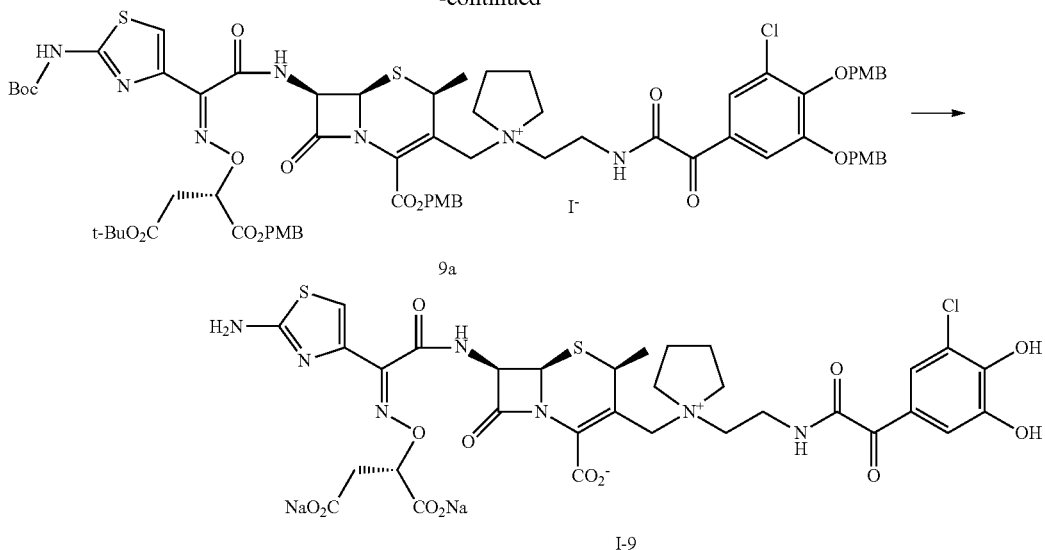

Step (1): Compound X-4+Compound 8e→Compound I-9

Compound X-4 (1082 mg, 1.00 mmol) and compound 8e (553 mg, 1.00 mmol) were used to synthesize the target compound in the same way as step 6 of Example 1.

Yielded amount: 414.9 mg, (38%)

$^1$H-NMR (D$_2$O) δ: 7.71 (1H, d, J=2.1 Hz), 7.37 (1H, d, J=2.1 Hz), 7.08 (1H, s), 5.74 (1H, d, J=4.6 Hz), 5.46 (1H, d, J=4.6 Hz), 5.09 (1H, d, J=14.2 Hz), 4.96 (1H, dd, J=9.9, 3.6 Hz), 4.27 (1H, d, J=14.2 Hz), 4.03 (1H, q, J=7.0 Hz), 3.98-3.91 (1H, m), 3.85-3.45 (7H, m), 2.77-2.64 (2H, m), 2.24 (4H, br s), 1.56 (3H, d, J=7.0 Hz).

Elem. Anal.: C32H31.4ClN7O13S2Na2.6 (H2O) 6.9

Calcd.: C, 38.22; H, 4.53; Cl, 3.53; N, 9.75; S, 6.38; Na, 5.94(%).

Found: C, 38.22; H, 4.53; Cl, 3.67; N, 9.84; S, 6.35; Na, 6.04(%).

Example 10: Synthesis of Compound I-10

[Chemical Formula 155]

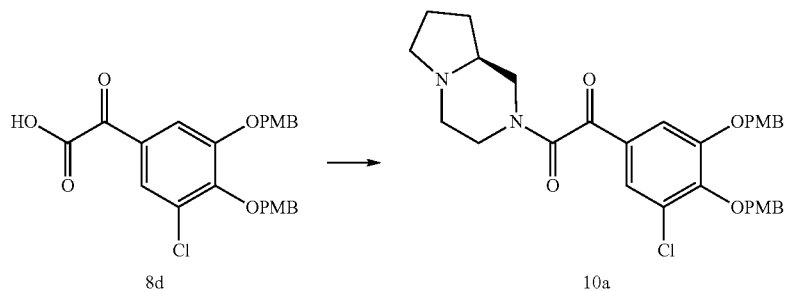

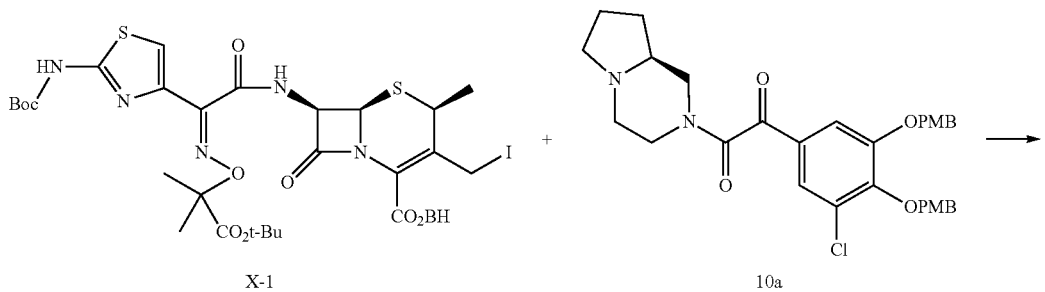

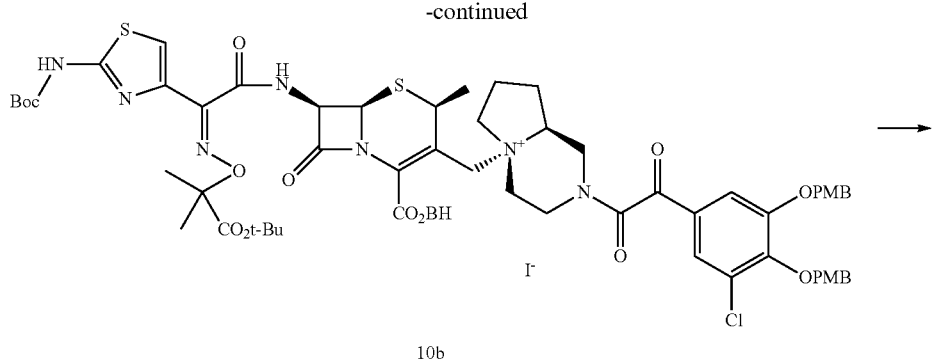

10b

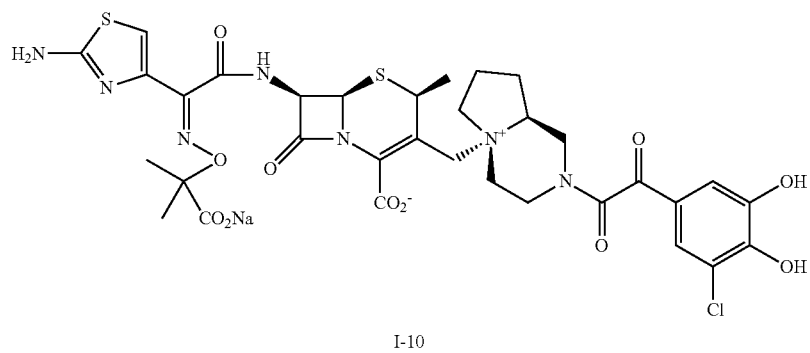

I-10

Step (1): Compound 8d→Compound 10a

Compound 8d (2.28 g, 5.00 mmol) was used to synthesize the target compound in the same way as step 5 of Example 8.

Yielded amount: 0.81 g, (29%)

$^1$H-NMR (CDCl$_3$) δ: 7.55 (1H, s), 7.52 (1H, s), 7.37 (2H, d, J=7.8 Hz), 7.30 (2H, d, J=7.8 Hz), 6.93 (2H, d, J=7.8 Hz), 6.82 (2H, d, J=7.8 Hz), 5.10 (4H, s), 4.78-4.61 (1H, m), 3.84 (3H, s), 3.80 (3H, s), 3.58-3.43 (1H, m), 3.29-2.96 (3H, m), 2.92-2.59 (1H, m), 2.28-2.12 (2H, m), 1.99-1.75 (4H, m), 1.51-1.31 (1H, m).

Step (2): Compound X-1+Compound 10a→Compound I-10

Compound X-1 (932 mg, 1.00 mmol) and compound 10a (565 mg, 1.00 mmol) were used to synthesize the target compound in the same way as step 6 of Example 1.

Yielded amount: 415.5 mg, (42%)

$^1$H-NMR (D$_2$O) δ: 7.58-7.56 (1H, m), 7.29 (1H, s), 7.02-7.01 (1H, m), 5.83-5.81 (1H, m), 5.46-5.44 (1H, m), 5.17-5.07 (1H, m), 4.37-4.25 (2H, m), 4.08-3.48 (8H, m), 2.50-2.00 (4H, m), 1.60-1.54 (3H, m), 1.53-1.52 (3H, m), 1.50-1.50 (3H, m).

Elem. Anal.: C33H34.5ClN7O11S2Na1.5 (H2O) 6.4

Calcd.: C, 41.52; H, 4.99; Cl, 3.71; N, 10.27; S, 6.72; Na, 3.61(%).

Found: C, 41.32; H, 5.00; Cl, 3.42; N, 10.56; S, 6.72; Na, 3.62(%).

Example 11: Synthesis of Compound I-11

[Chemical Formula 156]

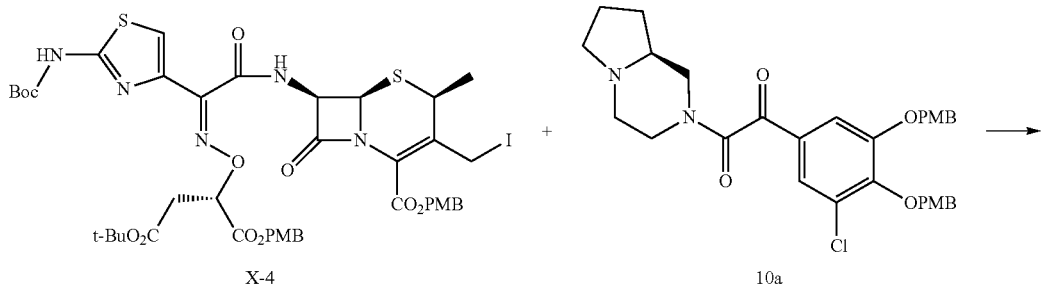

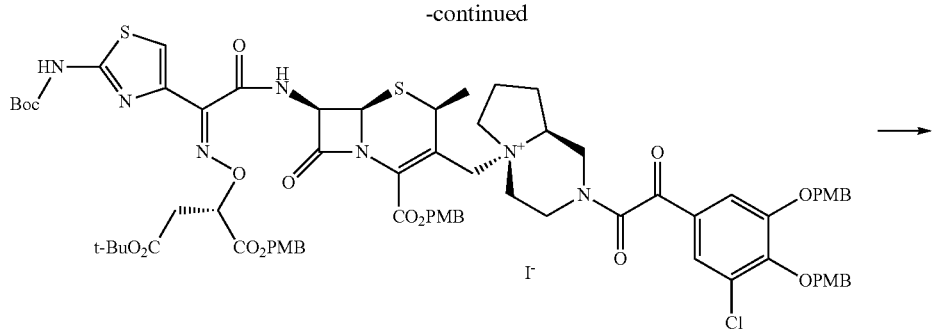
10b
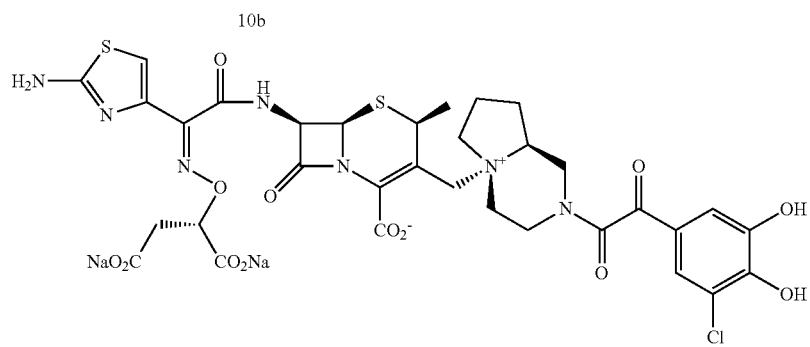
I-11
Step (1): Compound X-4+Compound 10a→Compound I-11
Compound X-4 (1082 mg, 1.00 mmol) and compound 10a (565 mg, 1.00 mmol) were used to synthesize the target compound in the same way as step 6 of Example 1.
Yielded amount: 379.3 mg, (35%)
$^1$H-NMR (D$_2$O) δ: 7.58-7.56 (1H, m), 7.26 (1H, s), 7.07-7.06 (1H, m), 5.78-5.76 (1H, m), 5.44-5.43 (1H, m), 5.22-5.10 (1H, m), 4.97-4.95 (1H, m), 4.39-4.27 (2H, m), 4.00-3.48 (8H, m), 2.76-2.64 (2H, m), 2.50-2.01 (4H, m), 1.59-1.53 (3H, m).
Elem. Anal.: C33H31.2ClN7O13S2Na2.8 (H2O) 8.2
Calcd.: C, 37.91; H, 4.59; Cl, 3.39; N, 9.38; S, 6.13; Na, 6.16(%).
Found: C, 37.92; H, 4.61; Cl, 3.41; N, 9.52; S, 6.02; Na, 6.21(%).
Example 12: Synthesis of Compound I-12
[Chemical Formula 157]
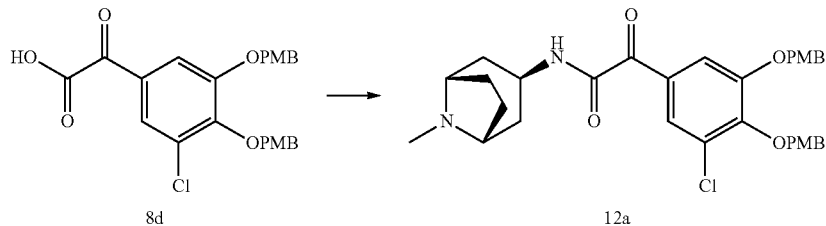
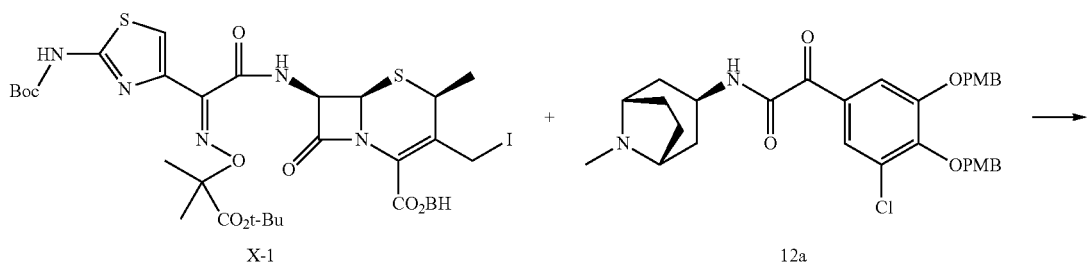

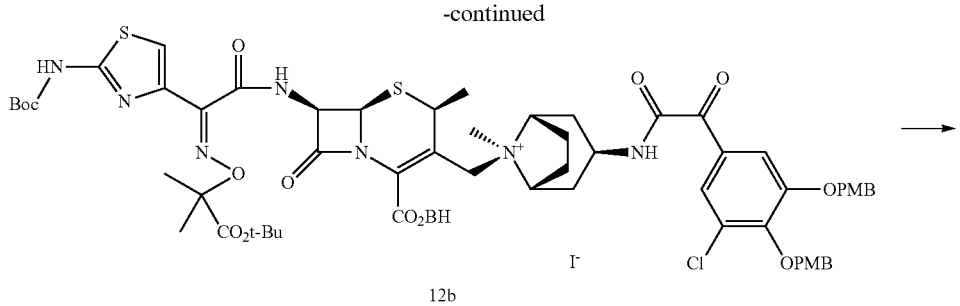

12b

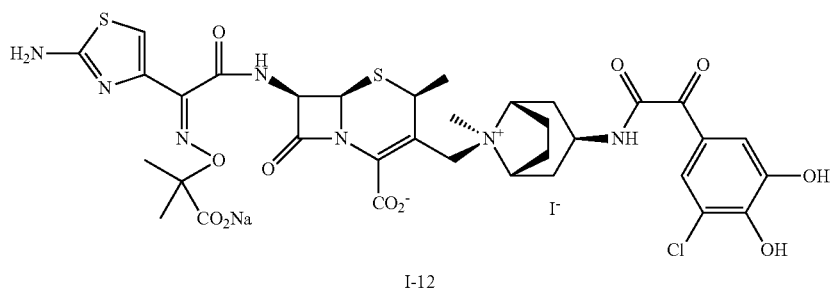

I-12

Step (1): Compound 8d→Compound 12a

Compound 8d (2.28 g, 5.00 mmol) was used to synthesize the target compound in the same way as step 4 of Example 8.

Yielded amount: 0.95 g, (33%)

$^1$H-NMR (CDCl$_3$) δ: 8.15 (1H, s), 8.08 (1H, s), 7.56 (1H, d, J=7.3 Hz), 7.38 (2H, d, J=8.1 Hz), 7.31 (2H, d, J=8.1 Hz), 6.93 (2H, d, J=8.1 Hz), 6.82 (2H, d, J=8.1 Hz), 5.10 (4H, s), 4.13 (1H, t, J=6.7 Hz), 3.83 (3H, s), 3.79 (3H, s), 3.19 (2H, br s), 2.30-2.17 (7H, m), 1.81-1.79 (2H, m), 1.72-1.69 (2H, m).

Step (2): Compound X-1+Compound 12a→Compound 12b

Compound X-1 (745 mg, 0.80 mmol) and compound 12a (463 mg, 0.80 mmol) were used to synthesize the target compound in the same way as step 6 of Example 1.

Yielded amount: 321 mg, (39%)

$^1$H-NMR (D$_2$O) δ: 7.65 (1H, d, J=2.3 Hz), 7.34 (1H, d, J=2.3 Hz), 7.03 (1H, s), 5.82 (1H, d, J=4.8 Hz), 5.47 (1H, d, J=4.8 Hz), 4.31-4.27 (1H, m), 4.12-4.05 (2H, m), 3.95 (1H, br s), 3.12-3.00 (3H, m), 2.86-2.74 (2H, m), 2.61-2.30 (4H, m), 2.19-2.15 (2H, m), 1.58 (3H, d, J=7.0 Hz), 1.53 (3H, s), 1.51 (3H, s).

Elem. Anal.: C34H36.8ClN7O11S2Na1.2 (H2O) 6.7

Calcd.: C, 42.21; H, 5.23; Cl, 3.66; N, 10.14; S, 6.63; Na, 2.85(%).

Found: C, 42.22; H, 5.26; Cl, 3.54; N, 10.28; S, 6.74; Na, 2.92(%).

Example 13: Synthesis of Compound I-13

[Chemical Formula 158]

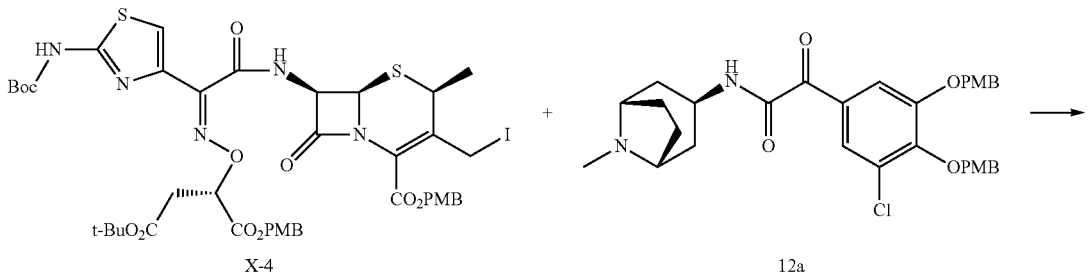

X-4  12a

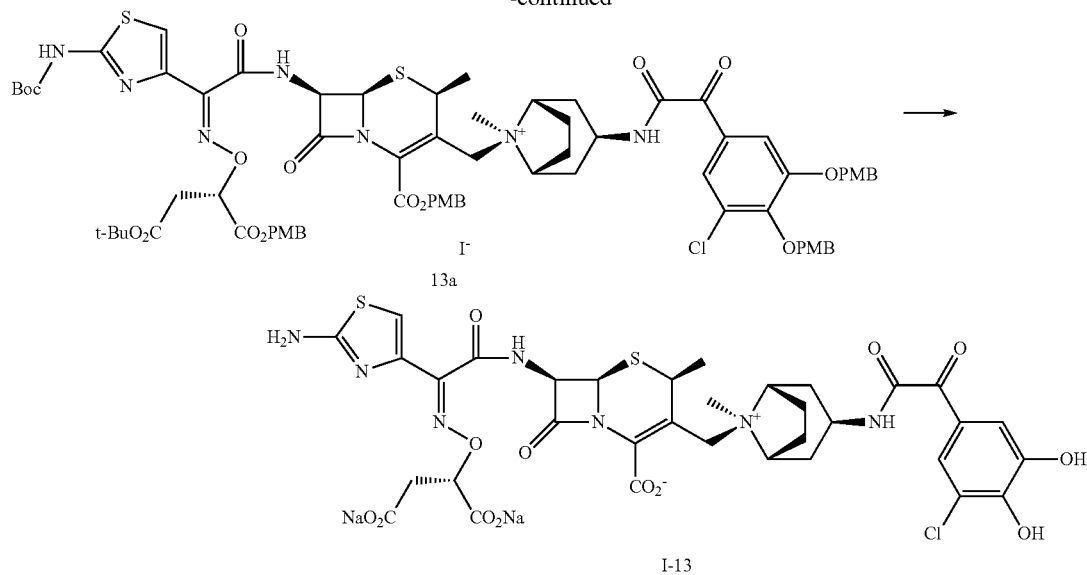

Step (1): Compound X-4+Compound 12a→Compound I-13

Compound X-4 (829 mg, 0.80 mmol) and compound 12a (463 mg, 0.80 mmol) were used to synthesize the target compound in the same way as in step 6 of Example 1.

Yielded amount: 370.4 mg, (41%)

$^1$H-NMR (D$_2$O) δ: 7.64 (1H, d, J=2.4 Hz), 7.32 (1H, d, J=2.4 Hz), 7.07 (1H, s), 5.77 (1H, d, J=4.6 Hz), 5.45 (1H, d, J=4.6 Hz), 4.96 (1H, dd, J=9.3, 4.0 Hz), 4.31-4.27 (1H, m), 4.09-4.02 (2H, m), 3.95 (2H, br s), 3.11-3.02 (3H, m), 2.86-2.65 (4H, m), 2.61-2.12 (7H, m), 1.56 (3H, d, J=7.0 Hz).

Elem. Anal.: C34H33.5ClN7O13S2Na2.5 (H2O) 7.5
Calcd.: C, 39.25; H, 4.70; Cl, 3.41; N, 9.42; S, 6.16; Na, 5.52(%).
Found: C, 39.51; H, 4.83; Cl, 3.68; N, 9.30; S, 5.78; Na, 5.46(%).

Example 14: Synthesis of Compound I-14

[Chemical Formula 159]

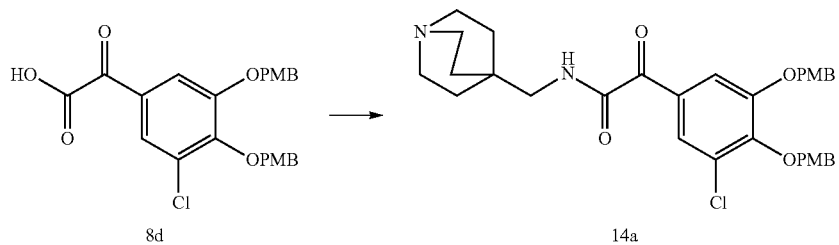

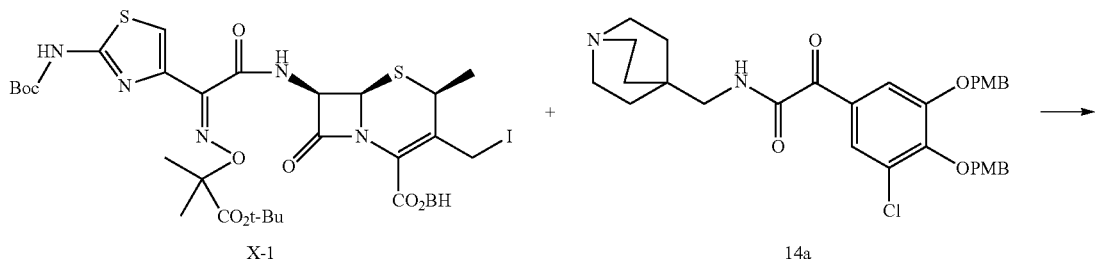

-continued

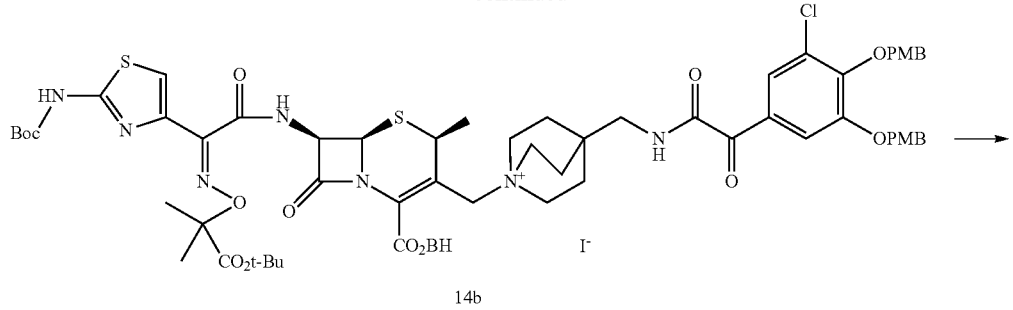

14b

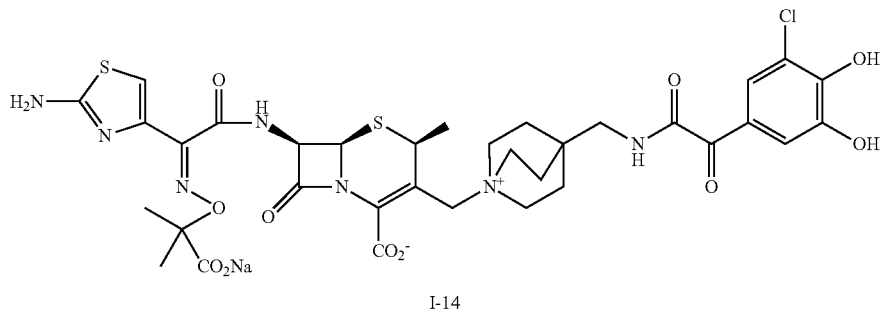

I-14

Step (1): Compound 8d→Compound 14a

Compound 8d (2.28 g, 5.00 mmol) was used to synthesize the target compound in the same way as step 4 of Example 8.

Yielded amount: 0.90 g, (31%)
$^1$H-NMR (DMSO-D$_6$) δ: 8.81 (1H, t, J=5.3 Hz), 7.64 (1H, s), 7.59 (1H, s), 7.45 (2H, d, J=7.1 Hz), 7.28 (2H, d, J=7.1 Hz), 6.99 (2H, d, J=7.1 Hz), 6.86 (2H, d, J=7.1 Hz), 5.18 (2H, s), 5.08 (2H, s), 3.78 (3H, s), 3.74 (3H, s), 3.02 (2H, d, J=5.3 Hz), 2.72 (6H, br s), 1.31 (6H, br s).

Step (2): Compound X-1+Compound 14a→Compound 14b

Compound X-1 (745 mg, 0.80 mmol) and compound 14a (450 mg, 0.78 mmol) were used to synthesize the target compound in the same way as in step 6 of Example 1.

Yielded amount: 447 mg, (%)
$^1$H-NMR (D$_2$O) δ: 7.66 (1H, d, J=2.0 Hz), 7.37 (1H, d, J=2.0 Hz), 7.00 (1H, s), 5.84 (1H, d, J=4.8 Hz), 5.44 (1H, d, J=4.8 Hz), 4.64 (1H, d, J=14.3 Hz), 4.08-4.05 (2H, m), 3.59-3.40 (6H, m), 3.36 (2H, s), 1.94 (6H, t, J=7.6 Hz), 1.56 (3H, d, J=7.2 Hz), 1.52 (3H, s), 1.51 (3H, s).

Example 15: Synthesis of Compound I-15

[Chemical Formula 160]

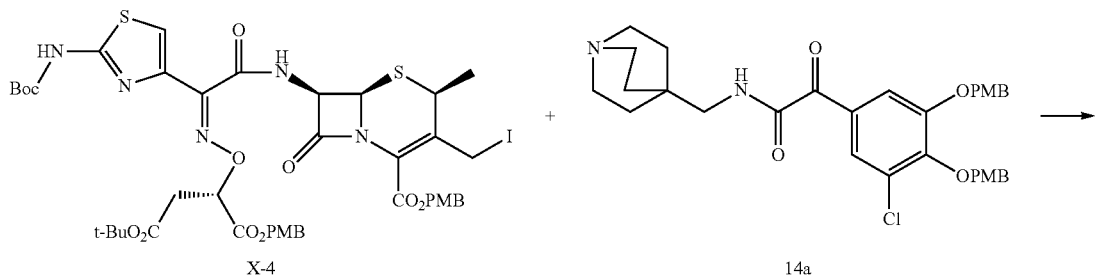

X-4        14a

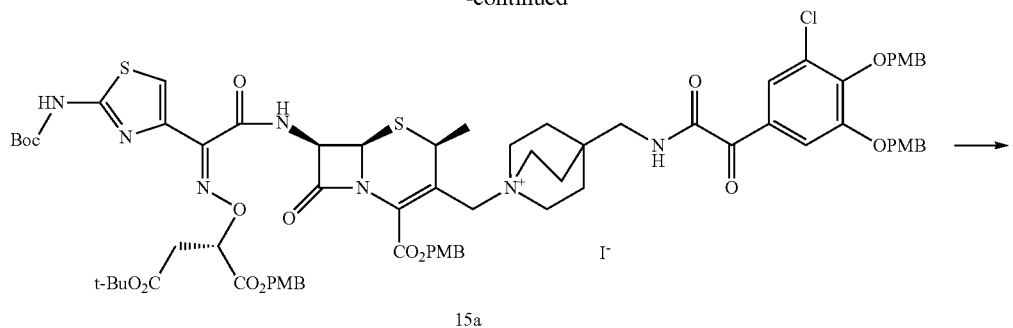
15a
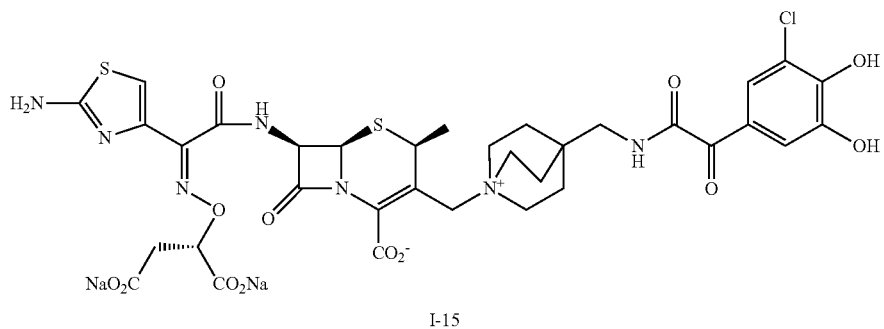
I-15
Step (1): Compound X-4+Compound 14a→Compound I-15
Compound X-4 (829 mg, 0.80 mmol) and compound 14a (450 mg, 0.78 mmol) were used to synthesize the target compound in the same way as in step 6 of Example 1.
Yielded amount: 388 mg
$^1$H-NMR (D$_2$O) δ: 7.67 (1H, d, J=2.3 Hz), 7.35 (1H, d, J=2.3 Hz), 7.05 (1H, s), 5.80 (1H, d, J=4.8 Hz), 5.43 (1H, d, J=4.8 Hz), 4.96 (1H, dd, J=9.2, 4.1 Hz), 4.68 (1H, d, J=14.2 Hz), 4.08-3.99 (2H, m), 3.60-3.43 (6H, m), 3.37 (2H, s), 2.74-2.71 (2H, m), 1.95 (6H, t, J=7.7 Hz), 1.55 (3H, d, J=7.0 Hz).
Example 16: Synthesis of Compound I-16
[Chemical Formula 161]
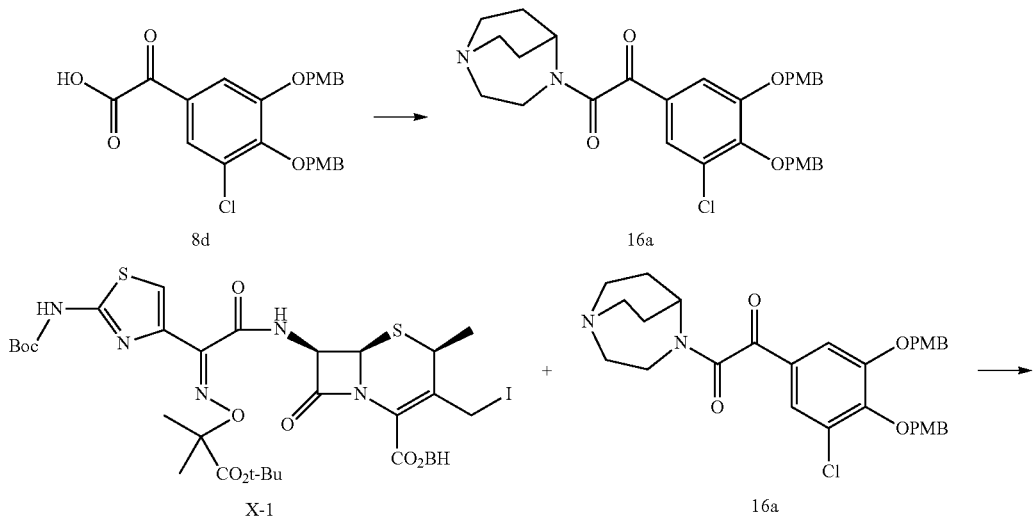

-continued

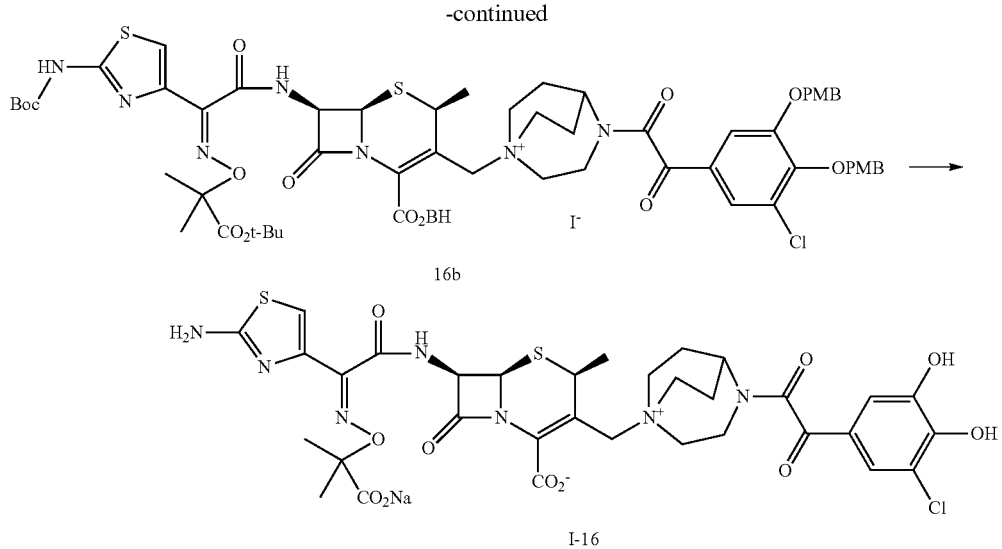

Step (1): Compound 8d→Compound 16a

Compound 8d (2.28 g, 5.00 mmol) was used to synthesize the target compound in the same way as step 4 of Example 8.

Yielded amount: 0.75 g, (27%)

$^1$H-NMR (DMSO-D$_6$) δ: 7.54 (1H, s), 7.46-7.44 (3H, m), 7.29 (2H, d, J=6.3 Hz), 7.00 (2H, d, J=6.3 Hz), 6.87 (2H, d, J=6.3 Hz), 5.22 (2H, s), 5.09 (2H, s), 4.54 (1H, s), 3.78-3.66 (8H, m), 3.01-2.78 (6H, m), 1.99-1.62 (4H, m).

Step (1): Compound X-1+Compound 16a→Compound I-16

Compound X-1 (606 mg, 0.65 mmol) and compound 16a (367 mg, 0.65 mmol) were used to synthesize the target compound in the same way as in step 6 of Example 1.

Yielded amount: 213.1 mg, (33%)

$^1$H-NMR (D$_2$O) δ: 7.54 (1H, s), 7.23 (1H, s), 7.00 (1H, s), 5.87-5.84 (1H, m), 5.47-5.45 (1H, m), 4.38-4.08 (4H, m), 3.88 (2H, br s), 3.82-3.46 (6H, m), 2.42-2.23 (4H, m), 1.61-1.57 (3H, m), 1.53-1.52 (3H, m), 1.51-1.50 (3H, m).

Elem. Anal.: C33H34.4ClN7O11S2Na1.6 (H2O) 6.7

Calcd.: C, 41.20; H, 5.01; Cl, 3.68; N, 10.19; S, 6.67; Na, 3.82(%).

Found: C, 40.92; H, 5.00; Cl, 3.48; N, 10.50; S, 6.87; Na, 3.77(%).

Example 17: Synthesis of Compound I-17

[Chemical Formula 162]

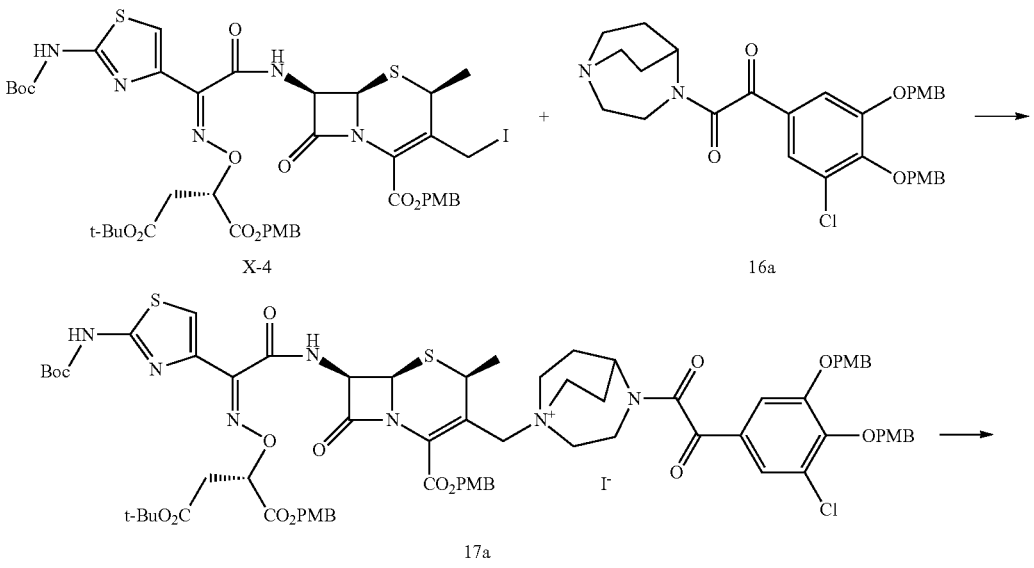

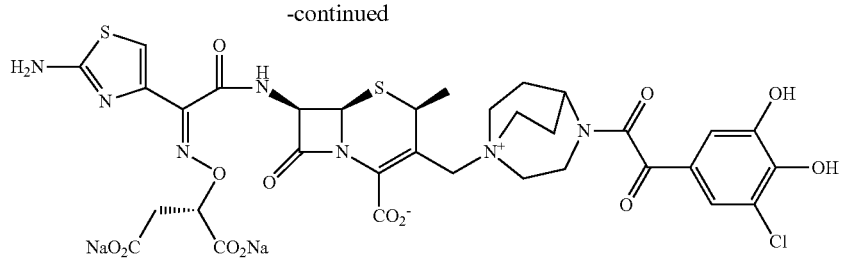
I-17
Step (1): Compound X-4+Compound 16a→Compound I-17
Compound X-4 (673 mg, 0.65 mmol) and compound 16a (367 mg, 0.65 mmol) were used to synthesize the target compound in the same way as step 6 of Example 1.
Yielded amount: 225.6 mg, (31%)
$^1$H-NMR (D$_2$O) δ: 7.54 (1H, s), 7.23 (1H, s), 7.04 (1H, s), 5.82-5.80 (1H, m), 5.44-5.43 (1H, m), 4.98-4.94 (1H, m), 4.38-4.07 (3H, m), 3.89 (2H, br s), 3.81-3.44 (6H, m), 2.75-2.65 (2H, m), 2.46-2.24 (4H, m), 1.60-1.56 (3H, m).
Elem. Anal.: C33H31ClN7O13S2Na3 (H2O) 7.9
Calcd.: C, 37.95; H, 4.52; Cl, 3.39; N, 9.39; S, 6.14; Na, 6.60(%).
Found: C, 37.93; H, 4.43; Cl, 3.34; N, 9.56; S, 6.18; Na, 6.59(%).
Example 18: Synthesis of Compound I-18
[Chemical Formula 163]
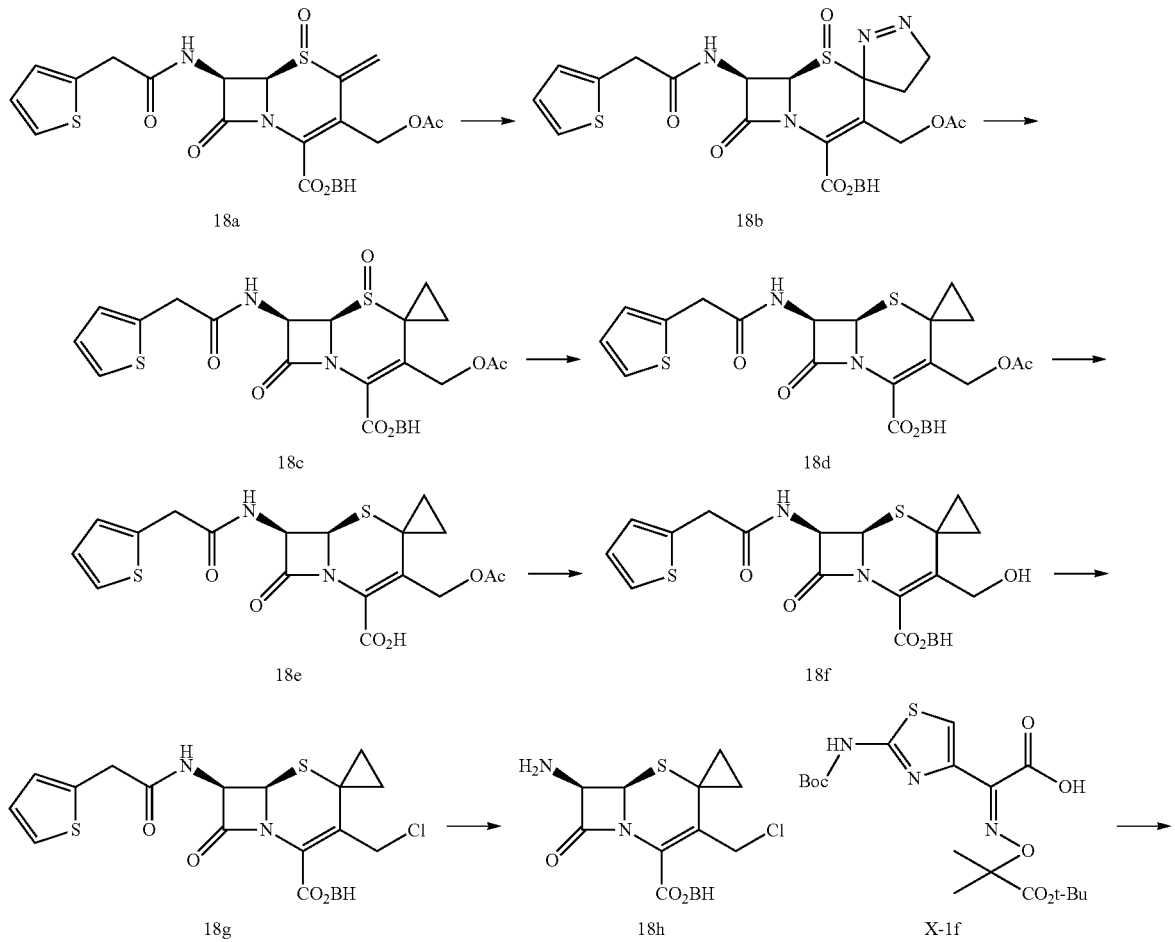

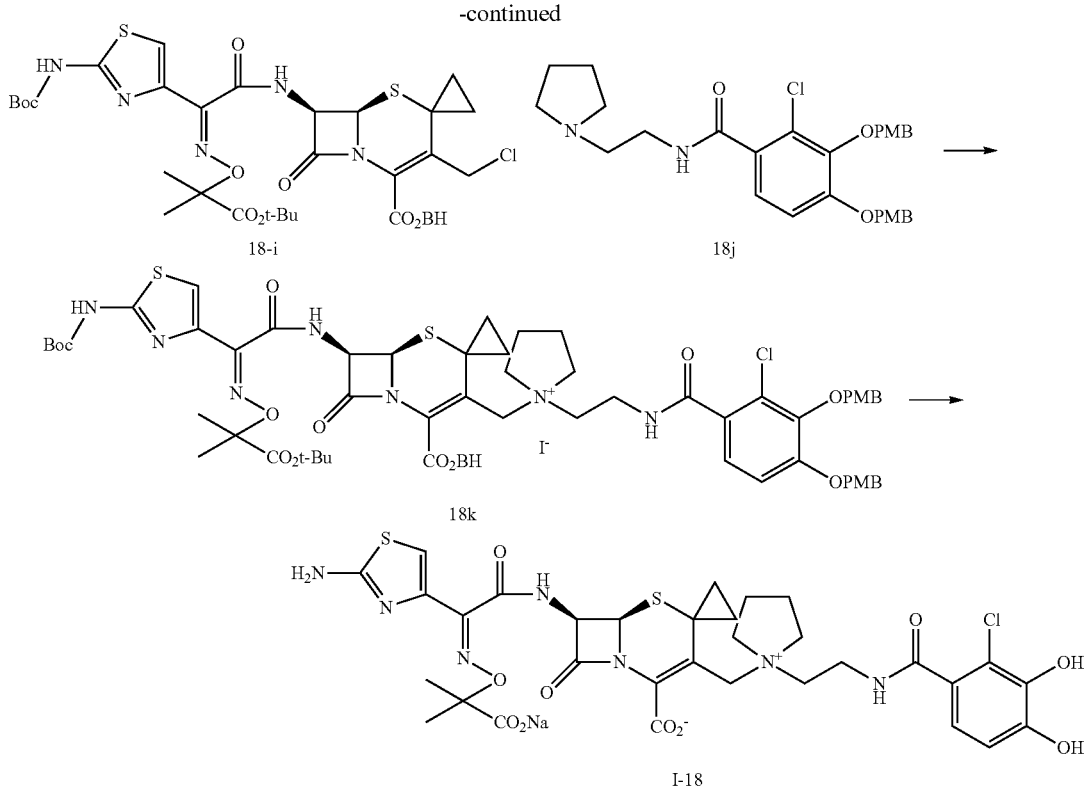

Step (1): Compound 18a→Compound 18b

Compound 18a (59.1 g, 100 mmol) which was synthesized according to the synthesis in U.S. Pat. No. 4,463,172A1 was dissolved into dichloromethane (600 ml) and thereto was then bubbled a diazomethane (170 mmol), prepared from N-methyl-N-nitroso-p-toluenesulfonamide (36.4 g, 170 mmol) at 0° C. The mixture was concentrated under reduced pressure. The precipitated solid was then collected by filtration, and washed with diisopropyl ether. In this way, compound 18b was yielded (64.98 g, 103%). Compound 18b yielded was used as it was, without being purified, in the next reaction.
MS (m+1)=633

Step (2): Compound 18b→Compound 18c

The total amount of compound 18b yielded (64.98 g, 100 mmol) was suspended into toluene (650 mL), and then stirred at 90° C. for 2 hours. The mixture was concentrated under reduced pressure. The compound-containing liquid was subjected to silica gel column chromatography to elute out the desired compound with chloroform/ethyl acetate. The desired-compound-containing fraction was concentrated under reduced pressure to yield compound 18c (23.5 g, 39%).
$^1$H-NMR (CDCl$_3$) δ: 7.41-7.29 (12H, m), 7.01-6.96 (3H, m), 6.85 (1H, d, J=10.0 Hz), 6.13 (1H, dd, J=10.0, 4.8 Hz), 4.87 (1H, d, J=12.8 Hz), 4.64 (1H, d, J=4.8 Hz), 4.38 (1H, d, J=12.8 Hz), 3.84 (2H, s), 1.91-1.75 (5H, m), 1.46-1.41 (1H, m), 0.92-0.86 (1H, m).

Step (3): Compound 18c→Compound 18d

Compound 18c (23.5 g, 39 mmol) was dissolved into dimethylacetoamide (230 ml) and thereto were then added potassium iodide (38.7 g, 233 mmol) and acetyl chloride (11.10 ml, 156 mmol) in turn at 0° C. The mixture was stirred at 0° C. for 4 hours. The reaction mixture was diluted with ethyl acetate and an aqueous sodium thiosulfate solution, then separated and washed with a saturated sodium hydrogen carbonate solution and a saturated salt solution, and dried over magnesium sulfate. Magnesium sulfate was filtrated off, and then the liquid was concentrated under reduced pressure. The compound-containing liquid was subjected to silica gel column chromatography to elute out the desired compound with hexane/ethyl acetate. The desired-compound-containing fraction was concentrated under reduced pressure to yield compound 18d (15.6 g, 68%).
$^1$H-NMR (CDCl$_3$) δ: 7.38-7.26 (11H, m), 7.03-6.95 (3H, m), 6.25-6.19 (1H, m), 5.93-5.89 (1H, m), 5.21-5.16 (1H, m), 4.44-4.35 (2H, m), 3.86-3.82 (2H, m), 1.95-1.91 (3H, m), 1.45-1.30 (3H, m), Step (4): Compound 18d→Compound 18e Compound 18d (15.6 g, 26.5 mmol) and anisole (5.79 mL, 53.0 mmol) were dissolved into dichloromethane (70 mL), and thereto was then added trifluoroacetic acid (70 mL) at 0° C. The mixture was stirred at 0° C. for 30 minutes. The reaction mixture was concentrated under reduced pressure. The precipitated solid was then collected by filtration, and washed with diisopropyl ether to yield compound 18e (10.5 g, 94%).
$^1$H-NMR (DMSO-D$_6$) δ: 13.66 (1H, s), 9.17 (1H, d, J=8.2 Hz), 7.38-7.35 (1H, m), 6.96-6.90 (2H, m), 5.81-5.78 (1H, m), 5.29-5.26 (1H, m), 4.48 (2H, s), 3.74 (2H, s), 2.00 (3H, s), 1.54-1.41 (2H, m), 1.35-1.30 (1H, m), 0.95-0.90 (1H, m).

Step (5): Compound 18e→Compound 18f

Compound 18e (8.9 g, 21.1 mmol) and sodium hydrogen carbonate (2.3 g, 27.4 mmol) were dissolved into boronic acid-ammonia buffer (150 mL, pH=8), and thereto was then added CAH immobilized enzyme (8.90 ml, 21.07 mmol) at rt (pH was adjusted ca.8 with 7% NH3 aq.). The mixture was stirred at rt for 5 hours (pH was adjusted ca.8 with 7% NH3 aq.). The reaction mixture was diluted with acetone (300 ml), then pH was adjusted ca. 3 with 2N HCl at 0° C. The reaction mixture was filtered and washed with acetone. To the filtrate diphenyl diazomethane (9.00 g, 46.3 mmol) in Acetone (10 ml) was added at 0° C. The resulting mixture was stirred at 0° C. for 2 hr. The reaction mixture was concentrated under reduced pressure. The precipitated solid was then collected by filtration, and washed with water and diisopropyl ether to yield compound 18f (10.19 g, 89%).

$^1$H-NMR (CDCl$_3$) δ: 7.42-7.28 (11H, m), 7.01 (1H, dd, J=5.1, 3.6 Hz), 6.96 (1H, d, J=3.3 Hz), 6.91 (1H, s), 6.22 (1H, d, J=8.9 Hz), 5.94 (1H, dd, J=9.0, 4.8 Hz), 5.12 (1H, d, J=4.8 Hz), 3.99 (1H, dd, J=12.8, 3.9 Hz), 3.84 (2H, s), 3.27-3.21 (1H, m), 2.61 (1H, dd, J=11.2, 3.9 Hz), 1.77-1.71 (1H, m), 1.39-1.31 (2H, m), 1.05-1.01 (1H, m).

Step (6): Compound 18f→Compound 18g

Compound 18f (10.2 g, 18.6 mmol) was suspended into dichloromethane (100 mL), and thereto were then added 2,6-lutidine (8.7 ml, 74.6 mmol) and triphosgene (2.8 g, 9.3 mmol) in turn at 0° C. The mixture was stirred at rt for 2 hours. The mixture was diluted with an aqueous hydrochloric acid solution and ethyl acetate, then separated and washed with a saturated sodium hydrogen carbonate and a saturated salt solution, and dried over magnesium sulfate. Magnesium sulfate was filtrated off, and then the liquid was concentrated under reduced pressure. The compound-containing liquid was subjected to silica gel column chromatography to elute out the desired compound with chloroform/ethyl acetate. The desired-compound-containing fraction was concentrated under reduced pressure to yield compound 18g (5.63 g, 53%).

$^1$H-NMR (CDCl$_3$) δ: 7.42-7.26 (11H, m), 7.02-6.95 (3H, m), 6.23 (1H, d, J=8.8 Hz), 5.90 (1H, dd, J=8.8, 4.9 Hz), 5.18 (1H, d, J=4.9 Hz), 4.15 (1H, d, J=11.8 Hz), 3.83 (2H, s), 3.77 (1H, d, J=11.8 Hz), 1.75-1.69 (1H, m), 1.45-1.38 (2H, m), 1.04-0.98 (1H, m).

Step (7): Compound 18g→Compound 18h

Phosphorus pentachloride (2.08 g, 10 mmol) was suspended into dichloromethane (30 mL), and thereto were then added pyridine (0.89 ml, 11 mmol) and compound 18g (2.83 g, 5.0 mmol) in turn at 0° C. The mixture was stirred at 0° C. for 1 hour. Thereto was then added methanol (6.1 mL, 150 mmol) at −40° C. The mixture was stirred at rt for 30 minutes. The mixture was diluted with water and dichloromethane, then separated and washed with a saturated sodium hydrogen carbonate solution and a saturated salt solution, and dried over magnesium sulfate. Magnesium sulfate was filtrated off, and then the liquid was concentrated under reduced pressure to yield compound 18h (2.98 g, 135%). Compound 18h yielded was used as it was, without being purified, in the next reaction.

MS (m+1)=633

Step (8): Compound X-1f+Compound 18h→Compound 18i

Compound 18h and compound X-1f were dissolved into dichloromethane (25 mL), and thereto were then added phenyl phosphorodichloridate (1.121 ml, 7.50 mmol) and NMM (1.924 ml, 17.50 mmol) in turn at −40° C. The mixture was stirred at −40~−20° C. for 1 hour. The mixture was diluted with a 0.2 mol/L aqueous hydrochloric acid solution and ethyl acetate, then separated and washed with a saturated sodium hydrogen carbonate and a saturated salt solution, and dried over magnesium sulfate. Magnesium sulfate was filtrated off, and then the liquid was concentrated under reduced pressure. The compound-containing liquid was subjected to silica gel column chromatography to elute out the desired compound with hexane/ethyl acetate. The desired-compound-containing fraction was concentrated under reduced pressure to yield compound 18i (2.28 g, 54%).

$^1$H-NMR (CDCl$_3$) δ: 8.23 (1H, d, J=8.7 Hz), 7.45-7.30 (13H, m), 7.00 (1H, s), 6.08 (1H, dd, J=8.7, 5.0 Hz), 5.29 (1H, d, J=5.0 Hz), 4.14 (1H, d, J=11.8 Hz), 3.81 (1H, d, J=11.8 Hz), 1.77-1.71 (1H, m), 1.53-1.37 (26H, m), 1.07-0.99 (1H, m).

Step (9): Compound 18i+Compound 18j→Compound I-18

Compound 18i (852 mg, 1.00 mmol), compound 18j (551 mg, 1.05 mmol) and sodium iodide (300 mg, 2.00 mmol) were used to synthesize the target compound in the same way as in step 6 of Example 1.

Yielded amount: 320.3 mg, (34%)

$^1$H-NMR (D$_2$O) δ: 6.93-6.91 (2H, m), 6.84 (1H, d, J=8.3 Hz), 5.66-5.63 (2H, m), 4.30 (1H, br s), 3.90-3.63 (9H, m), 2.28-2.16 (4H, m), 1.60-1.40 (9H, m), 1.22-1.17 (1H, m).

Elem. Anal.: C32H35ClN7O10S2Na (H2O) 5

Calcd.: C, 43.17; H, 5.09; Cl, 3.98; N, 11.01; S, 7.20; Na, 2.58(%).

Found: C, 43.12; H, 5.08; Cl, 4.24; N, 11.03; S, 7.08; Na, 2.47(%).

Example 19: Synthesis of Compound I-19

[Chemical Formula 164]

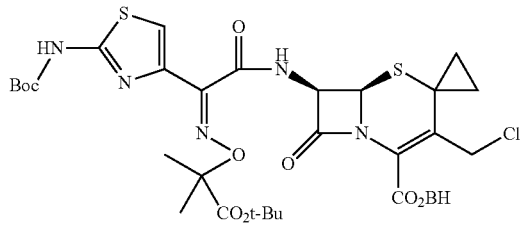

18i

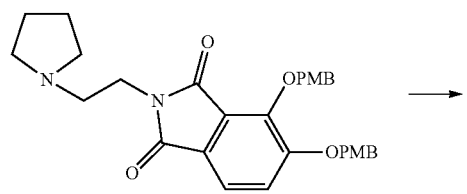

19a

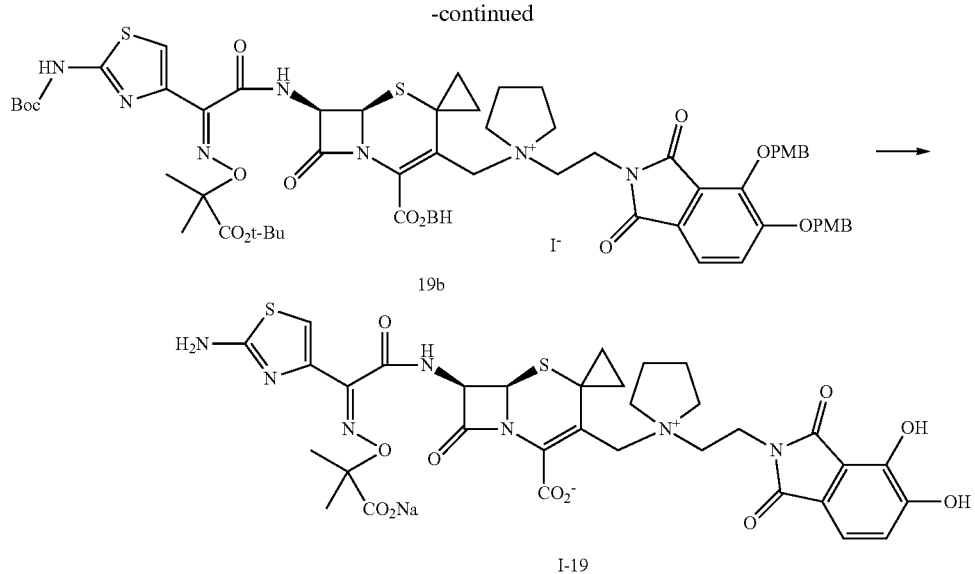
Step (1): Compound 18i+Compound 19a→Compound I-19
Compound 18i (852 mg, 1.00 mmol), compound 19a (542 mg, 1.05 mmol) and sodium iodide (300 mg, 2.00 mmol) were used to synthesize the target compound in the same way as step 6 of Example 1.
Yielded amount: 202.9 mg, (21%)
$^1$H-NMR (D$_2$O) δ: 7.12 (1H, d, J=7.5 Hz), 7.01 (1H, d, J=7.5 Hz), 6.94 (1H, s), 5.74-5.66 (2H, m), 4.36 (1H, br s), 4.09 (2H, br s), 3.94-3.58 (7H, m), 2.25-2.17 (4H, m), 1.63-1.43 (9H, m), 1.31-1.14 (1H, m).
Elem. Anal.: C33H34N7O11S2Na (H2O) 5.6
Calcd.: C, 44.40; H, 5.10; N, 10.98; S, 7.18; Na, 2.58(%).
Found: C, 44.40; H, 5.01; N, 11.02; S, 7.08; Na, 2.55(%).
Example 20: Synthesis of Compound I-20
[Chemical Formula 165]
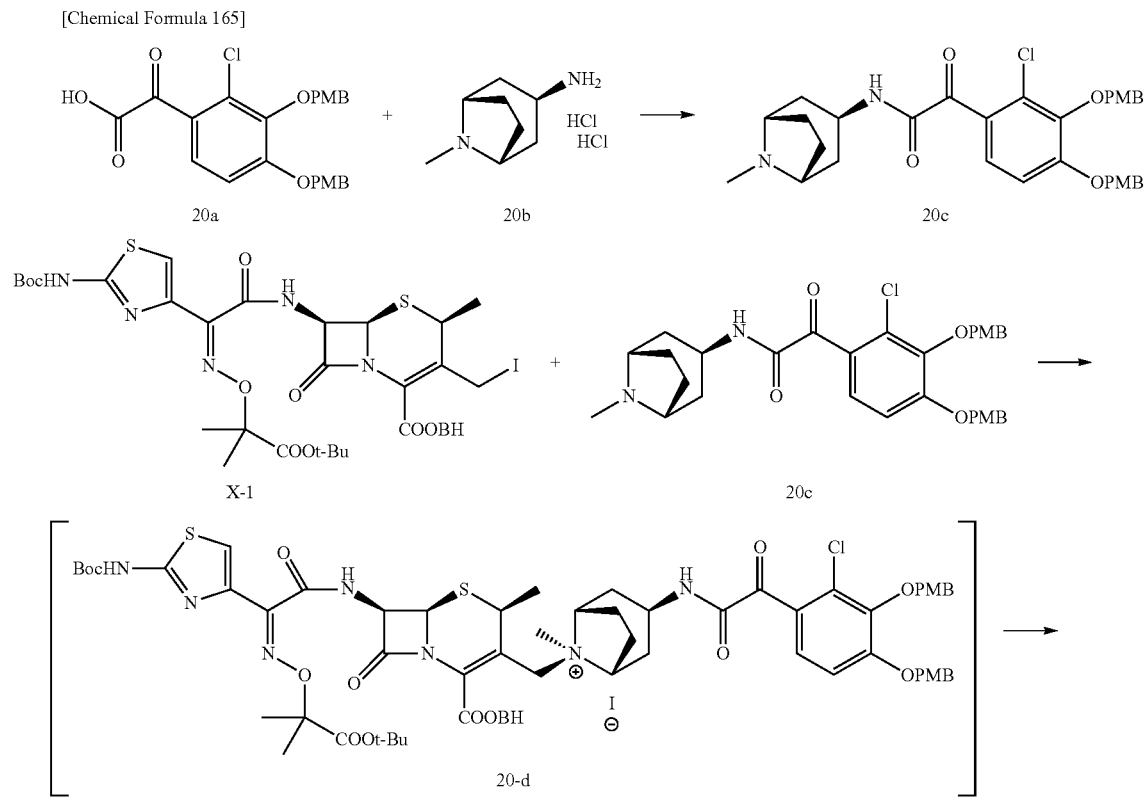

-continued

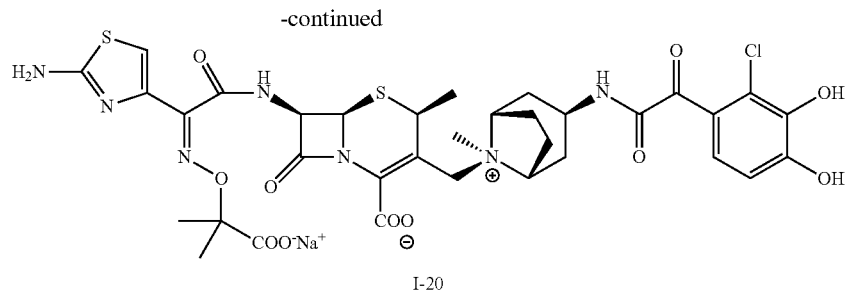

I-20

Step (1): Compound 20a+Compound 20b→Compound 20c

A solution of Compound 20a (1.00 g, 2.19 mmol) in 1 dichloromethane (10 mL) was cooled with ice, and thereto was added DIEA (573 µL, 3.28 mmol), and Diphenyl chlorophosphate (681 µL, 3.28 mmol). The liquid was stirred at 0° C. for 30 minutes.

A solution of Compound 20b (513 g, 2.41 mmol) in 1 dichloromethane (10 mL) was cooled with ice, and thereto was added triethylamine (698 µL, 5.03 mmol), and phosphate solution. After stirring at room temperature for 1 hour, aqueous sodium hydroxide was added to the reaction mixture, followed by extraction with ethyl acetate twice time. The combined organic layer was washed with water, then saturated brine, and then dried with anhydrous magnesium sulfate. The inorganic substance was removed by filtration, and then concentrated and subsequently drying under reduced pressure to yield Compound 20c as a yellow powder oil.

Yielded amount: 1.00 g (79%)

$^1$H-NMR (CDCl$_3$) δ: 1.75 (3H, d, J=14.56 Hz), 1.86 (2H, dd, J=15.31, 6.65 Hz), 2.18-2.21 (2H, m), 2.28-2.30 (2H, m), 2.33 (3H, s), 3.23 (2H, s), 3.80 (3H, s), 3.83 (3H, s), 4.96 (2H, s), 5.11 (2H, s), 6.83 (2H, d, J=8.53 Hz), 6.91-6.96 (3H, m), 7.33-7.36 (4H, m), 7.65 (1H, d, J=8.78 Hz).

Step (2): Compound X-1+Compound 20c→Compound 20d→Compound I-20

A solution of Compound 20c (579 mg, 1.0 mmol) in dimethylformamide (2.0 mL) was cooled with ice. The reaction vessel was then degassed under reduced pressure, and thereto was added Compound X-1 (932 mg, 1.0 mmol). After stirring at 0° C. for 7 hours, the reaction mixture was slowly added to 5% aqueous sodium chloride and sodium hydrogen sulfite cooled with ice. The precipitated solid was collected by filtration, washed with water, and suspended into water. The suspension was freeze-dried to yield Compound 20d as a brown solid. Compound 20d yielded was used as it was, without being purified, in the next reaction.

The total amount of compound 20d yielded was dissolved in dichloromethane (12 mL), and the solution was cooled to −40° C. Thereto were then added anisole (1.09 mL, 10 mmol) and a 2 mol/L aluminum chloride solution (5.0 mL, 10 mmol) in nitromethane in turn. The liquid was stirred at 0° C. for 30 minutes. To the reaction liquid were added diisopropyl ether and a small amount of water, and the resultant was stirred to generate a precipitate. The supernatant was removed by decantation. To the insoluble matter adhering to the vessel were added a diluted aqueous hydrochloric acid solution, and acetonitrile. The resultant was stirred to dissolve the matter completely. Thereto was then added diisopropyl ether, and the water phase was separated to be collected. The organic phase was again subjected to extraction with water, and then all of the resultant water phases were combined with each other. Thereto was added HP20-SS resin. Acetonitrile was then distilled off therefrom under reduced pressure. The resultant mixed liquid was purified by ODS column chromatography. The desired-compound-containing fraction was concentrated under reduced pressure, and then freeze-dried to yield compound I-20 as a yellow powder.

Yielded amount: 385 mg (43%)

$^1$H-NMR (D$_2$O) δ: 1.51 (3H, s), 1.53 (3H, s), 1.58 (3H, d, J=7.15 Hz), 2.17 (2H, d, J=16.81 Hz), 2.37-2.61 (5H, m), 2.71-2.85 (2H, m), 3.10 (3H, s), 3.95 (1H, s), 4.04-4.11 (3H, m), 4.24 (1H, t, J=7.53 Hz), 5.46 (1H, d, J=4.89 Hz), 5.83 (1H, d, J=4.89 Hz), 6.90 (1H, d, J=8.66 Hz), 7.02 (1H, s), 7.37 (1H, d, J=8.66 Hz).

MS (m+1)=820.28

Example 21: Synthesis of Compound I-21

[Chemical Formula 166]

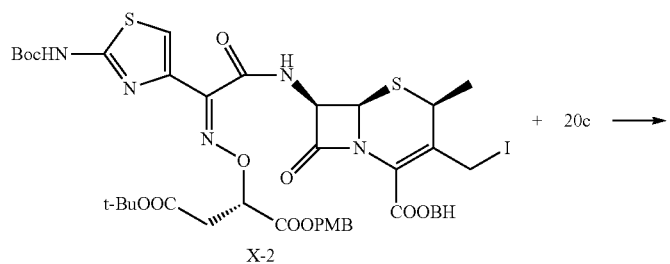

X-2

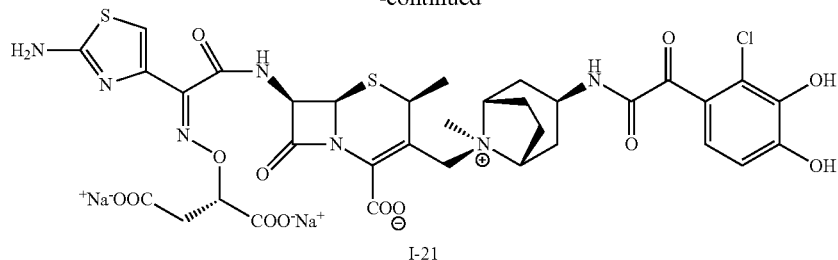

I-21

Step (1): Compound X-2+Compound 20c→Compound I-21

From Compound X-2 (1.082 g, 1.0 mmol) and Compound 20c (579 mg, 1.0 mmol), Compound I-21 was obtained as a yellow powder using the same method as Example 20.

Yield: 385 mg, (43%)

$^1$H-NMR (D$_2$O) δ: 1.56 (3H, d, J=7.15 Hz), 2.18 (2H, d, J=16.81 Hz), 2.27-2.83 (9H, m), 3.11 (3H, s), 3.95 (1H, s), 3.99-4.09 (3H, m), 4.24 (1H, t, J=7.47 Hz), 4.97 (1H, dd, J=9.22, 4.08 Hz), 5.44 (1H, d, J=4.77 Hz), 5.77 (1H, d, J=4.77 Hz), 6.87 (1H, d, J=8.66 Hz), 7.07 (1H, s), 7.37 (1H, d, J=8.66 Hz).

MS (m+1)=850.27

Example 22: Synthesis of Compound I-22

[Chemical Formula 167]

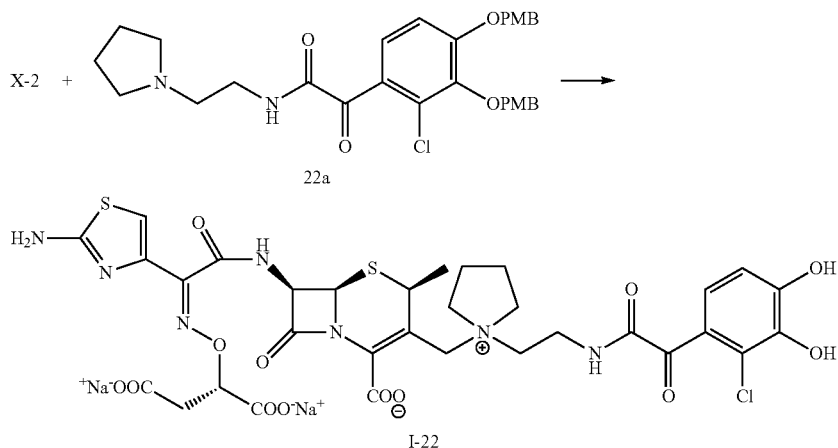

I-22

Step (1): Compound X-2+Compound 22a→Compound I-22

From Compound X-2 (866 mg, 0.80 mmol) and Compound 22a (442 mg, 0.80 mmol), Compound I-22 was obtained as a yellow powder using the same method as Example 20.

Yield: 85 mg, (12%)

$^1$H-NMR (D$_2$O) δ: 1.56 (3H, d, J=7.03 Hz), 2.24 (4H, s), 2.65-2.77 (2H, m), 3.53-4.04 (9H, m), 4.26 (1H, d, J=14.18 Hz), 4.96 (1H, dd, J=9.60, 3.58 Hz), 5.07 (1H, d, J=14.18 Hz), 5.45 (1H, d, J=4.64 Hz), 5.74 (1H, d, J=4.64 Hz), 6.87 (1H, d, J=8.66 Hz), 7.07 (1H, s), 7.34 (1H, d, J=8.66 Hz).

MS (m+1)=824.31

Example 23: Synthesis of Compound I-23

[Chemical Formula 168]

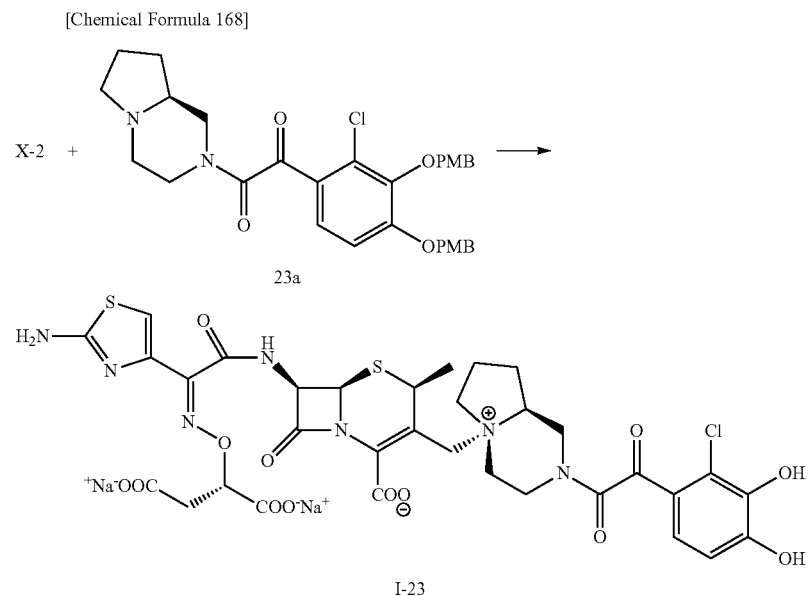

Step (1): Compound X-2+Compound 23a→Compound I-23

From Compound X-2 (1.082 g, 1.0 mmol) and Compound 23a (565 mg, 1.0 mmol), Compound I-23 was obtained as a yellow powder using the same method as Example 20.
Yield: 369 mg, (42%)
$^1$H-NMR (D$_2$O) δ: 1.57 (3H, dd, J=10.73, 7.09 Hz), 2.06-2.48 (4H, m), 2.70-2.74 (3H, m), 3.57-4.03 (8H, m), 4.29-4.35 (2H, m), 4.95-4.98 (1H, m), 5.12-5.21 (1H, m), 5.44 (1H, d, J=4.64 Hz), 5.77 (1H, dd, J=4.64, 2.13 Hz), 6.83 (1H, d, J=8.78 Hz), 7.06 (1H, d, J=2.26 Hz), 7.48 (1H, d, J=8.78 Hz).
MS (m+1)=836.19

Example 24: Synthesis of Compound I-24

Step (1): Compound X-2+Compound 24a→Compound I-24

From Compound X-2 (1.082 g, 1.0 mmol) and Compound 24a (579 mg, 1.0 mmol), Compound I-24 was obtained as a yellow powder using the same method as Example 20.
Yield: 442 mg, (49%)
$^1$H-NMR (D$_2$O) δ: 1.55 (3H, d, J=7.15 Hz), 1.94 (6H, t, J=7.72 Hz), 2.72 (2H, t, J=5.77 Hz), 3.35 (2H, s), 3.50 (6H, dt, J=29.32, 7.75 Hz), 3.98-4.08 (2H, m), 4.68 (1H, d, J=14.18 Hz), 4.96 (1H, dd, J=9.10, 4.33 Hz), 5.42 (1H, d, J=4.89 Hz), 5.80 (1H, d, J=4.89 Hz), 6.90 (1H, d, J=8.53 Hz), 7.05 (1H, s), 7.31 (1H, d, J=8.53 Hz).
MS (m+1)=850.20

[Chemical Formula 169]

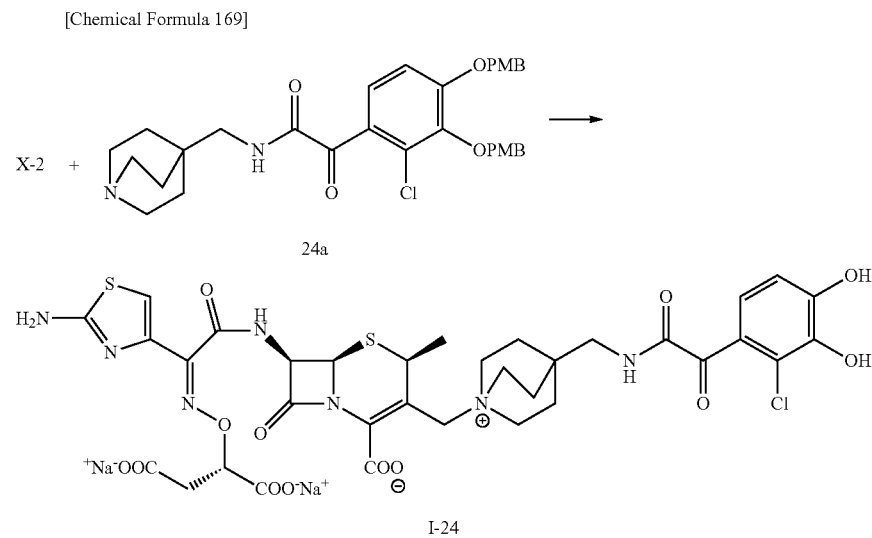

Example 25: Synthesis of Compound I-25
[Chemical Formula 170]
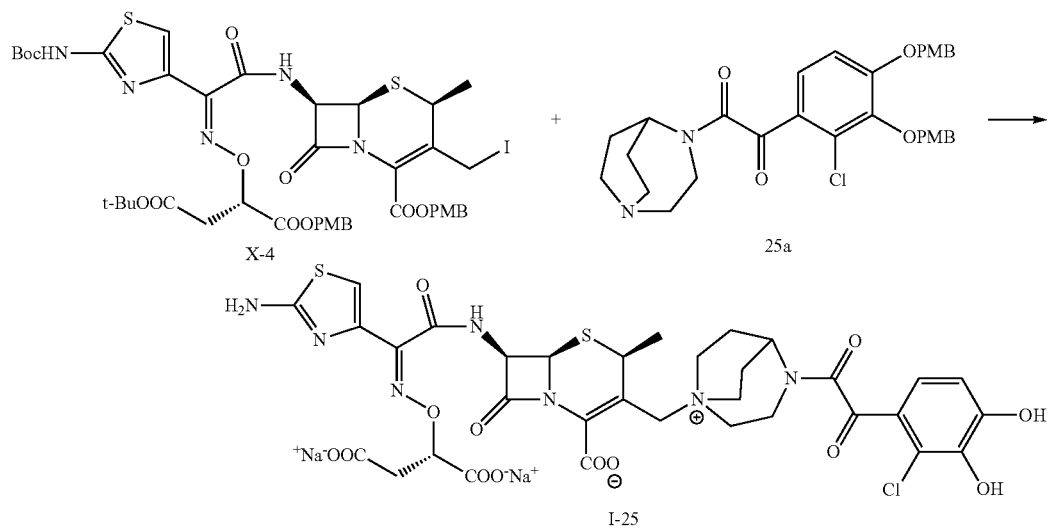
Step (1): Compound X-4+Compound 25a→Compound I-25
From Compound X-4 (1.036 g, 1.0 mmol) and Compound 25a (565 mg, 1.0 mmol), Compound I-25 was obtained as a yellow powder using the same method as Example 20.
Yield: 550 mg, (63%)
$^1$H-NMR (D$_2$O) δ: 1.58 (3H, dd, J=9.35, 7.22 Hz), 2.29-2.42 (4H, m), 2.70-2.74 (2H, m), 3.54-3.95 (7H, m), 4.02-4.10 (1H, m), 4.22-4.38 (2H, m), 4.87 (2H, d, J=13.93 Hz), 4.95-4.98 (1H, m), 5.43 (1H, d, J=4.77 Hz), 5.81 (1H, t, J=4.83 Hz), 6.83 (1H, dd, J=8.78, 6.84 Hz), 7.04 (1H, s), 7.48 (1H, d, J=8.78 Hz).
MS (m+1)=836.19
Example 26: Synthesis of Compound I-26
[Chemical Formula 171]
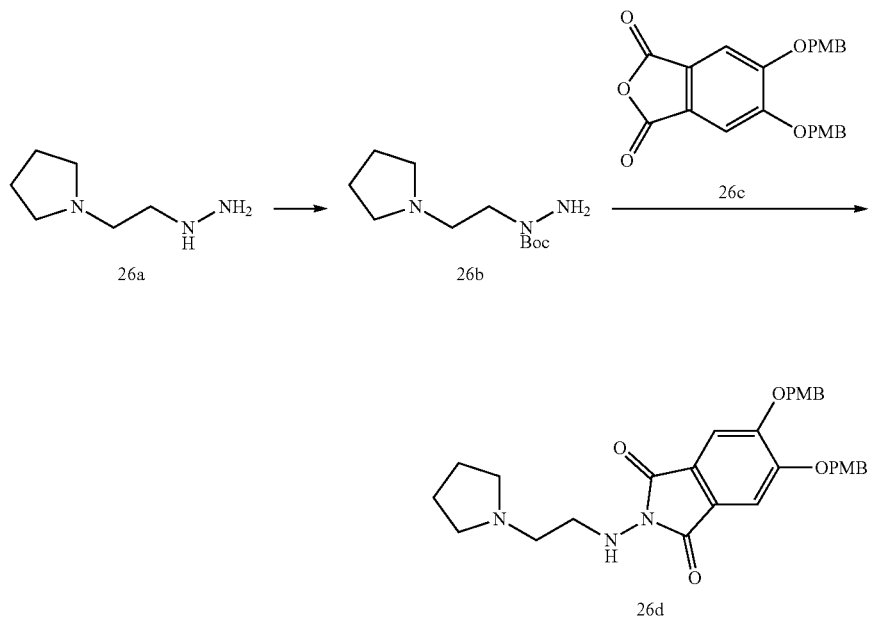

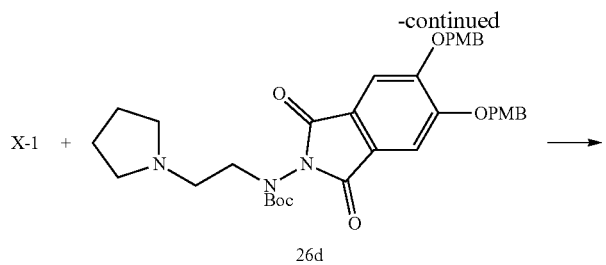

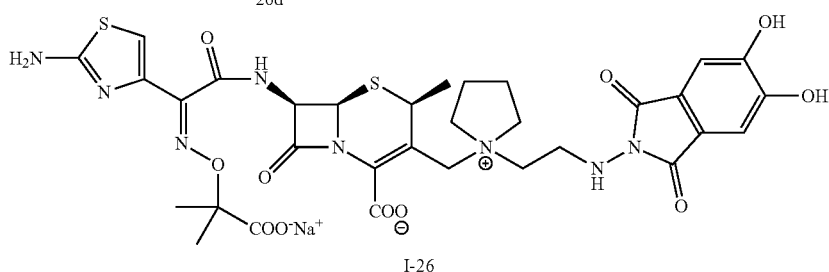

I-26

Step (1): Compound 26a→Compound 26b→Compound 26d

A solution of Compound 26a (1.29 g, 10 mmol) in ethanol (10 mL) was cooled with ice, and thereto was added Boc$_2$O solution (2.44 mL, 10.5 mmol) in ethanol (10 mL) dropwise. After stirring at room temperature for over night, the reaction mixture was concentrated and subsequently drying under reduced pressure to yield Compound 26b as colorless oil. The obtained Compound 26b was used in the next reaction without purification.

The total amount of Compound 26b yielded was dissolved in toluene (40 mL), and the solution was cooled with ice. Thereto was added Compound 26c (4.20 g, 10 mmol). After stirring at room temperature for 1 hour, then stirring at reflux for 6 hours, aqueous sodium hydroxide was added to the reaction mixture, followed by extraction with ethyl acetate. The inorganic substance was removed by filtration, and then concentrated under reduced pressure. The resulting crude product was purified by silica gel column chromatography (3% triethylamine in ethyl acetate/hexane) to yield Compound 26d as a white solid.

Yielded amount: 3.60 g (57%)
$^1$H-NMR (CDCl$_3$) δ: 1.51 (4H, s), 1.56 (9H, s), 2.42-2.46 (4H, m), 2.71 (2H, q, J=7.24 Hz), 3.71-3.79 (2H, m), 3.82 (6H, s), 5.18 (4H, s), 6.89-6.92 (4H, m), 7.33-7.37 (6H, m).

Step (2): Compound X-1+Compound 26d→Compound I-26

From Compound X-1 (932 mg, 1.0 mmol) and Compound 26d (632 mg, 1.0 mmol), Compound I-26 was obtained as a white powder using the same method as Example 20.

Yield: 449 mg, (57%)
$^1$H-NMR (D$_2$O) δ: 1.50 (3H, s), 1.51 (3H, s), 1.53 (3H, d, J=7.07 Hz), 2.22 (4H, s), 3.45-3.53 (6H, m), 3.64-3.77 (2H, m), 3.97 (1H, q, J=7.07 Hz), 4.26 (1H, d, J=14.31 Hz), 4.92 (1H, d, J=14.31 Hz), 5.39 (1H, d, J=4.77 Hz), 5.77 (1H, d, J=4.77 Hz), 6.98 (1H, s), 7.20 (2H, s).

MS (m+1)=773.33

Example 27: Synthesis of Compound I-27

[Chemical Formula 172]

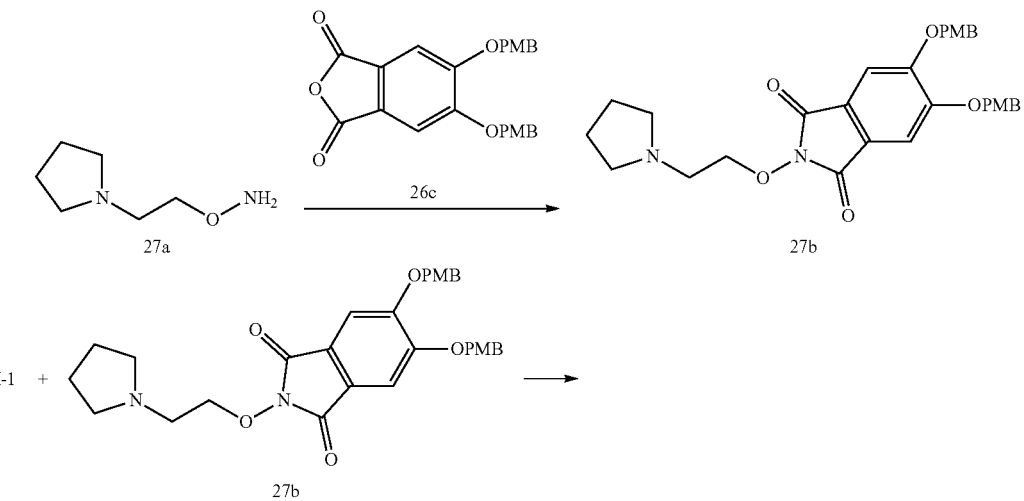

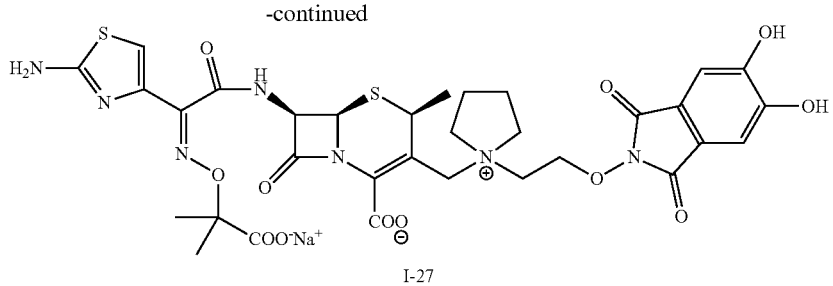

I-27

Step (1): Compound 27a→Compound 27b

A solution of Compound 27a (911 mg, 7.0 mmol) in toluene (30 mL) was cooled with ice, and thereto was added Compound 26c (2.94 g, 7.0 mmol). After stirring at room temperature for 30 minutes, thereto was added acetic acid (440 μL, 7.7 mmol). After stirring at reflux for 1 hour, aqueous sodium hydroxide was added to the reaction mixture, followed by extraction with ethyl acetate. The inorganic substance was removed by filtration, and then concentrated under reduced pressure. Thereto was added diisopropyl ether to precipitate a solid. The solid was collected by filtration, so as to yield compound 27b as a white solid.

Yielded amount: 2.60 g (70%)

$^1$H-NMR (CDCl$_3$) δ: 1.71-1.74 (4H, m), 2.58 (4H, s), 2.89 (2H, t, J=5.71 Hz), 3.81 (6H, s), 4.29 (2H, t, J=5.71 Hz), 5.17 (4H, s), 6.90 (4H, d, J=8.66 Hz), 7.32 (2H, s), 7.34 (4H, d, J=8.66 Hz).

Step (2): Compound 1a+Compound 9a→Compound (I-9)

From Compound 1a (932 mg, 1.0 mmol) and Compound 9a (632 mg, 1.0 mmol), Compound I-9 was obtained as a white powder using the same method as Example 1.

Yield: 453 mg, (57%)

$^1$H-NMR (D$_2$O) δ: 1.51 (3H, s), 1.53 (3H, s), 1.61 (3H, d, J=7.03 Hz), 2.27 (4H, s), 3.52-3.62 (2H, m), 3.71-3.78 (2H, m), 3.84-3.95 (2H, m), 4.10 (1H, q, J=7.03 Hz), 4.38 (1H, d, J=14.43 Hz), 4.56-4.69 (2H, m), 5.00 (1H, d, J=14.43 Hz), 5.47 (1H, d, J=4.77 Hz), 5.82 (1H, d, J=4.77 Hz), 7.01 (1H, s), 7.12 (2H, s).

MS (m+1)=774.34

Example 28: Synthesis of Compound I-28

[Chemical Formula 173]

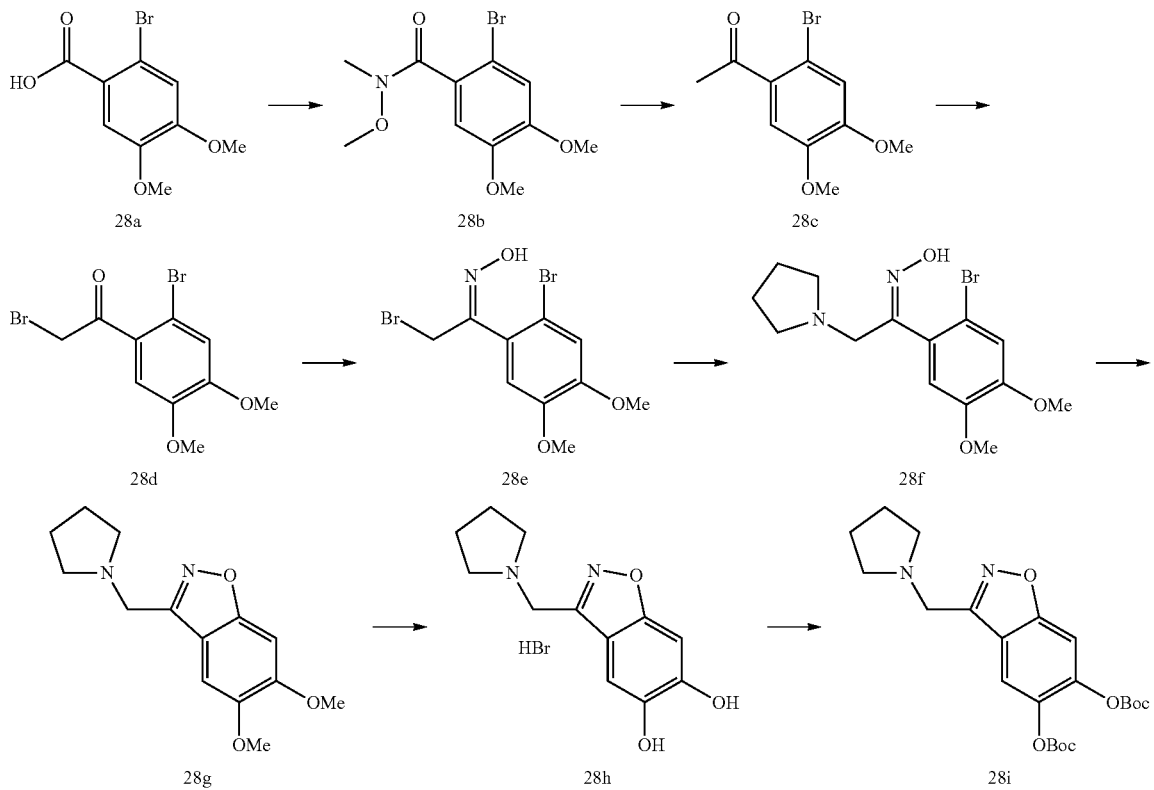

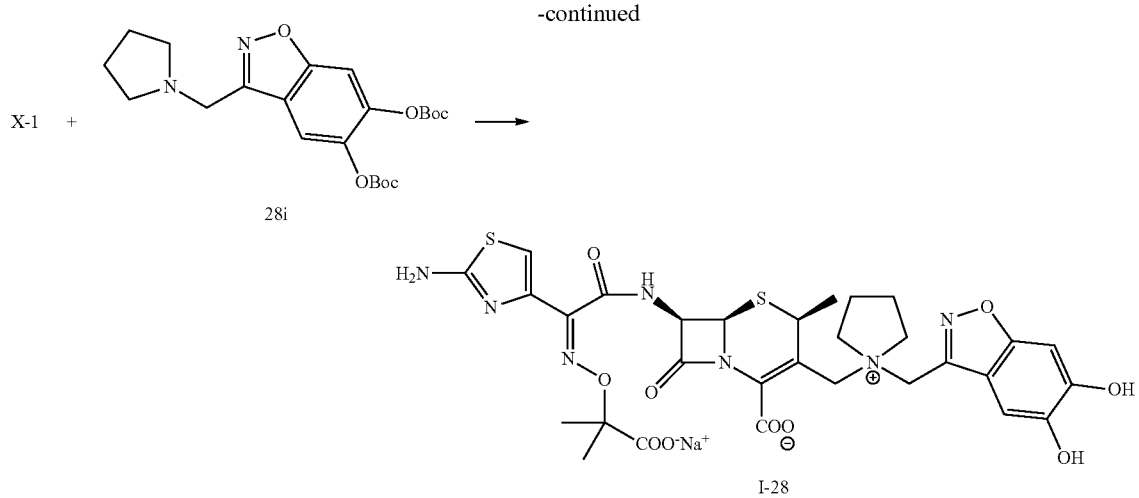

Step (1): Compound 28a→Compound 28b→Compound 28c

A solution of Compound 28a (24.4 g, 93 mmol) in dichloromethane (120 mL) was cooled with ice, and thereto was added N,O-dimethylhydroxylamine hydrochloride (16.4 g, 168 mmol) and 1-ethyl-3-(3-dimethylaminopropyl) carbodiimide hydrochloride (32.2 g, 168 mmol). After stirring at room temperature for 4.5 hours, water was added to the reaction mixture, followed by extraction with dichloromethane. The organic layer was washed with saturated brine, and then dried with anhydrous magnesium sulfate. The inorganic substance was removed by filtration, and then concentrated and subsequently drying under reduced pressure to yield Compound 28b as an orange oil. The obtained Compound 28b was used in the next reaction without purification.

The total amount of Compound 28b yielded was dissolved in tetrahydrofuran (500 mL), and the solution was cooled to 0° C. Thereto was added a 1 mol/L methylmagnesium bromide solution (186 mL, 186 mmol) in tetrahydrofuran. After stirring at room temperature for 5 hours, aqueous ammonium chloride was added to the reaction mixture, followed by extraction with ethyl acetate. The organic layer was washed with water, then saturated brine, and then dried with anhydrous magnesium sulfate. The inorganic substance was removed by filtration, and then concentrated under reduced pressure. Thereto was added diisopropyl ether to precipitate a solid. The solid was collected by filtration, so as to yield compound 28c.

Yielded amount: 23.5 g (97%)
$^1$H-NMR (CDCl$_3$) δ: 2.68 (3H, s), 3.90 (3H, s), 3.92 (3H, s), 7.05 (1H, s), 7.15 (1H, s).

Step (2): Compound 28c→Compound 28d

A solution of Copper bromide (7.97 g, 35.7 mmol) in ethyl acetate (20 mL) was heated to reflux, and thereto was added a solution of Compound 28c (5.0 g, 19.3 mmol) in chloroform (20 mL). After stirring at reflux for 2.5 hours, the insoluble matter was removed by filtration, and then concentrated under reduced pressure. The resulting crude product was purified by silica gel column chromatography (ethyl acetate/hexane) to yield Compound 28d as a yellow oil.

Yielded amount: 4.61 g (71%)

$^1$H-NMR (CDCl$_3$) δ: 3.90 (3H, s), 3.93 (3H, s), 4.59 (2H, s), 7.06 (1H, s), 7.13 (1H, s).

Step (3): Compound 28d→Compound 28e→Compound 28f

A solution of Compound 28d (4.61 g, 13.6 mmol) in methanol (180 mL) and water (30 mL) was added hydroxylamine hydrochloride (7.58 g, 109 mmol). After stirring at room temperature for over night, aqueous hydrochloric acid was added to the reaction mixture, followed by extraction with ethyl acetate. The organic layer was washed with water, then saturated brine, and then dried with anhydrous magnesium sulfate. The inorganic substance was removed by filtration, and then concentrated and subsequently drying under reduced pressure to yield Compound 28e as a yellow oil. The obtained Compound 28e was used in the next reaction without purification.

The total amount of Compound 28e yielded was dissolved in tetrahydrofuran (50 mL), and thereto was added pyrrolidine (3.38 mL, 40.9 mmol). After stirring at room temperature for 1 hour, water was added to the reaction mixture, followed by extraction with ethyl acetate. The organic layer was washed with water, then saturated brine, and then dried with anhydrous magnesium sulfate. The inorganic substance was removed by filtration, and then concentrated and subsequently drying under reduced pressure to yield Compound 28f as a yellow powder.

Yielded amount: 4.63 g (99%)
$^1$H-NMR (CDCl$_3$) δ: 1.77-1.80 (4H, m), 2.64 (4H, br s), 3.49 (2H, s), 3.86 (3H, s), 3.88 (3H, s), 6.68 (1H, s), 7.06 (1H, s).

Step (4): Compound 28f→Compound 28g

A solution of Compound 28f (4.29 g, 12.5 mmol) in 1,4-dioxane (300 mL) was added sodium tert-butoxide (1.80 g, 18.8 mmol). The reaction vessel was then degassed under reduced pressure, and thereto was added palladium acetate (421 mg, 1.88 mmol) and 1,3-bis(diphenylphosphino) propane (1.19 mg, 2.88 mmol). After stirring at 80° C. for 4.5 hours, water was added to the reaction mixture, followed by extraction with ethyl acetate twice time. The combined organic layer was washed saturated brine, and then dried with anhydrous sodium sulfate. The inorganic substance was removed by filtration, and then concentrated under reduced pressure. The resulting crude product was purified by silica gel column chromatography (ethyl acetate/hexane) to yield Compound 28g as a yellow oil.

Yielded amount: 1.82 g (56%)

$^1$H-NMR (CDCl$_3$) δ: 1.79-1.83 (4H, m), 2.60-2.63 (4H, m), 3.94 (3H, s), 3.97 (3H, s), 3.98 (2H, s), 7.02 (1H, s), 7.18 (1H, s).

Step (5): Compound 28g→Compound 28h→Compound 28i

A solution of Compound 28g (1.82 g, 6.94 mmol) in dichloromethane (20 mL) was cooled with ice, and thereto was added boron tribromide (1.97 mL, 20.8 mmol) dropwise. After stirring at room temperature for 1.5 hour, methanol was added to the reaction mixture at 0° C., and thereto was concentrated and subsequently drying under reduced pressure to yield Compound 28h as a brown solid. The obtained Compound 28h was used in the next reaction without purification.

The total amount of Compound 28h yielded was suspended in dichloromethane (20 mL), and the suspension was cooled with ice, and thereto was added triethylamine (1.44 mL, 10.4 mmol), DMAP (42 mg, 0.35 mmol), and Boc$_2$O (4.83 mL, 20.8 mmol). After stirring at room temperature for over night, water was added to the reaction mixture, followed by extraction with ethyl acetate. The organic layer was washed with water, then saturated brine, and then dried with anhydrous sodium sulfate. The inorganic substance was removed by filtration, and then concentrated under reduced pressure. The resulting crude product was purified by silica gel column chromatography (3% triethylamine in ethyl acetate/hexane) to yield Compound 28i as a yellow solid.

Yielded amount: 602 mg (20%)

$^1$H-NMR (CDCl$_3$) δ: 1.57 (18H, s), 1.78-1.81 (4H, m), 2.58-2.61 (4H, m), 4.00 (2H, s), 7.51 (1H, s), 7.78 (1H, s).

Step (6): Compound X-1+Compound 28i→Compound I-28

From Compound X-1 (932 mg, 1.0 mmol) and Compound 28i (434 mg, 1.0 mmol), Compound I-18 was obtained as a white powder using the same method as Example 20.

Yield: 344 mg, (47%)

$^1$H-NMR (D$_2$O) δ: 1.42 (3H, d, J=7.03 Hz), 1.48 (3H, s), 1.50 (3H, s), 2.28 (4H, s), 3.52-3.65 (3H, m), 3.81-3.84 (1H, m), 4.01 (1H, q, J=7.15 Hz), 4.40 (1H, d, J=14.05 Hz), 4.90 (2H, dd, J=32.12, 14.68 Hz), 5.07 (1H, d, J=14.05 Hz), 5.40 (1H, d, J=4.77 Hz), 5.79 (1H, d, J=4.77 Hz), 6.97 (1H, s), 7.18 (1H, s), 7.22 (1H, s).

MS (m+1)=716.06

Example 29: Synthesis of Compound I-29

[Chemical Formula 174]

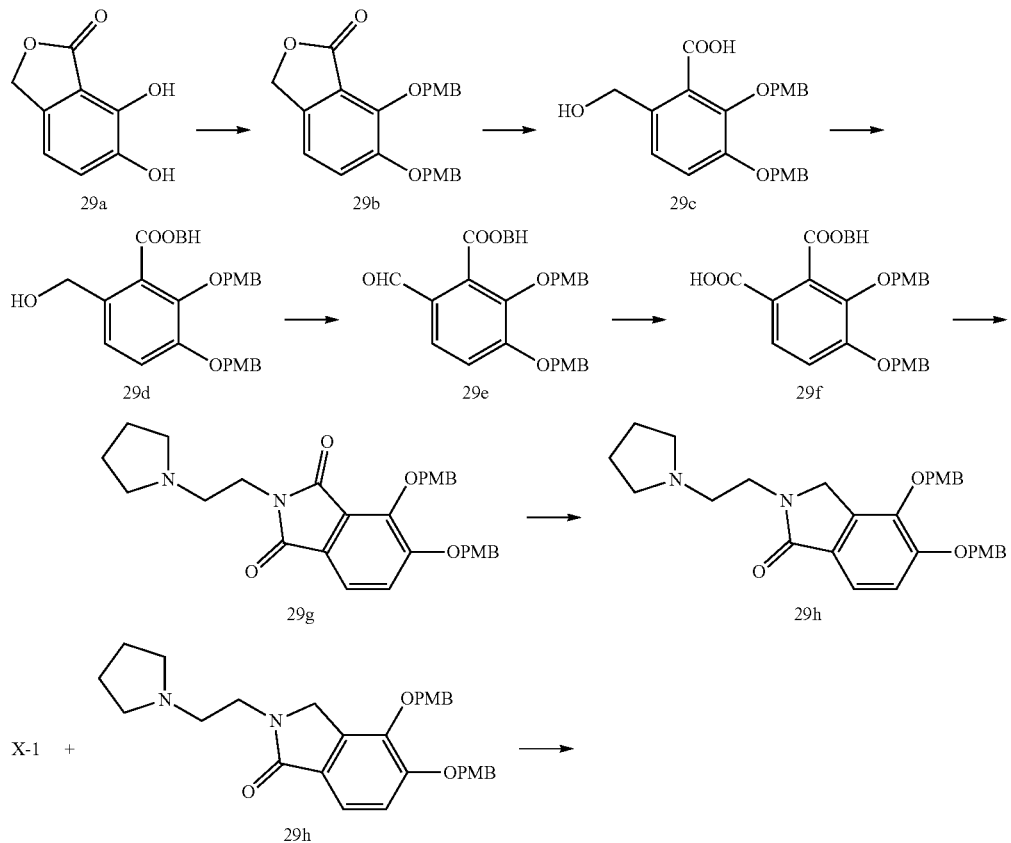

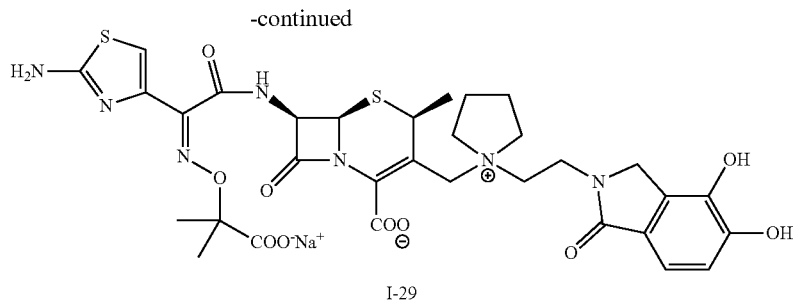

I-29

Step (1): Compound 29a→Compound 29b

To a solution of Compound 29a (12.6 g, 76 mmol) in DMF (120 mL) was added potassium carbonate (23.0 g, 166 mmol), 4-methoxybenzylchloride (22.7 mL, 166 mmol) and sodium iodide (5.67 g, 38 mmol), and the mixture was stirred at 70 degree for 1.5 hr. The solvent was removed by evaporation and the residue was diluted with water and ethyl acetate. The organic layer was washed with water and brine, dried over magnesium sulfate, filtered, and concentrated. The precipitated material was collected by filtration with diisopropyl ether and dried under high vacuum to afford Compound 29b (22.7 g, 74%) as a yellowish solid.

$^1$H-NMR (CDCl$_3$) δ: 3.79 (3H, s), 3.82 (3H, s), 5.05 (2H, s), 5.17 (2H, s), 5.26 (2H, s), 6.82 (2H, d, J=8.5 Hz), 6.89 (2H, d, J=8.5 Hz), 7.00 (1H, d, J=8.2 Hz), 7.22 (1H, d, J=8.2 Hz), 7.30 (2H, d, J=8.2 Hz), 7.42 (2H, d, J=8.4 Hz).

Step (2): Compound 29b→Compound 29c

To a solution of Compound 29b (22.4 g, 55 mmol) in methanol (55 mL) and tetrahydrofuran (55 mL) was added 2 mol/L sodium hydroxide (83 mL, 166 mmol), and the mixture was stirred at 70 degree for 1.5 hr. The resulting mixture was cooled to room temperature and then diluted with diethyl ether. The aqueous layer was separated and adjusted pH at 3.0 by adding 2 mol/L hydrochloric acid. The mixture was extracted with dichloromethane. The organic layer was washed with water and brine, dried over magnesium sulfate, evaporated and dried under high vacuum to afford Compound 29c (20.5 g, 88%) as a pale pink solid.

$^1$H-NMR (CDCl$_3$) δ: 3.80 (3H, s), 3.84 (3H, s), 4.67 (2H, s), 5.11 (2H, s), 5.12 (2H, s), 6.82 (2H, d, J=8.7 Hz), 6.95 (2H, d, J=8.7 Hz), 7.19-7.24 (4H, m), 7.39 (2H, d, J=8.7 Hz).

Step (3): Compound 29c→Compound 29d→Compound 29e

To a solution of Compound 29c (45.7 g, 108 mmol) in tetrahydrofuran (350 mL) was added a solution of diphenyldiazomethane (23.0 g, 118 mmol) in tetrahydrofuran (100 mL) over 20 min at room temperature. The mixture was stirred at room temperature over night and then the solvent was removed by evaporation. The residue was dried under high vacuum to give a crude material containing 13e as a major product which was used for the next step without further purification.

To a solution of Compound 29d prepared above in dichloromethane (640 mL) with stirring at 0 degree was added Dess-Martin periodinane (50.4 g, 119 mmol) and then the mixture was stirred at 0 degree for 2 hr. The mixture was diluted with water and the organic solvent was removed by evaporation. The resulting aqueous mixture was extracted with ethyl acetate. The organic layer was washed with water and brine, dried over magnesium sulfate, filtered and concentrated. The residue was triturated with diisopropyl ether and the solid was collected by filtration and dried under high vacuum to afford Compound 29e (51.1 g, 80%) was a colorless solid.

$^1$H-NMR (CDCl$_3$) δ: 3.79 (3H, s), 3.84 (3H, s), 4.86 (2H, s), 5.14 (2H, s), 6.68 (2H, d, J=8.66 Hz), 6.93 (2H, d, J=8.78 Hz), 6.97 (2H, d, J=8.66 Hz), 7.14 (1H, d, J=8.41 Hz), 7.19 (1H, s), 7.25-7.27 (5H, m), 7.36-7.38 (7H, m), 7.61 (1H, d, J=8.41 Hz), 9.74 (1H, s).

Step (4): Compound 29e→Compound 29f

To a solution of Compound 29e (51.1 g, 87 mmol) in 1,4-dioxane (600 mL) and water (200 mL) was added amidosulfuric acid (16.9 g, 174 mmol) and sodium chlorite (19.6 g, 174 mmol). The mixture was stirred at 0 degree for 30 min before an aqueous solution of sodium bisulfite (36.2 g, 348 mmol) was added. The mixture was extracted with ethyl acetate. The organic layer was washed with water and brine, dried over magnesium sulfate, filtered and concentrated. The solid precipitated by adding diisopropyl ether was collected by filtration and dried under high vacuum to afford Compound 29f (51.4 g, 98%) as a colorless solid.

$^1$H-NMR (DMSO-D$_6$) δ: 3.73 (3H, s), 3.77 (3H, s), 4.71 (2H, s), 5.20 (2H, s), 6.69 (2H, d, J=8.59 Hz), 6.85 (2H, d, J=8.59 Hz), 6.97-6.99 (3H, m), 7.26-7.28 (6H, m), 7.36-7.38 (5H, m), 7.45 (2H, d, J=8.59 Hz), 7.75 (1H, d, J=8.84 Hz).

Step (5): Compound 29f→Compound 29g

To a solution of Compound 29f (9.07 g, 15 mmol) in DMF (90 mL) with stirring at 0 degree was added 1-hydroxybenzotriazole (2.23 g, 16.5 mmol), 1-(2-aminoethyl)pyrrolidine (2.26 mL, 18 mmol) and EDC hydrochloride (3.74 g, 19.5 mmol) and then the mixture was stirred at room temperature for 3.5 hr. The organic solvent was removed by evaporation, and the residue was diluted with water. The mixture was extracted with ethyl acetate. The organic layer was washed with 1 mol/L sodium hydroxide, water and brine, and then dried over magnesium sulfate, filtered and concentrated. The precipitated material was collected by filtration and dried under high vacuum to afford Compound 29g (6.73 g, 87%) as a colorless solid.

$^1$H-NMR (CDCl$_3$) δ: 1.74-1.77 (4H, m), 2.57-2.60 (4H, m), 2.73 (2H, t, J=6.96 Hz), 3.78-3.81 (5H, m), 3.83 (3H, s), 5.09 (2H, s), 5.28 (2H, s), 6.82 (2H, d, J=8.66 Hz), 6.92 (2H, d, J=8.66 Hz), 7.12 (1H, d, J=8.03 Hz), 7.31 (2H, d, J=8.66 Hz), 7.38 (2H, d, J=8.66 Hz), 7.47 (1H, d, J=8.03 Hz).

Step (6): Compound 29g→Compound 29h

A solution of Compound 29g (1.55 g, 3.0 mmol) in acetic acid (60 mL) was added zinc powder (3.92 g, 60 mmol).

After stirring at 80° C. for 3 hours, the insoluble matter was removed by filtration, and then water was added to the filtrate, followed by extraction with ethyl acetate. The organic layer was washed with aqueous sodium hydroxide, then saturated brine, and then dried with anhydrous magnesium sulfate. The inorganic substance was removed by filtration, and then concentrated under reduced pressure. The resulting crude product was purified by silica gel column chromatography (3% triethylamine in ethyl acetate/hexane) to yield Compound 29h as a colorless oil.

Yield: 870 mg, (58%)

$^1$H-NMR (CDCl$_3$) δ: 1.74-1.78 (4H, m), 2.52-2.55 (4H, m), 2.64 (2H, t, J=6.90 Hz), 3.64 (2H, t, J=6.90 Hz), 3.79 (3H, s), 3.83 (3H, s), 4.09 (2H, s), 5.04 (2H, s), 5.14 (2H, s), 6.81 (2H, d, J=6.65 Hz), 6.93 (2H, d, J=8.66 Hz), 7.09 (1H, d, J=8.28 Hz), 7.20 (2H, d, J=8.66 Hz), 7.40 (2H, d, J=8.53 Hz), 7.50 (1H, d, J=8.28 Hz).

Step (7): Compound X-1+Compound 29h→Compound I-29

From Compound X-1 (745 mg, 0.80 mmol) and Compound 29h (402 mg, 0.80 mmol), Compound I-29 was obtained as a white powder using the same method as Example 20.

Yield: 244 mg, (40%)

$^1$H-NMR (D$_2$O) δ: 1.50 (3H, s), 1.52 (3H, s), 1.57 (3H, d, J=6.06 Hz), 2.22 (4H, s), 3.51-3.73 (6H, m), 4.05-4.10 (3H, m), 4.29 (1H, d, J=14.15 Hz), 4.49 (2H, s), 5.04 (1H, d, J=14.15 Hz), 5.47 (1H, d, J=2.53 Hz), 5.80 (1H, d, J=2.53 Hz), 7.00-7.04 (2H, m), 7.22 (1H, d, J=8.08 Hz).

MS (m+1)=744.21

Example 30: Synthesis of Compound I-30

[Chemical Formula 175]

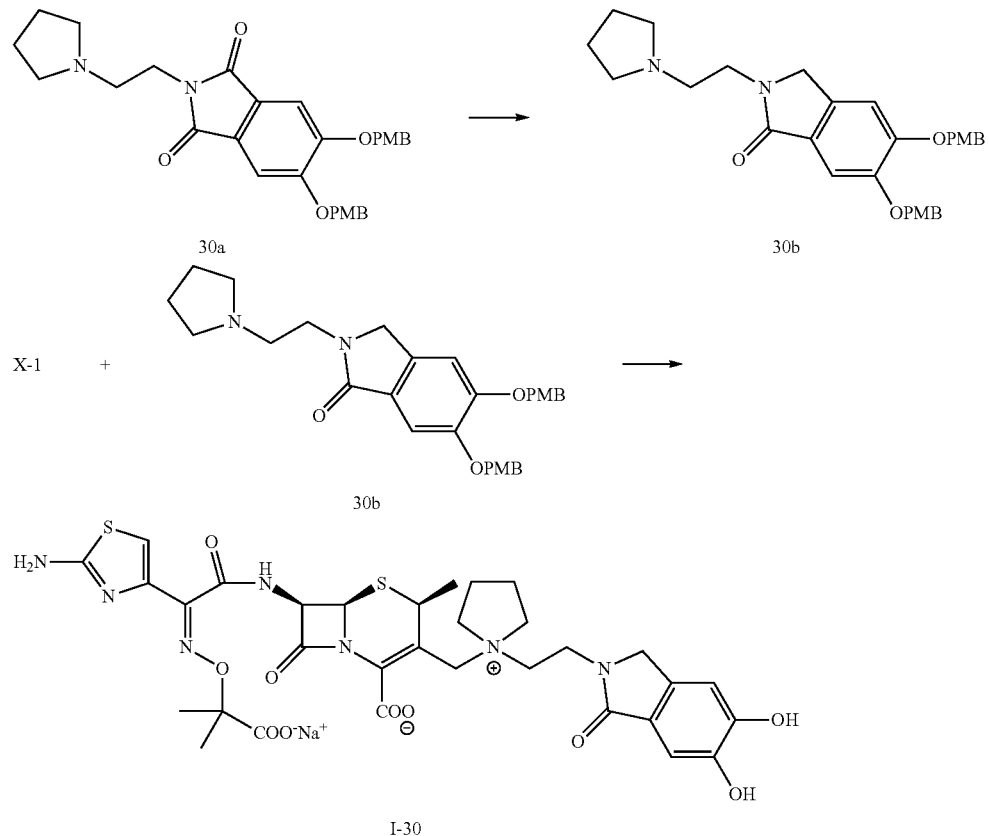

Step (1): Compound 30a→Compound 30b

From Compound 30a (1.03 g, 2.0 mmol), Compound 30b was obtained as a white solid using the same method as Example 29.

Yield: 585 mg, (58%)

$^1$H-NMR (CDCl$_3$) δ: 1.76 (4H, s), 2.56 (4H, s), 2.72 (2H, t, J=6.32 Hz), 3.70 (2H, t, J=6.32 Hz), 3.81 (6H, s), 4.34 (2H, s), 5.12 (4H, s), 6.89 (4H, d, J=8.59 Hz), 6.93 (1H, s), 7.33-7.38 (5H, m).

Step (2): Compound X-1+Compound 30b→Compound I-30

From Compound X-1 (745 mg, 0.80 mmol) and Compound 30b (402 mg, 0.80 mmol), Compound I-30 was obtained as a white powder using the same method as Example 20.

Yield: 236 mg, (39%)

$^1$H-NMR (D$_2$O) δ: 1.50 (3H, s), 1.52 (3H, s), 1.56 (3H, d, J=6.57 Hz), 2.23 (4H, s), 3.49-3.73 (6H, m), 4.02-4.10 (3H, m), 4.28 (1H, d, J=14.15 Hz), 4.42 (2H, s), 5.02 (1H, d, J=14.15 Hz), 5.46 (1H, d, J=3.28 Hz), 5.80 (1H, d, J=3.28 Hz), 7.01 (1H, s), 7.03 (1H, s), 7.17 (1H, s).

MS (m+1)=744.21

Example 31: Synthesis of Compound I-31
[Chemical Formula 176]
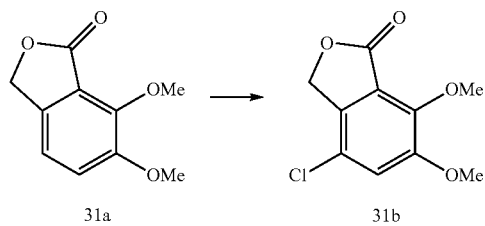
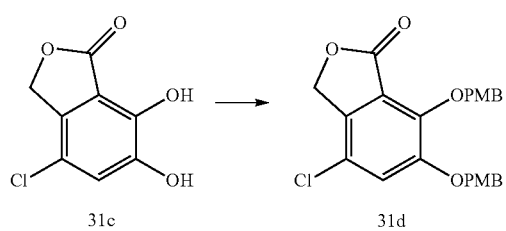
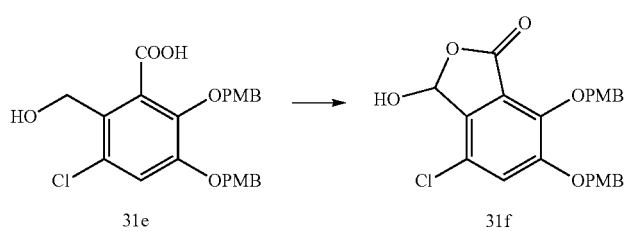
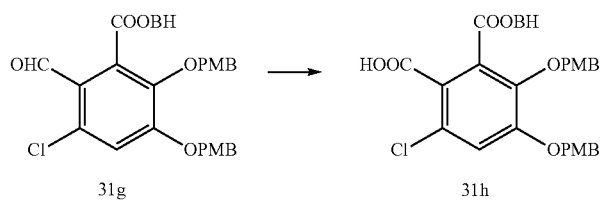
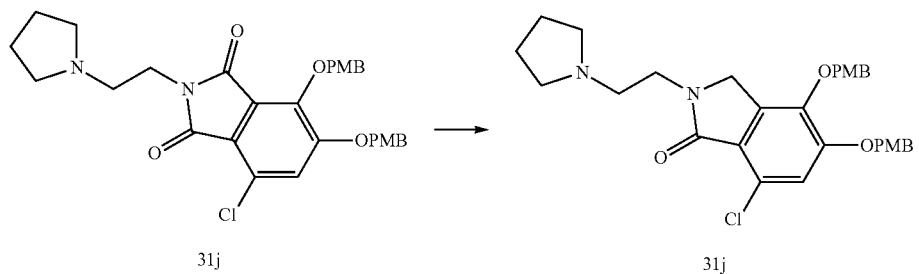

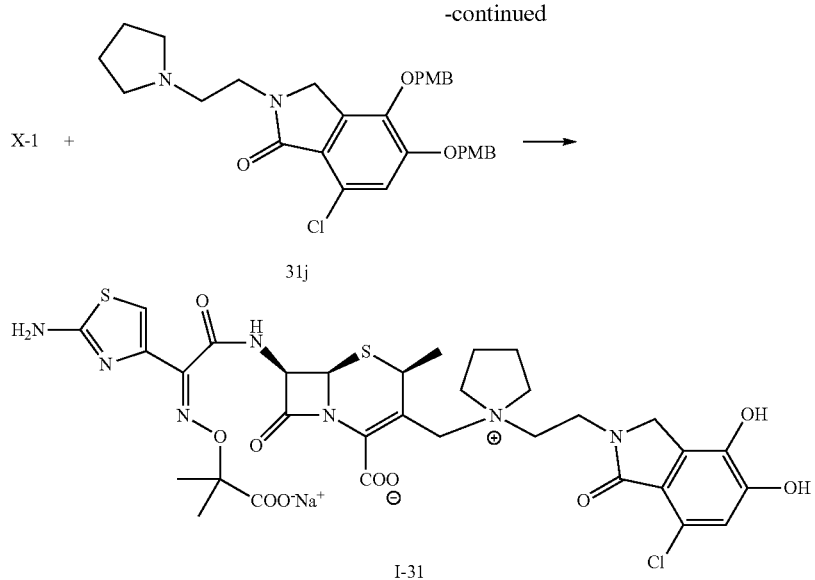

Step (1): Compound 31a→Compound 31b

A solution of Compound 31a (6.31 g, 32.5 mmol) in acetonitrile (60 mL) was added NCS (4.77 g, 35.7 mmol). After stirring at 60° C. for 1 hour, the insoluble matter was collected by filtration, so as to yield compound 31b.

Yield: 6.15 g, (83%)

$^1$H-NMR (CDCl$_3$) δ: 3.91 (3H, s), 4.09 (3H, s), 5.15 (2H, s), 7.16 (1H, s).

Step (2): Compound 31b→Compound 31c

A solution of Compound 31b (6.83 g, 30 mmol) in dichloromethane (60 mL) was cooled with ice, and thereto was added boron tribromide (9.43 mL, 100 mmol) dropwise. After stirring at room temperature for 2 hours, the reaction mixture was poured to ice, and thereto was concentrated dichloromethane. Then the solid was collected by filtration, so as to yield compound 31c.

Yield: 5.57 g, (93%)

$^1$H-NMR (DMSO-D$_6$) δ: 5.15 (2H, s), 7.10 (1H, s).

Step (3): Compound 31c→Compound 31d

From Compound 31c (5.57 g, 27.8 mmol), Compound 31d was obtained as a white solid using the same method as Example 29.

Yield: 8.45 g, (69%)

$^1$H-NMR (CDCl$_3$) δ: 3.79 (3H, s), 3.83 (3H, s), 5.03 (2H, s), 5.12 (2H, s), 5.24 (2H, s), 6.81 (2H, d, J=8.54 Hz), 6.91 (2H, d, J=8.54 Hz), 7.17 (1H, s), 7.30 (2H, d, J=8.39 Hz), 7.37 (2H, d, J=8.54 Hz).

Step (4): Compound 31d→Compound 31e

From Compound 31d (8.45 g, 19.2 mmol), Compound 31e was obtained as a white solid using the same method as Example 29.

Yield: 8.08 g, (92%)

$^1$H-NMR (DMSO-D$_6$) δ: 3.74 (3H, s), 3.77 (3H, s), 4.49 (2H, s), 4.85 (2H, s), 5.15 (2H, s), 6.85 (2H, d, J=8.54 Hz), 6.97 (2H, d, J=8.54 Hz), 7.23 (2H, d, J=8.54 Hz), 7.30 (1H, s), 7.42 (2H, d, J=8.54 Hz).

Step (5): Compound 31e→Compound 31f

A solution of Compound 31e (8.23 g, 17.9 mmol) in dichloromethane (80 mL) was cooled with ice, and thereto was added Dess-Martin Periodinane (8.37 g, 19.7 mmol). After stirring at room temperature for 30 minutes, water was added to the reaction mixture, followed by extraction with ethyl acetate. The organic layer was washed with water, then saturated brine, and then dried with anhydrous sodium sulfate. The inorganic substance was removed by filtration, and then concentrated under reduced pressure. Thereto was added diisopropyl ether to precipitate a solid. The solid was collected by filtration, so as to yield compound 31f.

Yield: 6.38 g, (78%)

$^1$H-NMR (DMSO-D$_6$) δ: 3.73 (3H, s), 3.77 (3H, s), 5.06 (2H, s), 5.15 (2H, s), 6.85 (2H, d, J=8.54 Hz), 6.97 (2H, d, J=8.54 Hz), 7.30 (2H, d, J=8.54 Hz), 7.38 (2H, d, J=8.39 Hz), 7.58 (1H, s).

Step (6): Compound 31f→Compound 31g→Compound 31h

A solution of Compound 31f (6.38 g, 14.0 mmol) in tetrahydrofuran (30 mL) was added drop-wise diphenyldiazomethane solution (2.98 g, 15.4 mmol) in tetrahydrofuran (30 mL). After stirring at room temperature for over night, the reaction mixture was concentrated under reduced pressure. Thereto was added diisopropyl ether to precipitate a solid. The solid was collected by filtration, so as to yield compound 31g.

From Compound 31g, Compound 31h was obtained as a white solid using the same method as Example 29.

Yield: 8.72 g, (98%)

$^1$H-NMR (DMSO-D$_6$) δ: 3.71 (3H, s), 3.77 (3H, s), 4.72 (2H, s), 5.19 (2H, s), 6.67 (2H, d, J=8.73 Hz), 6.79 (2H, d, J=8.73 Hz), 6.91 (1H, s), 6.98 (2H, d, J=8.73 Hz), 7.26-7.47 (13H, m).

Step (7): Compound 31h→Compound 31i

From Compound 31h (4.16 g, 6.51 mmol), Compound 31i was obtained as a white solid using the same method as Example 29.

Yield: 2.36 g, (66%)

$^1$H-NMR (CDCl$_3$) δ: 1.76 (4H, s), 2.58 (4H, s), 2.73 (2H, t, J=6.82 Hz), 3.78-3.81 (5H, m), 3.84 (3H, s), 5.06 (2H, s), 5.22 (2H, s), 6.81 (2H, d, J=8.59 Hz), 6.93 (2H, d, J=8.59 Hz), 7.03 (1H, s), 7.30-7.35 (4H, m).

Step (8): Compound 31i→Compound 31j

From Compound 31i (1.10 g, 2.0 mmol), Compound 31j was obtained as a colorless oil using the same method as Example 29.

Yield: 381 mg, (36%)

$^1$H-NMR (CDCl$_3$) δ: 1.76 (4H, s), 2.53 (4H, s), 2.63 (2H, t, J=6.19 Hz), 3.60 (2H, t, J=6.69 Hz), 3.79 (3H, s), 3.84 (3H, s), 4.00 (2H, s), 5.01 (2H, s), 5.11 (2H, s), 6.81 (2H, d, J=8.34 Hz), 6.94 (2H, d, J=8.08 Hz), 7.02 (1H, s), 7.17 (2H, d, J=7.33 Hz), 7.39 (2H, d, J=7.83 Hz).

Step (9): Compound X-1+Compound 31j→Compound I-31

From Compound X-1 (745 mg, 0.80 mmol) and Compound 31j (430 mg, 0.80 mmol), Compound I-31 was obtained as a white powder using the same method as Example 20.

Yield: 155 mg, (24%)

$^1$H-NMR (D$_2$O) δ: 1.50 (3H, s), 1.52 (3H, s), 1.58 (3H, d, J=7.03 Hz), 2.23 (4H, s), 3.49-3.64 (5H, m), 3.74-3.78 (1H, m), 4.00-4.11 (3H, m), 4.27 (1H, d, J=14.18 Hz), 4.39 (2H, s), 5.05 (1H, d, J=14.18 Hz), 5.48 (1H, d, J=4.77 Hz), 5.80 (1H, d, J=4.77 Hz), 6.87 (1H, s), 7.01 (1H, s).

MS (m+1)=778.23

Example 32: Synthesis of Compound I-32

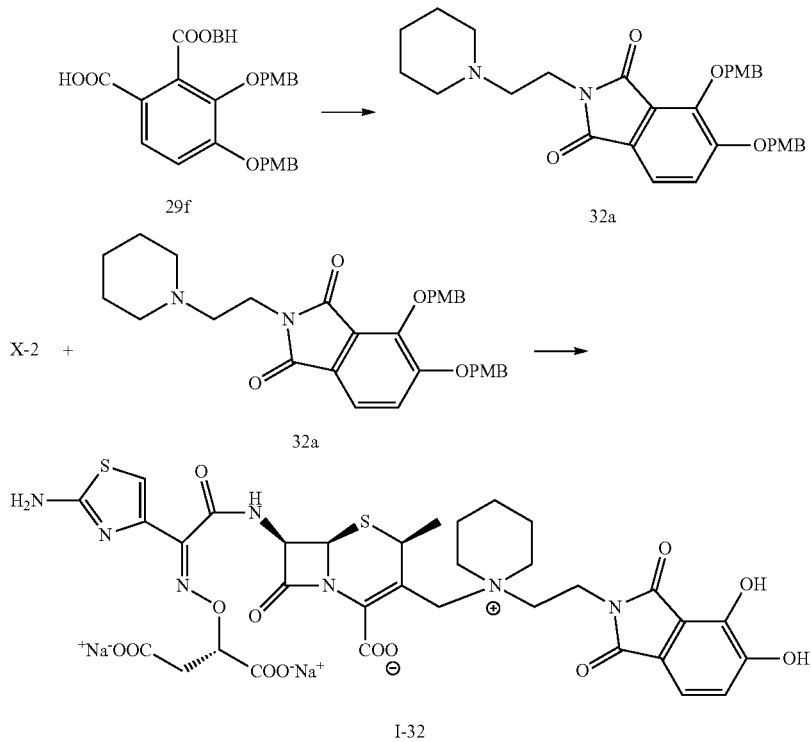

Step (1): Compound 29f→Compound 32a

From Compound 29f (3.02 g, 5.0 mmol) and 1-(2-aminoethyl)piperidine (775 μL, 5.5 mmol), Compound 32a was obtained as a white solid using the same method as Example 29.

Yield: 2.51 g, (95%)

$^1$H-NMR (CDCl$_3$) δ: 1.38-1.43 (2H, m), 1.51-1.56 (4H, m), 2.46 (4H, s), 2.57 (2H, t, J=6.96 Hz), 3.76-3.79 (5H, m), 3.83 (3H, s), 5.09 (2H, s), 5.28 (2H, s), 6.82 (2H, d, J=8.53 Hz), 6.92 (2H, d, J=8.53 Hz), 7.11 (1H, d, J=8.16 Hz), 7.30-7.39 (4H, m), 7.47 (1H, d, J=8.16 Hz).

Step (2): Compound X-2+Compound 32a→Compound I-32

From Compound X-2 (1.082 g, 1.0 mmol) and Compound 32a (624 mg, 1.0 mmol), Compound I-32 was obtained as a yellow powder using the same method as Example 20.

Yield: 176 mg, (21%)

$^1$H-NMR (D$_2$O) δ: 1.59 (3H, d, J=7.03 Hz), 1.80-1.99 (6H, m), 2.69-2.73 (2H, m), 3.29-3.39 (3H, m), 3.60-3.81 (3H, m), 4.05-4.09 (3H, m), 4.29 (1H, d, J=13.93 Hz), 4.96 (1H, dd, J=9.66, 3.76 Hz), 5.11 (1H, d, J=13.93 Hz), 5.49 (1H, d, J=4.64 Hz), 5.78 (1H, d, J=4.64 Hz), 7.02 (1H, d, J=7.78 Hz), 7.09 (1H, s), 7.19 (1H, d, J=7.78 Hz).

MS (m+1)=801.88

Example 33: Synthesis of Compound I-33

[Chemical Formula 178]

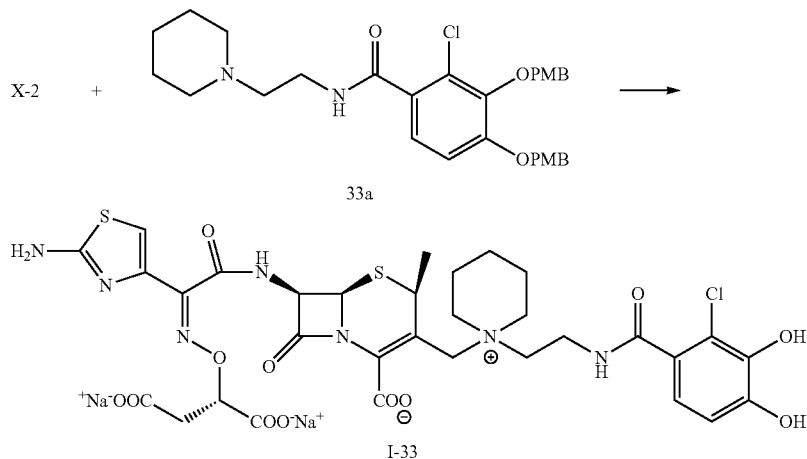

Step (1): Compound X-2+Compound 33a→Compound I-33

From Compound X-2 (1.082 g, 1.0 mmol) and Compound 33a (539 mg, 1.0 mmol), Compound I-33 was obtained as a white powder using the same method as Example 20.

Yield: 181 mg, (21%)

$^1$H-NMR (D$_2$O) δ: 1.57 (3H, d, J=7.03 Hz), 1.82-2.01 (5H, m), 2.68-2.72 (2H, m), 3.29-3.35 (3H, m), 3.61-3.96 (5H, m), 4.03 (1H, q, J=7.03 Hz), 4.23 (1H, d, J=13.93 Hz), 4.96 (1H, dd, J=9.47, 3.83 Hz), 5.05 (1H, d, J=13.93 Hz), 5.46 (1H, d, J=4.64 Hz), 5.77 (1H, d, J=4.64 Hz), 6.91 (1H, d, J=8.41 Hz), 7.00 (1H, d, J=8.41 Hz), 7.06 (1H, s).

MS (m+1)=809.98

Example 34: Synthesis of Compound I-34

Step (1): Compound X-2+Compound 29g→Compound I-34

From Compound X-2 (1.082 g, 1.0 mmol) and Compound 29g (517 mg, 1.0 mmol), Compound I-34 was obtained as a yellow powder using the same method as Example 20.

Yield: 414 mg, (50%)

$^1$H-NMR (D$_2$O) δ: 1.59 (3H, d, J=7.03 Hz), 2.23 (4H, s), 2.70-2.74 (2H, m), 3.53-3.71 (6H, m), 4.04-4.09 (3H, m), 4.32 (1H, d, J=14.18 Hz), 4.96 (1H, dd, J=9.79, 3.64 Hz), 5.12 (1H, d, J=14.18 Hz), 5.47 (1H, d, J=4.64 Hz), 5.76 (1H, d, J=4.64 Hz), 7.02 (1H, d, J=7.78 Hz), 7.08 (1H, s), 7.17 (1H, d, J=7.78 Hz).

MS (m+1)=788.02

[Chemical Formula 179]

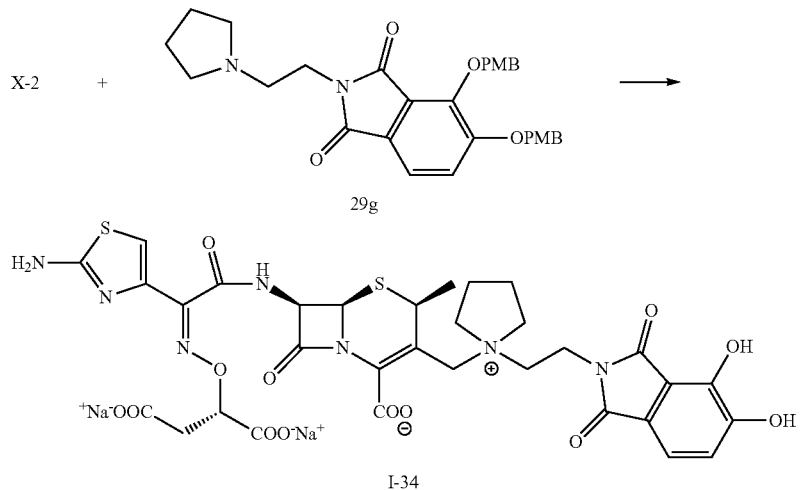

Example 35: Synthesis of Compound I-35

[Chemical Formula 180]

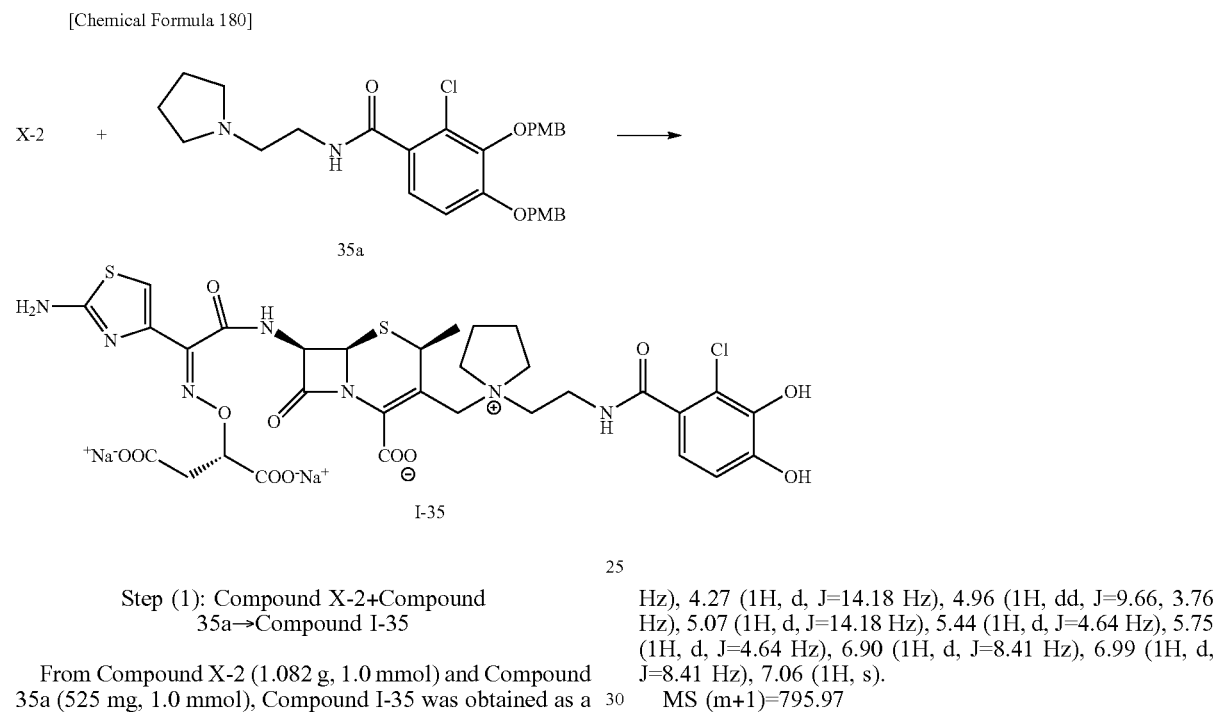

Step (1): Compound X-2+Compound 35a→Compound I-35

From Compound X-2 (1.082 g, 1.0 mmol) and Compound 35a (525 mg, 1.0 mmol), Compound I-35 was obtained as a white powder using the same method as Example 20.

Yield: 441 mg, (53%)

$^1$H-NMR (D$_2$O) δ: 1.56 (3H, d, J=7.15 Hz), 2.24 (4H, s), 2.69-2.72 (2H, m), 3.47-3.96 (9H, m), 4.01 (1H, q, J=7.07 Hz), 4.27 (1H, d, J=14.18 Hz), 4.96 (1H, dd, J=9.66, 3.76 Hz), 5.07 (1H, d, J=14.18 Hz), 5.44 (1H, d, J=4.64 Hz), 5.75 (1H, d, J=4.64 Hz), 6.90 (1H, d, J=8.41 Hz), 6.99 (1H, d, J=8.41 Hz), 7.06 (1H, s).

MS (m+1)=795.97

Example 36: Synthesis of Compound I-36

[Chemical Formula 181]

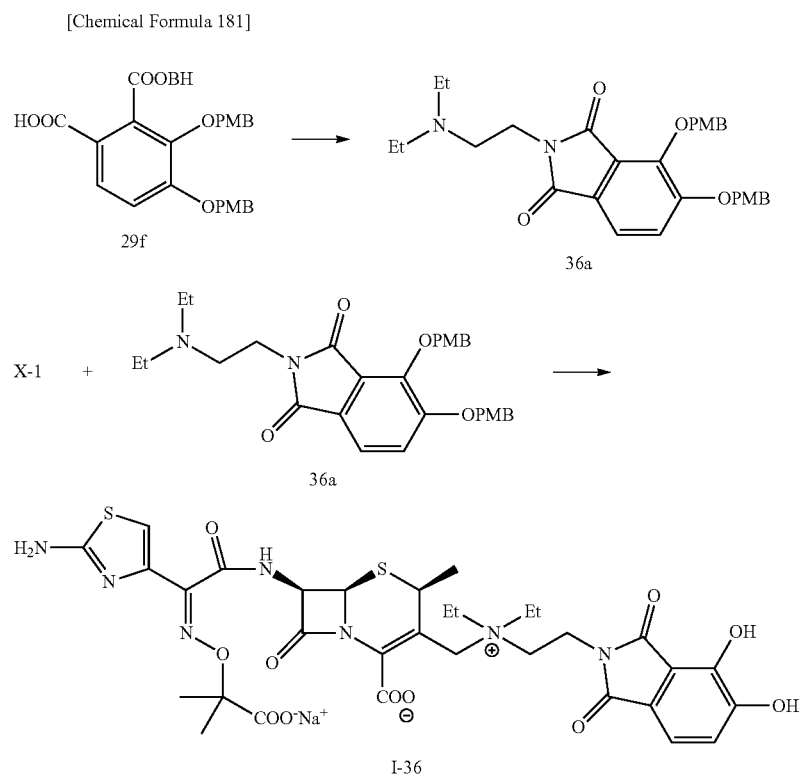

Step (1): Compound 29f→Compound 36a

From Compound 29f (3.63 g, 6.0 mmol) and N,N-diethylethylenediamine (1.01 mL, 7.2 mmol), Compound 36a was obtained as a white solid using the same method as Example 29.

Yield: 1.98 g, (64%)

$^1$H-NMR (CDCl$_3$) δ: 7.47 (1H, d, J=8.03 Hz), 7.38 (2H, d, J=8.53 Hz), 7.31 (2H, d, J=8.53 Hz), 7.11 (1H, d, J=8.03 Hz), 6.92 (2H, d, J=8.50 Hz), 6.82 (2H, d, J=8.53 Hz), 5.28 (2H, s), 5.08 (2H, s), 3.83 (3H, s), 3.79 (3H, s), 3.73 (2H, t, J=7.10 Hz), 2.69 (2H, t, J=7.09 Hz), 2.58 (4H, q, J=7.11 Hz), 1.01 (6H, t, J=7.09 Hz).

Step (2): Compound X-1+Compound 36a→Compound I-36

From Compound X-1 (559 mg, 0.60 mmol) and Compound 36a (311 mg, 0.60 mmol), Compound I-36 was obtained as a yellow powder using the same method as Example 20.

Yield: 110 mg, (24%)

$^1$H-NMR (D$_2$O) δ: 1.45 (6H, q, J=7.40 Hz), 1.50 (3H, s), 1.52 (3H, s), 1.59 (3H, d, J=6.90 Hz), 3.45-3.52 (6H, m), 3.95-4.11 (3H, m), 4.20 (1H, d, J=14.31 Hz), 5.03 (1H, d, J=14.31 Hz), 5.48 (1H, d, J=4.64 Hz), 5.77 (1H, d, J=4.64 Hz), 7.00 (1H, d, J=7.78 Hz), 7.04 (1H, s), 7.15 (1H, d, J=7.78 Hz).

MS (m+1)=760.08

Example 37: Synthesis of Compound I-37

[Chemical Formula 182]

Step (1): Compound 37a→Compound 37b

To a suspension of Compound 37a (4.29 g, 10 mmol) in dichloromethane (40 ml) with stirring in ice bath was added N,N-diethylethylenediamine (1.69 ml, 12 mmol), HOBt (1.62 g, 12 mmol) and EDC (2.30 g, 12 mmol), and then the mixture was stirred at room temperature over night. The resulting mixture was diluted with ethyl acetate and washed with a diluted aqueous solution of sodium hydroxide, water and brine. The organic layer was dried over magnesium sulfate, filtered and concentrated. The precipitated material was collected by filtration to afford Compound 37b (4.55 g, 86%).

$^1$H-NMR (CDCl$_3$) δ: 7.47 (1H, d, J=8.7 Hz), 7.35-7.34 (4H, m), 7.03 (1H, br s), 6.94-6.92 (3H, m), 6.83 (2H, d, J=8.4 Hz), 5.08 (2H, s), 4.95 (2H, s), 3.83 (3H, s), 3.80 (3H, s), 3.50 (2H, q, J=5.8 Hz), 2.64 (2H, t, J=5.8 Hz), 2.55 (4H, q, J=7.1 Hz), 1.01 (6H, t, J=7.1 Hz).

Step (2): Compound X-1+Compound 37b→Compound I-37

From Compound X-1 (932 mg, 1.0 mmol) and Compound 37b (527 mg, 1.0 mmol), Compound I-37 was obtained as a white powder using the same method as Example 20.

Yield: 320 mg, (41%)

$^1$H-NMR (D$_2$O) δ: 1.43 (6H, dd, J=10.73, 6.84 Hz), 1.49 (3H, s), 1.52 (3H, s), 1.57 (3H, d, J=7.03 Hz), 3.48 (6H, q, J=7.07 Hz), 3.74-3.95 (2H, m), 3.99 (1H, q, J=6.86 Hz), 4.17 (1H, d, J=14.31 Hz), 5.00 (1H, d, J=14.31 Hz), 5.45 (1H, d, J=4.64 Hz), 5.76 (1H, d, J=4.64 Hz), 6.90 (1H, d, J=8.41 Hz), 6.98 (1H, d, J=8.41 Hz), 7.03 (1H, s).

MS (m+1)=768.22

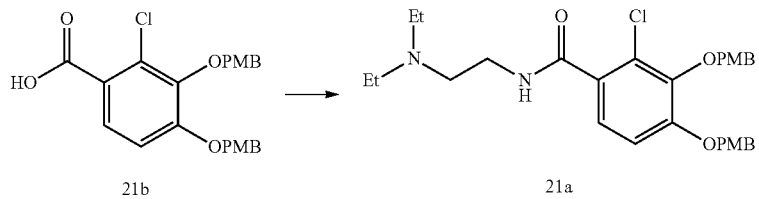

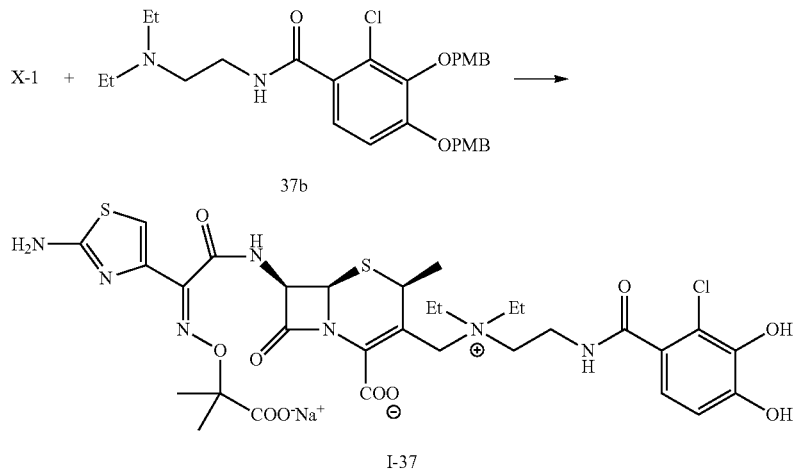

I-37

Example 38: Synthesis of Compound I-38

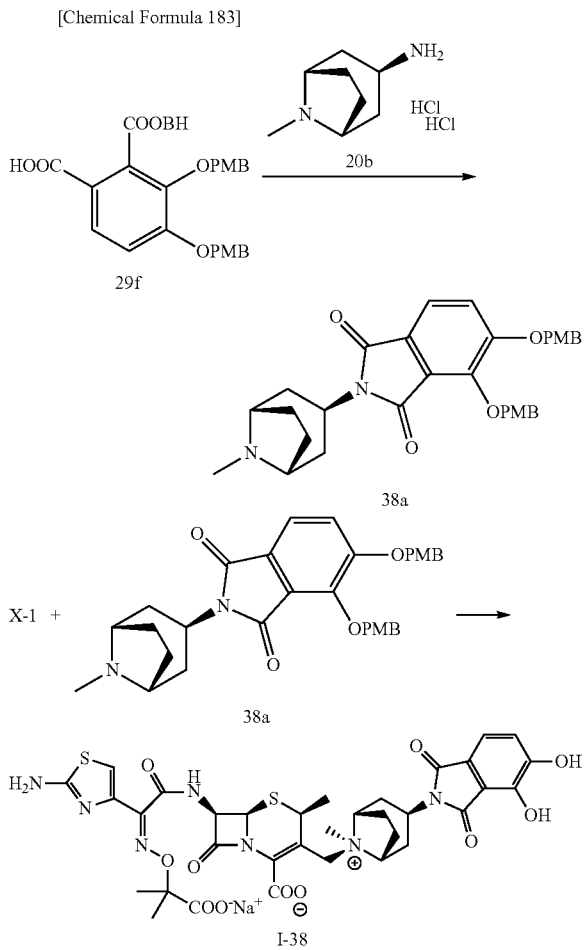

Step (1): Compound 29f→Compound 38a

From Compound 29f (3.02 g, 5.0 mmol), 20b (1.17 g, 5.5 mmol), and DIEA (1.92 mL, 11 mmol), Compound 38a was obtained as a colorless oil using the same method as Example 29.

Yield: 100 mg, (4%)

$^1$H-NMR (CDCl$_3$) δ: 1.74 (2H, dd, J=13.93, 6.27 Hz), 1.87-1.93 (2H, m), 2.13-2.16 (2H, m), 2.21 (3H, s), 2.26-2.34 (2H, m), 3.24 (2H, s), 3.79 (3H, s), 3.83 (3H, s), 4.55-4.65 (1H, m), 5.08 (2H, s), 5.25 (2H, s), 6.81 (2H, d, J=8.53 Hz), 6.91 (2H, d, J=8.53 Hz), 7.09 (1H, d, J=8.16 Hz), 7.30 (2H, d, J=8.66 Hz), 7.37 (2H, d, J=8.66 Hz), 7.42 (1H, d, J=8.16 Hz).

Step (2): Compound X-2+Compound 38a→Compound I-38

From Compound X-2 (466 mg, 0.50 mmol) and Compound 38a (271 mg, 0.50 mmol), Compound 3-38 was obtained as a yellow powder using the same method as Example 20.

Yield: 126 mg, (31%)

$^1$H-NMR (D$_2$O) δ: 1.51 (3H, s), 1.53 (3H, s), 1.59 (3H, d, J=7.15 Hz), 2.21 (2H, t, J=19.39 Hz), 2.51-2.66 (4H, m), 2.83-2.99 (2H, m), 3.12 (3H, s), 4.00 (1H, s), 4.07-4.15 (3H, m), 4.75 (2H, d, J=14.68 Hz), 5.47 (1H, d, J=4.89 Hz), 5.84 (1H, d, J=4.89 Hz), 7.02 (1H, s), 7.04 (1H, d, J=7.78 Hz), 7.17 (1H, d, J=7.78 Hz).

MS (m+1)=786.06

Example 39: Synthesis of Compound I-39

[Chemical Formula 184]

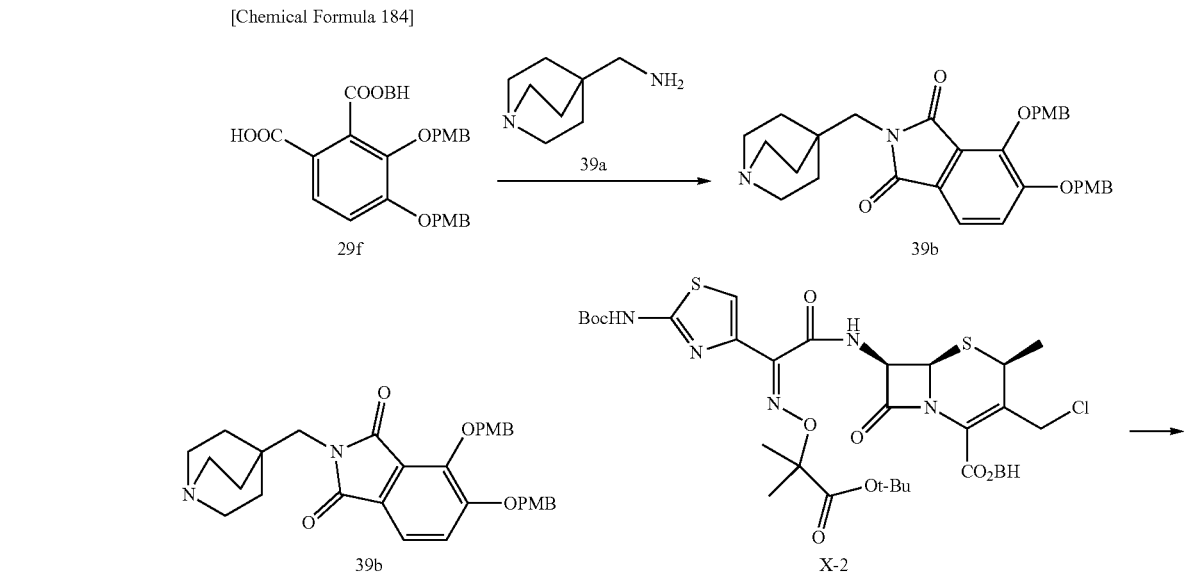

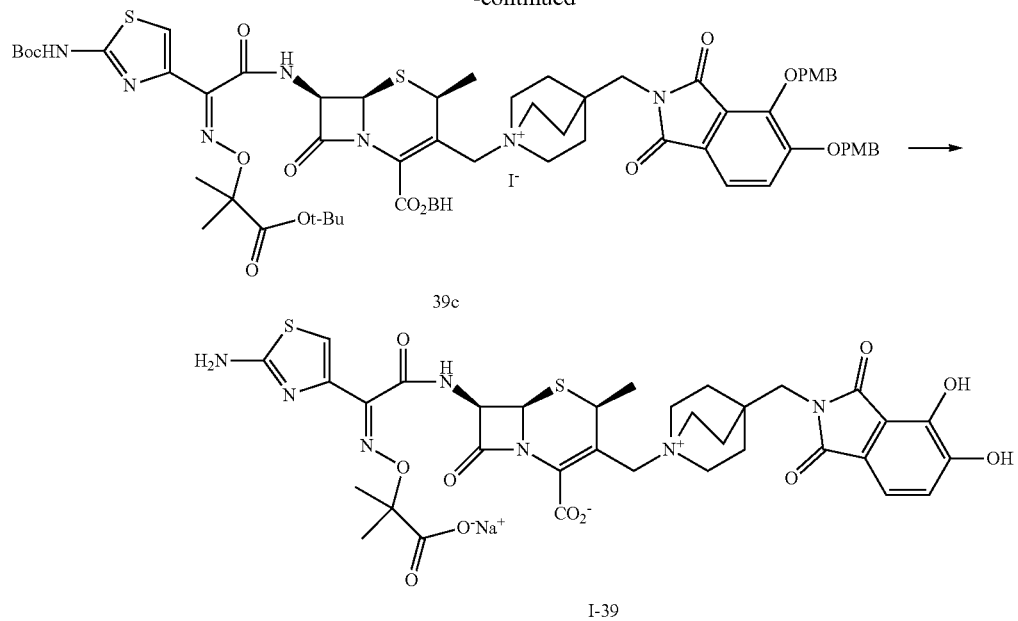

39c

I-39

Step (1): Compound 29f→Compound 39b

From Compound 29f (3.02 g, 5.0 mmol) and Compound 39a (771 mg, 5.5 mmol), Compound 39b was obtained as a white solid using the same method as Example 29.

$^1$H-NMR (CDCl$_3$) δ: 1.41 (6H, t, J=7.65 Hz), 2.85 (6H, t, J=7.65 Hz), 3.79 (3H, s), 3.83 (3H, s), 5.11 (2H, s), 5.28 (2H, s), 6.81 (2H, d, J=8.66 Hz), 6.92 (2H, d, J=8.66 Hz), 7.14 (1H, d, J=8.03 Hz), 7.33 (2H, d, J=8.66 Hz), 7.37 (2H, d, J=8.66 Hz), 7.48 (1H, d, J=8.03 Hz).

Step (2): Compound 39b+Compound X-2→Compound 39c

Compound 39b (543 mg, 1.0 mmol) was added to a solution of compound X-2 (932 mg, 1.0 mmol) in dimethylformamide (2 mL) at 0° C., and the resultant solution was stirred at 0° C. for 1 hour. The reaction mixture was slowly added to a 5% salt solution (30 ml) (containing 1.5 g of sodium bisulfite) at 0° C. The precipitated solid was collected by filtration, washed with water, and then suspended into water. The suspension was freeze-dried to yield compound 39c as an orange solid. Compound 39c yielded was used as it was, without being purified, in the next reaction.

Step (3): Compound 39c→Compound I-39

The total amount of compound 39c yielded was dissolved in dichloromethane (10 mL), and the solution was cooled to −40° C. Thereto were then added anisole (1.1 mL, 10 mmol) and a 2M aluminum chloride solution (5.00 mL, 10 mmol) in nitromethane in turn. The resultant was stirred at 0° C. for 30 minutes. The reaction mixture was dissolved in water, a 2 mol/L aqueous hydrochloric acid solution, and acetonitrile. The resultant solution was then washed with diisopropyl ether. To the water phase was added HP20-SS resin, and then acetonitrile was distilled off under reduced pressure. The resultant mixed liquid was purified by ODS column chromatography. To the resultant target-compound solution was added HP20-SS resin, and then acetonitrile was distilled off under reduced pressure. The resultant mixed liquid was purified by HP20-SS column chromatography. To the resultant target-compound solution was added a 0.2N aqueous sodium hydroxide solution until the whole gave a pH of 6.0. Thereafter, a piece of dry ice was added thereto. The resultant solution was concentrated under reduced pressure, and then freeze-dried to yield compound I-39 as an orange powder.

Yielded amount: 168 mg, (20%).

$^1$H-NMR (D$_2$O) δ: 1.50 (3H, s), 1.52 (3H, s), 1.55 (3H, d, J=7.15 Hz), 1.93 (6H, t, J=7.72 Hz), 3.41-3.53 (8H, m), 4.03-4.10 (2H, m), 4.61 (1H, d, J=14.43 Hz), 5.43 (1H, d, J=4.89 Hz), 5.84 (1H, d, J=4.89 Hz), 6.99 (1H, s), 7.04 (1H, d, J=7.91 Hz), 7.17 (1H, d, J=7.91 Hz).

MS (m+1)=784.06

Example 40: Synthesis of Compound I-40

[Chemical Formula 185]

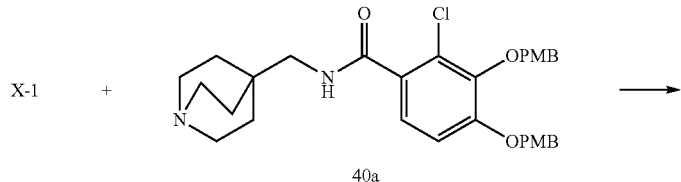

40a

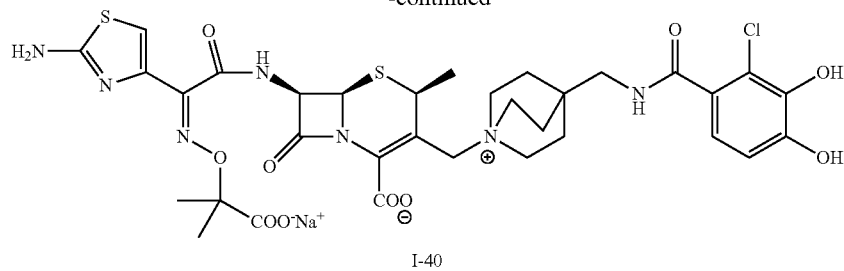

I-40

Step (1): Compound X-1+Compound 40a→Compound I-40

From Compound X-1 (932 mg, 1.0 mmol) and Compound 40a (543 mg, 1.0 mmol), Compound I-40 was obtained as a white powder using the same method as Example 20.

Yield: 523 mg, (64%)

$^1$H-NMR (D$_2$O) δ: 1.51 (3H, s), 1.53 (3H, s), 1.56 (3H, d, J=7.15 Hz), 1.96 (6H, t, J=7.59 Hz), 3.35 (2H, s), 3.45-3.57 (6H, m), 4.05-4.09 (2H, m), 4.64 (1H, d, J=14.31 Hz), 5.45 (1H, d, J=4.89 Hz), 5.85 (1H, d, J=4.89 Hz), 6.90 (1H, d, J=8.41 Hz), 6.95 (1H, d, J=8.41 Hz), 7.00 (1H, s).

MS (m+1)=792.01

Example 41: Synthesis of Compound I-41

[Chemical Formula 186]

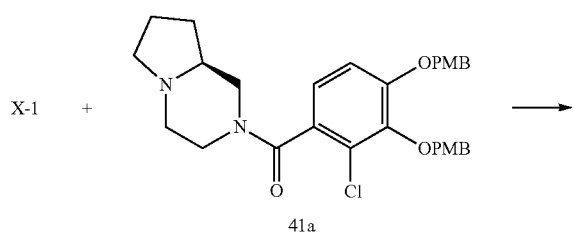

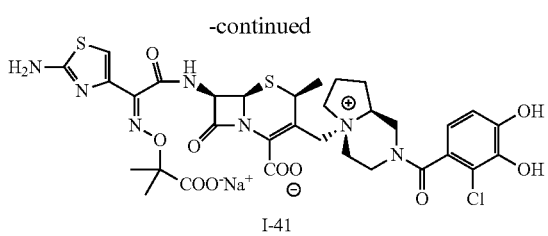

I-41

Step (1): Compound X-1+Compound 41a→Compound I-41

From Compound X-1 (932 mg, 1.0 mmol) and Compound 41a (537 mg, 1.0 mmol), Compound I-41 was obtained as a white powder using the same method as Example 20.

Yield: 443 mg, (55%)

$^1$H-NMR (D$_2$O) δ: 1.50 (3H, d, J=1.63 Hz), 1.52 (3H, d, J=1.88 Hz), 1.57 (3H, dd, J=17.69, 6.90 Hz), 2.02-2.46 (4H, m), 3.46-4.08 (9H, m), 4.25-4.53 (2H, m), 5.11 (1H, dd, J=19.89, 15.00 Hz), 5.45 (1H, d, J=4.64 Hz), 5.83 (1H, d, J=4.64 Hz), 6.83-6.88 (1H, m), 6.95-6.98 (1H, m), 7.01 (1H, s).

MS (m+1)=778.04

Example 42: Synthesis of Compound I-42

[Chemical Formula 187]

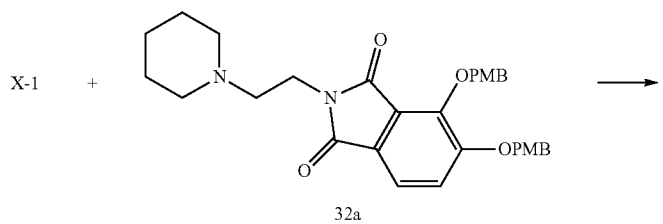

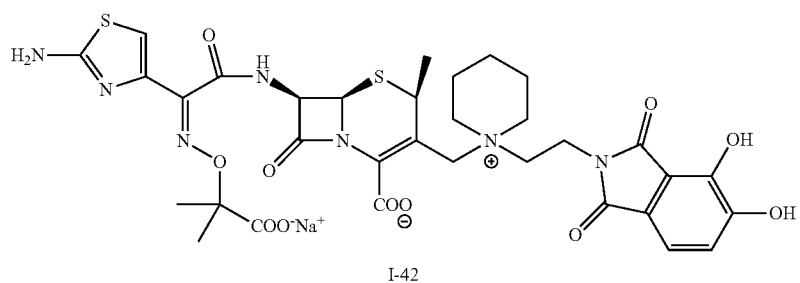

I-42

Step (1): Compound X-1+Compound 32a→Compound I-42

From Compound X-1 (932 mg, 1.0 mmol) and Compound 32a (624 mg, 1.0 mmol), Compound I-42 was obtained as a yellow powder using the same method as Example 20.
Yield: 192 mg, (24%)
$^1$H-NMR (D$_2$O) δ: 1.51 (3H, s), 1.53 (3H, s), 1.61 (3H, d, J=7.03 Hz), 1.81-2.00 (6H, m), 3.28-3.39 (3H, m), 3.59-3.80 (3H, m), 4.02-4.07 (2H, m), 4.16 (1H, q, J=7.03 Hz), 4.29 (1H, d, J=14.05 Hz), 5.07 (1H, d, J=14.05 Hz), 5.50 (1H, d, J=4.77 Hz), 5.83 (1H, d, J=4.77 Hz), 7.02-7.04 (2H, m), 7.17 (1H, d, J=7.78 Hz).
MS (m+1)=772.07

Example 43: Synthesis of Compound I-43

[Chemical Formula 188]

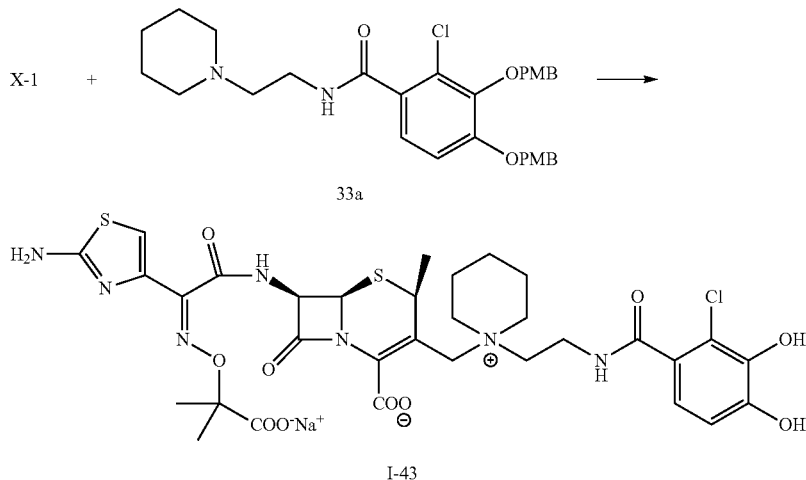

Step (1): Compound X-1+Compound 33a→Compound I-43

From Compound X-1 (932 mg, 1.0 mmol) and Compound 33a (539 mg, 1.0 mmol), Compound I-43 was obtained as a white powder using the same method as Example 20.
Yield: 272 mg, (29%)
$^1$H-NMR (D$_2$O) δ: 1.50 (3H, s), 1.52 (3H, s), 1.59 (3H, d, J=7.03 Hz), 1.82-2.01 (6H, m), 3.28-3.36 (3H, m), 3.62 (1H, d, J=11.92 Hz), 3.69-3.82 (3H, m), 3.89-3.96 (1H, m), 4.11 (1H, q, J=7.03 Hz), 4.23 (1H, d, J=14.18 Hz), 5.00 (1H, d, J=14.18 Hz), 5.48 (1H, d, J=4.77 Hz), 5.83 (1H, d, J=4.77 Hz), 6.87 (1H, d, J=8.28 Hz), 6.95 (1H, d, J=8.28 Hz), 7.02 (1H, s).

Example 44: Synthesis of Compound I-44

[Chemical Formula 189]

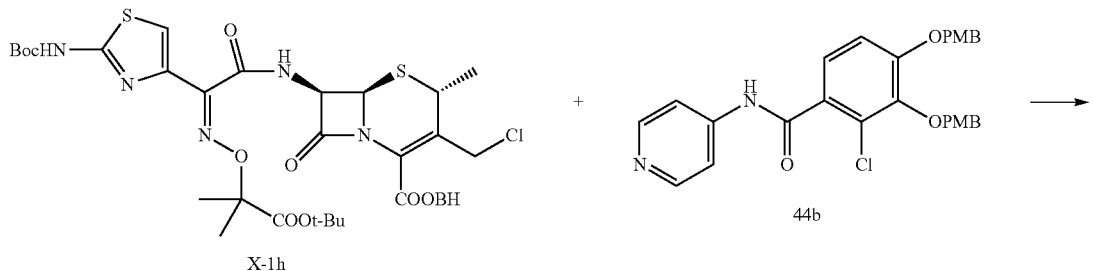

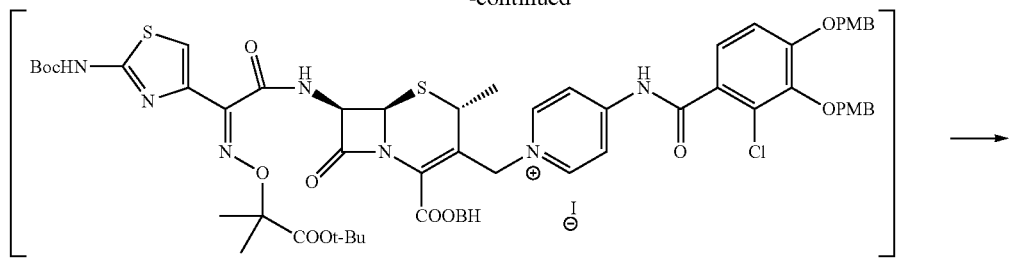

44c

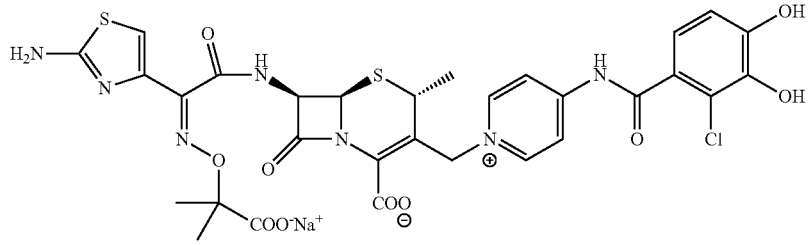

I-44

Step (1): Compound X-1h+Compound 44b→Compound 44c→Compound I-44

A solution of Compound 44b (404 mg, 0.80 mmol) in dimethylacetamide (2.0 mL) was cooled with ice, and thereto was added Compound X-1h (672 mg, 0.80 mmol). The reaction vessel was then degassed under reduced pressure, and thereto was added sodium iodide (240 mg, 1.6 mmol). After stirring at 15° C. for 7 hours, the reaction mixture was slowly added to 5% aqueous sodium chloride and sodium hydrogen sulfite cooled with ice. The precipitated solid was collected by filtration, washed with water, and suspended into water. The suspension was freeze-dried to yield Compound 44c as a brown solid. Compound 44c yielded was used as it was, without being purified, in the next reaction.

From Compound 44c, Compound I-44 was obtained as a white powder using the same method as Example 20.

Yield: 359 mg, (58%)

$^1$H-NMR (D$_2$O) δ: 1.44 (3H, s), 1.45 (3H, s), 1.61 (3H, d, J=6.78 Hz), 3.49 (1H, q, J=6.78 Hz), 5.12 (1H, d, J=14.68 Hz), 5.43-5.46 (2H, m), 5.92 (1H, d, J=4.39 Hz), 6.87 (1H, d, J=8.41 Hz), 6.90 (1H, s), 7.12 (1H, d, J=8.41 Hz), 8.09 (2H, d, J=6.53 Hz), 8.76 (2H, d, J=6.53 Hz).

MS (m+1)=745.97

Example 45: Synthesis of Compound I-45

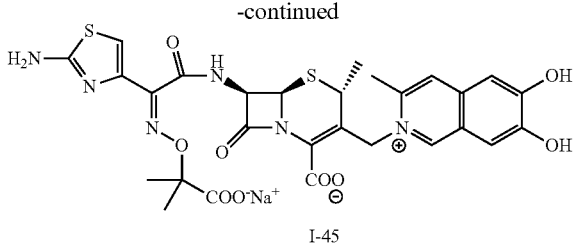

I-45

Step (1): Compound X-1h+Compound 45a→Compound I-45

From Compound X-1h (672 mg, 0.80 mmol) and Compound 45a (300 mg, 1.0 mmol), Compound I-45 was obtained as a white powder using the same method as Example 44.

Yield: 332 mg, (61%)

$^1$H-NMR (D$_2$O) δ: 1.39 (3H, d, J=7.15 Hz), 1.47 (6H, s), 2.69 (3H, s), 3.46 (1H, q, J=6.94 Hz), 5.22 (1H, d, J=15.31 Hz), 5.33 (1H, d, J=15.31 Hz), 5.47 (1H, d, J=4.89 Hz), 5.91 (1H, d, J=4.89 Hz), 6.88 (1H, s), 6.90 (1H, s), 7.29 (1H, s), 7.54 (1H, s), 8.83 (1H, s).

MS (m+1)=657.01

Example 46: Synthesis of Compound I-46

[Chemical Formula 190]

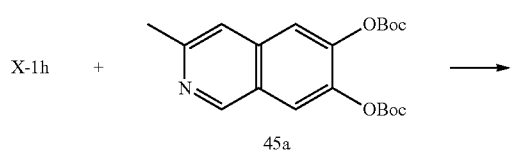

[Chemical Formula 191]

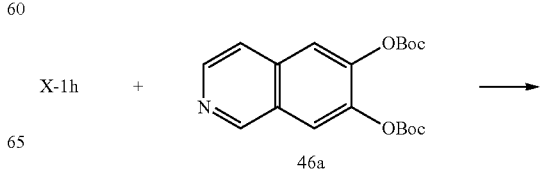

-continued

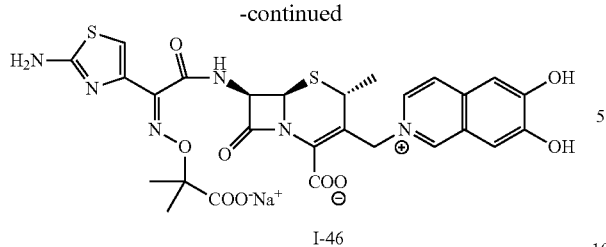

I-46

Step (1): Compound X-1h+Compound 46a→Compound I-46

From Compound X-1h (672 mg, 0.80 mmol) and Compound 46a (289 mg, 1.0 mmol), Compound I-46 was obtained as a white powder using the same method as Example 44.

Yield: 356 mg, (67%)

$^1$H-NMR (D$_2$O) δ: 1.43 (3H, s), 1.45 (3H, s), 1.57 (3H, d, J=7.15 Hz), 3.40 (1H, q, J=7.15 Hz), 5.12 (1H, d, J=14.68 Hz), 5.43-5.47 (2H, m), 5.88 (1H, d, J=4.77 Hz), 6.79 (1H, s), 7.06 (1H, s), 7.36 (1H, s), 7.72 (1H, d, J=6.90 Hz), 8.11 (1H, d, J=6.90 Hz), 9.01 (1H, s).

MS (m+1)=643.01

Example 47: Synthesis of Compound I-47

[Chemical Formula 192]

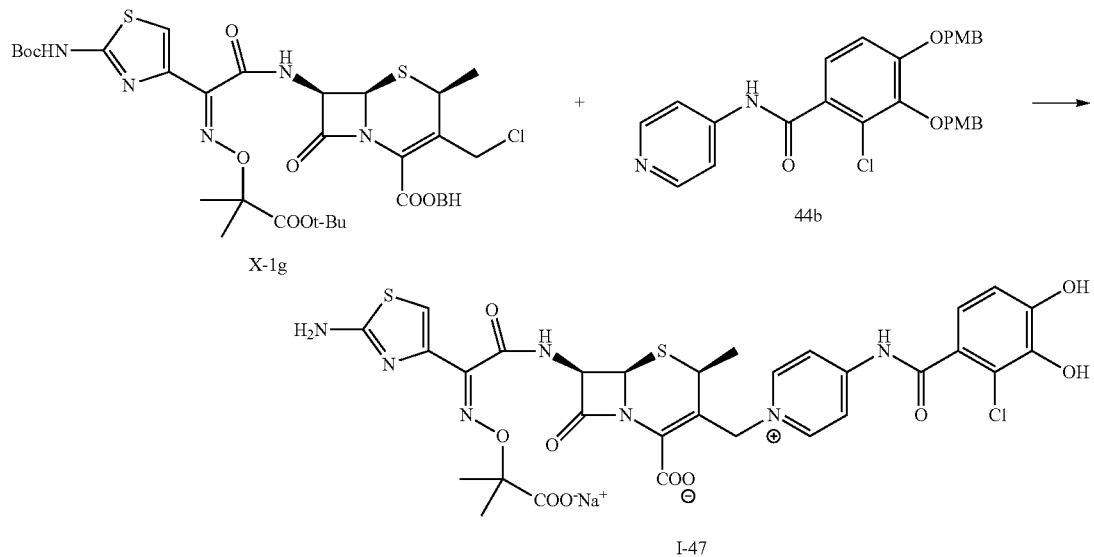

I-47

Step (1): Compound X-1g+Compound 44b→Compound I-47

From Compound X-1g (672 mg, 0.80 mmol) and Compound 44b (404 mg, 0.80 mmol), Compound I-47 was obtained as a white powder using the same method as Example 44.

Yield: 367 mg, (60%)

$^1$H-NMR (D$_2$O) δ: 1.27 (3H, d, J=7.16 Hz), 1.45 (3H, s), 1.48 (3H, s), 3.95 (1H, q, J=7.16 Hz), 5.28 (1H, d, J=15.16 Hz), 5.35-5.39 (2H, m), 5.74 (1H, d, J=4.80 Hz), 6.88 (1H, s), 6.91 (1H, d, J=8.34 Hz), 7.15 (1H, d, J=8.34 Hz), 8.19 (2H, d, J=7.33 Hz), 8.76 (2H, d, J=7.33 Hz).

MS (m+1)=745.93

Example 48: Synthesis of Compound I-48

[Chemical Formula 193]

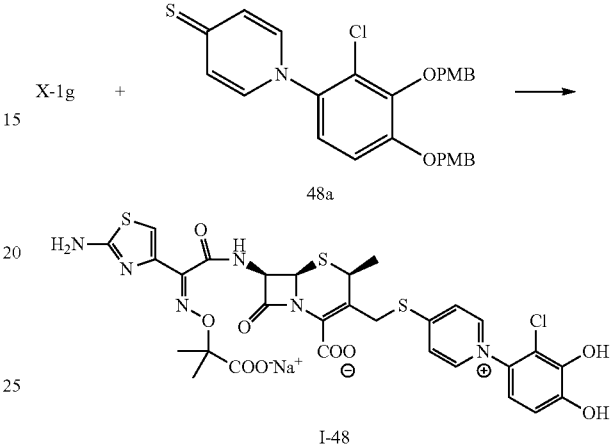

I-48

Step (1): Compound X-1g+Compound 48a→Compound I-48

From Compound X-1g (672 mg, 0.80 mmol) and Compound 48a (395 mg, 0.80 mmol), Compound I-48 was obtained as a white powder using the same method as Example 44.

Yield: 320 mg, (53%)

$^1$H-NMR (D$_2$O) δ: 1.50 (3H, s), 1.52 (3H, s), 1.56 (3H, d, J=7.15 Hz), 4.11 (1H, q, J=7.15 Hz), 4.17 (1H, d, J=13.80 Hz), 4.75 (1H, d, J=13.80 Hz), 5.30 (1H, d, J=4.64 Hz), 5.73

(1H, d, J=4.64 Hz), 7.00-7.02 (2H, m), 7.08 (1H, d, J=8.78 Hz), 7.91 (2H, d, J=6.90 Hz), 8.52 (2H, d, J=6.90 Hz).
MS (m+1)=734.92

Example 49: Synthesis of Compound I-49

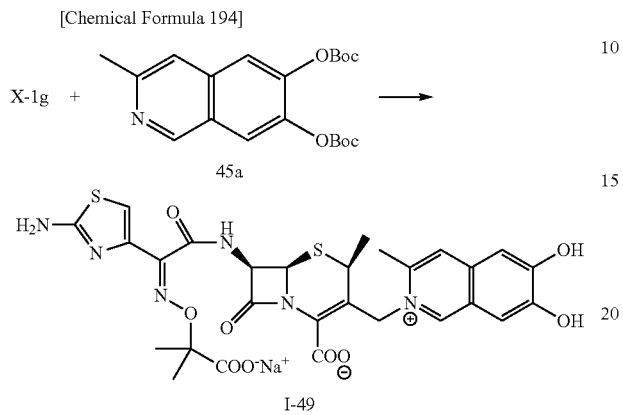

[Chemical Formula 194]

Step (1): Compound X-1g+Compound 45a→Compound I-49

From Compound X-1g (672 mg, 0.80 mmol) and Compound 45a (300 mg, 1.0 mmol), Compound I-49 was obtained as a white powder using the same method as Example 44.
Yield: 244 mg, (45%)
$^1$H-NMR (D$_2$O) δ: 1.25 (3H, d, J=7.15 Hz), 1.50 (3H, s), 1.51 (3H, s), 2.71 (3H, s), 3.95 (1H, q, J=7.15 Hz), 5.22 (1H, d, J=15.69 Hz), 5.44 (1H, d, J=15.69 Hz), 5.51 (1H, d, J=4.77 Hz), 5.80 (1H, d, J=4.77 Hz), 6.97-6.98 (2H, m), 7.34 (1H, s), 7.58 (1H, s), 8.83 (1H, s).
MS (m+1)=657.01

Example 50: Synthesis of Compound I-50

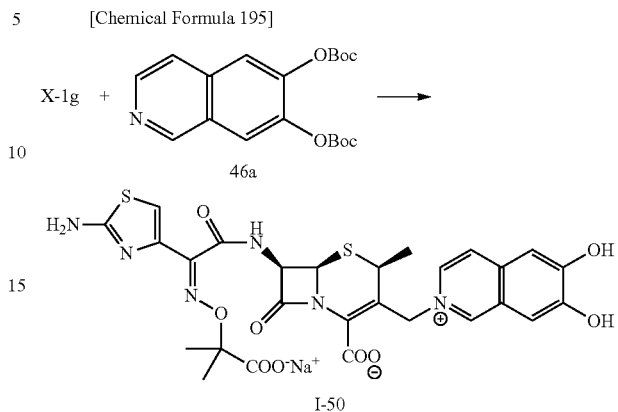

[Chemical Formula 195]

Step (1): Compound X-1g+Compound 46a→Compound I-50

From Compound X-1g (672 mg, 0.80 mmol) and Compound 46a (289 mg, 1.0 mmol), Compound I-50 was obtained as a white powder using the same method as Example 44.
Yield: 294 mg, (55%)
$^1$H-NMR (D$_2$O) δ: 1.35 (3H, d, J=7.33 Hz), 1.49 (3H, s), 1.51 (3H, s), 3.89 (1H, q, J=7.33 Hz), 5.30 (1H, d, J=14.91 Hz), 5.43 (1H, d, J=4.80 Hz), 5.46 (1H, d, J=14.91 Hz), 5.82 (1H, d, J=4.80 Hz), 6.98 (1H, s), 7.10 (1H, s), 7.41 (1H, s), 7.76 (1H, d, J=6.82 Hz), 8.00 (1H, d, J=6.82 Hz), 8.91 (1H, s).
MS (m+1)=643.01

Example 51: Synthesis of Compound I-51

[Chemical Formula 196]

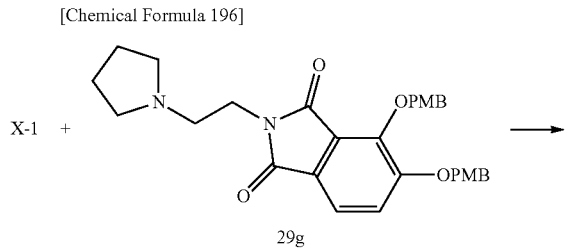

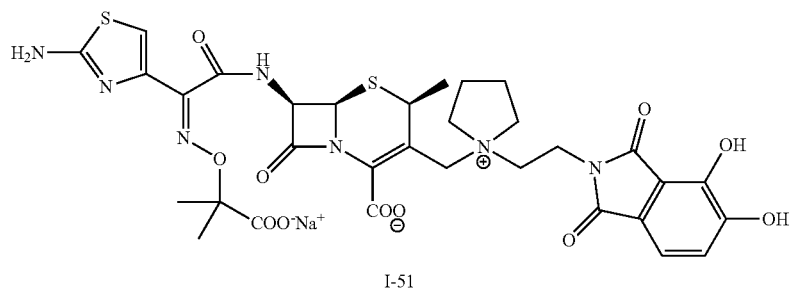

Step (1): Compound X-1+Compound 29g→Compound I-51

From Compound X-1 (932 mg, 1.0 mmol) and Compound 29g (517 mg, 1.0 mmol), Compound I-51 was obtained as a yellow powder using the same method as Example 20.
Yield: 222 mg, (29%)
$^1$H-NMR (D$_2$O) δ: 1.50 (3H, s), 1.53 (3H, s), 1.60 (3H, d, J=7.03 Hz), 2.23 (4H, s), 3.52-3.71 (6H, m), 3.99-4.16 (3H, m), 4.32 (1H, d, J=14.18 Hz), 5.07 (1H, d, J=14.18 Hz), 5.48 (1H, d, J=4.77 Hz), 5.81 (1H, d, J=4.77 Hz), 7.00-7.02 (2H, m), 7.15 (1H, d, J=7.78 Hz).
MS (m+1)=758.25

Example 52: Synthesis of Compound I-52

Thereto was added sodium iodide (240 mg, 1.6 mmol), and the solution was stirred at 15° C. for 6 hours. Dimethylformamide (5.0 mL) was added thereto, and the solution was cooled to −40° C. Thereto was added phosphorus tribromide (151 μL, 1.6 mmol). The solution was stirred at 0° C. for 30 minutes. The reaction mixture was slowly added to a 5% salt solution cooled with ice. The precipitated solid was collected by filtration, washed with water, and suspended into water. The suspension was freeze-dried to yield compound 52b as a brown solid. Compound 52b yielded was used as it was, without being purified, in the next reaction.

From Compound 52b, Compound I-52 was obtained as a white powder using the same method as Example 20.

[Chemical Formula 197]

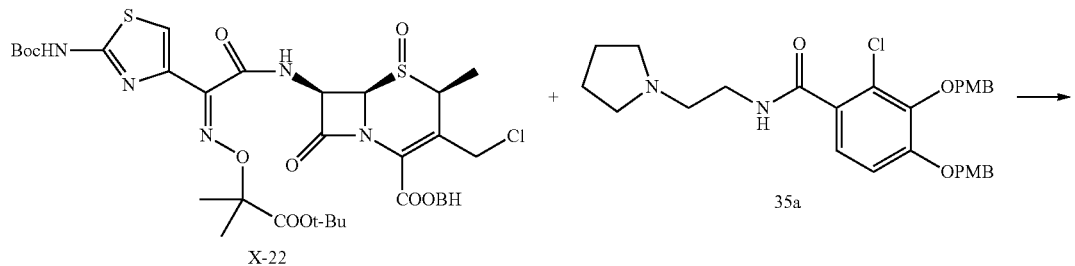

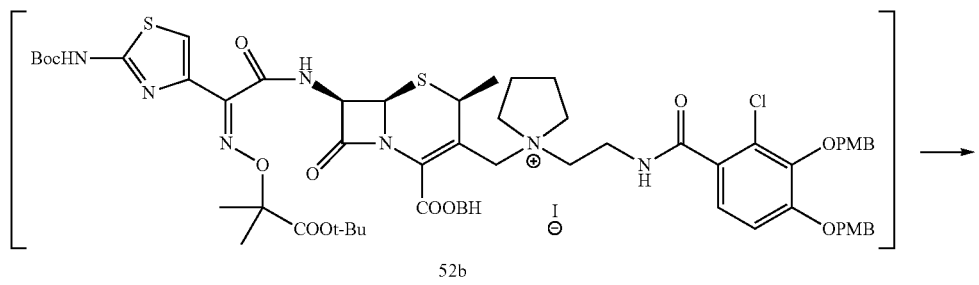

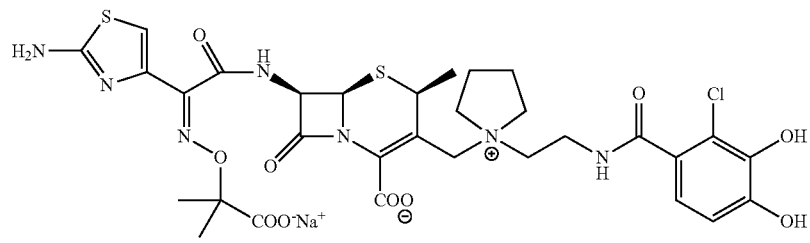

Step (1): Compound X-22+Compound 35a→Compound 52b→Compound I-52

A solution of Compound X-22 (420 mg, 0.80 mmol) in dimethylacetoamide (2.0 mL) was cooled with ice, and thereto was added compound 35a (685 mg, 0.80 mmol). The reaction vessel was then degassed under reduced pressure.

Yield: 269 mg, (43%)
$^1$H-NMR (D$_2$O) δ: 1.50 (3H, s), 1.52 (3H, s), 1.58 (3H, d, J=7.02 Hz), 2.23 (4H, s), 3.55-3.59 (2H, m), 3.73-3.88 (5H, m), 4.04-4.10 (1H, m), 4.22-4.29 (2H, m), 5.02 (1H, d, J=13.88 Hz), 5.45 (1H, d, J=5.03 Hz), 5.73 (1H, d, J=5.03 Hz), 6.88-6.90 (2H, m), 7.00 (1H, s).
MS (m+1)=766.62

Example 53: Synthesis of Compound I-53

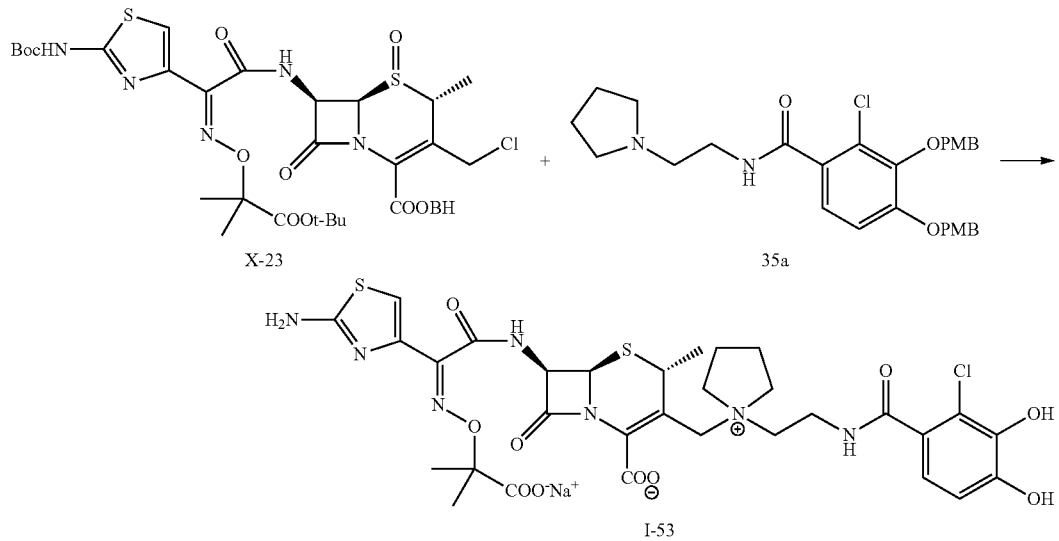

Step (1): Compound X-23+Compound 35a→Compound I-53

From Compound X-23 (514 mg, 0.60 mmol) and Compound 35a (315 mg, 0.60 mmol), Compound I-53 was obtained as a white powder using the same method as Example 52.

Yield: 198 mg, (42%)

$^1$H-NMR (D$_2$O) δ: 1.48 (6H, s), 1.64 (3H, d, J=6.86 Hz), 2.23 (4H, s), 3.55-3.59 (2H, m), 3.73-3.88 (6H, m), 4.22-4.29 (2H, m), 4.50 (1H, d, J=14.03 Hz), 5.47 (1H, d, J=5.03 Hz), 5.79 (1H, d, J=5.03 Hz), 6.82 (1H, d, J=8.39 Hz), 6.89 (1H, s), 6.98 (1H, d, J=8.39 Hz).

MS (m+1)=766.36

Example 54: Synthesis of Compound I-54

Step (1): Compound X-22+Compound 54a→Compound I-54

From Compound X-22 (685 mg, 0.80 mmol) and Compound 54a (441 mg, 0.80 mmol), Compound I-54 was obtained as a white powder using the same method as Example 51.

Yield: 164 mg, (25%)

$^1$H-NMR (D$_2$O) δ: 1.50 (3H, s), 1.52 (3H, s), 1.62 (3H, d, J=7.02 Hz), 2.17 (2H, dd, J=16.01, 6.86 Hz), 2.36-2.79 (7H, m), 3.14 (3H, s), 3.80 (1H, q, J=6.66 Hz), 4.01 (1H, s), 4.10-4.23 (3H, m), 5.43 (1H, d, J=4.88 Hz), 5.91 (1H, d, J=4.88 Hz), 6.89 (1H, d, J=8.39 Hz), 6.94 (1H, d, J=8.39 Hz), 6.98 (1H, s).

MS (m+1)=792.62

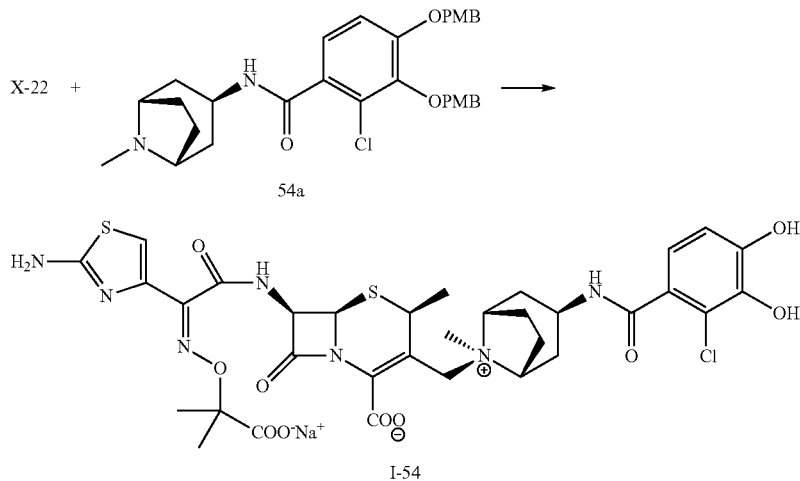

Example 55: Synthesis of Compound I-55
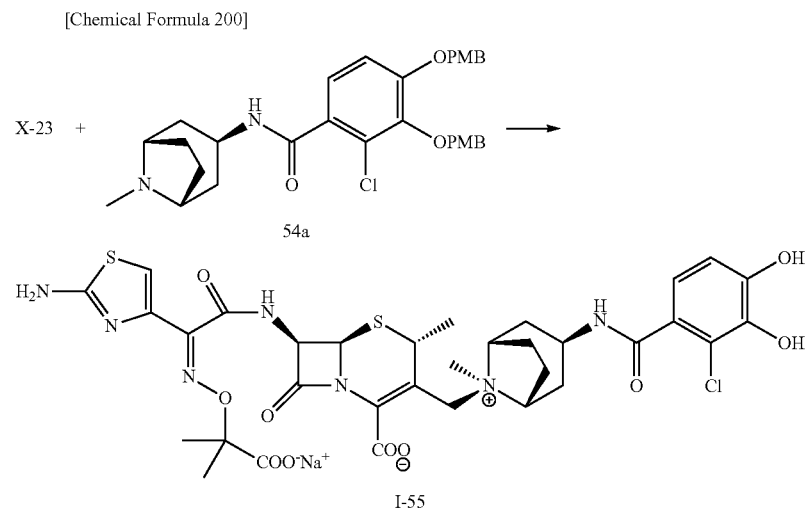
Step (1): Compound X-23+Compound 54a→Compound I-55
From Compound X-23 (514 mg, 0.60 mmol) and Compound 54a (331 mg, 0.60 mmol), Compound I-55 was obtained as a white powder using the same method as Example 51.
Yield: 30 mg, (6%)
$^1$H-NMR (D$_2$O) δ: 1.50 (3H, s), 1.52 (3H, s), 1.62 (3H, d, J=7.02 Hz), 2.17 (2H, dd, J=16.01, 6.86 Hz), 2.36-2.79 (7H, m), 3.14 (3H, s), 3.80 (1H, q, J=6.66 Hz), 4.01 (1H, s), 4.10-4.23 (3H, m), 5.43 (1H, d, J=4.88 Hz), 5.91 (1H, d, J=4.88 Hz), 6.89 (1H, d, J=8.39 Hz), 6.94 (1H, d, J=8.39 Hz), 6.98 (1H, s).
MS (m+1)=792.44
Example 56: Synthesis of Compound I-56
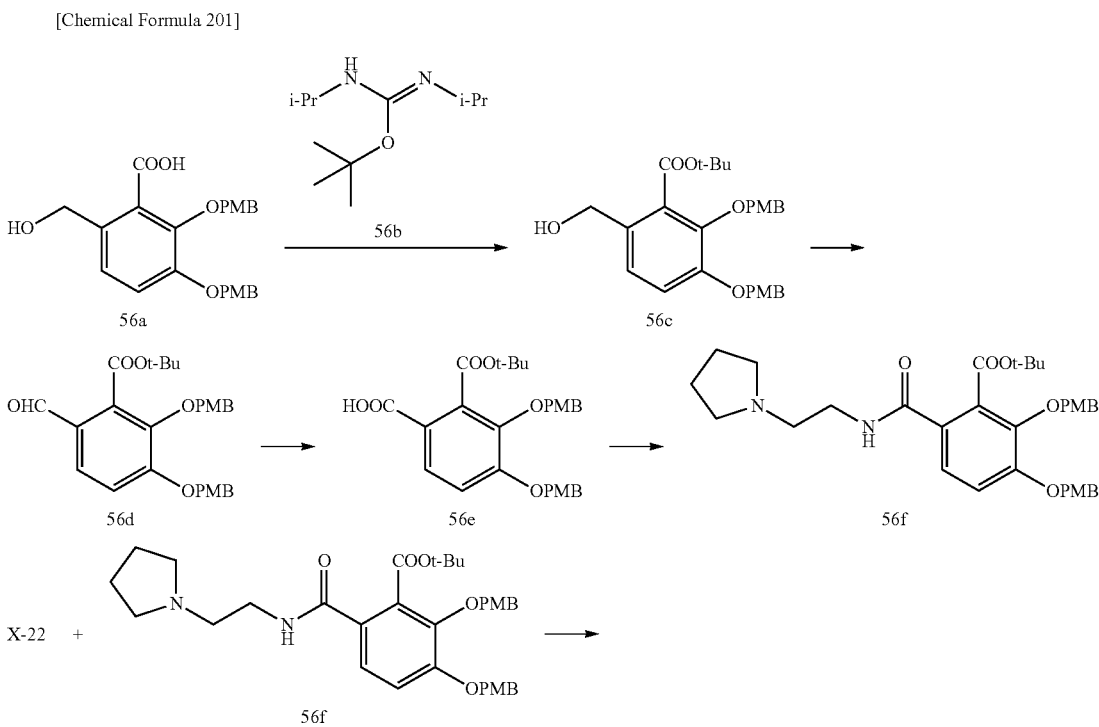

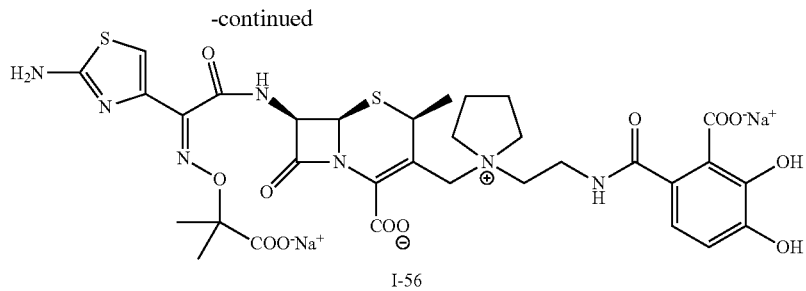

I-56

Step (1): Compound 56a→Compound 56c

To a solution of Compound 56a (10.19 g, 24.0 mmol) in dichloromethane (100 mL) was added Compound 56b (9.62 g, 48.0 mmol), and then the mixture was stirred at room temperature over night. The solvent was removed by evaporation and to the residue was added water and ethyl acetate. The organic layer separated was washed with water and brine, and then dried over MgSO4, filtered and concentrated. The residue was purified by column chromatography on silica gel eluted with n-hexane/ethyl acetate to afford Compound 56c (4.45 g, 39%) as an oil substance.

$^1$H-NMR (CDCl$_3$) δ: 1.55 (9H, s), 2.54 (1H, t, J=6.65 Hz), 3.80 (3H, s), 3.83 (3H, s), 4.52 (2H, d, J=6.65 Hz), 5.00 (2H, s), 5.05 (2H, s), 6.81 (2H, d, J=8.66 Hz), 6.90 (2H, d, J=8.66 Hz), 7.00 (1H, d, J=8.28 Hz), 7.08 (1H, d, J=8.28 Hz), 7.29 (2H, d, J=8.53 Hz), 7.35 (2H, d, J=8.53 Hz).

Step (2): Compound 56c→Compound 56d

To a solution of Compound 56c (4.45 g, 9.26 mmol) in dichloromethane (45 mL) was added Dess-Martin periodinane (4.32 g, 10.19 mmol) at 0 degree, and then the mixture was stirred at room temperature over night. To the resulting mixture was added water. The organic solvent was removed by evaporation and the aqueous residue was extracted with ethyl acetate. The organic layer was washed with water and brine, dried over magnesium sulfate, filtered and concentrated. The residue was purified by column chromatography on silica gel eluted with n-hexane/ethyl acetate to afford Compound 56d (2.91 g, 66%) as a colorless solid.

$^1$H-NMR (CDCl$_3$) δ: 1.56 (9H, s), 3.80 (3H, s), 3.84 (3H, s), 4.97 (2H, s), 5.14 (2H, s), 6.80 (2H, d, J=8.08 Hz), 6.93 (2H, d, J=8.34 Hz), 7.10 (1H, d, J=8.34 Hz), 7.26-7.28 (2H, m), 7.37 (2H, d, J=8.34 Hz), 7.60 (1H, d, J=8.34 Hz), 9.88 (1H, s).

Step (3): Compound 56d→Compound 56e

To a solution of Compound 56d (2.91 g, 6.08 mmol) in 1,4-dioxane (30 mL) and water (10 mL) with stirring in ice bath was added amidosulfuric acid (1.18 g, 12.16 mmol) and sodium chlorite (1.38 g, 12.16 mmol), and then the mixture was stirred at 0 degree for 30 min. To the resulting mixture was added sodium bisulfate (2.53 g, 24.32 mmol). The mixture was extracted with ethyl acetate. The organic layer was washed with water and brine, dried over magnesium sulfate, filtered, and concentrated. The residue was triturated with diisopropyl ether and the solid was collected by filtration and dried under high vacuum to afford Compound 56e (2.79 g, 93%) as a colorless solid.

$^1$H-NMR (DMSO-D$_6$) δ: 1.45 (9H, s), 3.74 (3H, s), 3.78 (3H, s), 4.84 (2H, s), 5.19 (2H, s), 6.83 (2H, d, J=8.66 Hz), 6.98 (2H, d, J=8.78 Hz), 7.20 (2H, d, J=8.66 Hz), 7.31 (1H, d, J=8.78 Hz), 7.46 (2H, d, J=8.66 Hz), 7.69 (1H, d, J=8.66 Hz).

Step (4): Compound 56e→Compound 56f

To a solution of Compound 56e (989 mg, 2.0 mmol) in dimethylformamide (3 mL) was added 1-hydroxybenzotriazole (324 mg, 2.4 mmol), 1-(2-aminoethyl)pyrrolidine (0.30 mL, 2.4 mmol) and EDC hydrochloride (460 mg, 2.4 mmol) at 0 degree. The mixture was stirred at room temperature for 4.5 hr. To the resulting mixture was added ice water and extracted with ethyl acetate. The organic layer was washed with 1 mol/L sodium hydroxide solution, water and brine, and then dried over magnesium sulfate, filtered, evaporated at 25 degree. The residue was dried under high vacuum to afford Compound 56f (1.16 g, 98%) as a yellowish oil.

$^1$H-NMR (CDCl$_3$) δ: 1.53 (9H, s), 1.79 (4H, br s), 2.58 (4H, br s), 2.70 (2H, t, J=5.81 Hz), 3.52 (2H, q, J=5.56 Hz), 3.79 (3H, s), 3.83 (3H, s), 4.97 (2H, s), 5.07 (2H, s), 6.80 (2H, d, J=8.34 Hz), 6.91 (2H, d, J=8.34 Hz), 6.96 (1H, d, J=8.59 Hz), 7.29 (2H, d, J=8.34 Hz), 7.33-7.36 (3H, m).

Step (5): Compound X-22+Compound 56f→Compound I-56

From Compound X-22 (475 mg, 0.59 mmol) and Compound 56f (346 mg, 0.59 mmol), Compound I-56 was obtained as a white powder using the same method as Example 52.

Yield: 51 mg, (11%)

$^1$H-NMR (D$_2$O) δ: 1.50 (3H, s), 1.52 (3H, s), 1.59 (3H, d, J=7.03 Hz), 2.24 (4H, s), 3.35-3.87 (8H, m), 4.11 (1H, q, J=7.03 Hz), 4.28 (1H, d, J=14.31 Hz), 5.00 (1H, d, J=14.31 Hz), 5.48 (1H, d, J=4.77 Hz), 5.82 (1H, d, J=4.77 Hz), 6.74 (1H, d, J=8.16 Hz), 6.96 (1H, d, J=8.16 Hz), 7.03 (1H, s).

MS (m+1)=776.03

Example 57: Synthesis of Compound I-57

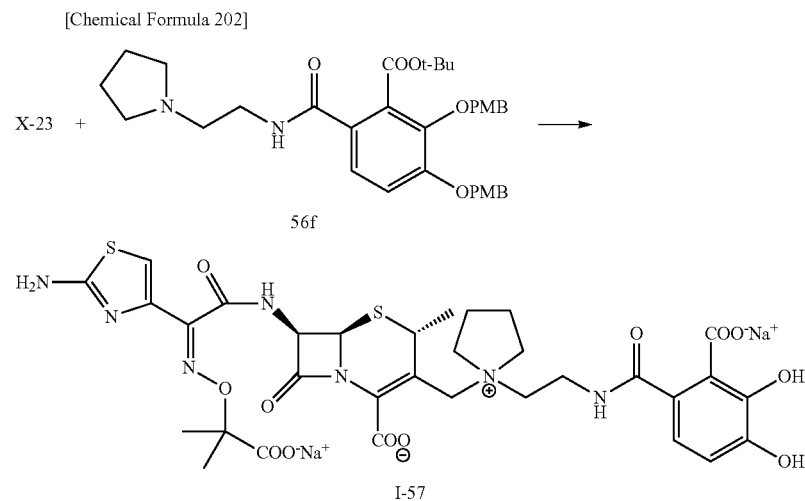

Step (1): Compound X-23+Compound 56f→Compound I-57

From Compound X-23 (685 mg, 0.80 mmol) and Compound 56f (473 mg, 0.80 mmol), Compound I-57 was obtained as a white powder using the same method as Example 52.

Yield: 52 mg, (8%)

$^1$H-NMR (D$_2$O) δ: 1.50 (6H, s), 1.65 (3H, d, J=6.82 Hz), 2.22 (4H, s), 3.58-3.87 (9H, m), 4.31 (1H, d, J=14.40 Hz), 4.46 (1H, d, J=14.40 Hz), 5.48 (1H, d, J=4.80 Hz), 5.83 (1H, d, J=4.80 Hz), 6.68 (1H, d, J=8.08 Hz), 6.93 (1H, d, J=8.08 Hz), 6.96 (1H, s).

MS (m+1)=776.06

Example 58: Synthesis of Compound I-58

Step (1): Compound X-23+Compound 29g→Compound I-58

From Compound X-23 (685 mg, 0.80 mmol) and Compound 29g (413 mg, 0.80 mmol), Compound I-58 was obtained as a yellow powder using the same method as Example 52.

Yield: 46 mg, (7%)

$^1$H-NMR (D$_2$O) δ: 1.46 (3H, s), 1.47 (3H, s), 1.68 (3H, d, J=6.78 Hz), 2.21 (4H, s), 3.49-3.55 (1H, m), 3.74-3.93 (6H, m), 4.02-4.05 (2H, m), 4.27 (1H, d, J=14.43 Hz), 4.55 (1H, d, J=13.93 Hz), 5.52 (1H, d, J=4.77 Hz), 5.87 (1H, d, J=4.77 Hz), 6.91 (1H, s), 6.96 (1H, s), 7.04 (1H, d, J=7.53 Hz).

MS (m+1)=758.03

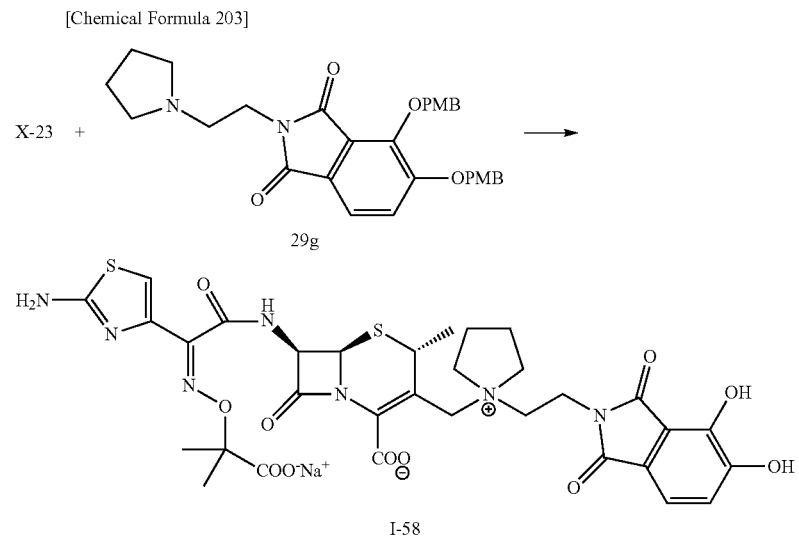

The compounds shown below were obtained from Compound X-1g and the each corresponding amine in the same way as example 39.

Example 59: Synthesis of Compound I-59

[Chemical Formula 204]

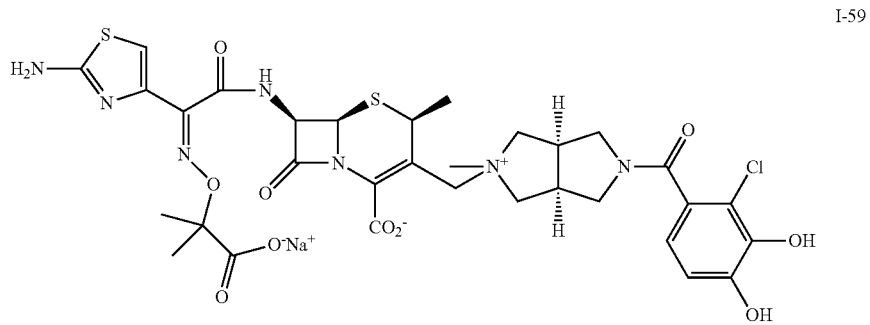

I-59

Yielded amount: 423 g (52%)
$^1$H-NMR (D$_2$O) δ: 6.93-6.91 (1H, m), 6.93-6.91 (1H, m), 6.81-6.77 (1H, m), 5.86-5.83 (1H, m), 5.47-5.44 (1H, m), 4.13-3.98 (4H, m), 3.69-3.63 (2H, m), 3.49-2.95 (7H, m), 1.59-1.56 (3H, m), 1.52 (3H, s), 1.50 (3H, s).
[M+H]=778.23

Example 60: Synthesis of Compound I-60

[Chemical Formula 205]

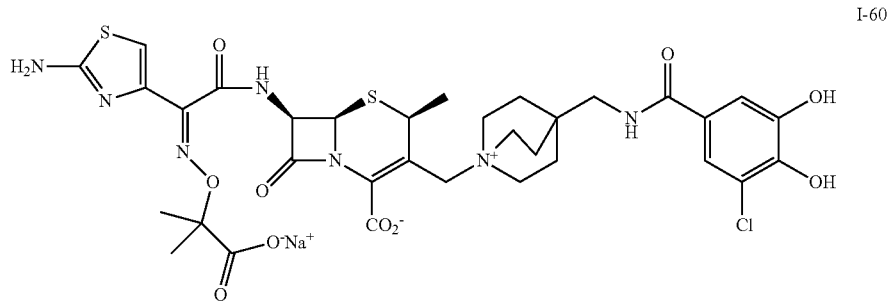

I-60

Yielded amount: 516 g (62%)
$^1$H-NMR (D$_2$O) δ: 7.39 (1H, s), 7.19 (1H, s), 7.01 (1H, s), 5.84 (1H, d, J=5.0 Hz), 5.45 (1H, d, J=5.0 Hz), 4.63 (1H, d, J=14.9 Hz), 4.09-4.04 (2H, m), 3.55-3.43 (6H, m), 3.35 (2H, br s), 1.93 (6H, t, J=7.8 Hz), 1.56 (3H, d, J=7.3 Hz), 1.52 (3H, s), 1.50 (3H, s).
[M+H]=792.27

Example 61: Synthesis of Compound I-61

[Chemical Formula 206]

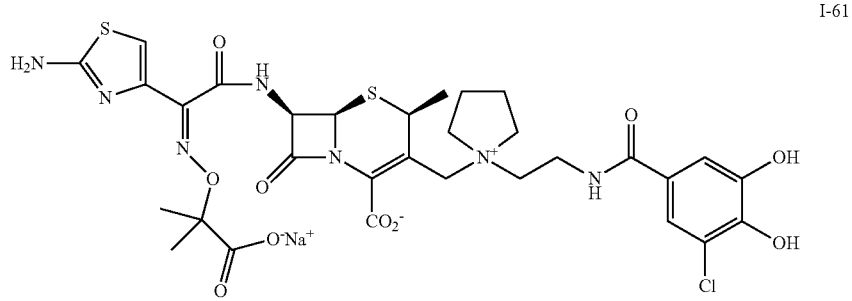

I-61

Yielded amount: 346 mg (42%)
$^1$H-NMR (D$_2$O) δ: 7.39 (1H, s), 7.23 (1H, s), 7.01 (1H, s), 5.80 (1H, d, J=4.8 Hz), 5.45 (1H, d, J=4.8 Hz), 5.03 (1H, d, J=14.3 Hz), 4.25 (1H, d, J=14.3 Hz), 4.09-4.04 (1H, m), 3.92-3.85 (1H, m), 3.79-3.70 (2H, m), 3.60-3.44 (5H, m), 2.29-2.15 (4H, m), 1.57 (3H, d, J=7.0 Hz), 1.52 (3H, s), 1.50 (3H, s).
[M+H]=766.24

Example 62: Synthesis of Compound I-62

[Chemical Formula 207]

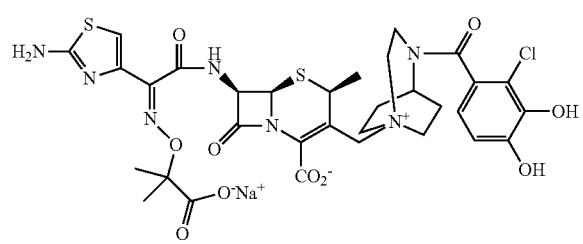

I-62

Yielded amount: 396 mg (48%)
$^1$H-NMR (D$_2$O) δ: 7.02-7.00 (1H, m), 6.92 (1H, d, J=8.3 Hz), 6.81-6.77 (1H, m), 5.86-5.83 (1H, m), 5.47-5.44 (1H, m), 4.13-3.98 (5H, m), 3.69-2.95 (11H, m), 1.58 (3H, t, J=6.6 Hz), 1.52 (3H, s), 1.50 (3H, s). [M+H]=778.20

Example 63: Synthesis of Compound I-63

[Chemical Formula 208]

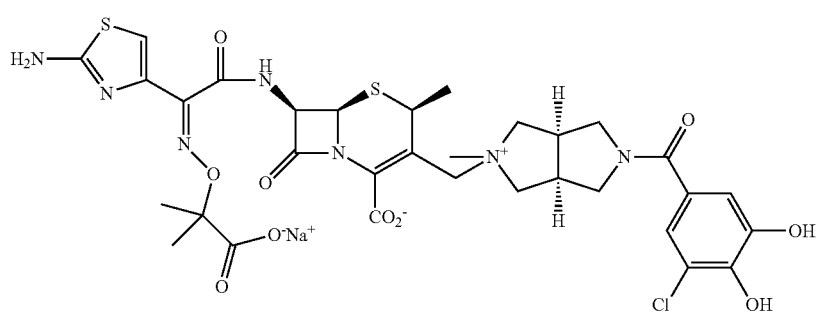

I-63

Yielded amount: 405 mg (50%)
$^1$H-NMR (D$_2$O) δ: 7.14 (1H, br s), 7.02-6.98 (2H, br m), 5.85-5.81 (1H, m), 5.45 (1H, d, J=4.9 Hz), 4.14-3.67 (8H, m), 3.42-2.95 (8H, m), 1.58-1.55 (3H, m), 1.52 (3H, br s), 1.50 (3H, br s).
[M+H]=778.20

Example 64: Synthesis of Compound I-64

[Chemical Formula 209]

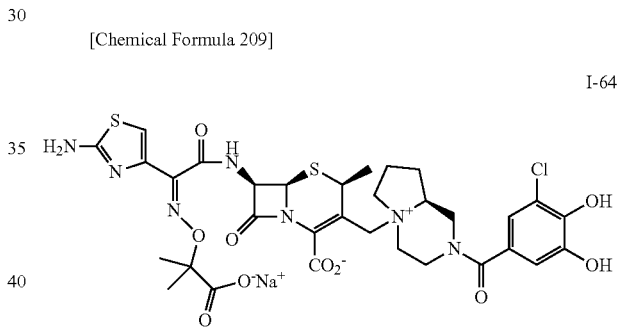

I-64

Yielded amount: 279 mg (35%)
$^1$H-NMR (D$_2$O) δ: 7.11 (1H, s), 7.02 (1H, s), 6.94 (1H, s), 5.83 (1H, d, J=4.8 Hz), 5.46 (1H, d, J=4.8 Hz), 5.12 (1H, d, J=14.3 Hz), 4.28 (1H, d, J=14.3 Hz), 4.07-3.55 (8H, m), 2.21-2.00 (4H, br m), 1.58 (3H, d, J=6.8 Hz), 1.53 (3H, s), 1.51 (3H, s). [M+H]=778.20

Example 65: Synthesis of Compound I-65
[Chemical Formula 210]
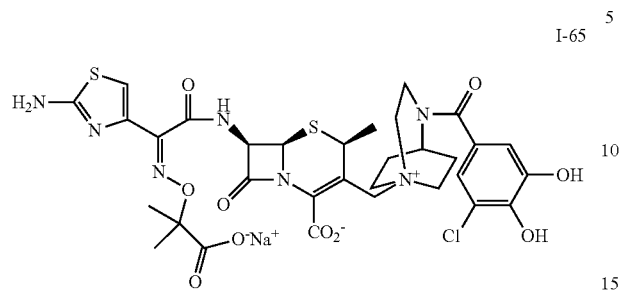
I-65
Yielded amount: 406 mg (50%)
$^1$H-NMR (D$_2$O) δ: 7.08-7.04 (1H, m), 6.99 (1H, br s), 6.93 (1H, br s), 5.89-5.84 (1H, br m), 5.47-5.44 (1H, br m), 4.31-3.47 (11H, m), 2.37-2.23 (4H, br m), 1.57 (3H, d, J=6.5 Hz), 1.52 (3H, br s), 1.50 (3H, br s).
[M+H]=778.23
Example 66: Synthesis of Compound I-66
[Chemical Formula 211]
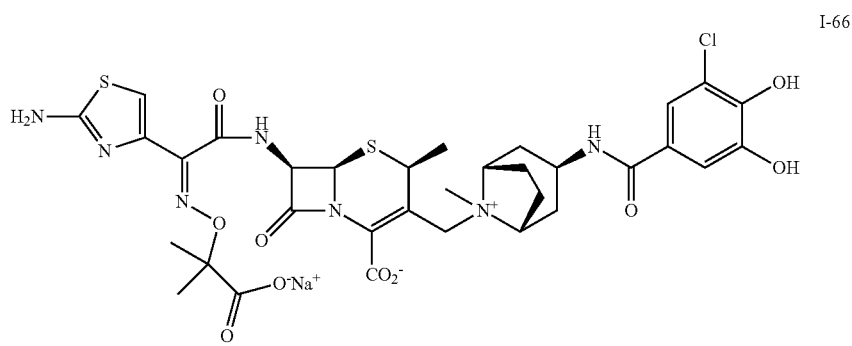
I-66
Yielded amount: 272 mg (33%)
$^1$H-NMR (D$_2$O) δ: 7.32 (1H, d, J=2.0 Hz), 7.17 (1H, s), 7.02 (1H, s), 5.82 (1H, d, J=4.8 Hz), 5.46 (1H, d, J=4.8 Hz), 4.21-3.94 (5H, m), 3.11 (3H, br s), 2.81-2.32 (7H, m), 2.19 (2H, d, J=17.2 Hz), 1.58 (3H, d, J=7.0 Hz), 1.53 (3H, s), 1.51 (3H, s).
[M+H]=792.24
Example 67: Synthesis of Compound I-67
[Chemical Formula 212]
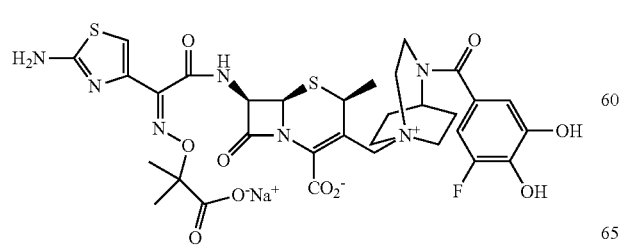
I-67

Yielded amount: 321 mg (40%)
$^1$H-NMR (D$_2$O) δ: 7.00 (1H, s), 6.89-6.81 (2H, m), 5.85 (1H, d, J=4.6 Hz), 5.45 (1H, d, J=4.6 Hz), 4.37-4.27 (1H, m), 4.11-4.03 (3H, m), 3.85-3.62 (7H, m), 2.35 (4H, br s), 1.58 (3H, d, J=6.0 Hz), 1.52 (3H, s), 1.50 (3H, s).
[M+H]=762.32
Example 68: Synthesis of Compound I-68
[Chemical Formula 213]
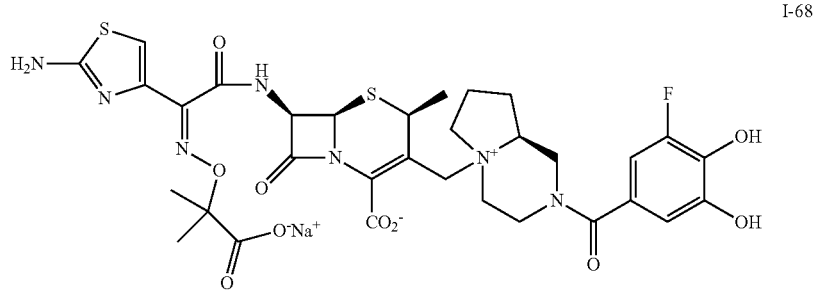
I-68
Yielded amount: 319 mg (40%)
$^1$H-NMR (D$_2$O) δ: 7.01 (1H, s), 6.92-6.89 (1H, br m), 6.84 (1H, s), 5.83 (1H, d, J=4.9 Hz), 5.46 (1H, d, J=4.9 Hz), 5.12 (1H, d, J=14.4 Hz), 4.30-3.52 (10H, m), 2.21-2.02 (4H, br m), 1.58 (3H, d, J=7.0 Hz), 1.53 (3H, s), 1.50 (3H, s).
[M+H]=762.32
Example 69: Synthesis of Compound I-69
[Chemical Formula 214]
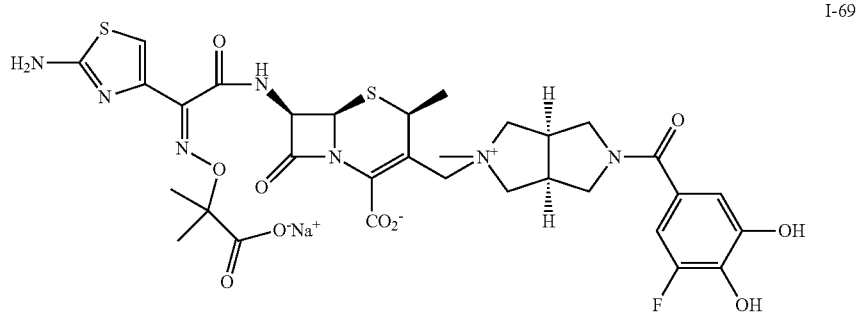
I-69
Yielded amount: 369 mg (47%)
$^1$H-NMR (D$_2$O) δ: 7.01 (1H, d, J=6.1 Hz), 6.95-6.92 (1H, m), 6.88 (1H, br s), 5.85-5.81 (1H, m), 5.45 (1H, d, J=4.9 Hz), 4.14-2.94 (16H, m), 1.57 (3H, d, J=7.0 Hz), 1.52 (3H, s), 1.50 (3H, s).
[M+H]=762.50

Example 70: Synthesis of Compound I-70
[Chemical Formula 215]
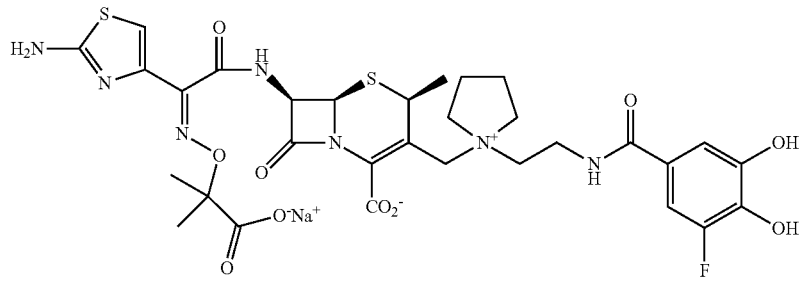
Yielded amount: 300 mg (37%)
$^1$H-NMR (D$_2$O) δ: 7.19-7.15 (2H, m), 7.01 (1H, s), 5.81 (1H, d, J=4.8 Hz), 5.46 (1H, d, J=4.8 Hz), 5.03 (1H, d, J=14.3 Hz), 4.25 (1H, d, J=14.3 Hz), 4.07 (1H, q, J=7.1 Hz), 3.92-3.86 (1H, m), 3.81-3.71 (2H, m), 3.62-3.44 (5H, m), 2.27-2.17 (4H, m), 1.57 (3H, d, J=7.2 Hz), 1.52 (3H, s), 1.50 (3H, s).
[M+H]=750.47
Example 71: Synthesis of Compound I-71
[Chemical Formula 216]
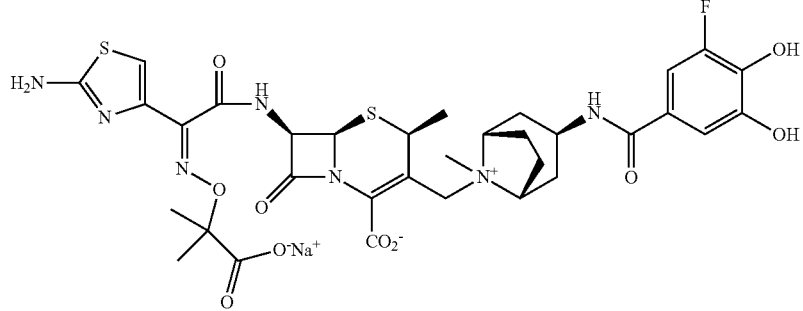
Yielded amount: 143 mg (17%)
$^1$H-NMR (D$_2$O) δ: 7.14-7.09 (2H, m), 7.02 (1H, s), 5.83 (1H, d, J=4.8 Hz), 5.47 (1H, d, J=4.8 Hz), 4.20 (1H, t, J=7.2 Hz), 4.13-4.05 (3H, m), 3.95 (1H, br s), 3.11 (3H, s), 2.81-2.41 (7H, m), 2.19 (2H, d, J=16.9 Hz), 1.58 (3H, d, J=7.0 Hz), 1.53 (3H, s), 1.51 (3H, s).
[M+H]=776.25

Example 72: Synthesis of Compound I-72
[Chemical Formula 217]
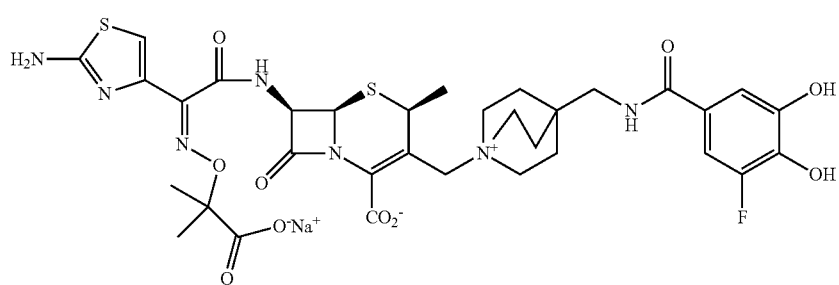
I-72
Yielded amount: 486 mg (60%)
$^1$H-NMR (D$_2$O) δ: 7.18-7.13 (2H, m), 7.00 (1H, s), 5.84 (1H, d, J=4.8 Hz), 5.44 (1H, d, J=4.8 Hz), 4.64 (1H, d, J=14.6 Hz), 4.07 (2H, dd, J=14.6, 8.2 Hz), 3.57-3.40 (6H, m), 3.35 (2H, s), 1.93 (6H, t, J=7.7 Hz), 1.56 (3H, d, J=7.2 Hz), 1.52 (3H, s), 1.50 (3H, s).
[M+H]=776.22
Example 73: Synthesis of Compound I-73
[Chemical Formula 218]
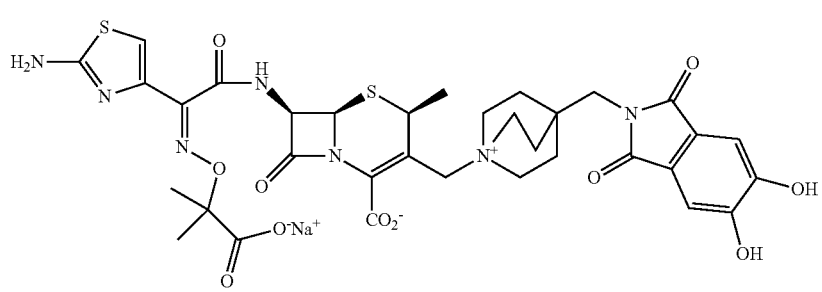
I-73
Yielded amount: 379 mg (45%)
$^1$H-NMR (D$_2$O) δ: 7.16 (2H, br s), 6.99 (1H, s), 5.83 (1H, d, J=4.8 Hz), 5.42 (1H, d, J=4.8 Hz), 4.62 (1H, d, J=14.4 Hz), 4.08-4.02 (2H, m), 3.52-3.40 (8H, m), 1.92 (6H, t, J=7.7 Hz), 1.54 (3H, d, J=7.2 Hz), 1.52 (3H, s), 1.50 (3H, s).
[M+H]=784.32
Example 74: Synthesis of Compound I-74
[Chemical Formula 219]
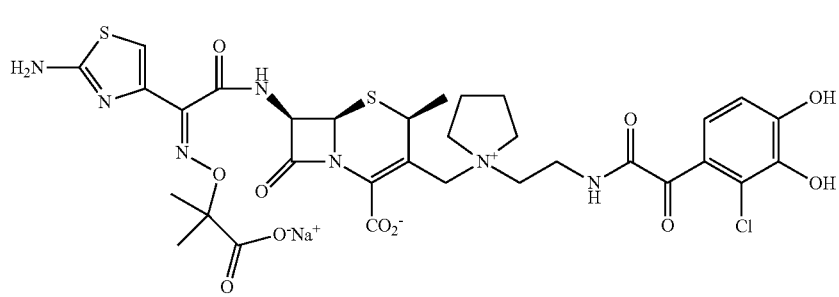
I-74

Yielded amount: 203 mg (23%)

$^1$H-NMR (D$_2$O) δ: 7.33 (1H, d, J=8.7 Hz), 7.02 (1H, d, J=2.4 Hz), 6.89 (1H, d, J=8.7 Hz), 5.80 (1H, d, J=4.8 Hz), 5.47 (1H, d, J=4.8 Hz), 5.03 (1H, d, J=14.3 Hz), 4.26 (1H, d, J=14.3 Hz), 4.07 (1H, q, J=7.1 Hz), 3.97-3.90 (1H, m), 3.84-3.77 (1H, m), 3.70-3.48 (6H, m), 2.27-2.18 (4H, br m), 1.57 (3H, d, J=7.0 Hz), 1.52 (3H, s), 1.50 (3H, s).

[M+H]=794.36

Example 75: Synthesis of Compound I-75

[Chemical Formula 220]

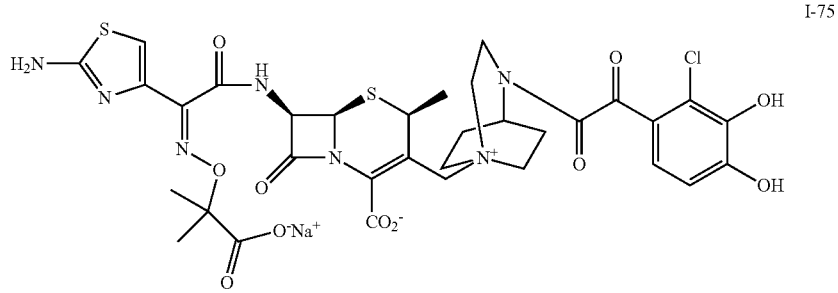

I-75

Yielded amount: 410 mg (45%)

$^1$H-NMR (D$_2$O) δ: 7.47 (1H, d, J=8.4 Hz), 7.00 (1H, br s), 6.81 (1H, br s), 5.86-5.83 (1H, br m), 5.46 (1H, br s), 4.86-4.83 (1H, br m), 4.38-4.31 (1H, m), 4.24 (1H, br s), 4.10-3.52 (8H, m), 2.41-2.27 (4H, br m), 1.60-1.56 (3H, m), 1.52 (3H, br s), 1.45 (3H, br s).

[M+H]=806.35

Example 76: Synthesis of Compound I-76

[Chemical Formula 221]

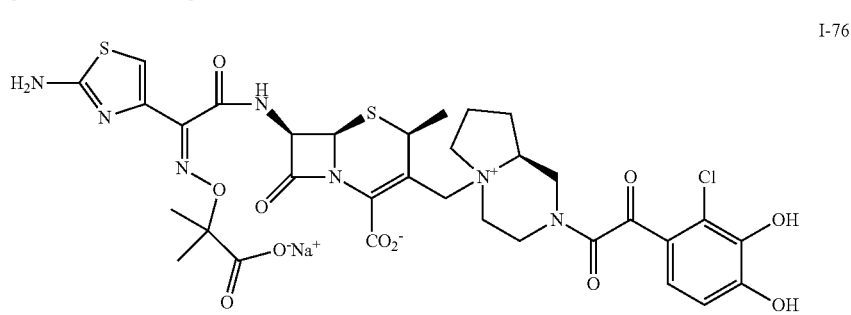

I-76

Yielded amount: 424 mg (48%)

$^1$H-NMR (D$_2$O) δ: 7.47 (1H, d, J=8.7 Hz), 7.02 (1H, s), 6.84 (1H, d, J=8.7 Hz), 5.82-5.81 (1H, br m), 5.46-5.45 (1H, br m), 5.17-5.08 (1H, m), 4.33-4.23 (2H, m), 4.07-3.56 (9H, m), 2.48-2.06 (4H, m), 1.60-1.55 (3H, m), 1.53 (3H, s), 1.51 (3H, s).

[M+H]=806.35

Example 77: Synthesis of Compound I-77
[Chemical Formula 222]
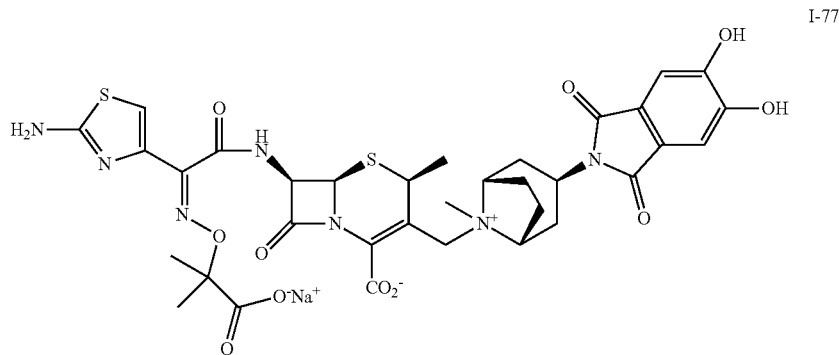
Yielded amount: 102 mg (12%)
$^1$H-NMR ($D_2O$) δ: 7.19 (2H, s), 7.02 (1H, s), 5.83 (1H, d, J=4.8 Hz), 5.47 (1H, d, J=4.8 Hz), 4.14-4.06 (3H, m), 3.99 (1H, br s), 3.12 (3H, s), 2.98-2.14 (10H, m), 1.59 (3H, d, J=7.2 Hz), 1.53 (3H, s), 1.51 (3H, s).
[M+H]=784.39
Example 78: Synthesis of Compound I-78
[Chemical Formula 223]
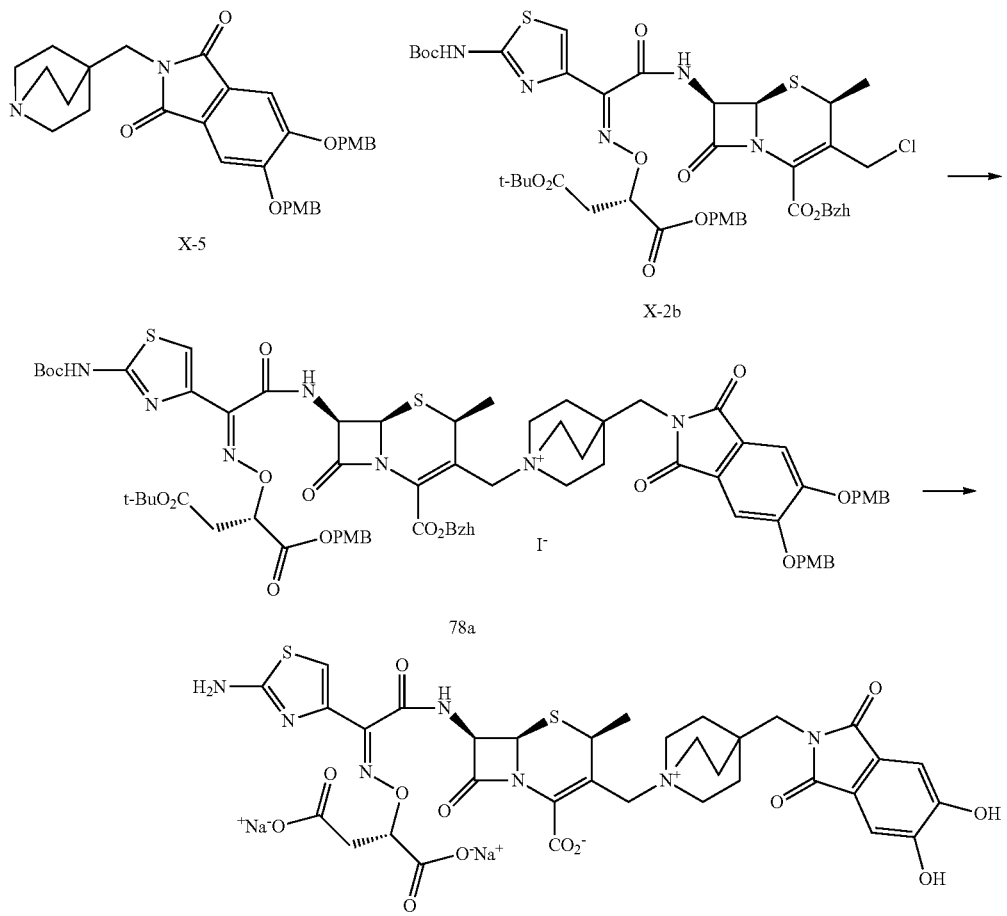

Compound X-5 (543 mg, 1.0 mmol) and Compound X-2b (1.3 g, 1.0 mmol) were used to synthesize the target compound I-78 in the same way as Example 39.

Yielded amount: 231 mg (25%)

$^1$H-NMR (D$_2$O) δ: 7.22 (2H, s), 7.03 (1H, s), 5.78 (1H, d, J=4.8 Hz), 5.41 (1H, d, J=4.8 Hz), 4.96 (1H, dd, J=9.1, 4.2 Hz), 4.67 (1H, t, J=12.9 Hz), 4.06-3.98 (2H, m), 3.54-3.33 (8H, m), 2.72-2.69 (2H, m), 1.93 (6H, t, J=7.7 Hz), 1.54 (3H, d, J=7.2 Hz).

[M+H]=814.27

The compounds shown below were obtained from Compound X-2b and the each corresponding amine in the same way as Example 78.

Example 79: Synthesis of Compound I-79

[Chemical Formula 224]

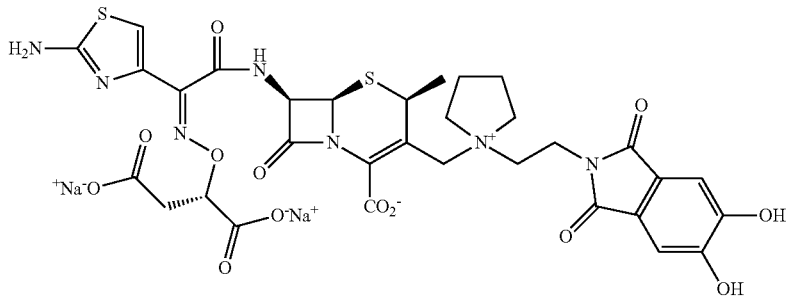

I-79

Yielded amount: 75 mg (8%)

$^1$H-NMR (D$_2$O) δ: 7.27 (2H, s), 7.08 (1H, s), 5.75 (1H, d, J=4.6 Hz), 5.46 (1H, d, J=4.6 Hz), 5.12 (1H, d, J=14.2 Hz), 4.96 (1H, dd, J=9.6, 3.8 Hz), 4.31 (1H, d, J=14.2 Hz), 4.13-4.02 (3H, m), 3.69-3.51 (6H, m), 2.77-2.65 (2H, m), 2.22-2.07 (4H, m), 1.58 (3H, d, J=7.0 Hz).

[M+H]=788.24

Example 80: Synthesis of Compound I-80

[Chemical Formula 225]

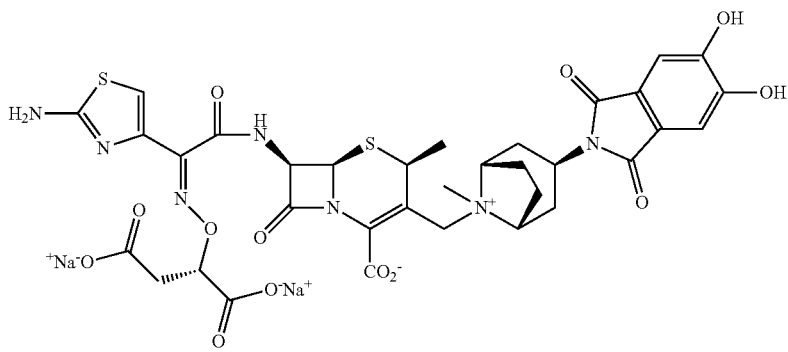

I-80

Yielded amount: 59 mg (5%)

$^1$H-NMR (D$_2$O) δ: 7.24 (2H, s), 7.07 (1H, s), 5.77 (1H, d, J=4.8 Hz), 5.45 (1H, d, J=4.8 Hz), 4.97 (2H, dd, J=9.2, 3.9 Hz), 4.10-3.99 (4H, m), 3.13 (3H, s), 3.03-2.46 (9H, m), 2.28-2.12 (2H, m), 1.58 (3H, d, J=7.2 Hz).

[M+H]=814.20

Example 81: Synthesis of Compound I-81
[Chemical Formula 226]
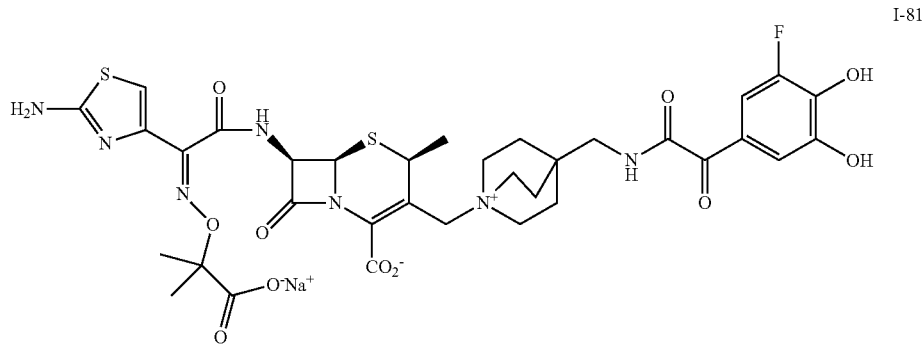
I-81
Yielded amount: 427 mg (49%)
1H-NMR (D$_2$O) δ: 7.44-7.41 (1H, m), 7.33 (1H, s), 7.01 (1H, s), 5.84 (1H, d, J=4.8 Hz), 5.45 (1H, d, J=4.8 Hz), 4.65 (1H, d, J=14.3 Hz), 4.07 (2H, t, J=6.9 Hz), 3.59-3.42 (6H, m), 3.37 (2H, s), 1.95 (6H, t, J=7.6 Hz), 1.56 (3H, d, J=7.0 Hz), 1.52 (3H, s), 1.51 (3H, s).
[M+H]=804.3
Example 82: Synthesis of Compound I-82
[Chemical Formula 227]
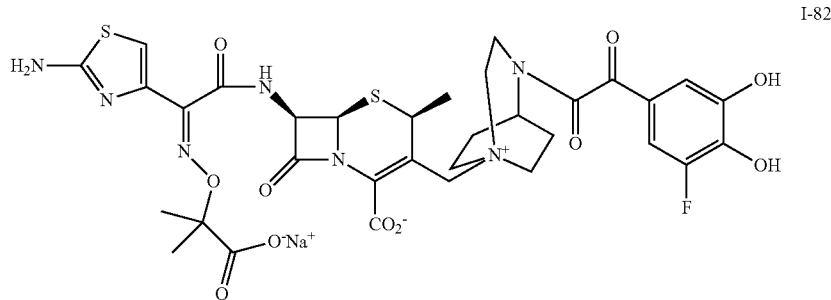
I-82
Yielded amount: 325 mg (51%)
$^1$H-NMR (D$_2$O) δ: 7.33-7.29 (1H, m), 7.22 (1H, br s), 7.00 (1H, br s), 5.85 (1H, t, J=5.5 Hz), 5.45 (1H, t, J=4.6 Hz), 4.38-4.27 (1H, m), 4.19-4.07 (2H, m), 3.88-3.49 (7H, m), 2.43-2.27 (4H, m), 1.61-1.56 (3H, m), 1.52 (3H, d, J=2.5 Hz), 1.50 (3H, d, J=1.9 Hz).
[M+H]=790.26
Example 83: Synthesis of Compound I-83
[Chemical Formula 228]
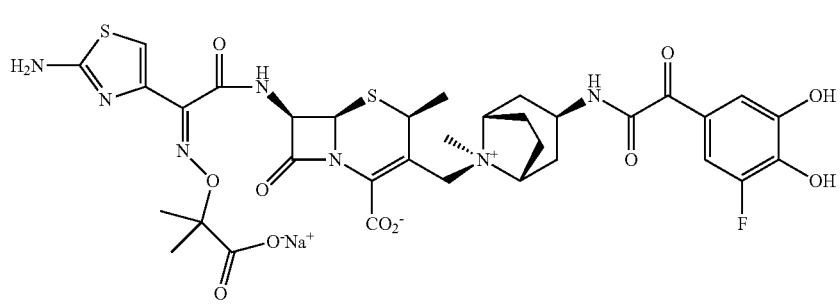
I-83

Yielded amount: 333 mg (40%)

$^1$H-NMR (D$_2$O) δ: 7.44-7.41 (1H, m), 7.34 (1H, s), 7.02 (1H, s), 5.82 (1H, d, J=4.9 Hz), 5.46 (1H, d, J=4.9 Hz), 4.29 (1H, t, J=7.4 Hz), 4.12-4.04 (3H, m), 3.95 (1H, br s), 3.11 (3H, s), 2.87-2.72 (2H, m), 2.55-2.32 (4H, m), 2.17 (2H, d, J=16.8 Hz), 1.58 (3H, d, J=7.0 Hz), 1.53 (3H, s), 1.51 (3H, s).

[M+H]=804.3

Example 84: Synthesis of Compound I-84

[Chemical Formula 229]

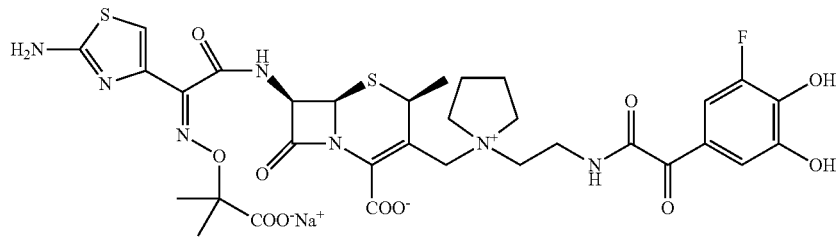

I-84

Yielded amount: 307 mg (38%)

$^1$H-NMR (D$_2$O) δ: 7.51-7.48 (1H, m), 7.40 (1H, s), 7.02 (1H, s), 5.80 (1H, d, J=4.8 Hz), 5.47 (1H, d, J=4.8 Hz), 5.04 (1H, d, J=14.3 Hz), 4.27 (1H, d, J=14.3 Hz), 4.09 (1H, dd, J=13.9, 6.8 Hz), 3.97-3.38 (8H, m), 2.23 (4H, dd, J=12.4, 7.5 Hz), 1.58 (3H, d, J=7.0 Hz), 1.52 (3H, s), 1.50 (3H, s).

[M+H]=778.27

Example 85: Synthesis of Compound I-85

[Chemical Formula 230]

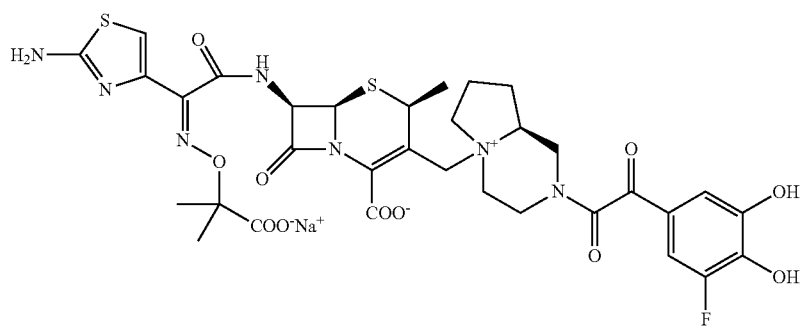

I-85

Yielded amount: 395 mg (49%)

$^1$H-NMR (D$_2$O) δ: 7.37-7.33 (1H, m), 7.25 (1H, s), 7.02-7.00 (1H, br m), 5.83-5.81 (1H, br m), 5.45 (1H, d, J=4.9 Hz), 5.13 (1H, dd, J=22.5, 14.3 Hz), 4.39-4.26 (2H, m), 4.09-3.52 (9H, m), 2.26-2.04 (4H, m), 1.60-1.54 (3H, br m), 1.52-1.52 (3H, br m), 1.50 (3H, br s).

[M+H]=790.26

Example 86: Synthesis of Compound I-86

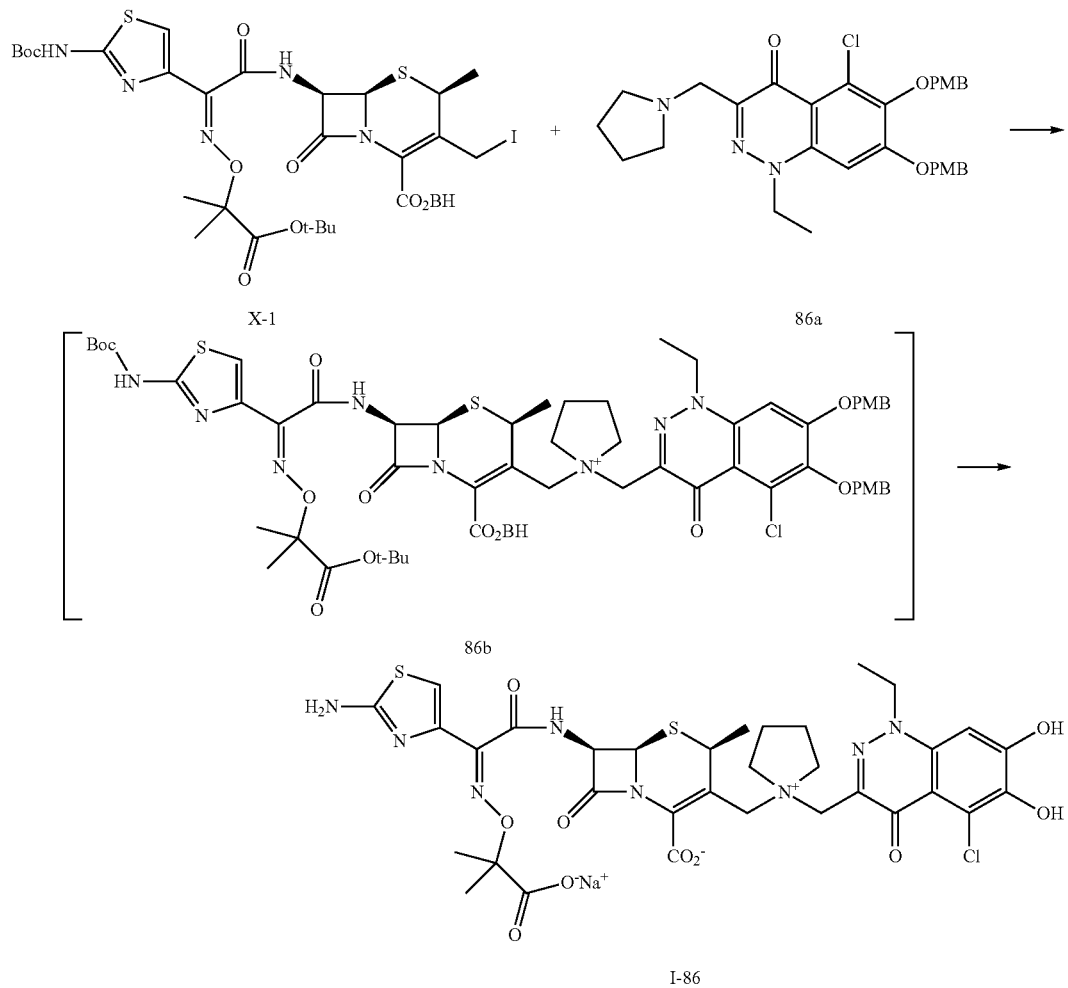

Step (1): Compound X-1+Compound 86a→Compound I-86

Compound X-1 (932 mg, 1.0 mmol) was added to a solution of compound 86a (564 mg, 1.00 mmol) in dimethylformamide (2 mL) at 0° C., and the resultant solution was stirred at 0° C. for 5 hours. The reaction mixture was slowly added to a 5% salt solution (30 ml) (containing 1.5 g of sodium bisulfite) at 0° C. The precipitated solid was collected by filtration, washed with water, and then suspended into water. The suspension was freeze-dried to yield compound 86b as an orange solid. Compound 86b yielded was used as it was, without being purified, in the next reaction.

The total amount of compound 86b yielded was dissolved in dichloromethane (10 mL), and the solution was cooled to −40° C. Thereto were then added anisole (1.1 mL, 10 mmol) and a 2 mol/L aluminum chloride solution (5.00 mL, 10 mmol) in nitromethane in turn. The resultant was stirred at 0° C. for 30 minutes. The reaction mixture was dissolved in water, a 2 mol/L aqueous hydrochloric acid solution, and acetonitrile. The resultant solution was then washed with diisopropyl ether. To the water phase was added HP20-SS resin, and then acetonitrile was distilled off under reduced pressure. The resultant mixed liquid was purified by ODS column chromatography. To the resultant target-compound solution was added HP20-SS resin, and then acetonitrile was distilled off under reduced pressure. The resultant mixed liquid was purified by HP20-SS column chromatography. To the resultant target-compound solution was added a 0.2N aqueous sodium hydroxide solution until the whole gave a pH of 6.0. Thereafter, a piece of dry ice was added thereto. The resultant solution was concentrated under reduced pressure, and then freeze-dried to yield compound I-86 as a yellow powder.

Yielded amount: 472 mg (53%).

$^1$H-NMR (D2O) δ: 7.00 (1H, s), 6.80 (1H, s), 5.82 (1H, d, J=4.8 Hz), 5.49 (1H, d, J=4.8 Hz), 4.99 (1H, d, J=14.3 Hz), 4.56 (2H, br s), 4.41-4.39 (3H, br m), 4.14 (1H, br s), 3.73 (1H, br s), 3.52-3.50 (3H, br m), 2.24 (4H, br s), 1.55-1.44 (12H, m).

[M+H]=805.4

Example 87: Synthesis of Compound I-87

[Chemical Formula 232]

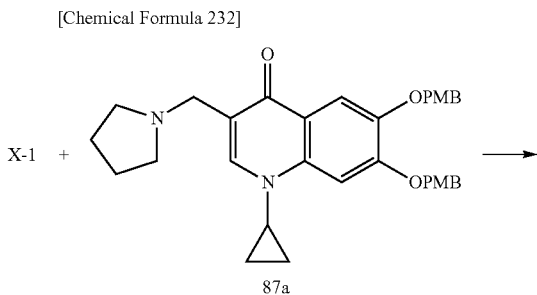

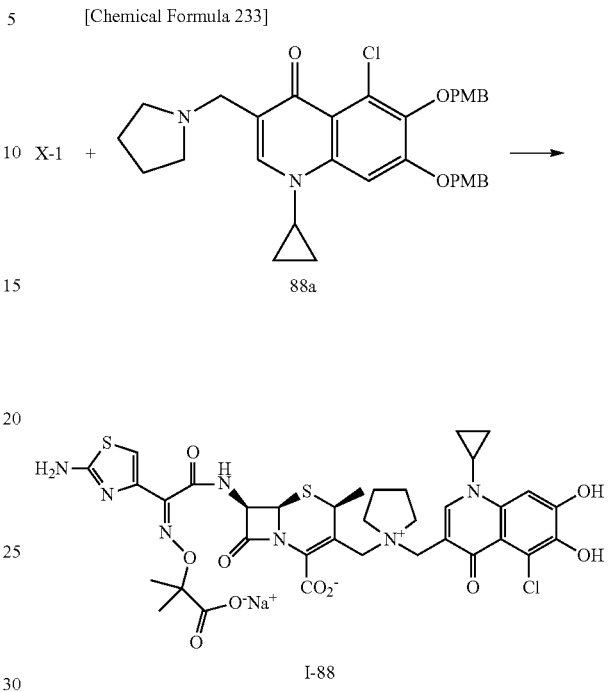

Step (1): Compound X-1+Compound 87a→Compound I-87

Compound X-1 (932 mg, 1.0 mmol) and compound 87a (541 mg, 1.0 mmol) were used to synthesize the target compound in the same way as Example 86.

Yielded amount: 298 mg (35%)

$^1$H-NMR (D2O) δ: 8.24 (1H, s), 7.48 (2H, d, J=7.3 Hz), 6.98 (1H, s), 5.82 (1H, d, J=4.9 Hz), 5.48 (1H, d, J=4.9 Hz), 4.89 (1H, d, J=14.3 Hz), 4.46-4.38 (2H, br m), 4.23 (1H, d, J=14.3 Hz), 4.16-4.10 (1H, br m), 3.59 (2H, br s), 3.36 (3H, br s), 2.22 (4H, d, J=7.2 Hz), 1.55-1.47 (9H, m), 1.44 (1H, d, J=5.6 Hz), 1.33-1.32 (2H, br m), 1.11 (2H, br s).

[M+H]=782.42

Example 88: Synthesis of Compound I-88

[Chemical Formula 233]

Step (1): Compound X-1+Compound 88a→Compound I-88

Compound X-1 (533 mg, 0.57 mmol) and compound 88a (329 mg, 0.57 mmol) were used to synthesize the target compound in the same way as Example 86.

Yielded amount: 136 mg (27%)

$^1$H-NMR (D2O) δ: 8.19 (1H, s), 7.41 (1H, s), 7.00 (1H, s), 5.83 (1H, d, J=4.9 Hz), 5.49 (1H, d, J=4.9 Hz), 4.89 (1H, d, J=14.2 Hz), 4.39 (2H, s), 4.22 (1H, d, J=14.2 Hz), 4.13 (1H, d, J=7.0 Hz), 3.56 (2H, s), 3.36 (3H, s), 2.21 (4H, s), 1.55-1.51 (9H, m), 1.32 (2H, s), 1.07 (2H, s).

[M+H]=816.21

Example 89: Synthesis of Compound I-89

[Chemical Formula 234]

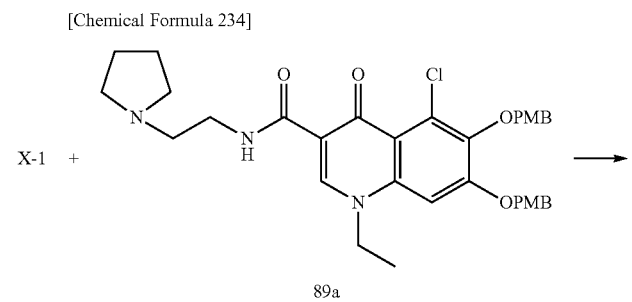

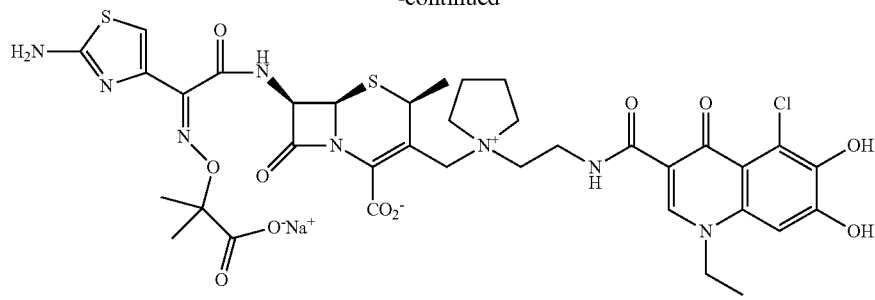

I-89

Step (1): Compound X-1+Compound 89a→Compound I-89

Compound X-1 (932 mg, 1 mmol) and compound 89a (620 mg, 1 mmol) were used to synthesize the target compound in the same way as Example 86.
Yielded amount: 135 mg (14%)
$^1$H-NMR (D2O) δ: 8.45 (1H, s), 7.00 (1H, s), 6.79 (1H, s), 5.82 (1H, d, J=4.6 Hz), 5.48 (1H, d, J=4.6 Hz), 5.03 (1H, d, J=14.4 Hz), 4.33-4.21 (3H, m), 4.07-3.91 (2H, m), 3.73-3.48 (6H, m), 2.24 (4H, br s), 1.57 (3H, d, J=7.0 Hz), 1.51-1.49 (9H, m), 1.42 (3H, t, J=6.4 Hz).
[M+H]=782.42

Example 90: Synthesis of Compound I-90

[Chemical Formula 235]

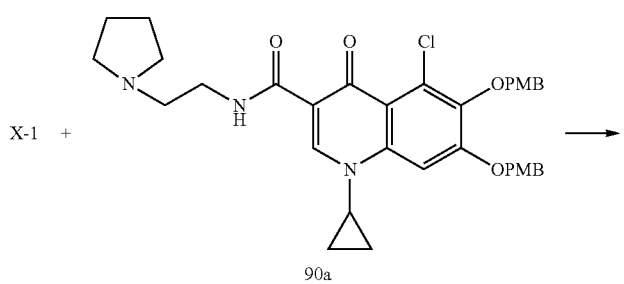

90a

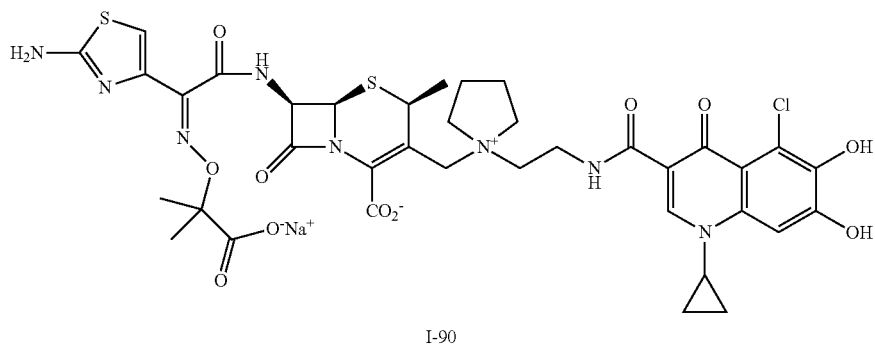

I-90

Step (1): Compound X-1+Compound 90a→Compound I-90

Compound X-1 (932 mg, 1 mmol) and compound 90a (632 mg, 1 mmol) were used to synthesize the target compound in the same way as Example 86.
Yielded amount: 234 mg (25%)
$^1$H-NMR (D2O) δ: 8.36 (1H, s), 7.23 (1H, s), 6.99 (1H, s), 5.83 (1H, d, J=4.6 Hz), 5.48 (1H, d, J=4.6 Hz), 5.03 (1H, d, J=14.2 Hz), 4.30 (1H, d, J=14.2 Hz), 4.06 (1H, br s), 3.90-3.36 (10H, m), 2.24 (4H, br s), 1.58 (3H, d, J=6.8 Hz), 1.51 (3H, s), 1.49 (3H, s), 1.44 (1H, d, J=5.6 Hz), 1.29 (2H, d, J=6.5 Hz), 1.03 (2H, br s).
[M+H]=873.35

Example 91: Synthesis of Compound I-91
[Chemical Formula 236]
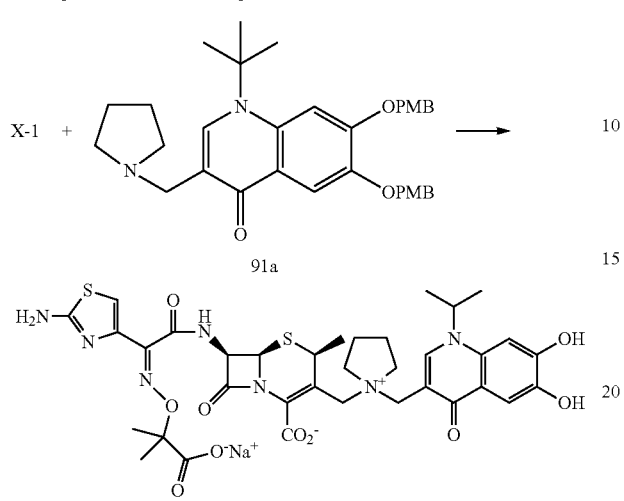
Step (1): Compound X-1+Compound 91a→Compound I-91
Compound X-1 (932 mg, 1 mmol) and compound 91a (557 mg, 1 mmol) were used to synthesize the target compound in the same way as Example 86.
Yielded amount: 334 mg (38%)
$^1$H-NMR (D2O) δ: 8.36 (1H, s), 7.68-7.65 (2H, m), 6.99 (1H, s), 5.83 (1H, d, J=4.9 Hz), 5.47 (1H, d, J=4.9 Hz), 4.90 (1H, d, J=15.2 Hz), 4.56-4.45 (2H, m), 4.25 (1H, d, J=13.9 Hz), 3.59 (1H, br s), 3.39-3.36 (3H, br m), 2.26-2.23 (4H, br m), 1.87 (9H, s), 1.56-1.49 (9H, m).
[M+H]=798.18.
Example 92: Synthesis of Compound I-92
[Chemical Formula 237]
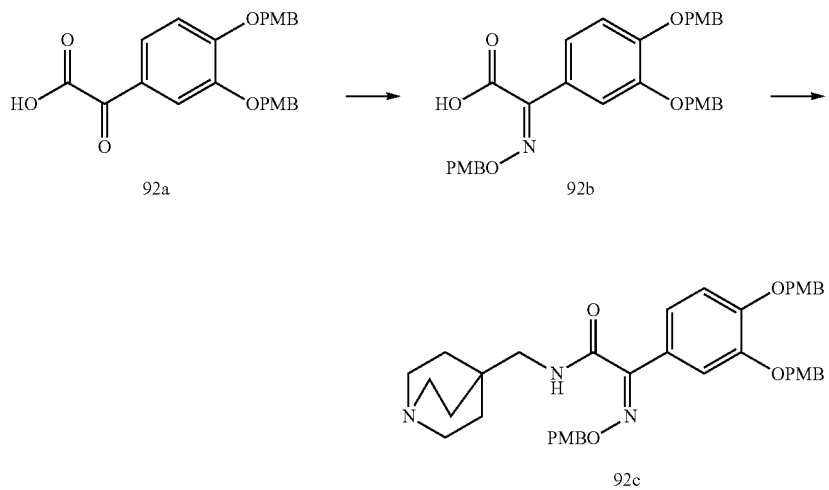
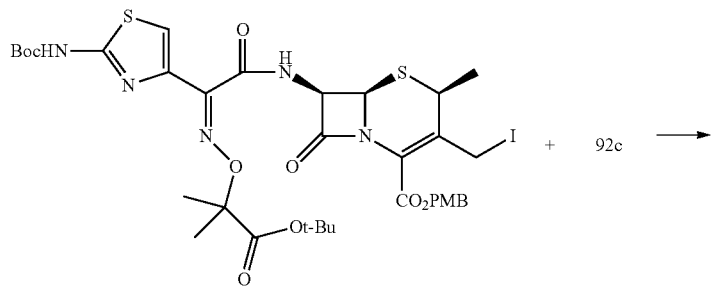

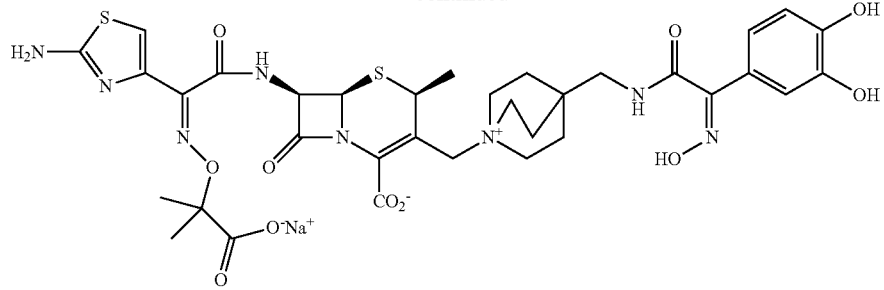

I-92

Step (1): Compound 92a→Compound 92b

To a solution of 92a (4 g, 9.47 mmol) in MeOH (35 ml) was added O-(4-methoxybenzyl)hydroxylamine (1.45 ml, 9.47 mmol) in MeOH (5 ml) at 0° C. under N2. The mixture was stirred at 0° C. for 1 h. The mixture was filtered off and the filtrate was washed IPE and Et$_2$O to yield compound 92b (3.87 g, 73%, E/Z=1:15).

Compound 92b
$^1$H-NMR (CDCl3) δ: 7.34-7.27 (5H, m), 7.05 (1H, dd, J=8.4, 1.6 Hz), 6.94-6.84 (9H, m), 5.16 (2H, s), 5.05 (4H, s), 4.63 (1H, s), 3.81 (3H, s), 3.79 (3H, s), 3.77 (3H, s).

Step (2): Compound 92b→Compound 92c

To a solution of 92b (1.11 g, 2.00 mmol) in DMA (10 ml) was added HOBt (0.35 g, 2.60 mmol) and WSCD HCl (0.46 g, 2.40 mmol) at 0° C. The mixture was stirred at 0° C. for 1 h. The reaction mixture was added quinuclidin-4-ylmethanamine (0.33 g, 2.40 mmol) at 0° C. and then the mixture was stirred at 0° C. for overnight. The reaction mixture was diluted with ethyl acetate, washed with an aqueous sodium hydroxide solution, water and a saturated salt solution, and dried over magnesium sulfate. Magnesium sulfate was filtrated off, and then the liquid was concentrated under reduced pressure. The compound-containing liquid was subjected to silica gel column chromatography to elute out the desired compound with hexane/ethyl acetate (containing 10% triethyl amine). The desired-compound-containing fraction was concentrated under reduced pressure to yield compound 92c (0.63 g, 46%, single isomer).

Compound 92c
$^1$H-NMR (DMSO-D$_6$) δ: 8.44-8.41 (1H, br m), 7.36-7.32 (6H, m), 7.24 (1H, d, J=1.8 Hz), 7.10 (1H, d, J=8.5 Hz), 6.98 (1H, dd, J=8.5, 1.8 Hz), 6.94-6.91 (6H, m), 5.06 (4H, s), 5.00 (2H, s), 3.75 (9H, s), 2.92 (2H, d, J=6.3 Hz), 2.54 (6H, t, J=7.7 Hz), 1.19 (6H, t, J=7.5 Hz).

Step (3): Compound X-24+Compound 92c→Compound I-92

Compound X-24 (886 mg, 1 mmol) and compound 92c (680 mg, 1 mmol) were used to synthesize the target compound in the same way as Example 86.

Yielded amount: 518 mg (60%)
$^1$H-NMR (D2O) δ: 7.15 (1H, d, J=1.8 Hz), 7.00-6.94 (3H, m), 5.85 (1H, d, J=4.9 Hz), 5.45 (1H, d, J=4.9 Hz), 4.63 (1H, d, J=14.3 Hz), 4.08-4.05 (2H, m), 3.54-3.38 (8H, m), 1.96-1.92 (6H, m), 1.56 (3H, d, J=7.2 Hz), 1.53 (3H, s), 1.51 (3H, s).
[M+H]=802.14.

Example 93: Synthesis of Compound I-93

[Chemical Formula 238]

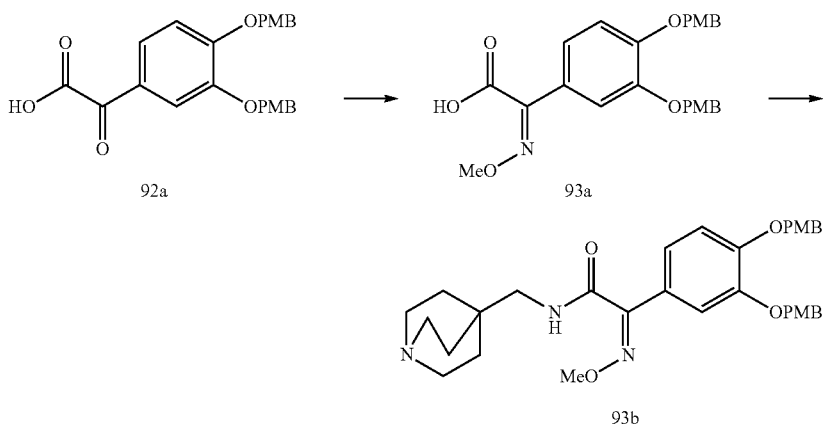

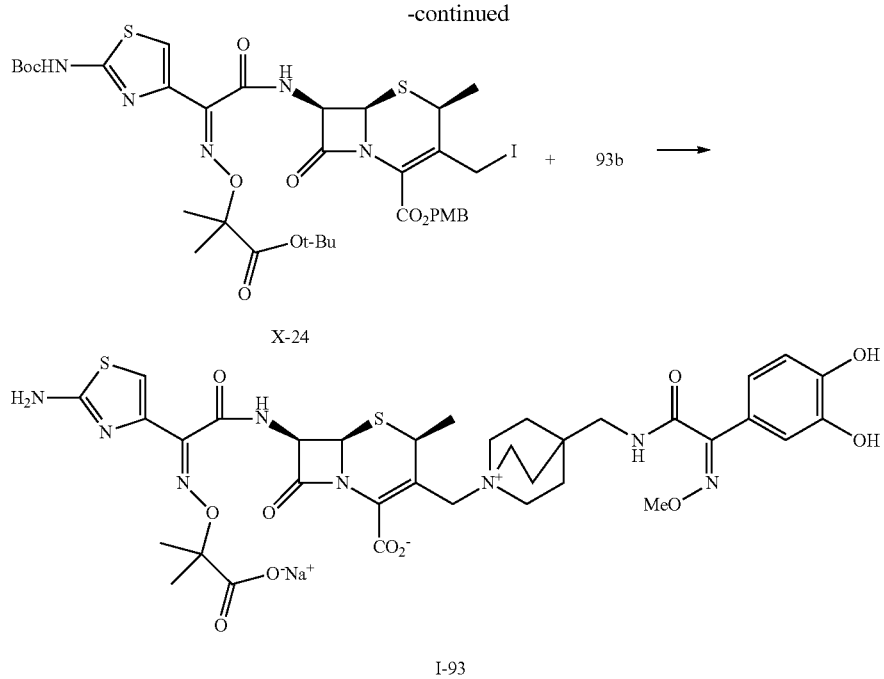

Step (1): Compound 92a→Compound 93a

To a solution of 92a (3 g, 7.10 mmol) in MeOH (30 ml) was added O-4-methylhydroxylammonium chloride (1.54 g, 18.46 mmol) and $Et_3N$ (2.75 ml, 19.8 mmol) at 0° C. under N2. The mixture was stirred at 0° C. for 5.5 h. The mixture was concentrated under reduced pressure. The reaction mixture was diluted with ethyl acetate, washed with an aqueous hydrochloric acid, water and a saturated salt solution, and dried over magnesium sulfate. Magnesium sulfate was filtrated off, and then the liquid was concentrated under reduced pressure to yield crude compound 93a (3.21 g)

Step (2): Compound 93a→Compound 93b

To a solution of 93a (3.21 g, 7.10 mmol) in DMA (20 ml) was added HOBt (1.24 g, 9.23 mmol) and WSCD HCl (1.63 g, 8.52 mmol) at 0° C. The mixture was stirred at 0° C. for 1 h. The reaction mixture was added quinuclidin-4-ylmethanamine (1.19 g, 8.52 mmol) at 0° C. and then the mixture was stirred at 0° C. for 1 h. The reaction mixture was diluted with ethyl acetate, washed with an aqueous sodium hydroxide solution, water and a saturated salt solution, and dried over magnesium sulfate. Magnesium sulfate was filtrated off, and then the liquid was concentrated under reduced pressure. The compound-containing liquid was subjected to silica gel column chromatography to elute out the desired compound with hexane/ethyl acetate (containing 10% triethyl amine). The desired-compound-containing fraction was concentrated under reduced pressure to yield compound 93b (1.59 g, 39%, E/Z=1:4) compound 93b $^1$H-NMR (DMSO-D6) δ: 8.46-8.43 (1H, m), 7.40-7.32 (4H, m), 7.27-7.24 (1H, m), 7.13-7.11 (1H, m), 7.01 (1H, dd, J=8.4, 1.9 Hz), 6.96-6.92 (4H, m), 5.07 (2H, s), 4.99 (2H, s), 3.87 (2H, s), 3.76-3.75 (6H, br m), 3.01-2.97 (2H, m), 2.71-2.68 (6H, m), 1.32-1.29 (6H, m).

Step (3): Compound X-24+Compound 93b→Compound I-93

Compound X-24 (886 mg, 1 mmol) and compound 93b (680 mg, 1 mmol) were used to synthesize the target compound in the same way as Example 86.

Yielded amount: 518 mg (60%)

$^1$H-NMR (D2O) δ: 7.17 (1H, s), 7.01-6.95 (3H, m), 5.85 (1H, d, J=4.8 Hz), 5.46 (1H, d, J=4.8 Hz), 4.64 (1H, d, J=14.2 Hz), 4.09-4.06 (2H, m), 3.98 (3H, s), 3.55-3.45 (6H, m), 3.38 (2H, br s), 1.95-1.91 (6H, m), 1.57 (3H, d, J=7.0 Hz), 1.52 (3H, s), 1.50 (3H, s).

[M+H]=815.22.

Example 94 and 95: Synthesis of Compound I-94 and I-95

[Chemical Formula 239]

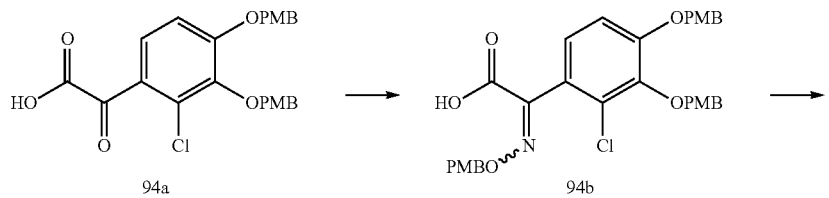

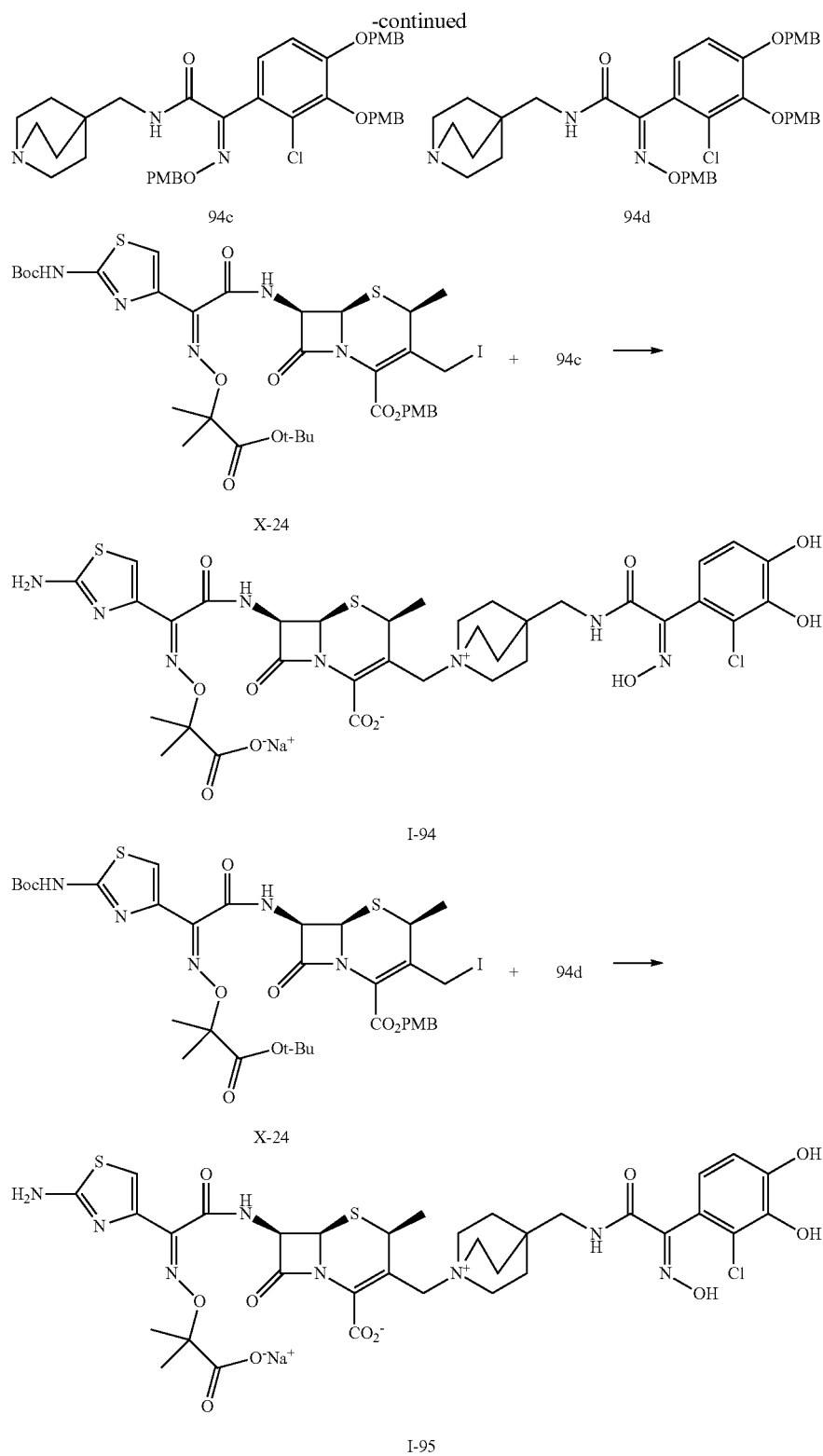

Step (1): Compound 94a→Compound 94b

To a solution of 94a (4 g, 8.76 mmol) in MeOH (40 ml) was added O-(4-methoxybenzyl)hydroxylamine (2.09 g, 9.63 mmol) at 0° C. under N2. The mixture was stirred at 0° C. for 1 h. The mixture was concentrated under reduced pressure. The reaction mixture was diluted with ethyl acetate, washed with an aqueous hydrochloric acid, water and a saturated salt solution, and dried over magnesium sulfate. Magnesium sulfate was filtrated off, and then the liquid was concentrated under reduced pressure to yield crude compound 94b (5.02 g, 8.76 mmol, E/Z=1:1.5)

Step (2): Compound 94b→Compound 94c and 94d

To a solution of 94b (1.77 g, 3 mmol) in DMA (10 ml) was added HOBt (0.52 g, 3.90 mmol) and WSCD HCl (0.69 g, 3.60 mmol) at 0° C. The mixture was stirred at 0° C. for 1 h. The reaction mixture was added quinuclidin-4-ylmethanamine (0.50 g, 3.60 mmol) at 0° C. and then the mixture was stirred at 0° C. for 1 h. The reaction mixture was diluted with ethyl acetate, washed with an aqueous sodium hydroxide solution, water and a saturated salt solution, and dried over magnesium sulfate. Magnesium sulfate was filtrated off, and then the liquid was concentrated under reduced pressure. The compound-containing liquid was subjected to silica gel column chromatography to elute out the desired compound with hexane/ethyl acetate (containing 10% triethyl amine). The desired-compound-containing fraction was concentrated under reduced pressure to yield compound 94c (0.88 g, 41%, E/Z=1:10) and compound 94d (0.61. 29%, E/Z=4.5:1).

Compound 94c $^1$H-NMR (DMSO-D6) δ: 8.35 (1H, t, J=6.3 Hz), 7.45 (2H, d, J=7.2 Hz), 7.39 (2H, d, J=8.5 Hz), 7.30 (2H, d, J=8.6 Hz), 7.25-7.18 (2H, m), 6.97 (4H, dd, J=11.7, 8.7 Hz), 6.86 (2H, d, J=31.6 Hz), 5.16 (2H, s), 5.10 (2H, s), 4.87 (2H, s), 3.78 (3H, s), 3.76 (3H, s), 3.75 (3H, s), 2.91 (2H, d, J=6.3 Hz), 2.58-2.54 (6H, m), 1.21-1.14 (6H, m).

Compound 94d $^1$H-NMR (DMSO-D6) δ: 7.98 (1H, t, J=6.3 Hz), 7.43 (2H, d, J=8.2 Hz), 7.31-7.24 (4H, m), 7.18 (2H, d, J=7.4 Hz), 6.98 (2H, d, J=8.5 Hz), 6.90 (2H, d, J=8.5 Hz), 6.85 (2H, d, J=8.2 Hz), 5.13 (2H, s), 5.11 (2H, s), 4.85 (2H, s), 3.77 (3H, s), 3.74 (6H, s), 2.96 (2H, d, J=6.3 Hz), 2.73-2.70 (6H, m), 1.30-1.26 (6H, m).

Step (3): Compound X-24+Compound 94c→Compound I-94

Compound X-24 (754 mg, 0.85 mmol) and compound 94c (608 mg, 0.85 mmol) were used to synthesize the target compound in the same way as Example 86.

Yielded amount: 410 mg (55%)

$^1$H-NMR (D2O) δ: 7.00 (1H, s), 6.97-6.90 (2H, m), 5.85 (1H, d, J=4.8 Hz), 5.45 (1H, d, J=4.8 Hz), 4.62 (1H, d, J=14.3 Hz), 4.09-4.04 (2H, m), 3.52-3.30 (8H, m), 1.93-1.90 (6H, m), 1.56 (3H, d, J=7.3 Hz), 1.52 (3H, s), 1.50 (3H, s). [M+H]=835.24.

Step (4): Compound X-24+Compound 94d→Compound I-95

Compound X-24 (886 mg, 1 mmol) and compound 94d (714 mg, 1 mmol) were used to synthesize the target compound in the same way as Example 86.

Yielded amount: 403 mg (46%)

$^1$H-NMR (D2O) δ: 7.00 (1H, s), 6.97-6.90 (1H, m), 6.78 (1H, d, J=8.3 Hz), 5.85 (1H, d, J=4.8 Hz), 5.45-5.42 (1H, m), 4.64-4.59 (2H, m), 4.07-3.97 (2H, m), 3.52-3.30 (8H, m), 1.94-1.87 (6H, m), 1.57-1.51 (9H, m). [M+H]=835.21

Example 96: Synthesis of Compound I-96

[Chemical Formula 240]

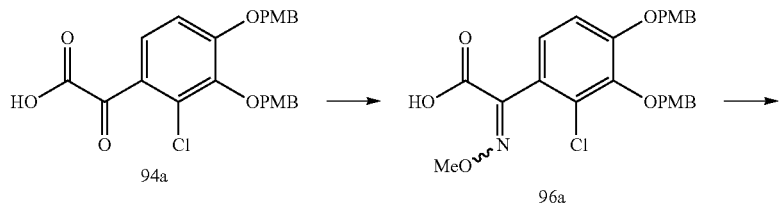

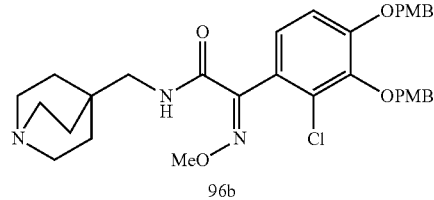

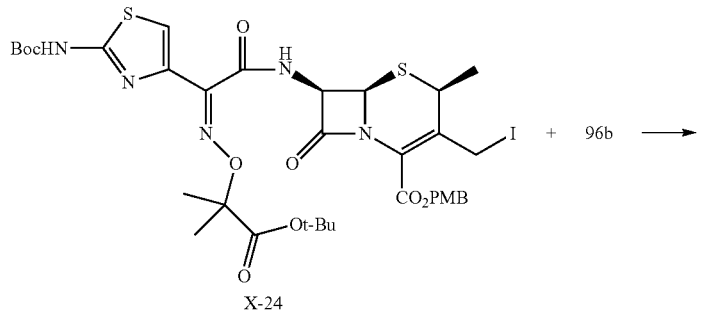

-continued

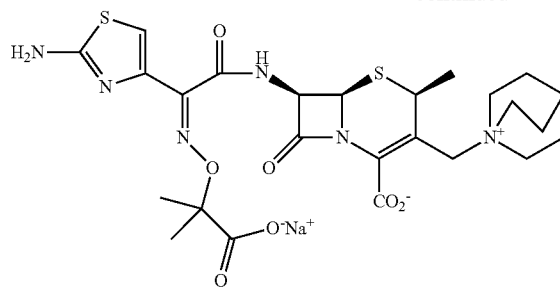

I-96

Step (1): Compound 94a→Compound 96a

To a solution of 94a (6 g, 13.1 mmol) in MeOH (60 ml) was added O-4-methylhydroxylammonium chloride (1.64 g, 19.7 mmol) and Et$_3$N (2.73 ml, 19.7 mmol) at 0° C. under N2. The mixture was stirred at 0° C. for 1.5 h. The mixture was concentrated under reduced pressure. The reaction mixture was diluted with ethyl acetate, washed with an aqueous hydrochloric acid, water and a saturated salt solution, and dried over magnesium sulfate. Magnesium sulfate was filtrated off, and then the liquid was concentrated under reduced pressure to yield crude compound 96a (6.38 g, E/Z=1:2.5)

Step (2): Compound 96a→Compound 96b

To a solution of 96a (6.38 g, 13.1 mmol) in DMA (50 ml) was added HOBt (2.3 g, 17.0 mmol) and WSCD HCl (3.02 g, 17.7 mmol) at 0° C. The mixture was stirred at 0° C. for 1 h. The reaction mixture was added quinuclidin-4-ylmethanamine (2.2 g, 15.7 mmol) at 0° C. and then the mixture was stirred at 0° C. for 1 h. The reaction mixture was diluted with ethyl acetate, washed with an aqueous sodium hydroxide solution, water and a saturated salt solution, and dried over magnesium sulfate. Magnesium sulfate was filtrated off, and then the liquid was concentrated under reduced pressure. The residue was recrystallized with hexane/ethyl acetate/a little of methanol to yield compound 96b (0.56 g, 7%, single isomer) compound 96b $^1$H-NMR (DMSO-D6) δ: 8.35 (1H, t, J=6.3 Hz), 7.44 (2H, d, J=8.5 Hz), 7.29 (2H, d, J=8.5 Hz), 7.23 (1H, d, J=8.9 Hz), 7.20 (1H, d, J=8.9 Hz), 6.98 (2H, d, J=8.5 Hz), 6.86 (2H, d, J=8.5 Hz), 5.15 (2H, s), 4.87 (2H, s), 3.90 (3H, s), 3.77 (3H, s), 3.74 (3H, s), 2.94 (2H, d, J=6.3 Hz), 2.71-2.67 (6H, m), 1.30-1.26 (6H, m).

Step (3): Compound X-24+Compound 96b→Compound I-96

Compound X-24 (743 mg, 0.84 mmol) and compound 96b (510 mg, 0.84 mmol) were used to synthesize the target compound in the same way as Example 86.

Yielded amount: 226 mg (28%)

$^1$H-NMR (D2O) δ: 7.01 (1H, s), 6.97 (1H, d, J=8.4 Hz), 6.91 (1H, d, J=8.4 Hz), 5.85 (1H, d, J=4.8 Hz), 5.45 (1H, d, J=4.8 Hz), 4.63 (1H, d, J=14.7 Hz), 4.09-4.00 (5H, m), 3.53-3.43 (6H, m), 3.33 (2H, s), 1.92-1.88 (6H, m), 1.54 (3H, d, J=7.3 Hz), 1.52 (3H, s), 1.50 (3H, s).

[M+H]=849.25

Example 97: Synthesis of Compound I-97

[Chemical Formula 241]

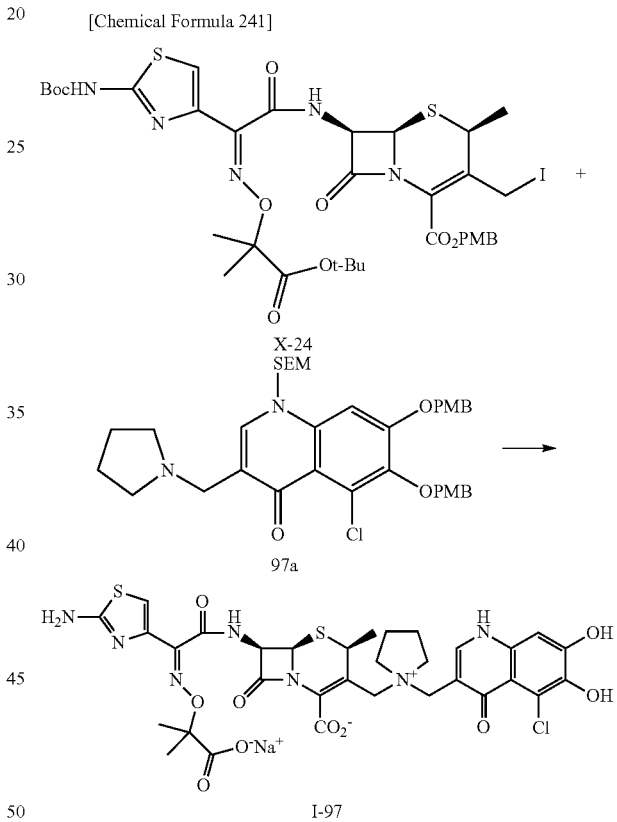

Step (1): Compound X-24+Compound 97a→Compound I-97

Compound X-24 (7.40 g, 8.37 mmol) and compound 97a (5.56 g, 8.37 mmol) were used to synthesize the target compound in the same way as Example 86.

Yielded amount: 1.81 g (26%)

$^1$H-NMR (D2O) δ: 7.98 (1H, s), 6.97 (1H, s), 6.62 (1H, s), 5.82 (1H, d, J=4.5 Hz), 5.50 (1H, d, J=4.5 Hz), 4.90 (1H, d, J=14.4 Hz), 4.36 (2H, s), 4.21-4.12 (2H, m), 3.56 (1H, br s), 3.36 (3H, br s), 2.24-2.21 (4H, br m), 1.54 (3H, d, J=7.7 Hz), 1.51 (3H, s), 1.49 (3H, s).

[M+H]=776.18

Example 98: Synthesis of Compound I-98

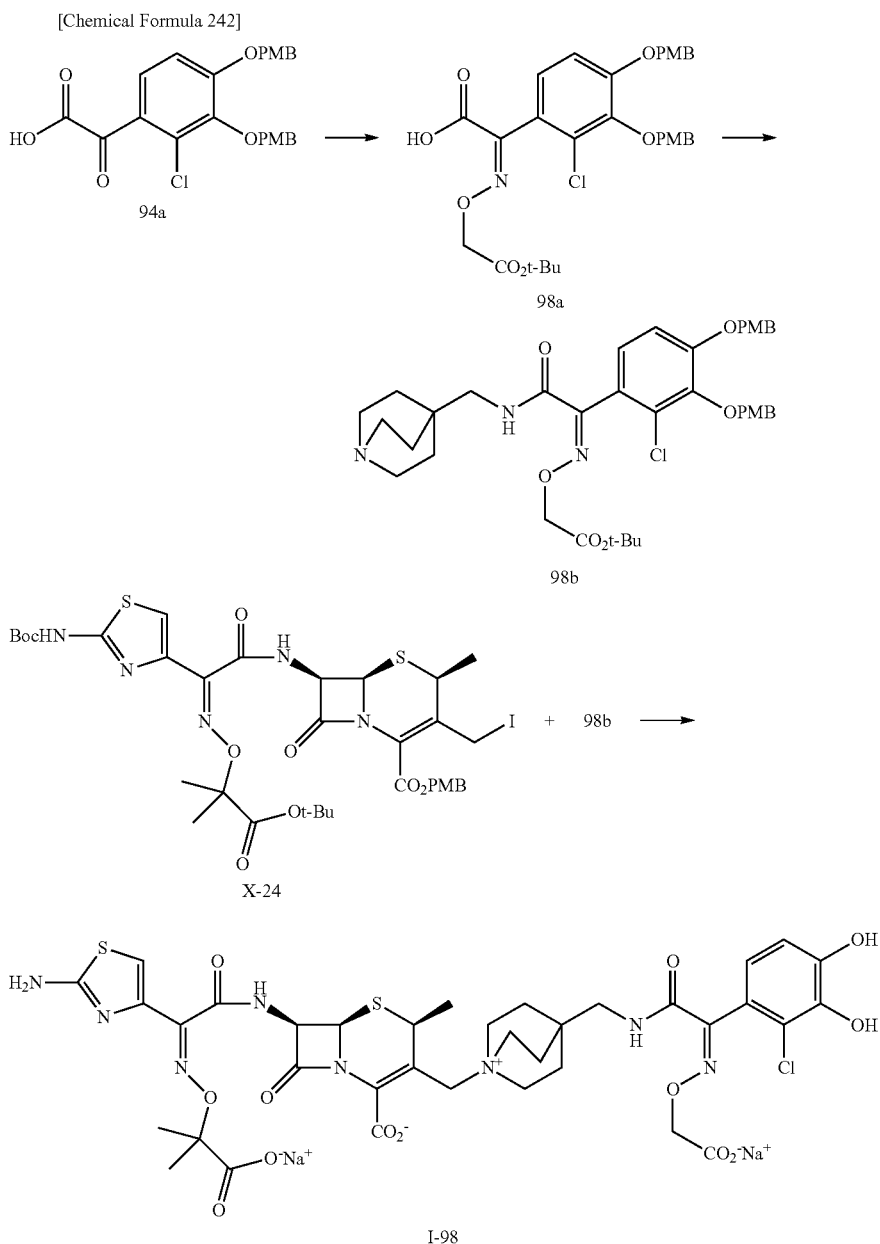

Step (1): Compound 94a+→Compound 98a

To a solution of 94a (1.37 g, 3 mmol) in MeOH (6 ml) was added tert-butyl 2-(aminooxy)acetate (0.44 g, 3 mmol) at 0° C. under N2. The mixture was stirred at rt for 1 h. The mixture was concentrated under reduced pressure. The reaction mixture was diluted with ethyl acetate, washed with an aqueous hydrochloric acid, water and a saturated salt solution, and dried over magnesium sulfate. Magnesium sulfate was filtrated off, and then the liquid was concentrated under reduced pressure. The residue was recrystallized with dichloromethane/diisopropyl ether to yield compound 98a (0.90 g, 51%, single isomer).

Compound 98a $^1$H-NMR (CDCl3) δ: 7.34 (4H, d, J=8.4 Hz), 7.23 (1H, d, J=8.5 Hz), 6.92 (3H, dd, J=8.4, 5.1 Hz), 6.83 (2H, d, J=8.5 Hz), 5.08 (2H, s), 4.95 (2H, s), 4.73 (2H, s), 3.83 (3H, s), 3.80 (3H, s), 1.51 (9H, s).

Step (2): Compound 98a→Compound 98b

Compound 98a (0.87 g, 1.49 mmol) and triethylamine (0.29 ml, 2.09 mmol) were dissolved into dimethylacetamide (6 mL), and thereto was then added Methanesulfonyl chloride (0.15 ml, 1.94 mmol) at −20° C. The mixture was stirred at −20° C. for 30 minutes. Thereto was then added quinuclidin-4-ylmethanamine (0.23 g, 1.64 mmol) at 0° C. The mixture was stirred at 0° C. for 1 h. The reaction mixture was diluted with ethyl acetate, washed with an aqueous sodium hydroxide solution, water and a saturated salt solution, and dried over magnesium sulfate. Magnesium sulfate was filtrated off, and then the liquid was concentrated under reduced pressure. The compound-containing liquid was subjected to silica gel column chromatography to elute out the desired compound with hexane/ethyl acetate (containing 10% triethyl amine). The desired-compound-containing fraction was concentrated under reduced pressure to yield compound 98b (0.72 g, 69%).

Compound 98b $^1$H-NMR (DMSO-D6) δ: 8.20 (1H, t, J=6.1 Hz), 7.44 (2H, d, J=8.5 Hz), 7.29 (2H, d, J=8.5 Hz), 7.24 (2H, d, J=7.5 Hz), 7.17 (2H, d, J=7.5 Hz), 6.98 (2H, d, J=8.5 Hz), 6.86 (2H, d, J=8.5 Hz), 5.16 (2H, s), 4.87 (2H, s), 4.69 (2H, s), 3.77 (3H, s), 3.74 (3H, s), 2.99 (2H, d, J=6.3 Hz), 2.72-2.68 (6H, m), 1.45 (9H, s), 1.33-1.29 (6H, m).

Step (3): Compound X-24+Compound 98b→Compound I-98

Compound X-24 (886 mg, 1 mmol) and compound 98b (708 mg, 1 mmol) were used to synthesize the target compound in the same way as Example 86.

Yielded amount: 567 mg (59%)

$^1$H-NMR (D2O) δ: 7.01-6.99 (2H, m), 6.94-6.91 (1H, m), 5.85 (1H, d, J=4.8 Hz), 5.46 (1H, d, J=4.8 Hz), 4.65-4.62 (3H, m), 4.11-4.05 (2H, m), 3.53-3.37 (9H, m), 1.95-1.91 (6H, m), 1.56 (3H, d, J=7.0 Hz), 1.52 (3H, s), 1.50 (3H, s).

[M+H]=893.23

Example 99: Synthesis of Compound I-99

[Chemical Formula 243]

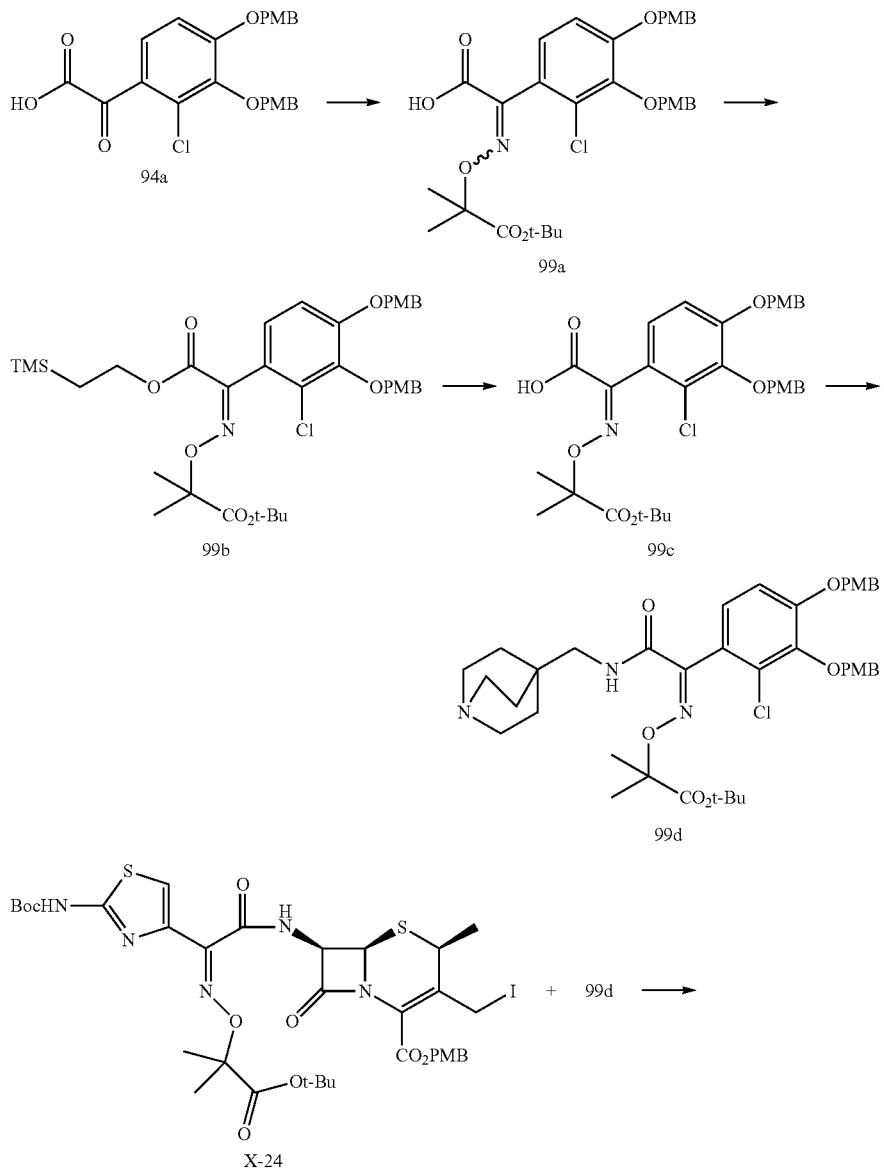

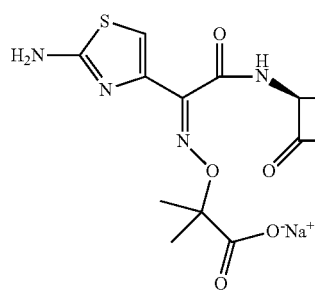
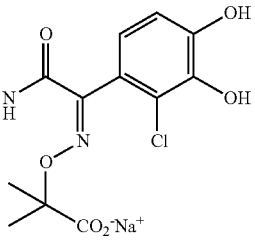

I-99

Step (1): Compound 94a→Compound 99a

To a solution of tert-butyl 2-(aminooxy)-2-methylpropanoate (5.25 g, 30 mmol) in MeOH (60 ml) was added 94a (9.16 g, 30 mmol) at 0° C. under N2. The mixture was stirred at rt for 1 h. The mixture was concentrated under reduced pressure. The reaction mixture was diluted with ethyl acetate, washed with an aqueous hydrochloric acid, water and a saturated salt solution, and dried over magnesium sulfate. Magnesium sulfate was filtrated off, and then the liquid was concentrated under reduced pressure. The residue was recrystallized with dichloromethane/diisopropyl ether to yield crude compound 99a (16 g, 87%, E/Z=1:1.5).

Step (2): Compound 99a→Compound 99b

To a solution of 99a (1.6 g, 2.61 mmol) in ethyl acetate (16 ml) was added WSCD HCl (0.55 g, 2.87 mmol) and DMAP (0.03 g, 0.26 mmol) and 2-(trimethylsilyl) ethanol (0.43 ml, 2.87 mmol) at 0° C. The mixture was stirred at rt for 1 h. The reaction mixture was diluted with ethyl acetate, washed with an aqueous hydrochloric acid, water and a saturated salt solution, and dried over magnesium sulfate. Magnesium sulfate was filtrated off, and then the liquid was concentrated under reduced pressure. The compound-containing liquid was subjected to silica gel column chromatography to elute out the desired compound with hexane/ethyl acetate to chloroform/methanol. The desired-compound-containing fraction was concentrated under reduced pressure to yield compound 99b (1.23 g, 66%, E/Z=1:10).

Compound 99b $^1$H-NMR (CDCl3) δ: 7.36 (4H, dd, J=8.5, 3.8 Hz), 7.07 (1H, d, J=8.5 Hz), 6.93 (3H, t, J=6.8 Hz), 6.83 (2H, d, J=8.5 Hz), 5.06 (2H, s), 4.97 (2H, s), 4.33 (2H, t, J=8.2 Hz), 3.84 (3H, s), 3.80 (3H, s), 1.47 (9H, s), 1.03 (2H, t, J=8.2 Hz), 0.02 (9H, s).

Step (3): Compound 99b→Compound 99c

To a solution of 99b (1.42 g, 2 mmol) in THF (14 ml) was added 1M TBAF in THF (4 ml, 4 mmol) at 0° C. The mixture was stirred at rt for 1 h. The reaction mixture was diluted with ethyl acetate, washed with an aqueous hydrochloric acid, water and a saturated salt solution, and dried over magnesium sulfate. Magnesium sulfate was filtrated off, and then the liquid was concentrated under reduced pressure to yield compound 99c (1.22 g).

Compound 99c $^1$H-NMR (CDCl3) δ: 7.37-7.33 (4H, m), 6.97 (2H, br s), 6.93 (2H, d, J=8.6 Hz), 6.83 (2H, d, J=8.6 Hz), 5.07 (2H, s), 4.99 (2H, s), 3.84 (3H, s), 3.80 (3H, s), 1.50 (6H, s), 1.47 (9H, s).

Step (4): Compound 99c→Compound 99d

Compound 99c (1.22 g, 2 mmol) and triethylamine (0.38 ml, 2.80 mmol) were dissolved into dimethylacetamide (13 mL), and thereto was then added Methanesulfonyl chloride (0.20 ml, 2.60 mmol) at −20° C. The mixture was stirred at −20° C. for 30 minutes. Thereto was then added quinuclidin-4-ylmethanamine (0.31 g, 2.20 mmol) at 0° C. The mixture was stirred at 0° C. for 1 h. The reaction mixture was diluted with ethyl acetate, washed with an aqueous sodium hydroxide solution, water and a saturated salt solution, and dried over magnesium sulfate. Magnesium sulfate was filtrated off, and then the liquid was concentrated under reduced pressure. The precipitated solid was then collected by filtration, and washed with diisopropyl ether to yield compound 99d (1.01 g, 51%, E/Z=1:10).

Compound 99d $^1$H-NMR (DMSO-D6) δ: 7.73 (1H, t, J=6.5 Hz), 7.45 (2H, d, J=8.2 Hz), 7.29 (2H, d, J=8.2 Hz), 7.24 (1H, d, J=8.5 Hz), 7.06 (1H, d, J=8.5 Hz), 6.99 (2H, d, J=8.2 Hz), 6.85 (2H, d, J=8.2 Hz), 5.15 (2H, s), 4.88 (2H, s), 3.78 (3H, s), 3.74 (3H, s), 2.96 (2H, d, J=6.4 Hz), 2.71-2.68 (6H, m), 1.42 (15H, s), 1.29-1.25 (6H, m).

Step (5): Compound X-24+Compound 99d→Compound I-99

Compound X-24 (901 mg, 1.02 mmol) and compound 99d (749 mg, 1.02 mmol) were used to synthesize the target compound in the same way as Example 86.

Yielded amount: 431 mg (45%)

$^1$H-NMR (D2O) δ: 7.01 (1H, s), 6.95 (1H, d, J=8.3 Hz), 6.88 (1H, d, J=8.3 Hz), 5.85 (1H, d, J=4.6 Hz), 5.46 (1H, d, J=4.6 Hz), 4.63 (1H, d, J=13.9 Hz), 4.09-4.04 (2H, m), 3.52-3.37 (6H, m), 3.30 (2H, br s), 1.92-1.89 (6H, m), 1.56 (3H, d, J=6.9 Hz), 1.52 (3H, s), 1.50 (3H, s), 1.44 (6H, s).

[M+H]=921.46

Example 100: Synthesis of Compound I-100

[Chemical Formula 244]

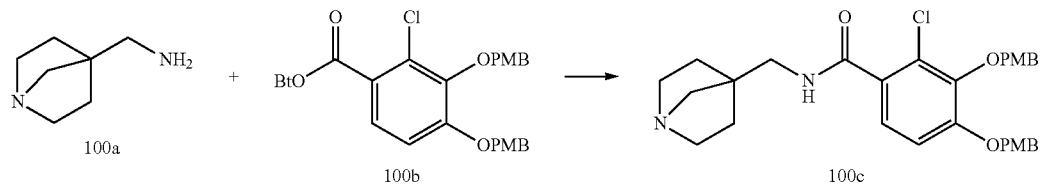

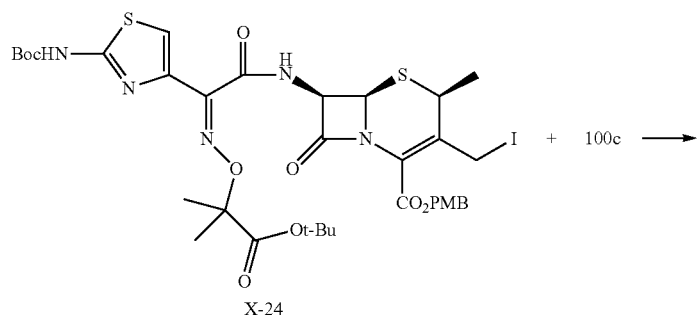

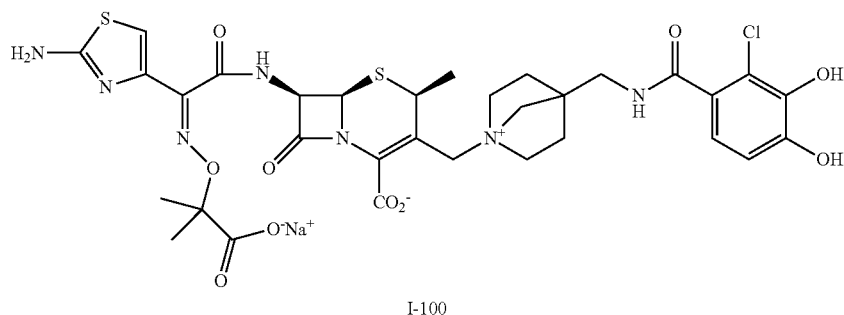

Step (1): Compound 100a+Compound 100b→Compound 100c

To a solution of 100b (28.9 g, 53 mmol) in THF (250 ml) was added 100a (6.69 g, 53 mmol) in THF (50 ml) at 0° C. The mixture was stirred at rt for 1 h. The reaction mixture was diluted with ethyl acetate, washed with an aqueous sodium hydroxide solution, water and a saturated salt solution, and dried over magnesium sulfate. Magnesium sulfate was filtrated off, and then the liquid was concentrated under reduced pressure. The precipitated solid was then collected by filtration, and washed with diisopropyl ether to yield compound 100c (24.1 g, 85%)
Compound 100c
$^1$H-NMR (DMSO-D6) δ: 8.40 (1H, t, J=6.0 Hz), 7.43 (2H, d, J=8.5 Hz), 7.33 (2H, d, J=8.5 Hz), 7.19 (1H, d, J=8.7 Hz), 7.13 (1H, d, J=8.7 Hz), 6.98 (2H, d, J=8.5 Hz), 6.89 (2H, d, J=8.5 Hz), 5.16 (2H, s), 4.89 (2H, s), 3.78 (3H, s), 3.76 (3H, s), 3.53 (2H, d, J=6.0 Hz), 2.85-2.78 (2H, m), 2.57-2.54 (2H, m), 2.25 (2H, s), 1.62-1.57 (2H, m), 1.24-1.18 (2H, m).

Step (2): Compound X-24+Compound 100c→Compound I-100

Compound X-24 (886 mg, 1 mmol) and compound 100c (537 mg, 1 mmol) were used to synthesize the target compound in the same way as Example 86.
Yielded amount: 500 mg (63%)
$^1$H-NMR (D2O) δ: 7.01 (1H, s), 6.95 (1H, d, J=8.4 Hz), 6.89 (1H, d, J=8.4 Hz), 5.82 (1H, d, J=4.8 Hz), 5.45 (1H, d, J=4.8 Hz), 4.92 (1H, d, J=14.6 Hz), 4.28 (1H, d, J=14.6 Hz), 4.07-4.02 (1H, m), 3.71-3.56 (6H, m), 3.44-3.42 (1H, br m), 3.35-3.33 (1H, br m), 2.24 (2H, br s), 2.01 (2H, br s), 1.57 (3H, d, J=7.2 Hz), 1.52 (3H, s), 1.50 (3H, s).
[M+H]=778.19

Example 101: Synthesis of Compound I-101

[Chemical Formula 245]

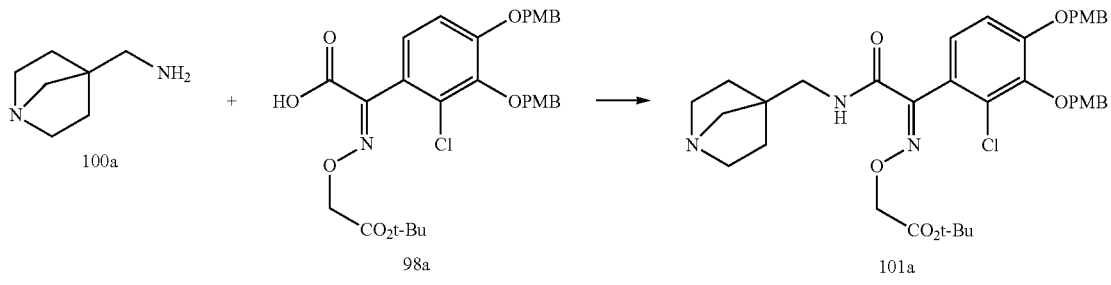

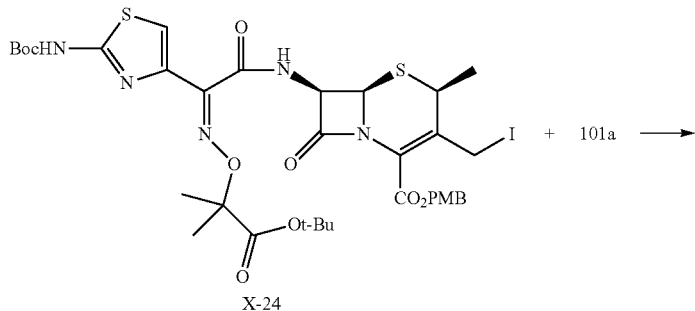

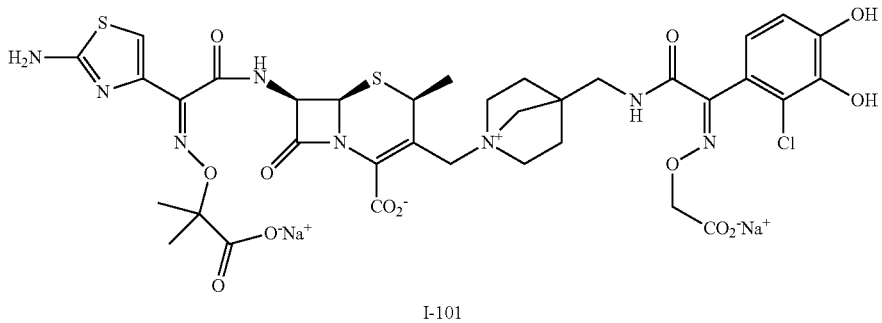

Step (1): Compound 100a+Compound 98a→Compound 101a

Compound 98a (1.17 g, 2 mmol) was used to synthesize the target compound 101a in the same way as in Step (2) of Example 98.

Yielded amount: 1.15 g (82%)

Compound 101a $^1$H-NMR (DMSO-D6) δ: 8.41 (1H, t, J=6.1 Hz), 7.43 (2H, d, J=8.4 Hz), 7.29 (2H, d, J=8.4 Hz), 7.25 (2H, d, J=8.9 Hz), 7.17 (2H, d, J=8.9 Hz), 6.98 (2H, d, J=8.5 Hz), 6.86 (2H, d, J=8.5 Hz), 5.16 (2H, s), 4.88 (2H, s), 4.66 (2H, s), 3.77 (3H, s), 3.74 (3H, s), 3.54 (2H, d, J=6.0 Hz), 2.79-2.73 (2H, m), 2.51-2.49 (2H, m), 2.18 (2H, s), 1.60-1.52 (2H, m), 1.44 (9H, s), 1.18-1.12 (2H, m).

Step (2): Compound X-24+Compound 101a→Compound I-101

Compound X-24 (1 g, 1.14 mmol) and compound 101a (788 mg, 1.14 mmol) were used to synthesize the target compound in the same way as Example 86.

Yielded amount: 453 mg (43%)

$^1$H-NMR (D2O) δ: 7.02-6.99 (2H, m), 6.93 (1H, d, J=8.4 Hz), 5.83 (1H, d, J=4.8 Hz), 5.47 (1H, d, J=4.8 Hz), 4.89 (1H, d, J=14.4 Hz), 4.62 (2H, s), 4.25 (1H, d, J=14.4 Hz), 3.97-3.92 (1H, m), 3.77-3.50 (6H, m), 3.37 (1H, d, J=8.4 Hz), 3.24 (1H, d, J=8.4 Hz), 2.22 (2H, br s), 1.98 (2H, br s), 1.54-1.51 (9H, m).

Elem. Anal.: C35H37ClN8Na2O13S2 (H2O) 8.6

Calcd.: C, 38.99; H, 5.07; N, 10.39; S, 5.95; Na, 4.26; Cl, 3.29(%).

Found: C, 38.88; H, 4.94; N, 10.53; S, 5.95; Na, 4.40; Cl, 3.57(%).

Example 102 and 103: Synthesis of Compound I-102 and I-103
[Chemical Formula 246]
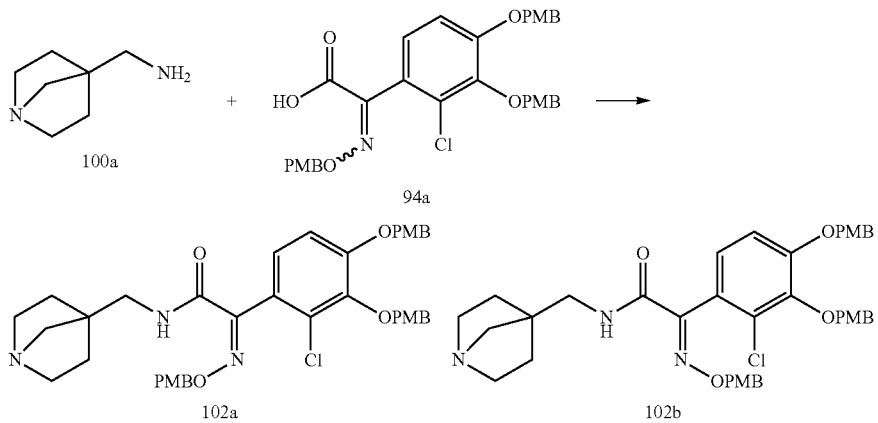
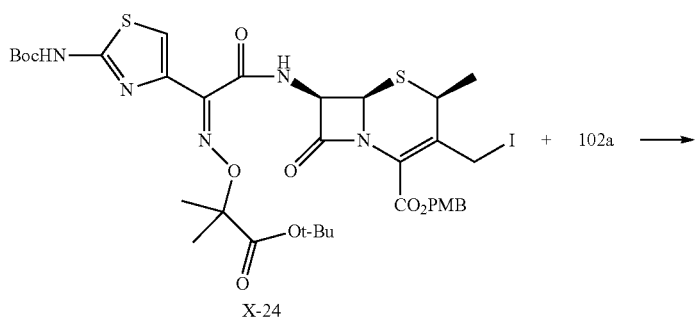
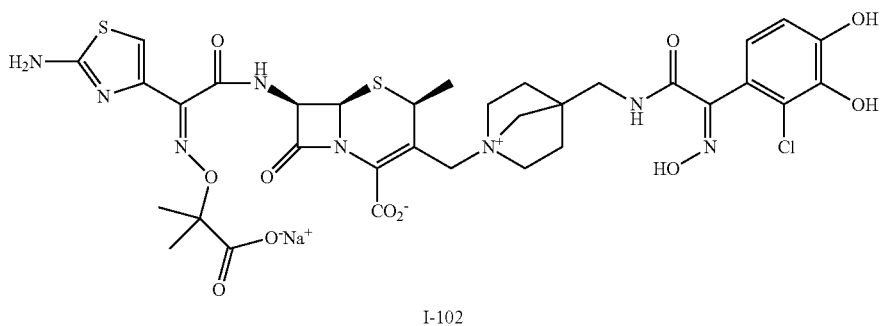
I-102
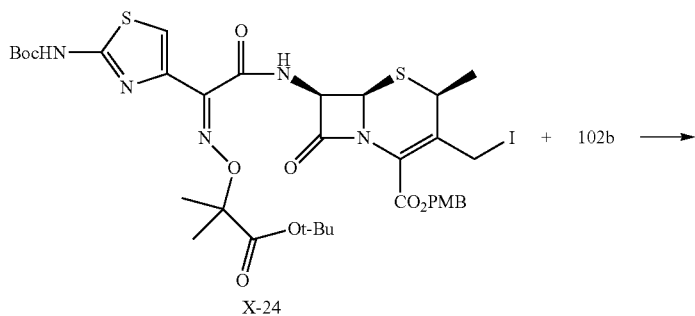

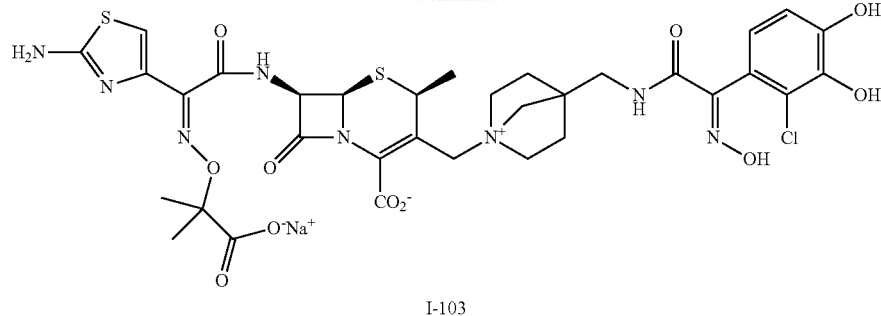

I-103

Step (1): Compound 100a+Compound 94b→Compound 102a and 102b

Compound 94b (5.76 g, 9.73 mmol) and triethylamine (1.88 ml, 13.6 mmol) were dissolved into dimethylacetamide (35 mL), and thereto was then added Methanesulfonyl chloride (0.98 ml, 12.6 mmol) at −20° C. The mixture was stirred at −20° C. for 30 minutes. Thereto was then added compound 100a (1.35 g, 10.7 mmol) in DMA (5 ml) at 0° C. The mixture was stirred at 0° C. for 1 h. The reaction mixture was diluted with ethyl acetate, washed with an aqueous sodium hydroxide solution, water and a saturated salt solution, and dried over magnesium sulfate. Magnesium sulfate was filtrated off, and then the liquid was concentrated under reduced pressure. The precipitated solid was then collected by filtration, and washed with ethyl acetate to yield compound 102a (3.2 g, 47%, single isomer). The residue was subjected to silica gel column chromatography to elute out the desired compound with ethyl acetate/methanol (containing 10% triethyl amine). The desired-compound-containing fraction was concentrated under reduced pressure to yield compound 102b (2 g, 29%, E/Z=10:1).

Compound 102a $^1$H-NMR (DMSO-D6) δ: 8.51 (1H, t, J=6.1 Hz), 7.44 (2H, d, J=8.5 Hz), 7.35 (2H, d, J=8.5 Hz), 7.28 (2H, t, J=8.5 Hz), 7.23 (1H, d, J=8.8 Hz), 7.18 (1H, d, J=8.8 Hz), 6.98 (2H, d, J=8.5 Hz), 6.93 (2H, d, J=8.5 Hz), 6.86 (2H, d, J=8.5 Hz), 5.15 (2H, s), 5.08 (2H, s), 4.87 (2H, s), 3.77 (3H, s), 3.76 (3H, s), 3.75 (3H, s), 3.45 (2H, d, J=6.1 Hz), 2.59-2.52 (2H, m), 2.31 (2H, br s), 2.03 (2H, br s), 1.44-1.38 (2H, m), 1.01-0.95 (2H, m).

Compound 102b $^1$H-NMR (DMSO-D6) δ: 8.26 (1H, t, J=6.3 Hz), 7.43 (2H, d, J=8.5 Hz), 7.30 (2H, d, J=8.5 Hz), 7.24 (2H, d, J=7.7 Hz), 7.17 (2H, d, J=7.7 Hz), 6.97 (2H, d, J=8.6 Hz), 6.90 (2H, dd, J=8.6, 1.9 Hz), 6.85 (2H, d, J=8.5 Hz), 5.12 (2H, s), 5.11 (2H, s), 4.86 (2H, s), 3.77 (3H, s), 3.74 (6H, s), 3.50 (2H, d, J=6.3 Hz), 2.76-2.72 (2H, m), 2.43-2.40 (2H, m), 1.54-1.48 (2H, m), 1.19-1.11 (2H, m).

Step (2): Compound X-24+Compound 102a→Compound I-102

Compound X-24 (886 mg, 1 mmol) and compound 102a (700 mg, 1 mmol) were used to synthesize the target compound in the same way as E Yielded amount: 432 mg (51%)

$^1$H-NMR (D2O) δ: 7.02 (1H, s), 6.94 (2H, dd, J=14.4, 8.3 Hz), 5.82 (1H, d, J=4.9 Hz), 5.46 (1H, d, J=4.9 Hz), 4.90 (1H, d, J=14.6 Hz), 4.24 (1H, d, J=14.6 Hz), 3.96-3.91 (1H, m), 3.75-3.51 (6H, m), 3.36 (1H, d, J=8.4 Hz), 3.23 (1H, d, J=8.4 Hz), 2.20 (2H, s), 1.96 (2H, s), 1.54-1.51 (9H, m).

Elem. Anal.: C33H36ClN8NaO11S2 (H2O) 6.7

Calcd.: C, 41.12; H, 5.17; N, 11.62; S, 6.65; Na, 2.38; Cl, 3.68(%).

Found: C, 41.02; H, 5.10; N, 11.69; S, 6.67; Na, 2.52; Cl, 3.83(%).

Step (3): Compound X-24+Compound 102b→Compound I-103

Compound X-24 (886 mg, 1 mmol) and compound 102b (700 mg, 1 mmol) were used to synthesize the target compound in the same way as Example 86.

Yielded amount: 365 mg (43%)

$^1$H-NMR (D2O) δ: 7.02 (1H, s), 6.96 (1H, d, J=12.3 Hz), 6.80 (1H, d, J=8.4 Hz), 5.82 (1H, d, J=4.8 Hz), 5.48 (1H, d, J=4.8 Hz), 4.89 (1H, d, J=14.6 Hz), 4.24 (1H, d, J=14.6 Hz), 3.99-3.92 (1H, m), 3.75-3.52 (6H, m), 3.34 (1H, d, J=8.5 Hz), 3.22 (1H, d, J=8.5 Hz), 2.18 (2H, br s), 1.95 (2H, br s), 1.54-1.51 (9H, m).

Elem. Anal.: C33H36ClN8NaO11S2 (H2O) 6.7 (NaHCO3) 0.1

Calcd.: C, 40.89; H, 5.13; N, 11.52; S, 6.59; Na, 2.60; Cl, 3.65(%).

Found: C, 40.70; H, 5.21; N, 11.60; S, 6.58; Na, 2.60; Cl, 3.84(%).

Example 104 and 105: Synthesis of Compound I-104 and I-105

[Chemical Formula 247]

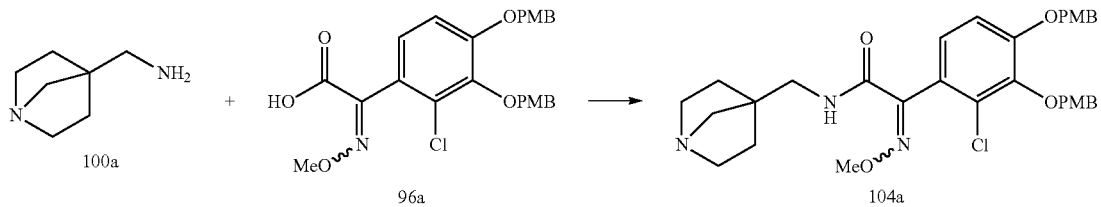

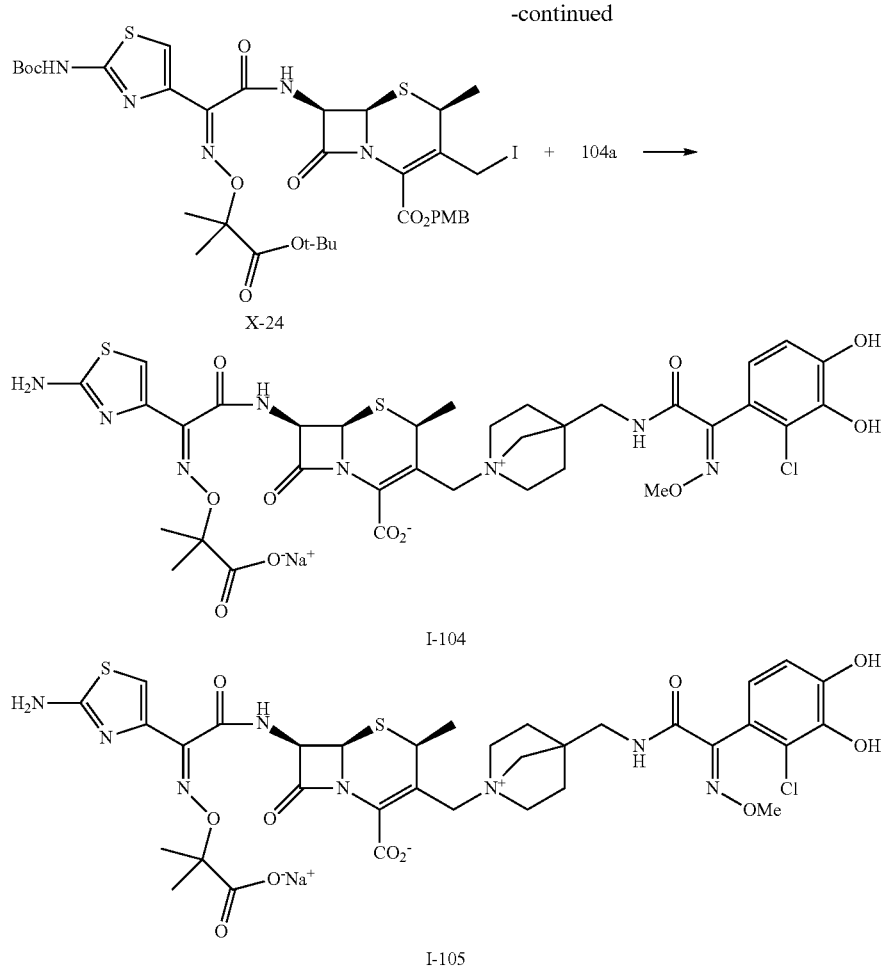

Step (1): Compound 100a+Compound 96a→Compound 104a

Compound 96b (1.38 g, 11 mmol) was used to synthesize the target compound in the same way as in Step (1) of Example 102.

Yielded amount: 3 g (50%, E/Z=1:1.5)
compound 104a $^1$H-NMR (DMSO-D6) δ: 8.58 (1H, t, J=6.0 Hz), 8.33 (1H, t, J=6.0 Hz), 7.44 (4H, d, J=7.7 Hz), 7.30 (4H, d, J=7.2 Hz), 7.25-7.14 (4H, m), 6.98 (4H, d, J=8.3 Hz), 6.86 (4H, d, J=8.3 Hz), 5.15 (4H, s), 4.88 (4H, s), 3.91 (3H, s), 3.90 (3H, s), 3.77 (6H, s), 3.74 (6H, s), 2.78-2.73 (4H, m), 2.47-2.42 (2H, m), 2.30 (2H, s), 2.16 (4H, s), 1.56-1.51 (4H, m), 1.18-1.13 (4H, m).

Step (2): Compound X-24+Compound 104a→Compound I-104 and I-105

Compound X-24 (969 mg, 1.1 mmol) and compound 104a (650 mg, 1.1 mmol) were used to synthesize the target compound in the same way as Example 86.

Yielded amount of I-104: 140 mg (15%)
Compound I-104

$^1$H-NMR (D2O) δ: 7.02 (1H, s), 6.92 (2H, dd, J=20.5, 6.0 Hz), 5.83 (1H, d, J=4.8 Hz), 5.46 (1H, d, J=4.8 Hz), 4.90 (1H, d, J=14.3 Hz), 4.25 (1H, d, J=14.3 Hz), 4.03 (3H, s), 3.96-3.91 (1H, m), 3.72-3.53 (6H, m), 3.33 (1H, d, J=8.5 Hz), 3.21 (1H, d, J=8.5 Hz), 2.18 (2H, s), 1.96 (2H, s), 1.54-1.51 (9H, m).

Elem. Anal.: C34H38ClN8NaO11S2 (H2O) 7.1 (NaHCO3) 0.2

Calcd.: C, 41.00; H, 5.27; N, 11.18; S, 6.40; Na, 2.75; Cl, 3.54(%).

Found: C, 40.69; H, 5.23; N, 11.48; S, 6.36; Na, 2.99; Cl, 3.51(%).

Yielded amount of I-105: 180 mg (19%)
Compound I-105

$^1$H-NMR (D2O) δ: 7.02 (1H, s), 6.95 (1H, d, J=8.4 Hz), 6.80 (1H, d, J=8.4 Hz), 5.82 (1H, d, J=4.8 Hz), 5.48 (1H, d, J=4.8 Hz), 4.90 (1H, d, J=14.4 Hz), 4.24 (1H, d, J=14.4 Hz), 4.03-3.95 (4H, m), 3.69-3.52 (6H, m), 3.35 (1H, d, J=8.7 Hz), 3.22 (1H, d, J=8.7 Hz), 2.18 (2H, s), 1.95 (2H, s), 1.55-1.51 (9H, m).

Elem. Anal.: C34H38ClN8NaO11S2 (H2O) 6.8

Calcd.: C, 41.68; H, 5.31; N, 11.44; S, 6.54; Na, 2.35; Cl, 3.62(%).

Found: C, 41.46; H, 5.24; N, 11.61; S, 6.80; Na, 2.49; Cl, 3.60(%).

Example 106: Synthesis of Compound I-106
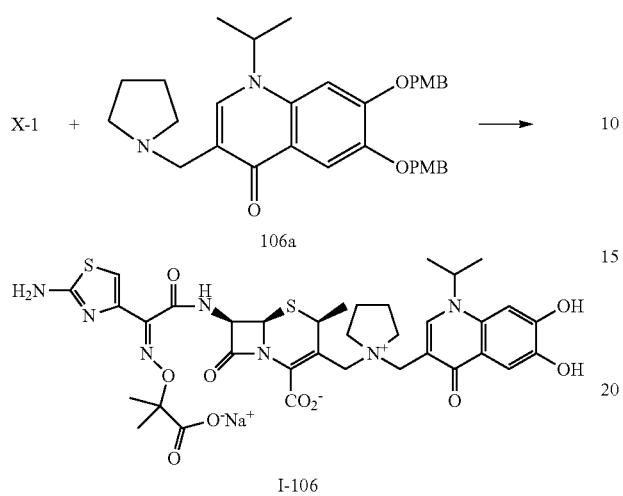
Step (1): Compound X-1+Compound 106a→Compound I-106
Compound X-1 (1.32 g, 1.32 mmol) and compound 106a (720 mg, 1.32 mmol) were used to synthesize the target compound in the same way as Example 86.
Yielded amount: 510 mg (47%)
$^1$H-NMR (D2O) δ: 8.26 (1H, s), 7.62 (1H, s), 7.30 (1H, s), 6.99 (1H, s), 5.83 (1H, d, J=4.9 Hz), 5.48 (1H, d, J=4.9 Hz), 5.01 (1H, t, J=6.6 Hz), 4.89 (1H, d, J=14.3 Hz), 4.54-4.47 (2H, m), 4.26 (1H, d, J=14.3 Hz), 4.16-4.10 (1H, m), 3.59 (1H, s), 2.26-2.23 (4H, m), 1.58 (6H, t, J=6.6 Hz), 1.53-1.49 (9H, m).
[M+H]=873.35
Example 107: Synthesis of Compound I-107
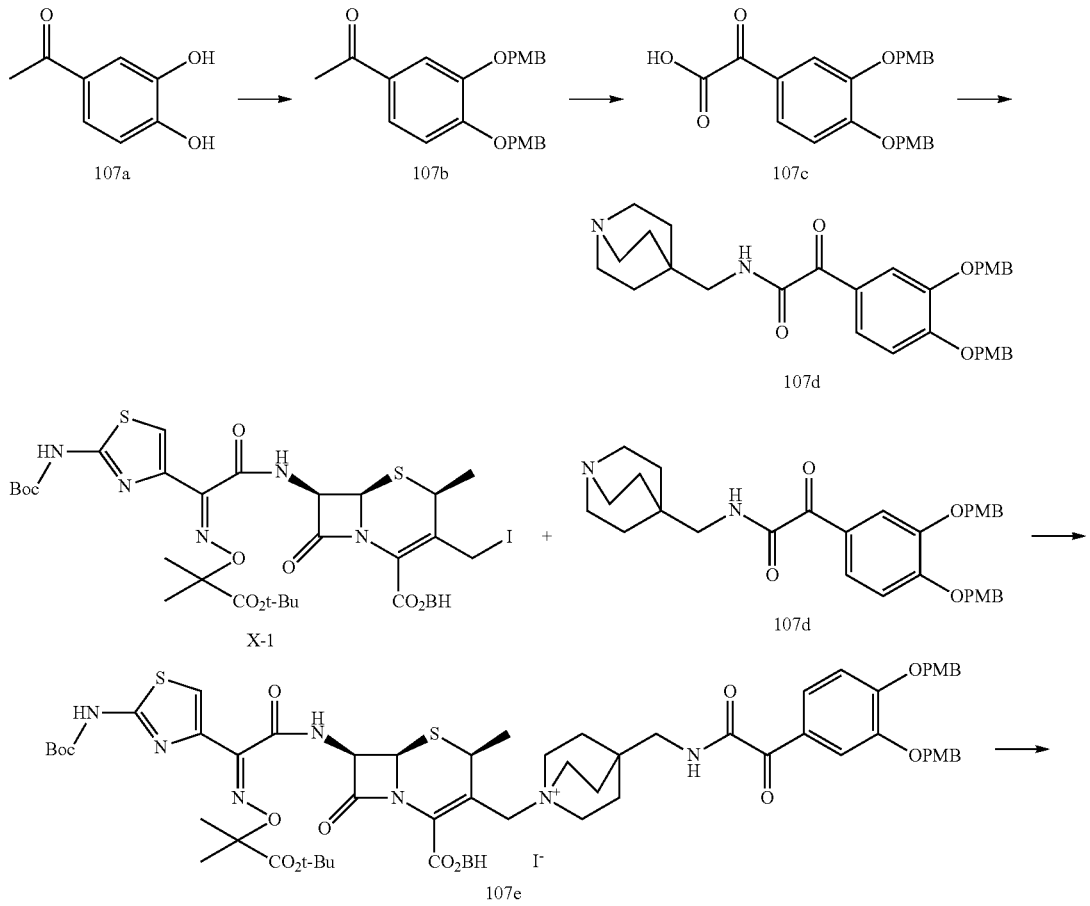

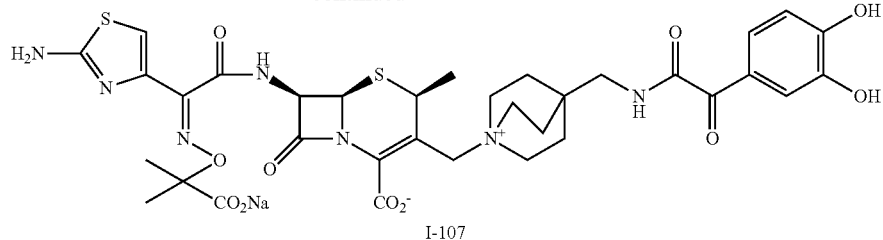

I-107

Step (1): Compound 107a→Compound 107b

Compound 107a (15.0 g, 99 mmol) was dissolved into dimethylacetamide (150 mL), and thereto were then added potassium carbonate (40.9 g, 296 mmol), p-methoxybenzyl chloride (32.2 ml, 237 mmol) and sodium iodide (14.78 g, 99 mmol) in turn. The mixture was stirred at 50° C. for 1.5 hours. The reaction mixture was poured into water. The precipitated solid was then collected by filtration, and washed with water and diisopropyl ether. In this way, compound 107c was yielded (35.58 g 92%).

$^1$H-NMR (CDCl$_3$) δ: 7.60 (1H, s), 7.52 (1H, d, J=8.4 Hz), 7.36 (4H, m), 6.93-6.89 (5H, m), 5.15 (2H, s), 5.11 (2H, s), 3.81 (6H, s), 2.51 (3H, s).

Step (2): Compound 107b→Compound 107c

Compound 107b (35.58 g, 91 mmol) was dissolved into pyridine (360 mL), and thereto was then added selenium dioxide (25.1 g, 227 mmol). The mixture was stirred at 80° C. for 1 day. The reaction mixture was filtered and evaporated. The residue was diluted with an aqueous hydrochloric acid solution and ethyl acetate, then separated and washed with water and a saturated salt solution, and dried over magnesium sulfate. Magnesium sulfate was filtrated off, and then the liquid was concentrated under reduced pressure. The precipitated solid was then collected by filtration, and washed with diisopropyl ether to yield compound 107c (22.0 g, 57%).

$^1$H-NMR (DMSO-D$_6$) δ: 7.51-7.50 (2H, m), 7.39-7.35 (4H, m), 7.27 (1H, d, J=8.3 Hz), 6.95-6.93 (4H, m), 5.18 (2H, s), 5.10 (2H, s), 3.75 (3H, s), 3.75 (3H, s).

Step (3): Compound 107c→Compound 107d

Compound 107c (4.00 g, 9.47 mmol) was dissolved into tetrahydrofuran (40 mL), and thereto were then added 1-chloro-N,N,2-trimethyl-1-propenylamine (1.503 ml, 11.36 mmol) at 0° C. The mixture was stirred at 0° C. for 1 hr. Thereto were then added 4-aminomethylquinuclidine (1.59 g, 11.36 mmol) 0° C. The mixture was stirred at rt for 1 hour. The reaction mixture was diluted with ethyl acetate and aqueous sodium hydroxide solution, then separated and washed with water and a saturated salt solution, and dried over magnesium sulfate. Magnesium sulfate was filtrated off, and then the liquid was concentrated under reduced pressure. The precipitated solid was then collected by filtration, and washed with diisopropyl ether to yield compound 107d (2.54 g, 49%).

$^1$H-NMR (DMSO-D$_6$) δ: 8.69 (1H, t, J=6.3 Hz), 7.56-7.55 (2H, m), 7.38-7.35 (4H, m), 7.25 (1H, d, J=8.8 Hz), 6.95- 6.92 (4H, m), 5.17 (2H, s), 5.07 (2H, s), 3.75-3.75 (6H, m), 3.01 (2H, d, J=6.3 Hz), 2.76-2.73 (6H, m), 1.34-1.31 (6H, m).

Step (4): Compound X-1+Compound 107d→Compound 107e→Compound I-107

Compound X-1 (932 mg, 1.0 mmol) was added to a solution of compound 107d (545 mg, 1.00 mmol) in dimethylformamide (2 mL) at 0° C., and the resultant solution was stirred at 0° C. for 3 hours. The reaction mixture was slowly added to a 5% salt solution (30 ml) (containing 1.5 g of sodium bisulfite) at 0° C. The precipitated solid was collected by filtration, washed with water, and then suspended into water. The suspension was freeze-dried to yield compound 107e as an orange solid. Compound 107e was used in the next reaction without further purification.

The total amount of compound 107e yielded was dissolved in dichloromethane (10 mL), and the solution was cooled to −40° C. Thereto were then added anisole (1.3 mL, 12 mmol) and a 2 mol/L aluminum chloride solution (6.00 mL, 12 mmol) in nitromethane in turn. The resultant was stirred at 0° C. for 30 minutes. The reaction mixture was dissolved in water, a 2 mol/L aqueous hydrochloric acid solution, and acetonitrile. The resultant solution was then washed with diisopropyl ether. To the water phase was added HP20-SS resin, and then acetonitrile was distilled off under reduced pressure. The resultant mixed liquid was purified by ODS column chromatography. To the resultant target-compound solution was added HP20-SS resin, and then acetonitrile was distilled off under reduced pressure. The resultant mixed liquid was purified by HP20-SS column chromatography. To the resultant target-compound solution was added a 0.2N aqueous sodium hydroxide solution until the whole gave a pH of 6.0. Thereafter, a piece of dry ice was added thereto. The resultant solution was concentrated under reduced pressure, and then freeze-dried to yield compound I-107 as a yellow powder.

Yielded amount: 592.4 mg, (64%).

$^1$H-NMR (D$_2$O) δ: 7.54-7.53 (2H, m), 7.00-6.99 (2H, m), 5.84 (1H, d, J=4.8 Hz), 5.44 (1H, d, J=4.8 Hz), 4.65 (1H, d, J=14.4 Hz), 4.08-4.06 (2H, m), 3.54-3.47 (6H, m), 3.37 (2H, s), 1.95-1.93 (6H, m), 1.56 (3H, d, J=7.1 Hz), 1.53 (3H, s), 1.51 (3H, s).

Elem. Anal.: C34H38N7O11S2Na (H2O) 5.2

Calcd.: C, 45.30; H, 5.41; N, 10.88; S, 7.11; Na, 2.55(%).

Found: C, 45.00; H, 5.43; N, 11.26; S, 6.98; Na, 2.56(%).

Example 108: Synthesis of Compound I-108

[Chemical Formula 250]

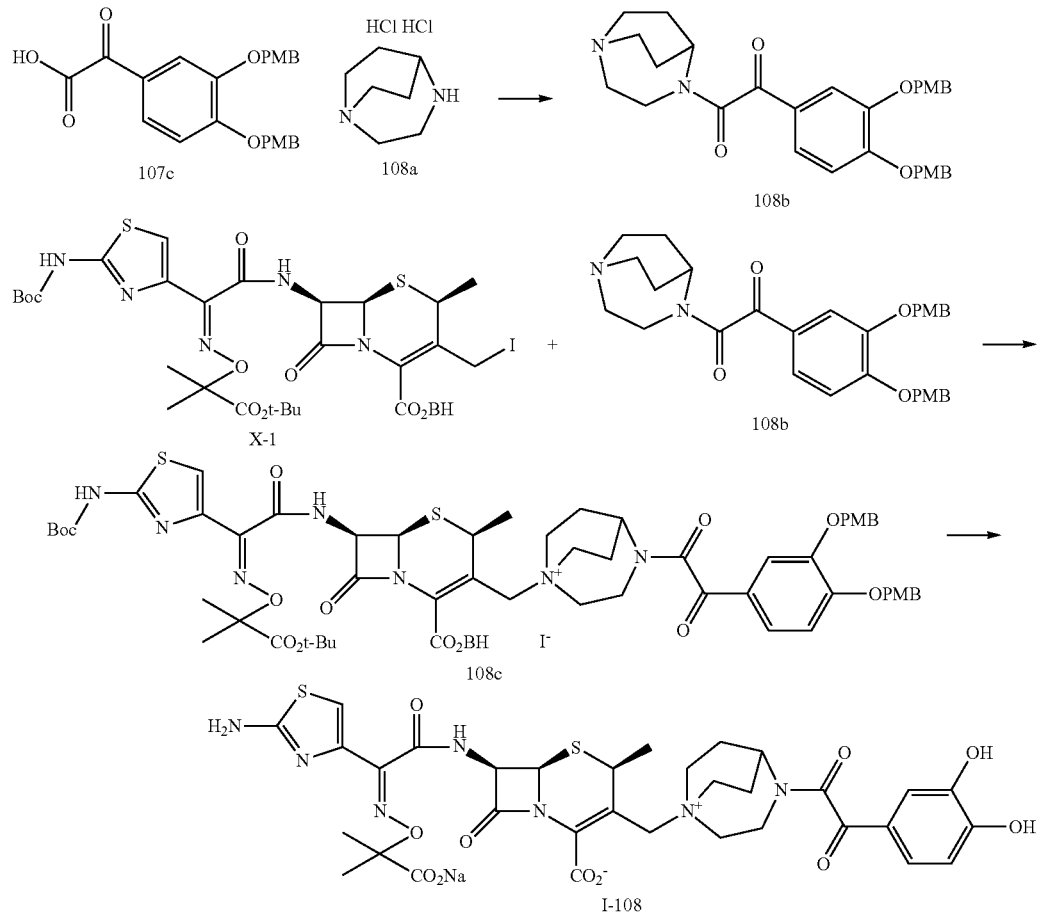

Step (1): Compound 107c+Compound 108a→Compound 108b

Compound 107c (4.00 g, 9.47 mmol) and compound 108a (2.26 g, 11.36 mmol) were used to synthesize compound 108b in the same way as in Step 3 of Example 107.
Yielded amount: 1.79 g, (36%)
$^1$H-NMR (DMSO-D$_6$) δ: 7.47-7.23 (7H, m), 6.95-6.93 (4H, m), 5.17 (2H, s), 5.10 (2H, s), 4.51 (1H, s), 3.72-3.66 (7H, m), 2.98-2.73 (6H, m), 2.00-1.98 (2H, m), 1.70-1.61 (3H, m).

Step (2): Compound X-1+Compound 108b→Compound 108c→Compound I-108

Compound X-1 (932 mg, 1.0 mmol) and compound 108b (531 mg, 1.0 mmol) were used to synthesize the target compound in the same way as in Step (4) of Example 107.
Yielded amount: 661.3 mg, (67%)
$^1$H-NMR (D$_2$O) δ: 7.45-7.42 (2H, m), 7.03-6.99 (2H, m), 5.87-5.83 (1H, m), 5.46-5.43 (1H, m), 4.95 (1H, br s), 4.85-4.81 (1H, m), 4.38-4.27 (1H, m), 4.16-4.07 (2H, m), 3.88-3.46 (7H, m), 2.47-2.22 (4H, m), 1.60-1.56 (3H, m), 1.53-1.50 (6H, m).
Elem. Anal.: C33H36N7O11S2Na (H2O) 5.3
Calcd.: C, 44.57; H, 5.28; N, 11.03; S, 7.21; Na, 2.59(%).
Found: C, 44.53; H, 5.24; N, 11.33; S, 7.11; Na, 2.68(%).

Example 109: Synthesis of Compound I-109

[Chemical Formula 251]

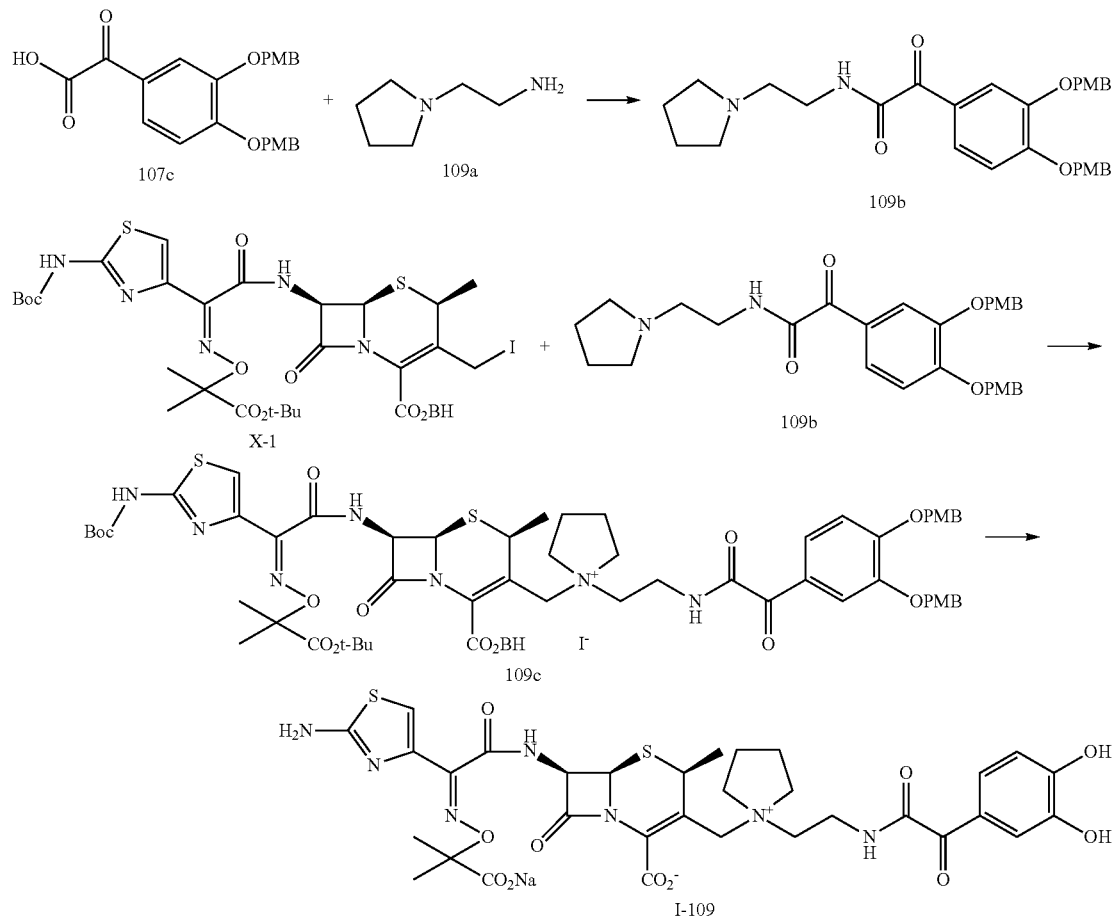

Step (1): Compound 107c+Compound 109a→Compound 109b

Compound 107c (1.00 g, 2.37 mmol) and compound 109a (0.36 ml, 2.84 mmol) were used to synthesize compound 109b in the same way as in Step (3) of Example 107.

Yielded amount: 459.4 mg, (37%)

$^1$H-NMR (DMSO-D$_6$) δ: 8.74 (1H, t, J=5.8 Hz), 7.65 (1H, dd, J=8.5, 1.8 Hz), 7.58 (1H, d, J=1.8 Hz), 7.39-7.34 (4H, m), 7.21 (1H, d, J=8.5 Hz), 6.96-6.91 (4H, m), 5.17 (2H, s), 5.08 (2H, s), 3.75 (3H, s), 3.75 (3H, s), 2.54 (2H, t, J=6.7 Hz), 2.49-2.46 (4H, m), 1.70-1.66 (4H, m).

Step (2): Compound X-1+Compound 109b→Compound 109c→Compound I-109

Compound X-1 (839 mg, 0.9 mmol) and compound 109b (467 mg, 0.9 mmol) were used to synthesize the target compound in the same way as in Step (4) of Example 107.

Yielded amount: 415.0 mg, (52%)

$^1$H-NMR (D$_2$O) δ: 7.60 (1H, dd, J=8.5, 2.0 Hz), 7.55 (1H, d, J=2.0 Hz), 7.01 (1H, s), 6.99 (1H, d, J=8.5 Hz), 5.80 (1H, d, J=4.8 Hz), 5.46 (1H, d, J=4.8 Hz), 5.04 (1H, d, J=14.3 Hz), 4.26 (1H, d, J=14.3 Hz), 4.07 (1H, q, J=7.0 Hz), 3.97-3.77 (2H, m), 3.73-3.67 (1H, m), 3.64-3.46 (5H, m), 2.28-2.20 (4H, m), 1.57 (3H, d, J=7.0 Hz), 1.52 (3H, s), 1.50 (3H, s).

Elem. Anal.: C32H36N7O11S2Na (H2O) 4.5
Calcd.: C, 44.54; H, 5.26; N, 11.36; S, 7.43; Na, 2.66(%).
Found: C, 44.50; H, 5.18; N, 11.51; S, 7.10; Na, 2.68(%).

Example 110: Synthesis of Compound I-110

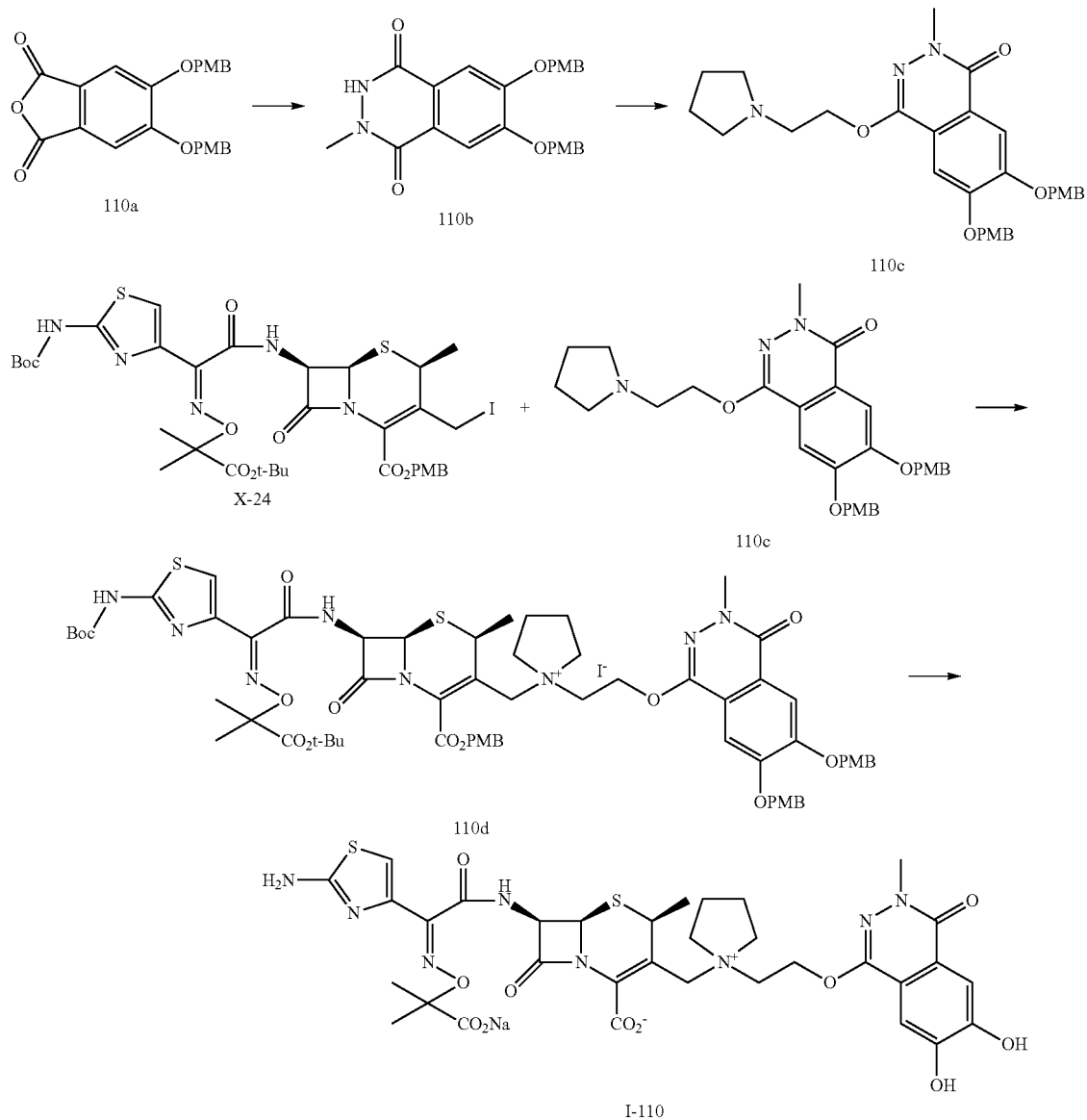

Step (1): Compound 110a→Compound 110b

Compound 110a (2.10 g, 5.00 mmol) was dissolved into ethanol (20 mL), and thereto was then added methyl hydrazine (0.28 ml, 5.25 mmol). The mixture was stirred at rt for 30 minutes, then reflux for 1 hour. The reaction mixture was evaporated. The precipitated solid was then collected by filtration, and washed with diisopropyl ether to yield compound 110b (2.28 g, 102%).

$^1$H-NMR (DMSO-D$_6$) δ: 7.68 (1H, s), 7.41-7.39 (5H, m), 6.96-6.94 (4H, m), 5.22 (2H, s), 5.21 (2H, s), 3.75 (6H, s), 3.53 (3H, s).

Step (2): Compound 110b→Compound 110c

Compound 110b (1.20 g, 2.68 mmol) was dissolved into tetrahydrofuran (12 mL), and thereto were then added diisopropyl azodicarboxylate (0.728 ml, 3.75 mmol) and triphenylphosphine (983 mg, 3.75 mmol) at 0° C. The mixture was stirred at 0° C. for 10 minutes. Thereto was then added 2-pyrrolidinoethanol (0.438 ml, 3.75 mmol) at 0° C. The mixture was stirred at rt for 1 hour. Thereto was then added diisopropyl ether (24 ml). The precipitated solid was then collected by filtration, and washed with diisopropyl ether to yield compound 110c (0.93 g, 64%).

$^1$H-NMR (CDCl$_3$) δ: 7.82 (1H, s), 7.41-7.34 (5H, m), 6.91-6.89 (4H, m), 5.22 (2H, s), 5.19 (2H, s), 4.42 (2H, t, J=5.9 Hz), 3.81 (3H, s), 3.81 (3H, s), 3.70 (3H, s), 2.95 (2H, t, J=5.9 Hz), 2.67-2.62 (4H, m), 1.85-1.78 (4H, m).

Step (3): Compound X-24+Compound 110c→Compound 110d→Compound I-110

Compound X-24 (886 mg, 1.0 mmol) and compound 110c (546 mg, 1.0 mmol) were used to synthesize the target compound in the same way as in Step (4) of Example 107.
Yielded amount: 238.2 mg, (25%)
$^1$H-NMR (D$_2$O) δ: 7.45 (1H, s), 7.14 (1H, s), 7.01 (1H, s), 5.83 (1H, d, J=4.6 Hz), 5.47 (1H, d, J=4.6 Hz), 4.34 (1H, d, J=14.6 Hz), 4.08 (1H, q, J=6.9 Hz), 3.96-3.82 (3H, m), 3.74-3.47 (7H, m), 2.26 (4H, br s), 1.54 (3H, d, J=6.9 Hz), 1.51 (3H, s), 1.49 (3H, s).
Elem. Anal.: C33H37N8O11S2Na (H2O) 5.8
Calcd.: C, 43.40; H, 5.36; N, 12.27; S, 7.02; Na, 2.52(%).
Found: C, 43.21; H, 5.29; N, 12.60; S, 6.97; Na, 2.65(%).

Example 111: Synthesis of Compound I-111

[Chemical Formula 253]

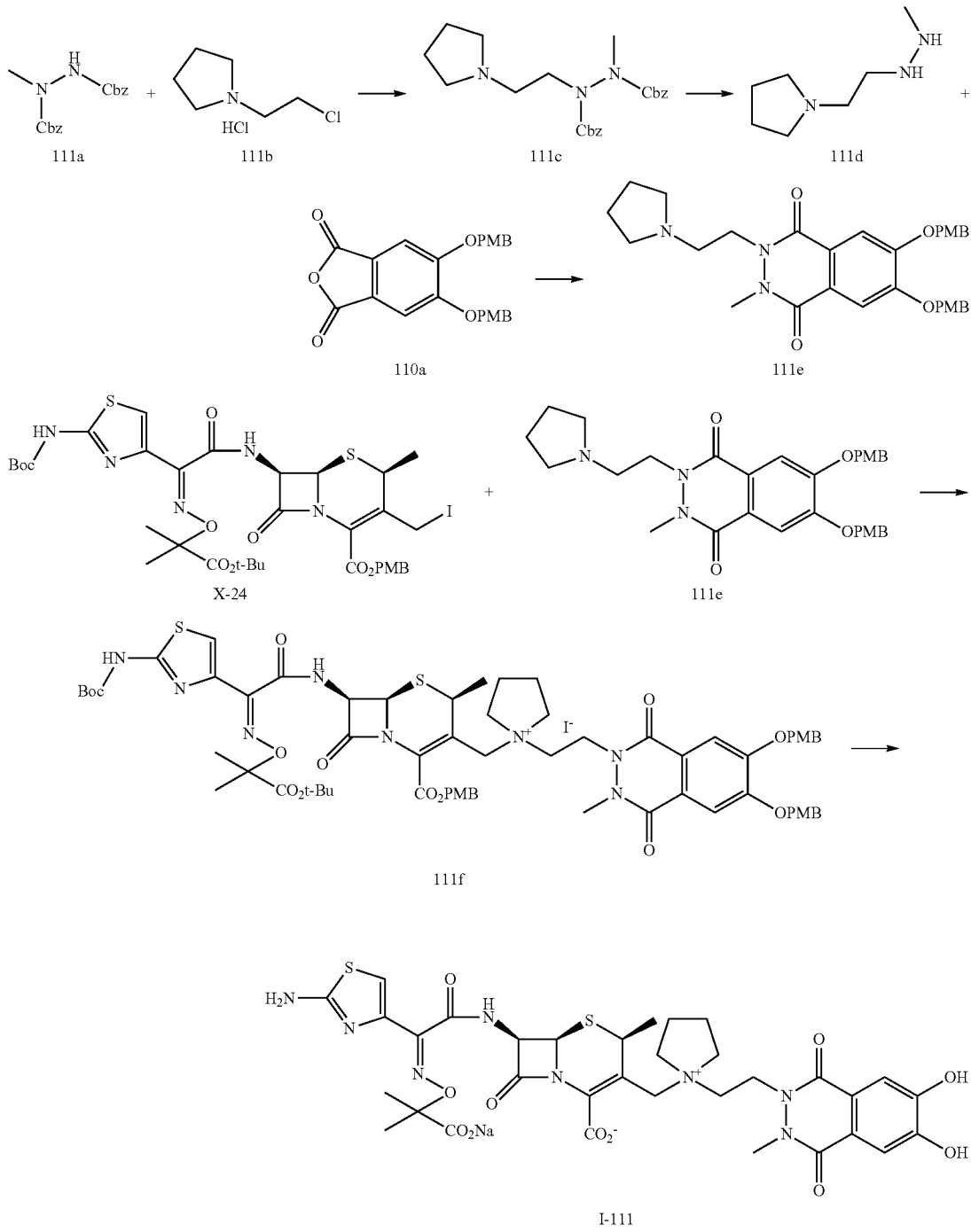

Step (1): Compound 111a+Compound 111b→Compound 111c

Compound 111a (10.0 g, 31.8 mmol) was dissolved into dimethylformamide (100 mL), and thereto was then added sodium hydride (3.05 g, 76.0 mmol) at 0° C. The mixture was stirred at 0° C. for 30 minutes. Thereto were then added compound 111b (5.95 g, 35.0 mmol) and sodium iodide (9.54 g, 63.6 mmol) in turn. The mixture was stirred at 60° C. for 2 hours. The reaction mixture was diluted with ethyl acetate and water, then separated and washed with a saturated salt solution, and dried over magnesium sulfate. Magnesium sulfate was filtrated off, and then the liquid was concentrated under reduced pressure. The compound-containing liquid was subjected to silica gel column chromatography to elute out the desired compound with ethyl acetate (3% triethylamine) The desired-compound-containing fraction was concentrated under reduced pressure to yield compound 111c (12.70 g, 97%).

$^1$H-NMR (DMSO-$D_6$) δ: 7.39-7.24 (10H, m), 5.19-4.95 (4H, m), 3.83-3.67 (1H, m), 3.13 (1H, s), 3.07 (2H, s), 2.61-2.55 (1H, m), 2.45-2.36 (4H, m), 1.66-1.61 (4H, m).

Step (2): Compound 111c→Compound 111d

Compound 111c (12.70 g, 30.9 mmol) was dissolved into methanol (120 mL), and thereto was then added 10% Pd/C (2.54 g, 50% wet). The mixture was stirred at rt under hydrogen atmosphere for 2 hours. The reaction mixture was filtered through celite, then concentrated under reduced pressure to yield compound 111d (4.90 g, 111%).

$^1$H-NMR (CDCl$_3$) δ: 3.94 (1H, t, J=6.8 Hz), 3.78 (1H, s), 2.96 (2H, t, J=6.8 Hz), 2.66-2.61 (3H, m), 2.58-2.52 (4H, m), 1.81-1.77 (4H, m).

Step (3): Compound 111d+Compound 110a→Compound 111e

Compound 111d (1.50 g, 10.47 mmol) was dissolved into ethanol (50 mL), and thereto was then added compound 110a (4.40 g, 10.47 mmol). The mixture was stirred at rt for 1 day, then reflux for 2 hour. The reaction mixture was evaporated. The compound-containing liquid was subjected to silica gel column chromatography to elute out the desired compound with ethyl acetate (3% triethylamine)/methanol. The desired-compound-containing fraction was concentrated under reduced pressure to yield compound 111e (2.10 g, 37%).

$^1$H-NMR (CDCl$_3$) δ: 7.73 (1H, s), 7.73 (1H, s), 7.40-7.38 (4H, m), 6.91-6.89 (4H, m), 5.21 (2H, s), 5.21 (2H, s), 4.30 (2H, t, J=7.3 Hz), 3.81 (6H, s), 3.68 (3H, s), 2.73 (2H, t, J=7.3 Hz), 2.59-2.54 (4H, m), 1.74-1.71 (4H, m).

Step (4): Compound X-24+Compound 111e→Compound 111f→Compound I-111

Compound X-24 (886 mg, 1.0 mmol) and compound 111e (546 mg, 1.0 mmol) were used to synthesize the target compound in the same way as in Step (4) of Example 107.

Yielded amount: 444.5 mg, (46%)

$^1$H-NMR (D$_2$O) δ: 7.19 (1H, s), 7.14 (1H, s), 6.99 (1H, s), 5.81 (1H, d, J=4.8 Hz), 5.48 (1H, d, J=4.8 Hz), 5.12 (1H, d, J=14.1 Hz), 4.58 (2H, br s), 4.33 (1H, d, J=14.1 Hz), 4.11 (1H, q, J=6.9 Hz), 3.84-3.51 (9H, m), 2.26 (4H, br s), 1.59 (3H, d, J=6.9 Hz), 1.52 (3H, s), 1.50 (3H, s).

Elem. Anal.: C33H37N8O11S2Na (H2O) 6
Calcd.: C, 43.23; H, 5.39; N, 12.22; S, 6.99; Na, 2.51(%).
Found: C, 42.94; H, 5.30; N, 12.54; S, 6.85; Na, 2.64(%).

Example 112: Synthesis of Compound I-112

[Chemical Formula 254]

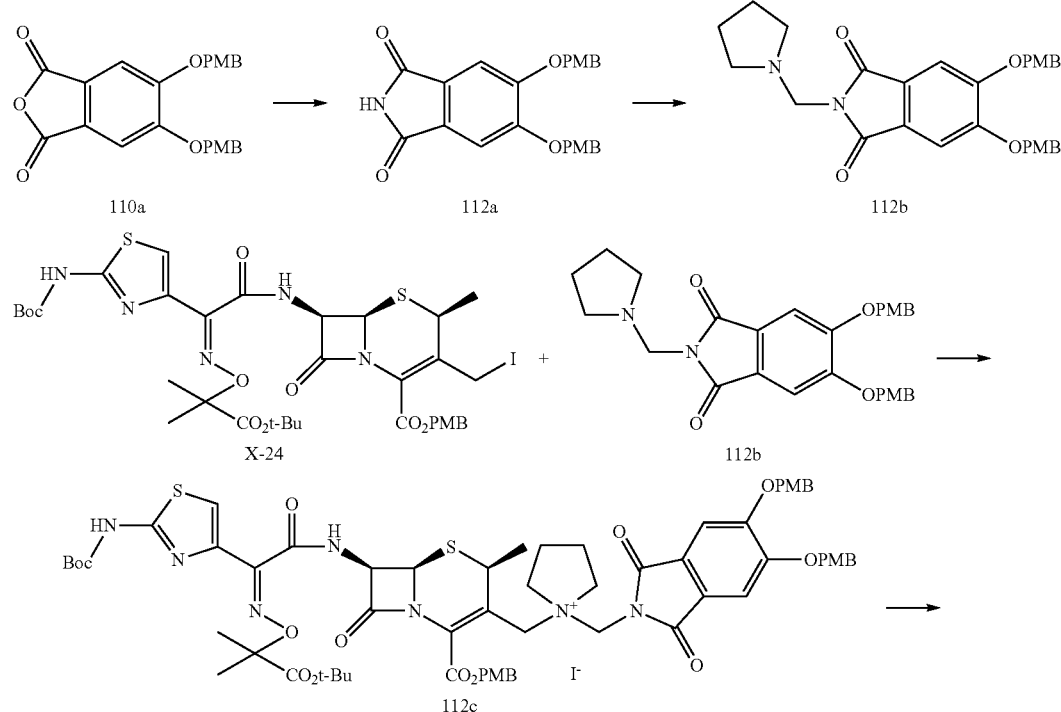

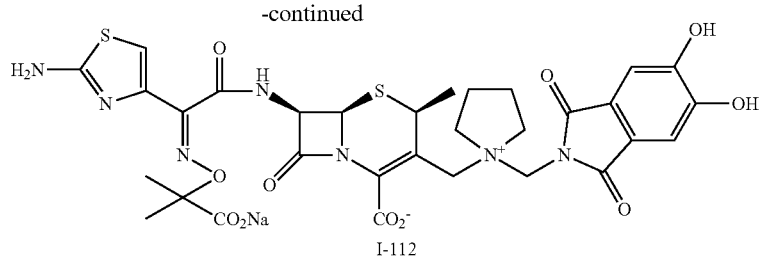

I-112

Step (1): Compound 110a→Compound 112a

Compound 110a (5.00 g, 11.89 mmol) was suspended into dimethylformamide (25 mL), and thereto were then added hexamethyldisilazane (24.93 ml, 119 mmol) and methanol (0.48 ml, 11.89 mmol) in turn. The mixture was stirred at rt for 1 day, then 50° C. for 2 hours, 80° C. for 2 hours. The reaction mixture was slowly added to a 1 mol/L aqueous hydrochloric acid solution (240 ml) at 0° C. The precipitated solid was collected by filtration, washed with water and diisopropyl ether to yield compound 112a (4.89 g, 98%).

$^1$H-NMR (CDCl$_3$) δ: 7.35 (4H, d, J=8.6 Hz), 7.33 (2H, s), 6.91 (4H, d, J=8.6 Hz), 5.18 (4H, s), 3.82 (6H, s).

Step (2): Compound 112a→Compound 112b

Compound 112a (1.00 g, 2.38 mmol) and paraformaldehyde (0.36 g, 11.92 mmol) were suspended into dimethylformamide (10 mL), and thereto was then added pyrrolidine (0.99 ml, 11.92 mmol). The mixture was stirred at rt for 2 hours. Thereto was then added water (20 ml). The precipitated solid was then collected by filtration, and washed with water to yield compound 112b (1.16 g, 97%).

$^1$H-NMR (CDCl$_3$) δ: 7.37-7.34 (6H, m), 6.90 (4H, d, J=8.6 Hz), 5.18 (4H, s), 4.64 (2H, s), 3.82 (6H, s), 2.71-2.66 (4H, m), 1.74-1.70 (4H, m).

Step (3): Compound X-24+Compound 112b→Compound I-112

Compound X-24 (886 mg, 1.0 mmol) and compound 112b (503 mg, 1.0 mmol) were used to synthesize the target compound in the same way as in Step (4) of Example 107.

Yielded amount: 111.0 mg, (9%)

$^1$H-NMR (D$_2$O) δ: 7.29 (2H, s), 7.01 (1H, s), 5.83 (1H, d, J=4.9 Hz), 5.48 (1H, d, J=4.9 Hz), 4.27 (1H, d, J=14.4 Hz), 4.11 (1H, q, J=7.2 Hz), 3.72 (1H, br s), 3.46-3.39 (3H, m), 3.28 (1H, t, J=7.2 Hz), 2.37-2.20 (4H, m), 2.00 (1H, t, J=7.2 Hz), 1.56 (3H, d, J=7.2 Hz), 1.52-1.49 (6H, m).

Elem. Anal.: C31H32N7O11S2Na (H2O) 5.2 (NaHCO3) 0.2

Calcd.: C, 42.77; H, 4.90; N, 11.19; S, 7.32; Na, 3.15(%).
Found: C, 42.49; H, 4.85; N, 11.97; S, 7.87; Na, 3.14(%).

Example 113: Synthesis of Compound I-113

[Chemical Formula 255]

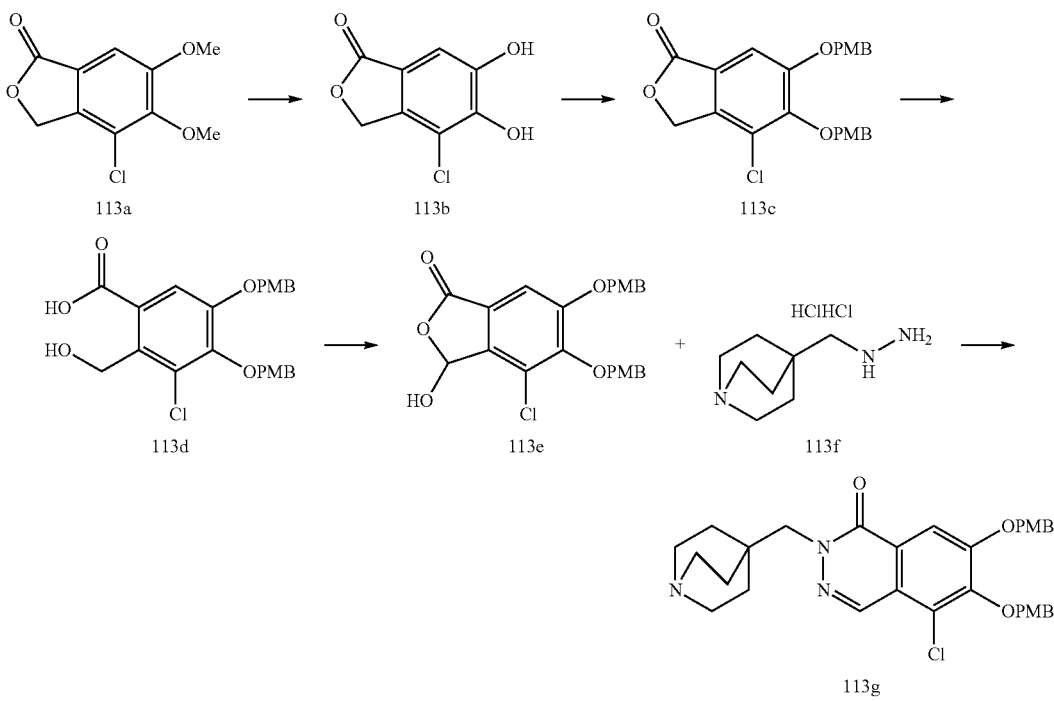

-continued

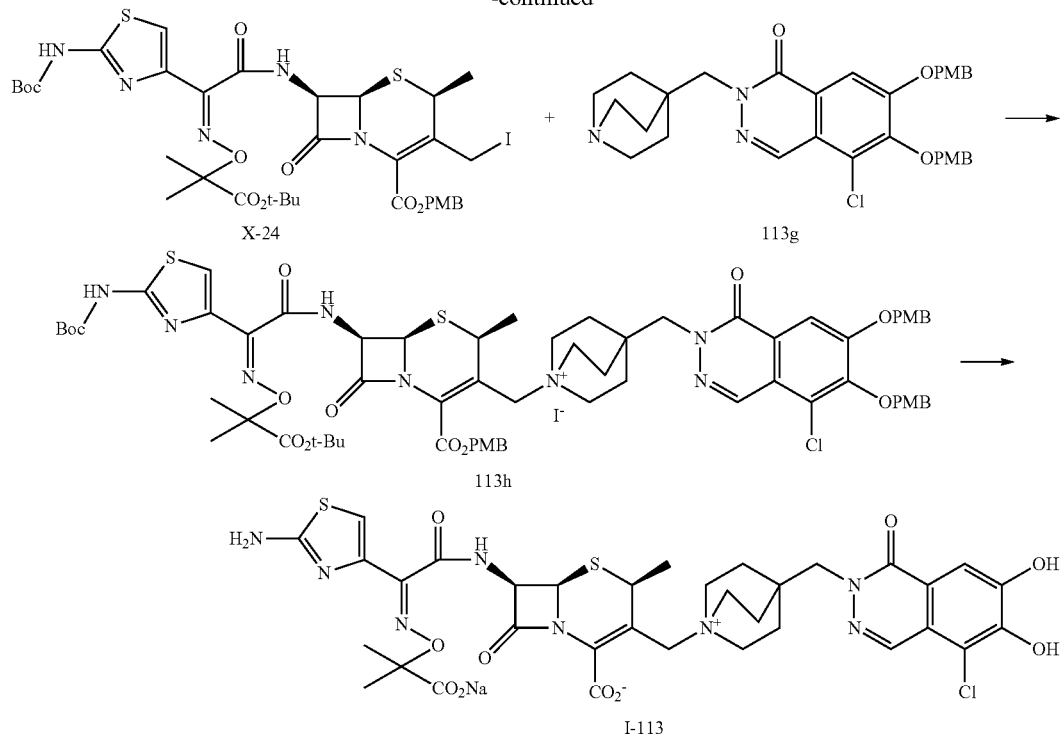

Step (1): Compound 113a→Compound 113b

Compound 113a (11.65 g, 51.0 mmol) was dissolved into dichloromethane (100 mL), and thereto were then added dropwise boron tribromide (25 g, 100 mmol) and 1 mol/L dichloromethane solution of boron tribromide (20 ml, 20 mmol) at 0° C. The mixture was stirred at rt for 1 hour. The reaction mixture was diluted with ice water, then extracted with ethyl acetate, and washed with a saturated salt solution, and dried over magnesium sulfate. Magnesium sulfate was filtrated off, and then the liquid was concentrated under reduced pressure to yield compound 113b (10.60 g, 104%). Compound 113b was used in the next reaction without further purification.

$^1$H-NMR (DMSO-$D_6$) δ: 10.54 (2H, br s), 7.09 (1H, s), 5.22 (2H, s).

Step (2): Compound 113b→Compound 113c

The total amount of compound 113b obtained in Step (1) was dissolved into dimethylacetamide (110 mL), and thereto were then added potassium carbonate (21.9 g, 159 mmol), p-methoxybenzyl chloride (17.3 ml, 127 mmol) and sodium iodide (7.92 g, 52.8 mmol) in turn. The mixture was stirred at 50° C. for 1 hour. The reaction mixture was poured into water. The precipitated solid was then collected by filtration, and washed with water and diisopropyl ether to yield compound 113c (20.71 g, 89%).

$^1$H-NMR (CDCl$_3$) δ: 7.39-7.36 (3H, m), 7.30 (2H, d, J=8.6 Hz), 6.94 (2H, d, J=8.6 Hz), 6.83 (2H, d, J=8.6 Hz), 5.18 (2H, s), 5.11 (2H, s), 5.09 (2H, s), 3.84 (3H, s), 3.80 (3H, s).

Step (3): Compound 113c→Compound 113d

A 2 mol/L aqueous sodium hydroxide solution (15 ml, 30 mmol) was added to a solution of compound 113c (4.41 g, 10 mmol) in tetrahydrofuran (5 mL) and methanol (5 mL). The resultant solution was stirred at 70° C. for 1 hour. To the reaction mixture was added water and 2 mol/L aqueous hydrochloric acid solutions (18 mL) at 0° C. The precipitated solid was then collected by filtration, and washed with water to yield compound 113d (5.33 g, 116%).

$^1$H-NMR (CDCl$_3$) δ: 7.61 (1H, s), 7.37-7.32 (4H, m), 6.92 (2H, d, J=7.9 Hz), 6.83 (2H, d, J=7.4 Hz), 5.09 (2H, s), 5.04 (2H, s), 4.98 (2H, s), 3.83 (3H, s), 3.80 (3H, s).

Step (4): Compound 113d→Compound 113e

The total amount of compound 113d yielded (5.33 g, 10 mmol) was suspended into acetone (50 mL), and thereto was then added Jone's reagent (2.67 mol/L, 7.5 mL, 20 mmol) at 0° C. The mixture was stirred at rt for 30 minutes. The reaction mixture was diluted with water, then added sodium bisulfite at 0° C. The mixture was evaporated to remove acetone, then the precipitated solid was collected by filtration, washed with water and diisopropyl ether to yield compound 113e (3.75 g, 82%).

$^1$H-NMR (CDCl$_3$) δ: 7.39-7.37 (3H, m), 7.31 (2H, d, J=8.3 Hz), 6.94 (2H, d, J=8.4 Hz), 6.83 (2H, d, J=8.3 Hz), 5.18 (1H, s), 5.11-5.07 (4H, m), 3.84 (3H, s), 3.80 (3H, s).

Step (5): Compound 113e+Compound 113f→Compound 113g

Compound 113e (777 mg, 3.40 mmol) was dissolved into dimethylacetamide (30 mL), and thereto was then added sodium acetate (1.40 g, 17.0 mmol). The mixture was stirred at rt for 30 minutes. Thereto was then added compound 113f (3.11 g, 6.81 mmol). The mixture was stirred at rt for 1 hour, then 70° C. for 1 hour. The reaction mixture was diluted with ethyl acetate and aqueous sodium hydroxide solution, then separated and washed with water and a saturated salt solution, and dried over sodium sulfate. Sodium sulfate was filtrated off, and then the liquid was concentrated under reduced pressure. The compound-containing liquid was subjected to silica gel column chromatography to elute out the desired compound with ethyl acetate (10% triethylamine)/methanol (10% triethylamine). The desired-compound-containing fraction was concentrated under reduced pressure to yield compound 113g (553 mg, 12%).

$^1$H-NMR (DMSO-D$_6$) δ: 8.37 (1H, s), 7.84 (1H, s), 7.49 (2H, d, J=8.3 Hz), 7.29 (2H, d, J=8.3 Hz), 7.01 (2H, d, J=8.3 Hz), 6.86 (2H, d, J=8.3 Hz), 5.33 (2H, s), 5.09 (2H, s), 3.96 (2H, s), 3.79 (3H, s), 3.74 (3H, s), 2.71 (6H, br s), 1.39 (6H, br s).

Step (6): Compound X-24+Compound 113g
Compound 113h→Compound I-113

Compound X-24 (886 mg, 1.0 mmol) and compound 113g (553 mg, 960 mmol) were used to synthesize the target compound in the same way as in Step (4) of Example 107.

Yielded amount: 547.4 mg, (58%)
$^1$H-NMR (D$_2$O) δ: 8.38 (1H, s), 7.37 (1H, s), 6.99 (1H, s), 5.83 (1H, d, J=4.9 Hz), 5.43 (1H, d, J=4.9 Hz), 4.61 (1H, d, J=14.4 Hz), 4.17 (2H, s), 4.09-4.02 (2H, m), 3.55-3.38 (6H, m), 1.99 (6H, s), 1.54 (3H, d, J=7.2 Hz), 1.51 (3H, s), 1.50 (3H, s).

Elem. Anal.: C34H36ClN8O10S2Na (H2O) 5 (NaHCO3) 0.4
Calcd.: C, 42.91; H, 4.86; N, 11.64; S, 6.66; Na, 3.34(%).
Found: C, 42.74; H, 4.97; N, 12.01; S, 6.81; Na, 3.33(%).

Example 114 and 115: Synthesis of Compound I-114 and I-115

[Chemical Formula 256]

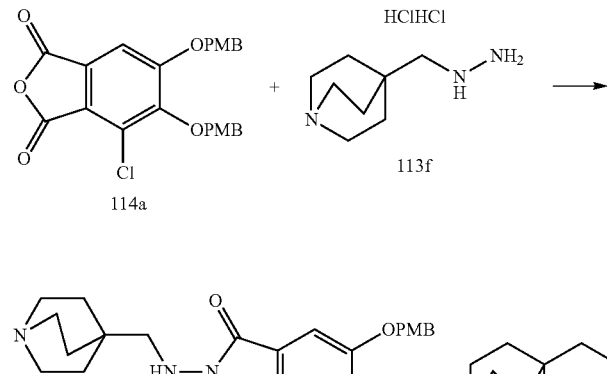

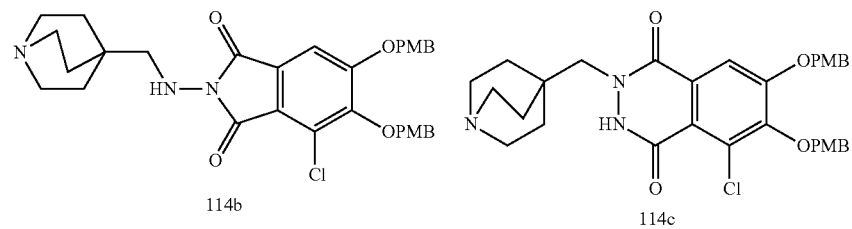

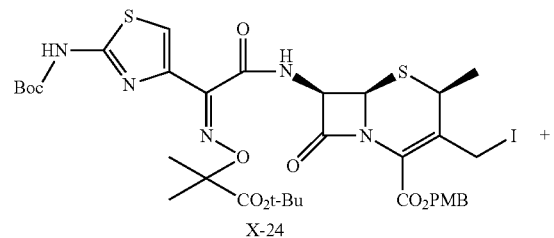

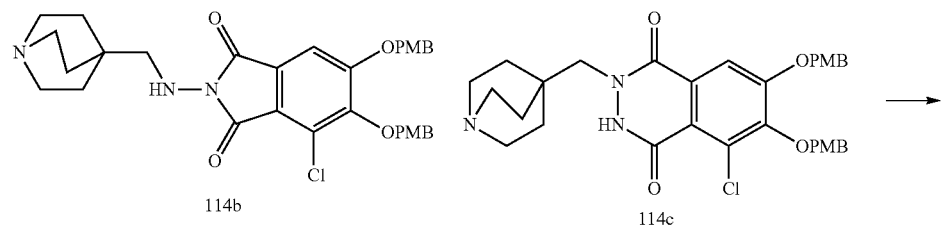

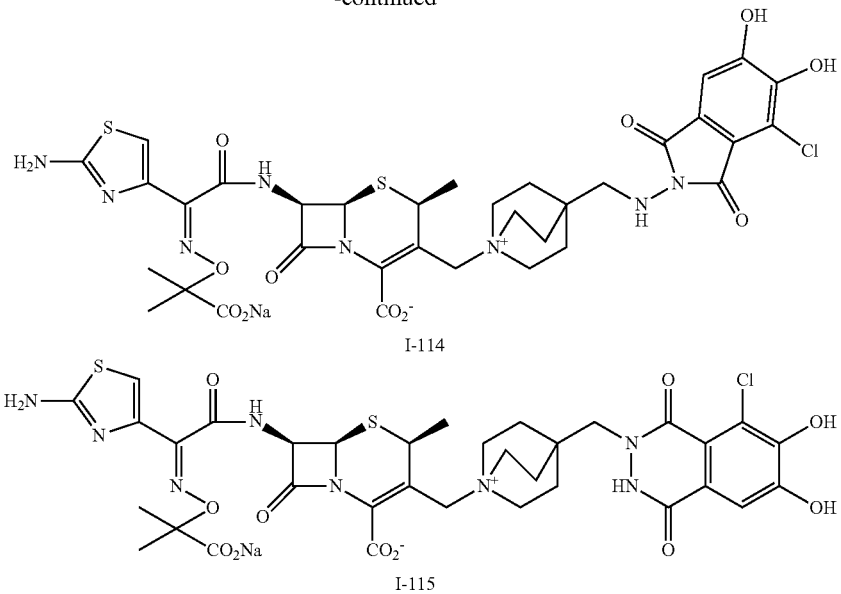

I-114

I-115

Step (1): Compound 114a+Compound 113f→Compound 114b

Compound 113f (311 mg, 1.36 mmol) and sodium acetate (559 mg, 6.82 mmol) were suspended into tetrahydrofuran (6 mL), and thereto was then added suspension of compound 114a (0.62 g, 1.36 mmol) in tetrahydrofuran (6 mL) at −20° C. The mixture was stirred at −20° C. for 1 hour. Thereto was then added acetic acid (0.39 ml, 6.82 mmol). The mixture was stirred at reflux for 1 day. The reaction mixture was diluted with ethyl acetate and aqueous sodium hydroxide solution, then separated and washed with water and a saturated salt solution, and dried over sodium sulfate. Sodium sulfate was filtrated off, and then the liquid was concentrated under reduced pressure. The precipitated solid was then collected by filtration, and washed with diisopropyl ether to yield a mixture of compound 114b and 114c (206 mg, 26%). The mixture was used in the next reaction without further purification.

MS (m+1)=592

Step (2): Compound X-24+Compound 114b and 114c→Compound I-114 and I-115

Compound X-24 (354 mg, 0.4 mmol) and compound 114b and 114c (206 mg, 0.35 mmol) were used to synthesize the target compound in the same way as in Step (4) of Example 107.

Yielded amount: Compound I-114 (165.6 mg, 45%), compound I-115 (16.6 mg, 5.5%)

Compound I-114

$^1$H-NMR (D$_2$O) δ: 7.10 (1H, s), 7.01 (1H, s), 5.85 (1H, d, J=4.6 Hz), 5.45 (1H, d, J=4.6 Hz), 4.63 (1H, d, J=13.9 Hz), 4.12-4.05 (2H, m), 3.59-3.41 (6H, m), 2.98 (2H, s), 1.97 (6H, t, J=7.2 Hz), 1.57 (3H, d, J=6.9 Hz), 1.52 (3H, s), 1.51 (3H, s).

Elem. Anal.: C34H36ClN8O11S2Na (H2O) 6.2 (NaHCO3) 0.5

Calcd.: C, 41.07; H, 4.89; Cl, 3.51; N, 11.11; S, 6.36; Na, 3.42(%).

Found: C, 40.68; H, 4.96; Cl, 3.53; N, 11.52; S, 6.41; Na, 3.32(%).

Compound I-115

$^1$H-NMR (D$_2$O) δ: 7.33 (1H, s), 6.92 (1H, s), 5.76 (1H, d, J=4.4 Hz), 5.36 (1H, d, J=4.4 Hz), 4.55 (1H, d, J=14.3 Hz), 3.99-3.91 (4H, m), 3.50-3.32 (6H, m), 1.96-1.92 (6H, m), 1.48-1.43 (9H, m).

MS (m+1)=833

Example 116: Synthesis of Compound I-116

[Chemical Formula 257]

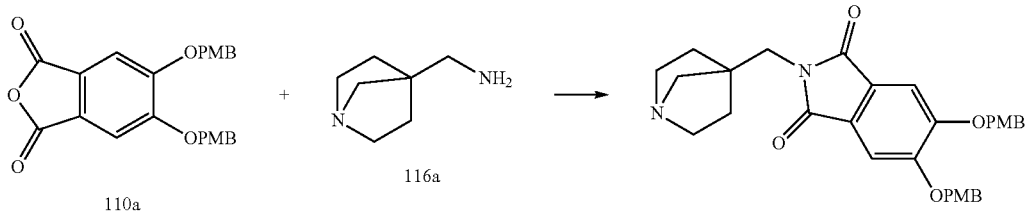

110a     116a     116b

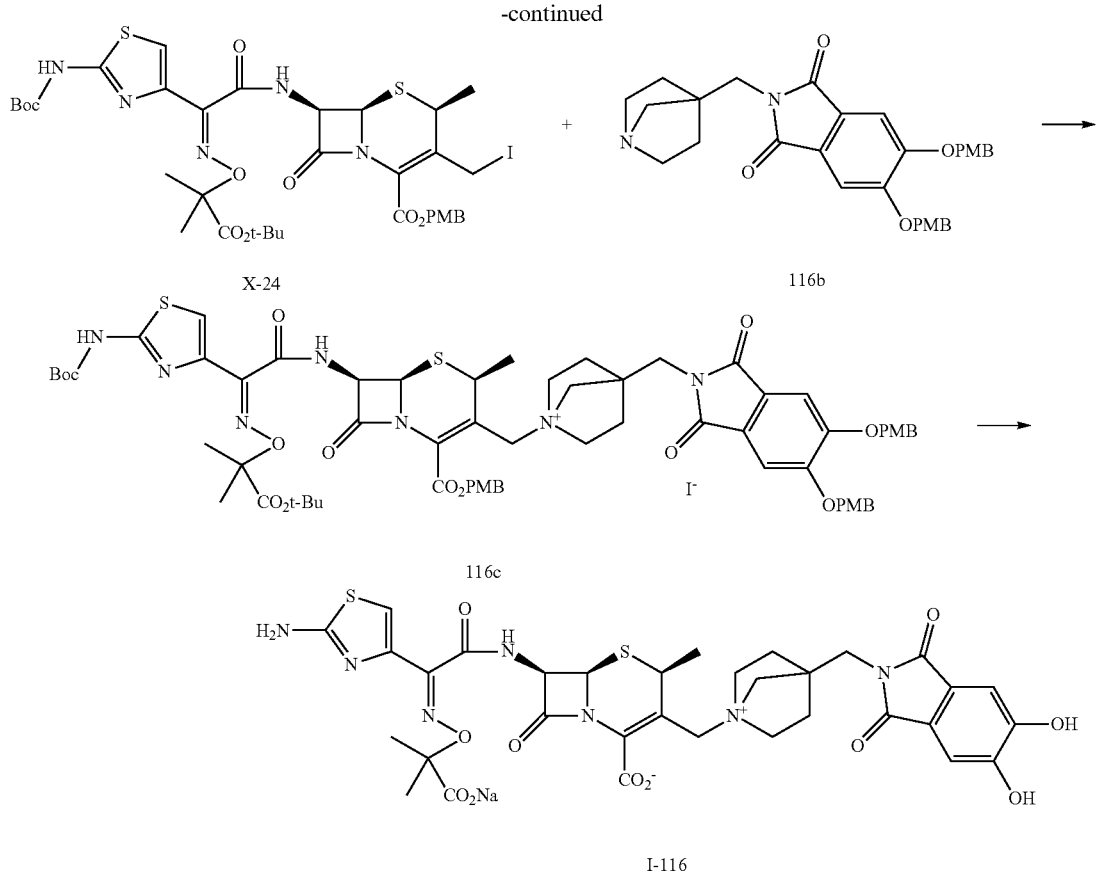

Step (1): Compound 110a+Compound 116a→Compound 116b

Compound 110a (1.26 g, 3.0 mmol) and compound 116a (379 mg, 3.0 mmol) were used to synthesize compound 116b in the same way as Reference Example 5.

Yielded amount: 1.35 g, (85%)

$^1$H-NMR (DMSO-D$_6$) δ: 7.49 (2H, s), 7.38 (4H, d, J=8.7 Hz), 6.95 (4H, d, J=8.7 Hz), 5.24 (4H, s), 3.82 (2H, s), 3.75 (6H, s), 2.74-2.68 (2H, m), 2.44-2.38 (2H, m), 2.11 (2H, s), 1.50-1.44 (2H, m), 1.14-1.08 (2H, m).

Step (2): Compound X-24+Compound 116b→Compound 116c→Compound I-116

Compound X-24 (886 mg, 1.0 mmol) and compound 116b (529 mg, 1.0 mmol) were used to synthesize the target compound in the same way as in Step (4) of Example 107.

Yielded amount: 568.0 mg, (62%)

$^1$H-NMR (D$_2$O) δ: 7.21 (2H, s), 7.00 (1H, s), 5.79 (1H, d, J=4.9 Hz), 5.40 (1H, d, J=4.9 Hz), 4.23 (1H, d, J=14.6 Hz), 4.06 (1H, q, J=7.2 Hz), 3.91 (2H, s), 3.70-3.47 (4H, m), 3.43 (1H, d, J=8.5 Hz), 3.33 (1H, d, J=8.5 Hz), 2.23-2.13 (2H, m), 2.00-1.92 (2H, m), 1.55 (3H, d, J=7.2 Hz), 1.52 (3H, s), 1.50 (3H, s).

Elem. Anal.: C33H34N7O11S2Na (H2O) 6.3

Calcd.: C, 43.78; H, 5.19; N, 10.83; S, 7.08; Na, 2.54(%).
Found: C, 43.76; H, 5.19; N, 10.87; S, 7.02; Na, 2.59(%).

Example 117: Synthesis of Compound I-117

[Chemical Formula 258]

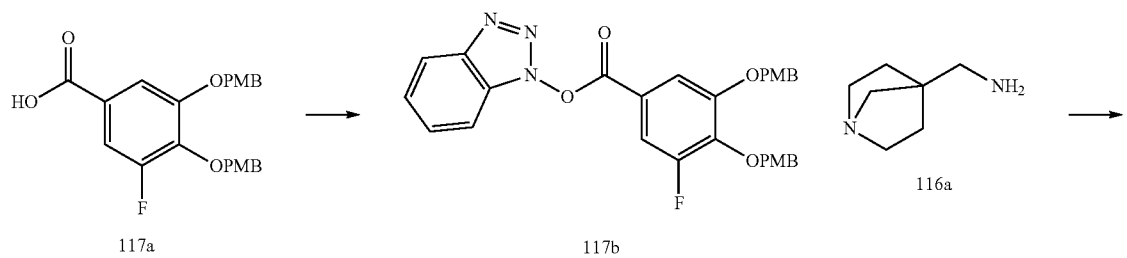

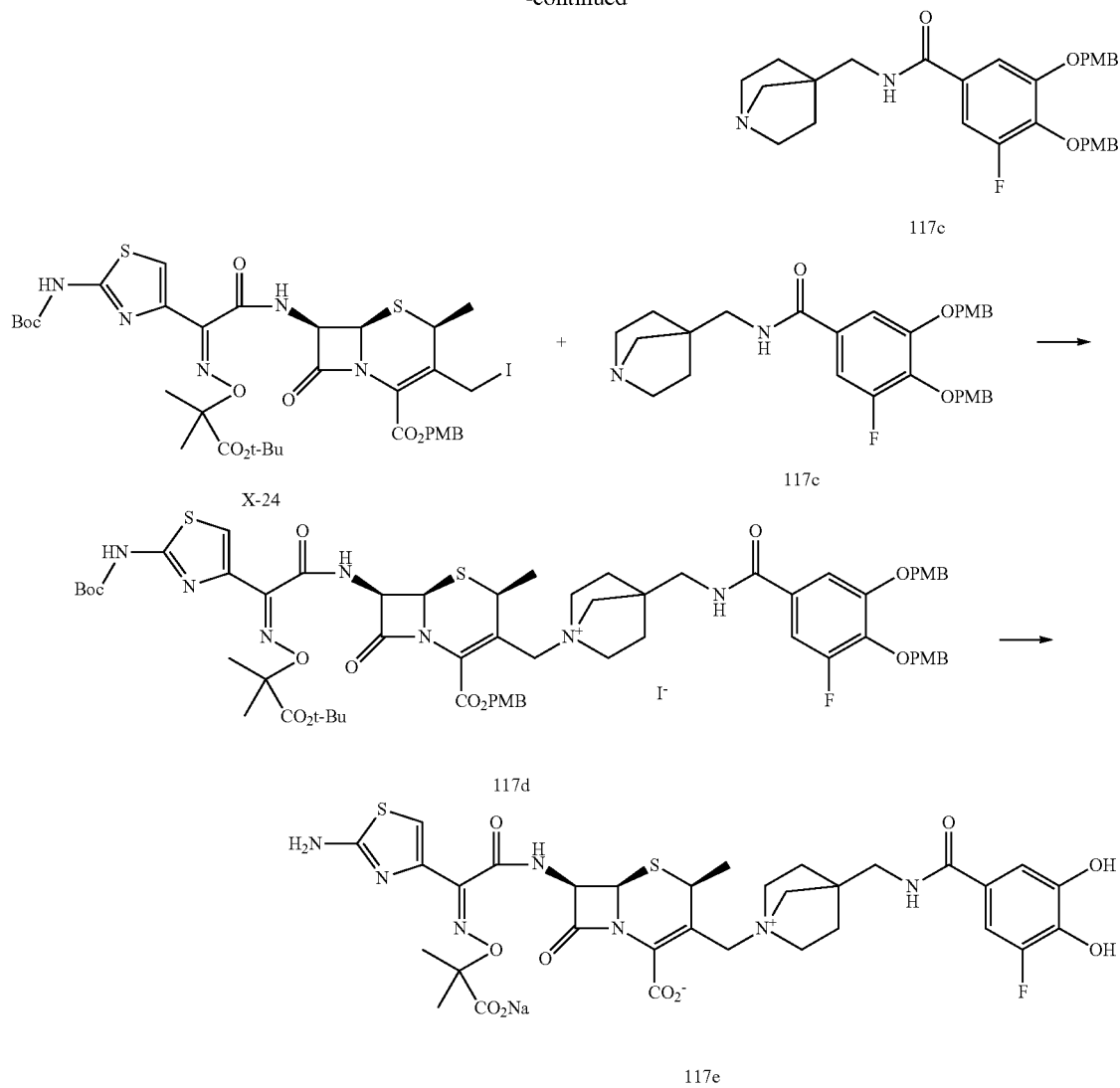

Step (1): Compound 117a→Compound 117b

Compound 117a (1.24 g, 3.0 mmol) and 1-hydroxybenzotriazole (446 mg, 3.3 mmol) were dissolved into dichloromethane (15 mL), and thereto was then added 1-ethyl-3-(3-dimethylaminopropyl) carbodiimide hydrochloride (690 mg, 3.6 mmol) at 0° C. The mixture was stirred at rt for 1 hour. The reaction mixture was diluted with dichloromethane and an aqueous hydrochloric acid solution, then separated and washed with water, a saturated sodium bicarbonate solution, and a saturated salt solution, and dried over magnesium sulfate. Magnesium sulfate was filtrated off, and then the liquid was concentrated under reduced pressure to yield compound 117b (1.72 g, 108%).

Compound 117b was used as it was, without being purified, in the next reaction.

$^1$H-NMR (CDCl$_3$) δ: 8.11 (1H, d, J=8.7 Hz), 7.68-7.62 (2H, m), 7.58-7.54 (1H, m), 7.47-7.44 (2H, m), 7.36 (2H, d, J=8.5 Hz), 7.31 (2H, d, J=8.5 Hz), 6.93 (2H, d, J=8.5 Hz), 6.85 (2H, d, J=8.5 Hz), 5.23 (2H, s), 5.12 (2H, s), 3.83 (3H, s), 3.81 (3H, s).

Step (2): Compound 117b+Compound 116a→Compound 117c

Compound 117b (1.59 g, 3.0 mmol) was dissolved into tetrahydrofuran (10 mL), and thereto was then added compound 116a (379 mg, 3.0 mmol) in tetrahydrofuran (10 mL) at 0° C. The mixture was stirred at rt for 1 hour. The reaction mixture was diluted with ethyl acetate and aqueous sodium hydroxide solution, then separated and washed with water and a saturated salt solution, and dried over sodium sulfate. Sodium sulfate was filtrated off, and then the liquid was concentrated under reduced pressure. The compound-containing liquid was subjected to silica gel column chromatography to elute out the desired compound with ethyl acetate (10% triethylamine)/methanol (10% triethylamine). The desired-compound-containing fraction was concentrated under reduced pressure to yield compound 117b (1.54 g, 99%).

$^1$H-NMR (DMSO-D$_6$) δ: 8.53 (1H, t, J=5.9 Hz), 7.48 (1H, s), 7.43 (2H, d, J=8.0 Hz), 7.33 (1H, d, J=11.0 Hz), 7.25 (2H, d, J=8.0 Hz), 6.98 (2H, d, J=8.0 Hz), 6.85 (2H, d, J=8.0 Hz), 5.14 (2H, s), 5.01 (2H, s), 3.78 (3H, s), 3.73 (3H, s), 3.58 (2H, d, J=5.9 Hz), 2.83-2.76 (2H, m), 2.20 (2H, s), 1.58-1.52 (2H, m), 1.21-1.15 (2H, m).

Step (3): Compound X-24+Compound 117c→Compound 117d→Compound I-117

Compound X-24 (886 mg, 1.0 mmol) and compound 117c (521 mg, 1.0 mmol) were used to synthesize the target compound in the same way as in Step (4). of Example 107.
Yielded amount: 202.3 mg, (22%)
$^1$H-NMR (D$_2$O) δ: 7.17 (1H, d, J=11.0 Hz), 7.13 (1H, s), 7.00 (1H, s), 5.79 (1H, d, J=4.0 Hz), 5.41 (1H, d, J=4.0 Hz), 4.89 (1H, d, J=14.7 Hz), 4.25 (1H, d, J=14.2 Hz), 4.05 (1H, q, J=7.2 Hz), 3.69-3.56 (6H, m), 3.40 (1H, d, J=8.4 Hz), 3.31 (1H, d, J=8.4 Hz), 2.25-2.17 (2H, m), 1.99-1.93 (2H, m), 1.55 (3H, d, J=7.2 Hz), 1.52 (3H, s), 1.50 (3H, s).

Elem. Anal.: C32H35FN7O10S2Na (H2O) 6.7 (NaHCO3) 0.1
Calcd.: C, 42.23; H, 5.36; F, 2.08; N, 10.74; S, 7.02; Na, 2.77(%).
Found: C, 42.17; H, 5.21; F, 2.02; N, 10.91; S, 7.06; Na, 2.77(%).

Example 118 Synthesis of Compound I-118

[Chemical Formula 259]

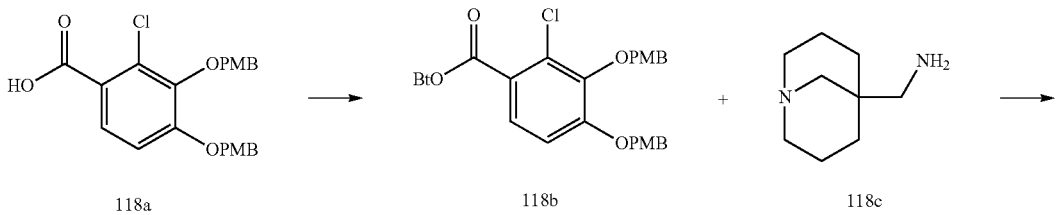

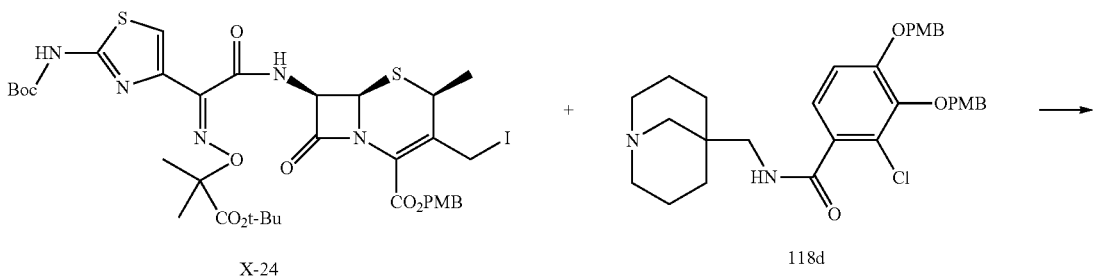

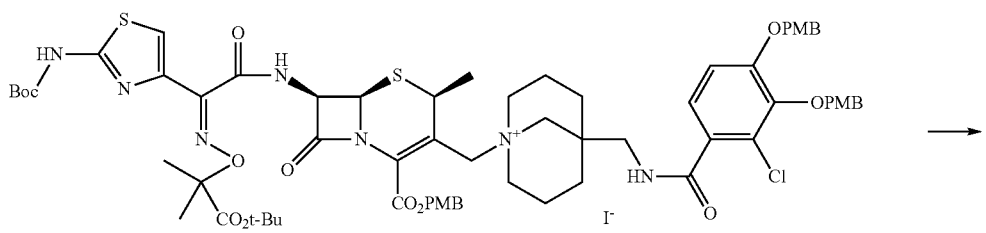

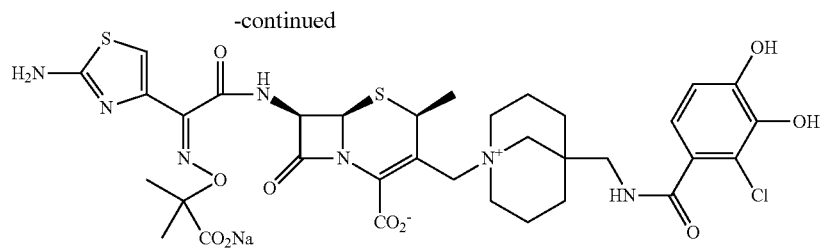

I-118

Step (1): Compound 118a→Compound 118b+Compound 118c→Compound 118d

Compound 118a was used to synthesize compound 118b in the same way as in Step (1). Of Example 117.

Compound 118a (1.67 g, 3.1 mmol) and compound 118b (472 mg, 3.1 mmol) were used to synthesize compound 118c in the same way as in Step (2) of Example 117.

Yielded amount: 1.36 g, (79%)

$^1$H-NMR (DMSO-D$_6$) δ: 8.23 (1H, t, J=6.2 Hz), 7.43 (2H, d, J=8.5 Hz), 7.33 (2H, d, J=8.5 Hz), 7.18 (1H, d, J=8.5 Hz), 7.12 (1H, d, J=8.5 Hz), 6.97 (2H, d, J=8.5 Hz), 6.88 (2H, d, J=8.5 Hz), 5.15 (2H, s), 4.88 (2H, s), 3.77 (3H, s), 3.75 (3H, s), 2.97-2.84 (6H, m), 2.60 (2H, s), 2.03-1.90 (2H, m), 1.68-1.53 (4H, m), 1.46-1.39 (2H, m).

Step (2): Compound X-24+Compound 118d→Compound 118e→Compound I-118

Compound X-24 (886 mg, 1.0 mmol) and compound 118d (565 mg, 1.0 mmol) were used to synthesize the target compound in the same way as in Step (4) of Example 107.

Yielded amount: 579.6 mg, (61%)

$^1$H-NMR (D$_2$O) δ: 6.96 (1H, d, J=8.3 Hz), 6.94 (1H, s), 6.90 (1H, d, J=8.3 Hz), 5.80 (1H, d, J=4.8 Hz), 5.43 (1H, d, J=4.8 Hz), 4.13 (1H, d, J=14.1 Hz), 3.98 (1H, q, J=7.2 Hz), 3.76-3.71 (1H, m), 3.50-3.13 (7H, m), 2.56-2.44 (2H, m), 2.02-1.95 (2H, m), 1.88-1.69 (4H, m), 1.55 (3H, d, J=7.2 Hz), 1.50 (3H, s), 1.48 (3H, s).

Elem. Anal.: C34H39ClN7O10S2Na (H2O) 6.4

Calcd.: C, 43.28; H, 5.53; Cl, 3.76; N, 10.39; S, 6.80; Na, 2.44(%).

Found: C, 43.17; H, 5.41; Cl, 3.69; N, 10.57; S, 6.85; Na, 2.47(%).

Example 119: Synthesis of Compound I-119

[Chemical Formula 260]

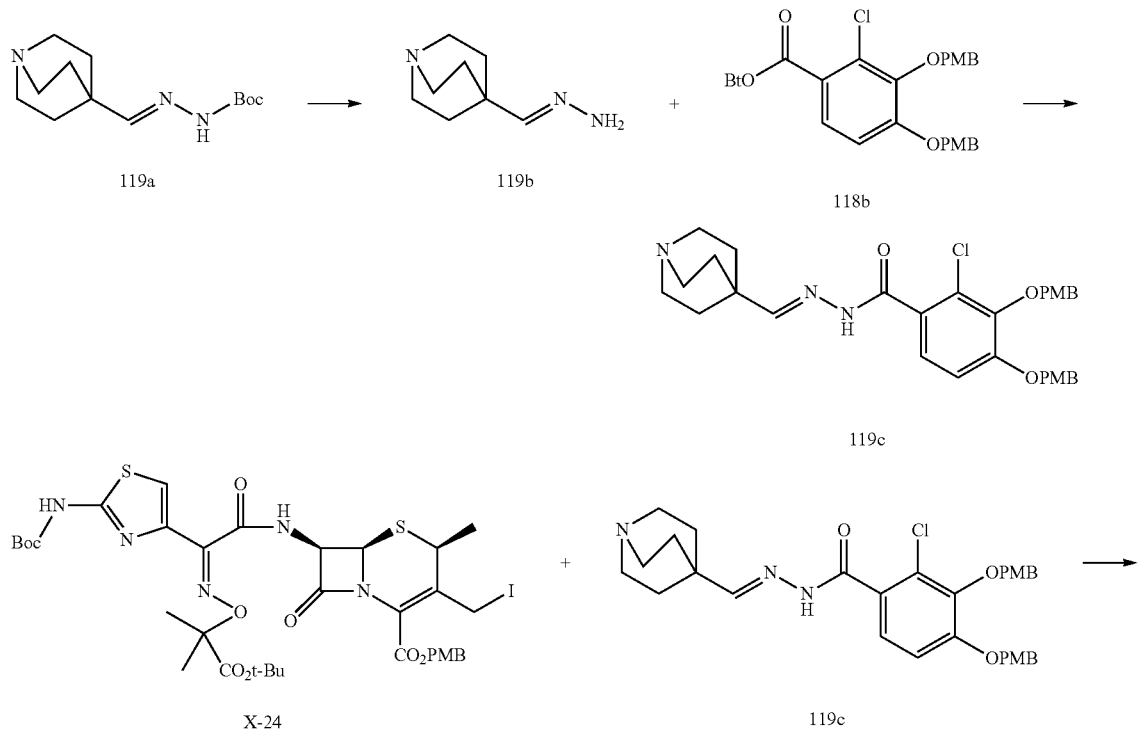

-continued

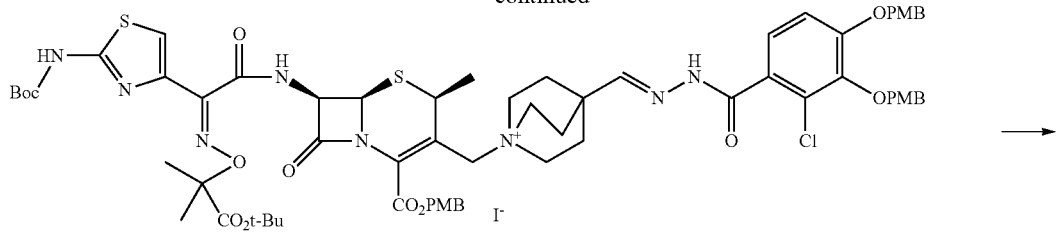

119d

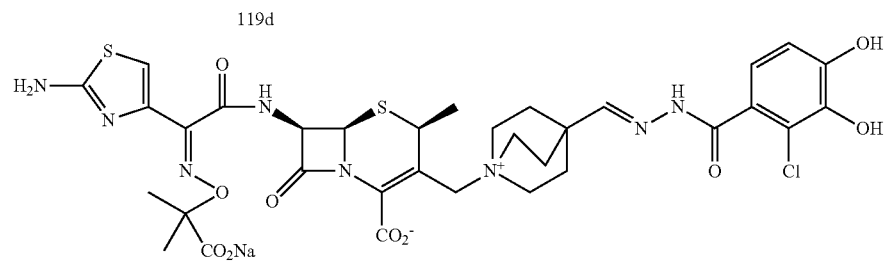

I-119

Step (1): Compound 119a→Compound 119b

Compound 119a (2.53 g, 10.0 mmol) was dissolved into methanol (12.5 mL), and thereto was then added 4 mol/L dioxane solution of hydrochloric acid (12.5 ml, 50 mmol) at 0° C. The mixture was stirred at rt for 4 hours, then the reaction mixture was evaporated. The precipitated solid was then collected by filtration, and washed with ethyl acetate/methanol (1/1) and ethyl acetate. The precipitated solid was suspended into methanol (25 mL), and thereto was then added sodium hydroxide (1.20 g, 30 mmol). The mixture was stirred at rt for 30 minutes, then a piece of dry ice was added thereto. The mixture was filtered, then the filtrate was concentrated under reduced pressure to yield compound 119b (2.67 g, 174%). The mixture was used in the next reaction without further purification.
MS (m+1)=154

Step (2): Compound 119b+Compound 118b→Compound 119c

Compound 118a (1.09 g, 2.0 mmol) and compound 119b (538 mg, 2.0 mmol) were used to synthesize compound 119c in the same way as in Step (2) of Example 117.

Yielded amount: 0.47 g, (42%)
MS (m+1)=564

Step (3): Compound X-24+Compound 119c→Compound 119d→Compound I-119

Compound X-24 (722 mg, 0.82 mmol) and compound 119c (460 mg, 0.82 mmol) were used to synthesize the target compound in the same way as in Step (4) of Example 107.
Yielded amount: 13 mg, (1.7%)
$^1$H-NMR (D$_2$O) δ: 7.58 (1H, s), 7.01 (1H, s), 6.75 (3H, s), 5.85 (1H, s), 5.46 (1H, d, J=5.3 Hz), 4.14-4.10 (4H, m), 3.62-3.55 (8H, m), 2.18 (6H, br s), 1.60-1.51 (9H, m).
MS (m+1)=783

Example 120: Synthesis of Compound I-130

[Chemical Formula 261]

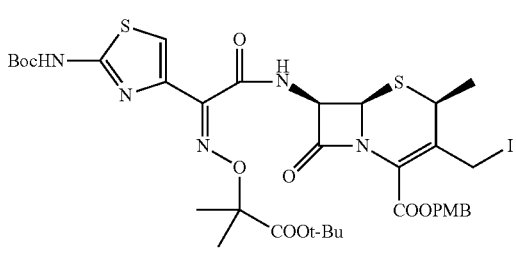

X-24

+

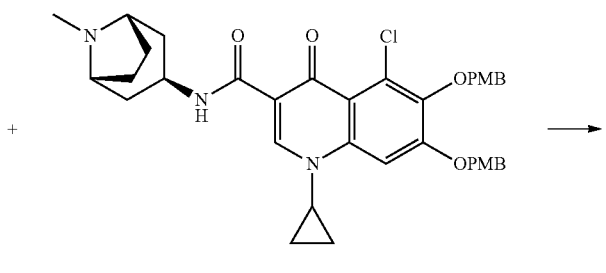

120a

-continued

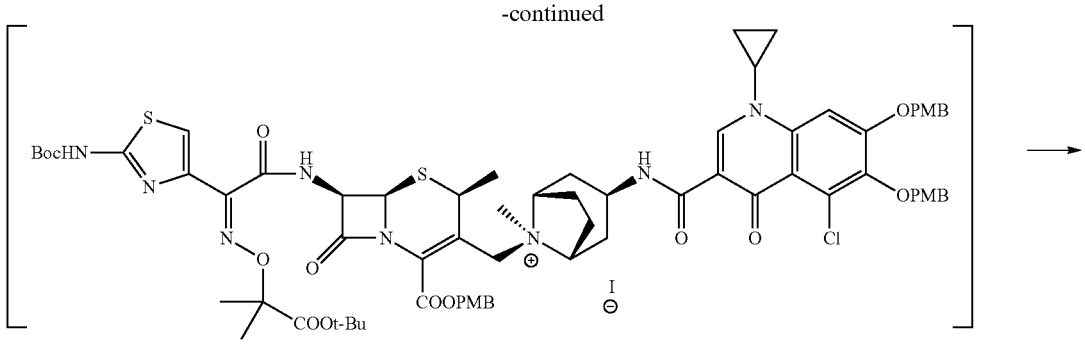

120b

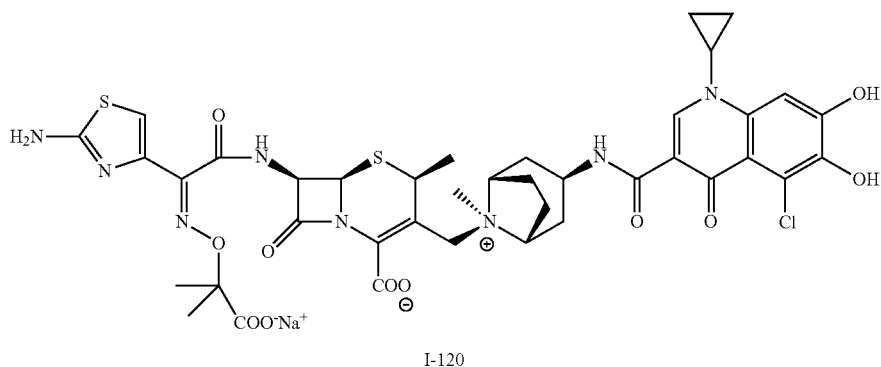

I-120

Step (1): Compound X-24+Compound 120a→Compound 120b→Compound I-120

A solution of Compound 120a (658 mg, 1.0 mmol) in dimethylformamide (2.0 mL) was cooled with ice. The reaction vessel was then degassed under reduced pressure, and thereto was added Compound X-24 (886 mg, 1.0 mmol). After stirring at 0° C. for 6 hours, the reaction mixture was slowly added to 5% aqueous sodium chloride and sodium hydrogen sulfite solution it was cooled with ice. The precipitated solid was collected by filtration, washed with water, and suspended into water. The suspension was freeze-dried to yield Compound 120b as a brown solid. Compound 120b yielded was used as it was, without being purified, in the next reaction.

The total amount of compound 120b yielded was dissolved in dichloromethane (10 mL), and the solution was cooled to −40° C. Thereto was then added anisole (1.09 mL, 10 mmol) and a 2 mol/L aluminum chloride solution (5.0 mL, 10 mmol) in nitromethane in turn. The liquid was stirred at 0° C. for 30 minutes. To the reaction liquid was added diisopropyl ether and a small amount of water, and the resultant was stirred to generate a precipitate. The supernatant was removed by decantation. To the insoluble matter adhering to the vessel were added a diluted aqueous hydrochloric acid solution, and acetonitrile. The resultant was stirred to dissolve the matter completely. Thereto was then added diisopropyl ether, and the water phase was separated to be collected. The organic phase was again subjected to extraction with water, and then all of the resultant water phases were combined with each other. Thereto was added HP20-SS resin. Acetonitrile was then distilled off therefrom under reduced pressure. The resultant mixed liquid was purified by ODS column chromatography. The desired-compound-containing fraction was added 0.2 mol/L sodium hydroxide aqueous solution until it gave a pH of 6.0, and thereto was added a piece of dry ice. The resultant solution was concentrated under reduced pressure, and then freeze-dried to yield compound I-120 as a yellow powder.

Yielded amount: 534 mg (58%)

$^1$H-NMR (D$_2$O) δ: 1.06 (2H, s), 1.29 (2H, d, J=6.65 Hz), 1.51 (3H, s), 1.53 (3H, s), 1.59 (3H, d, J=6.78 Hz), 2.06 (2H, t, J=13.55 Hz), 2.44-2.83 (5H, m), 3.13 (3H, s), 3.44 (1H, s), 4.01-4.22 (5H, m), 5.47 (1H, d, J=4.77 Hz), 5.83 (1H, d, J=4.77 Hz), 7.00 (1H, s), 7.23 (1H, s), 8.34 (1H, s).

Elem. Anal.: $C_{39}H_{42}ClN_8O_{11}S_2Na \cdot 7.0H_2O \cdot 0.1$ NaHCO$_3$

Calcd.: C, 44.48; H, 5.36; Cl, 3.36; N, 10.61; S, 6.07; Na, 2.40(%).

Found: C, 44.18; H, 5.34; Cl, 3.27; N, 10.91; S, 6.27; Na, 2.43(%).

MS (m+1)=899.38

Example 121: Synthesis of Compound I-121
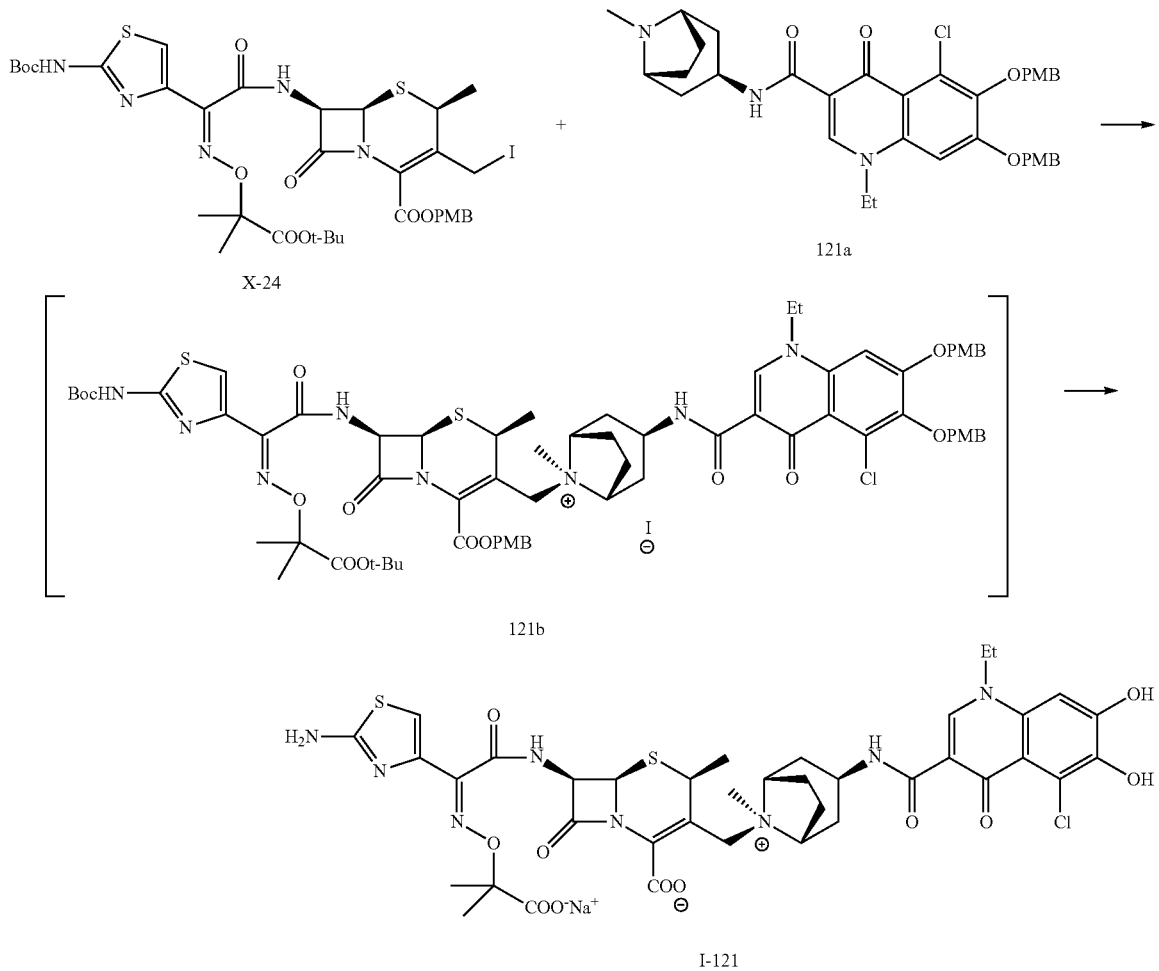
Step (1): Compound X-24+Compound 121a→Compound 121b→Compound I-121
From Compound X-24 (886 mg, 1.0 mmol) and Compound 121a (646 mg, 1.0 mmol), Compound I-121 was obtained as a yellow powder using the same method as Example 120.
Yielded amount: 127 mg, (14%)
$^1$H-NMR (D$_2$O) δ: 1.41 (3H, t, J=6.90 Hz), 1.51 (3H, s), 1.53 (3H, s), 1.59 (3H, d, J=6.90 Hz), 2.07-2.14 (2H, m), 2.45-2.87 (6H, m), 3.13 (3H, s), 4.00-4.29 (8H, m), 5.47 (1H, d, J=4.77 Hz), 5.83 (1H, d, J=4.77 Hz), 6.79 (1H, s), 7.01 (1H, s), 8.44 (1H, s).
MS (m+1)=887.32
Example 122: Synthesis of Compound I-122
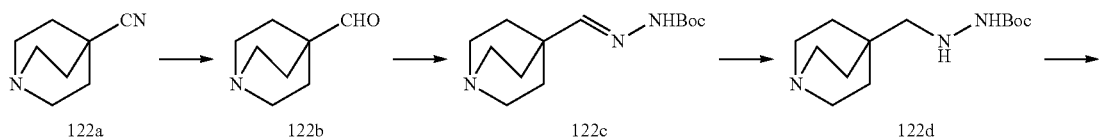

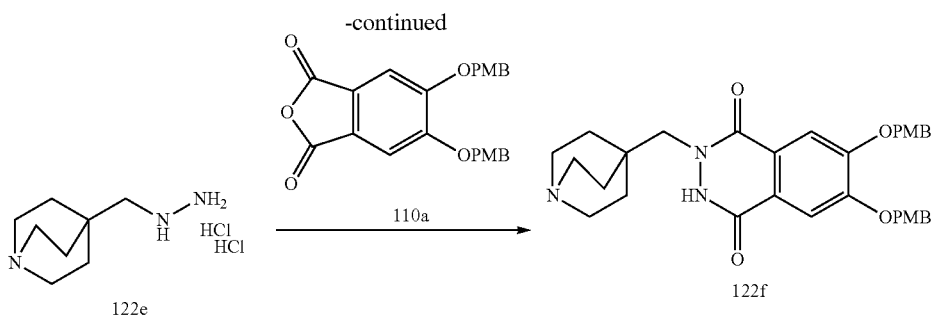

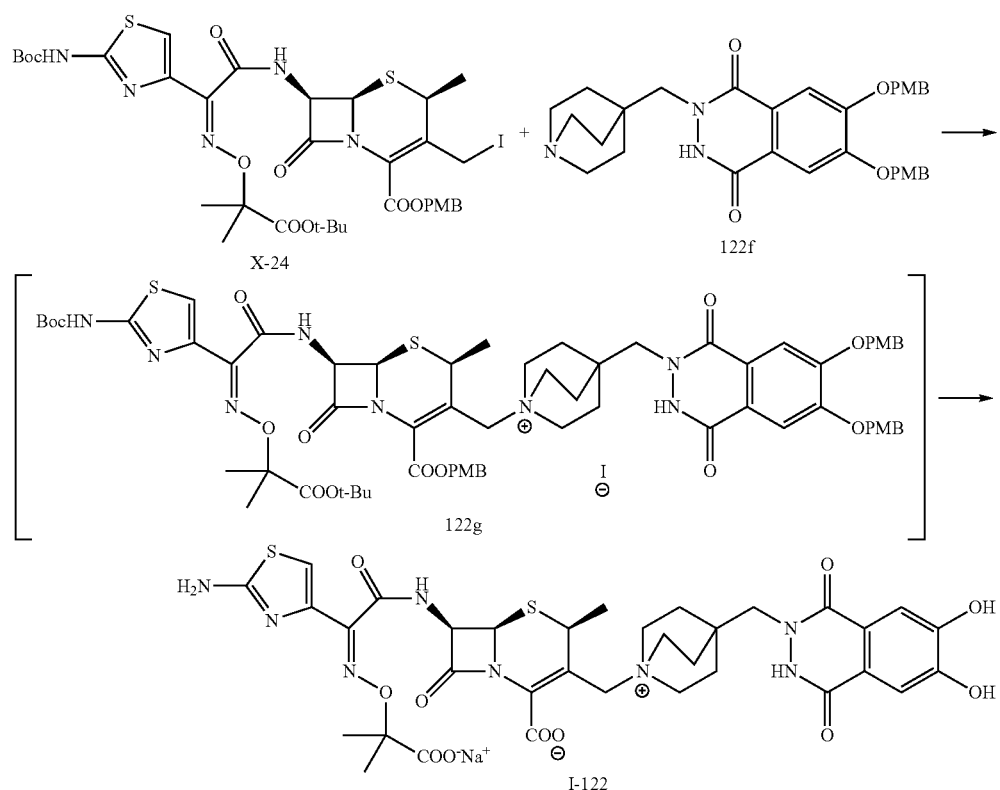

Step (1): Compound 122a→Compound 122b→Compound 122c

A solution of Compound 122a (22.84 g, 168 mmol) in toluene (114 mL) was cooled to −78° C., and thereto was added dropwise 1 mol/L DIBAL solution (335 mL, 335 mmol) in toluene for 50 minutes. After stirring at −78° C. for 50 minutes, the reaction mixture was warmed to 0° C., and thereto was added dropwise water (13.4 mL), 15% sodium hydroxide aqueous solution (13.4 mL), and water (33.5 mL) at 0° C. After stirring at room temperature for 10 minutes thereto was added methanol (114 mL), and tert-butyl hydrazinecarboxylate (26.6 g, 201 mmol). After stirring at room temperature for overnight, the insoluble substance was removed by filtration, and then concentrated. The residue was dissolved ethyl acetate and added saturated citric acid aqueous solution until it gave a pH of 4.0. The water phase was separated and added 8 mol/L sodium hydroxide aqueous solution until it gave a pH of 12.0, followed by extraction with chloroform twice time. The combined organic layer was dried with anhydrous sodium sulfate. The inorganic substance was removed by filtration, and then concentrated under reduced pressure. Thereto was added diisopropyl ether to precipitate a solid. The solid was collected by filtration, so as to yield compound 122c as a white solid.

Yielded amount: 28.7 g (68%)

$^1$H-NMR (CDCl$_3$) δ: 1.49 (9H, s), 1.60 (6H, t, J=7.72 Hz), 2.91 (6H, t, J=7.72 Hz), 6.92 (1H, s), 7.56 (1H, s).

Step (2): Compound 122c→Compound 122d→Compound 122e

A solution of Compound 122c (28.7 g, 113 mmol) in methanol (144 mL) was cooled with ice, and thereto was added sodium cyanoborohydride (14.24 g, 227 mmol), and then added 2 mol/L hydrochloric acid aqueous solution until it gave a pH of 4.0. After stirring at room temperature for 1.5 hours, and thereto was added 8 mol/L sodium hydroxide aqueous solution until it gave a pH of 12.0 at 0° C., and then concentrated, followed by extraction with ethyl acetate twice time. The combined organic layer was washed with saturated brine, and then was dried with anhydrous sodium sulfate. The inorganic substance was removed by filtration, and then concentrated and subsequently drying under reduced pressure to yield Compound 122d as a orange oil. Compound 122d yielded was used as it was, without being purified, in the next reaction.

The total amount of compound 122d yielded was dissolved in methanol (144 mL), and the solution was cooled with ice. Thereto was added slowly 4 mol/L hydrochloric acid solution (141 mL, 565 mmol) in 1,4-dioxane. After stirring at room temperature for overnight, and the reaction mixture was concentrated under reduced pressure. Thereto was added 50% methanol/ethyl acetate solution to precipitate a solid. The solid was collected by filtration, so as to yield compound 122e as a white solid.

Yielded amount: 24.6 g (95%)
$^1$H-NMR (D$_2$O) δ: 1.90 (6H, t, J=7.97 Hz), 2.99 (2H, s), 3.39 (6H, t, J=7.97 Hz).

Step (3): Compound 122e+Compound 110a→Compound 122f

A suspension of Compound 122e (17.6 g, 77 mmol) in 1,4-dioxane (144 mL) was added sodium acetate (31.6 g, 385 mmol) and Compound 110a (38.8 g, 92 mmol). After stirring at room temperature for 1 hour, thereto was added acetic acid (22.02 ml, 385 mmol). After stirring at room temperature for overnight, thereto was stirred at 70° C. for 1.5 hours. Then thereto was added 2 mol/L sodium hydroxide aqueous solution until it gave a pH of 12.0 at 0° C., followed by extraction with ethyl acetate twice time. The combined organic layer was washed with saturated brine, and then was dried with anhydrous sodium sulfate. The inorganic substance was removed by filtration, and then concentrated under reduced pressure. Thereto was added 5% triethylamine and methanol solution in ethyl acetate to precipitate a solid. The solid was collected by filtration, so as to yield compound 122f as a white solid.

Yielded amount: 30.96 g (72%)
$^1$H-NMR (DMSO-D$_6$) δ: 1.40 (6H, t, J=7.47 Hz), 2.64 (6H, t, J=7.47 Hz), 3.59 (2H, s), 3.75 (6H, s), 5.11 (2H, s), 5.12 (2H, s), 6.94 (4H, d, J=8.28 Hz), 7.38 (4H, d, J=8.28 Hz), 7.52 (2H, s).

Step (4): Compound X-24+Compound 122f→Compound 122g→Compound I-122

From Compound X-24 (10.0 g, 11.3 mmol) and Compound 122f (6.31 g, 11.3 mmol), Compound I-122 was obtained as a white powder using the same method as Example 120.

Yielded amount: 3.68 g, (40%)
$^1$H-NMR (D$_2$O) δ: 1.50 (3H, s), 1.51 (3H, s), 1.53 (3H, d, J=7.53 Hz), 2.00 (6H, t, J=7.22 Hz), 3.38-3.55 (6H, m), 3.97-4.06 (4H, m), 4.61 (1H, d, J=14.43 Hz), 5.42 (1H, d, J=4.77 Hz), 5.83 (1H, d, J=4.77 Hz), 6.97 (1H, s), 7.24 (1H, s), 7.39 (1H, s).

Elem. Anal.: $C_{33}H_{37}N_8O_{11}S_2Na_{1.2}$·5.9H$_2$O
Calcd.: C, 43.83; H, 5.28; N, 12.03; S, 6.88; Na, 2.96(%).
Found: C, 43.74; H, 5.35; N, 12.27; S, 7.03; Na, 2.86(%).
MS (m+1)=799.23

Example 123: Synthesis of Compound (I-123)

[Chemical Formula 265]

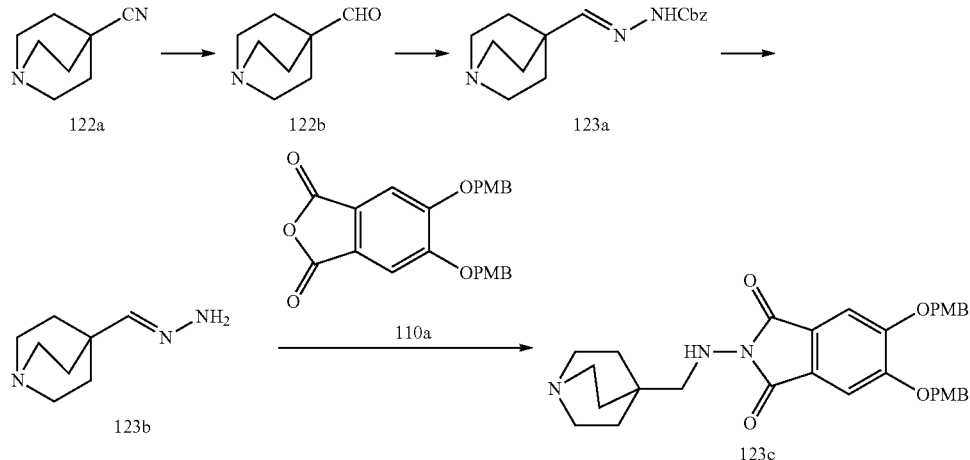

[Chemical Formula 266]

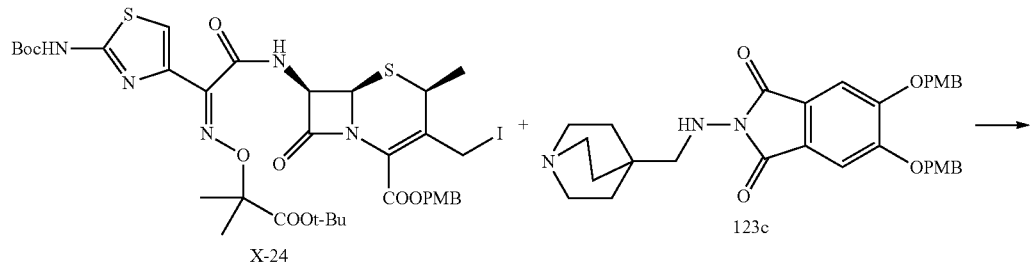

-continued

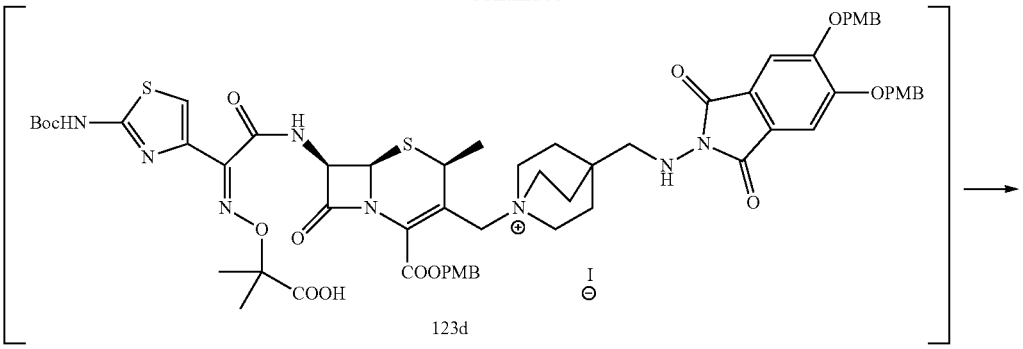

123d

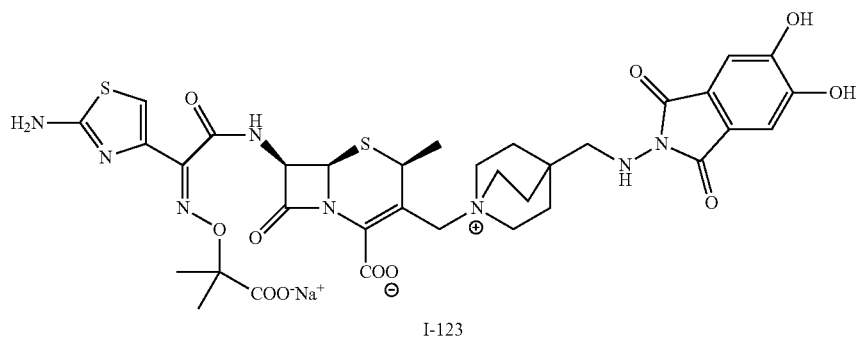

I-123

Step (1): Compound 122a→Compound 122b→Compound 123a

From Compound 122a (10.0 g, 73.4 mmol) and benzyl hydrazinecarboxylate (21.96 g, 132 mmol), Compound 123a was obtained as a white powder using the same method as in Step (1) of Example 122.

Yielded amount: 14.02 g, (66%)

$^1$H-NMR (DMSO-D$_6$) δ: 1.44 (6H, t, J=7.58 Hz), 2.74 (6H, t, J=7.58 Hz), 5.04 (2H, s), 7.09 (1H, s), 7.31-7.40 (6H, m).

Step (2): Compound 123a→Compound 123b

A solution of Compound 123a (11.49 g, 40 mmol) in methanol (180 mL) was added 5% palladium on carbon (3.6 g, 1.7 mmol). After stirring under hydrogen (1 atm) at room temperature for 2 hours, the insoluble substance was removed by filtration. Thereto was concentrated and subsequently drying under reduced pressure to yield Compound 123b as a white solid.

Yielded amount: 5.97 g, (97%)

$^1$H-NMR (DMSO-D$_6$) δ: 1.40 (6H, t, J=7.65 Hz), 2.73 (6H, t, J=7.65 Hz), 5.88 (2H, s), 6.76 (1H, s).

Step (3): Compound 123b+Compound 110a→Compound 123c

A suspension of Compound 123b (6.97 g, 45.5 mmol) in dimethylformamide (70 mL) was added Compound 110f (20.08 g, 47.8 mmol) at 0° C. After stirring at room temperature for 2 hours, thereto was added O-Benzotriazole-N,N,N',N'-tetramethyluronium hexafluorophosphate (20.70 g, 54.6 mmol) at 0° C. After stirring at room temperature for 4 hours, thereto was added acetic acid (26.0 ml, 455 mmol) and sodium cyanoborohydride (4.29 g, 68.2 mmol) at 0° C. After stirring at room temperature for overnight, thereto was added 2 mol/L sodium hydroxide aqueous solution, followed by extraction with ethyl acetate twice time. The combined organic layer was washed with water and saturated brine, and then was dried with anhydrous sodium sulfate. The inorganic substance was removed by filtration, and then concentrated under reduced pressure. Thereto was added diisopropyl ether to precipitate a solid. The solid was collected by filtration, so as to yield compound 123c as a yellow solid.

Yielded amount: 14.19 g, (56%)

$^1$H-NMR (DMSO-D$_6$) δ: 1.37 (6H, t, J=7.59 Hz), 2.65 (2H, d, J=6.02 Hz), 2.73 (6H, t, J=7.59 Hz), 3.75 (6H, s), 5.23 (4H, s), 6.95 (4H, d, J=8.66 Hz), 7.37 (4H, d, J=8.66 Hz), 7.46 (2H, s).

Step (4): Compound X-24+Compound 123c→Compound I-123

From Compound X-24 (11.52 g, 13 mmol) and Compound 123c (7.25 g, 13 mmol), Compound I-123 was obtained as a white powder using the same method as Example 120.

Yielded amount: 3.25 g, (30%)

$^1$H-NMR (D$_2$O) δ: 1.51 (3H, s), 1.52 (3H, s), 1.57 (3H, d, J=7.15 Hz), 1.97 (6H, t, J=7.65 Hz), 2.98 (2H, s), 3.41-3.58 (6H, m), 4.05-4.12 (2H, m), 4.63 (1H, d, J=14.81 Hz), 5.45 (1H, d, J=4.89 Hz), 5.85 (1H, d, J=4.89 Hz), 7.00 (1H, s), 7.19 (2H, s).

MS (m+1)=799.23

Example 124: Synthesis of Compound I-124

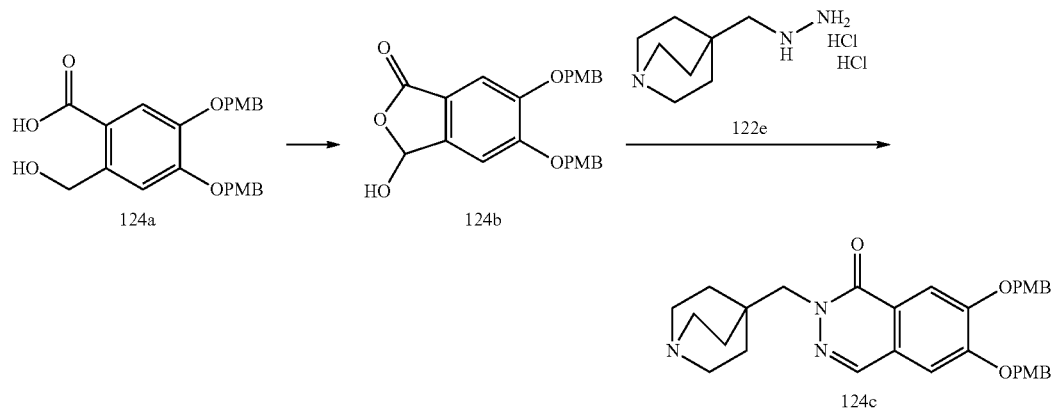

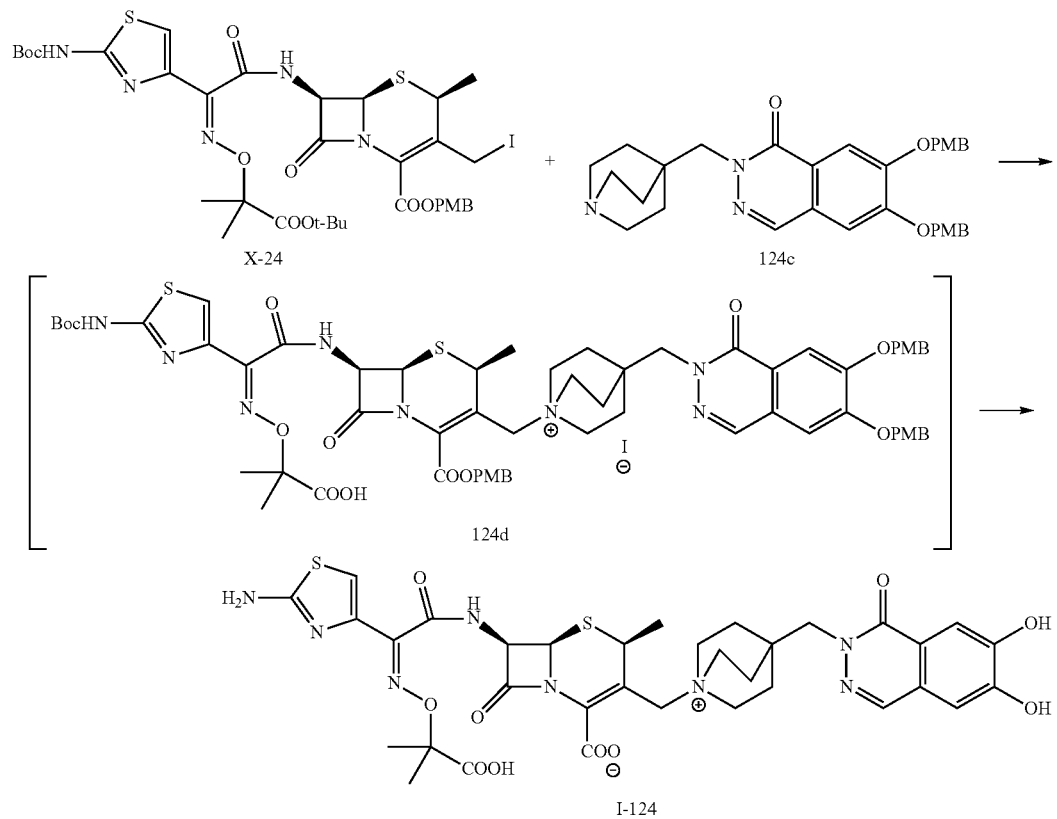

Step (1): Compound 124a→Compound 124b

A solution of Compound 124a (30.5 g, 72 mmol) in tetrahydrofuran (305 mL) was added manganese dioxide (62.5 g, 719 mmol). After stirring at room temperature for overnight, the insoluble substance was removed by filtration. And thereto was added 1 mol/L hydrochloric acid aqueous solution, followed by extraction with ethyl acetate twice time. The combined organic layer was washed with saturated brine, and then was dried with anhydrous magnesium sulfate. The inorganic substance was removed by filtration, and then concentrated under reduced pressure. Thereto was added diisopropyl ether to precipitate a solid. The solid was collected by filtration, so as to yield compound 124b as a brown solid.

Yielded amount: 22.76 g (75%)

$^1$H-NMR (DMSO-D$_6$) δ: 3.75 (3H, s), 3.76 (3H, s), 5.16 (2H, s), 5.17 (2H, s), 6.92-6.96 (4H, m), 7.35-7.40 (6H, m).

Step (2): Compound 124b+Compound 122e→Compound 5124cc

A solution of Compound 124b (30 g, 71 mmol) in dimethylformamide (300 mL) was added Compound 122e (19.44 g, 85 mmol) and sodium acetate (29.1 g, 355 mmol). After stirring at room temperature for 1 hour, thereto was added acetic acid (20.3 ml, 355 mmol). After stirring at room temperature for over night, thereto was added ice water and 2 mol/L sodium hydroxide aqueous solution until it gave a pH of 10.0 at 0° C. The precipitated solid was then collected by filtration and dissolved tetrahydrofuran. The resultant solution was dried with anhydrous sodium sulfate. The inorganic substance was removed by filtration, and then concentrated under reduced pressure. Thereto was added ethyl acetate to precipitate a solid. The solid was collected by filtration, so as to yield compound 124c as a white solid.

Yielded amount: 32.66 g (85%)

$^1$H-NMR (DMSO-D$_6$) δ: 1.42 (6H, t, J=7.59 Hz), 2.75 (6H, t, J=7.59 Hz), 3.75 (6H, s), 3.94 (2H, s), 5.20 (2H, s), 5.22 (2H, s), 6.94-6.97 (4H, m), 7.39 (2H, d, J=8.53 Hz), 7.42 (2H, d, J=8.53 Hz), 7.54 (1H, s), 7.71 (1H, s), 8.21 (1H, s).

Step (3): Compound X-24+Compound 124c→Compound I-124

From Compound X-24 (886 mg, 1.0 mmol) and Compound 124c (541 mg, 1.0 mmol), Compound I-124 was obtained as a yellow powder using the same method as Example 120.

Yielded amount: 440 mg, (55%)

$^1$H-NMR (D$_2$O) δ: 1.50 (3H, s), 1.52 (3H, s), 1.54 (3H, d, J=7.40 Hz), 1.98 (6H, s), 3.47 (6H, d, J=34.88 Hz), 4.02-4.13 (4H, m), 4.62 (1H, d, J=14.68 Hz), 5.42 (1H, d, J=4.77 Hz), 5.83 (1H, d, J=4.77 Hz), 6.97 (1H, s), 7.08 (1H, s), 7.41 (1H, s), 8.06 (1H, s).

Elem. Anal.: C$_{34}$H$_{37}$N$_8$O$_{10}$S$_2$Na.6.5H$_2$O.0.1NaHCO$_3$
Calcd.: C, 44.02; H, 5.43; N, 12.04; S, 6.89; Na, 2.72(%).
Found: C, 43.83; H, 5.45; N, 12.34; S, 6.81; Na, 2.70(%).
MS (m+1)=783.34

Example 125: Synthesis of Compound I-125

[Chemical Formula 269]

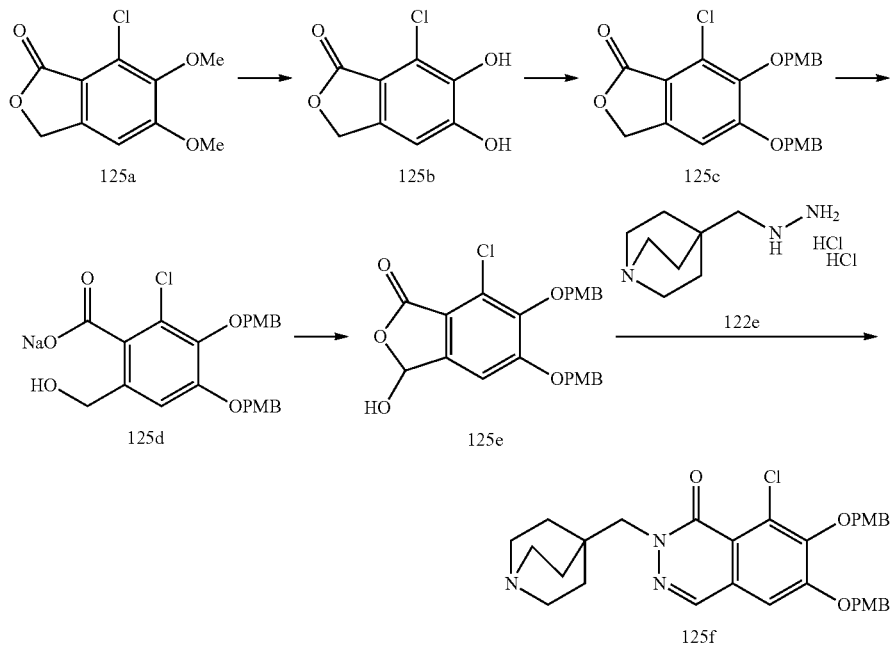

[Chemical Formula 270]

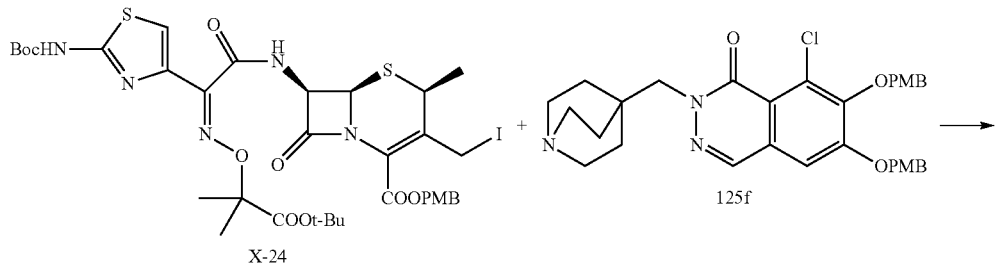

-continued

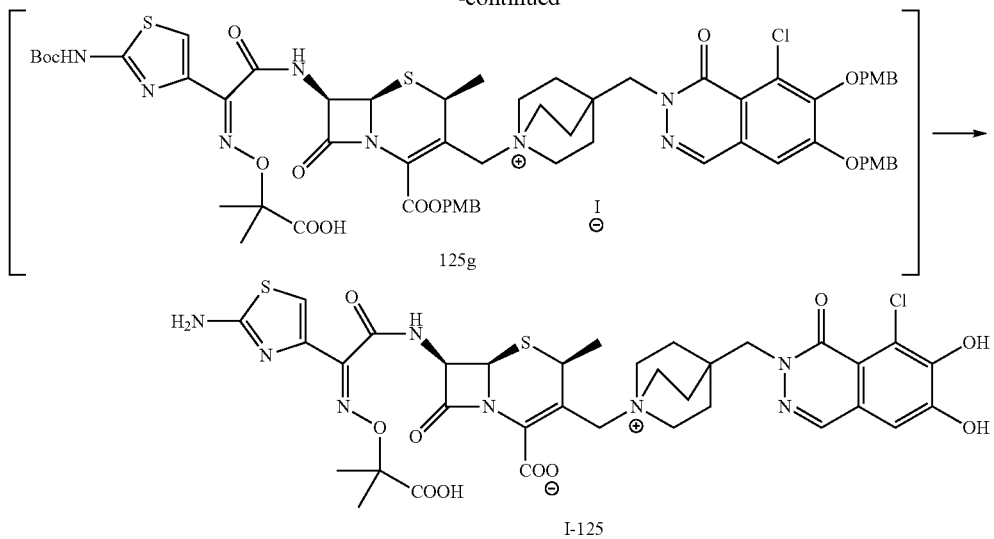

Step (1): Compound 125a→Compound 125b

A solution of Compound 125a (10.38 g, 45 mmol) in dichloromethane (100 mL) was cooled with ice, and thereto was added dropwise boron tribromide (10.3 mL, 109 mmol). After stirring at 0° C. for 1 hour, the reaction mixture was poured to ice, and thereto was concentrated. Then the precipitated solid was collected by filtration, so as to yield compound 125b as a brown solid.

Yielded amount: 8.89 g, (98%)

$^1$H-NMR (DMSO-$D_6$) δ: 5.14 (2H, s), 6.92 (1H, s).

Step (2): Compound 125b→Compound 125c

To a solution of compound 125b (9.89 g, 49 mmol) in dimethylformamide (100 mL) was added potassium carbonate (20.44 g, 148 mmol), 4-methoxybenzylchloride (16.12 mL, 118 mmol) and sodium iodide (7.39 g, 49 mmol). After stirring at 50° C. for 1 hour, the reaction mixture was poured to ice water. Then the precipitated solid was collected by filtration, so as to yield compound 125c as a brown solid.

Yielded amount: 20.18 g, (93%)

$^1$H-NMR (CDCl$_3$) δ: 3.80 (3H, s), 3.84 (3H, s), 4.99 (2H, s), 5.13 (2H, s), 5.15 (2H, s), 6.82 (2H, d, J=8.66 Hz), 6.90 (1H, s), 6.94 (2H, d, J=8.66 Hz), 7.32 (2H, d, J=8.66 Hz), 7.36 (2H, d, J=8.66 Hz).

Step (3): Compound 125c→Compound 125d

To a solution of compound 125c (17.35 g, 39 mmol) in methanol (17 mL) and tetrahydrofuran (17 mL) was added 2 mol/L sodium hydroxide (59 mL, 118 mmol) aqueous solution. After stirring at 70° C. for 1 hour, thereto was added ice water. Then the precipitated solid was collected by filtration, so as to yield compound 125d as a white solid.

Yielded amount: 18.60 g, (98%)

$^1$H-NMR (DMSO-$D_6$) δ: 3.75 (3H, s), 3.77 (3H, s), 4.33 (2H, s), 4.81 (2H, s), 5.06 (2H, s), 5.85 (1H, s), 6.87 (2H, d, J=8.66 Hz), 6.96 (2H, d, J=8.66 Hz), 7.05 (1H, s), 7.33 (2H, d, J=8.66 Hz), 7.41 (2H, d, J=8.66 Hz).

Step (4): Compound 125d→Compound 125e

A solution of Compound 125d (1.92 g, 4.0 mmol) in dichloromethane (15 mL) and methanol (4 mL) was added manganese dioxide (3.47 g, 40 mmol). After stirring at room temperature for 1 hour, thereto was concentrated and added ethyl acetate. The insoluble substance was removed by filtration. And thereto was added 1 mol/L hydrochloric acid aqueous solution, followed by extraction with ethyl acetate twice time. The combined organic layer was washed with saturated brine, and then was dried with anhydrous magnesium sulfate. The inorganic substance was removed by filtration, and then concentrated under reduced pressure. Thereto was added diisopropyl ether to precipitate a solid. The solid was collected by filtration, so as to yield compound 125e as a white solid.

Yielded amount: 1.25 g (69%)

$^1$H-NMR (CDCl$_3$) δ: 3.80 (3H, s), 3.84 (3H, s), 4.96 (2H, dd, J=13.87, 10.10 Hz), 5.14 (2H, dd, J=28.36, 11.04 Hz), 6.40 (1H, s), 6.81 (2H, d, J=8.53 Hz), 6.95 (2H, d, J=8.53 Hz), 7.06 (1H, s), 7.28 (2H, d, J=8.53 Hz), 7.38 (2H, d, J=8.53 Hz).

Step (5): Compound 125e+Compound 122e→Compound 125f

A solution of Compound 125e (949 mg, 2.08 mmol) in dimethylacetamide (9.5 mL) was added Compound 122e (521 mg, 2.29 mmol) and sodium acetate (852 mg, 10.4 mmol). After stirring at room temperature for 1 hour, thereto was added acetic acid (0.594 ml, 10.4 mmol). After stirring at 70° C. for over night, thereto was added ice water and 2 mol/L sodium hydroxide aqueous solution until it gave a pH of 10.0 at 0° C. The precipitated solid was then collected by filtration and dissolved tetrahydrofuran. The resultant solution was dried with anhydrous sodium sulfate. The inorganic substance was removed by filtration, and then concentrated under reduced pressure. Thereto was added ethyl acetate to precipitate a solid. The resulting crude product was purified by silica gel column chromatography (triethylamine/methanol/ethyl acetate), so as to yield compound 125f as a yellow solid.

Yielded amount: 435 mg (36%)

$^1$H-NMR (DMSO-$D_6$) δ: 1.46 (6H, t, J=7.53 Hz), 2.80 (6H, t, J=7.53 Hz), 3.74 (4H, s), 3.79 (3H, s), 3.92 (2H, s), 4.97 (2H, s), 5.27 (2H, s), 6.85 (2H, d, J=8.66 Hz), 7.01 (2H, d, J=8.66 Hz), 7.29 (2H, d, J=8.66 Hz), 7.50 (2H, d, J=8.66 Hz), 7.67 (1H, s), 8.24 (1H, s).

Step (6): Compound X-24+Compound 125f→Compound I-125

From Compound X-24 (668 mg, 0.755 mmol) and Compound 125f (435 mg, 0.755 mmol), Compound I-125 was obtained as a yellow powder using the same method as Example 120.

Yielded amount: 196 mg, (31%)

$^1$H-NMR (D$_2$O) δ: 1.50 (3H, s), 1.52 (3H, s), 1.54 (3H, d, J=7.15 Hz), 1.99 (6H, t, J=7.47 Hz), 3.39-3.55 (6H, m), 4.02-4.09 (4H, m), 4.61 (1H, d, J=14.31 Hz), 5.43 (1H, d, J=4.89 Hz), 5.83 (1H, d, J=4.89 Hz), 6.92 (1H, s), 6.98 (1H, s), 7.94 (1H, s).

Elem. Anal.: $C_{34}H_{36}ClN_8O_{10}S_2Na_{1.4}\cdot 7.2H_2O$

Calcd.: C, 41.75; H, 5.19; Cl, 3.62; N, 11.46; S, 6.56; Na, 3.29(%).

Found: C, 41.71; H, 5.15; Cl, 3.46; N, 11.73; S, 6.57; Na, 3.34(%).

MS (m+1)=817.42

Example 126: Synthesis of Compound I-126

[Chemical Formula 271]

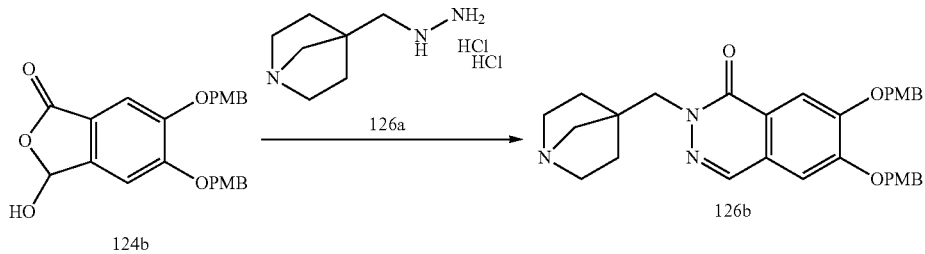

[Chemical Formula 272]

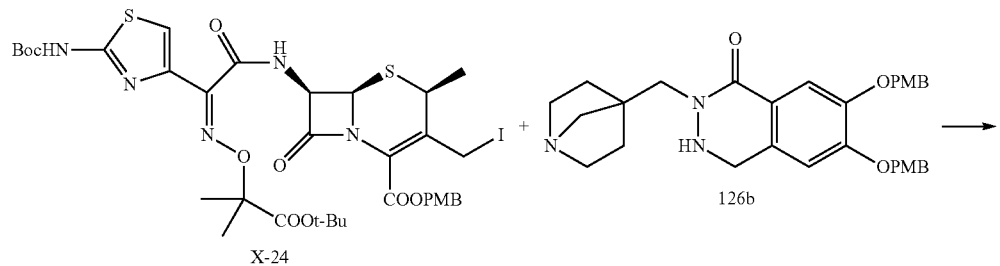

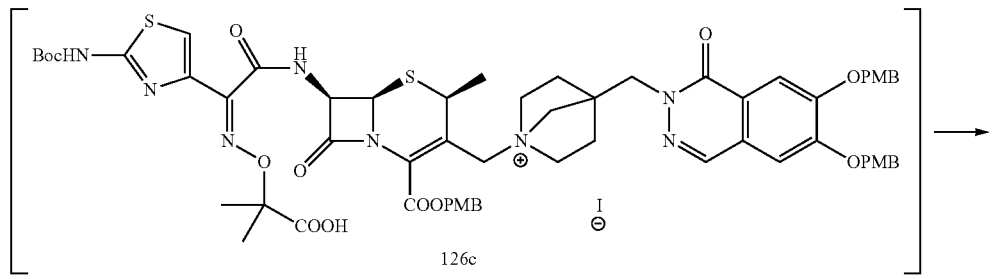

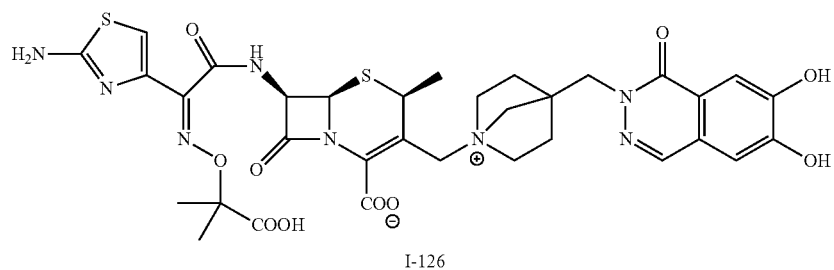

I-126

387

Step (1): Compound 124b+Compound 126a→Compound 126b

From Compound 124b (20.65 g, 49 mmol) and Compound 126a (14.65 g, 68 mmol), Compound 126b was obtained as a white powder using the same method as in Step (2) of Example 124.

[Chemical Formula 273]

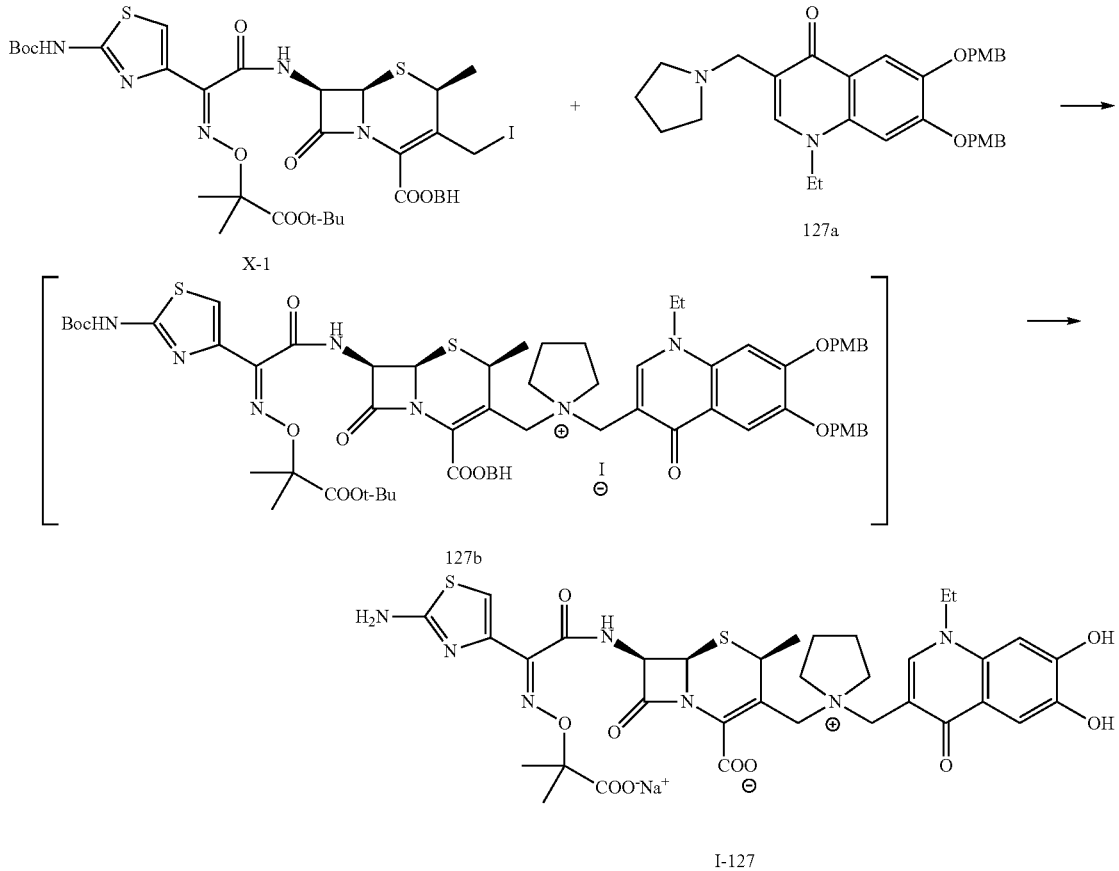

Yielded amount: 19.57 g, (76%)

$^1$H-NMR (DMSO-D$_6$) δ: 1.14-1.19 (2H, m), 1.48-1.54 (2H, m), 2.19 (2H, s), 2.39-2.45 (2H, m), 2.66-2.72 (2H, m), 3.75 (6H, s), 4.45 (2H, s), 5.20 (2H, s), 5.23 (2H, s), 6.94-6.97 (4H, m), 7.38-7.43 (4H, m), 7.55 (1H, s), 7.72 (1H, s), 8.24 (1H, s).

Step (2): Compound X-24+Compound 126b→Compound I-126

From Compound X-24 (886 mg, 1.0 mmol) and Compound 126b (528 mg, 1.0 mmol), Compound I-126 was obtained as a yellow powder using the same method as Example 120.

Yielded amount: 457 mg, (58%)

$^1$H-NMR (D$_2$O) δ: 1.49 (3H, s), 1.51 (3H, s), 1.53 (3H, d, J=7.15 Hz), 2.00 (2H, s), 2.19 (2H, s), 3.37-3.66 (6H, m), 4.04 (1H, q, J=7.15 Hz), 4.23 (1H, d, J=14.43 Hz), 4.48 (2H, dd, J=18.51, 14.62 Hz), 4.87 (1H, d, J=14.43 Hz), 5.34 (1H, d, J=4.89 Hz), 5.74 (1H, d, J=4.89 Hz), 6.96 (1H, s), 7.10 (1H, s), 7.43 (1H, s), 8.13 (1H, s).

388

Elem. Anal.: C$_{33}$H$_{35}$N$_8$O$_{10}$S$_2$Na.5.2H$_2$O
Calcd.: C, 44.81; H, 5.17; N, 12.67; S, 7.25; Na, 2.60(%).
Found: C, 44.77; H, 5.16; N, 12.77; S, 7.52; Na, 2.81(%).
MS (m+1)=769.48

Example 127: Synthesis of Compound I-127

Step (1): Compound X-1+Compound 127a→Compound I-127

From Compound X-1 (932 mg, 1.0 mmol) and Compound 127a (528 mg, 1.0 mmol), Compound I-127 was obtained as a yellow powder using the same method as Example 120.

Yielded amount: 161 mg, (20%)

$^1$H-NMR (D$_2$O) δ: 1.46 (3H, t, J=7.22 Hz), 1.49 (3H, s), 1.52-1.53 (6H, m), 2.22-2.25 (4H, m), 3.36-3.39 (3H, m), 3.59-3.61 (1H, m), 4.12 (1H, q, J=6.90 Hz), 4.22-4.32 (3H, m), 4.44 (2H, s), 4.90 (1H, d, J=13.93 Hz), 5.48 (1H, d, J=4.89 Hz), 5.83 (1H, d, J=4.89 Hz), 6.98 (1H, s), 7.07 (1H, s), 7.53 (1H, s), 8.20 (1H, s).

Elem. Anal.: C$_{34}$H$_{38}$N$_7$O$_{10}$S$_2$Na.8.1H$_2$O
Calcd.: C, 43.55; H, 5.83; N, 10.46; S, 6.84; Na, 2.45(%).
Found: C, 43.54; H, 5.85; N, 10.72; S, 6.58; Na, 2.48(%).
MS (m+1)=770.35

Example 128: Synthesis of Compound I-128

[Chemical Formula 274]

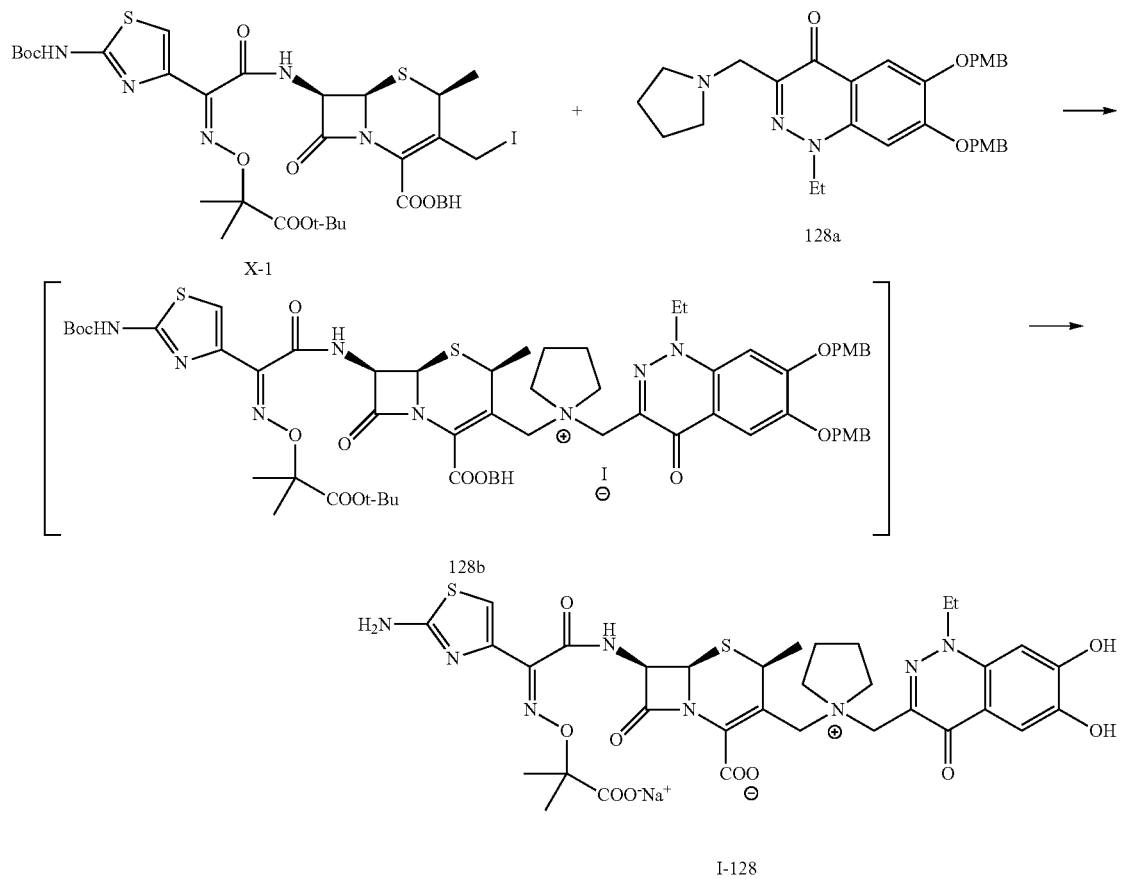

Step (1): Compound X-1+Compound 128a→Compound I-128

From Compound X-1 (932 mg, 1.0 mmol) and Compound 128a (530 mg, 1.0 mmol), Compound I-128 was obtained as a yellow powder using the same method as Example 120.
Yielded amount: 331 mg, (42%)
$^1$H-NMR (D$_2$O) δ: 1.48-1.54 (12H, m), 2.25 (4H, s), 3.42-3.48 (2H, m), 3.53-3.57 (1H, m), 3.74-3.76 (1H, m), 4.13 (1H, q, J=6.99 Hz), 4.40 (1H, d, J=14.43 Hz), 4.50 (2H, q, J=7.15 Hz), 4.60 (2H, s), 5.01 (1H, d, J=14.43 Hz), 5.48 (1H, d, J=4.77 Hz), 5.81 (1H, d, J=4.77 Hz), 6.99 (1H, s), 7.00 (1H, s), 7.33 (1H, s).
MS (m+1)=771.35

Example 129: Synthesis of Compound I-129

[Chemical Formula 275]

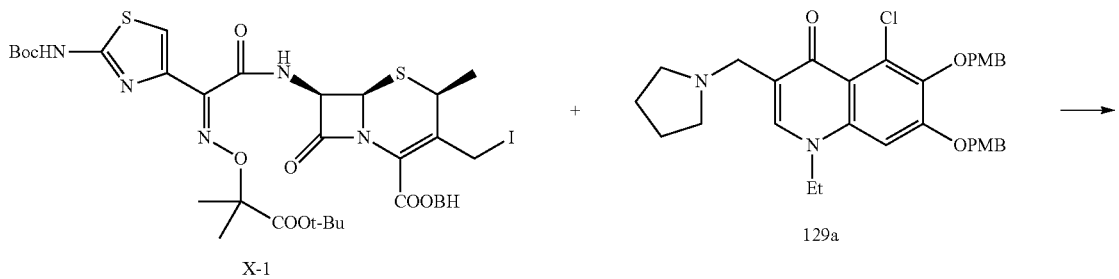

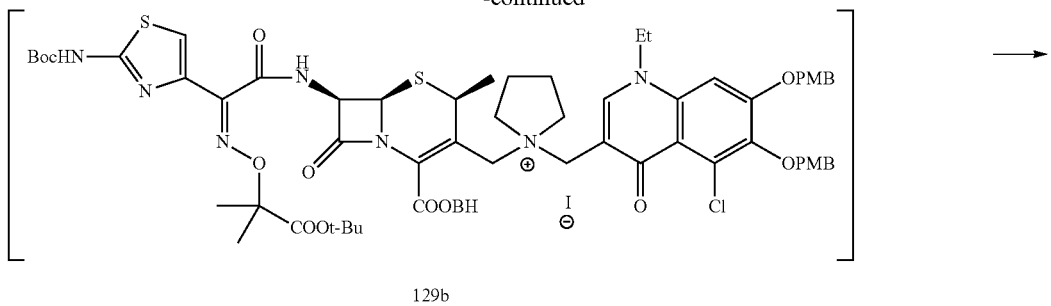

129b

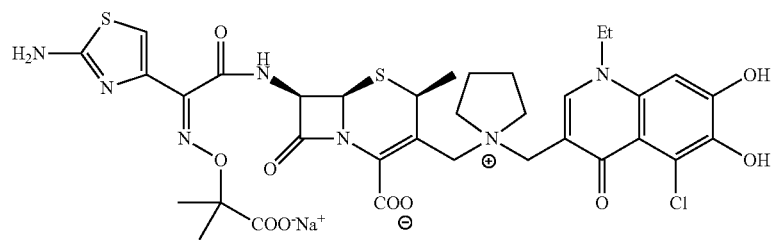

I-129

Step (1): Compound X-1+Compound 129a→Compound I-129

From Compound X-1 (932 mg, 1.0 mmol) and Compound 129a (563 mg, 1.0 mmol), Compound I-129 was obtained as a yellow powder using the same method as Example 120.

Yielded amount: 246 mg, (30%)

$^1$H-NMR (D$_2$O) δ: 1.40 (3H, t, J=7.03 Hz), 1.50 (3H, s), 1.52 (3H, s), 1.55 (3H, d, J=7.03 Hz), 2.23 (4H, d, J=10.42 Hz), 3.36 (3H, s), 3.56 (1H, s), 4.11-4.23 (4H, m), 4.37 (2H, s), 4.89 (1H, d, J=14.18 Hz), 5.50 (1H, d, J=4.89 Hz), 5.83 (1H, d, J=4.89 Hz), 6.87 (1H, s), 6.98 (1H, s), 8.09 (1H, s).

Elem. Anal.: C$_{34}$H$_{37}$ClN$_7$O$_{10}$S$_2$Na.7.4H$_2$O

Calcd.: C, 42.56; H, 5.44; Cl, 3.69; N, 10.22; S, 6.68; Na, 2.40(%).

Found: C, 42.53; H, 5.39; Cl, 3.51; N, 10.41; S, 6.69; Na, 2.56(%).

MS (m+1)=804.33

Example 130: Synthesis of Compound I-130

[Chemical Formula 276]

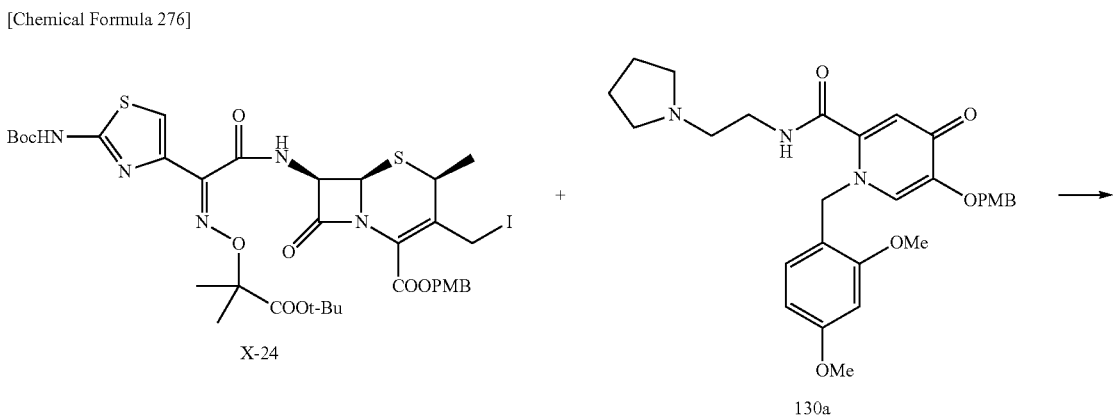

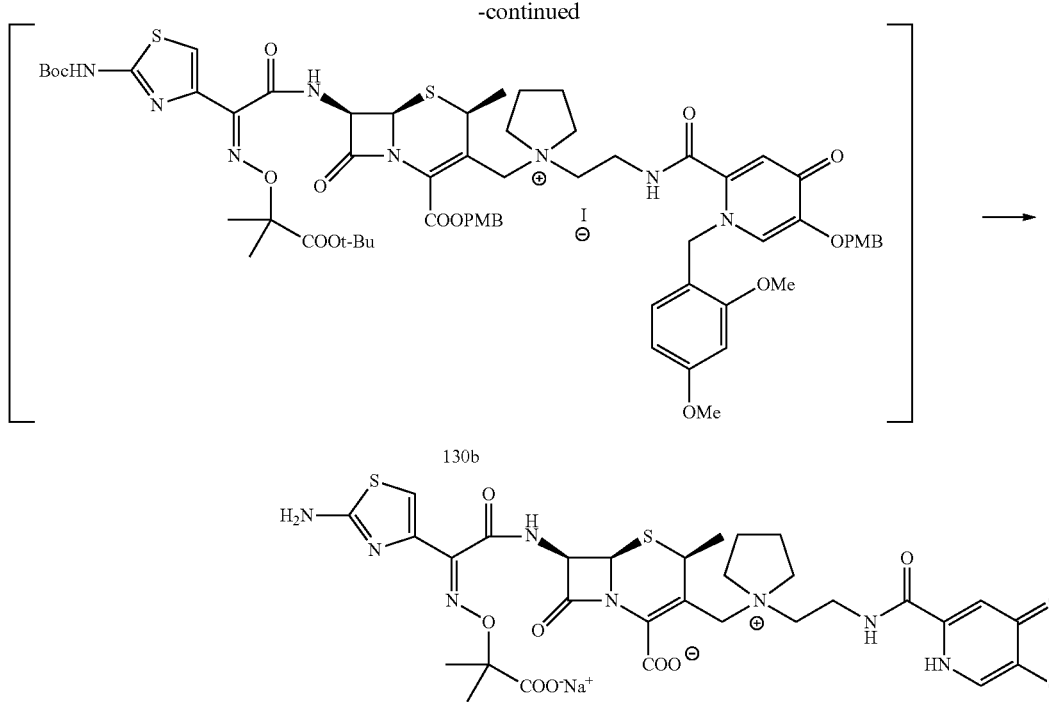
130b
I-130
Step (1): Compound X-24+Compound 130a→Compound I-130
From Compound X-24 (709 mg, 0.80 mmol) and Compound 130a (417 mg, 0.80 mmol), Compound I-130 was obtained as a white powder using the same method as Example 120.
Yielded amount: 177 mg, (29%)
$^1$H-NMR (D$_2$O) δ: 1.50 (3H, s), 1.52 (3H, s), 1.58 (3H, d, J=7.15 Hz), 2.21-2.25 (4H, m), 3.46-3.97 (8H, m), 4.09 (1H, q, J=7.15 Hz), 4.26 (1H, d, J=14.31 Hz), 5.04 (1H, d, J=14.31 Hz), 5.47 (1H, d, J=4.77 Hz), 5.82 (1H, d, J=4.77 Hz), 7.01 (1H, s), 7.12 (1H, s), 7.79 (1H, s).
MS (m+1)=733.35
Example 131: Synthesis of Compound I-131
[Chemical Formula 277]
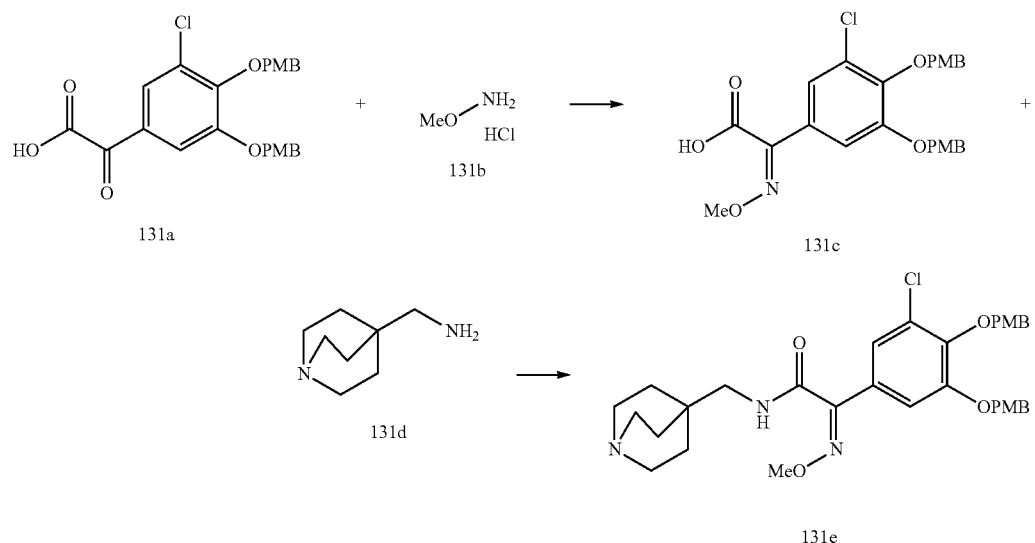

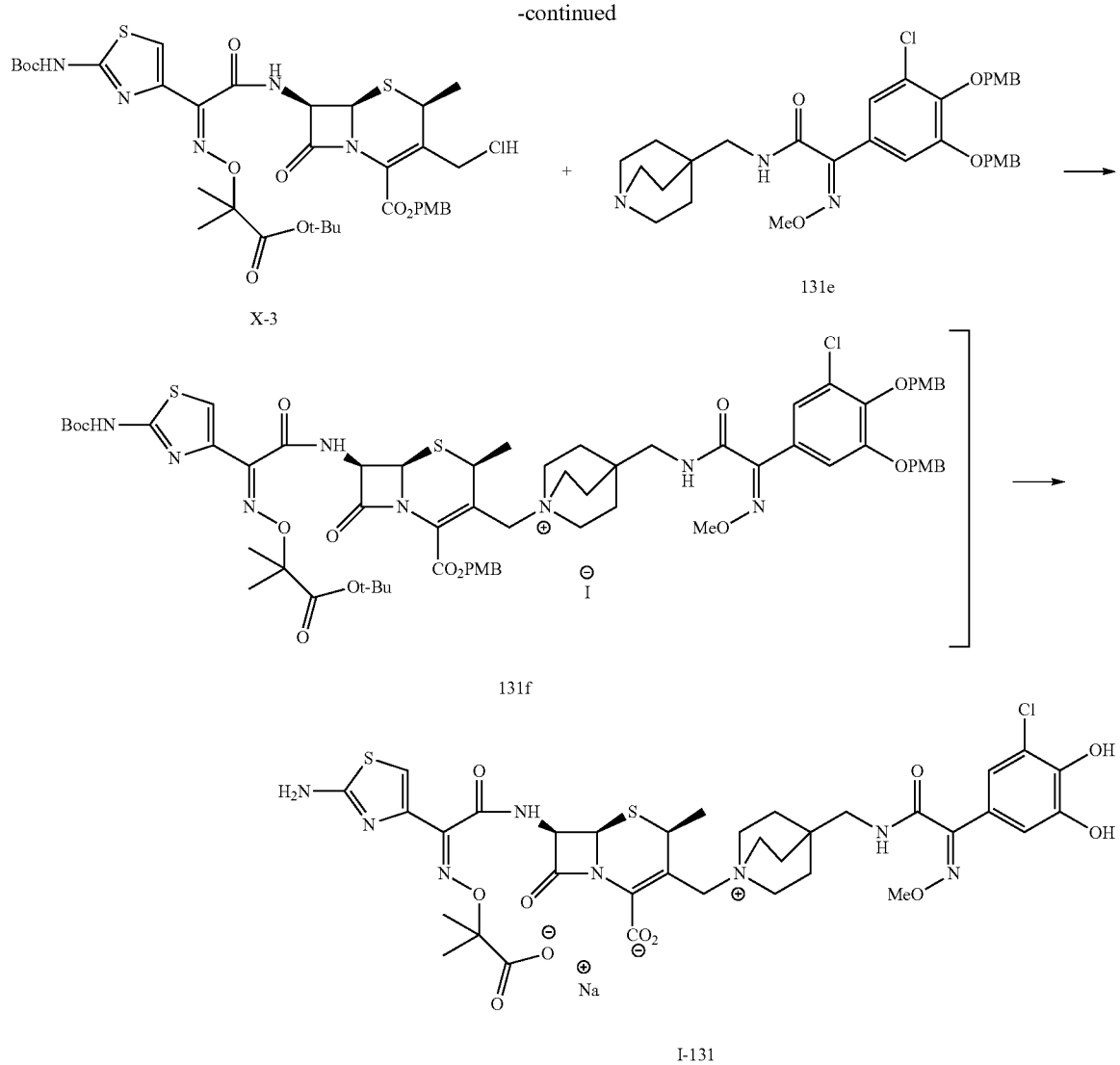

X-3

131e

131f

I-131

Step (1): Compound 131a+Compound 131b→Compound 131c

To a solution of Compound 131a (4.57 g, 10.0 mmol) in methanol (45 mL) was added Compound 131b (877 mg, 10.5 mmol) and triethylamine (1.46 mL, 10.5 mmol) at 0° C. After stirring at 0° C. for 1 hour, solvent was removed. The crude product was dissolved with ethyl acetate and washed with water, aqueous hydrochloride and brine. The organic layer was filtered, dryed over magnesium sulfate and concentrated under reduced pressure to yield Compound 131c as brown oil. Compound 131c was used in the next reaction without further purification.

Yielded amount: 4.86 g (100%)

$^1$H-NMR (CDCl$_3$) δ: 7.36 (2H, d, J=8.3 Hz), 7.32 (2H, d, J=8.6 Hz), 7.24 (2H, s), 6.92 (2H, d, J=8.6 Hz), 6.82 (2H, d, J=8.6 Hz), 5.06 (2H, s), 5.00 (2H, s), 4.09 (3H, s), 3.83 (3H, s), 3.80 (3H, s).

Step (2): Compound 131c+Compound 131d→Compound 131e

To a solution of Compound 131c (4.86 g, 10.0 mmol) in dimethylacetamide (40 mL) was added methanesulfonyl chloride (1.01 mL, 13.0 mmol) at −20° C. After the mixture was stirred at −20° C. for 30 minutes, the solution of Compound 131d (1.96 g, 14.0 mmol) in dimethylacetamide (10 mL) was added to the mixture and the reaction mixture was stirred at 0° C. for 30 minutes. Water and ethyl acetate were added to the reaction mixture, followed by extraction with ethyl acetate. The combined organic layer was washed with water, aqueous hydrochloric acid solution and brine. The organic layer was filtered, dryed over magnesium sulfate and concentrated under reduced pressure. The crude product was purified by silica gel chromatography to yield Compound 131e as brown foam.

Yielded amount: 4.10 g (67%)

$^1$H-NMR (CDCl$_3$) δ: 7.36 (2H, d, J=8.1 Hz), 7.31 (2H, d, J=8.3 Hz), 7.22-7.18 (2H, m), 6.92 (2H, t, J=8.6 Hz), 6.82 (2H, t, J=8.3 Hz), 5.94 (1H, t, J=6.6 Hz), 5.03 (2H, s), 4.99 (2H, s), 4.01 (3H, s), 3.83 (3H, s), 3.79 (3H, s), 3.24 (2H, d, J=6.6 Hz), 2.95 (6H, t, J=7.5 Hz), 1.47 (6H, t, J=7.3 Hz).

Step (3): Compound X-3+Compound 131e→Compound 131f→Compound I-131

To a solution of Compound X-3 (1.00 g, 1.26 mmol) in dimethylacetamide (2.0 mL) was added sodium iodide (377 mg, 2.56 mmo) and the mixture was stirred at room temperature for 30 minutes. The mixture was cooled to 0° C. and then a solution of Compound 131e (766 mg, 1.26 mmol) in dimethylacetamide (2.0 mL) was dropwised to it. The reaction mixture was slowly added to 5% aqueous sodium chloride after stirring at 0° C. for 2 hours. The precipitated solid was collected by filtration, washed with aqueous hydrochloride and water. The crude product Compound 131f was dissolved into dichloromethane (12 mL) and the solution was dryed over magnesium sulfate. Insoluble matter was removed by filtration to yield Compound 131f as a solution of dichloromethane. Compound 131f was used in the next reaction without further purification.

To a solution of Compound 131f in dichloromethane (12 mL) was added anisole (1.37 mL, 12.6 mmol) and a 2 mol/L aluminum chloride solution (6.3 mL, 12.6 mmol) in nitromethane in turn at −20° C. To the reaction mixture were added diisopropyl ether and a small amount of water after stirring at 0° C. for 30 minutes, and the resultant was stirred to generate a precipitate. The supernatant was removed by decantation. To the insoluble matter adhering to the vessel were added a diluted aqueous hydrochloric acid solution, and acetonitrile. The resultant was stirred to dissolve the matter completely. Thereto was added HP20-SS resin. Acetonitrile was then distilled off therefrom under reduced pressure. The resultant mixed liquid was purified by ODS column chromatography. The desired-compound-containing fraction was concentrated under reduced pressure, and then freeze-dried to yield compound I-131 as a yellow powder.

Yielded amount: 250 mg (24%)

$^1$H-NMR (D$_2$O) δ: 7.13 (1H, s), 7.06 (1H, s), 7.00 (1H, s), 5.84 (1H, d, J=4.5 Hz), 5.45 (1H, d, J=4.8 Hz), 4.65 (1H, d, J=14.4 Hz), 4.06 (2H, t, J=6.7 Hz), 3.99 (3H, s), 3.54-3.46 (6H, br m), 3.36 (2H, s), 1.92 (6H, s), 1.56 (3H, d, J=7.1 Hz), 1.52 (6H, d, J=7.6 Hz).

MS (m+1)=849.40

Example 132: Synthesis of Compound I-132

[Chemical Formula 278]

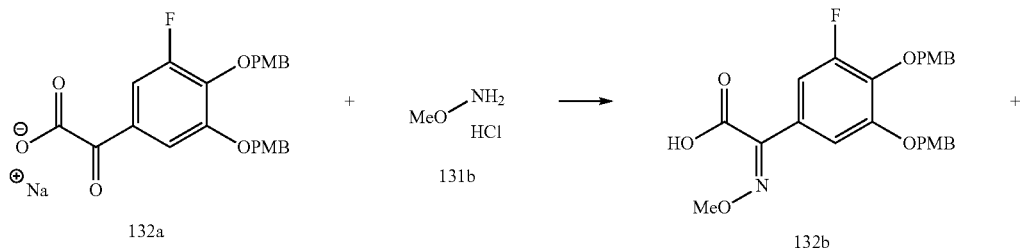

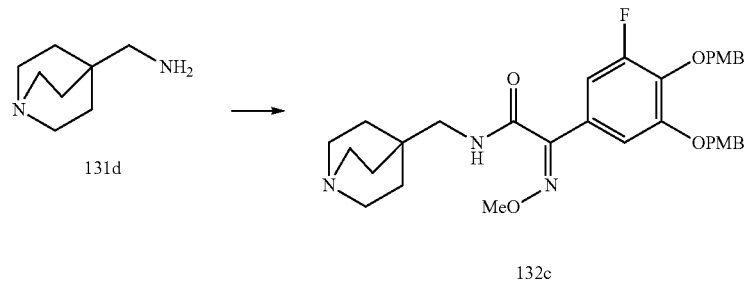

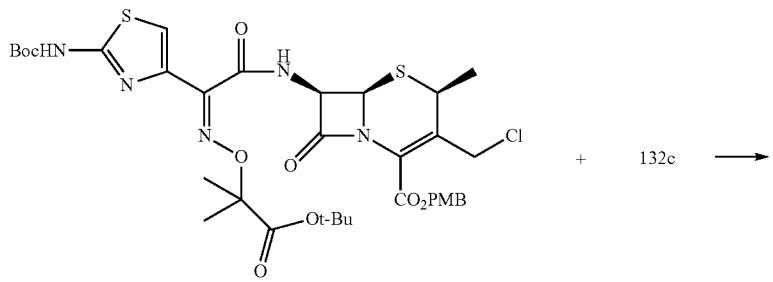

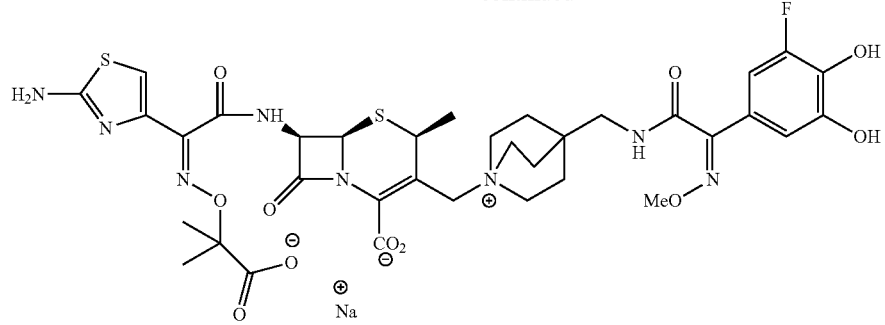

I-132

Step (1): Compound 132a+Compound 131b→Compound 132b

To a solution of Compound 132a (4.62 g, 10.0 mmol) in methanol (22 mL) and tetrahydrofuran (22 mL) was added Compound 131b (877 mg, 10.0 mmol) at 0° C. After stirring at 0° C. for 3 hour, solvent was removed. The crude product was dissolved with ethyl acetate and washed with water, aqueous hydrochloride and brine. The organic layer was filtered, dryed over magnesium sulfate and concentrated under reduced pressure to yield Compound 132b as brown oil. Compound 132b was used in the next reaction without further purification.

Yielded amount: 2.77 g (59%)

$^1$H-NMR (CDCl$_3$) δ: 7.34 (2H, d, J=8.5 Hz), 7.29 (2H, d, J=8.7 Hz), 7.08 (1H, s), 6.99 (1H, dd, J=10.9, 3.2 Hz), 6.91 (3H, d, J=8.7 Hz), 6.81 (2H, d, J=8.7 Hz), 5.05 (2H, s), 5.04 (2H, s), 4.06 (3H, s), 3.83 (3H, s), 3.79 (3H, s).

Step (2): Compound 132b+Compound 131d→Compound 132c

From Compound 132b (2.77 g, 5.9 mmol) and Compound 131d (1.16 g, 8.3 mmol), Compound 132c was obtained as a yellow foam using the same method as in Step (2) of Example 131.

Yielded amount: 1.03 g (29%)

$^1$H-NMR (CDCl$_3$) δ: 7.33 (2H, d, J=8.6 Hz), 7.28 (2H, d, J=8.6 Hz), 7.10 (1H, s), 7.01 (1H, dd, J=11.1, 1.5 Hz), 6.91 (2H, d, J=8.3 Hz), 6.81 (2H, d, J=8.3 Hz), 5.96 (1H, s), 5.04 (2H, s), 5.01 (2H, s), 4.01 (3H, s), 3.82 (3H, s), 3.79 (3H, s), 3.21 (2H, d, J=6.3 Hz), 2.91-2.89 (6H, br m), 1.43-1.41 (6H, br m).

Step (3): Compound X-3+Compound 132c→Compound I-132

From Compound X-3 (1.0 g, 1.26 mmol) and Compound 132c (745 mg, 1.26 mmol), Compound I-132 was obtained as a colorless powder using the same method as in Step (3) of Example 131.

Yielded amount: 314 mg (27%)

$^1$H-NMR (D$_2$O) δ: 7.01 (1H, s), 6.94 (1H, d, J=11.3 Hz), 6.91 (1H, s), 5.85 (1H, d, J=4.8 Hz), 5.46 (1H, d, J=4.8 Hz), 4.65 (1H, d, J=14.4 Hz), 4.07 (2H, t, J=7.5 Hz), 3.99 (3H, d, J=8.0 Hz), 3.50 (6H, t, J=18.1 Hz), 3.37 (2H, s), 1.93 (6H, t, J=7.5 Hz), 1.57 (3H, d, J=7.2 Hz), 1.53 (3H, s), 1.51 (3H, s).

MS (m+1)=833.41

Example 133: Synthesis of Compound I-133

[Chemical Formula 279]

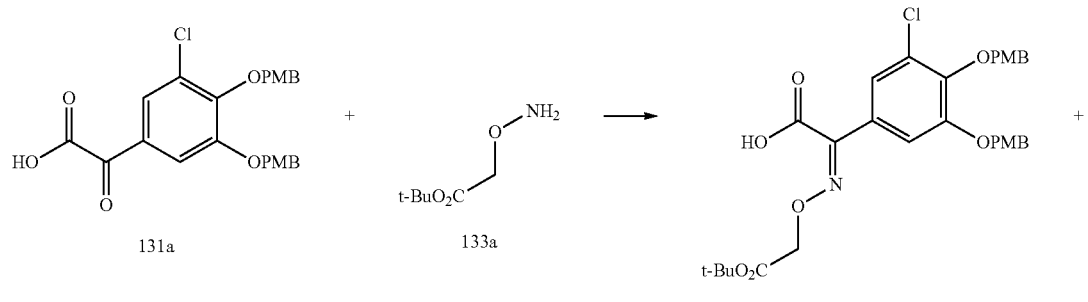

-continued

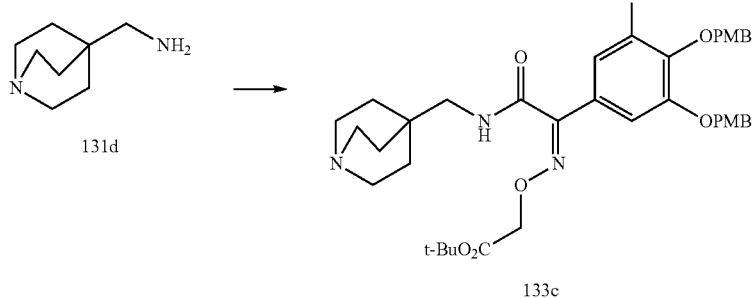

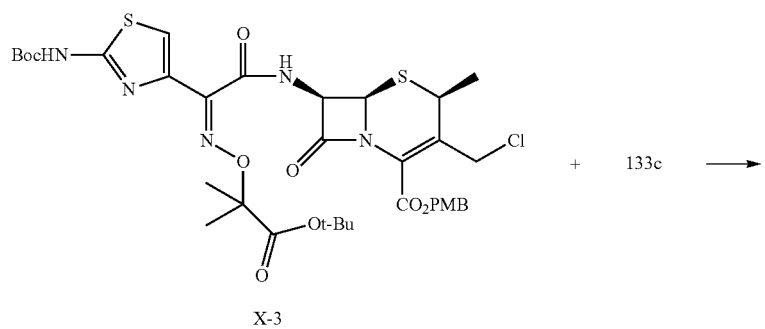

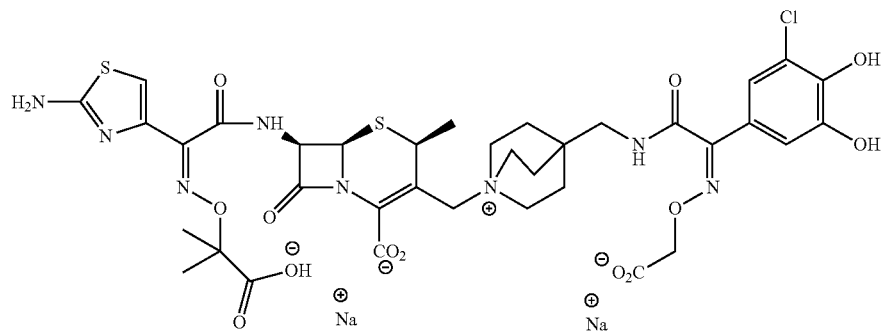

Step (1): Compound 131a+Compound 133a→Compound 133b

From Compound 131a (5.03 g, 11 mmol) and Compound 133a (1.62 g, 11 mmol), Compound 133b was obtained as a brown oil using the same method as in Step (1) of Example 131.

Yielded amount: 6.45 g (quant.)
$^1$H-NMR (CDCl$_3$) δ: 7.36-7.31 (5H, m), 7.17 (1H, d, J=7.3 Hz), 6.92 (2H, d, J=8.3 Hz), 6.82 (2H, d, J=8.3 Hz), 5.04 (2H, s), 5.00 (2H, s), 4.72 (2H, s), 3.83 (3H, s), 3.80 (3H, s), 1.51 (9H, s).

Step (2): Compound 133b+Compound 131d→Compound 133c

From Compound 133b (6.45 g, 11 mmol) and Compound 131d (2.16 g, 15.4 mmol), Compound 133c was obtained as a yellow foam using the same method as in Step (2) Example 131.

Yielded amount: 5.42 g (70%)
$^1$H-NMR (CDCl$_3$) δ: 7.45-7.28 (6H, m), 7.18-7.16 (1H, m), 6.92 (2H, d, J=8.6 Hz), 6.81 (2H, d, J=8.8 Hz), 5.03 (2H, s), 4.97 (2H, s), 4.67 (2H, s), 3.83 (3H, s), 3.79 (3H, s), 3.26 (2H, d, J=6.3 Hz), 2.93 (6H, t, J=7.1 Hz), 1.48-1.43 (15H, br m).

Step (3): Compound X-3+Compound 133c→Compound I-133

From Compound X-3 (1.0 g, 1.26 mmol) and Compound 133c (892 mg, 1.26 mmol), Compound I-133 was obtained as a yellow powder using the same method as in Step (3) Example 131.

Yielded amount: 260 mg (22%)
$^1$H-NMR (D$_2$O) δ: 7.15 (1H, s), 7.08 (1H, s), 7.01 (1H, s), 5.84 (1H, d, J=4.9 Hz), 5.46 (1H, d, J=4.8 Hz), 4.64 (1H, d, J=14.3 Hz), 4.57 (2H, s), 4.07 (2H, dd, J=10.5, 6.3 Hz), 3.49 (6H, t, J=19.1 Hz), 3.40 (3H, s), 1.95 (6H, t, J=7.6 Hz), 1.57 (3H, d, J=7.0 Hz), 1.52 (3H, s), 1.50 (3H, s).
MS (m+1)=894.38

Example 134: Synthesis of Compound I-134

[Chemical Formula 280]

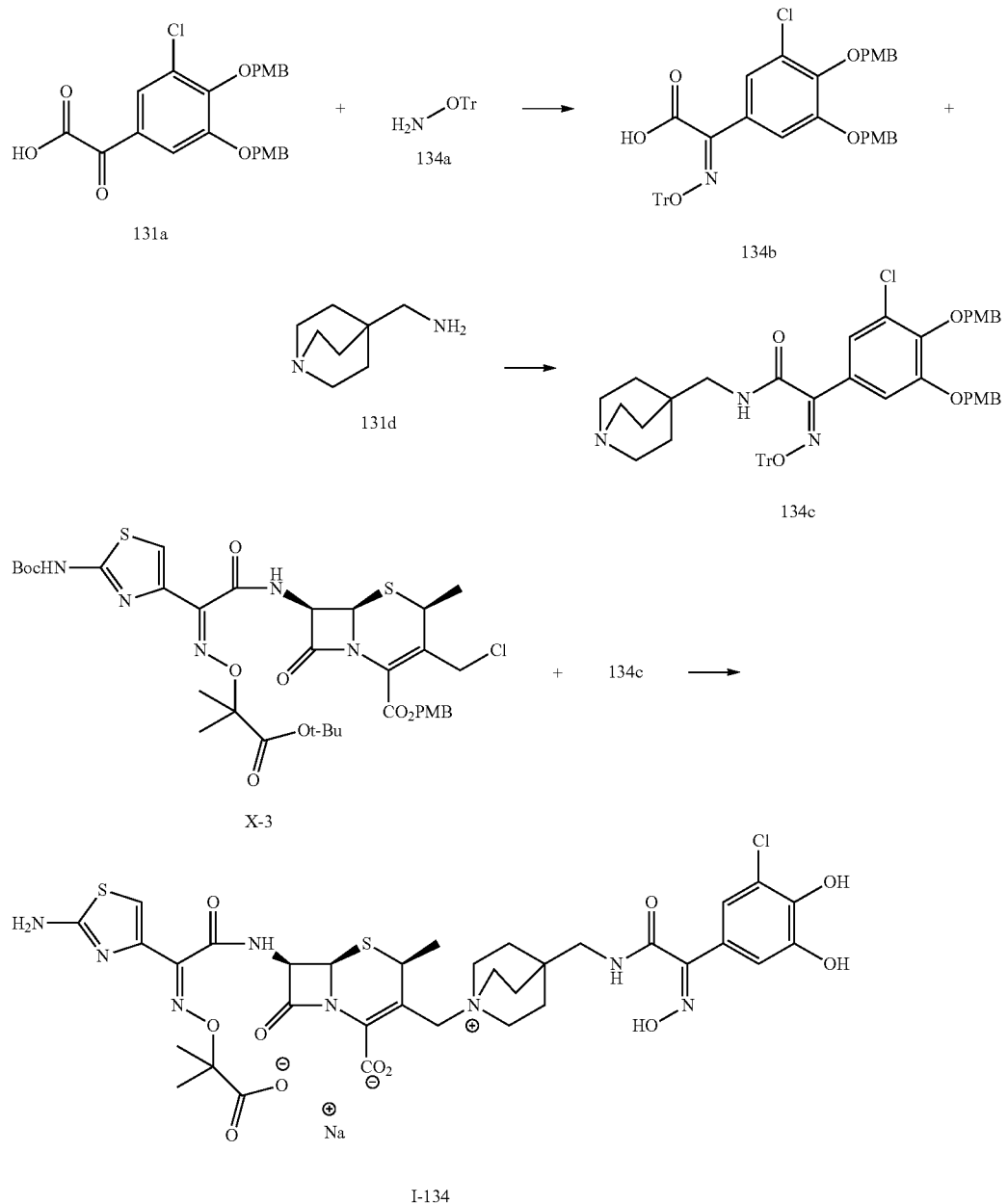

Step (1): Compound 131a+Compound 134a→Compound 134b

From Compound 131a (4.57 g, 10 mmol) and Compound 134a (3.03 g, 11 mmol), Compound 134b was obtained as a brown oil using the same method as in Step (1) of Example 131.

Yielded amount: 7.1 g (99%)

$^1$H-NMR (CDCl$_3$) δ: 7.49 (1H, d, J=1.8 Hz), 7.36-7.27 (20H, m), 6.88 (2H, d, J=8.6 Hz), 6.83 (2H, d, J=8.3 Hz), 5.06 (2H, s), 4.98 (2H, s), 3.81 (3H, s), 3.79 (3H, s).

Step (2): Compound 134b+Compound 131d→Compound 134c

From Compound 134b (7.1 g, 9.9 mmol) and Compound 131d (1.95 g, 13.9 mmol), Compound 134c was obtained as a brown oil using the same method as in Step (2) of Example 131.

Yielded amount: 1.67 g (20%)

$^1$H-NMR (CDCl$_3$) δ: 7.41-7.26 (29H, m), 6.86 (2H, d, J=8.3 Hz), 6.82 (2H, d, J=8.3 Hz), 6.31 (1H, t, J=6.3 Hz), 5.02 (2H, d, J=5.6 Hz), 4.95 (2H, d, J=8.6 Hz), 3.82 (3H, s), 3.78 (3H, s), 2.98 (2H, d, J=6.3 Hz), 2.83 (6H, t, J=7.3 Hz), 1.15 (6H, t, J=7.3 Hz).

Step (3): Compound X-3+Compound 134c→Compound I-134

From Compound X-3 (1.0 g, 1.26 mmol) and Compound 134c (1.05 g, 1.26 mmol), Compound I-134 was obtained as a colorless powder using the same method as in Step (3) of Example 131.

Yielded amount: 390 mg (28%)

$^1$H-NMR (D$_2$O) δ: 7.13 (1H, d, J=1.9 Hz), 7.01 (1H, s), 6.98 (1H, d, J=2.0 Hz), 5.84 (1H, d, J=4.9 Hz), 5.44 (1H, d, J=4.9 Hz), 4.64 (1H, d, J=14.4 Hz), 4.06 (2H, q, J=7.3 Hz), 3.54-3.39 (6H, m), 3.31 (2H, s), 1.91 (6H, t, J=7.8 Hz), 1.56 (3H, d, J=7.0 Hz), 1.53 (3H, s), 1.51 (3H, s).

MS (m+1)=835.42

Example 135: Synthesis of Compound I-135

[Chemical Formula 281]

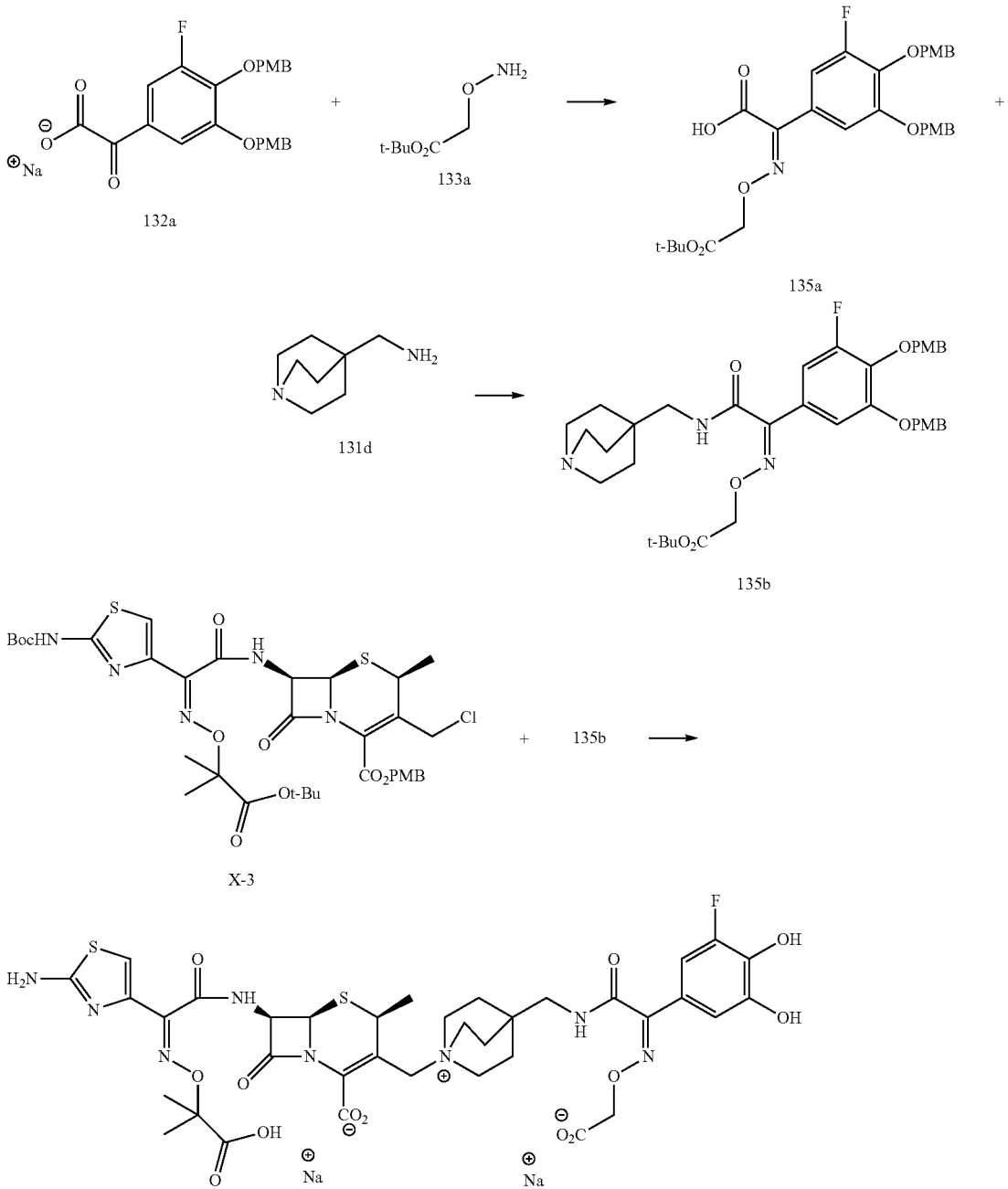

Step (1): Compound 132a+Compound 133d→Compound 3bb135a

To a solution of Compound 132a (4.99 g, 10.8 mmol) and aqueous hydrochloric acid (5.4 mL, 10.8 mmol) in methanol (25 mL) and tetrahydrofuran (25 mL) was added Compound 133d (1.77 g, 12.0 mmol) at 0° C. After stirring at 0° C. for 3 hour, solvent was removed. The crude product was dissolved with ethyl acetate and washed with water, aqueous hydrochloric acid and brine. The organic layer was filtered, dryed over magnesium sulfate and concentrated under reduced pressure to yield Compound 135a as brown oil. Compound 135a was used in the next reaction without further purification.

Yielded amount: 4.41 g (65%)
$^1$H-NMR (CDCl$_3$) δ: 7.34 (2H, d, J=8.1 Hz), 7.29 (2H, t, J=7.7 Hz), 7.11 (2H, t, J=13.0 Hz), 6.92 (3H, t, J=8.0 Hz), 6.82 (2H, d, J=8.3 Hz), 5.05 (2H, s), 5.03 (2H, s), 4.71 (2H, s), 3.83 (3H, s), 3.78 (3H, s), 1.51 (9H, s).

Step (2): Compound 135a+Compound 131d→Compound 135b

From Compound 135b (4.41 g, 6.5 mmol) and Compound 131d (1.27 g, 9.1 mmol), Compound 135b was obtained as a yellow foam using the same method as in Step (2) of Example 131.

Yielded amount: 2.73 g (62%)
$^1$H-NMR (CDCl$_3$) δ: 7.33 (2H, d, J=8.5 Hz), 7.29 (2H, d, J=8.8 Hz), 7.14 (1H, s), 7.04 (1H, dd, J=11.0, 6.5 Hz), 6.91 (2H, dd, J=5.5, 3.1 Hz), 6.81 (2H, d, J=8.7 Hz), 5.04 (2H, s), 5.01 (2H, s), 4.66 (2H, s), 3.83 (3H, s), 3.79 (3H, s), 3.29 (2H, d, J=6.4 Hz), 3.03-2.97 (6H, m), 1.60 (6H, m), 1.48 (9H, s).

Step (3): Compound X-3+Compound 135b→Compound I-135

From Compound X-3 (1.0 g, 1.26 mmol) and Compound 135b (853 mg, 1.26 mmol), Compound I-135 was obtained as a yellow powder using the same method as in Step (3) of Example 131.

Yielded amount: 175 mg (15%)
$^1$H-NMR (D$_2$O) δ: 7.01 (1H, s), 6.98-6.96 (2H, m), 5.84 (1H, d, J=4.8 Hz), 5.46 (1H, d, J=4.9 Hz), 4.64 (2H, d, J=13.9 Hz), 4.57 (2H, s), 4.08-4.06 (2H, m), 3.52-3.47 (6H, m), 3.40 (2H, s), 1.95 (6H, t, J=7.7 Hz), 1.57 (3H, s), 1.52 (3H, s), 1.50 (3H, d, J=5.8 Hz).
MS (m+1)=877.52

Example 136: Synthesis of Compound I-136

[Chemical Formula 282]

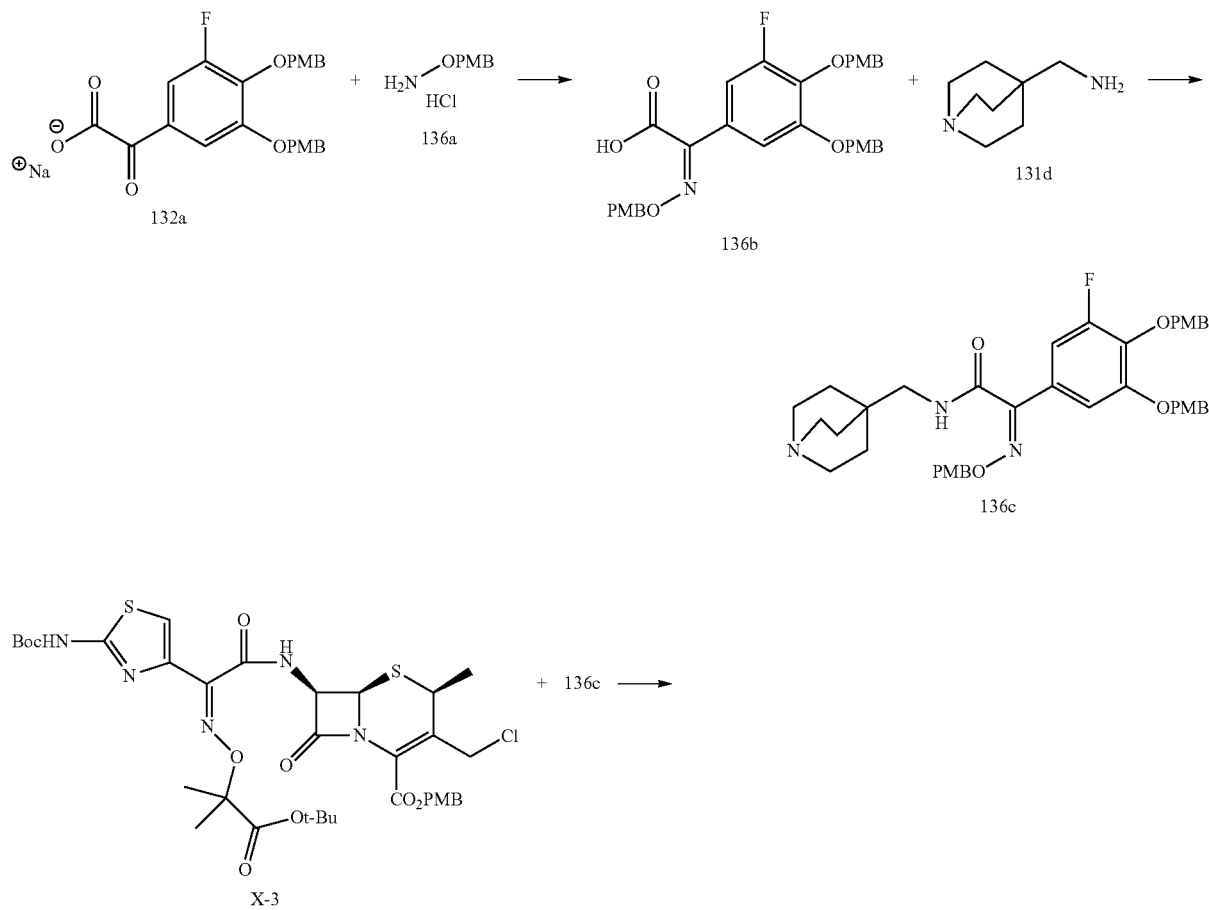

-continued

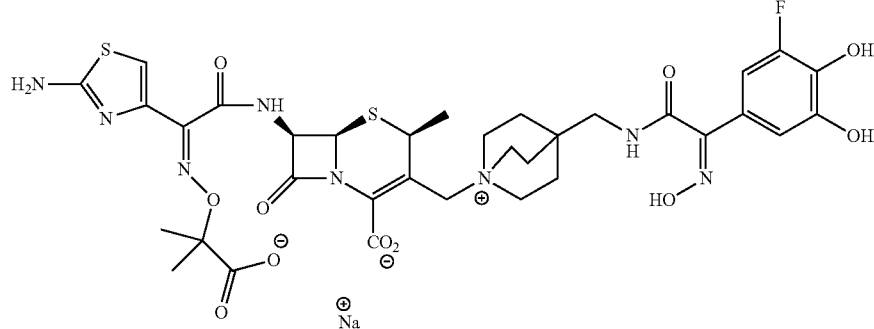

I-136

Step (1): Compound 132a+Compound 136a→Compound 136b

From Compound 132a (4.99 g, 10 mmol) and Compound 136a (1.90 g, 10 mmol), Compound 136b was obtained as a brown oil using the same method as in Step (1) of Example 132.

Yielded amount: 5.11 g (89%)

$^1$H-NMR (CDCl$_3$) δ: 7.32 (2H, d, J=8.5 Hz), 7.29 (2H, d, J=8.5 Hz), 7.11 (OH, d, J=188.6 Hz), 7.05 (1H, s), 6.98 (1H, dd, J=11.1, 1.6 Hz), 6.92-6.89 (4H, m), 6.81 (2H, d, J=8.7 Hz), 5.22 (2H, s), 5.05 (2H, s), 5.03 (2H, s), 3.83 (3H, s), 3.81 (3H, s), 3.79 (3H, s).

Step (2): Compound 136b+Compound 131d→Compound 136c

From Compound 136a (5.11 g, 8.9 mmol) and Compound 136a (1.75 g, 12.5 mmol), Compound 136b was obtained as a yellow foam using the same method as in Step (2) of Example 131.

Yielded amount: 2.4 g (39%)

$^1$H-NMR (CDCl$_3$) δ: 7.34-7.32 (4H, m), 7.29 (2H, d, J=8.5 Hz), 7.12 (1H, s), 7.03 (1H, dd, J=11.0, 1.8 Hz), 6.91 (4H, d, J=8.7 Hz), 6.81 (2H, d, J=8.5 Hz), 5.91 (1H, t, J=6.4 Hz), 5.15 (2H, s), 5.04 (2H, s), 5.03 (2H, s), 3.83 (3H, s), 3.82 (3H, s), 3.79 (3H, s), 3.14 (2H, d, J=6.5 Hz), 2.75-2.73 (6H, br m), 1.29-1.24 (6H, m).

Step (3): Compound X-3+Compound 136c→Compound I-136

From Compound X-3 (1.0 g, 1.26 mmol) and Compound 136c (878 mg, 1.26 mmol), Compound I-136 was obtained as a colorless powder using the same method as in Step (3) of Example 131.

Yielded amount: 400 mg (40%)

$^1$H-NMR (D$_2$O) δ: 7.00 (1H, s), 6.95 (1H, d, J=11.3 Hz), 6.92 (1H, s), 5.84 (1H, d, J=4.9 Hz), 5.45 (1H, d, J=4.8 Hz), 4.64 (1H, d, J=14.2 Hz), 4.06 (2H, t, J=7.0 Hz), 3.51-3.47 (6H, br m), 3.39 (3H, s), 1.96-1.94 (6H, br m), 1.56 (3H, d, J=7.0 Hz), 1.54 (3H, s), 1.50 (3H, s).

MS (m+1)=819.54

Example 137: Synthesis of Compound I-137

[Chemical Formula 283]

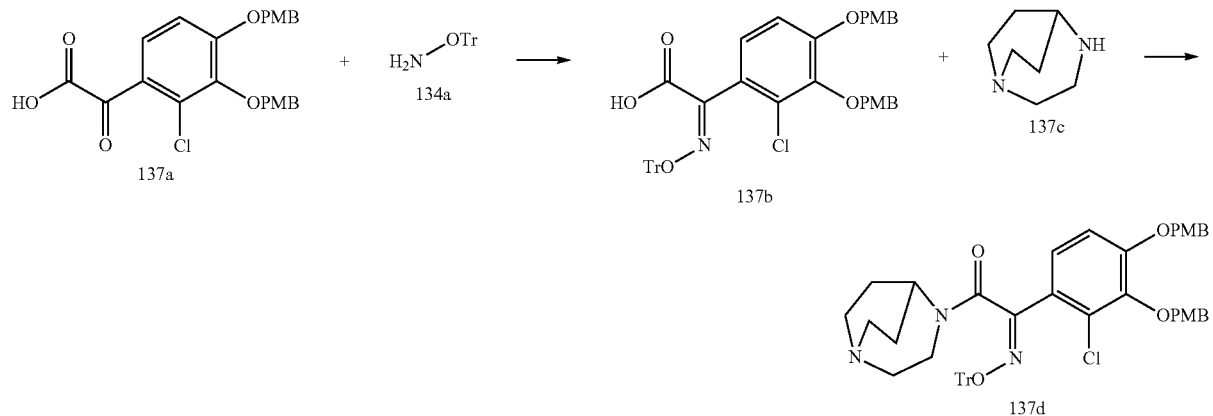

-continued

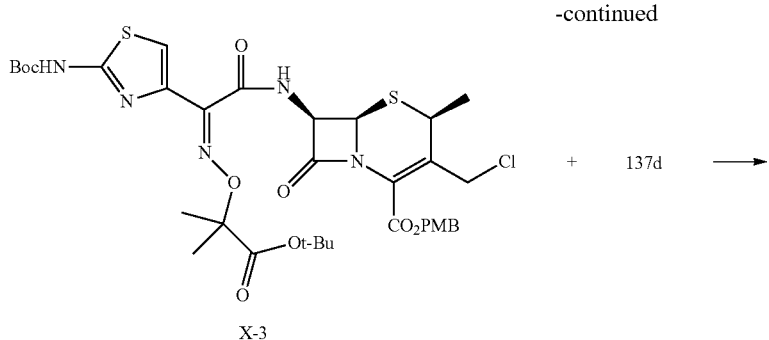

X-3

+ 137d ⟶

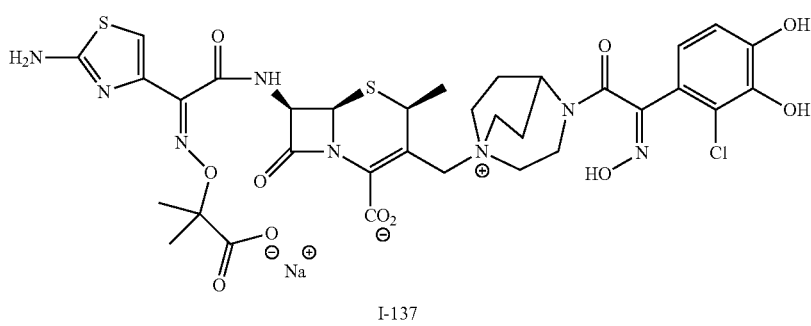

I-137

Step (1): Compound 137a+Compound 134a→Compound 137b

From Compound 137a (4.39 g, 9.60 mmol) and Compound 134a (2.64 g, 9.60 mmol), Compound 137b was obtained as a brown oil using the same method as in Step (1) of Example 131.

Yielded amount: 2.57 g (38%)

$^1$H-NMR (CDCl$_3$) δ: 7.51-7.43 (19H, m), 6.94-6.89 (2H, m), 6.82-6.79 (2H, m), 5.09-4.95 (4H, m), 3.84-3.74 (6H, m).

Step (2): Compound 137b+Compound 137c→Compound 137d

From Compound 3cc (2.57 g, 3.60 mmol) and Compound 7 (545 mg, 4.32 mmol), Compound 3cc was obtained as a brown oil using the same method as in Step (2) of Example 131.

Yielded amount: 940 mg (32%)

$^1$H-NMR (CDCl$_3$) δ: 7.34 (7H, dt, J=25.1, 7.5 Hz), 7.23 (13H, br s), 6.93 (2H, d, J=8.3 Hz), 6.77 (2H, d, J=8.3 Hz), 5.11 (2H, s), 4.98 (2H, s), 3.84 (3H, s), 3.73 (3H, s), 3.36 (2H, d, J=5.3 Hz), 2.99-2.79 (6H, m), 1.82-1.64 (6H, br m).

Step (3): Compound X-3+Compound 137d→Compound I-137

To a solution of Compound X-3 (908 mg, 1.14 mmol) in dimethylacetamide (2.0 mL) was added sodium iodide (342 mg, 2.29 mmo) and the mixture was stirred at room temperature for 30 minutes. The mixture was cooled to 0° C. and then a solution of Compound 137d (800 mg, 1.14 mmol) in dimethylacetamide (2.0 mL) was dropwised to it. The reaction mixture was slowly added to 5% aqueous sodium chloride after stirring at 0° C. for 2 hours. The precipitated solid was collected by filtration, washed with aqueous hydrochloride and water and suspended into water. The suspension was freeze-dried to yield the crude product as a brown solid. The crude product yielded was used as it was, without being purified, in the next reaction.

To a solution of the crude product in dichloromethane (12 mL) was added anisole (1.25 mL, 11.4 mmol) and a 2 mol/L aluminum chloride solution (5.7 mL, 11.4 mmol) in nitromethane in turn at −20° C. To the reaction mixture were added diisopropyl ether and a small amount of water after stirring at 0° C. for 30 minutes, and the resultant was stirred to generate a precipitate. The supernatant was removed by decantation. To the insoluble matter adhering to the vessel were added a diluted aqueous hydrochloric acid solution, and acetonitrile. The resultant was stirred to dissolve the matter completely. Thereto was added HP20-SS resin. Acetonitrile was then distilled off therefrom under reduced pressure. The resultant mixed liquid was purified by ODS column chromatography. The desired-compound-containing fraction was concentrated under reduced pressure, and then freeze-dried to yield compound I-137 as a yellow powder.

Yielded amount: 280 mg (29%)

$^1$H-NMR (D$_2$O) δ: 7.05-6.97 (3H, m), 5.87-5.86 (1H, m), 5.46-5.45 (1H, m), 4.31-4.07 (5H, m), 3.81-3.51 (7H, m), 2.36-2.31 (4H, m), 1.59 (3H, d, J=6.9 Hz), 1.53 (3H, s), 1.51 (3H, s).

Example 138: Synthesis of Compound I-138

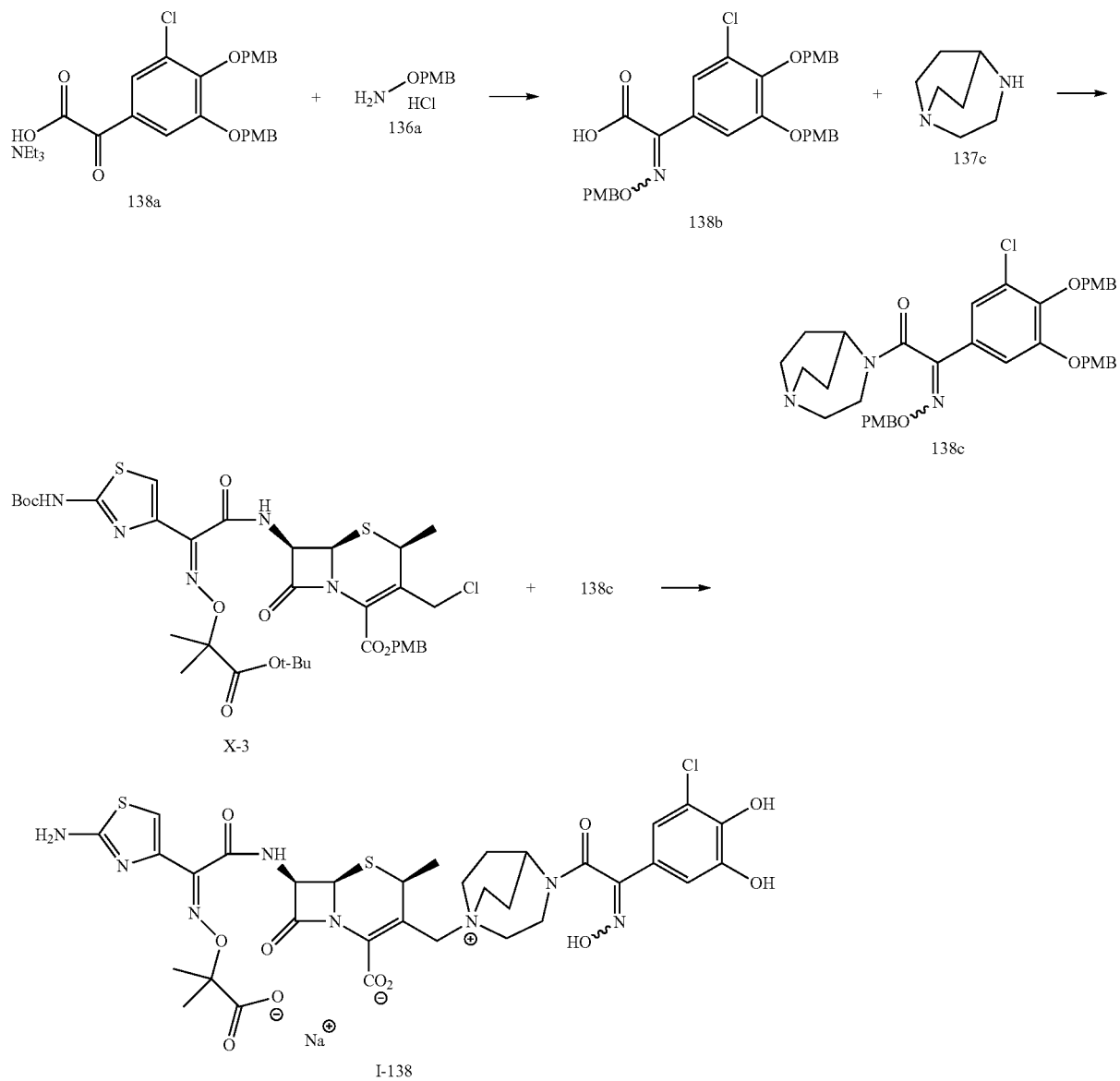

Step (1): Compound 138a+Compound 136a→Compound 138b

To a solution of Compound 138a (5.58 g, 10.0 mmol) in methanol (45 mL) was added acetic acid (0.572 mL, 10.0 mmol), Compound 136a (1.90 g, 10.0 mmol) and triethylamine (1.39 mL, 10.0 mmol) at 0° C. After stirring at 0° C. for 1 hour, solvent was removed. The crude product was dissolved with ethyl acetate and washed with water, aqueous hydrochloride and brine. The organic layer was filtered, dryed over magnesium sulfate and concentrated under reduced pressure to yield Compound 138b as brown oil. Compound 138b was used in the next reaction without further purification.

Yielded amount: 5.92 g (100%)

$^1$H-NMR (CDCl$_3$) δ: 7.36-7.31 (6H, m), 7.21 (2H, s), 6.92-6.90 (4H, m), 6.82 (2H, d, J=8.7 Hz), 5.23 (2H, s), 5.04 (2H, s), 4.99 (2H, s), 3.83 (3H, s), 3.81 (3H, s), 3.80 (3H, s).

Step (2): Compound 138b+Compound 137c→Compound 138c

From Compound 138b (1.78 g, 3.0 mmol) and Compound 137c (492 mg, 3.9 mmol), Compound 138c was obtained as a yellow foam using the same method as in Step (2) of Example 131.

Yielded amount: 800 mg (38%)

$^1$H-NMR (CDCl$_3$) δ: 7.38-7.30 (6H, m), 7.23 (1H, d, J=5.1 Hz), 7.16 (1H, t, J=4.3 Hz), 6.91-6.84 (6H, m), 5.15

(2H, s), 5.08-5.06 (2H, m), 5.02-5.00 (2H, m), 4.70 (1H, br s), 3.83-3.77 (9H, m), 3.29-2.55 (8H, m), 1.92-1.73 (3H, m), 1.22-1.17 (2H, m).

Step (3): Compound X-3+Compound 138c→Compound I-138

From Compound X-3 (908 mg, 1.14 mmol) and Compound 138c (800 mg, 1.14 mmol), Compound I-138 was obtained as a white powder using the same method as in Step (3) of Example 137.

Yielded amount: 320 mg (33%, E/Z=29:64 or 64:29)
$^1$H-NMR (D$_2$O) δ: 7.11-7.09 (2H, m), 7.00 (1H, s), 5.85-5.84 (1H, m), 5.44 (1H, s), 4.87 (2H, t, J=27.9 Hz), 4.32 (1H, t, J=15.0 Hz), 4.13-4.05 (2H, m), 3.81-3.67 (7H, br m), 2.37 (4H, s), 1.59-1.56 (3H, m), 1.52 (3H, s), 1.50 (3H, s).

MS (m+1)=822.5

Example 139: Synthesis of Compound I-139

Step (1): Compound 139a+Compound 137c→Compound 139b

From Compound 139a (2.88 g, 5.0 mmol) and Compound 137c (757 mg, 6.0 mmol), Compound 139b was obtained as a yellow foam using the same method as Step(2) of in Step (2) of Example 131.

Yielded amount: 861 mg (25%)
$^1$H-NMR (CDCl$_3$) δ: 7.34-7.27 (8H, m), 6.90-6.88 (4H, m), 6.82 (2H, d, J=8.6 Hz), 5.14 (2H, s), 5.09-5.00 (4H, m), 4.69 (1H, s), 3.82-3.80 (9H, m), 3.27-3.18 (2H, br m), 3.08-2.82 (4H, m), 2.81-2.70 (2H, m), 2.60-2.53 (1H, m), 2.03-1.70 (3H, m), 1.42 (1H, br s).

Step (2): Compound X-3+Compound 139b→Compound I-139

From Compound X-3 (1.0 g, 1.26 mmol) and Compound 139b (861 mg, 1.26 mmol), Compound I-139 was obtained as a colorless powder using the same method as in Step(3) of Example 137.

Yielded amount: 320 mg (31%, E/Z or Z/E=34:63)
$^1$H-NMR (D$_2$O) δ: 7.00 (1H, s), 6.96 (2H, d, J=11.7 Hz), 5.86-5.84 (1H, m), 5.45-5.44 (1H, m), 4.33 (2H, t, J=14.7 Hz), 4.13-4.07 (2H, m), 3.87-3.49 (8H, m), 2.38-2.36 (4H, br m), 1.59-1.57 (3H, m), 1.52 (3H, s), 1.50 (3H, s).

MS (m+1)=805.82

[Chemical Formula 285]

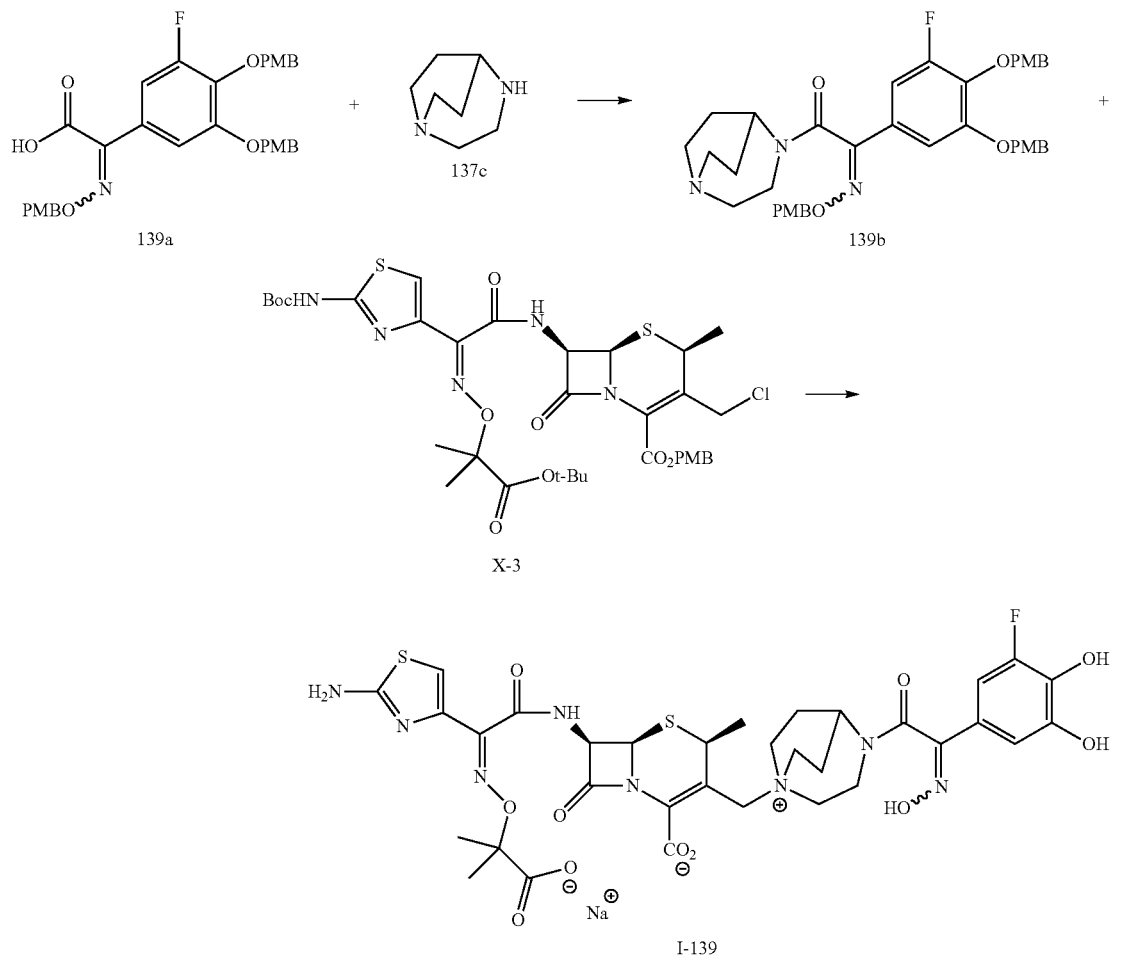

Example 140: Synthesis of Compound I-140

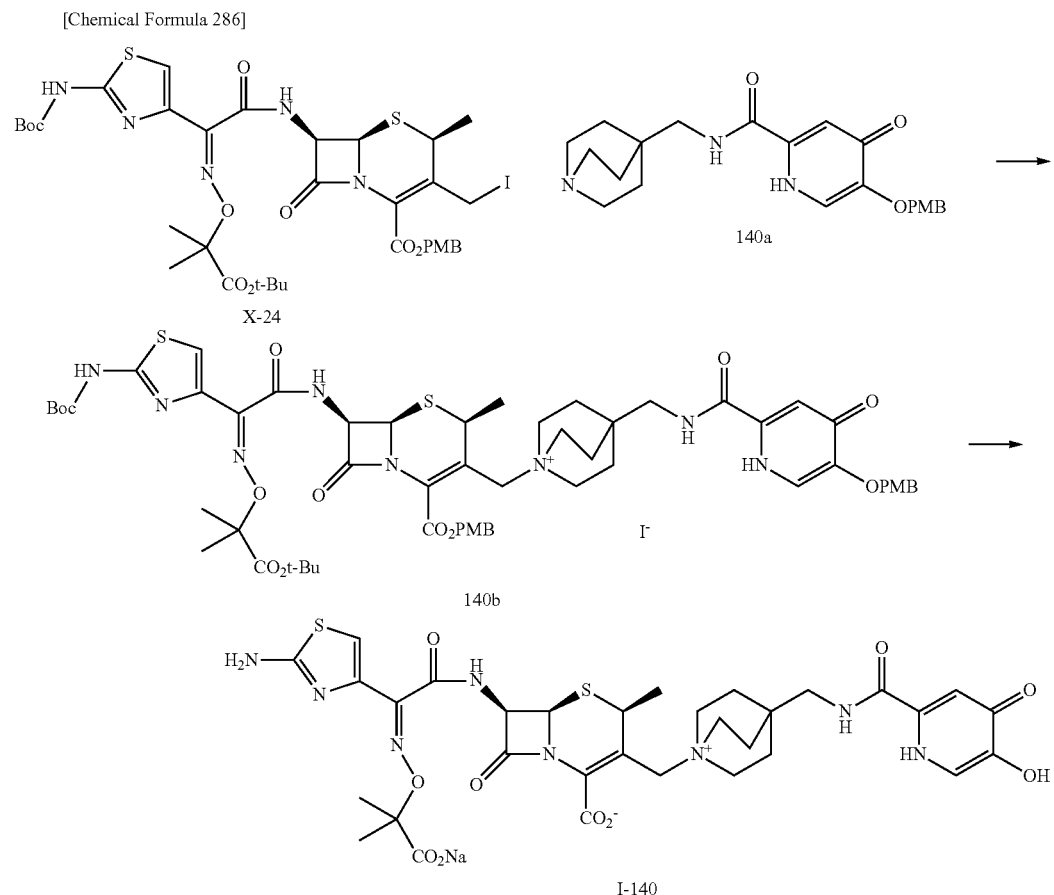

Step (1): Compound X-24+Compound 140a→Compound 140b→Compound I-140

Compound X-24 (886 mg, 1.0 mmol) and compound 140a (397 mg, 1.0 mmol) which was synthesized into according to the synthesis in WO2011125966A1 were used to synthesize the target compound in the same way as in Step (4) of Example 107.

Yielded amount: 334.2 mg, (37%)

$^1$H-NMR (D$_2$O) δ: 7.78 (1H, s), 7.12 (1H, s), 7.00 (1H, s), 5.84 (1H, d, J=4.9 Hz), 5.45 (1H, d, J=4.9 Hz), 4.64 (1H, d, J=14.3 Hz), 4.11-4.05 (2H, m), 3.58-3.42 (6H, m), 3.39 (2H, s), 1.94 (6H, t, J=7.8 Hz), 1.56 (3H, d, J=7.2 Hz), 1.52 (3H, s), 1.50 (3H, s).

Elem. Anal.: C32H37N8O10S2Na (H2O) 6.1
Calcd.: C, 43.15; H, 5.57; N, 12.58; S, 7.20; Na, 2.58(%).
Found: C, 43.10; H, 5.45; N, 12.82; S, 7.21; Na, 2.64(%).

Example 141: Synthesis of Compound I-141

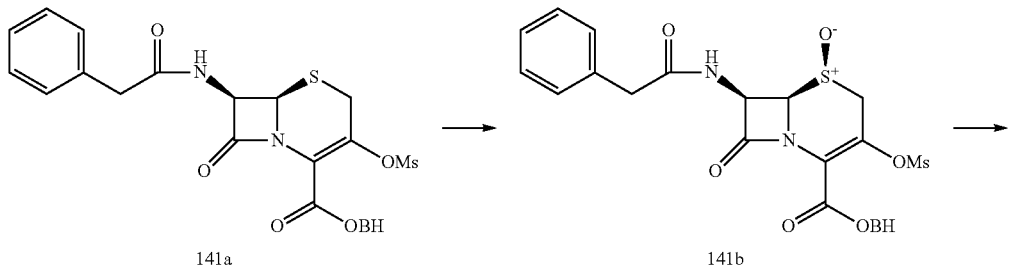

-continued
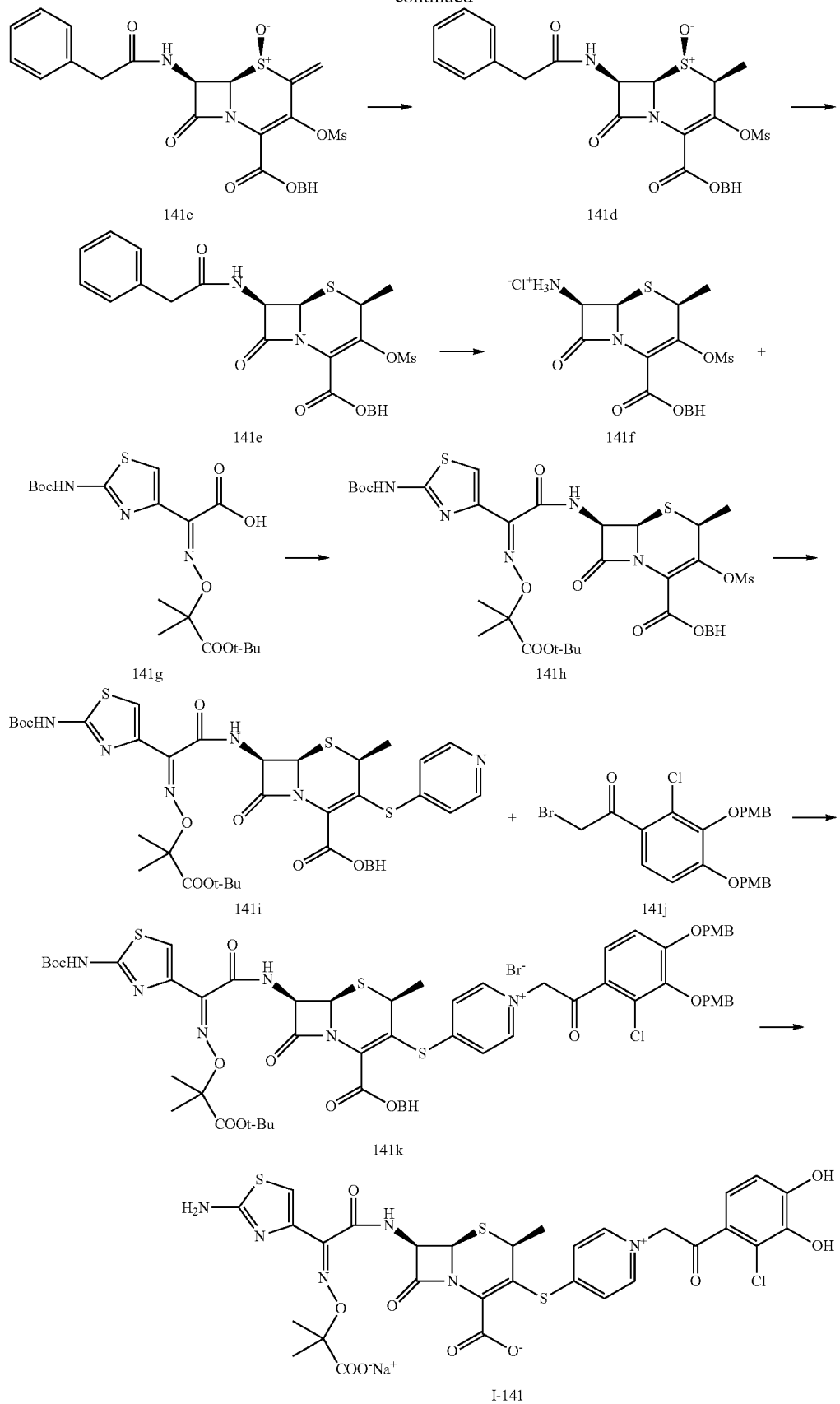

Step (1): Compound 141a→Compound 141b

To a cooled (0° C.) solution of compound 141a (17.4 g, 30.0 mmol) in DMA (200 ml) was added 39% peracetic acid (5.69 ml, 33.0 mmol). After stirring for 1 hr at 0° C., the mixture was quenched by 50 mL of 10% sodium bisulfite aqueous solution. The resulting solid was collected by filtration and washed with water and isopropanol to afford 17.4 g of compound 141b (98%).

$^1$H-NMR (DMSO-D$_6$) δ: 8.57 (d, J=8.1 Hz, 1H), 7.50 (d, J=7.7 Hz, 2H), 7.42-7.21 (m, 13H), 6.97 (s, 1H), 5.91 (dd, J=8.1, 4.5 Hz, 1H), 5.03 (d, J=4.5 Hz, 1H), 4.20 (d, J=18.1 Hz, 1H), 4.01 (d, J=18.1 Hz, 1H), 3.69 (d, J=14.0 Hz, 1H), 3.55 (d, J=14.0 Hz, 1H), 3.12 (s, 3H).

Step (2): Compound 141b→Compound 141c

To a solution of compound 141b (17 g, 28.6 mmol) in DMF (170 ml) was added dimethylamine hydrochloride (2.33 g, 28.6 mmol) and 36%~38% formalin (4.26 ml, 57.2 mmol). After stirring for 30 min at 50° C., the resulting mixture was poured into water then the resulting solid was collected by filtration to afford 13.2 g of compound 141c (76%)

$^1$H-NMR (DMSO-D$_6$) δ: 8.59 (d, J=8.3 Hz, 1H), 7.53 (d, J=7.7 Hz, 2H), 7.42-7.23 (m, 14H), 6.95 (s, 1H), 6.51 (s, 1H), 6.45 (s, 1H), 6.05 (dd, J=8.3, 5.0 Hz, 1H), 5.25 (d, J=5.0 Hz, 1H), 3.69 (d, J=14.1 Hz, 1H), 3.58 (d, J=14.1 Hz, 1H), 3.23 (s, 3H).

Step (3): Compound 141c→Compound 141d

To a cooled (−40° C.) solution of sodium borohydride (937 mg, 24.8 mmol) in MeOH (300 ml) was added dropwise a solution of compound 141c (12.5 g, 20.6 mmol) in 250 ml of THF under −40° C. After the mixture was stirred at −40° C. for 30 min, TFA (0.163 ml, 2.12 mmol) was added. Then the mixture was concentrated in vacuo. The resulting precipitate was collected by filtration and washed by MeOH to afford 9.40 g of compound 141d (75%).

$^1$H-NMR (DMSO-D$_6$) δ: 8.61 (d, J=8.1 Hz, 1H), 7.49 (d, J=7.7 Hz, 2H), 7.44-7.22 (m, 13H), 6.95 (s, 1H), 5.94 (dd, J=3.5, 8.1 Hz, 1H), 5.18 (d, J=3.5 Hz, 1H), 4.06 (q, J=7.7 Hz, 1H), 3.68 (d, J=14.3 Hz, 1H), 3.57 (d, J=14.3 Hz, 1H), 3.04 (s, 3H), 1.55 (d, J=7.7 Hz, 3H).

Step (4): Compound 141d→Compound 141e

To a cooled (−40° C.) solution of compound 141d (9.39 g, 15.4 mmol) in DMF (100 ml) was added phosphorous tribromide (1.75 ml, 18.5 mmol). After the reaction mixture was stirred for 15 min at −40° C., the mixture was diluted with water. The resulting solid was collected by filtration and washed by water to afford 9.40 g of compound 141e.

$^1$H-NMR (DMSO-D$_6$) δ: 9.22 (d, J=8.4 Hz, 1H), 7.48 (d, J=7.8 Hz, 2H), 7.42-7.19 (m, 13H), 6.90 (s, 1H), 5.83 (dd, J=8.4, 5.0 Hz, 1H), 5.41 (d, J=5.0 Hz, 1H), 4.26 (q, J=7.1 Hz, 1H), 3.60-3.50 (m, 2H), 3.07 (s, 3H), 1.48 (d, J=7.1 Hz, 3H).

Step (5): Compound 141e→Compound 141f

To a cooled (−20° C.) slurry of phosphorus pentachloride (4.01 g, 19.2 mmol) in dichloromethane (60.0 ml) was added pyridine (1.67 ml, 21.2 mmol) followed by compound 141e (5.7 g, 9.62 mmol). After the mixture was stirred for 45 min at 0° C., the mixture was cooled to −40° C. then MeOH (23.4 ml, 577 mmol) was added to this mixture in one portion. The mixture was warmed to room temperature and diluted with water and dichloromethane. The aqueous layer was extracted with dichloromethane. The combined organic layers were washed with water and brine, dried over MgSO$_4$, filtered. To this mixture was added 4 mmol/l HCl in EtOAc (3.61 ml) then this solution was concentrated in vacuo. The resulting residue compound 141f was used in next Step without further purification.

Step (6): Compound 141f+Compound 141g→Compound 141h

To a cooled (−50° C.) solution of compound 141f (9.62 mmol) in dichloro methane (50.0 ml) were added compound 141g (4.96 g, 11.5 mmol) and phenyl dichlorophosphate (1.87 ml, 12.5 mmol) followed by N-methyl morpholine (4.23 ml, 38.5 mmol). After 1 hr at −50° C., the reaction mixture was poured into water. Then the aqueous layer was extracted with ethyl acetate and the combined extracts were washed with water and brine, dried (MgSO4), filtered, and concentrated in vacuo. The residue was purified by silica gel chromatography to afford 1.25 g of compound 141h (25%).

$^1$H-NMR (CDCl$_3$) δ: 8.29 (d, J=9.0 Hz, 1H), 7.42-7.28 (m, 11H), 6.94 (s, 1H), 6.06 (dd, J=9.0, 5.1 Hz, 1H), 5.29 (d, J=5.0 Hz, 1H), 4.15-4.02 (m, 1H), 2.62 (s, 3H), 1.63 (d, J=10.0 Hz, 3H), 1.52 (s, 15H), 1.41 (s, 9H).

Step (7): Compound 141h→Compound 141i

To a cooled (0° C.) solution of compound 141h (4.93 g, 5.57 mmol) in tetrahydrofuran (50.0 ml) were added magnesium bromide diethyl etherate (7.19 g, 27.9 mmol), pyridine-4-thiol (1.36 g, 12.3 mmol) and potassium carbonate (1.69 g, 12.3 mmol). After stirring for 2 hr at 0° C., the reaction mixture was poured into water. Then the aqueous layer was extracted with ethyl acetate and the combined extracts were washed with water and brine, dried (MgSO4), filtered, and concentrated in vacuo. The residue was purified by silica gel chromatography to afford 1.25 g of compound 5i (25%).

$^1$H-NMR (CDCl$_3$) δ: 8.39-8.32 (m, 1H), 7.44-7.21 (m, 13H), 7.08 (d, J=5.9 Hz, 2H), 6.98 (s, 1H), 6.05 (dd, J=8.8, 5.1 Hz, 1H), 5.38 (d, J=5.1 Hz, 1H), 3.82 (q, J=7.2 Hz, 1H), 1.63 (d, J=9.7 Hz, 6H), 1.53 (s, 9H), 1.42 (s, 9H).

Step (8): Compound 141i+Compound 141j→Compound 141k

To a cooled (0° C.) solution of compound 141i (0.90 g, 1.00 mmol) in DMF (3.00 ml) was added compound 141j (0.56 g, 1.10 mmol; ref. WO2013002215A1). After stirring overnight at 0° C., the reaction mixture was poured into water. Then the aqueous layer was extracted with ethyl acetate and the combined extracts were washed with water and brine, dried (MgSO4), filtered, and concentrated in vacuo. The resulting residue compound 141k was used in next Step without further purification.

Step (9): Compound 141k→Compound I-141

To a cooled (−20° C.) solution of compound 141k in dichloromethane (15.0 ml) was added anisole (1.09 ml, 10.0 mmol) followed by 2 mol/L aluminum chloride solution (5.00 mL, 10.0 mmol) in nitromethane in one portion. After stirring for 30 min at −20° C., the mixture was quenched with water (15.0 ml). The resulting precipitate was dissolved in 2 mol/L aqueous hydrochloric acid solution and acetonitrile. The water phase was washed with diisopropyl ether. To this water phase was added HP20SS resin and involved acetonitrile was distilled off under reduced pressure. The residual suspension was loaded HP20SS precolum connected ODS column and purified. To the resultant target-compound solution was added a 0.2 mol/L aqueous sodium hydroxide solution until the whole gave a pH of 6.0. Then a piece of dry ice was added thereto. The resultant solution was concentrated under reduced pressure, and then freeze-dried to afford 508 mg of compound I-141 (65% from compound 141i)

$^1$H-NMR (D$_2$O) δ: 8.38 (d, J=6.6 Hz, 2H), 7.87 (d, J=6.6 Hz, 2H), 7.53 (d, J=8.6 Hz, 1H), 6.99 (s, 1H), 6.93 (d, J=8.6 Hz, 1H), 5.85 (d, J=5.1 Hz, 1H), 5.65 (d, J=5.1 Hz, 1H), 4.22 (q, J=7.2 Hz, 1H), 1.54-1.50 (m, 9H).

Elemental Analysis: C30H26ClN6NaO10S3 (H2O) 5

Calcd.: C, 41.17; H, 4.15; N, 9.60; S, 10.99; Cl, 4.05; Na, 2.63(%).

Found: C, 40.88; H, 4.16; N, 9.72; S, 11.00; Cl, 4.26; Na, 2.93(%).

Example 142: Synthesis of Compound I-142

[Chemical Formula 288]

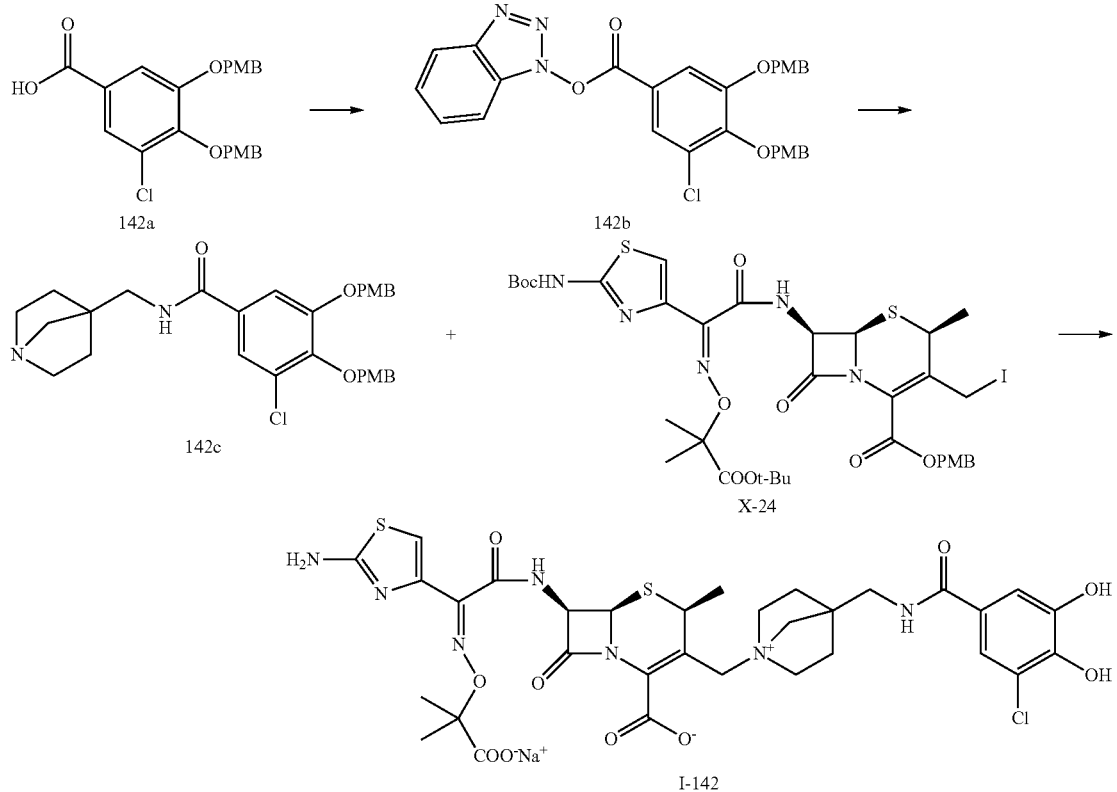

Step (1): Compound 142a→Compound 142b

Compound 142a (12.8 g, 30.0 mmol) was used to synthesized the compound 142b in the same way as in Step (1) of example 117.

Yielded amount: 14.1 g, (86%)

$^1$H-NMR (CDCl$_3$) δ: 8.11 (d, J=8.6 Hz, 1H), 7.97 (s, 1H), 7.74 (s, 1H), 7.60-7.53 (m, 1H), 7.49-7.43 (m, 2H), 7.39 (d, J=8.3 Hz, 2H), 7.33 (d, J=8.3 Hz, 2H), 6.94 (d, J=8.3 Hz, 2H), 6.85 (d, J=8.3 Hz, 2H), 5.17 (s, 2H), 5.14 (s, 2H), 3.84 (s, 3H), 3.81 (s, 3H).

Step (2): Compound 142b→Compound 142c

Compound 142b (1.63 g, 3.00 mmol) was used to synthesized the compound 142c in the same way as in Step (2) of example 117.

Yielded amount: 1.53 g (95%)

$^1$H-NMR (CDCl$_3$) δ: 7.41 (d, J=1.6 Hz, 1H), 7.37 (d, J=8.5 Hz, 2H), 7.32 (d, J=8.5 Hz, 2H), 6.93 (d, J=8.4 Hz, 2H), 6.82 (d, J=8.4 Hz, 2H), 6.09 (t, J=5.8 Hz, 1H), 5.10 (s, 2H), 5.03 (s, 2H), 3.83 (s, 3H), 3.80 (s, 3H), 3.78 (d, J=6.3 Hz, 2H), 3.04-2.92 (m, 2H), 2.66-2.60 (m, 2H), 2.34 (s, 2H), 1.35-1.22 (m, 2H).

Step (3): Compound 142c+Compound X-24→Compound I-142

Compound X-24 (0.886 g, 1.00 mmol) and compound 142c (0.537 g, 1.00 mmol) were used to synthesized the target compound in the same way as in Step (4) of example 107.

Yielded amount: 0.291 g (36%)

$^1$H-NMR (D$_2$O) δ: 7.38 (d, J=1.8 Hz, 1H), 7.22 (d, J=1.8 Hz, 1H), 6.99 (s, 1H), 5.77 (d, J=4.7 Hz, 1H), 5.40 (d, J=4.7 Hz, 1H), 4.90 (d, J=14.4 Hz, 1H), 4.24 (d, J=14.4 Hz, 1H), 4.04 (q, J=7.1 Hz, 1H), 3.74-3.51 (m, 6H), 3.41 (d, J=8.5 Hz, 1H), 3.31 (d, J=8.5 Hz, 1H), 2.29-2.15 (m, 2H), 2.02-1.92 (m, 2H), 1.55 (d, J=7.1 Hz, 3H), 1.52-1.48 (m, 6H).

Elemental Analysis: C32H35ClN7NaO10S2 (H2O) 6.4

Calcd.: C, 41.98; H, 5.26; N, 10.71; Cl, 3.87; Na, 2.51(%).

Found: C, 41.94; H, 5.16; N, 10.87; Cl, 3.72; Na, 2.61(%).

Example 143: Synthesis of Compound I-143

Step (1): Compound X-24→Compound 143a)

Compound 143a: 1-((6,7-bis((4-methoxybenzyl)oxy)-1-methyl-4-oxo-1,4-dihydroquinolin-3-yl)methyl)-1-(((4S,6R,7R)-7-((Z)-2-(((1-(tert-butoxy)-2-methyl-1-oxopropan-2-yl)oxy)imino)-2-(2-((tert-butoxycarbonyl)amino)thiazol-4-yl)acetamido)-2-(((4-methoxybenzyl)oxy)carbonyl)-4-methyl-8-oxo-5-thia-1-azabicyclo[4.2.0]oct-2-en-3-yl)methyl)pyrrolidin-1-ium, Iodide

[Chemical Formula 289]

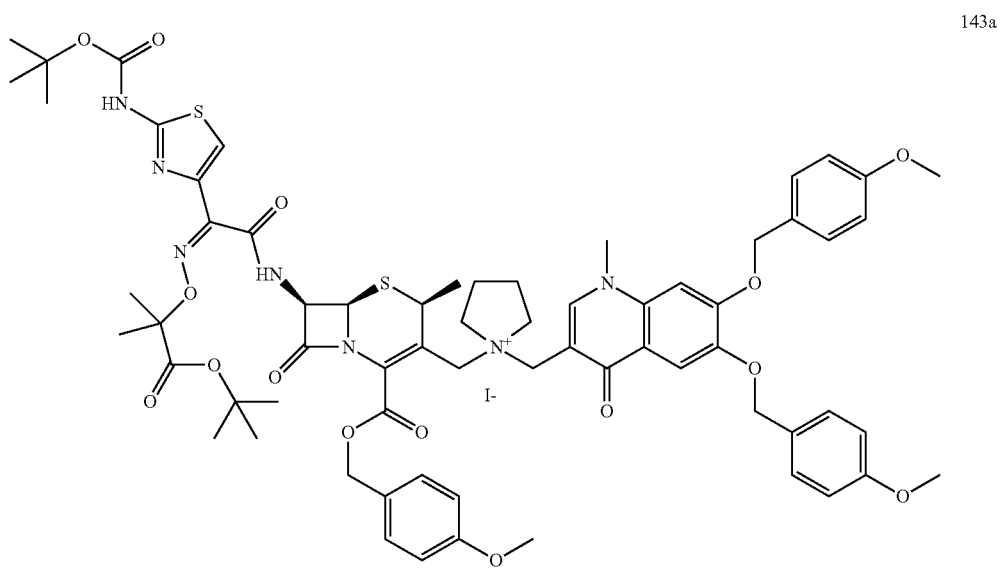

143a 6,7-bis((4-methoxybenzyl)oxy)-1-methyl-3-(pyrrolidin-1-ylmethyl)quinolin-4(1H)-one (WO2013052568A1 0.588 g, 1.14 mmol) in DMF (5 mL) at 0° C. under nitrogen was added compound X-24 (1.063 g, 1.200 mmol) (in DMF (5 mL). The mixture was stirred at the same temperature over 3 h, and was left in a freezer overnight. The solution was poured into ice-cooled 5% NaCl aq (100 mL) containing NaHSO$_3$ (1 g) and was stirred for 15 min. The solid was collected by filtration, washed with water and dried, and purified by automated silica gel chromatography (Combi-flash RF), eluting with MeOH/DCM (0-20%) to afford compound 143a (0.269 g, 15% yield) as a brown solid. LCMS: (M+H)$^+$: 1273.5.

Step (2): Compound 143a→Compound I-143

Compound I-143: (4S,6R,7R)-7-((Z)-2-(2-aminothi-azol-4-yl)-2-(((2-carboxypropan-2-yl)oxy)imino)acetamido)-3-((1-((6,7-dihydroxy-1-methyl-4-oxo-1,4-dihydroquinolin-3-yl)methyl)pyrrolidin-1-ium-1-yl) methyl)-4-methyl-8-oxo-5-thia-1-azabicyclo[4.2.0]oct-2-ene-2-carboxylate, Sodium salt

[Chemical Formula 290]

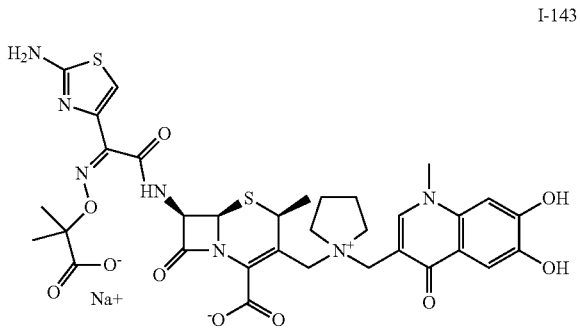

I-143 compound 143a (0.269 g, 0.142 mmol) in DCM (1.5 mL) at 0° C. was added anisole (0.16 mL, 1.42 mmol), followed by TFA (0.50 mL, 6.5 mmol). The mixture was warmed up to rt and then stirred overnight. Diisopropyl ether (30 mL) was added, and the mixture was stirred for 10 min. The resulting precipitate was collected by filtration, and washed twice with diisopropyl ether (2×5 mL). The solid was dissolved in a mixture of MeCN (6 mL), water (6 mL), and 2M HCl aq (1.5 mL), and HP20SS resin (6 g) was added. The mixture was concentrated to dryness, and the resin was loaded onto a pre-column containing HP20SS resin (10 g), and purified by automated reverse phase chromatography eluting with 0-20% MeCN/water to afford (4S,6R,7R)-7-((Z)-2-(2-aminothiazol-4-yl)-2-(((2-carboxypropan-2-yl)oxy)imino)acetamido)-3-((1-((6,7-dihydroxy-1-methyl-4-oxo-1,4-dihydroquinolin-3-yl)methyl)pyrrolidin-1-ium-1-yl) methyl)-4-methyl-8-oxo-5-thia-1-azabicyclo[4.2.0]oct-2-ene-2-carboxylate (67 mg, 62% yield) as an off-white solid. A portion of this product (56 mg, 0.074 mmol) was suspended in water (HPLC grade, 10 mL) and cooled to 0° C. To the vigorously stirring suspension was added 0.1N NaOH aq (0.74 mL, 0.074 mmol) slowly using an Eppendorf pipette. After the addition was complete, a small piece of dry ice was added to quench any extra NaOH. The pale yellow solution was then frozen and lyophilized to afford compound I-143 (57 mg) as an off-white solid.

LCMS: (M+H)$^+$: 756.2. $^1$H NMR (400 MHz, D$_2$O) δ ppm 1.32-1.43 (m, 9H) 2.10 (d, J=10.86 Hz, 4H) 3.25 (br. s., 3H) 3.48 (br. s., 1H) 3.80 (s, 3H) 4.00 (d, J=6.57 Hz, 1H) 4.11 (d, J=14.40 Hz, 1H) 4.33 (s, 2H) 4.78-4.81 (m, 1H) 5.35 (d, J=4.80 Hz, 1H) 5.70 (d, J=4.80 Hz, 1H) 6.87 (s, 1H) 6.96 (s, 1H) 7.48 (s, 1H) 8.05 (s, 1H).

The compounds shown below were obtained from Compound X-24 and the each corresponding amine which was synthesized according to the synthesis in WO2013052568A1 in the same way as example 143.

Example 144: Synthesis of Compound I-144

Compound I-144: (4S,6R,7R)-7-((Z)-2-(2-aminothi-azol-4-yl)-2-(((2-carboxypropan-2-yl)oxy)imino)acetamido)-3-((1-((1-ethyl-5-fluoro-6,7-dihydroxy-4-oxo-1,4-dihydroquinolin-3-yl)methyl)pyrrolidin-1-ium-1-yl)methyl)-4-methyl-8-oxo-5-thia-1-azabicyclo[4.2.0]oct-2-ene-2-carboxylate, Sodium salt

[Chemical Formula 291]

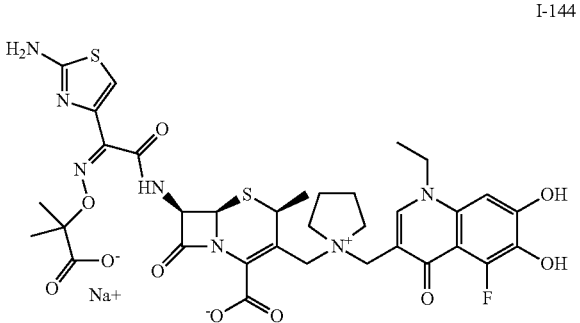

I-144

LCMS: (M+H)$^+$: 788.1. $^1$H NMR (400 MHz, D$_2$O) δ ppm 1.24-1.48 (m, 12H) 1.99-2.23 (m, 4H) 3.22 (br. s., 3H) 3.46 (d, J=3.28 Hz, 1H) 3.96-4.17 (m, 4H) 4.27 (br. s., 2H) 4.79 (d, J=7.33 Hz, 1H) 5.35 (d, J=4.80 Hz, 1H) 5.70 (d, J=4.80 Hz, 1H) 6.70 (s, 1H) 6.85 (s, 1H) 8.03 (s, 1H).

Example 145: Synthesis of Compound I-145

Compound I-145: (4S,6R,7R)-7-((Z)-2-(2-aminothi-azol-4-yl)-2-(((2-carboxypropan-2-yl)oxy)imino)acetamido)-3-((1-((5-chloro-6,7-dihydroxy-1-methyl-4-oxo-1,4-dihydroquinolin-3-yl)methyl)pyrrolidin-1-ium-1-yl)methyl)-4-methyl-8-oxo-5-thia-1-azabicyclo[4.2.0]oct-2-ene-2-carboxylate, Sodium salt

[Chemical Formula 292]

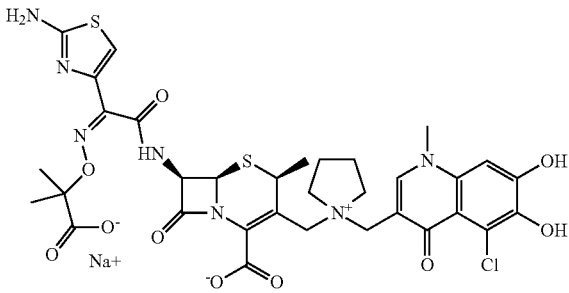

I-145

LCMS: (M+H)$^+$: 790.0. $^1$H NMR (400 MHz, D$_2$O) δ ppm 1.27-1.50 (m, 9H) 2.08 (br. s., 4H) 3.21 (d, J=6.32 Hz, 3H) 3.45 (br. s., 1H) 3.63 (br. s., 3H) 3.95-4.12 (m, 2H) 4.21 (br. s., 2H) 4.78 (d, J=11.62 Hz, 1H) 5.36 (d, J=4.80 Hz, 1H) 5.70 (d, J=4.80 Hz, 1H) 6.65 (br. s., 1H) 6.85 (s, 1H) 7.91 (br. s., 1H).

Example 146: Synthesis of Compound I-146

Step (1):
6,7-dimethoxyquinazolin-4(3H)-one→Compound 146a

Compound 146a: 3-(2-chloroethyl)-6,7-dimethoxy-quinazolin-4(3H)-one

[Chemical Formula 293]

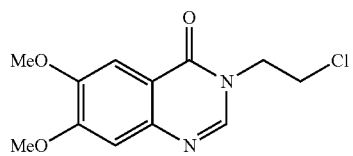

To a solution of 6,7-dimethoxyquinazolin-4(3H)-one (5.0 g, 24 mmol) in DMF (100 mL) was added 1-chloro-2-iodoethane (3.48 mL, 48.5 mmol) dropwise at 50° C., and the mixture was stirred overnight. Water was added, the mixture was extracted with ethyl acetate. The organic layer was dried (Na$_2$SO$_4$), concentrated and purified by automated silica gel chromatography (10% MeOH in DCM) to afford compound 146a (6.5 g, 96% yield) as a yellow solid. LCMS: (M+H)$^+$: 269.0.

Step (2): Compound 146a→Compound 146b

Compound 146b: 3-(2-chloroethyl)-6,7-dihydroxy-quinazolin-4(3H)-one

[Chemical Formula 294]

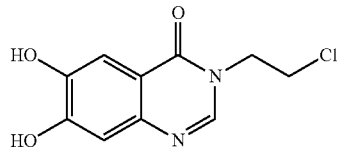

To a solution of compound 146a in DCM (100 mL) was added BBr$_3$ dropwise at −70° C., and the mixture was allowed to warm up to room temperature and stirred for 1 h. MeOH was added to the mixture dropwise at 0° C., and then the solvent was removed in vacuo. The residue was purified by silica gel chromatography (20% MeOH in DCM) to afford compound 146b (5.7 g, 91% yield). LCMS: (M+H)$^+$: 241.2.

Step (3): Compound 146b→Compound 146c

Compound 146c: 3-(2-chloroethyl)-6,7-bis((4-methoxybenzyl)oxy)quinazolin-4(3H)-one

[Chemical Formula 295]

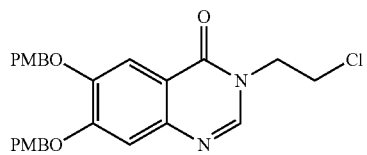

To a solution of 1-(chloromethyl)-4-methoxybenzene (14.8 g, 95.0 mmol) in DMF (100 mL) was added potassium carbonate (16.4 g, 118 mmol) and 1-(chloromethyl)-4-methoxybenzene (14.8 g, 95.0 mmol), and this mixture was stirred at 50° C. overnight. Water was added, and the mixture was extracted with ethyl acetate. The organic layer was dried (Na$_2$SO$_4$), filtered, and concentrated, and the residue was purified using silica gel chromatography (Combiflash RF) to afford compound 146c (7.8 g, 69% yield). LCMS: (M+H)$^+$: 480.9.

Step (4): Compound 146c→Compound 146d

Compound 146d: 6,7-bis((4-methoxybenzyl)oxy)-3-(2-(pyrrolidin-1-yl)ethyl)quinazolin-4(3H)-one

[Chemical Formula 296]

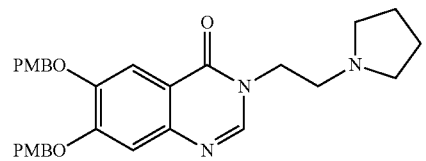

To a solution of compound 146c (7.00 g, 14.6 mmol) in DCM (150 mL) were added DIPEA (6.36 mL, 36.4 mmol) and pyrrolidine (3.01 mL, 36.4 mmol), and the mixture was heated to 80° C. The reaction mixture was washed with 5% NaHCO$_3$ aq (40 mL), brine, and H$_2$O, and the organic layer was dried (Na$_2$SO$_4$), filtered, and concentrated, and the residue was purified by automated silica gel chromatography (20% MeOH in DCM) to afford compound 146d (2.9 g, 39% yield). LCMS: (M+H)$^+$: 516.3.

Step (5): Compound X-24+Compound 146d→Compound I-146

Compound I-146 (4S,6R,7R)-7-((Z)-2-(2-aminothiazol-4-yl)-2-(((2-carboxypropan-2-yl)oxy)imino)acetamido)-3-((1-(2-(6,7-dihydroxy-4-oxoquinazolin-3(4H)-yl)ethyl)pyrrolidin-1-ium-1-yl)methyl)-4-methyl-8-oxo-5-thia-1-azabicyclo[4.2.0]oct-2-ene-2-carboxylate, Sodium salt

[Chemical Formula 297]

I-146

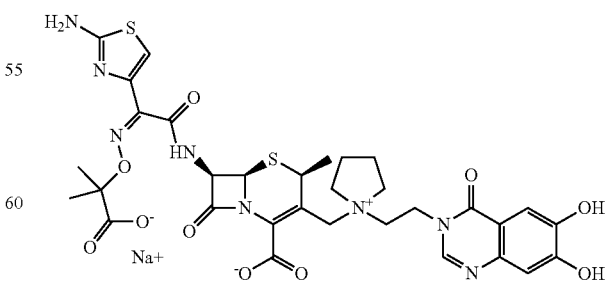

This compound was prepared according to the two-step sequence of Example 143, using compound 146d and compound X-24.

¹H NMR (400 MHz, D₂O) δ ⌊ppm 1.37 (s, 3H) 1.39 (s, 3H) 1.47 (d, J=7.07 Hz, 3H) 2.13 (br. s., 4H) 3.35-3.60 (m, 5H) 3.68 (d, J=10.61 Hz, 1H) 3.99 (q, J=6.99 Hz, 1H) 4.19 (d, J=14.15 Hz, 1H) 4.24-4.41 (m, 2H) 5.00 (d, J=14.15 Hz, 1H) 5.34 (d, J=5.05 Hz, 1H) 5.69 (d, J=4.80 Hz, 1H) 6.72 (s, 1H) 6.86 (s, 1H) 7.11 (s, 1H) 8.00 (s, 1H).

Example 147: Synthesis of Compound I-147

Step (1): 6,7-dimethoxyquinazoline-2,4(1H,3H)-dione→Compound 147a

Compound 147a: 6,7-dimethoxy-1-methylquinazoline-2,4(1H,3H)-dione

[Chemical Formula 298]

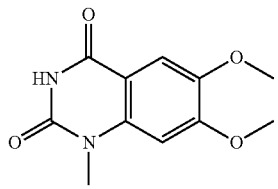

To a suspension of 6,7-dimethoxyquinazoline-2,4(1H,3H)-dione (40.0 g, 180 mmol) in anhydrous chloroform (300 mL) was added (E)-trimethylsilyl N-(trimethylsilyl)acetamidate (156 mL, 630 mmol), and the mixture was stirred at room temperature until a clear solution was obtained (2 h). Iodomethane (168 mL, 2700 mmol) was then added. The reaction mixture was heated to reflux temperature for 48 h. After the solution was cooled to room temperature, sat. NaHCO₃ aq (30 mL) was added, and the precipitate was collected by filtration to afford compound 147a (38 g, 89% yield) as a white solid. LCMS: (M+H)⁺:237.1.

Step (2): Compound 147a→Compound 147b

Compound 147b: 3-(2-chloroethyl)-6,7-dimethoxy-1-methylquinazoline-2,4(1H,3H)-dione

[Chemical Formula 299]

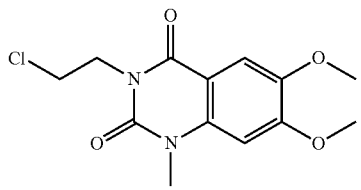

To a solution of compound 147a (28.0 g, 119 mmol) in DMF (20 mL) was added cesium carbonate (77.0 g, 237 mmol), followed by 1-chloro-2-iodoethane (21.6 mL, 237 mmol). The reaction mixture was stirred at 50° C. overnight. Water was added and the mixture was stirred at rt for 15 min. The white precipitate was collected by filtration and washed with water to afford compound 147b (29 g, 82% yield). The crude mixture was used in next Step without purification. LCMS: (M+H)⁺: 299.0.

Step (3): Compound 147b→Compound 147c

Compound 147c 5-chloro-3-(2-chloroethyl)-6,7-dimethoxy-1-methylquinazoline-2,4(1H,3H)-dione

[Chemical Formula 300]

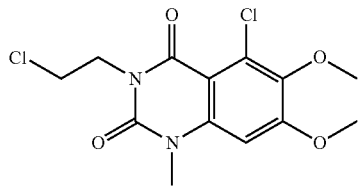

3-(2-chloroethyl)-6,7-dimethoxy-1-methylquinazoline-2,4(1H,3H)-dione compound 147b (29 g, 97 mmol) and 1-chloropyrrolidine-2,5-dione (19.5 g, 146 mmol) were suspended in DMF (40 mL) and heated at 95° C. for 0.5 h. Water and ethyl acetate (300 mL) were added to the mixture. The organic phase was separated, and the aqueous phase was extracted with ethyl acetate (2×300 mL). The combined organic phases were dried, filtered and concentrated. The residue was purified by silica gel chromatography (0-15%, EtOAc in hexane) to afford compound 147c (10 g, 31% yield). LCMS: (M+H)⁺: 333.0.

Step (4): Compound 147c→Compound 147d

Compound 147d: 5-chloro-3-(2-chloroethyl)-6,7-dihydroxy-1-methylquinazoline-2,4(1H,3H)-dione

[Chemical Formula 301]

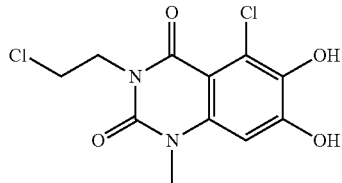

To a solution of compound 147c (10 g, 30.0 mmol) in DCM (25 mL) was added BBr₃ (14.2 mL, 150 mmol) at −78° C. The mixture was allowed to warm up to rt, and stirred for 2 h. The mixture was diluted with MeOH and stripped several times to afford compound 147d (8.8 g, 96% yield) as a yellow solid. The crude product was used in next Step without further purification. LCMS: (M+H)⁺: 304.9.

Step (5): Compound 147d→Compound 147e

Compound 147e: 5-chloro-3-(2-chloroethyl)-6,7-bis((4-methoxybenzyl)oxy)-1-methylquinazoline-2,4(1H,3H)-dione

[Chemical Formula 302]

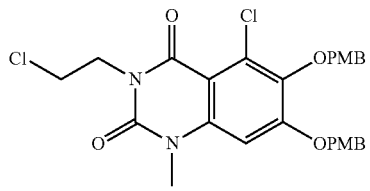

To a solution of compound 147d (4.40 g, 10.1 mmol) in DMF (120 mL) was added cesium carbonate (9.87 g, 30.3 mmol), followed by 1-(chloromethyl)-4-methoxybenzene (5.50 mL, 40.4 mmol). The reaction mixture was stirred at 50° C. for 5 h. Water was added and the mixture was stirred at rt for 15 min. The yellow precipitate was collected by filtration and washed with water. The crude material was purified by automated silica gel chromatography, using a 40 g column and eluting with EA/Hexane (0-30%) to afford compound 147e (2.3 g, 42% yield) as a yellow solid. LCMS: (M+H)$^+$: 545.1.

Step (6): Compound 147e→Compound 147f

Compound 147f: 5-chloro-6,7-bis((4-methoxybenzyl)oxy)-1-methyl-3-(2-(pyrrolidin-1-yl)ethyl)quinazoline-2,4(1H,3H)-dione

[Chemical Formula 303]

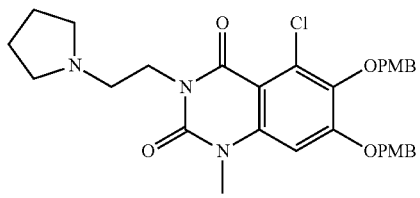

A solution of compound 147e (2.3 g, 4.2 mmol), DIPEA (1.363 g, 10.54 mmol), and pyrrolidine (0.750 g, 10.5 mmol) in acetonitrile (100 mL) was heated at reflux temperature for 6 h. Water was added, and the product was extracted with DCM. The organic phase was washed with NaHCO$_3$ aq, brine and then dried over Na$_2$SO$_4$, filtered and concentrated. The crude material was purified by automated silica gel chromatography using a 24 g column and eluting with 0-5% MeOH in DCM to afford compound 147f (1 g, 41% yield) as a yellow solid. LCMS: (M+H)$^+$: 580.3.

Step (7): Compound X-24+Compound 147f→Compound I-147

Compound I-147: (4S,6R,7R)-7-((Z)-2-(2-aminothiazol-4-yl)-2-(((2-carboxypropan-2-yl)oxy)imino)acetamido)-3-((1-(2-(5-chloro-6,7-dihydroxy-1-methyl-2,4-dioxo-1,2-dihydroquinazolin-3(4H)-yl)ethyl)pyrrolidin-1-ium-1-yl)methyl)-4-methyl-8-oxo-5-thia-1-azabicyclo[4.2.0]oct-2-ene-2-carboxylate, Sodium salt

[Chemical Formula 304]

I-147

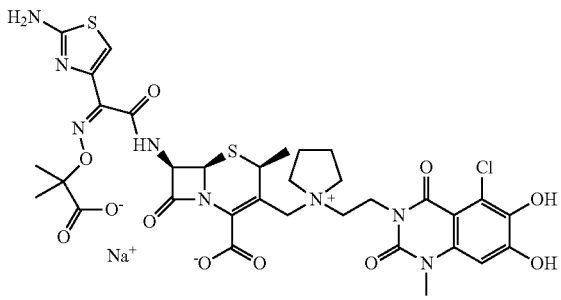

This compound was prepared according to the two-step sequence of Example 143, using compound 147f and compound X-24.

LCMS: (M+H)$^+$: 821.0. $^1$H NMR (400 MHz, D$_2$O) δ ppm 1.38 (s, 3H) 1.40 (s, 3H) 1.48 (d, J=6.82 Hz, 3H) 2.12 (br. s., 4H) 3.32 (br. s., 3H) 3.35-3.66 (m, 6H) 3.98-4.07 (m, 1H) 4.16-4.36 (m, 3H) 4.98 (d, J=14.15 Hz, 1H) 5.37 (d, J=4.80 Hz, 1H) 5.68 (d, J=4.29 Hz, 1H) 6.48 (s, 1H) 6.91 (s, 1H).

Example 148: Synthesis of Compound I-148

Step (1): Methyl 2-amino-4,5-difluorobenzoate→Compound 148a

Compound 148a: Methyl 2-amino-3-chloro-4,5-difluorobenzoate

[Chemical Formula 305]

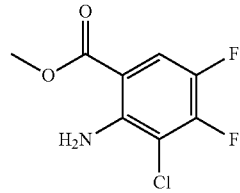

Methyl 2-amino-4,5-difluorobenzoate (40.0 g, 214 mmol) and NCS (25.9 g, 194 mmol) were suspended in DMF (10 mL) and heated at 95° C. for 30 min. Water and DCM were added to the mixture. The organic phase was separated. The water phase was extracted with DCM (2×10 mL). The combined organic phase was dried, filtered and concentrated. The resulting residue was purified via normal phase chromatography (0-40% EtOAc in hexane) to afford Compound 148a (11 g, 26% yield) as a white solid. LCMS: (M+H)$^+$: 221.9.

Step (2): Compound 148a→Compound 148b

Compound 148b: 8-chloro-2-(chloromethyl)-6,7-difluoroquinazolin-4(3H)-one

[Chemical Formula 306]

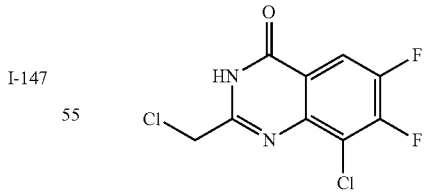

Hydrogen chloride gas was bubbled through a solution of compound 148a (150 mL, 2380 mmol) until the precipitate that initially formed had dissolved. This mixture was stirred at rt overnight. Water was added to the reaction mixture, and the resulting precipitate was collected by filtration and dried under high vacuum to afford Compound 148b (8.0 g, 67% yield) as gray solid.

LCMS: (M+H)$^+$: 264.9.

Step (3): Compound 148b→Compound 148c

Compound 148c: 8-chloro-6,7-difluoro-2-(pyrrolidin-1-ylmethyl)quinazolin-4(3H)-one

[Chemical Formula 307]

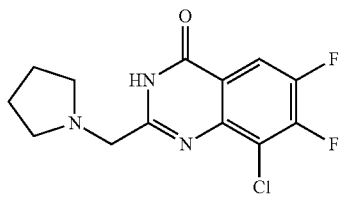

To a solution of Compound 148b (5.00 g, 18.9 mmol) in DCM (120 mL) was added a solution of pyrrolidine (3.90 mL, 47.2 mmol) in DCM dropwise, and this mixture was stirred at rt for 2 h. The reaction mixture was washed with brine (3×), and the organic layer was dried with $Na_2SO_4$, filtered, and concentrated to Compound 148c (5.0 g, 88% yield) as a white solid. LCMS: $(M+H)^+$: 300.3.

Step (4): Compound 148c→Compound 148d

Compound 148d: 8-chloro-6,7-bis((4-methoxybenzyl)oxy)-2-(pyrrolidin-1-ylmethyl)quinazolin-4(3H)-one

[Chemical Formula 308]

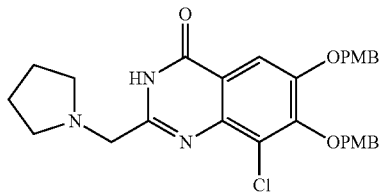

A mixture of (4-methoxyphenyl)methanol (46.1 g, 334 mmol) and Compound 148c (5.00 g, 16.7 mmol) was heated at 80° C. over the weekend. Water was added to the reaction mixture, and the pH was adjusted to 2 using 2N HCl aq, and the product was extracted with DCM. The organic layer was washed with brine and concentrated, and the residue was purified by automated reverse phase chromatography (70% MeCN in $H_2O$ containing 0.1% TFA). The combined fractions were then neutralized using 2N NaOH, and the product was extracted with DCM. The organic layer was dried, filtered, concentrated and then repurified by automated silica gel chromatography to afford Compound 148d (350 mg, 3.9% yield).

LCMS: $(M+H)^+$: 536.0.

Step (5): Compound X-24+Compound 148d→Compound I-148

Compound I-148: (4S,6R,7R)-7-((Z)-2-(2-aminothiazol-4-yl)-2-(((2-carboxypropan-2-yl)oxy)imino)acetamido)-3-((1-((8-chloro-6,7-dihydroxy-4-oxo-3,4-dihydroquinazolin-2-yl)methyl)pyrrolidin-1-ium-1-yl)methyl)-4-methyl-8-oxo-5-thia-1-azabicyclo[4.2.0]oct-2-ene-2-carboxylate, Sodium salt

[Chemical Formula 309]

I-148

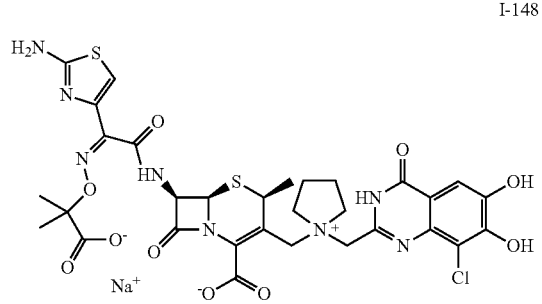

This compound was prepared according to the two-Step sequence of Example 143, using compound 148d and compound X-24.

LCMS: $(M+H)^+$: 777.1. $^1H$ NMR (400 MHz, $D_2O$) δ ppm 1.35 (s, 9H) 2.14 (br. s., 4H) 3.51-4.03 (m, 6H) 4.43 (q, J=15.49 Hz, 2H) 4.93 (d, J=13.89 Hz, 2H) 5.10 (d, J=5.05 Hz, 1H) 5.63 (d, J=4.80 Hz, 1H) 6.86 (s, 1H) 7.29 (s, 1H).

Example 149: Synthesis of Compound I-149

Step (1): 2,4,5-trifluorobenzoyl chloride→Compound 149a

Compound 149a: Ethyl 3-(dimethylamino)-2-(2,4,5-trifluorobenzoyl)acrylate

[Chemical Formula 310]

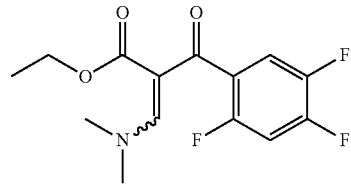

A solution of 2,4,5-trifluorobenzoyl chloride (50 g, 257 mmol) in toluene was added dropwise to a solution of triethylamine (107 mL, 771 mmol) and ethyl 3-(dimethylamino)acrylate (44.2 g, 308 mmol) in toluene (500 mL). The mixture was stirred at 90° C. for 3 h. The reaction mixture was cooled down and then was washed with water and extracted with EtOAc. The organic layer was dried over $Na_2SO_4$, filtered and concentrated to afford compound 149a (75 g, 97% yield) as brown oil. The crude product was used in next Step without further purification. LCMS: $(M+H)^+$: 302.0,

Step (2): Compound 149a→Compound 149b

Compound 149b: Ethyl 6,7-difluoro-1-methyl-4-oxo-1,4-dihydroquinoline-3-carboxylate

[Chemical Formula 311]

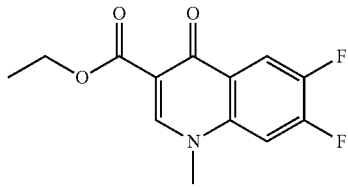

A solution of compound 149a (70 g, 232 mmol) in ethanol (200 mL) and diethyl ether (400 mL) was added to methanamine (54.7 mL, 465 mmol). After the mixture was stirred for 2 h at rt, analysis of the mixture by LCMS indicated that the reaction was complete. The reaction mixture was concentrated under reduced pressure, the oily residue was dissolved in DMF (500 mL) and potassium carbonate (96.0 g, 697 mmol) was added. The mixture was stirred at 100° C. for 2 h. Cold water was added to the reaction mixture. The resulting precipitate was collected by filtration and dried to afford compound 149b (45 g, 73% yield). LCMS: (M+H)$^+$: 267.9.

Step (3): Compound 149b→Compound 149c

Compound 149c: 6,7-Dimethoxy-1-methyl-4-oxo-1,4-dihydroquinoline-3-carboxylic acid

[Chemical Formula 312]

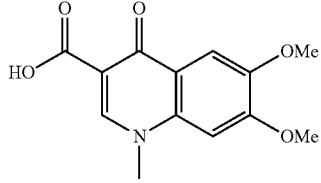

A mixture of compound 149b (45.0 g, 168 mmol), potassium hydroxide (472 g, 8420 mmol) and methanol (1 L) was heated at reflux temperature for 6 h. The pH of the solution was adjusted to 2, and the mixture was concentrated in vacuo. The obtained residue was triturated with water to afford compound 149c (35 g, 79% yield) as a pale yellow solid. The crude product was used in next Step without further purification. LCMS: (M+H)$^+$: 264.0.

Step (4): Compound 149c→Compound 149d

Compound 149d: 6,7-Dimethoxy-1-methyl-5-nitro-4-oxo-1,4-dihydroquinoline-3-carboxylic acid

[Chemical Formula 313]

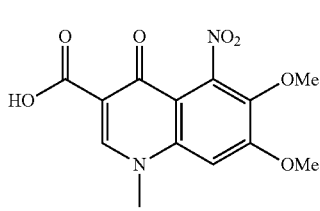

A thick, dark solution of compound 149c (35 g, 133 mmol) dissolved in sulfuric acid (354 mL, 6648 mmol) was cooled to 0° C. and potassium nitroperoxous acid (16.1 g, 160 mmol) was added in small portions. The temperature of the reaction mixture was maintained below 10° C. by use of an ice-water bath. After the addition was complete, the mixture was maintained under 10° C. for 1 h, and was then allowed to warm up to rt. The mixture was stirred at this temperature for 2 h, after which time it was poured onto ice-water (800 mL). The yellow solid that precipitated was collected by filtration, and washed with water and ethanol. The solid was dried in vacuo to afford compound 148d (30 g, 73% yield) as a pale yellow solid. The crude product was used in next Step without further purification. LCMS: (M+H)$^+$: 337.4

Step (5): Compound 149d→Compound 149e

Compound 149e: 5-Amino-6,7-dimethoxy-1-methyl-4-oxo-1,4-dihydroquinoline-3-carboxylic acid

[Chemical Formula 314]

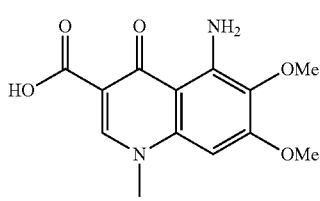

A solution of ethyl compound 149d (30 g, 89 mmol) in a mixture of ethanol (300 mL) and water (300 mL) was treated with sodium sulfide.9H$_2$O (214 g, 892 mmol) for 2 h at 90° C. After the mixture was cooled down, it was poured into cold water, and the solution was adjusted to pH 2. The resulting yellow precipitate was collected by filtration, washed with water and dried to afford compound 148e (24 g, 97% yield) as a yellow solid. The crude product was used in next Step without further purification.

LCMS: (M+H)$^+$: 279.0

Step (6): Compound 149e→Compound 149f

Compound 149f: 5-Chloro-6-hydroxy-7-methoxy-1-methyl-4-oxo-1,4-dihydroquinoline-3-carboxylic acid

[Chemical Formula 315]

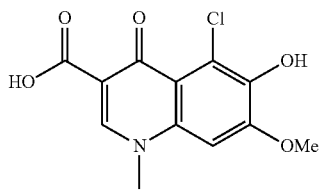

To a pale brown suspension of compound 149e (24 g, 69 mmol) in conc. HCl aq (120 mL) was added dropwise a solution of sodium nitrosamide (4.69 g, 69.0 mmol) in water (40 mL) at 0° C. The mixture was stirred at 0° C. for 1 h. To the orange suspension was added HCl aq (180 mL), and the mixture was heated at 95° C. for 6 h. The reaction mixture was cooled down to rt and then poured into water, and the precipitate was collected by filtration and dried to afford compound 149f (13 g, 66% yield) as a pale yellow solid. The crude product was used in next Step without further purification. LCMS: $(M+H)^+$: 283.9.

Step (7): Compound 149f→Compound 149g

Compound 149g: 5-Chloro-6,7-dihydroxy-1-methyl-4-oxo-1,4-dihydroquinoline-3-carboxylic acid

[Chemical Formula 316]

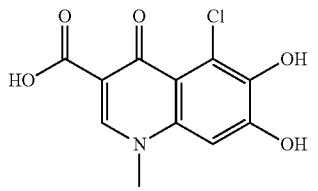

To a solution of compound 149f (17.6 mL, 45.8 mmol) in DCM (300 mL) was added BBr$_3$ (15.2 mL, 160 mmol) at −78° C. The mixture was allowed to warm up to rt, and stirred overnight. The mixture was diluted with MeOH and stripped several times to afford compound 149g (11 g, 89% yield) as a yellow solid. The crude product was used in next Step reaction without further purification. LCMS: $(M+H)^+$: 269.9.

Step (8): Compound 149g→Compound 149h

Compound 149h: 4-methoxybenzyl 5-chloro-6,7-bis((4-methoxybenzyl)oxy)-1-methyl-4-oxo-1,4-dihydroquinoline-3-carboxylate

[Chemical Formula 317]

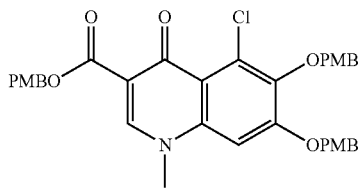

To a solution of compound 149g (11 g, 40.8 mmol) in DMF (250 mL) was added cesium carbonate (39.9 g, 122 mmol), followed by 1-(chloromethyl)-4-methoxybenzene (22.2 mL, 163 mmol). The reaction mixture was stirred at 55° C. for 5 h. Water was added, and the mixture was stirred at rt for 15 min. The yellow precipitate was collected by filtration and washed with water to afford compound 149h (20 g, 78% yield) as a yellow solid. The crude mixture was used in next Step without purification. LCMS: $(M+H)^+$: 630.3.

Step (9): Compound 149h→Compound 149j

Compound 149j: 5-Chloro-6,7-bis((4-methoxybenzyl)oxy)-1-methyl-4-oxo-1,4-dihydroquinoline-3-carboxylic acid

[Chemical Formula 318]

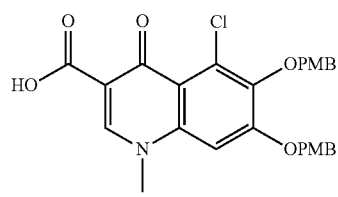

To a suspension of compound 149h (20.0 g, 31.7 mmol) in a mixture of methanol (120 mL) and water (60 mL) was added KOH (3.56 g, 63.5 mmol) portionwise. The resulting mixture was stirred at 90° C. for 3 h. The reaction mixture was cooled down to rt and concentrated. The residue was then diluted with water and the solution was adjusted to pH 1 using 2N HCl aq. The precipitate was collected by filtration and dried to afford compound 149j (13.5 g, 83% yield) as a pale yellow solid. The crude product was used in the next Step without further purification. LCMS: $(M+H)^+$: 510.2

Step (10): Compound 149j→Compound 149k

Compound 149k: 5-Chloro-6,7-bis((4-methoxybenzyl)oxy)-1-methyl-4-oxo-N-(2-(pyrrolidin-1-yl)ethyl)-1,4-dihydroquinoline-3-carboxamide

[Chemical Formula 319]

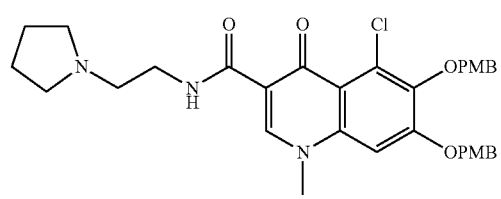

To a solution of compound 149j (2.0 g, 2.7 mmol) in DMF (100 mL) were added HATU (1.03 g, 2.71 mmol) and DIPEA (1.42 mL, 8.12 mmol), and the mixture was stirred for 0.5 h. To this mixture was added 2-(pyrrolidin-1-yl)ethanamine (0.34 mL, 2.7 mmol). Analysis of the reaction mixture by LCMS indicated that the reaction was complete in 1 h. Water was added, and the mixture was extracted with DCM and washed with brine. The crude material was purified by automated silica gel chromatography using a 24 g column and eluting with 0-20% MeOH/DCM. The pure product was then washed by sodium bicarbonate aq, and further purified using a 4 g silica gel column and eluting with 0-20% MeOH/DCM to afford compound 149k (1.3 g, 79% yield) as a yellow solid. LCMS: $(M+H)^+$: 606.3

Step (11): Compound X-24+Compound 149k→Compound I-149

Compound I-149: (4S,6R,7R)-7-((Z)-2-(2-aminothiazol-4-yl)-2-(((2-carboxypropan-2-yl)oxy)imino)acetamido)-3-((1-(2-(5-chloro-6,7-dihydroxy-1-methyl-4-oxo-1,4-dihydroquinoline-3-carboxamido)ethyl)pyrrolidin-1-ium-1-yl)methyl)-4-methyl-8-oxo-5-thia-1-azabicyclo[4.2.0]oct-2-ene-2-carboxylate, Sodium salt

[Chemical Formula 320]

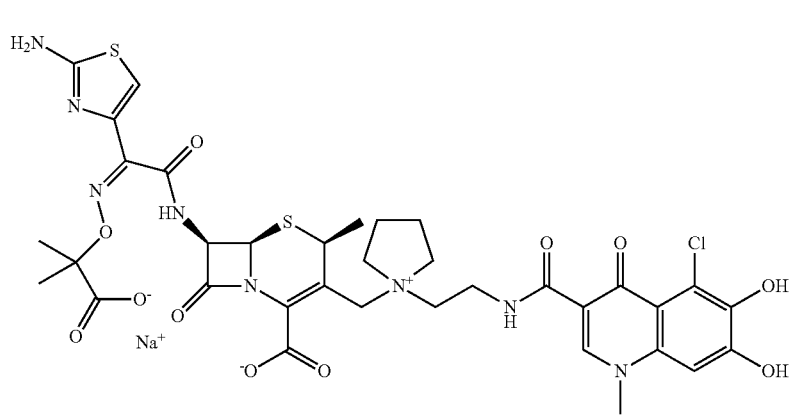

I-149

This compound was prepared according to the two-Step sequence of Example 143, using compound 149k and compound X-24.

LCMS: (M+H)$^+$: 777.1. $^1$H NMR (400 MHz, D$_2$O) δ ppm 1.36 (s, 3H) 1.40 (s, 3H) 1.47 (br. s., 3H) 1.99-2.22 (m, 4H) 3.27-4.28 (m, 13H) 4.90 (br. s., 1H) 5.37 (d, J=4.80 Hz, 1H) 5.76 (br. s., 1H) 6.47 (br. s., 1H) 6.85 (s, 1H) 8.10 (br. s., 1H).

Example 150: Synthesis of Compound I-150

Step (1):
4,5-dihydroxy-2-nitrobenzaldehyde→Compound 150a

Compound 150a:
4,5-Bis((4-methoxybenzyl)oxy)-2-nitrobenzaldehyde

[Chemical Formula 321]

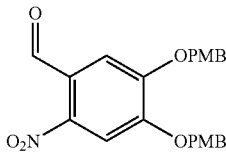

To a solution of 4,5-dihydroxy-2-nitrobenzaldehyde (79.0 g, 431 mmol) in DMF (500 mL) was added K$_2$CO$_3$ (179 g, 1300 mmol), followed by 1-(chloromethyl)-4-methoxybenzene (129 mL, 949 mmol). The reaction mixture was stirred at 50° C. for 2 h. The mixture was poured into ice-water, and the resulting suspension was filtered to afford a yellow solid that was dried and used in the next Step without further purification (152 g, 83% yield).

Step (2): Compound 150a→Compound 150b

Compound 150b: Methyl 4,5-bis((4-methoxybenzyl)oxy)-2-nitrobenzoate

[Chemical Formula 322]

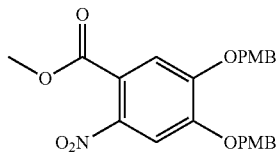

To a suspension of compound 150a (152 g, 359 mmol) in MeOH (1.2 L) and DCM (300 mL), were added KOH (101 g, 1800 mmol) and I$_2$ (182 g, 718 mmol). The reaction mixture was stirred for 1.5 h. A saturated aqueous sodium bisulphite solution (300 mL) was added, and it was noted that the chestnut color of the mixture disappeared. The organic phase was concentrated and then EtOAc (500 mL) was added to the mixture. The organic phase was separated, and the aqueous phase was extracted with EtOAc (2×500 mL). The combined organic phase was dried, filtered and concentrated to afford compound 150b (128 g, 79% yield) as a red oil. LCMS: (M+H)$^+$: 454.1.

443

Step (3): Compound 150b→Compound 150c

Compound 150c: Methyl 2-amino-4,5-bis((4-methoxybenzyl)oxy)benzoate

[Chemical Formula 323]

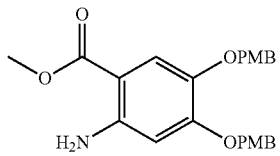

A mixture of compound 150b (128 g, 282 mmol), iron (126 g, 2260 mmol) and ammonium chloride (151 g, 2820 mmol) in water (400 mL) and methanol (1200 mL) was heated at reflux for 1 h. The mixture was filtered, and the collected solid was washed with DCM. The filtrate was concentrated in vacuo to remove organic solvents. Then DCM (500 mL) was added to the resulting aqueous solution, the organic phase was separated, and the aqueous phase was extracted with DCM (2×300 mL). The combined organic extracts were concentrated to afford compound 150c (100 g, 84% yield) as a grey solid. LCMS: $(M+H)^+$: 424.0.

Step (4): Compound 150c→Compound 150d

Compound 150d: 2-Amino-4,5-bis((4-methoxybenzyl)oxy)benzoic acid

[Chemical Formula 324]

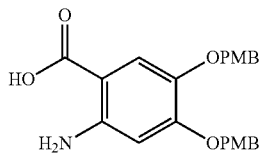

To a solution of compound 150c (10.0 g, 23.6 mmol) in water (100 mL) and methanol (100 mL) was added sodium hydroxide (4.72 g, 118 mmol). The mixture was stirred at 80° C. for 1 h. The methanol was removed under vacuum, and citric acid was added to adjust the pH of the solution to 6. The mixture was then extracted with DCM (3×100 mL). The combined organic extracts were washed with water, dried ($Na_2SO_4$), filtered and concentrated to afford compound 150d (8.2 g, 85% yield) as a slight yellow solid. LCMS: $(M+H)^+$: 410.3.

Step (5): Compound 150d→Compound 150e

Compound 150e: 2-amino-4,5-bis((4-methoxybenzyl)oxy)-N-(quinuclidin-4-ylmethyl)benzamide

[Chemical Formula 325]

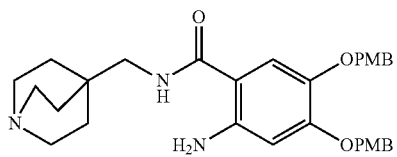

444

To a solution of compound 150d (3.00 g, 7.33 mmol) in DMF (50 mL) was added HATU (3.34 g, 8.79 mmol) and DIPEA (3.84 mL, 22.0 mmol), and the resulting mixture was stirred at rt for 30 min. Then, quinuclidin-4-ylmethanamine (WO2011125966Ai, 1.13 g, 8.06 mmol) was added, and the resulting mixture was stirred at rt for 1 h. Water and EtOAc were added to the mixture. The organic phase was separated, the aqueous phase was extracted with EtOAc three times. The combined organic extracts were washed with brine, dried ($Na_2SO_4$), filtered, and concentrated under vacuum. The residue was purified by automated silica gel chromatography (0-10% solvent B in solvent A; solvent A=DCM, solvent B=10:90:1 MeOH:DCM:$NH_4OH$, 40 g column) to afford compound 150e (2.88 g, 74% yield) as a brown solid. LCMS: $(M+H)^+$: 532.5.

Step (6): Compound 150e→Compound 150f

Compound 150f: 6,7-bis((4-methoxybenzyl)oxy)-3-(quinuclidin-4-ylmethyl)quinazolin-4(3H)-one

[Chemical Formula 326]

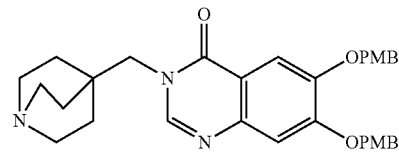

A mixture of compound 150e (2.88 g, 5.42 mmol) and trimethoxymethane (2.97 mL, 27.1 mmol) in methanol (100 mL) was heated to 120° C. overnight. The solvent was removed under vacuum, and the residue was purified by Combiflash silica gel chromatography (0-10% solvent B in solvent A; solvent A=DCM, solvent B=10:90:1 MeOH:DCM:$NH_4OH$, 24 g column). The collected brown solid was dissolved in DCM and washed with water. The organic layer was concentrated, and the residue was further purified by automated silica gel chromatography (0-10% MeOH/DCM, 4 g column) to afford compound 150f (0.68 g, 23% yield) as a white yellow solid. LCMS: $(M+H)^+$: 542.5.

Step (11): Compound X-24+Compound 150f→Compound I-150

Compound I-150: (4S,6R,7R)-7-((Z)-2-(2-aminothiazol-4-yl)-2-(((2-carboxypropan-2-yl)oxy)imino)acetamido)-3-((4-((6,7-dihydroxy-4-oxoquinazolin-3(4H)-yl)methyl)quinuclidin-1-ium-1-yl)methyl)-4-methyl-8-oxo-5-thia-1-azabicyclo[4.2.0]oct-2-ene-2-carboxylate, Sodium salt

[Chemical Formula 327]

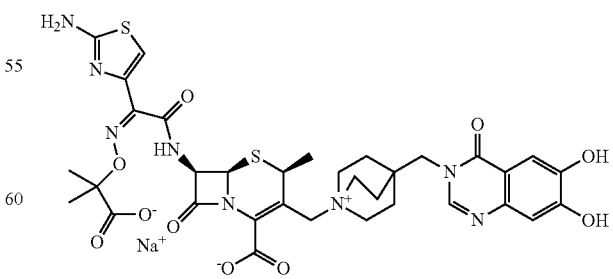

I-150

This compound was prepared according to the two-Step sequence of Example 143, using compound 150f and compound X-24.

LCMS: (M+H)⁺: 783.7. ¹H NMR (400 MHz, D₂O) δ ⌊ ppm 1.36 (s, 3H) 1.38 (s, 3H) 1.40 (d, J=7.07 Hz, 3H) 1.84 (t, J=7.58 Hz, 6H) 3.23-3.47 (m, 6H) 3.85-3.99 (m, 4H) 4.48 (d, J=14.40 Hz, 1H) 5.29 (d, J=5.05 Hz, 1H) 5.70 (d, J=4.80 Hz, 1H) 6.84 (d, J=2.02 Hz, 2H) 7.25 (s, 1H) 7.91 (s, 1H).

Example 151: Synthesis of Compound I-151

Step (1): Compound 150d→Compound 151a

Compound 151a 2-Amino-4,5-bis((4-methoxybenzyl)oxy)-N-(2-(pyrrolidin-1-yl) ethyl)benzamide Chemical Formula 168]

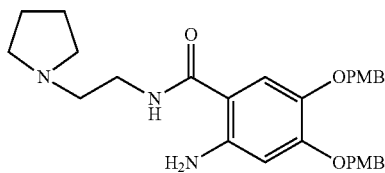

To a solution of compound 150d (1.57 g, 3.83 mmol) in MeCN (20 mL) were added HATU (1.60 g, 4.22 mmol) and DIPEA (1.27 mL, 7.67 mmol). The mixture was stirred for 0.5 h, and then 2-(pyrrolidin-1-yl)ethanamine (0.58 mL, 4.6 mmol) was added. The mixture was stirred for 1 h, and then a standard aqueous work-up afforded compound 151a (1.8 g, 93% yield). The crude product was directly used for the next Step without any purification.
LCMS: (M+H)⁺: 506.5

Step (2): Compound 151a→Compound 151b

Compound 151b: 6,7-bis((4-methoxybenzyl)oxy)-3-(2-(pyrrolidin-1-yl)ethyl)quinazoline-2,4(1H,3H)-dione

[Chemical Formula 328]

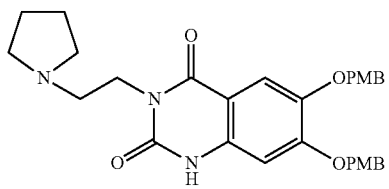

A mixture of compound 151a (1.8 g, 3.6 mmol) and CDI (1.155 g, 7.120 mmol) in THF (30 mL) was heated at reflux temperature for 4 h. The solution was cooled down and was partitioned between DCM and water. The organic layer was washed with aq NaHCO₃, brine, dried over Na₂SO₄, filtered and concentrated. The crude material was purified by automated silica gel chromatography (Combiflash RF), using a 40 g column and eluting with 0-10% MeOH/DCM with each solvent containing 0.1% NEt₃. The desired product was washed with water, and further purified by normal phase chromatography, using a 4 g column and eluting with 0-10% MeOH/DCM to afford compound 151b (700 mg, 37% yield) as a yellow solid. LCMS: (M+H)⁺: 532.5

Step (3): Compound X-24+Compound 151b→Compound I-151

Compound I-151: (4S,6R,7R)-7-((Z)-2-(2-aminothiazol-4-yl)-2-(((2-carboxypropan-2-yl)oxy)imino) acetamido)-3-((1-(2-(6,7-dihydroxy-2,4-dioxo-1,2-dihydroquinazolin-3(4H)-yl)ethyl)pyrrolidin-1-ium-1-yl)methyl)-4-methyl-8-oxo-5-thia-1-azabicyclo[4.2.0]oct-2-ene-2-carboxylate, Sodium salt

[Chemical Formula 329]

I-151

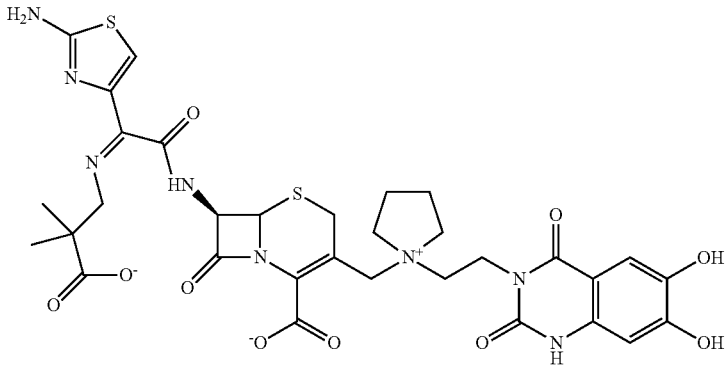

This compound was prepared according to the two-Step sequence of Example 143, using compound 151b and compound X-24.
LCMS: (M+H)⁺: 773.0. ¹H NMR (400 MHz, D₂O) δ ⌊ ppm 1.38 (s, 3H) 1.40 (s, 3H) 1.47 (d, J=7.07 Hz, 3H) 2.10 (br. s., 4H) 3.30-3.64 (m, 6H) 4.02 (q, J=7.07 Hz, 1H) 4.16-4.36 (m, 3H) 4.95 (d, J=14.15 Hz, 1H) 5.34 (d, J=4.55 Hz, 1H) 5.68 (d, J=4.55 Hz, 1H) 6.39 (s, 1H) 6.89 (s, 1H) 7.13 (s, 1H).

The compounds shown below were obtained from Compound X-24 and the each corresponding amine which was synthesized according to the synthesis in WO2013052568A1 in the same way as example 143.
LCMS: (M+H)⁺: 506.5

Example 152: Synthesis of Compound I-152

Compound I-152: (4S,6R,7R)-7-((Z)-2-(2-aminothiazol-4-yl)-2-(((2-carboxypropan-2-yl)oxy)imino)acetamido)-3-((1-(2-(1-ethyl-6,7-dihydroxy-4-oxo-1,4-dihydrocinnoline-3-carboxamido)ethyl)pyrrolidin-1-ium-1-yl)methyl)-4-methyl-8-oxo-5-thia-1-azabicyclo[4.2.0]oct-2-ene-2-carboxylate, Sodium salt

[Chemical Formula 330]

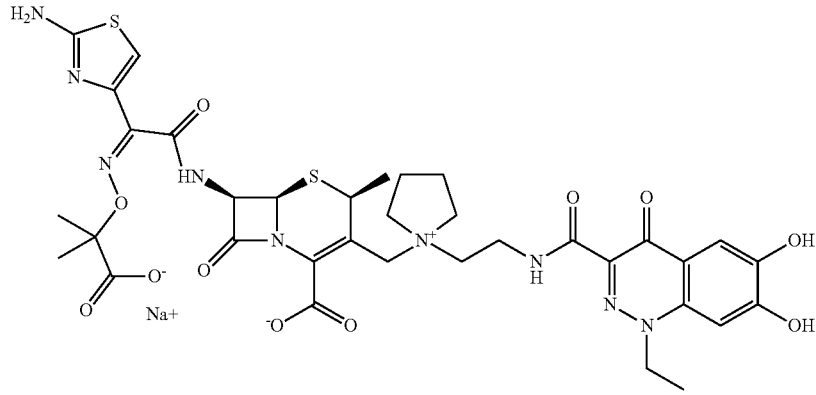

I-152

LCMS: (M+H)$^+$: 828.0. $^1$H NMR (400 MHz, D$_2$O) δ ppm 1.32-1.39 (m, 9H) 1.45 (d, J=6.82 Hz, 3H) 2.11 (br. s., 4H) 3.29-3.69 (m, 6H) 3.75-3.91 (m, 2H) 3.98 (q, J=7.07 Hz, 1H) 4.18 (d, J=14.15 Hz, 1H) 4.41 (q, J=6.99 Hz, 2H) 4.94 (d, J=14.15 Hz, 1H) 5.35 (d, J=4.80 Hz, 1H) 5.69 (d, J=4.80 Hz, 1H) 6.86 (s, 1H) 6.91 (s, 1H) 7.24 (s, 1H).

Example 153: Synthesis of Compound I-153

Compound I-153: (4S,6R,7R)-7-((Z)-2-(2-aminothiazol-4-yl)-2-(((2-carboxypropan-2-yl)oxy)imino)acetamido)-3-((1-(2-(1-ethyl-6,7-dihydroxy-4-oxo-1,4-dihydroquinoline-3-carboxamido)ethyl)pyrrolidin-1-ium-1-yl)methyl)-4-methyl-8-oxo-5-thia-1-azabicyclo[4.2.0]oct-2-ene-2-carboxylate, Sodium salt

[Chemical Formula 331]

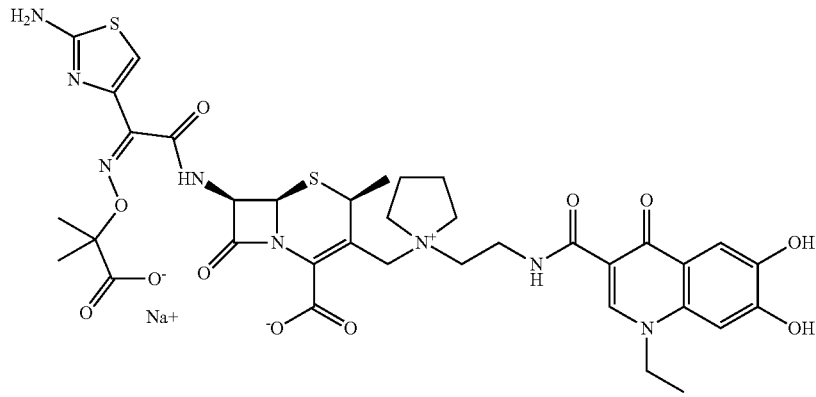

I-153

LCMS: (M+H)⁺: 826.9. ¹H NMR (400 MHz, D$_2$O) δ ppm 1.28 (t, J=7.07 Hz, 3H) 1.34 (s, 3H) 1.36 (s, 3H) 1.44 (d, J=7.07 Hz, 3H) 2.11 (br. s., 4H) 2.99-3.03 (m, 1H) 3.29-3.54 (m, 5H) 3.60 (br. s., 1H) 3.68-3.86 (m, 2H) 3.97 (d, J=7.07 Hz, 1H) 4.05 (d, J=7.07 Hz, 2H) 4.16 (d, J=14.15 Hz, 1H) 4.93 (d, J=14.15 Hz, 1H) 5.35 (d, J=4.80 Hz, 1H) 5.68 (d, J=4.55 Hz, 1H) 6.77 (s, 1H) 6.85 (s, 1H) 7.23 (s, 1H) 8.29 (s, 1H).

Example 154: Synthesis of Compound I-154

Compound I-154: (4S,6R,7R)-7-((Z)-2-(2-aminothiazol-4-yl)-2-(((2-carboxypropan-2-yl)oxy)imino)acetamido)-3-((4-((6,7-dihydroxy-2,4-dioxo-1,2-dihydroquinazolin-3(4H)-yl)methyl)quinuclidin-1-ium-1-yl)methyl)-4-methyl-8-oxo-5-thia-1-azabicyclo[4.2.0]oct-2-ene-2-carboxylate, Sodium salt

[Chemical Formula 332]

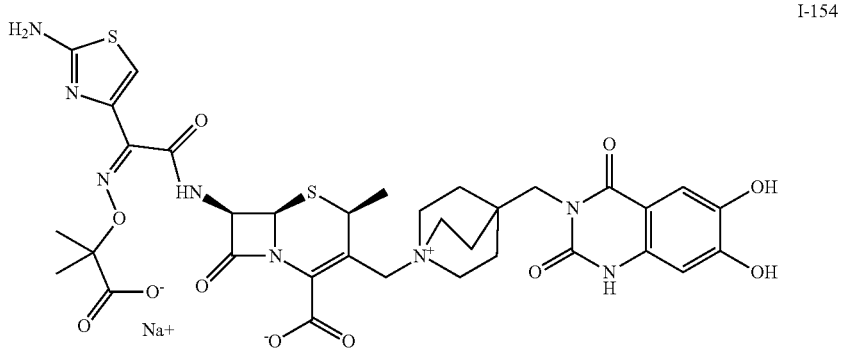

I-154

LCMS: (M+H)⁺: 798.9. ¹H NMR (400 MHz, D$_2$O) δ ppm 1.36 (s, 3H) 1.38 (s, 3H) 1.41 (d, J=7.07 Hz, 3H) 1.82 (t, J=7.58 Hz, 6H) 3.20-3.44 (m, 6H) 3.78-3.98 (m, 4H) 4.46 (d, J=14.40 Hz, 1H) 5.29 (d, J=5.05 Hz, 1H) 5.70 (d, J=4.80 Hz, 1H) 6.42 (s, 1H) 6.85 (s, 1H) 7.15 (s, 1H).

Example 155: Synthesis of Compound I-155

Step (1):
2-chloro-3,4-dimethoxybenzaldehyde→Compound 155a

Compound 155a:
2-Chloro-3,4-dimethoxy-6-nitrobenzaldehyde

[Chemical Formula 333]

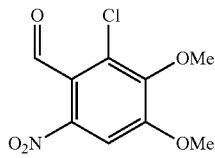

Trifluoromethanesulfonic acid (26.6 mL, 299 mmol) was added to a solution of 2-chloro-3,4-dimethoxybenzaldehyde (20 g, 100 mmol) and potassium nitrate (30.2 g, 299 mmol) in acetic acid (80 mL) with stirring at 0° C., and the resulting mixture was stirred at room temperature overnight. The reaction mixture was then poured into water, neutralized with a saturated aqueous sodium hydrogencarbonate solution. The precipitate was collected by filtration and dried to afford compound 155a (19 g, 78% yield)

LCMS: (M+H)⁺: 246.1.

Step (2): Compound 155a→Compound 155b

Compound 155b:
2-Chloro-3,4-dimethoxy-6-nitrobenzoic acid

[Chemical Formula 334]

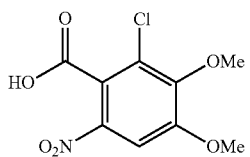

To a solution of compound 155a (19 g, 77 mmol) in THF (100 mL) and t-Butanol (100 mL) was added 2-methylbut-2-ene (387 mL, 774 mmol) at 10° C. Subsequently, a solution of sodium chlorite (21.0 g, 232 mmol) and sodium dihydrogenphosphate (27.8 g, 232 mmol) in water (50 mL) was added dropwise to the solution and the suspension was stirred vigorously for 1 h at rt. The mixture was then diluted with saturated NH$_4$Cl aq and the product was extracted with DCM. The combined organic extracts were washed with brine, dried over Na$_2$SO$_4$, filtered, and concentrated in vacuo to afford a yellow solid that was used in the next Step without further purification (20 g, 99%). LCMS: (M+H-H$_2$O)$^+$: 244.1.

Step (3): Compound 155b→Compound 155c

Compound 155c:
6-Amino-2-chloro-3,4-dimethoxybenzoic acid

[Chemical Formula 335]

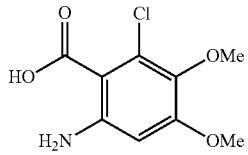

A mixture of compound 155b (10 g, 38 mmol) and Pd/C (1.0 g, 38 mmol) in methanol (100 mL) was stirred overnight under an atmosphere of hydrogen. The mixture was filtered, and the solvent was evaporated to afford compound 155c (8 g, 90% yield) as a brown solid. LCMS: (M+H)$^+$: 232.1.

Step (4): Compound 155c→Compound 155d

Compound 155d:
5-Chloro-6,7-dimethoxyquinazolin-4(3H)-one

[Chemical Formula 336]

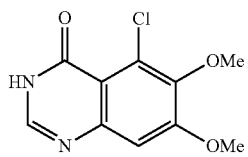

In a 100 mL flask were placed compound 155c (7.0 g, 30 mmol), trimethoxymethane (64.1 g, 604 mmol), ammonium acetate (23.3 g, 302 mmol) and methanol (20 mL). The reaction mixture was stirred at 120° C. for 3 h. The reaction mixture was concentrated. Water (100 mL) was added to the reaction mixture, and the resulting mixture was stirred for 15 min and filtered to afford compound 155d (6.5 g, 89% yield) as a brown crystalline product.
LCMS: (M+H)$^+$: 241.1.

Step (5): Compound 155d→Compound 155e

Compound 155e: 5-chloro-3-(2-chloroethyl)-6,7-dimethoxyquinazolin-4(3H)-one

[Chemical Formula 337]

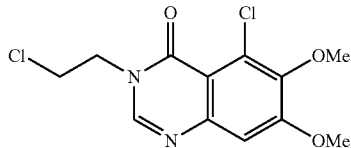

To a solution of compound 155d (3.0 g, 12.5 mmol) in DMF (5 mL) was added cesium carbonate (8.12 g, 24.9 mmol), followed by 1-chloro-2-iodoethane (2.27 mL, 24.9 mmol). The reaction mixture was stirred at 50° C. for 0.5 h. Water was added and the mixture was stirred at rt for 15 min. The white precipitate was collected by filtration and washed with water to afford compound 155e (3 g, 79% yield). The crude mixture was used in next Step without purification. LCMS: (M+H)$^+$: 303.2.

Step (6): Compound 155e→Compound 155f

Compound 155f: 5-Chloro-3-(2-chloroethyl)-6,7-dihydroxyquinazolin-4(3H)-one

[Chemical Formula 338]

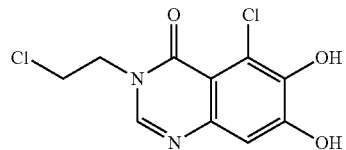

To a solution of compound 155e (3.0 g, 9.9 mmol) in DCM (10 mL) was added tribromoborane (3.40 mL, 34.6 mmol) at −78° C. The mixture was allowed to warm up to rt, and was stirred overnight. The mixture was diluted with MeOH and concentrated, and this procedure was repeated several times to afford compound 155f (2.5 g, 92% yield). The crude product was used in next Step without further purification. LCMS: (M+H)$^+$: 275.1.

Step (7): Compound 155f→Compound 155g

Compound 155g: 5-chloro-3-(2-chloroethyl)-6,7-bis((4-methoxybenzyl)oxy)quinazolin-4(3H)-one

[Chemical Formula 339]

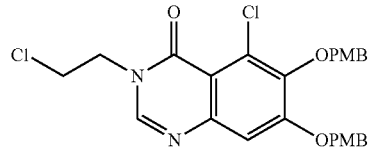

To a solution of compound 155f (2.5 g, 9.1 mmol) in DMF (30 mL) was added K$_2$CO$_3$ (5.02 g, 36.4 mmol), followed by 1-(chloromethyl)-4-methoxybenzene (5.12 mL, 36.4 mmol). The reaction mixture was stirred at 50° C. for 2 h. Water was added, and the mixture was stirred at rt for 15 min. The yellow precipitate was collected by filtration and washed with water to afford compound 155g (4 g, 73% yield) as a yellow solid. The crude mixture was used in next Step without purification. LCMS: (M+H)$^+$: 515.4.

Step (8): Compound 155g→Compound 155h

Compound 155h: 5-Chloro-6,7-bis((4-methoxybenzyl)oxy)-3-(2-(pyrrolidin-1-yl)ethyl)quinazolin-4(3H)-one

[Chemical Formula 340]

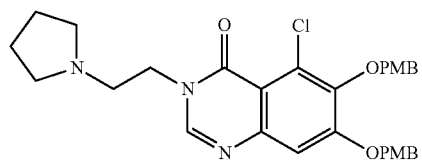

A solution of compound 155g (4.0 g, 7.8 mmol), DIPEA (2.57 mL, 15.5 mmol), and pyrrolidine (1.28 mL, 15.5 mmol) in acetonitrile (100 mL) was heated to reflux temperature for 12 h. Water was added to the reaction mixture, which was then extracted with DCM. The organic layer was washed with NaHCO$_3$, brine and dried over Na$_2$SO$_4$, filtered and concentrated in vacuo. The crude material was purified by automated silica gel chromatography using an 80 g column and eluting with 0-5% MeOH in DCM over 45 min, to provide 1 g of pure product as a grey solid. Contaminated fractions were concentrated and washed by MeCN to give another 800 mg product, affording a total of 1.8 g product (42% yield). LCMS: (M+H)$^+$: 550.5.

Step (9): Compound X-24+Compound 155h→Compound I-155

Compound I-155: (4S,6R,7R)-7-((Z)-2-(2-aminothiazol-4-yl)-2-(((2-carboxypropan-2-yl)oxy)imino)acetamido)-3-((1-(2-(5-chloro-6,7-dihydroxy-4-oxoquinazolin-3(4H)-yl)ethyl)pyrrolidin-1-ium-1-yl)methyl)-4-methyl-8-oxo-5-thia-1-azabicyclo[4.2.0]oct-2-ene-2-carboxylate, Sodium salt

[Chemical Formula 341]

I-155

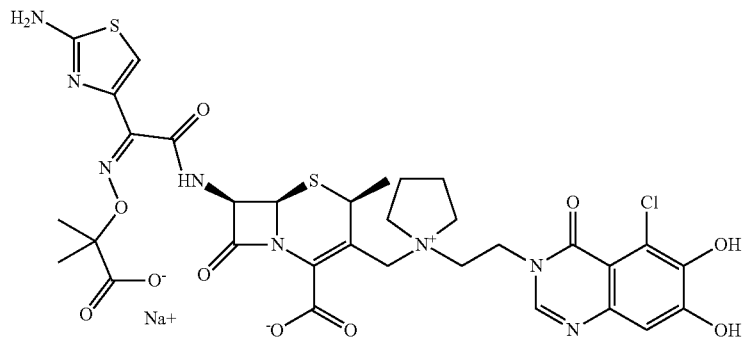

This compound was prepared according to the two-Step sequence of Example 143, using compound 155h and compound X-24.

LCMS: (M+H)$^+$: 791.4. $^1$H NMR (400 MHz, D$_2$O) δ ppm 1.37 (s, 3H) 1.39 (s, 3H) 1.47 (d, J=7.07 Hz, 3H) 2.14 (br. s., 4H) 3.34-3.59 (m, 5H) 3.68 (br. s., 1H) 3.99 (q, J=6.65 Hz, 1H) 4.13-4.36 (m, 3H) 5.00 (d, J=14.15 Hz, 1H) 5.36 (d, J=4.80 Hz, 1H) 5.70 (d, J=4.80 Hz, 1H) 6.58 (s, 1H) 6.87 (s, 1H) 7.99 (s, 1H).

Example 156: Synthesis of Compound I-156

Step (1): 6,7-bis((4-methoxybenzyl)oxy)-1-methyl-4-oxo-1,4-dihydroquinoline-3-carboxylic acid-→Compound 156a Compound 156a: 6,7-Bis((4-methoxybenzyl)oxy)-1-methyl-4-oxo-N-(quinuclidin-4-ylmethyl)-1,4-dihydroquinoline-3-carboxamide

[Chemical Formula 342]

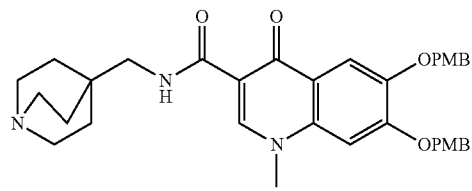

To a solution of 6,7-bis((4-methoxybenzyl)oxy)-1-methyl-4-oxo-1,4-dihydroquinoline-3-carboxylic acid (WO2013052568A1, 3.0 g, 5.5 mmol) in DMF (100 mL) were added HATU (3.13 g, 8.23 mmol) and DIPEA (2.88 mL, 16.5 mmol), and the mixture was stirred for 0.5 h. Quinuclidin-4-ylmethanamine (WO2011125966A1, 1.28 mL, 8.23 mmol) was then added, and the mixture was stirred for 2 h. Sodium bicarbonate was added, and the mixture was stirred for 15 min. The yellow precipitate was collected by filtration, washed with water and purified by automated silica gel chromatography using a 24 g column and eluting with 0-20% MeOH in DCM to afford compound 156a (2 g, 61% yield) as a yellow solid. LCMS: (M+H)$^+$: 598.6.

Step (2): Compound X-24+Compound 156a→Compound I-156

Compound I-156: (4S,6R,7R)-7-((Z)-2-(2-aminothiazol-4-yl)-2-(((2-carboxypropan-2-yl)oxy)imino)acetamido)-3-((4-((6,7-dihydroxy-1-methyl-4-oxo-1,4-dihydroquinoline-3-carboxamido)methyl)quinuclidin-1-ium-1-yl)methyl)-4-methyl-8-oxo-5-thia-1-azabicyclo[4.2.0]oct-2-ene-2-carboxylate, Sodium salt

[Chemical Formula 343]

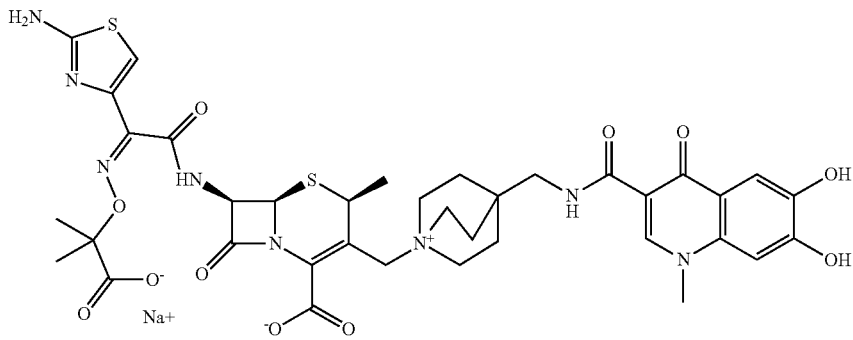

I-156

This compound was prepared according to the two-Step sequence of Example 143, using compound 156a and compound X-24.

LCMS: (M+H)$^+$: 839.3. $^1$H NMR (400 MHz, D$_2$O) δ ppm 1.37 (s, 3H) 1.39 (s, 3H) 1.43 (d, J=7.07 Hz, 3H) 1.82 (br. s., 6H) 3.17-3.53 (m, 8H) 3.64 (s, 3H) 3.89-4.02 (m, 2H) 4.52 (d, J=14.40 Hz, 1H) 5.31 (d, J=4.55 Hz, 1H) 5.71 (d, J=4.80 Hz, 1H) 6.64 (br. s., 1H) 6.85 (s, 1H) 7.16 (s, 1H) 8.20 (s, 1H).

Example 157: Synthesis of Compound I-157

Compound I-157: (4S,6R,7R)-7-((Z)-2-(2-aminothiazol-4-yl)-2-(((2-carboxypropan-2-yl)oxy)imino)acetamido)-3-((1-(2-(6,7-dihydroxy-1-methyl-4-oxo-1,4-dihydroquinoline-3-carboxamido)ethyl)pyrrolidin-1-ium-1-yl)methyl)-4-methyl-8-oxo-5-thia-1-azabicyclo[4.2.0]oct-2-ene-2-carboxylate, Sodium salt

[Chemical Formula 344]

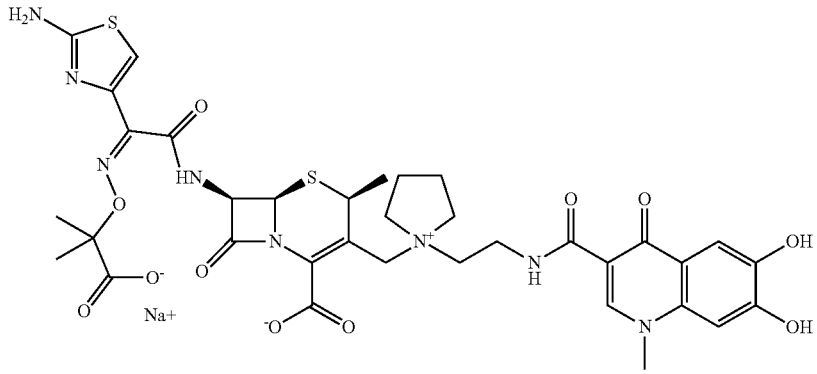

I-157

This compound was prepared according to the two-Step sequence of Example 143, using 6,7-bis((4-methoxybenzyl)oxy)-1-methyl-4-oxo-N-(2-(pyrrolidin-1-yl)ethyl)-1,4-dihydroquinoline-3-carboxamide (which was synthesized according to the synthesis in WO2013052568A1) and compound X-24. LCMS: (M+H)$^+$: 813.2. $^1$H NMR (400 MHz, D$_2$O) δ ⌊ ppm 1.34 (s, 3H) 1.37 (s, 3H) 1.47 (d, J=6.82 Hz, 3H) 2.11 (br. s., 4H) 3.42 (br. s., 4H) 3.49 (br. s., 3H) 3.56-3.82 (m, 4H) 4.00 (d, J=6.82 Hz, 1H) 4.15 (d, J=14.15 Hz, 1H) 4.95 (d, J=14.15 Hz, 1H) 5.37 (d, J=4.55 Hz, 1H) 5.73 (d, J=4.80 Hz, 1H) 6.46 (br. s., 1H) 6.82 (s, 1H) 6.97 (s, 1H) 7.96 (s, 1H).

Example 158: Synthesis of Compound I-158

Step (1): Compound 155d→Compound 158a

Compound 158a: 5-Chloro-3-(3-chloropropyl)-6,7-dimethoxyquinazolin-4(3H)-one

[Chemical Formula 345]

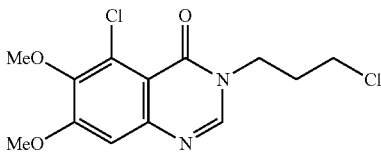

To a solution of compound 155d (2.50 g, 10.4 mmol) in DMF (100 mL) was added 1-chloro-3-iodopropane (1.60 mL, 20.8 mmol) dropwise at 50° C., and the mixture was stirred overnight. Water was added, and the mixture was extracted with EtOAc. The organic layer was dried over Na$_2$SO$_4$, filtered and concentrated. The residue was purified by automated silica gel chromatography (10% MeOH in DCM) to afford compound 158a (2.0 g, 61% yield) as a yellow solid. LCMS: (M+H)$^+$: 316.8.

Step (2): Compound 158a→Compound 158b

Compound 158b: 5-Chloro-3-(3-chloropropyl)-6,7-dihydroxyquinazolin-4(3H)-one

[Chemical Formula 346]

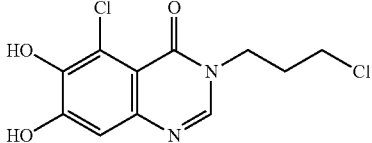

To a solution of compound 158a (2.0 g, 6.3 mmol) in DCM (100 mL) was added boron tribromide (2.98 mL, 31.5 mmol) dropwise at −78° C. The reaction mixture was allowed to warm up slowly to rt and was stirred overnight. The mixture was diluted with MeOH and concentrated, and this process was repeated three times to afford compound 158b (1.7 g, 93% yield). LCMS: (M+H)$^+$: 288.8.

Step (3): Compound 158b→Compound 158c

Compound 158c: 5-Chloro-3-(3-chloropropyl)-6,7-bis((4-methoxybenzyl)oxy)quinazolin-4(3H)-one

[Chemical Formula 347]

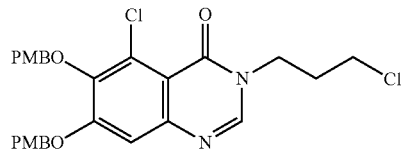

To a solution of compound 158b (3.68 g, 23.5 mmol) in DMF (100 mL) was added potassium carbonate (4.06 g, 29.4 mmol) and 1-(chloromethyl)-4-methoxybenzene (3.68 g, 23.5 mmol), and this mixture was stirred at 50° C. overnight. Water was added, and the mixture was extracted with EtOAc. The organic layer was dried (Na$_2$SO$_4$), filtered and concentrated. The residue was purified by automated silica gel chromatography to afford compound 158c (3 g, 96% yield). LCMS: (M+H)$^+$: 529.1.

Step (4): Compound 158c→Compound 158d

Compound 158d: 5-Chloro-6,7-bis((4-methoxybenzyl)oxy)-3-(3-(pyrrolidin-1-yl)propyl)quinazolin-4(3H)-one

[Chemical Formula 348]

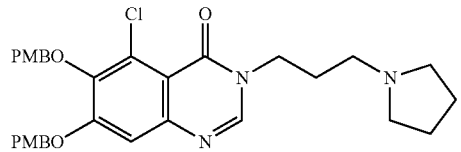

To a solution of compound 158c (3.3 g, 6.2 mmol) in MeCN (100 mL) were added DIPEA (2.72 mL, 15.6 mmol) and pyrrolidine (1.29 mL, 15.6 mmol), and this mixture was heated to 80° C. Analysis of the reaction mixture by LCMS indicated that the starting material was not fully consumed. Sodium iodide (1.121 g, 7.480 mmol) was added to the reaction mixture, which was then stirred overnight at the same temperature. The volatiles were removed, and the residue was dissolved in EtOAc, washed with brine, NaHCO$_3$ aq, and water, dried over Na$_2$SO$_4$, filtered and then purified by automated silica gel chromatography (10% MeOH in DCM) to afford compound 158d (0.9 g, 26% yield). LCMS: (M+H)$^+$: 564.5.

Step (5): Compound X-24+Compound 158d→Compound I-158

Compound I-158: (4S,6R,7R)-7-(((Z)-2-(2-aminothiazol-4-yl)-2-(((2-carboxypropan-2-yl)oxy)imino)acetamido)-3-((1-(3-(5-chloro-6,7-dihydroxy-4-oxoquinazolin-3(4H)-yl)propyl)pyrrolidin-1-ium-1-yl)methyl)-4-methyl-8-oxo-5-thia-1-azabicyclo[4.2.0]oct-2-ene-2-carboxylate, Sodium salt

[Chemical Formula 349]

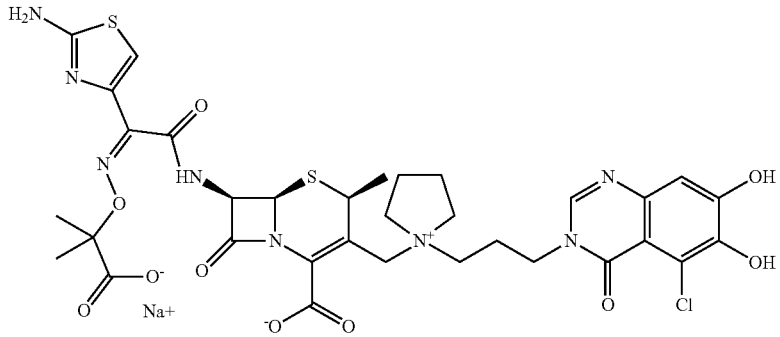

I-158

This compound was prepared according to the two-Step sequence of Example 143, using compound 158d and compound X-24.

LCMS: (M+H)$^+$: 804.9. $^1$H NMR (400 MHz, D$_2$O) δ ppm 1.27 (d, J=7.07 Hz, 3H) 1.34 (s, 3H) 1.36 (s, 3H) 2.06 (br. s., 4H) 2.17 (br. s., 2H) 3.27 (s, 2H) 3.31-3.50 (m, 6H) 3.89-4.12 (m, 3H) 5.07 (d, J=4.80 Hz, 1H) 5.57 (d, J=4.80 Hz, 1H) 6.78 (s, 1H) 6.81 (s, 1H) 8.04 (s, 1H).

Example 159: Synthesis of Compound I-159

Step (1): 6,7-bis((4-methoxybenzyl)oxy)-4-oxo-1,4-dihydroquinoline-3-carboxylate→Compound 159a Compound 159a: Ethyl 6,7-bis((4-methoxybenzyl)oxy)-1-methyl-4-oxo-1,4-dihydroquinoline-3-carboxylate

[Chemical Formula 350]

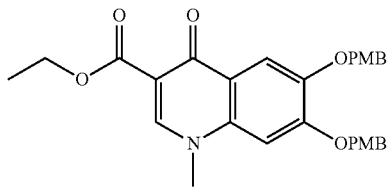

To a suspension of ethyl 6,7-bis((4-methoxybenzyl)oxy)-4-oxo-1,4-dihydroquinoline-3-carboxylate (10.0 g, 20.4 mmol) in DMF (100 mL) was added K$_2$CO$_3$ (7.06 g, 51.1 mmol) and iodomethane (3.18 mL, 51.1 mmol). The mixture was stirred at 50° C. for 2 h. Water was added, the precipitate was collected by filtration to afford compound 159a (9 g, 87% yield) as a yellow solid that was used for the next Step without further purification.

LCMS: (M+H)$^+$: 504.1.

Step (2): Compound 159a→Compound 159b

Compound 159b: 6,7-Bis((4-methoxybenzyl)oxy)-1-methyl-4-oxo-1,4-dihydroquinoline-3-carboxylic acid

[Chemical Formula 351]

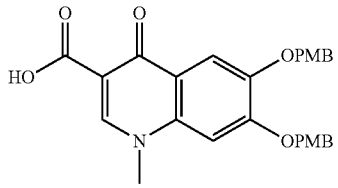

To a suspension of compound 159a (9.0 g, 17.9 mmol) in a mixture of methanol (10 mL) and water (5 mL) was added KOH (5.0 g, 89 mmol) portionwise. The resulting mixture was stirred at 90° C. for 3 h. The reaction mixture was cooled down to rt and concentrated. The residue was diluted with water and the pH of the solution was adjusted to 1 using 2N HCl aq. The precipitate was collected by filtration and dried to afford compound 159b (9 g, 92% yield) as a pale yellow solid. The crude product was used in next Step without further purification. LCMS: (M+H)$^+$: 476.4.

Step (3): Compound 159b→Compound 159c

Compound 159c: 3-(1,4-diazabicyclo[3.2.2]nonane-4-carbonyl)-6,7-bis((4-methoxybenzyl)oxy)-1-methylquinolin-4(1H)-one

[Chemical Formula 352]

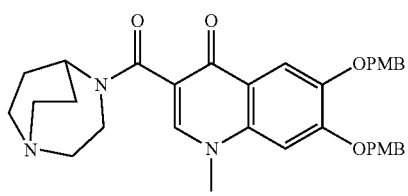

To a solution of compound 159b (3.0 g, 5.5 mmol) in DMF (30 mL) were added HATU (3.13 g, 8.23 mmol) and DIPEA (2.88 mL, 16.5 mmol). The mixture was stirred for 0.5 h, and 1,4-diazabicyclo[3.2.2]nonane (1.16 mL, 8.23 mmol) was added. The reaction mixture was stirred for 1 h. Water was added and the product was extracted with DCM and washed with sodium bicarbonate. The crude material was purified by automated silica gel chromatography using a 24 g column and eluting with 0-20% MeOH in DCM to afford compound 159c (1.8 g, 56% yield) as a yellow solid. LCMS: (M+H)$^+$: 584.6

Step (4): Compound X-24+Compound 159c→Compound I-159

Compound I-159: (4S,6R,7R)-7-((Z)-2-(2-aminothiazol-4-yl)-2-(((2-carboxypropan-2-yl)oxy)imino)acetamido)-3-((4-(6,7-dihydroxy-1-methyl-4-oxo-1,4-dihydroquinoline-3-carbonyl)-1,4-diazabicyclo[3.2.2]nonan-1-ium-1-yl)methyl)-4-methyl-8-oxo-5-thia-1-azabicyclo [4.2.0]oct-2-ene-2-carboxylate, Sodium salt

[Chemical Formula 353]

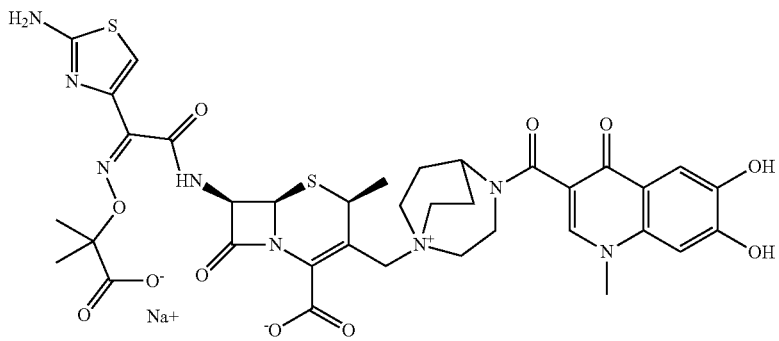

I-159

This compound was prepared according to the two-Step sequence of Example 143, using compound 159c and compound X-24. LCMS: (M+H)$^+$: 825.1. $^1$H NMR (400 MHz, D$_2$O) δ | ppm 1.33-1.51 (m, 9H) 2.27 (br. s., 4H) 3.31-3.87 (m, 10H) 3.92-4.07 (m, 2H) 4.11-4.28 (m, 2H) 4.75-4.80 (m, 1H) 5.32 (d, J=5.05 Hz, 1H) 5.68-5.76 (m, 1H) 6.84-6.90 (m, 1H) 6.98 (br. s., 1H) 7.46-7.54 (m, 1H) 7.96-8.06 (m, 1H).

Example 160: Synthesis of Compound I-160

Step (1): Compound 149j→Compound 160a

Compound 160a: 3-(1,4-diazabicyclo[3.2.2]nonane-4-carbonyl)-5-chloro-6,7-bis((4-methoxybenzyl)oxy)-1-methylquinolin-4(1H)-one

[Chemical Formula 354]

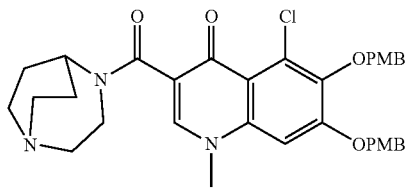

To a solution of compound 149j (2.5 g, 4.9 mmol) in DMF (50 mL) were added HATU (2.80 g, 7.35 mmol) and DIPEA (3.43 mL, 19.6 mmol), and the resulting mixture was stirred at rt for 30 min. Then 1,4-diazabicyclo[3.2.2]nonane (0.804 g, 6.37 mmol) was added, and the resulting mixture was stirred at rt for 1 h. Water and EtOAc were added to the mixture. The organic phase was separated, and the aqueous phase was extracted with EtOAc three times. The combined organic extracts were washed with brine, dried over Na$_2$SO$_4$, filtered, and concentrated under vacuum. The residue was purified by automated silica gel chromatography (0-10% solvent B in solvent A; solvent A=DCM, solvent B=10:90:1 MeOH:DCM:NH$_4$OH, 24 g column). The collected brown solid was dissolved in DCM and washed with water, and then the organic layer was concentrated. The residue was further purified by automated silica gel chromatography (0-10% MeOH in DCM, 4 g column) to afford compound 160a (1.17 g, 39% yield) as a brown solid. LCMS: (M+H)$^+$: 618.5.

Step (2): Compound X-24+Compound 160a→Compound I-160

Compound I-160: (4S,6R,7R)-7-((Z)-2-(2-aminothiazol-4-yl)-2-(((2-carboxypropan-2-yl)oxy)imino)acetamido)-3-((4-(5-chloro-6,7-dihydroxy-1-methyl-4-oxo-1,4-dihydroquinoline-3-carbonyl)-1,4-diazabicyclo[3.2.2]nonan-1-ium-1-yl)methyl)-4-methyl-8-oxo-5-thia-1-azabicyclo[4.2.0]oct-2-ene-2-carboxylate, Sodium salt

[Chemical Formula 355]

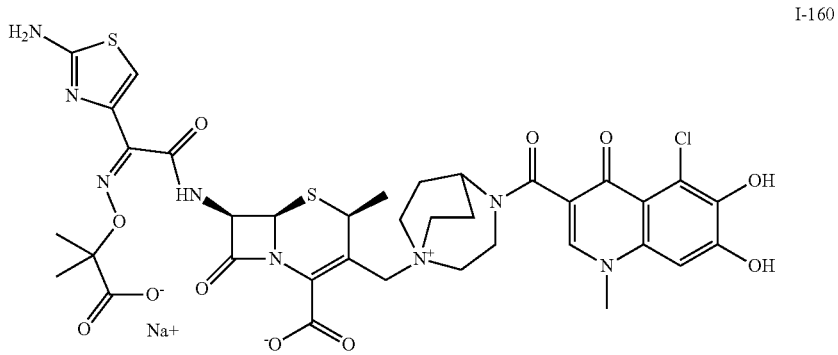

I-160

This compound was prepared according to the two-Step sequence of Example 143, using compound 160a and compound X-24.

LCMS: (M+H)$^+$: 859.2. $^1$H NMR (400 MHz, D$_2$O) δ ppm 1.33-1.55 (m, 9H) 2.07-2.34 (m, 4H) 3.31-3.91 (m, 11H) 4.20 (br. s., 3H) 4.76 (d, J=6.32 Hz, 1H) 5.32 (d, J=4.80 Hz, 1H) 5.72 (d, J=4.80 Hz, 1H) 6.84 (s, 1H) 6.85-6.88 (m, 1H) 7.86-7.95 (m, 1H).

Example 161: Synthesis of Compound I-161

Step (1): Compound 155d→Compound 147a

Compound 161a: 5-chloro-6,7-dimethoxy-3-methylquinazolin-4(3H)-one

[Chemical Formula 356]

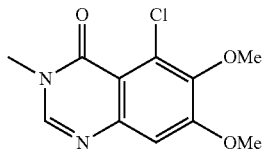

To a mixture of K$_2$CO$_3$ (24.5 g, 177 mmol) and compound 155d (21.3 g, 89.0 mmol) in DMF (100 mL) was added iodomethane (11.02 mL, 177 mmol) at rt, and the resulting mixture was stirred at 50° C. for 1 h. The mixture was cooled down to room temperature and poured into ice-water (700 mL). The resulting aqueous mixture was stirred for 15 min and filtered to afford compound 161a (19.3 g, 86% yield) as a yellow solid. LCMS: (M+H)$^+$: 255.2.

Step (2): Compound 161a→Compound 161b

Compound 161b: 5-chloro-6,7-dihydroxy-3-methylquinazolin-4(3H)-one

[Chemical Formula 357]

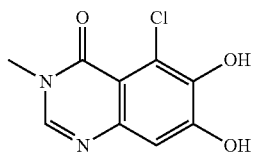

To a solution of compound 161a (18.0 g, 70.7 mmol) in DCM (150 mL) was added tribromoborane (24.30 mL, 247.0 mmol) at −78° C. The mixture was allowed to warm up to rt, and stirred overnight. The mixture was diluted with MeOH and concentrated, diluted again with MeOH and concentrated, and this procedure was repeated several times to afford compound 161b (16.3 g, 99% yield). LCMS: (M+H)$^+$: 227.1.

Step (3): Compound 161b→Compound 161c

Compound 161c: 5-chloro-6,7-bis((4-methoxybenzyl)oxy)-3-methylquinazolin-4(3H)-one

[Chemical Formula 358]

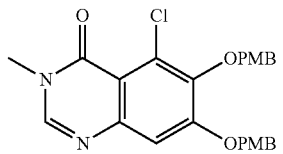

To a solution of compound 161b (16.3 g, 71.9 mmol) in DMF (250 mL) was added K$_2$CO$_3$ (29.8 g, 216 mmol), followed by 1-(chloromethyl)-4-methoxybenzene (29.4 mL, 216 mmol). Then the reaction mixture was stirred at 50° C. for 2 h. Water was added and the mixture was stirred at rt for 15 min. The yellow precipitate was collected by filtration and washed with water to afford compound 161c (40 g, 98% yield). LCMS: (M+H)$^+$: 467.2.

Step (4): Compound 161c→Compound 161d

Compound 161d: Potassium 6-amino-2-chloro-3,4-bis((4-methoxybenzyl)oxy)benzoate

[Chemical Formula 359]

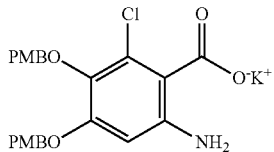

To a solution of compound 161c (36 g, 63 mmol) in methanol (300 mL) and water (200 mL) was added KOH (355 g, 6320 mmol). The mixture was heated at reflux temperature overnight. The mixture was cooled to rt and water (100 mL) was added. The resulting yellow precipitate was collected by filtration and washed with water (20 mL). The residue was diluted with diisopropyl ether and DCM (2:1 ratio, 900 mL), and the solid was collected by filtration, rinsing with the same solvent mixture (2×60 mL), to afford compound 161d (23.6 g, 77% yield) as a light brown solid.

LCMS: (M+H)$^+$: 444.2.

Step (5): Compound 161ad→Compound 161e

Compound 161e: 5-chloro-6,7-bis((4-methoxybenzyl)oxy)-3-(quinuclidin-4-ylmethyl)quinazolin-4(3H)-one

[Chemical Formula 360]

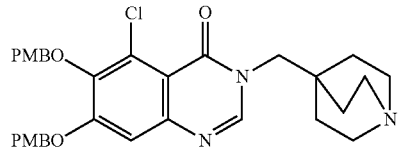

To a mixture of compound 161e (5.0 g, 10.4 mmol) in DMF (25 mL) were added trimethoxymethane (56.7 mL, 519 mmol), DIPEA (18.12 mL, 104.0 mmol) and quinuclidin-4-ylmethanamine, 2 Hydrochloride (ref: WO2011125966A1, 3.29 g, 15.6 mmol). The mixture was stirred at 115° C. for 6 h. Water was added, and the mixture was extracted with DCM and washed with 2N NaOH aq. The organic extract was purified by automated normal phase chromatography using a 160 g basic alumina column and eluting with 30-80% solvent A in solvent B (solvent A=EtOAc/EtOH/Et$_3$N, 76:24:1 ratio; solvent B=Hexane) to afford compound 161e (3.0 g, 50% yield) as a yellow solid. LCMS: (M+H)$^+$: 576.4.

Step (6): Compound X-24+Compound 161e→Compound I-161

Compound I-161 (4S,6R,7R)-7-((Z)-2-(2-aminothiazol-4-yl)-2-(((2-carboxypropan-2-yl)oxy)imino)acetamido)-3-((4-((5-chloro-6,7-dihydroxy-4-oxoquinazolin-3(4H)-yl)methyl)quinuclidin-1-ium-1-yl)methyl)-4-methyl-8-oxo-5-thia-1-azabicyclo[4.2.0]oct-2-ene-2-carboxylate, Sodium salt

[Chemical Formula 361]

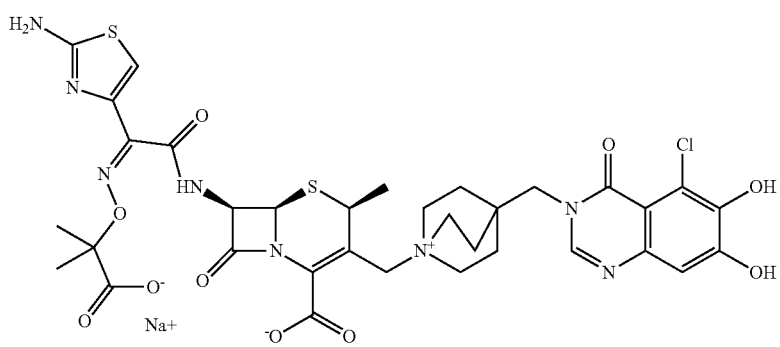

I-161

This compound was prepared according to the two-Step sequence of Example 143, using compound 161e and compound X-24. LCMS: (M+H)+: 817.4. ¹H NMR (400 MHz, D₂O) δ ⌊ ppm 1.37 (s, 3H) 1.39 (s, 3H) 1.42 (d, J=7.07 Hz, 3H) 1.86 (t, J=7.71 Hz, 6H) 3.25-3.46 (m, 6H) 3.85-4.00 (m, 4H) 4.49 (d, J=14.40 Hz, 1H) 5.30 (d, J=5.05 Hz, 1H) 5.71 (d, J=4.80 Hz, 1H) 6.84 (br. s., 1H) 6.86 (s, 1H) 7.96 (s, 1H).

Example 162: Synthesis of Compound I-162

Step (1): 6-amino-2-chloro-3,4-bis((4-methoxybenzyl)oxy)benzoate→Compound 162a

Compound 162a: 6-amino-2-chloro-3,4-bis((4-methoxybenzyl)oxy)-N-(quinuclidin-4-ylmethyl) benzamide

[Chemical Formula 362]

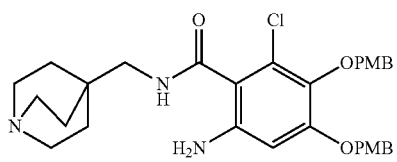

To a solution of potassium 6-amino-2-chloro-3,4-bis((4-methoxybenzyl)oxy)benzoate (5.0 g, 10.4 mmol) in acetonitrile (400 mL) were added HATU (3.94 g, 10.4 mmol) and DIPEA (9.06 mL, 51.9 mmol), and the mixture was stirred for 0.5 h at rt. Quinuclidin-4-ylmethanamine, 2 Hydrochloride (WO2011125966A1, 2.65 g, 12.5 mmol) was then added, and the mixture was stirred for 1 h at rt. Water was added, and the mixture was extracted with DCM and washed with aq sodium bicarbonate. The crude material was purified by automated silica column chromatography using a 24 g column and eluting with 40-90% solvent A in solvent B (solvent A=EtOAc/EtOH/Et₃N, 76:24:1 ratio; solvent B=Hexane) to afford compound 162a (2.46 g, 42% yield) as a yellow solid. LCMS: (M+H)+: 566.4.

Step (2): Compound 162a→Compound 162b

Compound 162b: 5-chloro-6,7-bis((4-methoxybenzyl)oxy)-3-(quinuclidin-4-ylmethyl)quinazoline-2,4(1H,3H)-dione

[Chemical Formula 363]

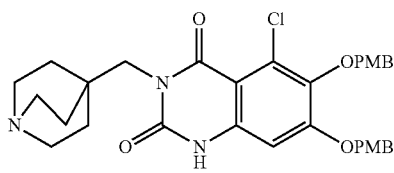

A mixture of compound 162a (100 mg, 0.177 mmol) and CDI (86 mg, 0.53 mmol) in THF (20 mL) was heated to reflux temperature for 24 h. The solution was cooled to rt and was partitioned between EtOAc and water. The organic phase was dried over Na₂SO₄, filtered and concentrated. The crude material was purified by automated silica gel chromatography using a 24 g column and eluting with 0-20% MeOH (containing 1% NH₄OH) in DCM to afford compound 162b (100 mg, 96% yield). LCMS: (M+H)+: 592.4.

Step (3): Compound X-24+Compound 162b→Compound 162c

Compound 162c: 1-(((4S,6R,7R)-7-((Z)-2-(((1-(tert-butoxy)-2-methyl-1-oxopropan-2-yl)oxy)imino)-2-(2-(((tert-butoxycarbonyl)amino)thiazol-4-yl)acetamido)-2-(((4-methoxybenzyl)oxy)carbonyl)-4-methyl-8-oxo-5-thia-1-azabicyclo[4.2.0]oct-2-en-3-yl)methyl)-4-((5-chloro-6,7-bis((4-methoxybenzyl)oxy)-2,4-dioxo-1,2-dihydroquinazolin-3(4H)-yl)methyl)quinuclidin-1-ium, Iodide

[Chemical Formula 364]

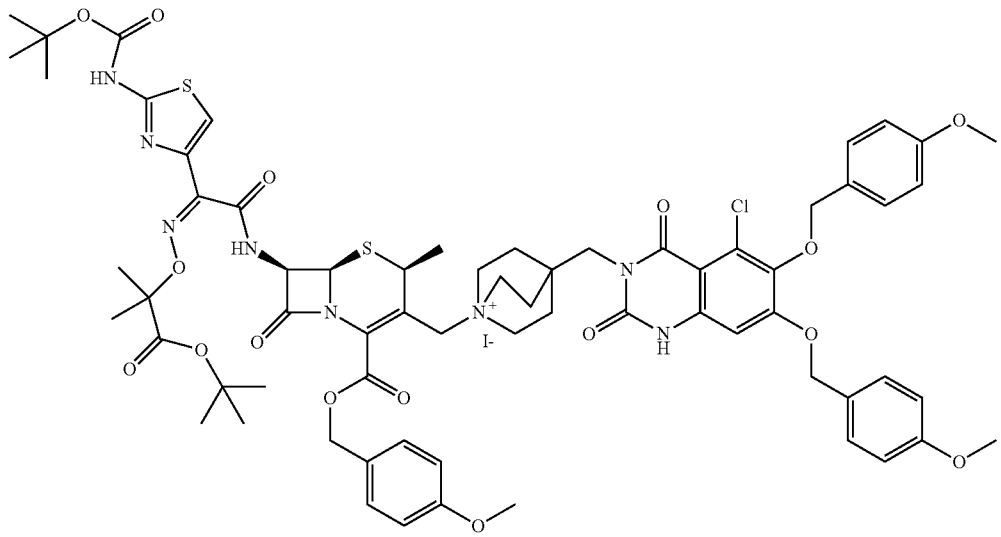

To a mixture of compound 162b (0.101 g, 0.171 mmol) in DMF (2 mL) at 0° C. was added compound X-24 (0.166 g, 0.188 mmol). The mixture was stirred at the same temperature over 1 h. The solution was poured into ice-cooled 5% NaCl aq (20 mL) and the resulting slurry was stirred for 15 min. The solid was collected by filtration, rinsed with water (2×), and dried under high vacuum to afford the desired product as a yellow solid (0.27 g, 70% yield)

LCMS: (M+H)$^+$: 1349.6.

Step (4): Compound 162c→Compound I-162

Compound I-162: (4S,6R,7R)-7-((Z)-2-(2-aminothiazol-4-yl)-2-(((2-carboxypropan-2-yl)oxy)imino)acetamido)-3-((4-((5-chloro-6,7-dihydroxy-2,4-dioxo-1,2-dihydroquinazolin-3(4H)-yl)methyl)quinuclidin-1-ium-1-yl)methyl)-4-methyl-8-oxo-5-thia-1-azabicyclo[4.2.0]oct-2-ene-2-carboxylate, Sodium salt

[Chemical Formula 365]

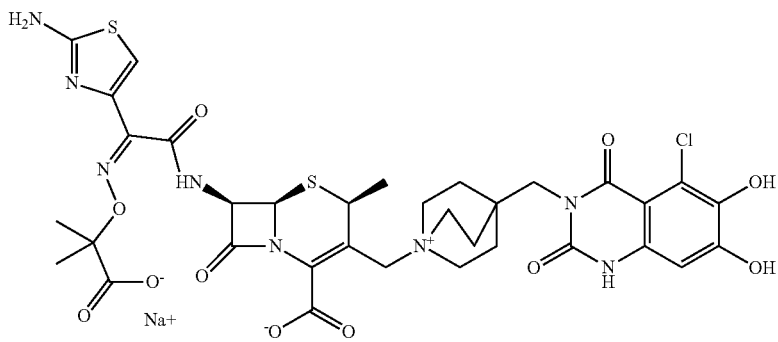

To a solution of compound 162c (0.233 g, 0.102 mmol) in DCM (1 mL) at 0° C. was added anisole (0.11 mL, 1.03 mmol), followed by TFA (0.30 mL, 3.89 mmol). The mixture was stirred overnight at rt. Diisopropyl ether (10 mL) was then added. The mixture was stirred for 10 min, and the precipitate was collected by filtration, and rinsed twice with diisopropyl ether (2×2 mL) The solid was dissolved in a mixture of MeCN (2 mL), water (2 mL), and 2M HCl aq (0.5 mL), and HP20SS resin (2 g) was added. The mixture was concentrated to dryness, and the resin was loaded onto a pre-column containing HP20SS resin (4 g). The pre-column was installed on the Combiflash instrument and washed with water (flow rate=75 mL/min) until the eluting fractions were at pH 4.5 (~5 min). The product was then purified by automated reverse phase chromatography (100 g C18 Gold column, 10% MeCN/water for 8 min, then 18% MeCN/water for 15 min) to afford (4S,6R,7R)-7-((Z)-2-(2-aminothiazol-4-yl)-2-(((2-carboxypropan-2-yl)oxy)imino)acetamido)-3-((4-((5-chloro-6,7-dihydroxy-2,4-dioxo-1,2-dihydroquinazolin-3(4H)-yl)methyl)quinuclidin-1-ium-1-yl)methyl)-4-methyl-8-oxo-5-thia-1-azabicyclo[4.2.0]oct-2-ene-2-carboxylate (53 mg) as an off white solid. This compound was suspended in water (HPLC grade, 10 mL), and cooled to 0° C. To the vigorously stirring suspension was added 0.1N NaOH aq slowly using an Eppendorf pipette until the pH of the solution was 5.5, and a small piece of dry ice was added to quench any excess NaOH. The resulting clear solution was then frozen and lyophilized to afford compound I-162 (53 mg, 59% yield) as an off-white solid. LCMS: (M+H)$^+$: 833.1. $^1$H NMR (400 MHz, D$_2$O) δ | ppm 1.36 (s, 3H) 1.38 (s, 3H) 1.41 (d, J=6.57 Hz, 3H) 1.83 (br. s., 6H) 3.14-3.48 (m, 6H) 3.91 (d, J=15.92 Hz, 4H) 4.46 (d, J=13.89 Hz, 1H) 5.30 (br. s., 1H) 5.71 (d, J=4.55 Hz, 1H) 6.17-6.33 (m, 1H) 6.86 (s, 1H).

Example 163: Synthesis of Compound I-163

Step (1): Compound 150d→Compound 163a

Compound 163a: 2-amino-4,5-bis((4-methoxybenzyl)oxy)-N-(8-methyl-8-azabicyclo[3.2.1]octan-3-yl)benzamide

[Chemical Formula 366]

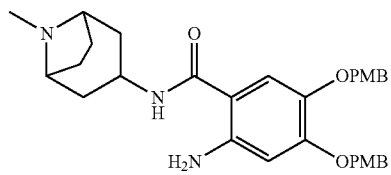

To a solution of compound 150d (4.0 g, 9.8 mmol) in acetonitrile (300 mL) were added HATU (4.46 g, 11.7 mmol) and DIPEA (8.53 mL, 48.8 mmol), and the mixture was stirred for 0.5 h at rt. (1R,5S)-8-methyl-8-azabicyclo[3.2.1]octan-3-amine, 2 Hydrochloride (2.499 g, 11.72 mmol) was then added, and the mixture was stirred for 2 h at rt. Water was added and the mixture was extracted with DCM and washed with sodium bicarbonate. The organic extract was purified by automated silica gel chromatography using a 24 g column and eluting with 0-20% MeOH (containing 1% NH$_4$OH) in DCM to afford compound 163a (3.4 g, 66% yield) as a yellow solid. LCMS: (M+H)$^+$:532.4.

Step (2): Compound 163a→Compound 163b

Compound 163b: 6,7-Bis((4-methoxybenzyl)oxy)-3-(8-methyl-8-azabicyclo[3.2.1]octan-3-yl)quinazolin-4(3H)-one

[Chemical Formula 367]

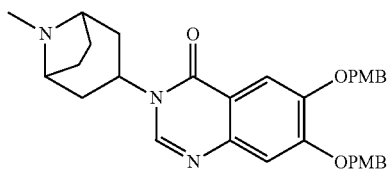

A mixture of compound 163a (1.5 g, 2.8 mmol), trimethoxymethane (30.9 mL, 282 mmol) and methanol (30 mL) was heated to 100° C. for 7 d. Water was added, and the mixture was extracted with DCM and washed with aq sodium bicarbonate. The organic extract was purified by automated silica gel chromatography using a 24 g column and eluting with 0-15% MeOH (containing 1% NH$_4$OH) in DCM to afford compound 163b (1.2 g, 79% yield) as a yellow solid.
LCMS: (M+H)$^+$: 542.4

Step (3): Compound X-24+Compound 163b→Compound I-163

Compound I-163: (4S,6R,7R)-7-((Z)-2-(2-aminothiazol-4-yl)-2-(((2-carboxypropan-2-yl)oxy)imino)acetamido)-3-(((1R,5S,8s)-3-(6,7-dihydroxy-4-oxoquinazolin-3(4H)-yl)-8-methyl-8-azabicyclo[3.2.1]octan-8-ium-8-yl)methyl)-4-methyl-8-oxo-5-thia-1-azabicyclo[4.2.0]oct-2-ene-2-carboxylate, Sodium salt

[Chemical Formula 368]

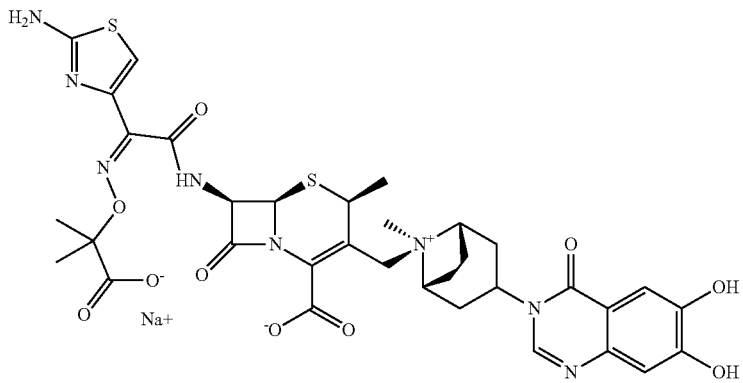

I-163

This compound was prepared according to the two-step sequence of Example 162, using compound 163b and compound X-24. LCMS: (M+H)$^+$: 783.4. $^1$H NMR (400 MHz, D$_2$O) δ | ppm 1.38 (s, 3H) 1.40 (s, 3H) 1.46 (d, J=7.07 Hz, 3H) 2.18 (t, J=16.42 Hz, 2H) 2.25-2.36 (m, 2H) 2.37-2.55 (m, 2H) 2.82-3.00 (m, 2H) 3.03 (s, 3H) 3.84-4.09 (m, 5H) 4.80-4.92 (m, 1H) 5.35 (d, J=4.80 Hz, 1H) 5.71 (d, J=4.80 Hz, 1H) 6.82 (s, 1H) 6.88 (s, 1H) 7.27 (s, 1H) 8.09 (s, 1H).

Example 164: Synthesis of Compound I-164

Step (1):
2-amino-4,5-bis((4-methoxybenzyl)oxy)benzoic acid→Compound 164a

Compound 164a: 3-(1-azabicyclo[2.2.1]heptan-4-ylmethyl)-6,7-bis((4-methoxybenzyl)oxy)quinazolin-4 (3H)-one

[Chemical Formula 369]

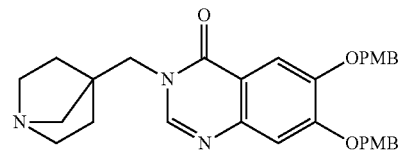

To a solution of 2-amino-4,5-bis((4-methoxybenzyl)oxy) benzoic acid (1.0 g, 2.4 mmol) in DMF (10 mL) were added trimethoxymethane (24.05 mL, 220.0 mmol), DIPEA (1.280 mL, 7.33 mmol) and 1-azabicyclo[2.2.1]heptan-4-ylmethanamine, 2 Hydrochloride (0.730 g, 3.66 mmol). The mixture was stirred at 115° C. for 2 h. Water was added, and the mixture was extracted with DCM and washed with 2N NaOH aq. The organic extract was purified by automated silica gel chromatography, using a 24 g column and eluting with 0-15% MeOH (containing 1% NH$_4$OH) in DCM to afford compound 164a (0.43 g, 33% yield) as a slightly yellow solid. LCMS: (M+H)$^+$: 528.4.

Step (2): Compound X-24+Compound 164a→Compound I-141

Compound I-164: (4S,6R,7R)-7-((Z)-2-(2-aminothiazol-4-yl)-2-(((2-carboxypropan-2-yl)oxy)imino)acetamido)-3-((4-((6,7-dihydroxy-4-oxoquinazolin-3(4H)-yl)methyl)-1-azabicyclo[2.2.1]heptan-1-ium-1-yl)methyl)-4-methyl-8-oxo-5-thia-1-azabicyclo[4.2.0]oct-2-ene-2-carboxylate, Sodium salt

[Chemical Formula 370]

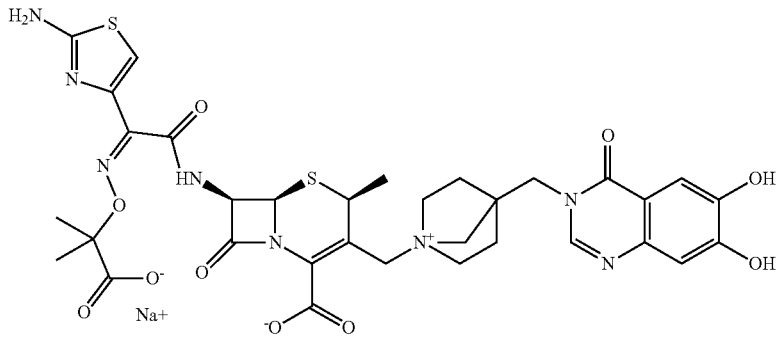

I-164

This compound was prepared according to the two-step sequence of Example 162, using compound 164a and compound X-24. LCMS: (M+H)$^+$: 769.4. $^1$H NMR (400 MHz, D$_2$O) δ ∟ppm 1.36 (s, 3H) 1.38 (s, 3H) 1.41 (d, J=7.07 Hz, 3H) 1.90 (br. s., 2H) 2.08 (br. s., 2H) 3.21-3.62 (m, 6H) 3.92 (d, J=7.07 Hz, 1H) 4.12 (d, J=14.40 Hz, 1H) 4.27 (br. s., 2H) 4.74-4.77 (m, 1H) 5.24 (d, J=4.80 Hz, 1H) 5.65 (d, J=4.80 Hz, 1H) 6.86 (s, 1H) 6.91 (s, 1H) 7.34 (s, 1H) 8.03 (s, 1H).

Example 165: Synthesis of Compound I-165

Step (1): Compound 161d→Compound 165a

Compound 165a: 3-(1-azabicyclo[2.2.1]heptan-4-ylmethyl)-5-chloro-6,7-bis((4-methoxybenzyl)oxy)quinazolin-4(3H)-one

[Chemical Formula 371]

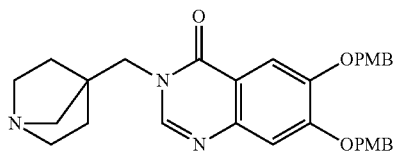

To a mixture of compound 161d (1.0 g, 2.07 mmol) in DMF (10 mL) were added trimethoxymethane (20.43 mL, 187.0 mmol), DIPEA (1.09 mL, 6.22 mmol) and 1-azabicyclo[2.2.1]heptan-4-ylmethanamine, 2 Hydrochloride (0.620 g, 3.11 mmol). Then, the mixture was stirred at 115° C. for 2 h. Water was added, and the mixture was extracted with DCM and washed with 2N NaOH aq. The crude product was purified by automated silica gel chromatography using a 24 g column and eluting with 0-15% MeOH (containing 1% NH$_4$OH) in DCM to afford compound 165a (0.36 g, 31% yield) as a slight yellow solid. LCMS: (M+H)$^+$: 562.4.

Step (2): Compound X-24+Compound 165a→Compound I-165

Compound I-165: (4S,6R,7R)-7-((Z)-2-(2-aminothiazol-4-yl)-2-(((2-carboxypropan-2-yl)oxy)imino)acetamido)-3-((4-((5-chloro-6,7-dihydroxy-4-oxoquinazolin-3(4H)-yl)methyl)-1-azabicyclo[2.2.1]heptan-1-ium-1-yl)methyl)-4-methyl-8-oxo-5-thia-1-azabicyclo[4.2.0]oct-2-ene-2-carboxylate, Sodium salt

[Chemical Formula 372]

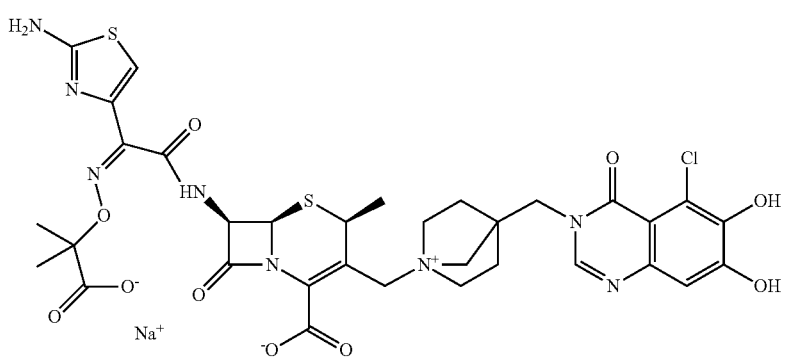

This compound was prepared according to the two-step sequence of Example 162, using compound 165a and compound X-24.

LCMS: (M+H)$^+$: 802.8. $^1$H NMR (400 MHz, D$_2$O) δ ppm 1.36 (s, 3H) 1.38 (s, 3H) 1.41 (d, J=7.33 Hz, 3H) 1.92 (d, J=16.17 Hz, 2H) 2.08 (br. s., 2H) 3.20-3.62 (m, 6H) 3.93 (q, J=6.99 Hz, 1H) 4.11 (d, J=14.40 Hz, 1H) 4.23 (s, 2H) 4.75 (s, 1H) 5.26 (d, J=4.80 Hz, 1H) 5.65 (d, J=4.55 Hz, 1H) 6.80 (s, 1H) 6.87 (s, 1H) 8.02 (s, 1H).

Example 166: Synthesis of Compound I-166

Step (1): 4-nitrobenzene-1,2-diol→Compound 166a

Compound 166a: 4,4'-(((4-nitro-1,2-phenylene)bis(oxy))bis(methylene))bis(methoxybenzene)

[Chemical Formula 373]

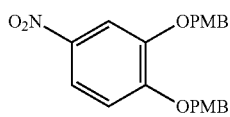

To a solution of 4-nitrobenzene-1,2-diol (9.6 g, 62 mmol) in DMF (100 mL) was added K$_2$CO$_3$ (25.7 g, 186 mmol) followed by 1-(chloromethyl)-4-methoxybenzene (21.0 mL, 155 mmol). The reaction mixture was stirred at 50° C. for 2 h. Water was added, and the mixture was stirred at room temperature for 15 min. The resulting yellow precipitate was collected by filtration and washed with water to afford compound 166a (25.8 g, 95% yield) as a yellow solid. This material was used in the next Step without purification. LCMS: (M+H+Na)$^+$: 418.1.

Step (2): Compound 166a→Compound 166b

Intermediate 3,4-bis((4-methoxybenzyl)oxy)aniline

[Chemical Formula 374]

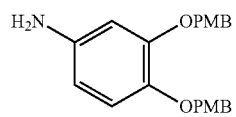

Under an atmosphere of nitrogen, a mixture of compound 166a (29.5 g, 74.6 mmol), ethanol (150 mL), and water (150 mL) was treated with Na$_2$S.9H$_2$O (179 g, 746 mmol) for 2 h at 100° C. The mixture was allowed to cool down, and then was poured into cold water. The resulting yellow precipitate was collected by filtration, washed with water and dried to afford compound 166b (26.3 g, 96% yield) as a yellow solid. This material was used in next Step without purification. LCMS: (M+H)$^+$: 366.1.

Step (3): Compound 166b→Compound 166c

Compound 166c: 5-(((3,4-bis((4-methoxybenzyl)oxy)phenyl)amino)methylene)-2, 2-dimethyl-1,3-dioxane-4,6-dione

[Chemical Formula 375]

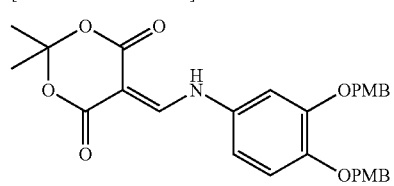

To a solution of compound 166b (19.5 g, 53.4 mmol) in iPrOH (150 mL) was added 5-(methoxymethylene)-2,2-dimethyl-1,3-dioxane-4,6-dione (9.64 mL, 55.9 mmol) at room temperature. The resulting mixture was heated to 80° C. for 20 min. Over this time, the mixture became a thick slurry that was difficult to stir. The reaction mixture was cooled to room temperature, diluted with a small amount of iPrOH to afford a more fluid slurry, and then filtered through a Buchner funnel rinsing with iPrOH. The collected yellow solid was used in the next Step without further purification. LCMS: $(M+H+Na)^+$: 542.2.

Step (4): Compound 166c→Compound 166d

Compound 166d: 6,7-bis((4-methoxybenzyl)oxy)quinolin-4(1H)-one

[Chemical Formula 376]

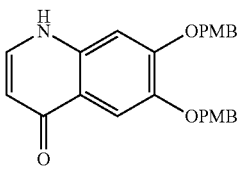

Diphenylether (60 mL) was heated to a boil using a heating mantle. Solid compound 166c (14.0 g, 26.9 mmol) was added portionwise, and the resulting solution was heated for 5 min. The mixture was cooled until it was lukewarm, and then hexane was added. The mixture was stirred well, and then filtered through a Buchner funnel. The collected solid was again suspended in hexane, stirred for 30 min, and then filtered to afford compound 166d (11 g, 82% yield). This material was used in the next Step without further purification. LCMS: $(M+H)^+$: 418.1.

Step (5): Compound 166d→Compound 166e

Compound 166e: 3-(hydroxymethyl)-6,7-bis((4-methoxybenzyl)oxy)quinolin-4(1H)-one

[Chemical Formula 377]

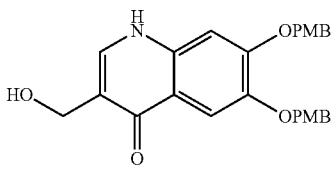

A slurry of compound 166d (5.10 g, 12.2 mmol) in ethanol (30 mL) was heated to 80° C. for 20 min to aid solubility of the starting material. (Note: the starting material does not completely dissolve at elevated temperature, but all clumps are broken up.) The mixture was removed from the oil bath to add 1M sodium hydroxide aq (30.5 mL, 30.5 mmol) and formaldehyde (37% aq solution, 25.5 mL, 342 mmol), and this mixture was heated at 80° C. for 4 h. The reaction mixture was cooled to room temperature by adding ice, and the resulting slurry was stirred for 20 min to break up the clumps. The product was collected by filtration through a Buchner funnel. The solid was washed with water followed by hexanes, and was dried under vacuum overnight to afford compound 166e (4.69 g, 86% yield) as a tan solid. This material was used without purification. LCMS: $(M+H)^+$: 448.2.

Step (6): Compound 166e→Compound 166f

Compound 166f: 3-(hydroxymethyl)-6,7-bis((4-methoxybenzyl)oxy)-1-((2-(trimethylsilyl)ethoxy)methyl)quinolin-4(1H)-one

[Chemical Formula 378]

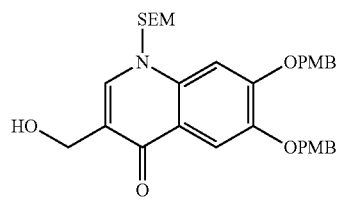

To a suspension of sodium hydride (0.326 g, 8.14 mmol) in THF (72.6 mL) was added compound 166e (4.6 g, 7.4 mmol), and the mixture was stirred at room temperature for 30 min. Then, SEMCl (1.44 mL, 8.14 mmol) was added, and the mixture was stirred at room temperature for 3 h. The mixture was concentrated onto silica gel, and the resulting residue was purified by automated silica gel chromatography (100% DCM, then 0-10% MeOH/DCM over 10 min, 40 g column) to afford compound 166f (2.2 g, 51% yield) as a dark brown solid. LCMS: $(M+H)^+$: 578.2.

Step (7): Compound 166f→Compound 166g

Compound 166g: 6,7-bis((4-methoxybenzyl)oxy)-4-oxo-1-((2-(trimethylsilyl)ethoxy)methyl)-1,4-dihydroquinoline-3-carbaldehyde

[Chemical Formula 379]

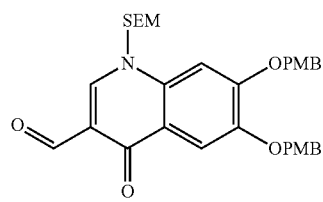

To a solution of compound 166f (2.2 g, 3.8 mmol) in DCM (50 mL) was added manganese dioxide (4.97 g, 57.1 mmol), and the mixture was stirred at room temperature overnight. The mixture was filtered through a celite cake rinsing with DCM, and the filtrate was concentrated to afford compound 166g (2.1 g, 96% yield) as a yellow solid. This material was used in the next Step without purification. LCMS: $(M+H)^+$: 576.2.

Step (8): Compound 166g→Compound 166h

Compound 166h: 6,7-bis((4-methoxybenzyl)oxy)-3-(pyrrolidin-1-ylmethyl)-1-((2-(trimethylsilyl)ethoxy)methyl)quinolin-4(1H)-one

[Chemical Formula 380]

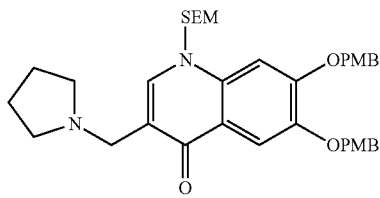

To a solution of compound 166g (2.1 g, 3.7 mmol) in DCM (40 mL) was added pyrrolidine (0.452 mL, 5.47 mmol) and acetic acid (10.4 µL, 0.182 mmol), and the homogeneous solution was stirred at room temperature for 30 min. Then, NaBH(OAc)$_3$ (1.55 g, 7.30 mmol) was added, and the mixture was stirred for 1.5 h. The reaction mixture was diluted with DCM, and then washed successively with saturated NaHCO$_3$ (aq), NaOH (aq), and brine. The organic layer was concentrated, and then MeOH (30 mL) and 5N NaOH (2 mL) were added. The resulting mixture was stirred at room temperature for 0.5 h. The volatiles were removed, and the residue was purified twice via automated silica gel chromatography to afford compound 166h (1.65 g, 72% yield) as a pale yellow solid. LCMS: (M+H)$^+$: 631.3. $^1$H NMR (DMSO-d$_6$): ☐7.96 (s, 1H), 7.64 (s, 1H), 7.41 (d, J=8.6 Hz, 2H), 7.38 (d, J=8.6 Hz, 2H), 6.96 (d, J=6.6 Hz, 2H), 6.94 (d, J=6.6 Hz, 2H), 5.61 (s, 2H), 5.19 (s, 2H), 5.12 (s, 2H), 3.76 (s, 3H), 3.75 (s, 3H), 3.51 (t, J=8.3 Hz, 2H), 3.47 (s, 2H), 2.44-2.50 (m, 4H), 1.62-1.74 (m, 4H), 0.78-0.89 (m, 2H), −0.08 (s, 9H).

Step (9): Compound X-24+Compound 166h→Compound I-166

Compound I-166: (4S,6R,7R)-7-((Z)-2-(2-aminothiazol-4-yl)-2-(((2-carboxypropan-2-yl)oxy)imino)acetamido)-3-((1-((6,7-dihydroxy-4-oxo-1,4-dihydroquinolin-3-yl)methyl)pyrrolidin-1-ium-1-yl)methyl)-4-methyl-8-oxo-5-thia-1-azabicyclo[4.2.0]oct-2-ene-2-carboxylate, Sodium salt

[Chemical Formula 381]

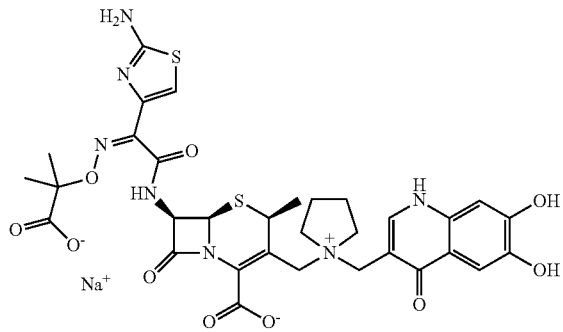

I-166

This compound was prepared according to the two-step sequence of Example 162, using compound 166h and compound X-24. LCMS: (M+H)$^+$: 742.1. 742.4. $^1$H NMR (D$_2$O): 8.05 (s, 1H), 7.41 (s, 1H), 6.89 (s, 1H), 6.86 (s, 1H), 5.70 (d, J=4.8 Hz, 1H), 5.34 (d, J=4.8 Hz, 1H), 4.76-4.83 (m, 2H), 4.27-4.44 (m, 2H), 4.11 (d, J=13.9 Hz, 1H), 3.91-4.04 (m, 1H), 3.39-3.55 (m, 1H), 3.16-3.34 (m, 3H), 1.96-2.20 (m, 4H), 1.34-1.39 (m, 9H).

Example 167: Synthesis of Compound I-167

Step (1): 6,7-dimethoxyquinolin-4(1H)-one→Compound 167a

Compound 167a: 6,7-Dimethoxy-5-Nitroquinolin-4(1H)-One

[Chemical Formula 382]

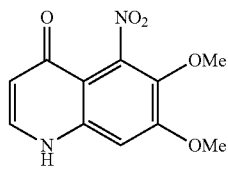

A thick, dark solution of 6,7-dimethoxyquinolin-4(1H)-one (10 g, 48.7 mmol) in sulfuric acid (40 mL, 750 mmol) was cooled to 0° C., and potassium nitrate (4.93 g, 48.7 mmol) was added in small portions, maintaining the temperature below 10° C. After the addition was complete, the mixture was stirred for 10 min and was poured onto ice-water (300 mL). A yellow solid precipitated which was collected by filtration and washed with water and ethanol. The solid was collected and dried in vacuo to afford compound 167a (13.2 g, 108% yield) as a pale yellow solid. This crude material was used in next Step without purification. LCMS: (M+H)$^+$: 250.9.

Step (2): Compound 167a→Compound 167b

Compound 167b: 5-amino-6,7-dimethoxyquinolin-4(1H)-one

[Chemical Formula 383]

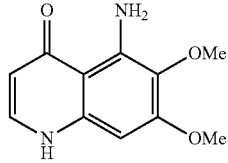

A solution of compound 166a (13.2 g, 52.8 mmol) in EtOH (40 mL) and DCM (80 mL) was placed under vacuum, flushed with an atmosphere of hydrogen, and this process was repeated six times. Then, 10% Pd/C (5.61 g, 5.28 mmol) was added. The mixture was stirred for 12 h and then filtered rinsing with generous amounts of ethanol. The filtrate was concentrated to afford compound 167b e (11.3 g, 88% yield) as a yellow solid. LCMS: (M+H)$^+$: 220.9.

Step (3): Compound 167b→Compound 167c

Compound 167c:
5-chloro-6-hydroxy-7-methoxyquinolin-4(1H)-one

[Chemical Formula 384]

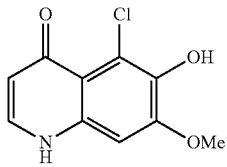

To a stirring mixture of compound 167b (12.2 g, 55.4 mmol) in conc. HCl aq (50 mL, 1650 mmol) at 0° C. was added a solution of sodium nitrite (4.01 g, 58.2 mmol) in water (17 mL), dropwise. The mixture was stirred at 0° C. for 10 min, at which point LCMS indicated the formation of a diazo-intermediate having one methoxy group de-methylated. To the orange suspension was added conc. HCl aq (50 mL), and the resulting mixture was heated to 95° C. for 1 h. The reaction mixture was cooled down to room temperature, and was filtered and dried to afford compound 167c (10.2 g, 76% yield) as a pale yellow solid. The crude product was used in next Step without purification. LCMS: (M+H)$^+$: 225.9.

Step (4): Compound 167c→Compound 167d

Compound 167d:
5-chloro-6,7-dihydroxyquinolin-4(1H)-one

[Chemical Formula 385]

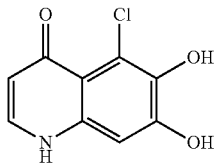

To a solution of compound 167c (9.0 g, 40 mmol) in DCM (100 mL) was added tribromoborane (5.66 mL, 59.8 mmol) at −78° C. The mixture was stirred for 2 h at room temperature. The mixture was diluted with MeOH (50 mL) and concentrated, and this process was repeated five times to afford compound 167d (12.5 g, 148% yield) as a brown solid. This material was carried forward to the next Step without purification. LCMS: (M+H)$^+$: 211.9.

Step (5): Compound 167d→Compound 167e

Compound 167e: 5-chloro-6,7-bis((4-methoxybenzyl)oxy)quinolin-4(1H)-one

[Chemical Formula 386]

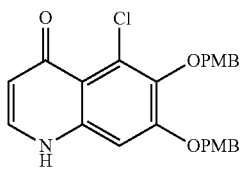

To a solution of compound 167f (10.5 g, 29.8 mmol) in DMF (100 mL) was added K$_2$CO$_3$ (8.23 g, 59.5 mmol), followed by 1-(chloromethyl)-4-methoxybenzene (8.07 mL, 59.5 mmol). The reaction mixture was stirred at 50° C. for 2 h. Water (200 mL) and DCM (150 mL) were added, and the mixture was stirred at room temperature for 15 min. The aqueous phase was extracted with DCM (two times). The combined organic phases were dried, filtered, and concentrated to afford a residue that was purified via automated normal phase chromatography (0-10% MeOH in DCM) to afford compound 167e (5.3 g, 39% yield) as a crimson solid. LCMS: (M+H)$^+$: 452.1.

Step (6): Compound 167e→Compound 167f

Compound 167f: 5-chloro-3-(hydroxymethyl)-6,7-bis((4-methoxybenzyl)oxy)quinolin-4(1H)-one

[Chemical Formula 387]

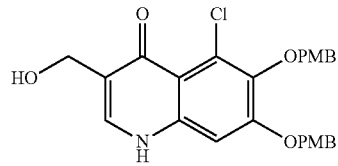

A slurry of compound 167e (25 g, 55 mmol) in ethanol (200 mL) was heated to 80° C. to aid solubility of the starting material. (Note: the starting material does not completely dissolve at elevated temperature, but all clumps are broken up.) The mixture was removed from the oil bath to add 1M sodium hydroxide (aq) (277 mL, 277 mmol) and formaldehyde (37% aq solution, 82 mL, 1100 mmol), and this mixture was heated at 80° C. for 3 h. The reaction mixture was cooled to room temperature, and the resulting slurry was filtered through a Büchner funnel. The solid was washed with water, followed by hexanes to afford compound 167f (20.4 g, 77% yield) as a tan solid. LCMS: (M+H)$^+$: 482.0. $^1$H NMR (DMSO-d$_6$): 11.55 (d, J=5.8 Hz, 1H), 7.70 (d, J=5.8 Hz, 1H), 7.48 (d, J=8.6 Hz, 2H), 7.30 (d, J=8.8 Hz, 2H), 7.09 (s, 1H), 7.01 (d, J=8.6 Hz, 2H), 6.85 (d, J=8.6 Hz, 2H), 5.17 (s, 2H), 4.86 (s, 2H), 4.32 (d, J=5.1 Hz, 2H), 3.79 (s, 3H), 3.74 (s, 3H).

Step (7): Compound 167f→Compound 167g

Compound 167g: 5-chloro-3-(hydroxymethyl)-6,7-bis((4-methoxybenzyl)oxy)-1-((2-(trimethylsilyl)ethoxy)methyl)quinolin-4(1H)-one

[Chemical Formula 388]

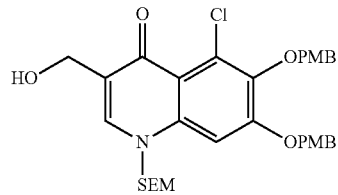

To a suspension of compound 167f (28 g, 51.1 mmol) in DMF (800 mL) was added sodium hydride (2.05 g, 51.1 mmol) and the mixture was stirred at room temperature for 30 min. Then, (2-(chloromethoxy)ethyl)trimethylsilane (9.05 mL, 51.1 mmol) was added, and the mixture was stirred at room temperature for 1 h. Analysis of the reaction mixture by LC-MS indicated that some starting material was still present. Water was added to the reaction mixture, and the precipitate was collected by filtration. Silica gel and DCM were added to the precipitate, and the resulting mixture was concentrated and purified by automated silica gel chromatography (100% DCM, then 0-10% MeOH/DCM) to afford compound 167g (11 g, 19% yield) as a brown oil. LCMS: (M+H)$^+$: 612.2.

Step (8): Compound 167g→Compound 167h

Compound 167h: 5-chloro-6,7-bis((4-methoxybenzyl)oxy)-4-oxo-1-((2-(trimethylsilyl)ethoxy)methyl)-1,4-dihydroquinoline-3-carbaldehyde

[Chemical Formula 389]

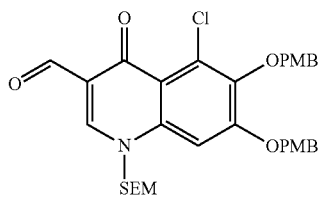

To a solution of 5-chloro-3-(hydroxymethyl)-6,7-bis((4-methoxybenzyl)oxy)-1-((2-(trimethylsilyl)ethoxy)methyl)quinolin-4(1H)-one (5.48 g, 6.62 mmol) in DCM (90 mL) was added manganese(IV) oxide (8.64 g, 99.0 mmol), and the mixture was stirred at room temperature overnight. The mixture was filtered through a celite cake, rinsed with DCM, and the filtrate was concentrated in vacuo to afford compound 167h (4.2 g, 80% yield). This material was used in the next Step without further purification. LCMS: (M+H)$^+$: 610.2.

Step (9): Compound 167h→Compound 167i

Compound 167i: 5-chloro-6,7-bis((4-methoxybenzyl)oxy)-4-oxo-1-((2-(trimethylsilyl)ethoxy)methyl)-1,4-dihydroquinoline-3-carboxylic acid

[Chemical Formula 390]

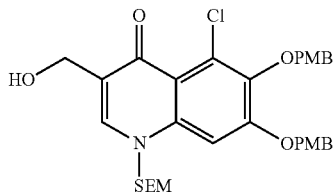

To a solution of compound 167h (3.64 g, 4.59 mmol) in THF (140 mL) and t-Butanol (140 mL) was added 2-methylbut-2-ene (22.97 mL, 45.90 mmol) at 10° C. Subsequently, a solution of sodium chlorite (1.246 g, 13.78 mmol) and sodium dihydrogenphosphate (1.653 g, 13.78 mmol) in water (45 mL) was added dropwise to the first solution, and the mixture was stirred overnight at room temperature. The mixture was then diluted with sat NH$_4$Cl (aq) and extracted with DCM. The combined organic extracts were washed with brine, dried over Na$_2$SO$_4$, filtered, and concentrated in vacuo to afford compound 167i (2.56 g, 89% yield) as a white solid that was used in the next Step without further purification. LCMS: (M+H)$^+$: 626.1. $^1$H NMR (DMSO-d$_6$): 9.08 (s, 1H), 7.57 (s, 1H), 7.49 (d, J=8.6 Hz, 2H), 7.30 (d, J=8.6 Hz, 2H), 7.01 (d, J=8.6 Hz, 2H), 6.86 (d, J=8.6 Hz, 2H), 5.91 (s, 2H), 5.33 (s, 2H), 4.95 (s, 2H), 3.79 (s, 3H), 3.75 (s, 3H), 3.62 (t, J=8.0 Hz, 2H), 0.88 (t, J=8.0 Hz, 2H), −0.05 (s, 9H).

Step (10): Compound 167i→Compound 167j

Compound 167j: 5-chloro-6,7-bis((4-methoxybenzyl)oxy)-4-oxo-N-(2-(pyrrolidin-1-yl)ethyl)-1-((2-(trimethylsilyl) ethoxy)methyl)-1,4-dihydroquinoline-3-carboxamide

[Chemical Formula 391]

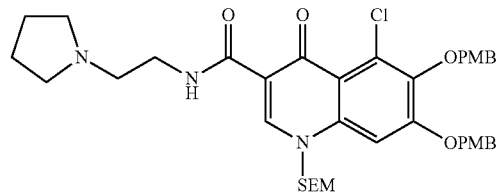

To a solution of compound 167i (2.20 g, 3.51 mmol) in DMF (50 mL) was added HATU (1.60 g, 4.22 mmol) and DIPEA (1.84 mL, 10.5 mmol), and the resulting mixture was stirred at room temperature for 30 min. Then, 2-(pyrrolidin-1-yl)ethanamine (0.47 mL, 3.7 mmol) was added, and the resulting mixture was stirred at room temperature for 1 h. Water and EtOAc were added to the mixture, and the aqueous phase was extracted with EtOAc three times. The combined organic extracts were washed with brine, dried over Na$_2$SO$_4$, filtered, and concentrated in vacuo. The resulting residue was purified via automated normal phase chromatography (24 g column, 0-10% solvent B in solvent A; solvent A=DCM, solvent B=10:90:1 MeOH:DCM:NH$_4$OH). The collected solid was dissolved in DCM and washed with water, and then the organic layer was concentrated in vacuo. The residue was passed through a small (4 g) silica gel column (0-10% MeOH in DCM) to afford compound 167j (1.31 g, 52% yield) as a brown solid. LCMS: (M+H)$^+$: 722.3. $^1$H NMR (DMSO-d$_6$): 9.88 (t, J=5.6 Hz, 1H), 8.84 (s, 1H), 7.48 (d, J=8.6 Hz, 2H), 7.45 (s, 1H), 7.30 (d, J=8.6 Hz, 2H), 7.01 (d, J=8.8 Hz, 2H), 6.85 (d, J=8.6 Hz, 2H), 5.81 (s, 1H), 5.28 (s, 2H), 4.91 (s, 2H), 3.79 (s, 3H), 3.75 (s, 3H), 3.59 (t, J=7.8 Hz, 2H), 3.44 (q, J=6.3 Hz, 2H), 2.58 (t, J=6.4 Hz, 2H), 2.44-2.50 (m, 4H), 1.64-1.74 (m, 4H), 0.87 (t, J=7.8 Hz, 2H), −0.06 (s, 9H).

Step (11): Compound X-24+Compound 167j→Compound I-167

Compound I-167: (4S,6R,7R)-7-((Z)-2-(2-aminothiazol-4-yl)-2-(((2-carboxypropan-2-yl)oxy)imino)acetamido)-3-((1-(2-(5-chloro-6,7-di hydroxy-4-oxo-1,4-dihydroquinoline-3-carboxamido)ethyl)pyrrolidin-1-ium-1-yl)methyl)-4-methyl-8-oxo-5-thia-1-azabicyclo[4.2.0]oct-2-ene-2-carboxylate, Sodium salt

[Chemical Formula 392]

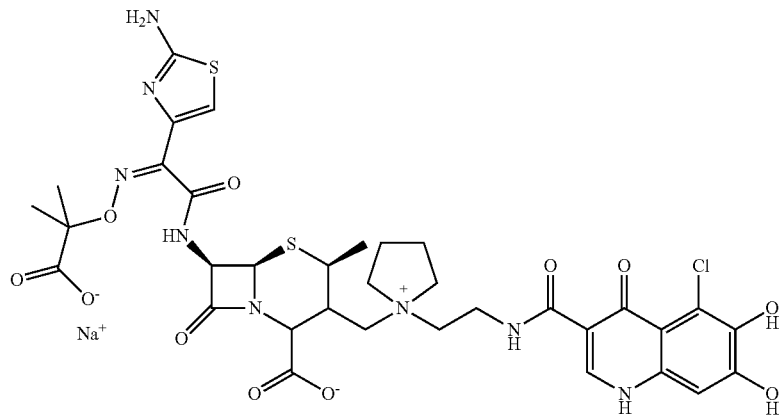

This compound was prepared according to the two-step sequence of Example 162, using compound 167j and compound X-24.

LCMS: (M+H)$^+$: 833.2. $^1$H NMR (D$_2$O): 8.26 (br. s., 1H), 6.87 (s, 1H), 6.47-6.57 (m, 1H), 5.70 (d, J=4.5 Hz, 1H), 5.35 (d, J=4.5 Hz, 1H), 4.90 (d, J=14.9 Hz, 1H), 4.17 (d, J=14.1 Hz, 1H), 3.96 (d, J=5.3 Hz, 1H), 3.69-3.90 (m, 2H), 3.56-3.67 (m, 1H), 3.26-3.55 (m, 6H), 2.10 (br. s., 4H), 1.45 (d, J=6.6 Hz, 3H), 1.38 (s, 3H), 1.36 (s, 3H).

Example 168: Synthesis of Compound I-168

Step (1): 5-chloro-1-ethyl-6,7-bis((4-methoxybenzyl)oxy)-4-oxo-1,4-dihydroquinoline-3-carboxylic acid→Compound 168a Compound 168a: 5-chloro-1-ethyl-6,7-bis((4-methoxybenzyl)oxy)-4-oxo-N-(quinuclidin-4-ylmethyl)-1,4-dihydroquinoline-3-carboxamide

[Chemical Formula 393]

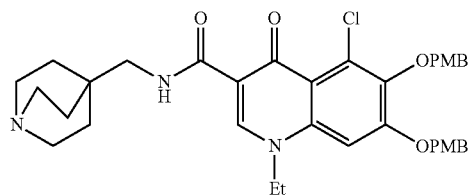

To a solution of 5-chloro-1-ethyl-6,7-bis((4-methoxybenzyl)oxy)-4-oxo-1,4-dihydroquinoline-3-carboxylic acid (ref: WO2013052568, 6.11 g, 11.7 mmol) and quinuclidin-4-ylmethanamine (1.799 g, 12.83 mmol) in DCM (700 mL) was added DIPEA (3.05 mL, 17.5 mmol) and PyBOP (7.28 g, 14.0 mmol) at room temperature, and the reaction mixture was stirred overnight. The mixture was concentrated and the residue was purified via automated silica gel chromatography (120 g column, 0-10% MeOH in DCM), and the isolated product was washed with saturated NaHCO$_3$ aq, brine, and water successively. The resulting material was eluted through a smaller (24 g) silica gel column (0-10% MeOH in DCM) to afford product (2.28 g, 30% yield) as a white solid. This material was not very reactive in the subsequent Step and was determined by $^1$H NMR to exist in a salt form, presumably with some form of silica gel as the counterion. The material was suspended in MeOH and 1 equiv of 5N NaOH (aq) was added. The mixture was stirred for 15 min and then filtered and rinsed with MeOH to afford compound 168a (1.82 g). LCMS: (M+H)$^+$: 646.1. $^1$H NMR (DMSO-d$_6$): 10.04 (t, J=6.1 Hz, 1H), 8.74 (s, 1H), 7.51 (d, J=8.8 Hz, 2H), 7.31 (d, J=8.6 Hz, 2H), 7.29 (br. s., 1H), 7.02 (d, J=8.6 Hz, 2H), 6.86 (d, J=8.6 Hz, 2H), 5.36 (s, 2H), 4.91 (s, 2H), 4.50 (q, J=6.8 Hz, 2H), 3.79 (s, 3H), 3.75 (s, 3H), 3.11 (d, J=5.8 Hz, 2H), 2.69-2.79 (m, 6H), 1.28-1.37 (m, 9H).

Step (2): Compound X-24+Compound 168a→Compound I-168

Compound I-168: (4S,6R,7R)-7-((Z)-2-(2-aminothiazol-4-yl)-2-(((2-carboxypropan-2-yl)oxy)imino)acetamido)-3-((4-((5-chloro-1-ethyl-6,7-dihydroxy-4-oxo-1,4-dihydroquinoline-3-carboxamido)methyl)quinuclidin-1-ium-1-yl)methyl)-4-methyl-8-oxo-5-thia-1-azabicyclo[4.2.0]oct-2-ene-2-carboxylate, Sodium salt

[Chemical Formula 394]

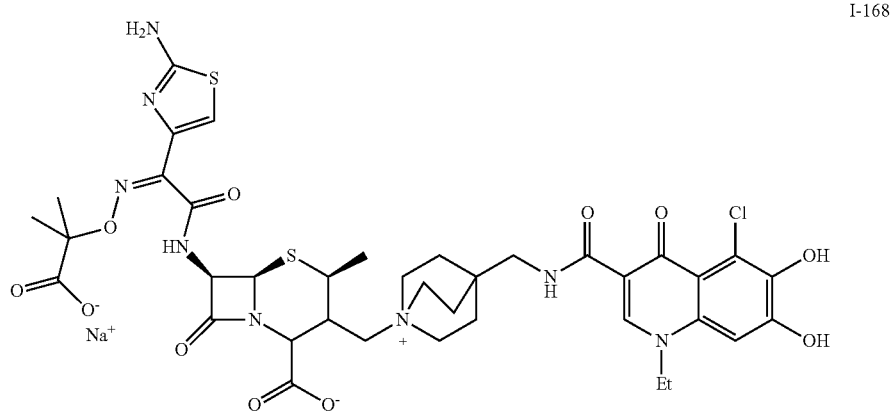

I-168

This compound was prepared according to the two-Step sequence of Example 162, using compound 168a and compound X-24.

LCMS: (M+H)+: 887.4. $^1$H NMR (D$_2$O): 8.31 (s, 1H), 6.85 (s, 1H), 6.70 (br. s., 1H), 5.70 (d, J=4.5 Hz, 1H), 5.30 (d, J=4.8 Hz, 1H), 4.52 (d, J=14.1 Hz, 1H), 3.99-4.16 (m, 2H), 3.86-3.98 (m, 2H), 3.24-3.50 (m, 8H), 1.83 (br. s., 6H), 1.42 (d, J=6.8 Hz, 3H), 1.38 (s, 3H), 1.36 (s, 3H), 1.22-1.30 (m, 3H).

Example 169: Synthesis of Compound I-169

Step (1): Compound 167i→Compound 169a

Compound 169a: 5-chloro-6,7-bis((4-methoxybenzyl)oxy)-4-oxo-N-(quinuclidin-4-ylmethyl)-1-((2-(trimethylsilyl)ethoxy)methyl)-1,4-dihydroquinoline-3-carboxamide

[Chemical Formula 395]

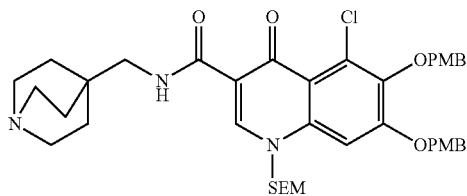

To a solution of compound 167i (980 mg, 1.56 mmol) in DMF (25 mL) was added HATU (714 mg, 1.88 mmol) and DIPEA (1.09 mL, 6.26 mmol), and the resulting mixture was stirred at room temperature for 30 min. Then quinuclidin-4-ylmethanamine, 2 Hydrochloride (WO 2011125966A1, 367 mg, 1.72 mmol) was added and the resulting mixture was stirred at room temperature for 1 h. Water and EtOAc were added to the mixture, and the aqueous phase was extracted with EtOAc three times. The combined organic extracts were washed with brine, dried over Na$_2$SO$_4$, filtered, and concentrated in vacuo. The residue was purified via automated normal phase chromatography (24 g column, 45-90% solvent B in solvent A; solvent A=hexanes, solvent B=3:1 EtOAc/EtOH containing 2% NH$_4$OH) to afford the desired product as a brown solid. The 1H NMR of this material suggested that the product exists as a salt form. To the solid suspended in MeOH was added 200 μL of 6N NaOH aq, at which point the mixture became homogeneous. After stirring the solution for 5 min, it was then passed through an SCX column, eluting with MeOH. The product was then recovered by eluting with MeOH containing 1% NH$_4$OH. The collected material was concentrated, then redissolved in MeOH and concentrated another two times to ensure all the NH$_4$OH was removed. This process afforded compound 169a (0.896 g, 76% yield) as a brown solid.

LCMS: (M+H)+: 748.7. $^1$H NMR (DMSO-d$_6$): 9.94 (t, J=6.1 Hz, 1H), 8.86 (s, 1H), 7.48 (d, J=8.8 Hz, 2H), 7.46 (s, 1H), 7.30 (d, J=8.6 Hz, 2H), 7.01 (d, J=8.8 Hz, 2H), 6.85 (d, J=8.8 Hz, 2H), 5.82 (s, 2H), 5.28 (s, 2H), 4.91 (s, 2H), 3.79 (s, 3H), 3.75 (s, 3H), 3.59 (t, J=8.0 Hz, 2H), 3.13 (d, J=6.1 Hz, 2H), 2.72-2.82 (m, 6H), 1.30-1.40 (m, 6H), 0.87 (t, J=7.8 Hz, 2H), −0.06 (s, 9H).

Step (2): Compound X-24+Compound 169a→Compound I-169

Compound I-169: (4S,6R,7R)-7-((Z)-2-(2-aminothiazol-4-yl)-2-(((2-carboxypropan-2-yl)oxy)imino)acetamido)-3-((4-((5-chloro-6,7-dihydroxy-4-oxo-1,4-dihydroquinoline-3-carboxamido)methyl)quinuclidin-1-ium-1-yl)methyl)-4-methyl-8-oxo-5-thia-1-azabicyclo[4.2.0]oct-2-ene-2-carboxylate, Sodium salt

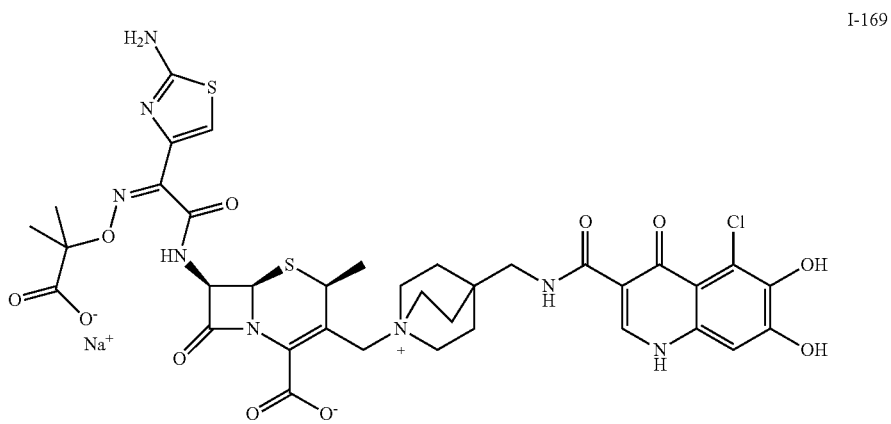

I-169

This compound was prepared according to the two-Step sequence of Example 162, using compound 169a and compound X-24.

LCMS: (M+H)+: 859.5. $^1$H NMR (D$_2$O) □: 8.10 (s, 1H), 6.85 (s, 1H), 6.41 (s, 1H), 5.71 (d, J=4.8 Hz, 1H), 5.32 (d, J=4.8 Hz, 1H), 4.52 (d, J=14.1 Hz, 1H), 3.82-4.03 (m, 2H), 3.29-3.53 (m, 6H), 3.23 (br. s., 2H), 1.76-1.89 (m, 6H), 1.43 (d, J=6.8 Hz, 3H), 1.39 (s, 3H), 1.37 (s, 3H).

The compounds shown below were obtained from Compound X-24 and the each corresponding amine which was synthesized in the same way as example 163 to 169.

Example 170: Synthesis of Compound I-170

Compound I-170: (4S,6R,7R)-7-((Z)-2-(2-aminothiazol-4-yl)-2-(((2-carboxypropan-2-yl)oxy)imino)acetamido)-3-((4-((5-chloro-1-cyclopropyl-6,7-dihydroxy-4-oxo-1,4-dihydroquinoline-3-carboxamido)methyl)quinuclidin-1-ium-1-yl)methyl)-4-methyl-8-oxo-5-thia-1-azabicyclo[4.2.0]oct-2-ene-2-carboxylate, Sodium salt

[Chemical Formula 397]

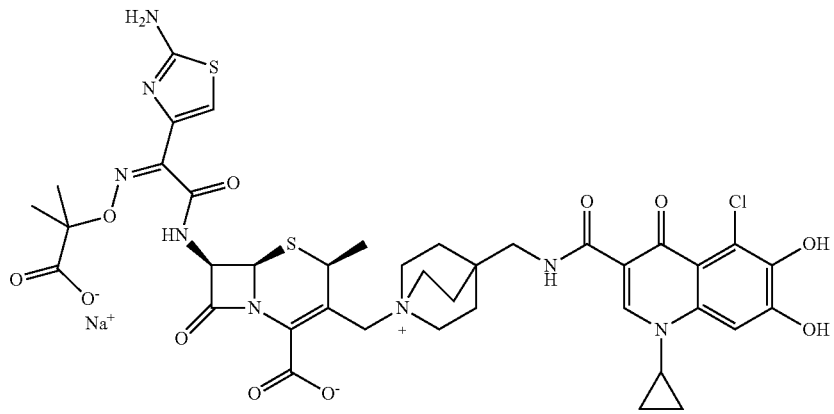

I-170

LCMS: (M+H)⁺: 899.5. ¹H NMR (D₂O): 8.29 (s, 1H), 7.14 (s, 1H), 6.85 (s, 1H), 5.66-5.73 (m, 1H), 5.70 (d, J=4.8 Hz, 1H), 5.30 (d, J=4.8 Hz, 1H), 4.51 (d, J=14.4 Hz, 1H), 3.88-4.00 (m, 2H), 3.30-3.50 (m, 7H), 3.23 (br. s., 2H), 1.82 (br. s., 6H), 1.42 (d, J=6.8 Hz, 3H), 1.38 (s, 3H), 1.36 (s, 3H), 1.16 (d, J=6.3 Hz, 2H), 0.92 (br. s., 2H).

Example 171: Synthesis of Compound I-171

Compound I-171: (4S,6R,7R)-7-((Z)-2-(2-aminothiazol-4-yl)-2-(((2-carboxypropan-2-yl)oxy)imino)acetamido)-3-(((1R,5S,8s)-3-(5-chloro-6,7-dihydroxy-4-oxo-1,4-dihydroquinoline-3-carboxamido)-8-methyl-8-azabicyclo[3.2.1]octan-8-ium-8-yl)methyl)-4-methyl-8-oxo-5-thia-1-azabicyclo[4.2.0]oct-2-ene-2-carboxylate, Sodium salt

[Chemical Formula 398]

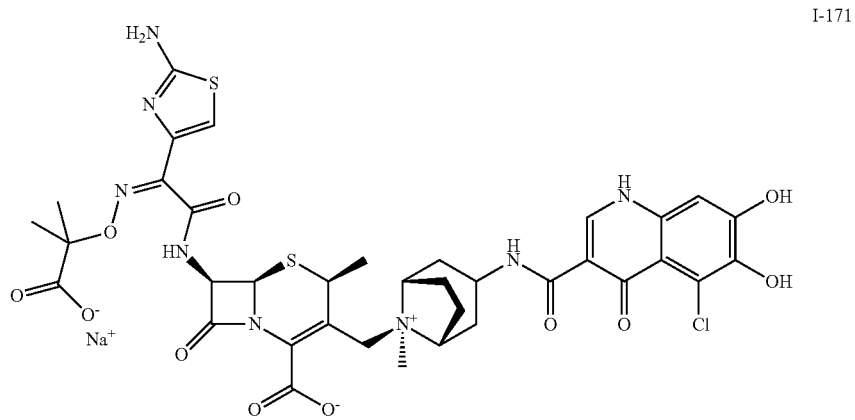

I-171

LCMS: (M+H)⁺: 859.2. ¹H NMR (D₂O): 8.19 (br. s., 1H), 6.88 (s, 1H), 6.54 (br. s., 1H), 5.70 (d, J=4.8 Hz, 1H), 5.34 (d, J=4.5 Hz, 1H), 4.07-4.26 (m, 1H), 3.91-4.04 (m, 3H), 3.86 (br. s., 1H), 2.98 (br. s., 3H), 2.41-2.81 (m, 5H), 2.22-2.40 (m, 3H), 1.90-2.05 (m, 2H), 1.45 (d, J=6.3 Hz, 3H), 1.40 (s, 3H), 1.38 (s, 3H).

Example 172: Synthesis of Compound I-172

Compound I-172: (4S,6R,7R)-7-((Z)-2-(2-aminothiazol-4-yl)-2-(((2-carboxypropan-2-yl)oxy)imino)acetamido)-3-((4-((5-chloro-6,7-dihydroxy-1-methyl-4-oxo-1,4-dihydroquinoline-3-carboxamido)methyl)quinuclidin-1-ium-1-yl)methyl)-4-methyl-8-oxo-5-thia-1-azabicyclo[4.2.0]oct-2-ene-2-carboxylate, Sodium salt

[Chemical Formula 399]

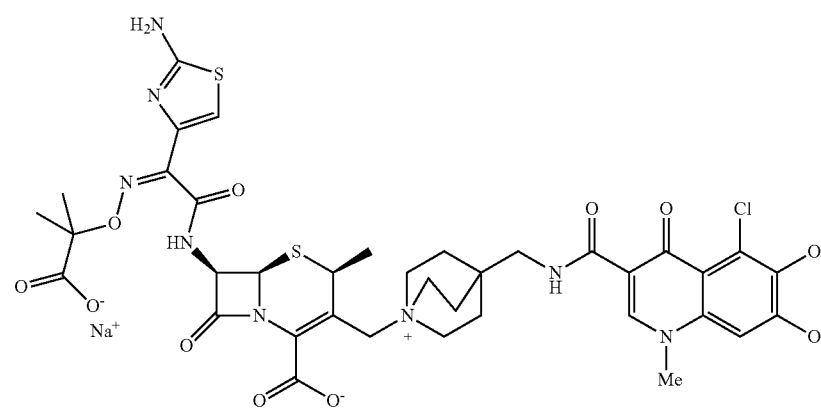

I-172

LCMS: (M+H)+: 873.5. ¹H NMR (D₂O) □: 8.11 (br. s., 1H), 6.86 (s, 1H), 6.45 (br. s., 1H), 5.71 (d, J=4.0 Hz, 1H), 5.33 (m, 1H), 4.53 (d, J=14.1 Hz, 1H), 3.94 (m, 2H), 3.54 (m, 3H), 3.32-3.50 (m, 7H), 3.23 (m, 2H), 1.83 (m, 6H), 1.43 (d, J=6.3 Hz, 3H), 1.39 (s, 3H), 1.38 (s, 3H).

Example 173: Synthesis of Compound I-173

Compound I-171: (4S,6R,7R)-7-((Z)-2-(2-aminothiazol-4-yl)-2-(((2-carboxypropan-2-yl)oxy)imino)acetamido)-3-(((1R,5S,8s)-3-(5-chloro-6,7-dihydroxy-1-methyl-4-oxo-1,4-dihydroquinoline-3-carboxamido)-8-methyl-8-azabicyclo[3.2.1]octan-8-ium-8-yl)methyl)-4-methyl-8-oxo-5-thia-1-azabicyclo[4.2.0]oct-2-ene-2-carboxylate, Sodium salt

[Chemical Formula 400]

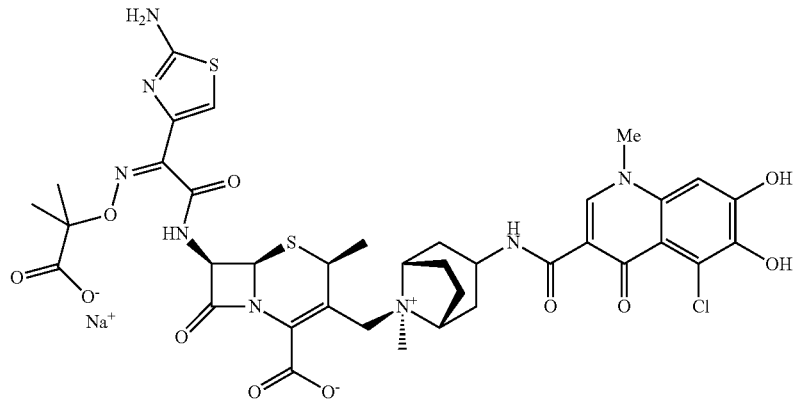

I-173

LCMS: (M+H)+: 873.5. ¹H NMR (D₂O): 8.28 (s, 1H), 6.89 (s, 1H), 6.64 (br. s., 1H), 5.67-5.74 (m, 1H), 5.71 (d, J=4.5 Hz, 1H), 5.35 (d, J=4.5 Hz, 1H), 4.64-4.67 (m, 1H), 4.13-4.20 (m, 1H), 3.94-4.05 (m, 3H), 3.83-3.91 (m, 1H), 3.68 (s, 3H), 3.01 (s, 3H), 2.58-2.80 (m, 3H), 2.44-2.57 (m, 2H), 2.30-2.41 (m, 2H), 1.93-2.06 (m, 3H), 1.46 (d, J=6.8 Hz, 3H), 1.40 (s, 3H), 1.38 (s, 3H).

Example 174: Synthesis of Compound I-174

Step (1): Compound 166b→Compound 174a

Compound 174a: diethyl 2-(((3,4-bis((4-methoxybenzyl)oxy)phenyl)amino)methylene) malonate

[Chemical Formula 401]

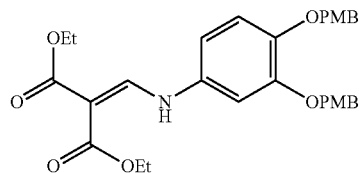

To a solution of compound 166b (100 g, 274 mmol) in iPrOH (800 mL) was added diethyl 2-(ethoxymethylene) malonate (60.3 mL, 301 mmol) at room temperature. The resulting solution was heated to 80° C. for 40 min. Over this time, the suspension became much thicker and was difficult to stir. The mixture was cooled to room temperature, diluted with a small amount of iPrOH to make the slurry more fluid, and filtered through a Büchner funnel rinsing with iPrOH to afford compound 174a (140 g, 96% yield). LCMS: (M+H)+: 536.4.

Step (2): Compound 174a→Compound 174b

Compound 174b: ethyl 6,7-bis((4-methoxybenzyl)oxy)-4-oxo-1,4-dihydroquinoline-3-carboxylate

[Chemical Formula 402]

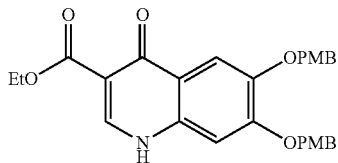

Diphenyl ether (167 mL) was heated to a boil using a heating mantle. compound 174a (15.6 g, 29.0 mmol) was added portionwise and the resulting solution was heated for 10 min. The resulting dark solution was cooled to room temperature, diluted with hexane. This entire procedure was performed 8 more times (a total of 140 g of starting material was processed), and the hexane mixtures from each batch were combined and filtered to afford crude product as a grey solid. The solid was diluted again with hexane, and the resulting slurry was stirred for 30 min and filtered. The collected solid was diluted with MeOH, heated to 80° C. for 30 min, and then filtered to afford compound 174b (75 g, 59% yield)

LCMS: (M+H)$^+$: 490.3.

Step (3): Compound 174b→Compound 174c

Compound 174c: ethyl 6,7-bis((4-methoxybenzyl)oxy)-4-oxo-1-((2-(trimethylsilyl)ethoxy) methyl)-1,4-dihydroquinoline-3-carboxylate

[Chemical Formula 403]

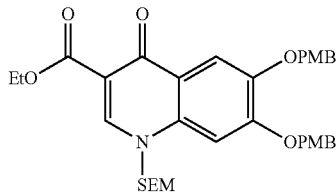

To a suspension of compound 174b (20.0 g, 40.9 mmol) in THF (300 mL) was added $K_2CO_3$ (8.47 g, 61.3 mmol) and SEMCl (7.97 ml, 44.9 mmol). The mixture was stirred at room temperature for 3 h. Water was added to the mixture and the THF was evaporated. The remaining mixture was extracted with DCM (3×200 mL). The combined organic phases were dried, filtered and concentrated to afford compound 174c (23 g, 91% yield) as a dark red oil. This material was used in the next Step without purification. LCMS: (M+H)$^+$: 620.5.

Step (4): Compound 174c→Compound 174d

Compound 174d: 6,7-bis((4-methoxybenzyl)oxy)-4-oxo-1-((2-(trimethylsilyl)ethoxy)methyl)-1,4-dihydroquinoline-3-carboxylic acid

[Chemical Formula 404]

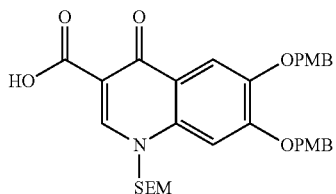

To a solution of compound 174c (23 g, 37 mmol) in water (200 mL) and MeOH (200 mL) was added NaOH (7.42 g, 186 mmol). The mixture was stirred at 80° C. for 1 h. The methanol was evaporated, and HCl aq was added to the solution to adjust the pH to 6. The precipitated solid was collected by filtration to afford compound 174d (19.8 g, 90% yield) as a grey solid. LCMS: (M+H)$^+$: 592.2. $^1$H NMR (DMSO-d$_6$): 8.63 (s, 1H), 7.75 (s, 1H), 7.41 (d, J=8.6 Hz, 2H), 7.37 (d, J=8.6 Hz, 2H), 7.34 (s, 1H), 6.92-6.97 (m, J=8.6 Hz, 2H), 6.92-6.97 (m, J=9.0 Hz, 2H), 5.66 (s, 2H), 5.19 (s, 2H), 5.09 (s, 2H), 3.76 (s, 3H), 3.75 (s, 3H), 3.54 (t, J=7.8 Hz, 2H), 0.84 (t, J=7.8 Hz, 2H), −0.07 (s, 9H).

Step (5): Compound 174d→Compound 174e

Compound 174e: 3-(1,4-diazabicyclo[3.2.2]nonane-4-carbonyl)-6,7-bis((4-meth oxybenzyl)oxy)-1-((2-(trimethylsilyl)ethoxy)methyl)quinolin-4(1H)-one

[Chemical Formula 405]

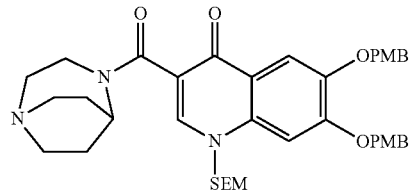

To a solution of compound 174d (24.0 g, 40.6 mmol) in DMF (250 mL) was added HATU (18.5 g, 48.7 mmol) and DIPEA (28.3 mL, 162 mmol), and the resulting mixture was stirred at room temperature for 30 min. Then, 1,4-diazabicyclo[3.2.2]nonane (5.63 g, 44.6 mmol) was added, and the mixture was stirred at room temperature for 1 h. Water and EtOAc were added and the aqueous phase was extracted with EtOAc three times. The combined organic extracts were washed with brine, dried over Na$_2$SO$_4$, filtered, and concentrated in vacuo. The residue was purified via normal phase chromatography (24 g column, 0-10% solvent B in solvent A; solvent A=DCM, solvent B=10:90:1 MeOH:DCM:NH$_4$OH). The isolated solid was dissolved in DCM, washed with water, and then the organic later was concentrated. The residue was eluted through a small silica gel column (4 g, 0-10% MeOH/DCM) to afford compound 174e (16.4 g, 58% yield) as a brown solid. LCMS: (M+H)$^+$: 700.6. $^1$H NMR (DMSO-d$_6$): 8.22 (s, 1H), 7.67 (s, 1H), 7.41 (d, J=8.8 Hz, 2H), 7.39 (d, J=9.1 Hz, 2H), 7.35 (s, 1H), 6.95 (d, J=8.8 Hz, 2H), 6.95 (d, J=8.8 Hz, 2H), 5.63 (s, 2H), 5.21 (s, 2H), 5.14 (s, 2H), 4.53 (br. s., 1H), 3.76 (s, 6H), 3.46-3.59 (t, J=8.1 Hz, 2H), 3.36-3.42 (m, 1H), 2.78-3.04 (m, 6H), 1.43-2.02 (m, 4H), 0.88-1.34 (m, 3H), 0.84 (t, J=8.0 Hz, 2H), −0.07 (s, 9H). Note: This intermediate exists as a mixture of amide rotamers, as observed by $^1$H NMR. Only the shifts for the major rotamer are reported.

Step (4): Compound X-24+Compound 174e→Compound I-174

Compound I-174: (4S,6R,7R)-7-((Z)-2-(2-aminothiazol-4-yl)-2-(((2-carboxypropan-2-yl)oxy)imino)acetamido)-3-((4-(6,7-dihydroxy-4-oxo-1,4-dihydroquinoline-3-carbonyl)-1,4-diazabicyclo[3.2.2]nonan-1-ium-1-yl)methyl)-4-methyl-8-oxo-5-thia-1-azabicyclo[4.2.0]oct-2-ene-2-carboxylate, Sodium salt

[Chemical Formula 406]

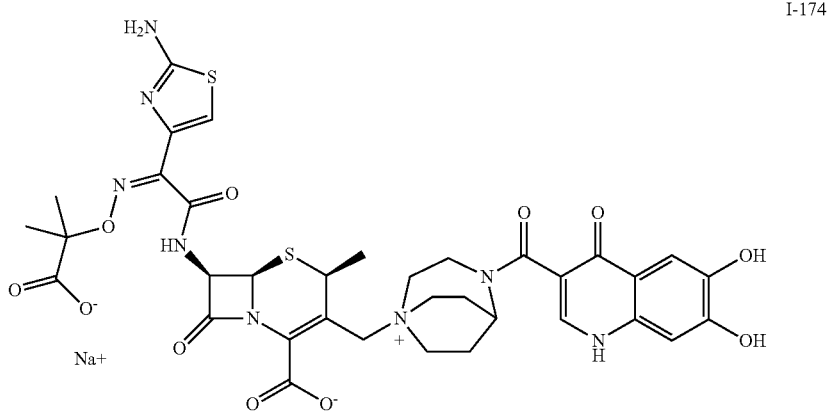

I-174

This compound was prepared according to the two-Step sequence of Example 162, using compound 174e and compound X-24.

LCMS: (M+H)$^+$: 811.3. $^1$H NMR (D$_2$O) □: 8.00 (s, 1H), 7.42 (s, 1H), 6.91 (s, 1H), 6.85 (s, 1H), 5.71 (d, J=4.8 Hz, 1H), 5.32 (d, J=5.1 Hz, 1H), 4.77 (br. s., 1H), 4.17 (d, J=14.1 Hz, 1H), 3.87-4.08 (m, 2H), 3.26-3.85 (m, 8H), 2.26 (m, 3H), 1.45 (d, J=7.3 Hz, 3H), 1.39 (s, 3H), 1.37 (s, 3H). Note: This analog exists as a mixture of amide rotamers, as observed by $^1$H NMR. Only the shifts for the major rotamer are reported.

The compounds shown below were obtained from Compound X-24 and the each corresponding amine which was synthesized according to the synthesis in WO2013052568A1 in the same way as above example.

Example 175: Synthesis of Compound I-175

Compound I-175: (4S,6R,7R)-7-((Z)-2-(2-aminothiazol-4-yl)-2-(((2-carboxypropan-2-yl)oxy)imino)acetamido)-3-((4-((6,7-dihydroxy-4-oxo-1,4-dihydroquinoline-3-carboxamido)methyl)quinuclidin-1-ium-1-yl)methyl)-4-methyl-8-oxo-5-thia-1-azabicyclo[4.2.0]oct-2-ene-2-carboxylate, Sodium salt

[Chemical Formula 407]

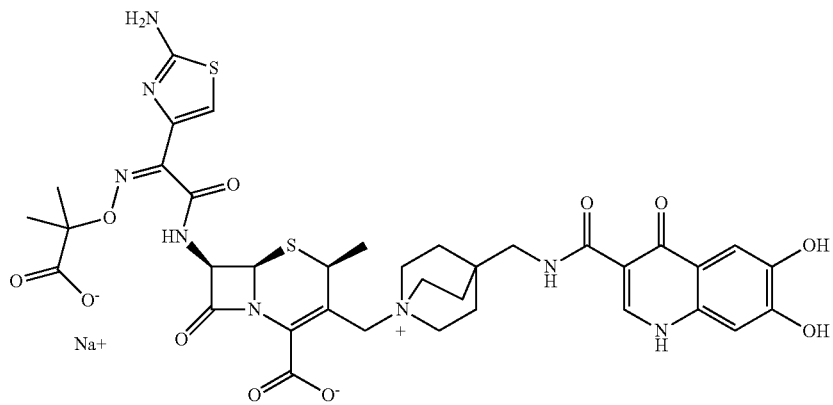

I-175

LCMS: (M+H)⁺: 825.6. ¹H NMR (D₂O): 8.39 (s, 1H), 7.34 (s, 1H), 6.86 (s, 1H), 6.68 (br. s., 1H), 5.71 (d, J=4.8 Hz, 1H), 5.31 (d, J=4.5 Hz, 1H), 4.50 (d, J=14.4 Hz, 1H), 3.85-4.02 (m, 2H), 3.38-3.54 (m, 3H), 3.22-3.37 (m, 5H), 1.82 (br. s., 6H), 1.42 (d, J=6.6 Hz, 3H), 1.39 (s, 3H), 1.37 (s, 3H).

Example 176: Synthesis of Compound I-176

Compound I-176: (4S,6R,7R)-7-((Z)-2-(2-aminothiazol-4-yl)-2-(((2-carboxypropan-2-yl)oxy)imino)acetamido)-3-((1-(2-(6,7-dihydroxy-4-oxo-1,4-dihydroquinoline-3-carboxamido)ethyl)pyrrolidin-1-ium-1-yl)methyl)-4-methyl-8-oxo-5-thia-1-azabicyclo[4.2.0]oct-2-ene-2-carboxylate, Sodium salt

[Chemical Formula 408]

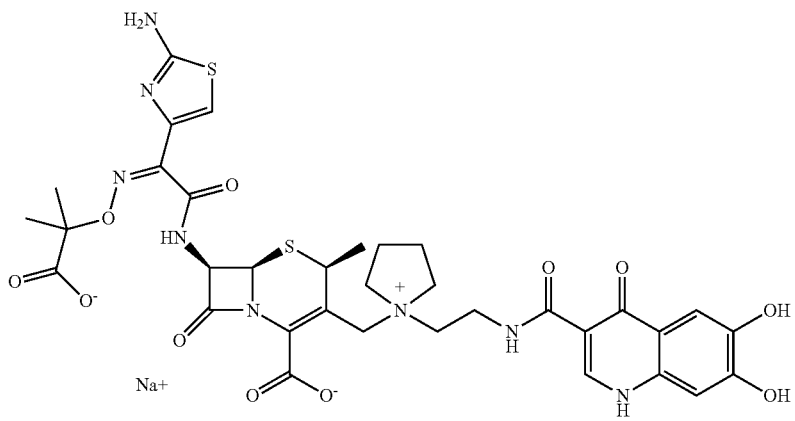

I-176

LCMS: (M+H)⁺: 799.6. ¹H NMR (D₂O): 8.19 (s, 1H), 7.14 (s, 1H), 6.84 (s, 1H), 6.63 (s, 1H), 5.70 (d, J=4.5 Hz, 1H), 5.35 (d, J=4.8 Hz, 1H), 4.91 (d, J=14.1 Hz, 1H), 4.16 (d, J=14.4 Hz, 1H), 3.92-4.01 (m, 1H), 3.66-3.88 (m, 2H), 3.56-3.65 (m, 1H), 3.31-3.52 (m, 5H), 1.98-2.19 (m, 4H), 1.45 (d, J=7.1 Hz, 3H), 1.37 (s, 3H), 1.35 (s, 3H).

Example 177: Synthesis of Compound I-177

Compound I-177: (4S,6R,7R)-7-((Z)-2-(2-aminothiazol-4-yl)-2-(((2-carboxypropan-2-yl)oxy)imino)acetamido)-3-((4-(5-chloro-6,7-dihydroxy-4-oxo-1,4-dihydroquinoline-3-carbonyl)-1,4-diazabicyclo[3.2.2]nonan-1-ium-1-yl)methyl)-4-methyl-8-oxo-5-thia-1-azabicyclo[4.2.0]oct-2-ene-2-carboxylate, Sodium salt

[Chemical Formula 409]

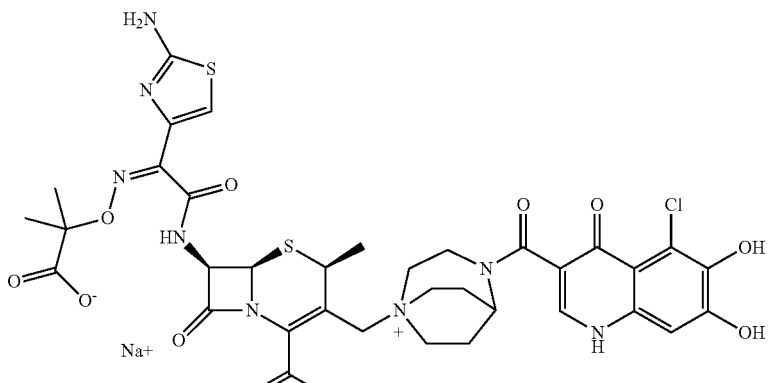

I-177

GSK3185871A

LCMS: (M+H)⁺: 845.3. ¹H NMR (D$_2$O): 7.87 (br. s., 1H), 6.84 (s, 1H), 6.70 (br. s., 1H), 5.71 (d, J=4.8 Hz, 1H), 5.31 (d, J=4.8 Hz, 1H), 4.74-4.81 (m, 1H), 4.14-4.28 (m, 2H), 3.92-4.08 (m, 1H), 3.28-3.91 (m, 8H), 2.03-2.34 (m, 4H), 1.44 (d, J=7.1 Hz, 3H), 1.38 (s, 3H), 1.36 (s, 3H). Note: This analog exists as a mixture of amide rotamers, as observed by ¹H NMR. Only the shifts for the major rotamer are reported.

Example 178: Synthesis of Compound I-178

Step (1): Compound 167i→Compound 178a

Compound 178a: N-(1-azabicyclo[2.2.1]heptan-4-ylmethyl)-5-chloro-6,7-bis((4-methoxybenzyl)oxy)-4-oxo-1-((2-(trimethylsilyl)ethoxy)methyl)-1,4-dihydroquinoline-3-carboxamide

[Chemical Formula 410]

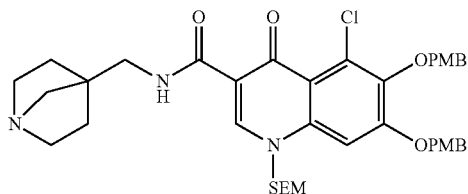

To a solution of compound 167i (2.56 g, 3.27 mmol) in DMF (80 mL) was added HATU (1.49 g, 3.92 mmol) and DIPEA (2.29 mL, 13.1 mmol), and the resulting mixture was stirred at room temperature for 30 min. Then, 1-azabicyclo[2.2.1]heptan-4-ylmethanamine, 2 Hydrochloride (WO 2011125966A1, 0.716 g, 3.60 mmol) was added, and the resulting mixture was stirred at room temperature for 1 h. Water and EtOAc were added to the mixture, and the aqueous phase was extracted with EtOAc three times. The combined organic extracts were washed with brine, dried over Na$_2$SO$_4$, filtered, and concentrated in vacuo. The residue was purified on a Combiflash instrument using a Biotage KP-NH column (45-90% 3:1 EtOAc/EtOH in hexanes) to afford compound 178a (560 mg, 23% yield) as a pale yellow solid. LCMS: (M+H)⁺: 734.4. ¹H NMR (DMSO-d$_6$): 10.01 (t, J=5.8 Hz, 1H), 8.87 (s, 1H), 7.48 (d, J=8.6 Hz, 2H), 7.46 (s, 1H), 7.30 (d, J=8.3 Hz, 2H), 7.01 (d, J=8.6 Hz, 2H), 6.85 (d, J=8.6 Hz, 2H), 5.82 (s, 2H), 5.28 (s, 2H), 4.91 (s, 2H), 3.79 (s, 3H), 3.74 (s, 3H), 3.67 (d, J=5.8 Hz, 2H), 3.55-3.62 (m, 4H), 2.70-2.84 (m, 2H), 2.16 (s, 2H), 1.73-1.81 (m, 2H), 1.46-1.58 (m, 2H), 1.13-1.28 (m, 2H), 0.87 (t, J=8.0 Hz, 2H), −0.06 (s, 9H).

Step (2): Compound X-24+Compound 178a→Compound 178b

Compound 178b: 1-(((4S,6R,7R)-7-((Z)-2-(((1-(tert-butoxy)-2-methyl-1-oxopropan-2-yl)oxy)imino)-2-(2-((tert-butoxycarbonyl)amino)thiazol-4-yl)acetamido)-2-(((4-methoxybenzyl)oxy)carbonyl)-4-methyl-8-oxo-5-thia-1-azabicyclo[4.2.0]oct-2-en-3-yl)methyl)-4-((5-chloro-6,7-bis((4-methoxybenzyl)oxy)-4-oxo-1-((2-(trimethylsilyl)ethoxy)methyl)-1,4-dihydroquinoline-3-carboxamido)methyl)-1-azabicyclo[2.2.1]heptan-1-ium

[Chemical Formula 411]

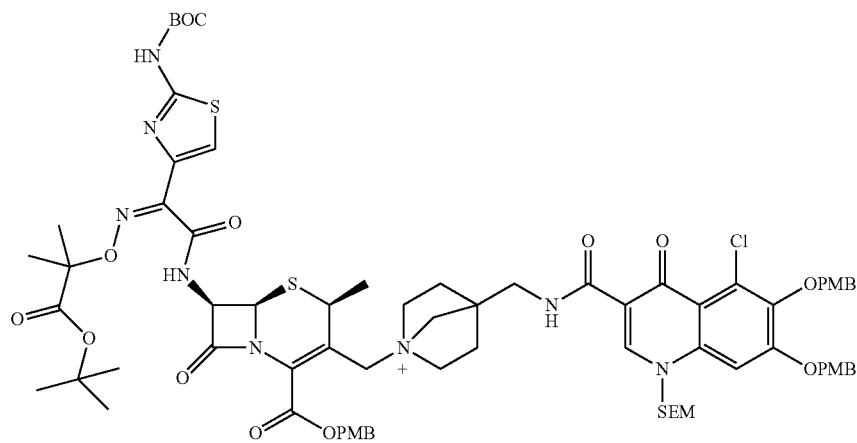

To a solution of compound 178a (0.840 g, 1.075 mmol) in DMF (3.60 mL) at 0° C., was added a solution of compound X-24 (1.00 g, 1.13 mmol) in DMF (3.60 mL), and the mixture was stirred for 30 min at 0° C. An ice-cold solution of NaCl (5% aq, 30 mL) was added, and the resulting slurry was stirred at 0° C. for 15 min, filtered and dried in vacuo to afford compound 178b (1.64 g, 72% yield). This material was used in the next Step without purification.

LCMS: $(M+H)^+$: 1492.5.

Step (3): Compound 178b→Compound 178c

Compound 178c: (4S,6R,7R)-7-((Z)-2-(2-aminothiazol-4-yl)-2-(((2-carboxypropan-2-yl)oxy)imino)acetamido)-3-((4-((5-chloro-6,7-dihydroxy-4-oxo-1,4-dihydroquinoline-3-carboxamido)methyl)-1-azabicyclo[2.2.1]heptan-1-ium-1-yl)methyl)-4-methyl-8-oxo-5-thia-1-azabicyclo[4.2.0]oct-2-ene-2-carboxylate

[Chemical Formula 412]

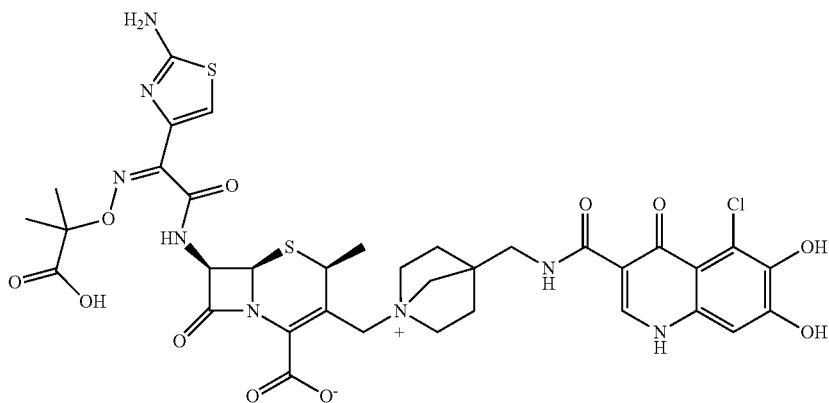

To a solution of compound 178b (1.64 g, 0.769 mmol) in DCM (15 mL) at −40° C., was added anisole (0.840 mL, 7.69 mmol) and 1M $AlCl_3$ in nitromethane (7.69 mL, 7.69 mmol). The resulting clumpy mixture was stirred at 0° C. for 30 min, and a solution of MeCN, water, and 1N HCl aq (1:1:0.25 ratio, 30 mL) was added followed by 30 mL of $iPr_2O$. The organic layer was extracted with a solution of 20% MeCN in 0.5M HCl aq (2×30 mL). To the combined aqueous layers was added HP20SS resin (8 g), and the mixture was concentrated until all the MeCN was removed. This sample was filtered through a loading cartridge that was pre-loaded with more HP20SS resin (15 g). The cartridge was attached to a Combiflash and 100% water was eluted through the cartridge until the fractions were pH>4. A reverse phase Combiflash column was attached (100 g C18 column) and the product was eluted using 0-20% MeCN/water for 10 min, and then 30% MeCN/water over 15 min. Pure fractions were collected to afford compound 178c (370 mg, 55% yield). LCMS: $(M+H)^+$: 845.3. $^1$H NMR (DMSO-$d_6$): 10.38-10.54 (m, 1H), 9.86 (br. s., 1H), 8.43 (s, 1H), 7.31 (br. s., 2H), 6.92 (br. s., 1H), 6.72 (s, 1H), 5.71-5.84 (m, 1H), 5.26 (d, J=5.1 Hz, 1H), 4.93 (m, 1H), 3.92-4.00 (m, 1H), 3.81-3.92 (m, 1H), 3.48-3.63 (m, 6H), 3.22-3.28 (m, 2H), 1.94-2.10 (m, 2H), 1.71 (br. s., 2H), 1.47 (s, 3H), 1.44 (s, 3H), 1.11-1.33 (m, 3H).

Step (4): Compound 178c→Compound I-178

Compound I-178: (4S,6R,7R)-7-((Z)-2-(2-aminothiazol-4-yl)-2-(((2-carboxypropan-2-yl)oxy)imino)acetamido)-3-((4-((5-chloro-6,7-dihydroxy-4-oxo-1,4-dihydroquinoline-3-carboxamido)methyl)-1-azabicyclo[2.2.1]heptan-1-ium-1-yl)methyl)-4-methyl-8-oxo-5-thia-1-azabicyclo[4.2.0]oct-2-ene-2-carboxylate, Sodium salt

[Chemical Formula 413]

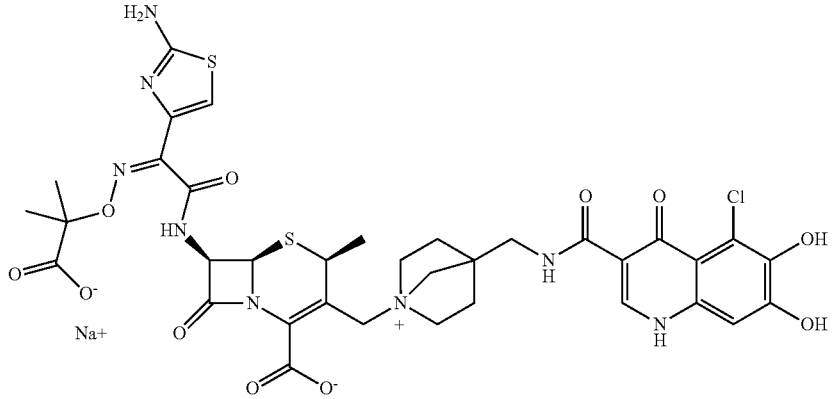

I-178

A vigorously stirring solution of compound 178c (140 mg, 0.164 mmol) in water (11 mL) and acetonitrile (5.52 mL) was cooled to 0° C. using an ice bath, and 0.1M NaOH aq was added dropwise until the pH was 5.5. A small piece of dry ice was added to quench any excess sodium hydroxide, and then the acetonitrile was removed in vacuo. The remaining solution was concentrated by lyophilization to afford compound I-178 (139 mg, 97% yield).

LCMS: (M+H)$^+$: 845.3. $^1$H NMR (D$_2$O): 8.12 (s, 1H), 6.80 (s, 1H), 6.40 (s, 1H), 5.63 (d, J=4.8 Hz, 1H), 5.24 (d, J=4.5 Hz, 1H), 4.75-4.80 (m, 1H), 4.15 (d, J=14.7 Hz, 1H), 3.98 (m, 1H), 3.60 (m, 6H), 3.33 (d, J=7.6 Hz, 1H), 3.21 (d, J=7.8 Hz, 1H), 2.11 (m, 2H), 1.87 (m, 2H), 1.42 (d, J=6.8 Hz, 3H), 1.36 (s, 3H), 1.34 (s, 3H).

Example 179: Synthesis of Compound I-179

Step (1): Compound 151d→Compound 179a

Compound 179a: N-(1-azabicyclo[2.2.1]heptan-4-ylmethyl)-6,7-bis((4-methoxybenzyl)oxy)-4-oxo-1-((2-(trimethylsilyl)ethoxy)methyl)-1,4-dihydroquinoline-3-carboxamide

[Chemical Formula 414]

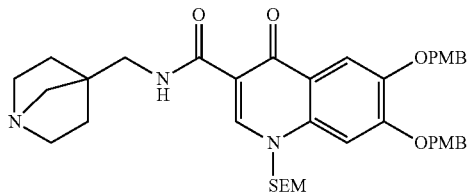

To a solution of compound 151d (1.00 g, 1.69 mmol) in DMF (25 mL) was added HATU (0.771 g, 2.03 mmol) and DIPEA (1.18 mL, 6.76 mmol), and the resulting mixture was stirred at room temperature for 30 min. Then, 1-azabicyclo[2.2.1]heptan-4-ylmethanamine (WO 2011125966A1, 0.337 g, 1.690 mmol) was added, and the resulting mixture was stirred at room temperature for 1 h. Water and EtOAc were added to the mixture, and the aqueous phase was extracted three times with EtOAc. The combined organic extracts were washed with brine, dried over Na$_2$SO$_4$, filtered and concentrated in vacuo. The residue was purified by automated chromatography (100% hexanes, then 0-45% 3:1 EtOAc/EtOH in hexanes, 55 g Biotage® KP-NH column) to afford compound 179a (560 mg, 47% yield) as a brown solid. LCMS: (M+H)$^+$:700.4. $^1$H NMR (DMSO-d$_6$): 10.21 (t, J=5.3 Hz, 1H), 8.86 (s, 1H), 7.78 (s, 1H), 7.44 (s, 1H), 7.42 (d, J=8.6 Hz, 2H), 7.38 (d, J=8.6 Hz, 2H), 6.95 (d, J=8.1 Hz, 2H), 6.96 (d, J=7.8 Hz, 2H), 5.81 (s, 2H), 5.23 (s, 2H), 5.18 (s, 2H), 3.76 (s, 3H), 3.75 (s, 3H), 3.67 (d, J=5.3 Hz, 2H), 3.55 (t, J=7.8 Hz, 2H), 2.69-2.87 (m, 2H), 2.43-2.50 (m, 2H), 2.18 (s, 2H), 1.46-1.62 (m, 2H), 1.21-1.28 (m, 2H), 0.83 (t, J=7.8 Hz, 2H), −0.08 (s, 9H).

Step (2): Compound X-24+Compound 179a→Compound 179b

Compound 179b: 4-((6,7-bis((4-methoxybenzyl)oxy)-4-oxo-1-((2-(trimethylsilyl)ethoxy)methyl)-1,4-dihydroquinoline-3-carboxamido)methyl)-1-(((4S,6R,7R)-7-((Z)-2-(((1-(tert-butoxy)-2-methyl-1-oxopropan-2-yl)oxy)imino)-2-(2-(((tert-butoxycarbonyl)amino)thiazol-4-yl)acetamido)-2-(((4-methoxybenzyl)oxy)carbonyl)-4-methyl-8-oxo-5-thia-1-azabicyclo[4.2.0]oct-2-en-3-yl)methyl)-1-aza bicyclo[2.2.1]heptan-1-ium

[Chemical Formula 415]

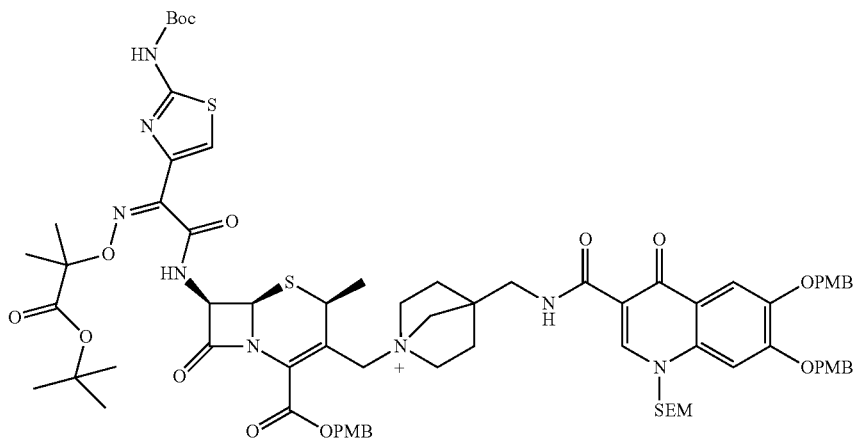

To a solution of compound 179a (560 mg, 0.784 mmol) in DMF (2.61 mL) at 0° C., was added a solution of compound X-24 (729 mg, 0.823 mmol) in DMF (2.61 mL) and the mixture was stirred for 30 min at 0° C. A cold solution of NaCl (5% aq, 30 mL) was added, and the resulting slurry was stirred at 0° C. for 15 min, filtered and dried under vacuum to afford compound 179b (1.15 g, 92% yield). This material was used in the next Step without purification.
LCMS: (M+H)⁺: 1457.5.

Step (3): Compound 179b→Compound 179c

Compound 179c: (4S,6R,7R)-7-((Z)-2-(2-aminothiazol-4-yl)-2-(((2-carboxypropan-2-yl)oxy)imino)acetamido)-3-((4-((6,7-dihydroxy-4-oxo-1,4-dihydroquinoline-3-carboxamido)methyl)-1-azabicyclo[2.2.1]heptan-1-ium-1-yl)methyl)-4-methyl-8-oxo-5-thia-1-azabicyclo[4.2.0]oct-2-ene-2-carboxylate

[Chemical Formula 416]

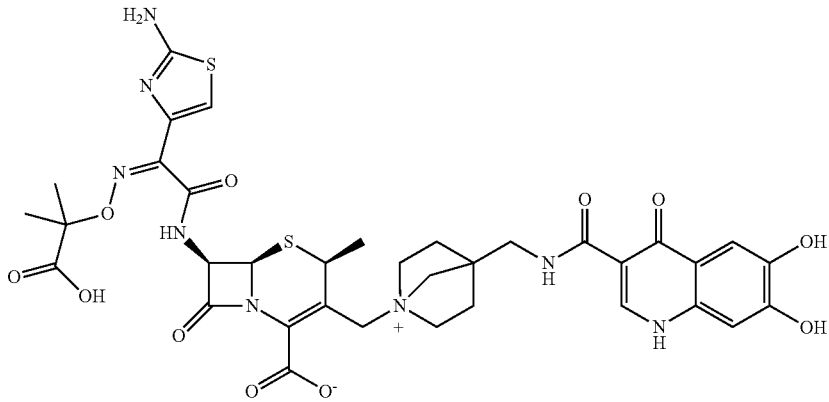

To a solution of compound 179b (1.13 g, 0.646 mmol) in DCM (15 mL) at −40° C., were added anisole (0.84 mL, 7.7 mmol) and 1M AlCl₃ in nitromethane (6.46 mL, 6.46 mmol). The resulting clumpy mixture was stirred at 0° C. for 30 min. A mixture of MeCN, water, and 1N HCl aq (1:1:0.25 ratio, 30 mL) was added, followed by 30 mL of iPr₂O. The organic layer was extracted with a solution of 20% MeCN in 0.5M HCl aq (2×30 mL). To the combined aqueous layers was added HP20SS resin (10 g), and the mixture was concentrated to remove the acetonitrile. The remaining slurry was filtered through a loading cartridge that was pre-loaded with HP20SS resin (20 g). The cartridge was attached to a Combiflash instrument and flushed with 100% water until the fractions were pH>4. A Yamazen Ultrapack ODS-S-50C glass column was attached, and the product was eluted with 100% H₂O, 5 min, 0-18% MeCN/H₂O over 30 min, and 18% MeCN/H₂O for 10 min. The purest fractions were collected to afford compound 179c (200 mg, 38% yield).

LCMS: (M+H)⁺: 811.4. ¹H NMR (DMSO-d₆): 12.82 (br. s., 1H), 10.53 (t, J=5.3 Hz, 1H), 10.37 (br. s., 1H), 10.06 (br. s., 1H), 9.44 (br. s., 1H), 8.47 (br. s., 1H), 7.52 (s, 1H), 7.33 (br. s., 2H), 7.00 (s, 1H), 6.70 (s, 1H), 5.75 (dd, J=7.3, 5.3 Hz, 1H), 5.26 (d, J=5.1 Hz, 1H), 4.99-5.18 (m, 1H), 3.91-4.09 (m, 2H), 3.43-3.62 (m, 8H), 1.92-2.13 (m, 2H), 1.64-1.78 (m, 2H), 1.46 (s, 3H), 1.44 (s, 3H), 1.19-1.38 (m, 3H).

Step (4): Compound 179c→Compound I-179

Compound I-179: (4S,6R,7R)-7-((Z)-2-(2-aminothiazol-4-yl)-2-(((2-carboxypropan-2-yl)oxy)imino)acetamido)-3-((4-((6,7-dihydroxy-4-oxo-1,4-dihydroquinoline-3-carboxamido)methyl)-1-azabicyclo[2.2.1]heptan-1-ium-1-yl)methyl)-4-methyl-8-oxo-5-thia-1-azabicyclo[4.2.0]oct-2-ene-2-carboxylate, Sodium salt

[Chemical Formula 417]

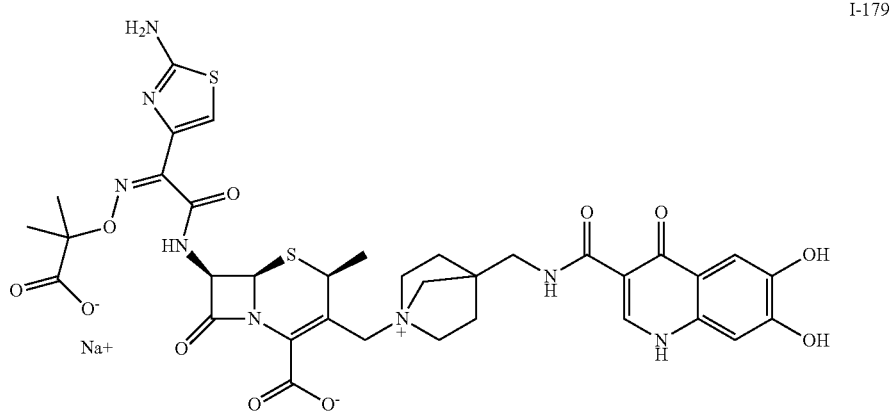

I-179 compound 179c (200 mg, 0.245 mmol) in water (11 mL) and acetonitrile (5.50 mL) was cooled to 0° C. using an ice bath, and 0.2M NaOH aq was added dropwise until the pH was 5.5. A small piece of dry ice was added to quench any excess sodium hydroxide, and then the acetonitrile was removed in vacuo. The remaining solution was concentrated by lyophilization to afford compound I-179 (203 mg, 99% yield). LCMS: (M+H)⁺: 811.2. ¹H NMR (D₂O): 8.30 (s, 1H), 7.18 (s, 1H), 6.80 (s, 1H), 6.64 (s, 1H), 5.61 (d, J=4.8 Hz, 1H), 5.20 (d, J=4.8 Hz, 1H), 4.73-4.78 (m, 1H), 4.14 (d, J=14.4 Hz, 1H), 3.97 (q, J=7.3 Hz, 1H), 3.64 (d, J=6.8 Hz, 2H), 3.42-3.60 (m, 4H), 3.31 (d, J=8.3 Hz, 1H), 3.23 (d, J=8.6 Hz, 1H), 2.01-2.20 (m, 2H), 1.79-1.93 (m, 2H), 1.41 (d, J=7.1 Hz, 3H), 1.35 (s, 3H), 1.33 (s, 3H).

Example 180: Synthesis of Compound I-180

[Chemical Formula 418]

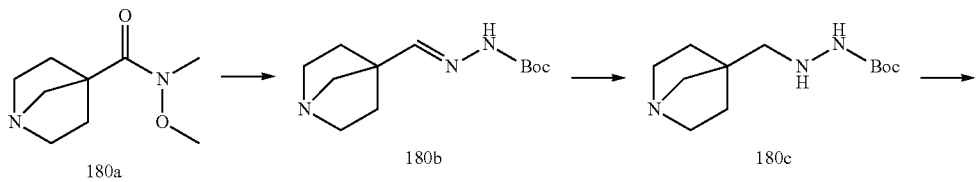

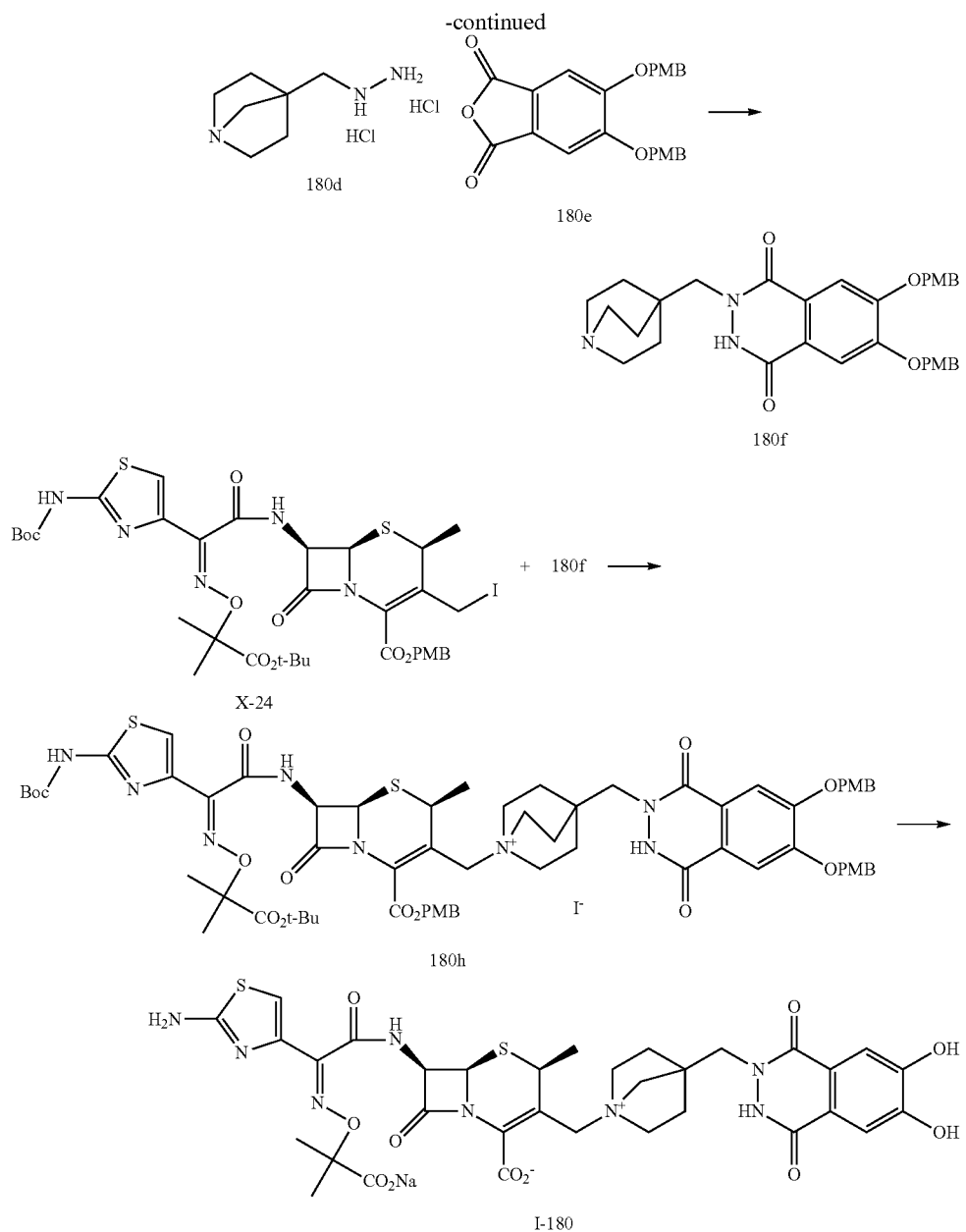

Step (1): Compound 180a→Compound 180b

Compound 180a (1.45 g, 7.9 mmol) was dissolved into tetrahydrofuran (15 mL), and thereto was then added lithium aluminium hydride (0.3 g, 7.9 mmol) at 0° C. The mixture was stirred at 0° C. for 1 hour. To the reaction mixture was then added sodium sulfate decahydrate at 0° C. The mixture was stirred at rt for 1 hour. To the reaction mixture was then added tert-butyl hydrazinecarboxylate (2.1 g, 15.7 mmol). After stirring at room temperature for overnight, the insoluble substance was removed by filtration, and then dissolved ethyl acetate and added saturated citric acid aqueous solution. The water phase was separated and extracted with chloroform. The combined organic layer was dried with anhydrous magnesium sulfate. Magnesium sulfate was filtrated off, and then the liquid was under reduced pressure to yield compound 180b (2.28 g, 113%). Compound 180b yielded was used as it was, without being purified, in the next reaction.

$^1$H-NMR (DMSO-D$_6$) δ: 10.52 (1H, s), 7.55 (1H, s), 2.85-2.77 (2H, m), 2.29 (2H, s), 1.78-1.70 (2H, m), 1.42 (9H, s), 1.38 (2H, s), 1.26-1.16 (2H, m).

Step (2): Compound 180b→Compound 180c

The total amount of compound 180b yielded (2.28 g) was dissolved into methanol (25 mL), and thereto was then added sodium cyanoborohydride (1.2 g, 19.1 mmol) at 0° C. The mixture was stirred at 0° C. for 10 minutes, and then added 2 mol/L hydrochloric acid aqueous solution until it gave a pH of 4.0. After stirring at room temperature for 2 hours, the mixture was concentrated and thereto was added 8 mol/L sodium hydroxide aqueous solution, and then extracted with ethyl acetate. The combined organic layer was dried with anhydrous sodium sulfate. Sodium sulfate was filtrated off, and then the liquid was under reduced pressure to yield compound 180c (2.99 g, 130%). Compound 180c yielded was used as it was, without being purified, in the next reaction.

$^1$H-NMR (DMSO-D$_6$) δ: 8.22 (1H, s), 4.30 (1H, s), 2.98 (2H, d, J=4.0 Hz), 2.75-2.69 (2H, m), 2.47-2.41 (2H, m), 2.14 (2H, s), 1.53-1.38 (13H, m).

Step (3): Compound 180c→Compound 180d

The total amount of compound 180c yielded (2.99 g) was dissolved in methanol (24 mL), and thereto was then added 4 mol/L hydrochloric acid solution (23.8 mL, 95 mmol) in 1,4-dioxane at 0° C. After stirring at room temperature for over night, and the reaction mixture was concentrated under reduced pressure. The precipitated solid was then collected by filtration, and washed with 50% methanol/ethyl acetate solution to yield compound 180d (2.31 g, 113%)

$^1$H-NMR (DMSO-D$_6$) δ: 10.78 (1H, s), 7.45-7.20 (4H, m), 3.28-3.22 (2H, m), 3.18 (2H, s), 3.07 (2H, s), 1.97-1.91 (2H, m), 1.72-1.66 (2H, m).

Step (4): Compound X-180d+Compound 180e→Compound 180f

To a suspension of the total amount of compound 180d yielded (2.31 g) in 1,4-dioxane (45 mL) was added sodium acetate (3.91 g, 47.7 mmol) and compound 180e (4.81 g, 11.4 mmol). After stirring at room temperature for 1 hour, thereto was stirred at 70° C. for 2 hours. The reaction mixture was diluted with a mixture of ethyl acetate/tetrahydrofuran and aqueous sodium hydroxide solution, then separated and washed with water and a saturated salt solution, and dried over sodium sulfate. Sodium sulfate was filtrated off, and then the liquid was concentrated under reduced pressure. The compound-containing liquid was subjected to silica gel column chromatography to elute out the desired compound with ethyl acetate (10% triethylamine)/methanol (10% triethylamine). The desired-compound-containing fraction was concentrated under reduced pressure to yield compound 180f (1.79 g, 35%).

$^1$H-NMR (DMSO-D$_6$) δ: 7.60 (1H, s), 7.49 (1H, s), 7.40-7.36 (4H, m), 6.96-6.93 (4H, m), 5.16 (2H, s), 5.15 (2H, s), 4.18 (2H, s), 3.75 (3H, s), 3.75 (3H, s), 2.74-2.68 (2H, m), 2.47-2.41 (2H, m), 2.30 (2H, s), 1.57-1.51 (2H, m), 1.20-1.14 (2H, m).

Step (4): Compound X-24+Compound 180f→Compound 180f→Compound I-180

Compound X-24 (886 mg, 1.0 mmol) and compound 180f (544 mg, 1.0 mmol) were used to synthesize the target compound in the same way as Example 120.

Yielded amount: 225 mg, (28%)

$^1$H-NMR (D$_2$O) δ: 7.47 (1H, s), 7.27 (1H, s), 6.98 (1H, s), 5.76 (1H, d, J=4.3 Hz), 5.37 (1H, d, J=4.3 Hz), 4.88 (1H, d, J=14.4 Hz), 4.34 (2H, s), 4.24 (1H, d, J=14.4 Hz), 4.06 (1H, q, J=7.0 Hz), 3.64-3.43 (6H, m), 2.23-2.15 (2H, m), 2.04-1.97 (2H, m), 1.54 (3H, d, J=7.0 Hz), 1.51 (3H, s), 1.49 (3H, s). LCMS (m+1)=785

The compounds shown in the following tables can be obtained in the same way exemplified above.

TABLE 1

| Example No. | Structure |
|---|---|
| II-1 | 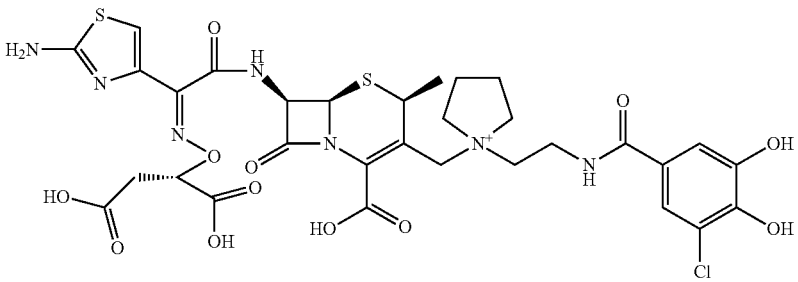 [SMILES: C[C@@H]1S[C@@H]2[C@H](NC(=O)/C(=N\O[C@@H](CC(=O)O)C(=O)O)c3csc(N)n3)C(=O)N2C(C(=O)O)=C1C[N+]1(CCNC(=O)c2cc(O)c(O)c(Cl)c2)CCCC1] |
| II-2 | 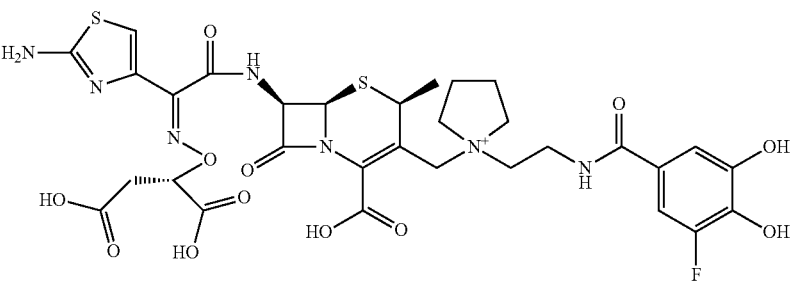 [SMILES: C[C@@H]1S[C@@H]2[C@H](NC(=O)/C(=N\O[C@@H](CC(=O)O)C(=O)O)c3csc(N)n3)C(=O)N2C(C(=O)O)=C1C[N+]1(CCNC(=O)c2cc(O)c(O)c(F)c2)CCCC1] |

TABLE 1-continued
| Example No. | Structure |
|---|---|
| II-3 | 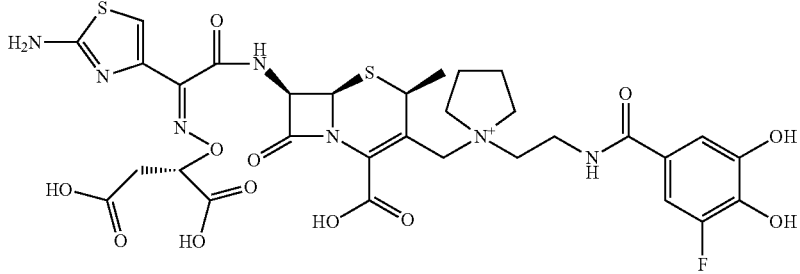 [SMILES: C[C@@H]1S[C@@H]2[C@H](NC(=O)/C(=N\O[C@@H](CC(=O)O)C(=O)O)c3csc(N)n3)C(=O)N2C(C(=O)O)=C1C[N+]1(CCNC(=O)c2cc(O)c(O)c(F)c2)CCCC1] |
| II-4 | 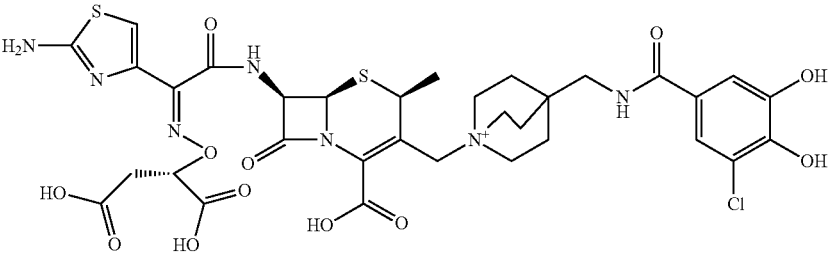 [SMILES: C[C@@H]1S[C@@H]2[C@H](NC(=O)/C(=N\O[C@@H](CC(=O)O)C(=O)O)c3csc(N)n3)C(=O)N2C(C(=O)O)=C1C[N+]12CCC(CNC(=O)c3cc(O)c(O)c(Cl)c3)(CC1)CC2] |
| II-5 | 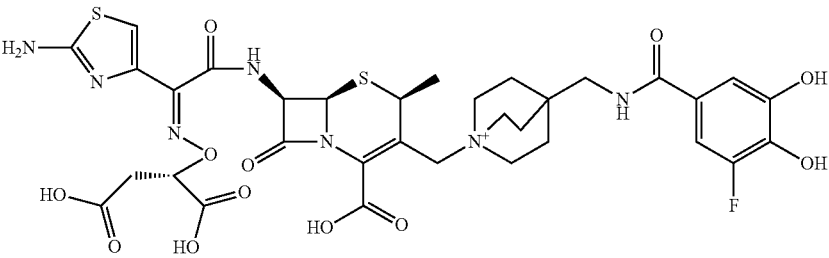 [SMILES: C[C@@H]1S[C@@H]2[C@H](NC(=O)/C(=N\O[C@@H](CC(=O)O)C(=O)O)c3csc(N)n3)C(=O)N2C(C(=O)O)=C1C[N+]12CCC(CNC(=O)c3cc(O)c(O)c(F)c3)(CC1)CC2] |
| II-6 | 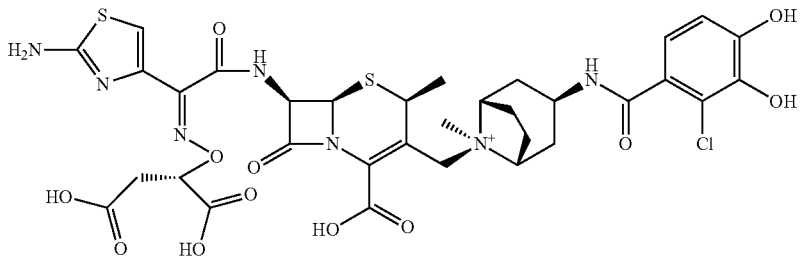 [SMILES: C[C@@H]1S[C@@H]2[C@H](NC(=O)/C(=N\O[C@@H](CC(=O)O)C(=O)O)c3csc(N)n3)C(=O)N2C(C(=O)O)=C1C[N@+]1(C)[C@@H]2CC[C@H]1C[C@@H](NC(=O)c1ccc(O)c(O)c1Cl)C2] |
| II-7 | 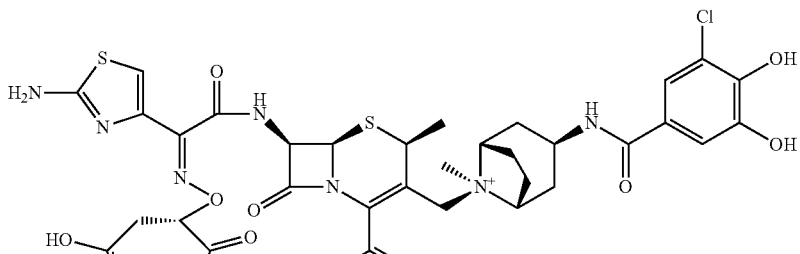 |

TABLE 1-continued
| Example No. | Structure |
|---|---|
| II-8 | 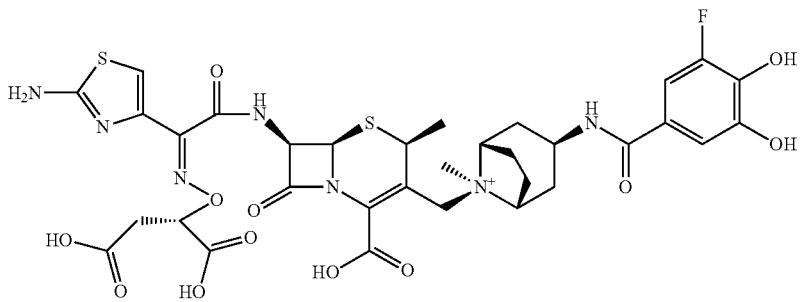 [SMILES: C[C@@H]1S[C@@H]2[C@H](NC(=O)/C(=N\O[C@@H](CC(=O)O)C(=O)O)c3csc(N)n3)C(=O)N2C(C(=O)O)=C1C[N@+]1(C)[C@@H]2CC[C@H]1C[C@@H](NC(=O)c1cc(O)c(O)c(Cl)c1)C2] |
TABLE 2
| Example No. | Structure |
|---|---|
| II-9 | 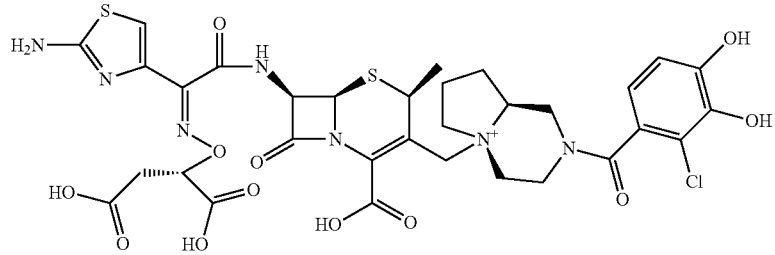 [SMILES: C[C@@H]1S[C@@H]2[C@H](NC(=O)/C(=N\O[C@@H](CC(=O)O)C(=O)O)c3csc(N)n3)C(=O)N2C(C(=O)O)=C1C[N@+]12CCC[C@H]1CN(C(=O)c1ccc(O)c(O)c1Cl)CC2] |
| II-10 | 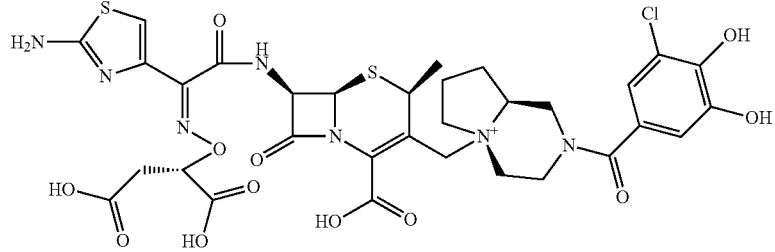 |
| II-11 | 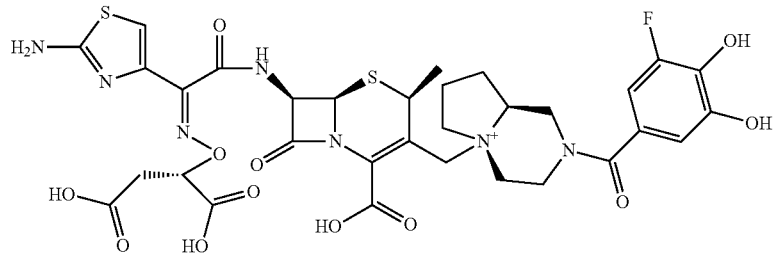 [SMILES: C[C@@H]1S[C@@H]2[C@H](NC(=O)/C(=N\O[C@@H](CC(=O)O)C(=O)O)c3csc(N)n3)C(=O)N2C(C(=O)O)=C1C[N@+]12CCC[C@H]1CN(C(=O)c1cc(O)c(O)c(Cl)c1)CC2] |
| II-12 | 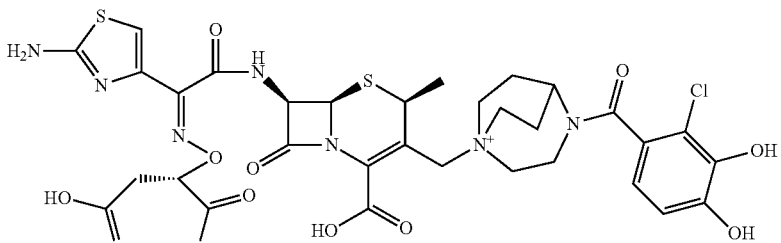 |

519 520
TABLE 2-continued
| Example No. | Structure |
|---|---|
| II-13 | 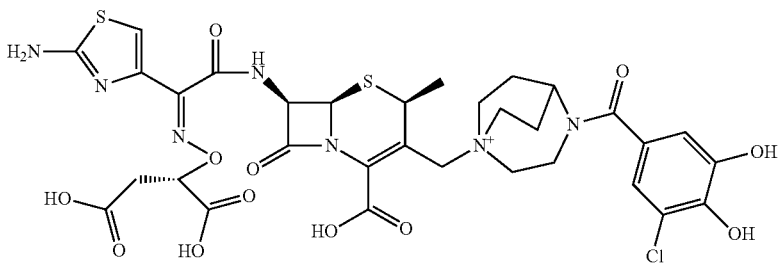 [SMILES: C[C@@H]1S[C@@H]2[C@H](NC(=O)/C(=N\O[C@@H](CC(=O)O)C(=O)O)c3csc(N)n3)C(=O)N2C(C(=O)O)=C1C[N+]12CCC(CC1)N(C(=O)c1cc(O)c(O)c(Cl)c1)CC2] |
| II-14 | 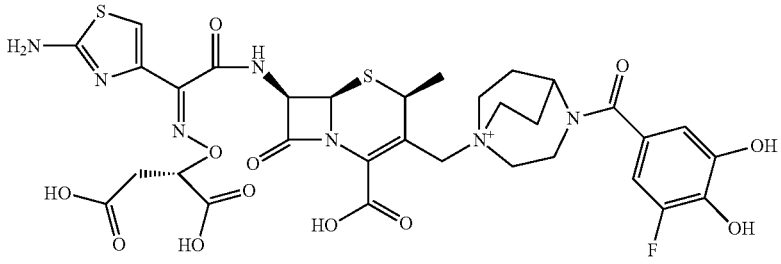 [SMILES: C[C@@H]1S[C@@H]2[C@H](NC(=O)/C(=N\O[C@@H](CC(=O)O)C(=O)O)c3csc(N)n3)C(=O)N2C(C(=O)O)=C1C[N+]12CCC(CC1)N(C(=O)c1cc(O)c(O)c(F)c1)CC2] |
| II-15 | 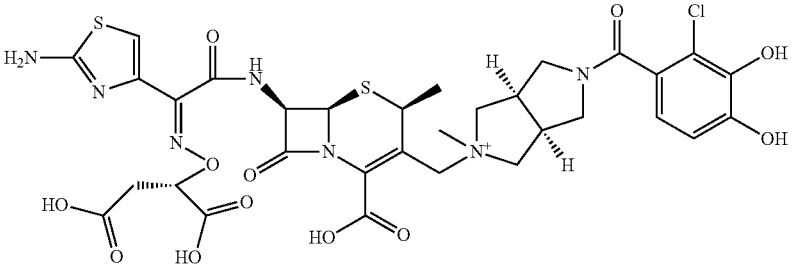 [SMILES: C[C@@H]1S[C@@H]2[C@H](NC(=O)/C(=N\O[C@@H](CC(=O)O)C(=O)O)c3csc(N)n3)C(=O)N2C(C(=O)O)=C1C[N+]1(C)C[C@H]2CN(C(=O)c3ccc(O)c(O)c3Cl)C[C@H]2C1] |
| II-16 | 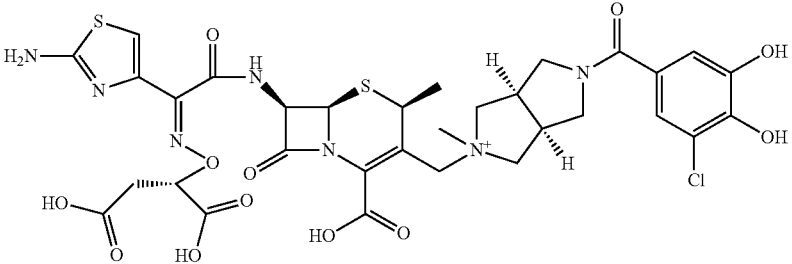 [SMILES: C[C@@H]1S[C@@H]2[C@H](NC(=O)/C(=N\O[C@@H](CC(=O)O)C(=O)O)c3csc(N)n3)C(=O)N2C(C(=O)O)=C1C[N+]1(C)C[C@H]2CN(C(=O)c3cc(O)c(O)c(Cl)c3)C[C@H]2C1] |
TABLE 3
| Example No. | Structure |
|---|---|
| II-17 | 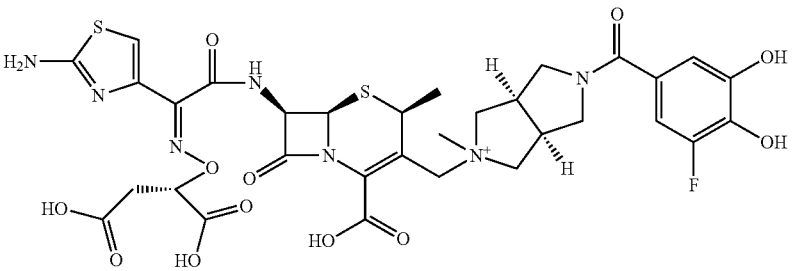 [SMILES: C[C@@H]1S[C@@H]2[C@H](NC(=O)/C(=N\O[C@@H](CC(=O)O)C(=O)O)c3csc(N)n3)C(=O)N2C(C(=O)O)=C1C[N+]1(C)C[C@H]2CN(C(=O)c3cc(O)c(O)c(F)c3)C[C@H]2C1] |

TABLE 3-continued
| Example No. | Structure |
|---|---|
| II-18 | 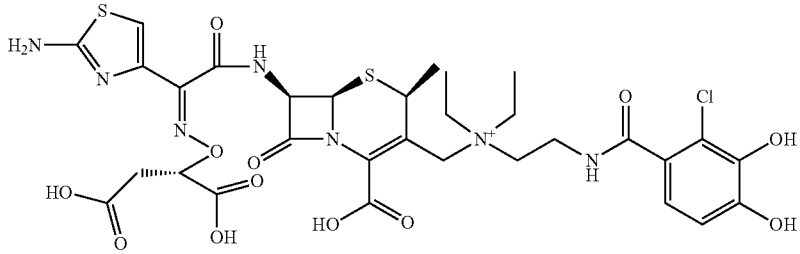 [SMILES: CC[N+](CC)(CCNC(=O)c1ccc(O)c(O)c1Cl)CC1=C(C(=O)O)N2C(=O)[C@@H](NC(=O)/C(=N\O[C@@H](CC(=O)O)C(=O)O)c3csc(N)n3)[C@H]2S[C@H]1C] |
| II-19 | 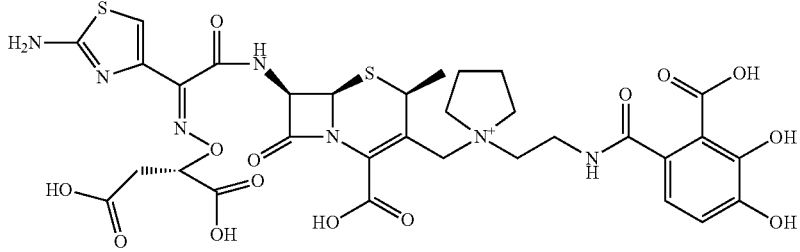 [SMILES: C[C@@H]1S[C@@H]2[C@H](NC(=O)/C(=N\O[C@@H](CC(=O)O)C(=O)O)c3csc(N)n3)C(=O)N2C(C(=O)O)=C1C[N+]1(CCNC(=O)c2ccc(O)c(O)c2C(=O)O)CCCC1] |
| II-20 | 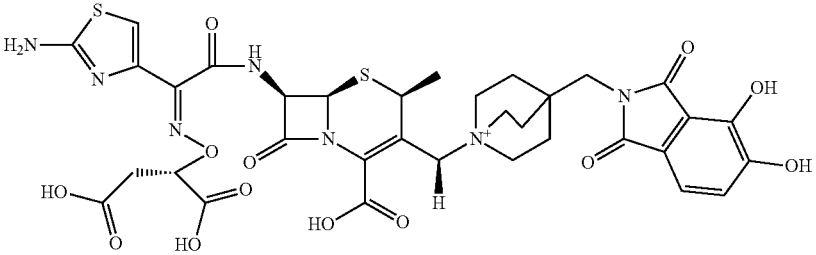 |
| II-21 | 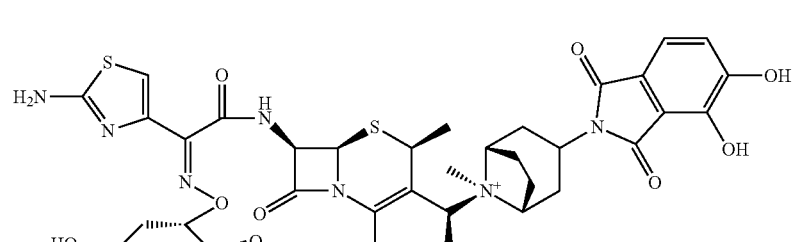 |
| II-22 | 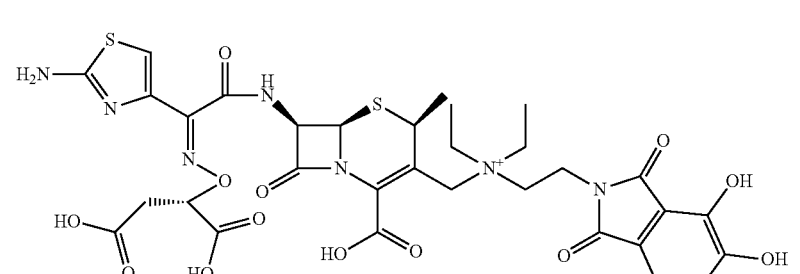 |

TABLE 3-continued
| Example No. | Structure |
|---|---|
| II-23 | 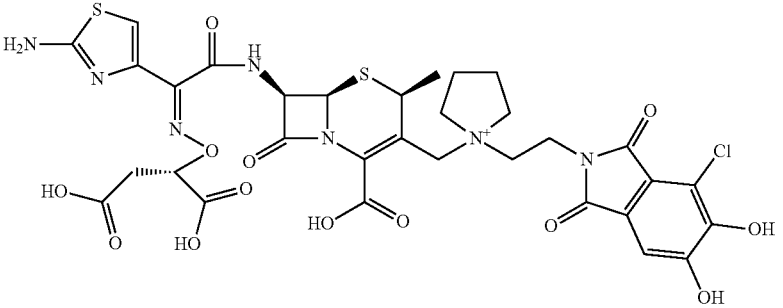 [SMILES: C[C@@H]1S[C@@H]2[C@H](NC(=O)/C(=N\O[C@@H](CC(=O)O)C(=O)O)c3csc(N)n3)C(=O)N2C(C(=O)O)=C1C[N+]1(CCN2C(=O)c3cc(O)c(O)c(Cl)c3C2=O)CCCC1] |
| II-24 | 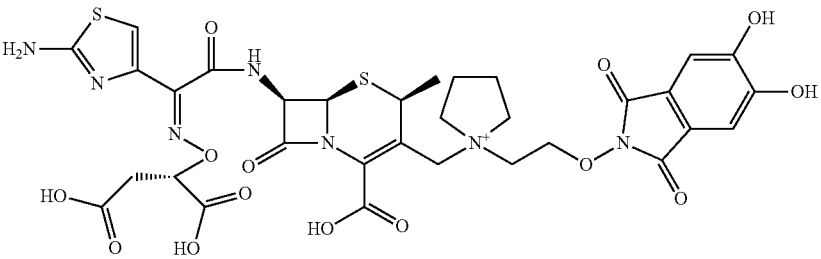 [SMILES: C[C@@H]1S[C@@H]2[C@H](NC(=O)/C(=N\O[C@@H](CC(=O)O)C(=O)O)c3csc(N)n3)C(=O)N2C(C(=O)O)=C1C[N+]1(CCON2C(=O)c3cc(O)c(O)cc3C2=O)CCCC1] |
TABLE 4
| Example No. | Structure |
|---|---|
| II-25 | 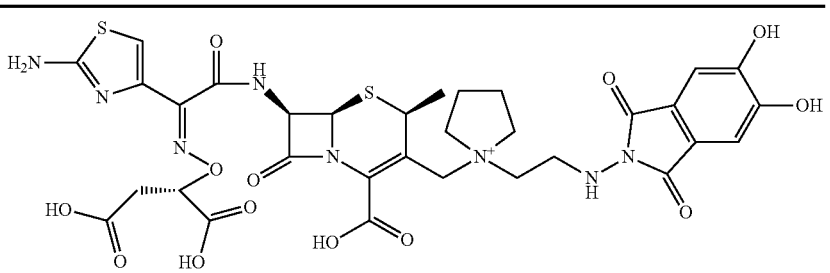 |
| II-26 | 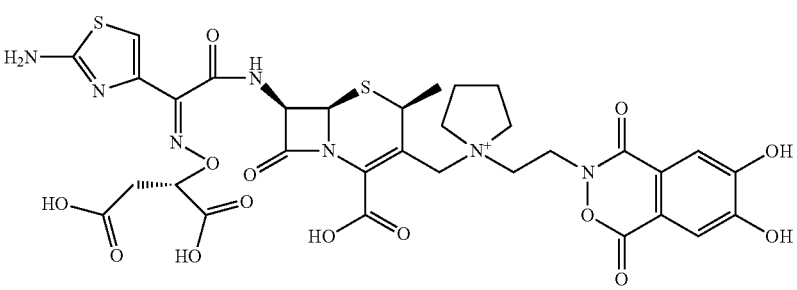 [SMILES: C[C@@H]1S[C@@H]2[C@H](NC(=O)/C(=N\O[C@@H](CC(=O)O)C(=O)O)c3csc(N)n3)C(=O)N2C(C(=O)O)=C1C[N+]1(CCn2oc(=O)c3cc(O)c(O)cc3c2=O)CCCC1] |
| II-27 | 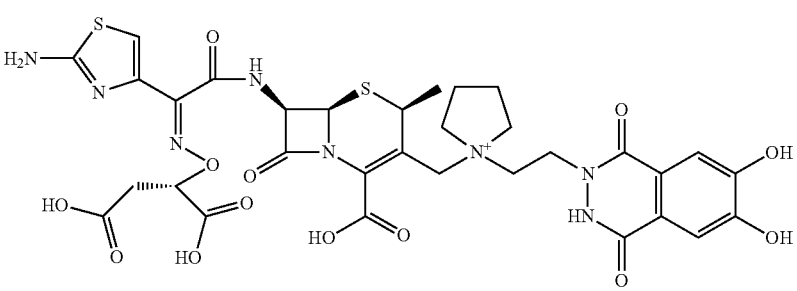 [SMILES: C[C@@H]1S[C@@H]2[C@H](NC(=O)/C(=N\O[C@@H](CC(=O)O)C(=O)O)c3csc(N)n3)C(=O)N2C(C(=O)O)=C1C[N+]1(CCn2[nH]c(=O)c3cc(O)c(O)cc3c2=O)CCCC1] |

TABLE 4-continued
| Example No. | Structure |
|---|---|
| II-28 | 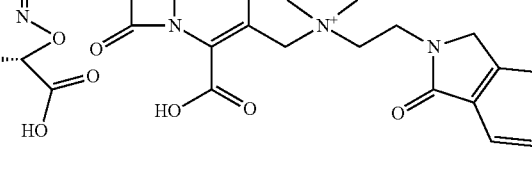 |
| II-29 | 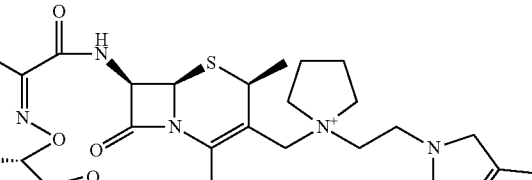 |
| II-30 | 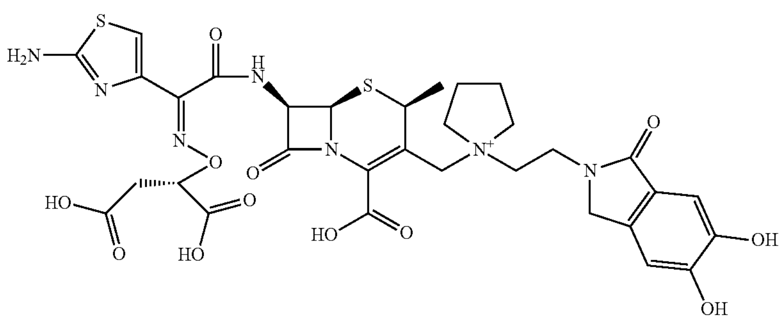 [SMILES: C[C@@H]1S[C@@H]2[C@H](NC(=O)/C(=N\O[C@@H](CC(=O)O)C(=O)O)c3csc(N)n3)C(=O)N2C(C(=O)O)=C1C[N+]1(CCN2Cc3cc(O)c(O)cc3C2=O)CCCC1] |
| II-31 | 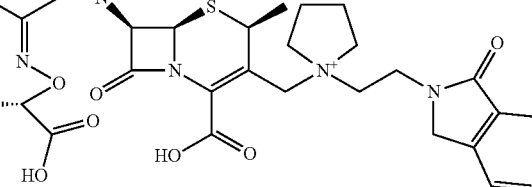 |
| II-32 | 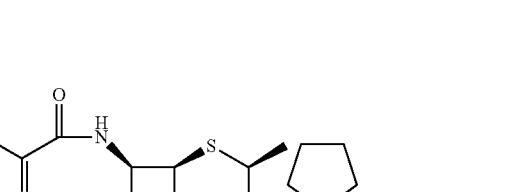 |

TABLE 5

| Example No. | Structure |
| --- | --- |
| II-33 | 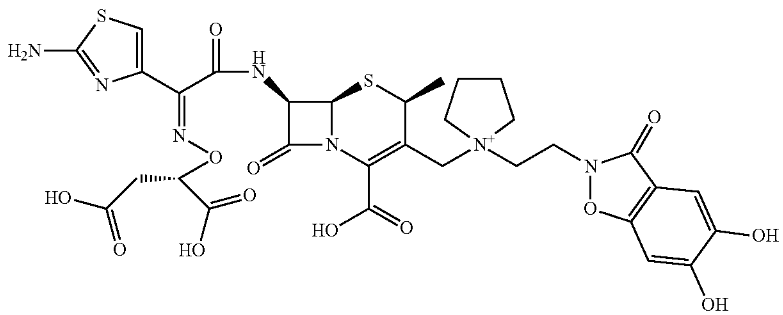 [SMILES: C[C@@H]1S[C@@H]2[C@H](NC(=O)/C(=N\O[C@@H](CC(=O)O)C(=O)O)c3csc(N)n3)C(=O)N2C(C(=O)O)=C1C[N+]1(CCn2sc3cc(O)c(O)cc3c2=O)CCCC1] |
| II-34 | 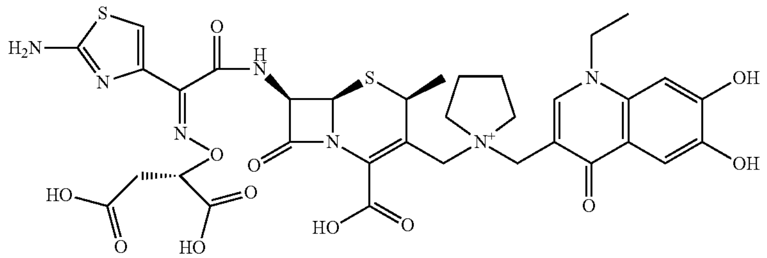 |
| II-35 | 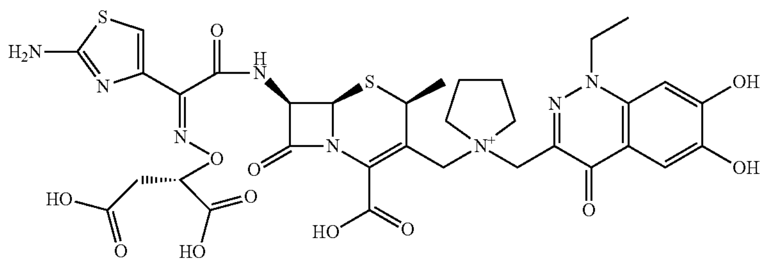 [SMILES: CCn1nc(C[N+]2(CC3=C(C(=O)O)N4C(=O)[C@@H](NC(=O)/C(=N\O[C@@H](CC(=O)O)C(=O)O)c5csc(N)n5)[C@H]4S[C@H]3C)CCCC2)c(=O)c2cc(O)c(O)cc21] |
| II-36 | 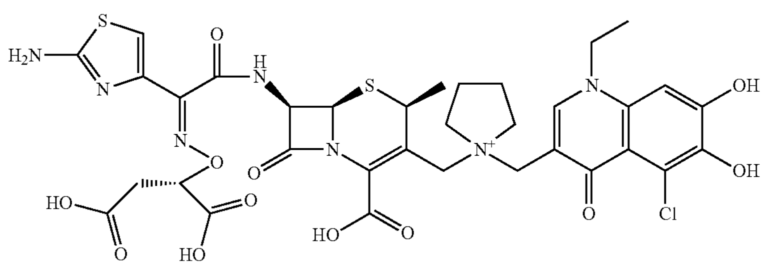 [SMILES: CCn1cc(C[N+]2(CC3=C(C(=O)O)N4C(=O)[C@@H](NC(=O)/C(=N\O[C@@H](CC(=O)O)C(=O)O)c5csc(N)n5)[C@H]4S[C@H]3C)CCCC2)c(=O)c2c(Cl)c(O)c(O)cc21] |
| II-37 | 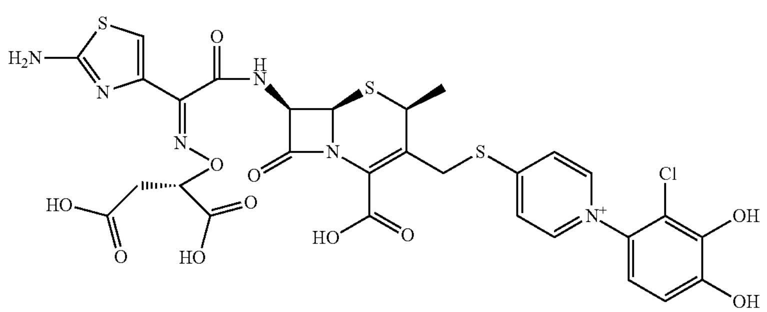 [SMILES: C[C@@H]1S[C@@H]2[C@H](NC(=O)/C(=N\O[C@@H](CC(=O)O)C(=O)O)c3csc(N)n3)C(=O)N2C(C(=O)O)=C1CSc1cc[n+](-c2ccc(O)c(O)c2Cl)cc1] |

TABLE 5-continued

| Example No. | Structure |
|---|---|
| II-38 | (chemical structure) |
| II-39 | (chemical structure) |
| II-40 | (chemical structure) |

TABLE 6

| Example No. | Structure |
|---|---|
| II-41 | (chemical structure) |
| II-42 | (chemical structure) |

TABLE 6-continued

| Example No. | Structure |
|---|---|
| II-43 | 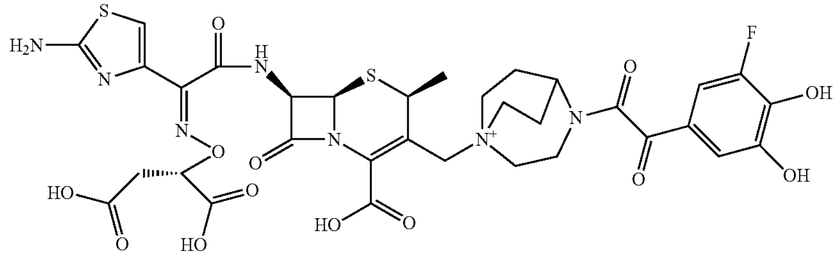 [SMILES: C[C@@H]1S[C@@H]2[C@H](NC(=O)/C(=N\O[C@@H](CC(=O)O)C(=O)O)c3csc(N)n3)C(=O)N2C(C(=O)O)=C1C[N+]12CCC(CC1)N(C(=O)C(=O)c1cc(O)c(O)c(F)c1)CC2] |
| II-44 | 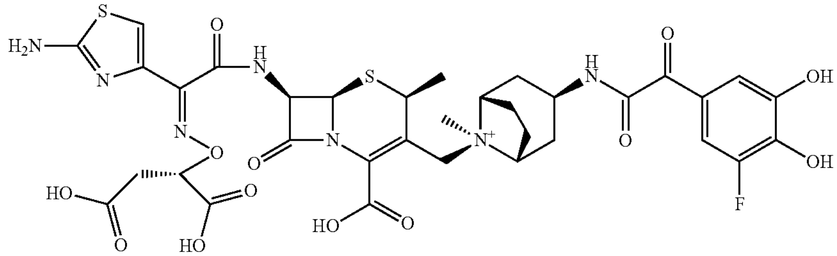 [SMILES: C[C@@H]1S[C@@H]2[C@H](NC(=O)/C(=N\O[C@@H](CC(=O)O)C(=O)O)c3csc(N)n3)C(=O)N2C(C(=O)O)=C1C[N@+]1(C)[C@@H]2CC[C@H]1C[C@@H](NC(=O)C(=O)c1cc(O)c(O)c(F)c1)C2] |
| II-45 | 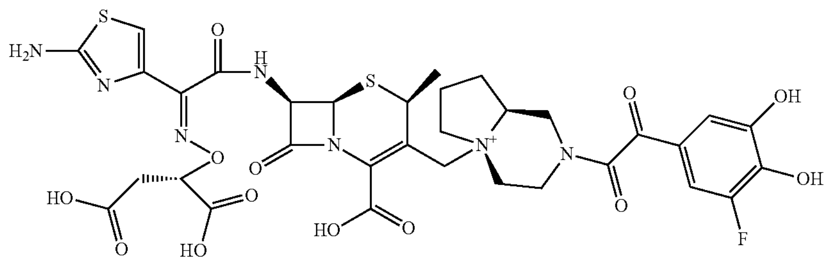 [SMILES: C[C@@H]1S[C@@H]2[C@H](NC(=O)/C(=N\O[C@@H](CC(=O)O)C(=O)O)c3csc(N)n3)C(=O)N2C(C(=O)O)=C1C[N@+]12CCC[C@H]1CN(C(=O)C(=O)c1cc(O)c(O)c(F)c1)CC2] |
| II-46 | 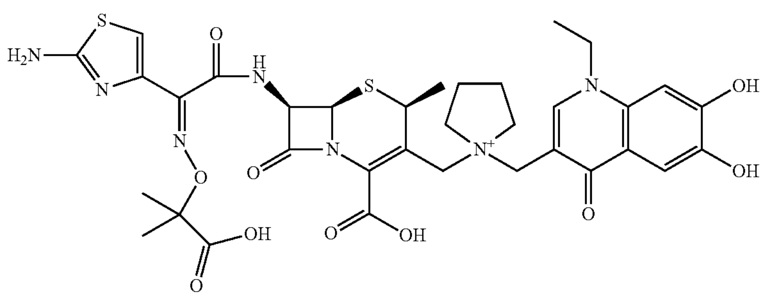 |
| II-47 | 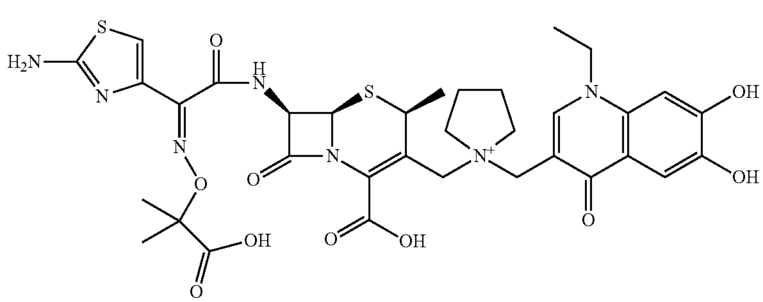 |

TABLE 6-continued

| Example No. | Structure |
|---|---|
| II-48 | 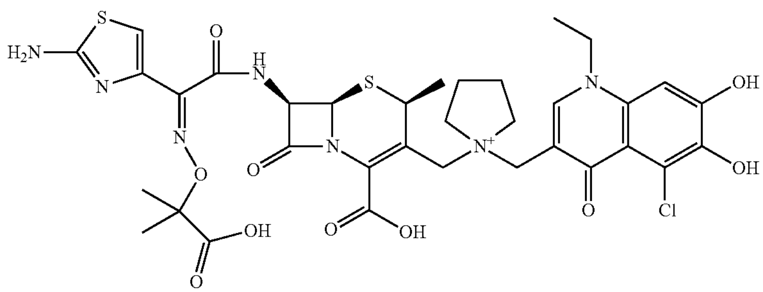 [SMILES: CCn1cc(C[N+]2(CC3=C(C(=O)O)N4C(=O)[C@@H](NC(=O)/C(=N\OC(C)(C)C(=O)O)c5csc(N)n5)[C@H]4S[C@H]3C)CCCC2)c(=O)c2c(Cl)c(O)c(O)cc21] |

TABLE 7

| Example No. | Structure |
|---|---|
| II-49 | 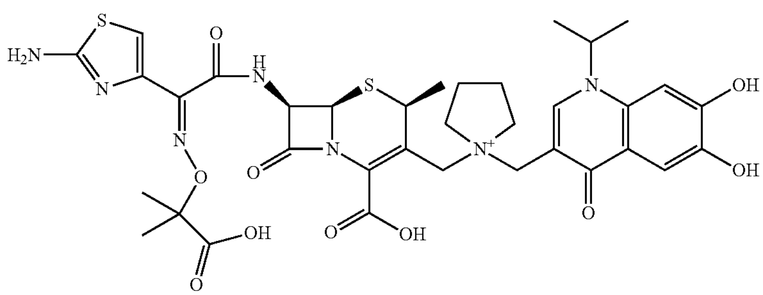 [SMILES: CC(C)n1cc(C[N+]2(CC3=C(C(=O)O)N4C(=O)[C@@H](NC(=O)/C(=N\OC(C)(C)C(=O)O)c5csc(N)n5)[C@H]4S[C@H]3C)CCCC2)c(=O)c2cc(O)c(O)cc21] |
| II-50 | 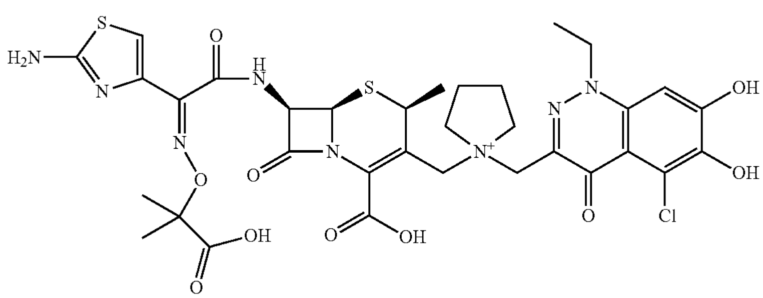 |
| II-51 | 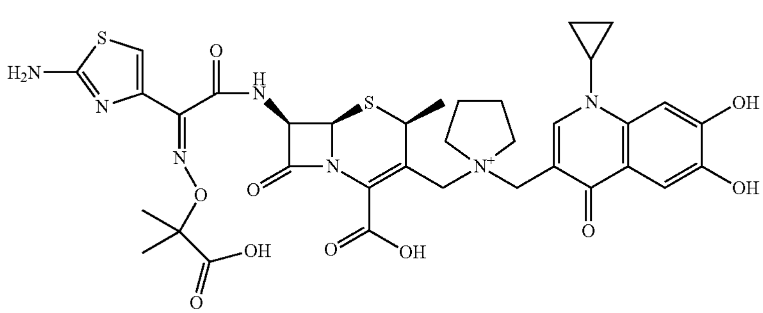 [SMILES: C[C@@H]1S[C@@H]2[C@H](NC(=O)/C(=N\OC(C)(C)C(=O)O)c3csc(N)n3)C(=O)N2C(C(=O)O)=C1C[N+]1(Cc2cn(C3CC3)c3cc(O)c(O)cc3c2=O)CCCC1] |

TABLE 7-continued
| Example No. | Structure |
|---|---|
| II-52 | 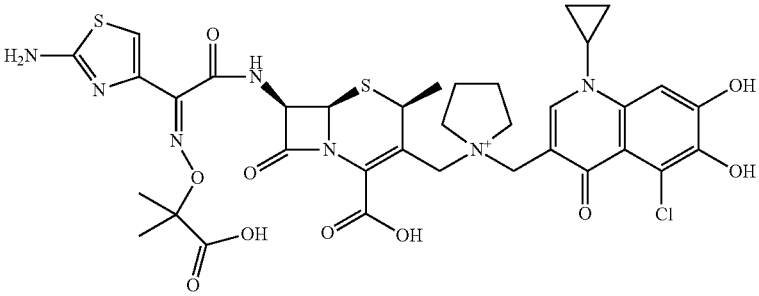 |
| II-53 | 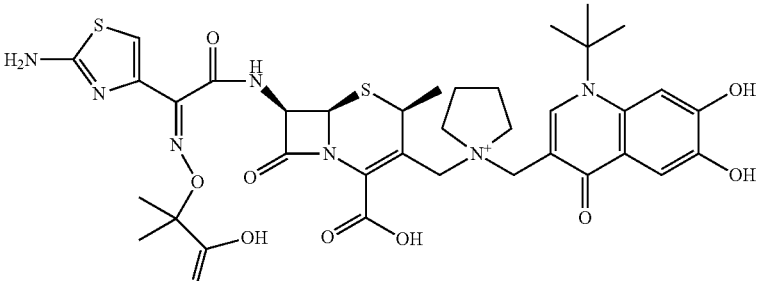 |
| II-54 | 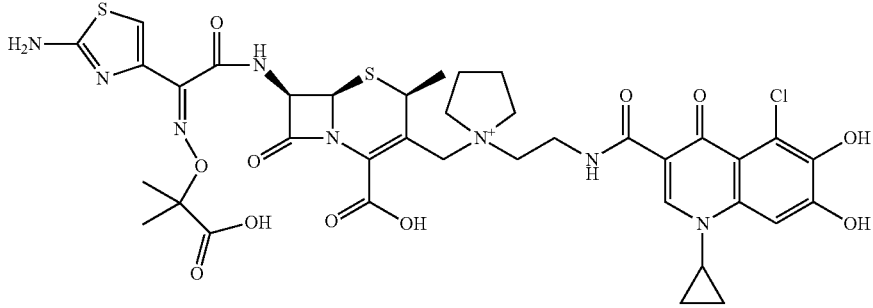 [SMILES: C[C@@H]1S[C@@H]2[C@H](NC(=O)/C(=N\OC(C)(C)C(=O)O)c3csc(N)n3)C(=O)N2C(C(=O)O)=C1C[N+]1(CCNC(=O)c2cn(C3CC3)c3cc(O)c(O)c(Cl)c3c2=O)CCCC1] |
| II-55 | 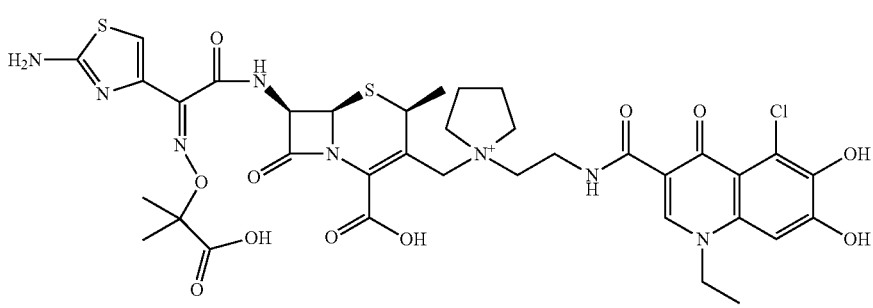 [SMILES: CCn1cc(C(=O)NCC[N+]2(CC3=C(C(=O)O)N4C(=O)[C@@H](NC(=O)/C(=N\OC(C)(C)C(=O)O)c5csc(N)n5)[C@H]4S[C@H]3C)CCCC2)c(=O)c2c(Cl)c(O)c(O)cc21] |

Test Example 1

Compound (I) of the invention was evaluated for in vitro antimicrobial activity thereof.

(Method)

Measurement of Minimum Inhibitory Concentration (MIC: µg/mL) was conducted according to CLSI (Clinical and Laboratory Standards Institute) method, and the amount of bacteria for inoculation was $5 \times 10^5$ cfu/mL, and cation-adjusted Iso-Sensitest broth containing human Apo-transferrin was used as a test medium, and the experiment was conducted using broth microdilution method. The bacteria used are listed below.

TABLE 8

| No. | Species | Strain Name | Enzyme Produced | Strain Type |
|---|---|---|---|---|
| 1 | E. Coli | JMI1890 | PER-1, TEM-1 | ESBL producing strain |
| 2 | A. baumannii | JMI7 | PER-1, OXA-23, 51 | ESBL and OXA-type carbapenemase producing strain |
| 3 | A. baumannii | JMI2346 | OXA-51, TEM | ESBL and OXA-type carbapenemase producing strain |
| 4 | K. pneumoniae | SR01358 | KPC-2 | ESBL and KPC-type carbapenemase producing strain |

(Results)

The test results are shown in Tables below. The values of inhibitory activity are expressed in microgram/mL (µg/ml).

TABLE 9

| Compound | E. Coli JMI:1890 | A. baumannii JMI:7 | A. baumannii JMI:2346 | K. pneumoniae SR01358 |
|---|---|---|---|---|
| I-1 | 1 | 1 | 16 | ≤0.031 |
| I-3 | 0.5 | 0.5 | 2 | ≤0.031 |
| I-8 | 1 | 1 | 16 | 0.25 |
| I-10 | 1 | 1 | 8 | ≤0.031 |
| I-11 | 2 | 2 | 16 | 0.063 |
| I-12 | 0.25 | 1 | 4 | ≤0.031 |
| I-13 | 1 | 2 | 8 | 0.063 |
| I-14 | 1 | 2 | 8 | ≤0.031 |
| I-15 | 1 | 4 | 16 | |
| I-16 | 0.5 | 1 | 8 | ≤0.031 |
| I-17 | 2 | 4 | 16 | ≤0.031 |
| I-20 | 0.063 | 0.125 | 0.5 | ≤0.031 |
| I-21 | 0.5 | 0.5 | 2 | 0.063 |
| I-22 | 0.5 | 0.5 | 4 | ≤0.031 |
| I-23 | 1 | 1 | 4 | 0.063 |
| I-24 | 2 | 1 | 8 | 0.125 |
| I-25 | 0.25 | 0.5 | 2 | ≤0.031 |
| I-26 | 0.5 | 0.5 | 4 | ≤0.031 |
| I-27 | 0.5 | 0.5 | 4 | ≤0.031 |
| I-32 | 1 | 0.5 | 2 | 0.125 |
| I-33 | 0.25 | 1 | 4 | 0.063 |
| I-35 | 0.5 | 1 | 16 | ≤0.031 |
| I-36 | 0.5 | 0.5 | 4 | 0.125 |
| I-37 | 0.5 | 1 | 4 | 0.125 |
| I-38 | 0.25 | 0.25 | 0.5 | 0.063 |
| I-39 | 0.25 | 0.125 | 1 | 0.063 |
| I-40 | 0.5 | 1 | 4 | 0.063 |
| I-41 | 1 | 1 | 4 | 0.063 |
| I-42 | 0.5 | 0.5 | 2 | 0.063 |
| I-43 | 0.5 | 1 | 4 | 0.063 |

TABLE 10

| Compound | E. Coli JMI:1890 | A. baumannii JMI:7 | A. baumannii JMI:2346 | K. pneumoniae SR01358 |
|---|---|---|---|---|
| I-51 | 0.5 | 2 | 8 | 0.125 |
| I-52 | 0.25 | 1 | 4 | ≤0.031 |
| I-53 | 0.25 | 2 | 4 | 0.25 |
| I-60 | 1 | 1 | 4 | ≤0.031 |
| I-61 | 2 | 2 | 16 | 0.063 |
| I-62 | 0.063 | 0.5 | 2 | ≤0.031 |
| I-63 | 1 | 1 | | ≤0.031 |
| I-64 | 0.125 | 2 | 4 | ≤0.031 |
| I-65 | 0.125 | 0.5 | 2 | ≤0.031 |
| I-66 | 0.063 | 0.25 | 1 | ≤0.031 |
| I-67 | 0.25 | 1 | 2 | ≤0.031 |
| I-68 | 0.5 | 2 | 8 | ≤0.031 |
| I-69 | 0.25 | 1 | 8 | ≤0.031 |
| I-71 | 0.25 | 0.5 | 2 | ≤0.031 |
| I-72 | 0.125 | 1 | 4 | ≤0.031 |
| I-73 | 0.063 | 0.25 | 2 | ≤0.031 |
| I-74 | 0.25 | 0.25 | 4 | ≤0.031 |
| I-75 | 0.125 | 0.25 | 4 | ≤0.031 |
| I-76 | 0.25 | 0.5 | 4 | ≤0.031 |
| I-77 | 0.25 | 0.5 | 1 | ≤0.031 |
| I-78 | 0.25 | 0.5 | 8 | ≤0.031 |
| I-83 | 0.063 | 0.5 | 2 | ≤0.031 |
| I-84 | 2 | 1 | 16 | ≤0.031 |
| I-85 | 0.5 | 2 | 8 | 0.25 |

TABLE 11

| Compound | E. Coli JMI:1890 | A. baumannii JMI:7 | A. baumannii JMI:2346 | K. pneumoniae SR01358 |
|---|---|---|---|---|
| I-90 | 1 | 0.5 | 8 | ≤0.031 |
| I-92 | 2 | 4 | 16 | 0.125 |
| I-94 | 0.5 | 1 | 4 | 0.063 |
| I-96 | 0.125 | 1 | 8 | ≤0.031 |
| I-98 | 0.063 | 0.5 | 4 | ≤0.031 |
| I-99 | 1 | 2 | 16 | ≤0.031 |
| I-100 | 0.125 | 0.5 | 1 | 0.063 |
| I-101 | 0.063 | 0.25 | 0.5 | ≤0.031 |
| I-102 | 0.125 | 0.5 | 2 | ≤0.031 |
| I-103 | 0.25 | 0.5 | 2 | ≤0.031 |
| I-104 | 0.125 | 1 | 1 | ≤0.031 |
| I-105 | 0.25 | 2 | 4 | ≤0.031 |
| I-107 | 0.5 | 2 | 4 | ≤0.031 |
| I-108 | 0.5 | 0.5 | 2 | ≤0.031 |
| I-109 | 0.5 | 1 | 8 | 0.063 |
| I-113 | 0.25 | 0.25 | 4 | ≤0.031 |
| I-114 | 0.125 | 0.5 | 4 | ≤0.031 |
| I-115 | 0.25 | 0.25 | 2 | ≤0.031 |
| I-116 | ≤0.031 | 0.25 | 1 | ≤0.031 |
| I-117 | ≤0.031 | 0.5 | 1 | 0.25 |
| I-118 | ≤0.031 | 0.25 | 0.5 | 0.063 |
| I-120 | 0.063 | 0.5 | 2 | ≤0.031 |
| I-121 | 0.063 | 0.5 | 2 | ≤0.031 |

TABLE 11-continued

| Compound | E. Coli JMI:1890 | A. baumannii JMI:7 | A. baumannii JMI:2346 | K. pneumoniae SR01358 |
|---|---|---|---|---|
| I-122 | 0.25 | 0.5 | 2 | ≤0.031 |
| I-123 | 0.125 | 0.5 | 4 | ≤0.031 |
| I-124 | 0.125 | 0.5 | 2 | ≤0.031 |
| I-125 | 0.125 | 0.5 | 8 | ≤0.031 |

TABLE 12

| Compound | E. Coli JMI:1890 | A. baumannii JMI:7 | A. baumannii JMI:2346 | K. pneumoniae SR01358 |
|---|---|---|---|---|
| I-4 | 2 | 1 | | ≤0.031 |
| I-54 | 0.125 | 0.5 | 1 | ≤0.031 |
| I-81 | 0.5 | 2 | 8 | ≤0.031 |
| I-126 | 0.063 | 0.25 | 0.5 | ≤0.031 |
| I-130 | 8 | | | ≤0.031 |
| I-131 | 0.125 | 2 | 2 | 0.063 |
| I-132 | 0.25 | 1 | 4 | ≤0.031 |
| I-133 | 0.063 | 0.5 | 2 | ≤0.031 |
| I-134 | 0.125 | 1 | 2 | ≤0.031 |
| I-135 | 0.125 | 1 | 4 | ≤0.031 |
| I-136 | 0.5 | 1 | 2 | ≤0.031 |
| I-137 | 0.25 | 0.5 | 2 | ≤0.031 |
| I-138 | 0.25 | 0.5 | 4 | ≤0.031 |
| I-140 | 0.5 | 4 | | ≤0.031 |
| I-142 | 0.25 | 0.5 | 2 | ≤0.031 |
| I-150 | 2 | 0.5 | 2 | ≤0.031 |
| I-160 | ≤0.031 | 0.25 | 0.5 | 0.063 |
| I-161 | 0.125 | 0.25 | 4 | ≤0.031 |
| I-164 | ≤0.031 | 0.5 | 2 | ≤0.031 |
| I-165 | ≤0.031 | 0.5 | 1 | ≤0.031 |
| I-169 | 0.063 | 0.25 | 0.5 | ≤0.031 |
| I-174 | 4 | 0.25 | 1 | ≤0.031 |
| I-177 | 0.063 | 0.25 | 0.5 | ≤0.031 |
| I-180 | ≤0.031 | 0.5 | 1 | ≤0.031 |

As shown above, Compounds (I) of the invention have a wide antimicrobial spectrum, in particular, potent antimicrobial spectrum against Gram negative bacteria, and/or effectiveness against multidrug-resistant bacteria, and further to exhibit high stability against beta-lactamase producing Gram negative bacteria.

Formulation Example 1

Powder of a compound of the present invention is formulated to prepare an injecting agent.

INDUSTRIAL APPLICABILITY

The compounds of the present invention have a wide antimicrobial spectrum against Gram negative bacteria and Gram positive bacteria, and are effective as an antimicrobial drug having high stability against beta-lactamase producing Gram negative bacteria. Moreover, the present compounds have good disposition, and high water solubility, and thus particularly effective as an injecting agent.

The invention claimed is:

1. A compound which is:

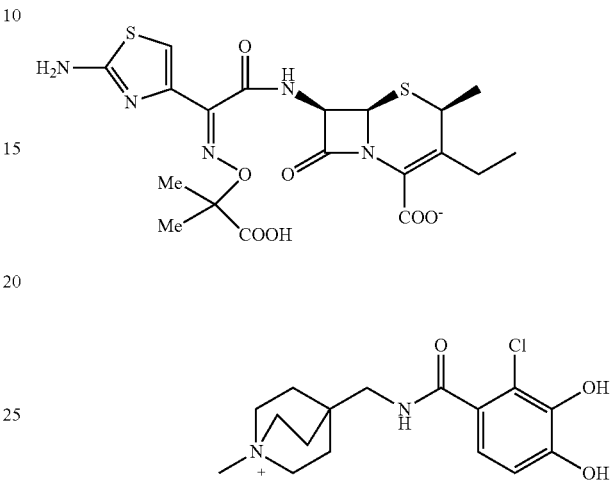

or a pharmaceutically acceptable salt thereof.

2. A compound which is:

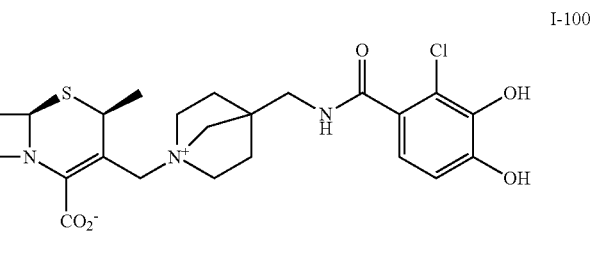

I-100

3. A pharmaceutical composition, which comprises a compound or a pharmaceutically acceptable salt thereof according to claim 1 and at least one or more pharmaceutically acceptable excipients.

4. A pharmaceutical composition, which comprises a compound according to claim 2 and at least one or more pharmaceutically acceptable excipients.

5. A method of treating bacterial infections, which comprises administering a therapeutically effective amount of a compound or a pharmaceutically acceptable salt thereof according to claim 1 to a subject in need thereof.

6. The method according to claim 5, wherein the bacterial infections are caused by Gram-Negative bacteria or Gram-Positive bacteria.

7. A method of treating bacterial infections, which comprises administering a pharmaceutical composition according to claim 3 to a subject in need thereof.

8. A method of treating a bacterial infection, which comprises administering a compound or pharmaceutically acceptable salt thereof according to claim 1 to a subject in need thereof.

9. The method according to claim 8, wherein the bacterial infection is caused by Gram-Negative bacteria or Gram-Positive bacteria.

10. The method according to claim 8, wherein the compound or a pharmaceutically acceptable salt thereof according to claim 1 exhibits potent antimicrobial activity against beta-lactamase producing Gram negative bacteria.

11. The method according to claim 9, wherein the Gram negative bacteria is selected from:
- Gram negative bacteria of enterobacteria selected from *E. coli, Klebsiella, Serratia, Enterobacter, Citrobacter, Morganella, Providencia* or *Proteus;*
- Gram negative bacteria colonized in respiratory system selected from *Haemophilus, Moraxella;*
- Gram negative bacteria of glucose non fermentation selected from *Pseudomonas aeruginosa, Pseudomonas* other than *P. aeruginosa, Stenotrophomonas, Burkholderia* or *Acinetobacter;*
- Gram negative multidrug-resistant bacteria selected from Class B type metallo-betalactamase producing Gram negative bacteria, and extended-spectrum beta-lactamase (ESBL) producing bacteria; or
- Gram beta-lactam drug resistant Gram negative bacteria selected from ESBL producing bacteria.

12. The method according to claim 9, wherein the Gram positive bacteria is selected from methicillin-resistant *Staphylococcus aureus* (MRSA) or penicillin-resistant *Streptococcus pneumoniae* (PRSP).

13. A method for treating biothreat organism(s), which comprises administering a compound or a pharmaceutically acceptable salt thereof according to claim 1 or a pharmaceutically acceptable salt thereof to a subject in need thereof; wherein:
- the biothreat organism(s) is or are selected from *Yersinia pestis, Bacillus anthracis, Francisella tularensis, Burkholderia mallei, Burkholderia pseudomallei, Brucella suis, Brucella melitensis* or *Brucella abortus.*

14. A method for treating a biothreat organism or biothreat organisms, which comprises administering a compound according to claim 3 to a subject in need thereof; wherein the biothreat organism(s) is or are selected from *Yersinia pestis, Bacillus anthracis, Francisella tularensis, Burkholderia mallei, Burkholderia pseudomallei, Brucella suis, Brucella melitensis* or *Brucella abortus.*

15. A method for treating a Gram-negative bacteria infection, which comprises administering a compound or a pharmaceutically aceeptable salt thereof according to claim 1 to a subject in need thereof.

16. The method according to claim 15, wherein the bacterial infection is caused by Gram-Negative bacteria or Gram-Positive bacteria.

17. The method according to claim 16, wherein the Gram negative bacteria is selected from:
- Gram negative bacteria of enterobacteria selected from *E. coli, Klebsiella, Serratia, Enterobacter, Citrobacter, Morganella, Providencia* or *Proteus;*
- Gram negative bacteria colonized in respiratory system selected from *Haemophilus, Moraxella;*
- Gram negative bacteria of glucose non fermentation selected from *Pseudomonas aeruginosa, Pseudomonas* other than *P. aeruginosa, Stenotrophomonas, Burkholderia* or *Acinetobacter;*
- Gram negative multidrug-resistant bacteria selected from Class B type metallo-betalactamase producing Gram negative bacteria, and extended-spectrum beta-lactamase (ESBL) producing bacteria; or
- Gram beta-lactam drug resistant Gram negative bacteria selected from ESBL producing bacteria.

18. A method for treating a Gram-negative bacterial infection, which comprises administering a pharmaceutical composition according to claim 3 to a subject in need thereof.

19. A method for treating Gram-positive bacterial infections, which comprises administering a compound or a pharmaceutically acceptable salt thereof according to claim 1 to a subject in need thereof.

20. The method according to claim 19, wherein the bacterial infection is caused by Gram-Positive bacteria.

21. The method according to claim 20, wherein the Gram positive bacteria is selected from methicillin-resistant *Staphylococcus aureus* (MRSA) or penicillin-resistant *Streptococcus pneumoniae* (PRSP).

22. A method for treating Gram-positive bacterial infections, which comprises administering a pharmaceutical composition according to claim 3 to a subject in need thereof.

23. A method of treating a bacterial infection, which comprises administering a compound according to claim 3 to a subject in need thereof.

\* \* \* \* \*